US007491698B2

(12) United States Patent
Hey et al.

(10) Patent No.: US 7,491,698 B2
(45) Date of Patent: Feb. 17, 2009

(54) MIXING AND MATCHING TC PROTEINS FOR PEST CONTROL

(75) Inventors: Timothy D. Hey, Zionsville, IN (US); Amanda D. Schleper, Westfield, IN (US); Scott A. Bevan, Indianapolis, IN (US); Scott B. Bintrim, Westfield, IN (US); Jon C. Mitchell, West Lafayette, IN (US); Ze Sheng Li, Westfield, IN (US); Weiting Ni, Carmel, IN (US); Baolong Zhu, San Diego, CA (US); Donald J. Merlo, Carmel, IN (US); Patricia C. Apel-Birkhold, Zionsville, IN (US); Thomas Meade, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/754,115

(22) Filed: Jan. 7, 2004

(65) Prior Publication Data

US 2004/0208907 A1    Oct. 21, 2004

Related U.S. Application Data

(60) Provisional application No. 60/441,723, filed on Jan. 21, 2003.

(51) Int. Cl.
*A61K 38/16*    (2006.01)
*A01N 33/04*    (2006.01)
*C07K 14/195*   (2006.01)

(52) U.S. Cl. .................. 514/12; 424/405; 530/350

(58) Field of Classification Search ............... 514/12; 424/405; 530/350
See application file for complete search history.

(56) References Cited

U.S. PATENT DOCUMENTS 6,048,838 A    4/2000   Ensign et al.

(Continued)

FOREIGN PATENT DOCUMENTS

WO    WO 95/00647 A1    1/1995

(Continued)

OTHER PUBLICATIONS

Morgan et al., "Sequence analysis of insecticidal genes from *Xenorhabdus nematophilus* PMFI296," Appl Environ Microbiol 67:2062-2069, 2001.*

(Continued)

*Primary Examiner*—Rebecca E. Prouty
*Assistant Examiner*—Rosanne Kosson
(74) *Attorney, Agent, or Firm*—Baker & Daniels LLP

(57) ABSTRACT

The subject invention relates to the surprising discovery that toxin complex (TC) proteins, obtainable from *Xenorhabdus*, *Photorhabdus*, and *Paenibacillus*, can be used interchangeably with each other. In particularly preferred embodiments of the subject invention, the toxicity of a "stand-alone" TC protein (from *Photorhabdus*, *Xenorhabdus*, or *Paenibacillus*, for example) is enhanced by one or more TC protein "potentiators" derived from a source organism of a different genus from which the toxin was derived. As one skilled in the art will recognize with the benefit of this disclosure, this has broad implications and expands the range of utility that individual types of TC proteins will now be recognized to have. Among the most important advantages is that one skilled in the art will now be able to use a single set of potentiators to enhance the activity of a stand-alone *Xenorhabdus* protein toxin as well as a stand-alone *Photorhabdus* protein toxin. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes, and transformation events, needed to be expressed by a transgenic plant to achieve effective control of a wider spectrum of target pests. Certain preferred combinations of heterologous TC proteins are also disclosed herein. Other objects, advantages, and features of the subject invention will be apparent to one skilled in the art having the benefit of the subject disclosure.

19 Claims, 7 Drawing Sheets

Schematic Diagram of pET/pCot Constructions

U.S. PATENT DOCUMENTS

Figure 1:
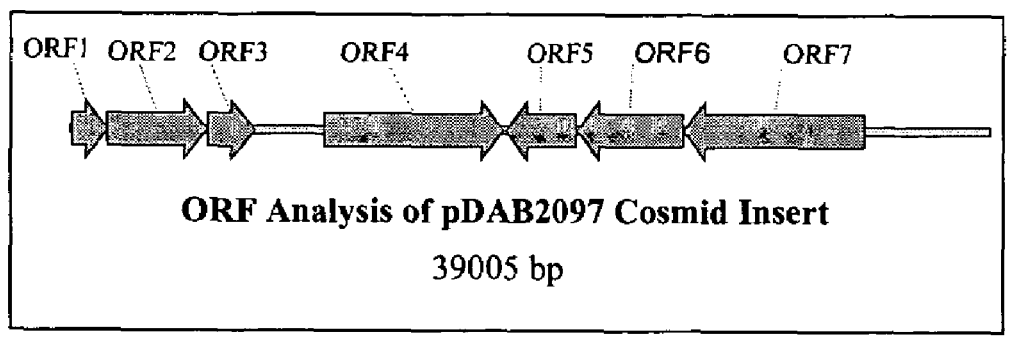

| | | | |
|---|---|---|---|
| 6,174,860 | B1 | 1/2001 | Kramer et al. |
| 6,277,823 | B1 | 8/2001 | Kramer et al. |
| 6,281,413 | B1 * | 8/2001 | Kramer et al. ............... 800/302 |
| 6,590,142 | B1 | 7/2003 | Petell et al. |
| 2002/0078478 | A1 | 6/2002 | Ffrench-Constant |
| 2004/0103455 | A1 * | 5/2004 | Ffrench-Constant et al. ......................... 800/279 |

FOREIGN PATENT DOCUMENTS

| | | |
|---|---|---|
| WO | WO 97/17432 A1 | 5/1997 |
| WO | WO 98/08388 A1 | 3/1998 |
| WO | WO 98/08932 A1 | 3/1998 |
| WO | WO 98/50427 A1 | 11/1998 |
| WO | WO 99/03328 A1 | 1/1999 |
| WO | WO 99/42589 A2 | 8/1999 |
| WO | WO 99/54472 A1 | 10/1999 |
| WO | WO 00/30453 A2 | 6/2000 |
| WO | WO 00/42855 A1 | 7/2000 |
| WO | WO 01/11029 A1 | 2/2001 |
| WO | WO 02/094867 A2 | 11/2002 |
| WO | WO 0294867 A2 * | 11/2002 |
| WO | WO 2004/002223 A2 | 1/2004 |

OTHER PUBLICATIONS

Result 1 from searching SEQ ID No. 34 in the UniProt database on Feb. 17, 2006, alignment with the sequence of Morgan et al. cited in U above.*

Result 1 from searching SEQ ID No. 45 in the published patent applications protein database on Feb. 17, 2006, alignment with SEQ ID No. 10 of French-Constant et al. cited in A above.*

Result 3 from searching SEQ ID No. 45 in the Geneseq protein database on Feb. 17, 2006, alignment with SEQ ID No. 3319 of Duchaud et al. cited in N above.*

Result 1 from searching SEQ ID No. 47 in the published patent applications protein database on Feb. 17, 2006, alignment with SEQ ID No. 12 of Ffrench-Constant et al. cited in A above.*

Result 1 from searching SEQ ID No. 47 in the issued patents protein database on Feb. 17, 2006, alignment with SEQ ID No. 12 of Kramer et al. cited in B above.*

Alignment of SEQ ID No. 34 and the protein encoded by SEQ ID No. 21, TcdA1 (GenBank record No. AAF05542), from the GenBank Blast web site, http://www.ncbi.nlm.nih.gov/blast/bl2seq/wblast2.cgi, Jun. 21, 2006.*

Written Description Guidelines, pp. 35-40, http://www.uspto.gov/web/offices/pac/writtendesc.pdf.*

H. Guo et al., "Protein Tolerance to Random Amino Acid Change", PNAS 101(25):9205-9210, 2004.*

Bowen et al., "Insecticidal toxins from the bacterium *Photorhabdus luminescens*," Science 280 (5372), 2129-2132 (1998).

Bowen et al., Insecticidal toxin complex protein TcaC (*Photorhabdus luminescens*), Genbank Accession No. AAC38625 (gi:3265037), Jun. 30, 1998.

Bowen et al., Insecticidal toxin complex protein TcbA (*Photorhabdus luminescens*), Genbank Accession No. AAC38627 (gi:3265040), Jun. 30, 1998.

Ffrench-Constant et al., "*Photorhabdus* toxins: novel biological insecticides," Current Opinion in Microbiology (1999), p. 284-288, vol. 12.

Ffrench-Constant et al., "Novel insecticidal toxins from nematode-symbiotic bacteria," Cellular and Mol. Life Sciences (May. 2000), p. 828-833, vol. 57, No. 5.

Ffrench-Constant et al., "A Genomic Sample Sequence of the Entomopathogenic Bacterium *Photorhabdus* . . . ," Appl. Environ. Microbiol. (Aug. 2000), p. 3310-3329, vol. 66, No. 8.

Forst et al., "Molecular Biology of the Symbiotic-Pathogenic Bacteria *Xenorhabdus* spp. and *Photorhabdus* spp.,"Microbiological Reviews (Mar. 1996), p. 21-43, vol. 60, No. 1.

Hurst et al., "Plasmid-Located Pathogenicity Determinants of *Serratia entomophila* . . . ," Journal of Bacteriology (Sep. 2000), p. 5127-5138, vol. 182, No. 18.

Hurst et al., SepA (*Serratia entomophila*), Genbank Accession No. AAG09642 (gi:9963678) Nov. 5, 2003.

Hurst et al., SepB (*Serratia entomophila*), Genbank Accession No. AAG09643 (gi:9963679) Nov. 5, 2003.

Hurst et al., SepA (*Serratia entomophila*), Genbank Accession No. AAG09642 (gi:9963678).

Hurst et al., SepB (*Serratia entomophila*), Genbank Accession No. AAG09643 (gi:9963679).

Hurst et al., SepC (*Serratia entomophila*), Genbank Accession No. AAG09644 (gi:9963980) Nov. 5, 2003.

Merlo et al., Toxin A (*Photorhabdus luminescens*), Genbank Accession No. AAF05542 (gi:6176340), Nov. 2, 1999.

Morgan et al., "Sequence Analysis of Insecticidal Genes from *Xenorhabdus nematophilus* PMFI296," Appl. Environ. Microbiol. (May 2001), p. 2062-2069, vol. 67, No. 5.

Morgan et al., *Xenorhabdus nematophilus* genes, Genbank Accession No. AJ308438, May 11, 2001.

Morgan et al., Putative chitinase (*Xenorhabdus nematophila*), Genbank Accession No. CAC38398 (gi:14041727), May 11, 2001.

Morgan et al., XptA1 protein (*Xenorhabdus nematophila*), Genbank Accession No. CAC38401 (gi:14041730), May 11, 2001.

Morgan et al., XptB1 protein (*Xenorhabdus nematophila*), Genbank Accession No. CAC38402 (gi:14041731), May 11, 2001.

Morgan et al., XptC1 protein (*Xenorhabdus nematophila*), Genbank Accession No. CAC38403 (gi:14041732), May 11, 2001.

Morgan et al., XptA2 protein (*Xenorhabdus nematophila*), Genbank Accession No. CAC38404 (gi:14041733), May 11, 2001.

NCBI Microbial Genomes Annotation Project, COG3209: Rhs family protein (*Pseudomonas* . . . ), Genbank Accession No. ZP_00083266 (gi:23058175) Apr. 9, 2004.

Hurst et al., SepC (*Serratia entomophila*), Genbank Accession No. AAG09644 (gi:9963980).

NCBI Microbial Genomes Annotation Project, Hypothetical protein (*Pseudomonas fluorescens* . . . ), Genbank Accession No. ZP_00084399 (gi:23059431) Apr. 9, 2004.

NCBI Microbial Genomes Annotation Project, COG3209: Rhs family protein (*Pseudomonas* . . . ), Genbank Accession No. ZP_00084400 (gi:23059432) Apr. 9, 2004.

NCBI Microbial Genomes Annotation Project, COG3209: Rhs family protein (*Pseudomonas* . . . ), Genbank Accession No. ZP_00084401 (gi:23059433) Apr. 9, 2004.

NCBI Microbial Genomes Annotation Project, COG3209: Rhs family protein (*Pseudomonas* . . . ), Genbank Accession No. ZP_00084403 (gi:23059435) Apr. 9, 2004.

NCBI Microbial Genomes Annotation Project, COG3209: Rhs family protein (*Pseudomonas* . . . ), Genbank Accession No. ZP_00125560 (gi:23470227) Sep. 23, 2003.

NCBI Microbial Genomes Annotation Project, Hypothetical protein (*Pseudomonas syringae* . . . ), Genbank Accession No. ZP_00126265 (gi:23470933) Sep. 23, 2003.

NCBI Microbial Genomes Annotation Project, COG3209: Rhs family protein (*Pseudomonas* . . . ), Genbank Accession No. ZP_00127864 (gi:23472540) Apr. 9, 2004.

NCBI Microbial Genomes Annotation Project, COG3209: Rhs family protein (*Pseudomonas* . . . ), Genbank Accession No. ZP_00127865 (gi:23472541) Apr. 9, 2004.

NCBI Microbial Genomes Annotation Project, Hypothetical protein (*Pseudomonas syringae* . . . ), Genbank Accession No. ZP_00127867 (gi:23472543) Apr. 9, 2004.

NCBI Microbial Genomes Annotation Project, COG3209: Rhs family protein (*Pseudomonas* . . . ), Genbank Accession No. ZP_00083267 (gi:23058176).

NCBI Microbial Genomes Annotation Project, Hypothetical protein (*Pseudomonas fluorescens* . . . ), Genbank Accession No. ZP_00084399 (gi:23059431).

NCBI Microbial Genomes Annotation Project, COG3209: Rhs family protein (*Pseudomonas* . . . ), Genbank Accession No. ZP_00084400 (gi:23059432).

NCBI Microbial Genomes Annotation Project, COG3209: Rhs family protein (*Pseudomonas* . . . ), Genbank Accession No. ZP_00084401 (gi:23059433).

NCBI Microbial Genomes Annotation Project, COG3209: Rhs family protein (*Pseudomonas* . . . ), Genbank Accession No. ZP_00084403 (gi:23059435).
NCBI Microbial Genomes Annotation Project, COG3209: Rhs family protein (*Pseudomonas* . . . ), Genbank Accession No. ZP_00125560 (gi:23470227).
NCBI Microbial Genomes Annotation Project, Hypothetical protein (*Pseudomonas syringae* . . . ), Genbank Accession No. ZP_00126265 (gi:23470933).
NCBI Microbial Genomes Annotation Project, COG3209: Rhs family protein (*Pseudomonas* . . . ), Genbank Accession No. ZP_00127864 (gi:23472540).
NCBI Microbial Genomes Annotation Project, COG3209: Rhs family protein (*Pseudomonas* . . . ), Genbank Accession No. ZP_00127865 (gi:23472541).
NCBI Microbial Genomes Annotation Project, Hypothetical protein (*Pseudomonas syringae* . . . ), Genbank Accession No. ZP_00127867 (gi:23472543).
NCBI Microbial Genomes Annotation Project, Hypothetical protein (*Pseudomonas syringae* . . . ), Genbank Accession No. ZP_00127868 (gi:23472544) Apr. 9, 2004.
NCBI Microbial Genomes Annotation Project, COG3209: Rhs family protein (*Pseudomonas* . . . ), Genbank Accession No. ZP_00127869 (gi:23472545) Apr. 9, 2004.
NCBI Microbial Genomes Annotation Project, COG3209: Rhs family protein (*Pseudomonas* . . . ), Genbank Accession No. ZP_001237870 (gi:23472546) Apr. 9, 2004.
NCBI Microbial Genomes Annotation Project, COG3209: Rhs family protein (*Pseudomonas* . . . ), Genbank Accession No. ZP_00123877 (gi:23468542) Apr. 9, 2004.
Pettersson et al., "Transfer of *Bacillus lentimorbus* and *Bacillus popilliae* to the genus *Paenibacillus* . . . ," Int. J. Syst. Bacteriol. (1999), p. 531-540, vol. 49, No. 2 (abstract).
Shida et al., "Emended description of *Paenibacillus amylolyticus* and description of *Paenibacillus* . . . ," Int. J. Syst. Bacteriol. (1997), p. 299-306, vol. 47, No. 2 (abstract).
Waterfield et al., "Oral Toxicity of *Photorhabdus luminescens* W14 Toxin Complexes in *Escherichia coli*," Appl. Environ. Microbiol. (Nov. 2001), p. 5017-5024, vol. 67, No. 11.
Waterfield et al., "The toxin complex genes of *Photorhabdus*: a growing gene family," Trends in Microbiology (Apr. 2001), p. 185-191, vol. 9, No. 4.
Waterfield et al., "Genomic islands in *Photorhabdus*," Trends Microbiol. 10 (12), 541-545 (2002).
Waterfield et al., Toxin complex protein (*Photorhabdus luminescens*), Genbank Accession No. AAL18473 (gi:16416915) Oct. 25, 2001.
NCBI Microbial Genomes Annotation Project, Hypothetical protein (*Pseudomonas syringae* . . . ), Genbank Accession No. ZP_00127868 (gi:23472544).
NCBI Microbial Genomes Annotation Project, COG3209: Rhs family protein (*Pseudomonas* . . . ), Genbank Accession No. ZP_00127869 (gi:23472545).
NCBI Microbial Genomes Annotation Project, COG3209: Rhs family protein (*Pseudomonas* . . . ), Genbank Accession No. ZP_001237870 (gi:23472546).
NCBI Microbial Genomes Annotation Project, COG3209: Rhs family protein (*Pseudomonas* . . . ), Genbank Accession No. ZP_00123877 (gi:23468542).
Waterfield et al., Toxin complex protein (*Photorhabdus luminescens*), Genbank Accession No. AAL18473 (gi:16416915).
Waterfield et al., TcdA1; toxin complex protein (*Photorhabdus luminescens*), Genbank Accession No. AAL18486 (gi:16416929) Jul. 17, 2003.
Waterfield et al., TcdB1; toxin complex protein (*Photorhabdus luminescens*), Genbank Accession No. AAL18487 (gi:16416930) Jul. 17, 2003.
Waterfield et al., TccC2 (*Photorhabdus luminescens*), Genbank Accession No. AAL18492 (gi:27479639) Jul. 17, 2003.
Waterfield et al., TccC4 (*Photorhabdus luminescens*), Genbank Accession No. AAO17196 (gi:27479669) Jul. 17, 2003.
Waterfield et al., TcdA2 (*Photorhabdus luminescens*), Genbank Accession No. AAO17201 (gi:27479674) Jul. 17, 2003.
Waterfield et al., TcdB2 (*Photorhabdus luminescens*), Genbank Accession No. AAO17202 (gi:27479675) Jul. 17, 2003.
Waterfield et al., TccC3 (*Photorhabdus luminescens*), Genbank Accession No. AAO17204 (gi:27479677) Jul. 17, 2003.
Waterfield et al., TcdA4 (*Photorhabdus luminescens*), Genbank Accession No. AAO17209 (gi:27479682) Jul. 17, 2003.
Waterfield et al., TccC5 (*Photorhabdus luminescens*), Genbank Accession No. AAO17210 (gi:27479683) Jul. 17, 2003.
Waterfield et al., TcdA1; toxin complex protein (*Photorhabdus luminescens*), Genbank Accession No. AAL18486 (gi:16416929).
Waterfield et al., TcdB1; toxin complex protein (*Photorhabdus luminescens*), Genbank Accession No. AAL18487 (gi:16416930).
Waterfield et al., TccC2 (*Photorhabdus luminescens*), Genbank Accession No. AAL18492 (gi:27479639).
Waterfield et al., TccC4 (*Photorhabdus luminescens*), Genbank Accession No. AAO17196 (gi:27479669).
Waterfield et al., TcdA2 (*Photorhabdus luminescens*), Genbank Accession No. AAO17201 (gi:27479674).
Waterfield et al., TcdB2 (*Photorhabdus luminescens*), Genbank Accession No. AAO17202 (gi:27479675).
Waterfield et al., TccC3 (*Photorhabdus luminescens*), Genbank Accession No. AAO17204 (gi:27479677).
Waterfield et al., TcdA4 (*Photorhabdus luminescens*), Genbank Accession No. AAO17209 (gi:27479682).
Waterfield et al., TccC5 (*Photorhabdus luminescens*), Genbank Accession No. AAO17210 (gi:27479683).

* cited by examiner

Figure 1. Orientation of ORFs identified in pDAB2097

Figure 2:
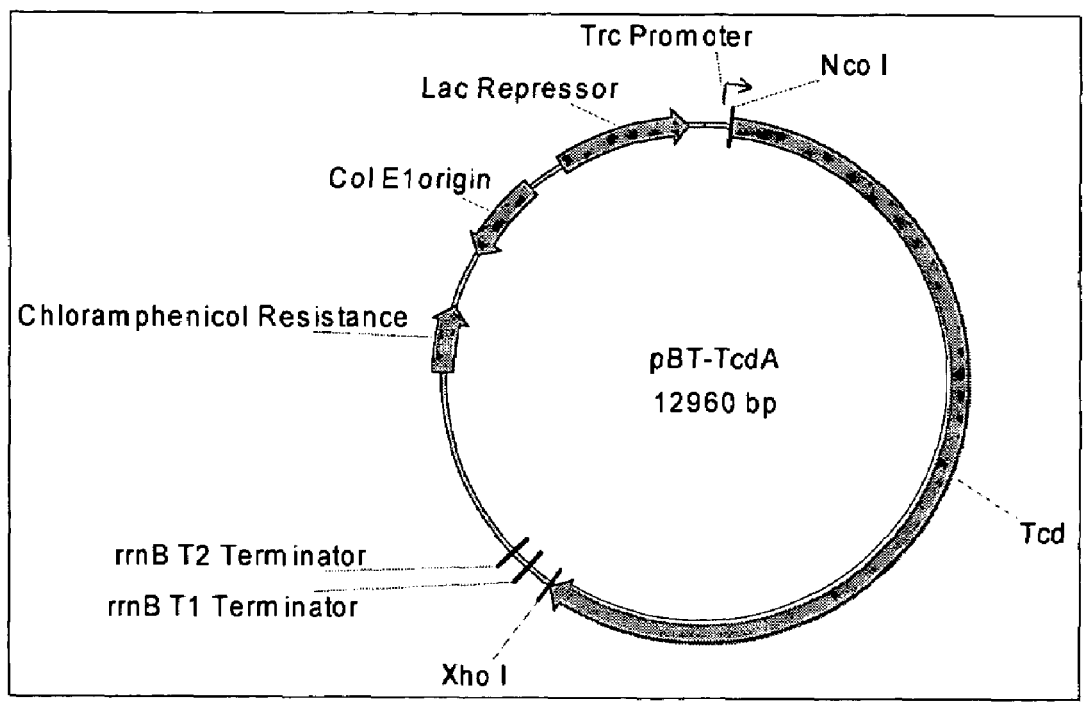

Figure 2. Expression Plasmid pBT-TcdA.

Figure 3:
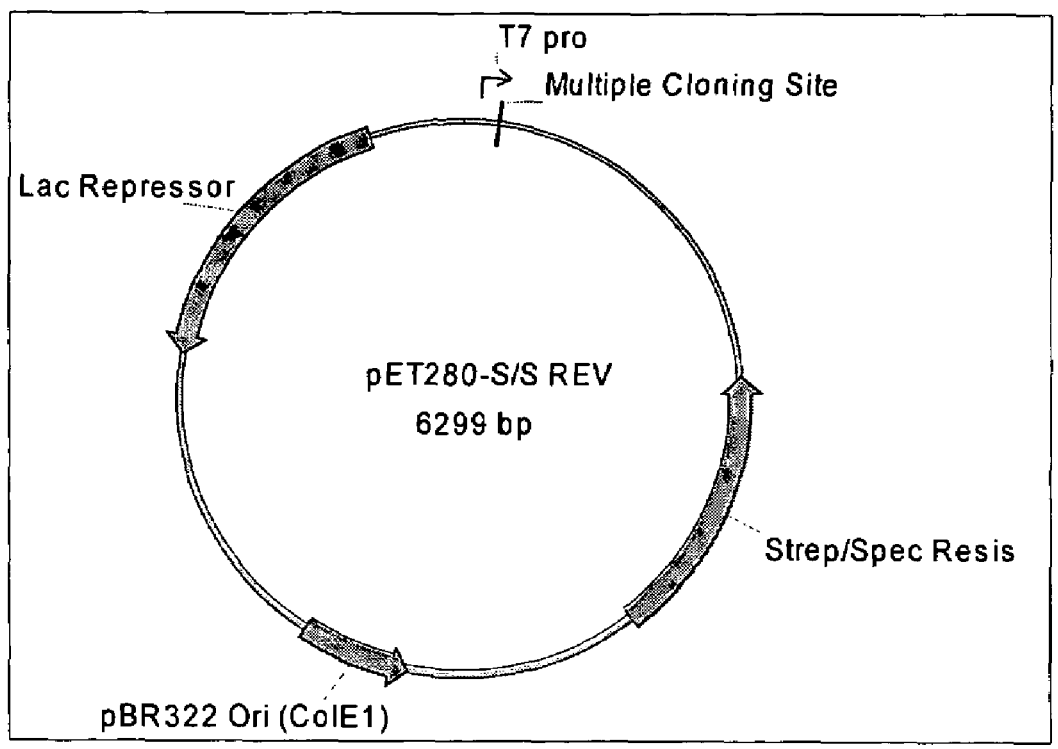

Figure 3. Expression Vector Plasmid pET280 Vector

Figure 4:
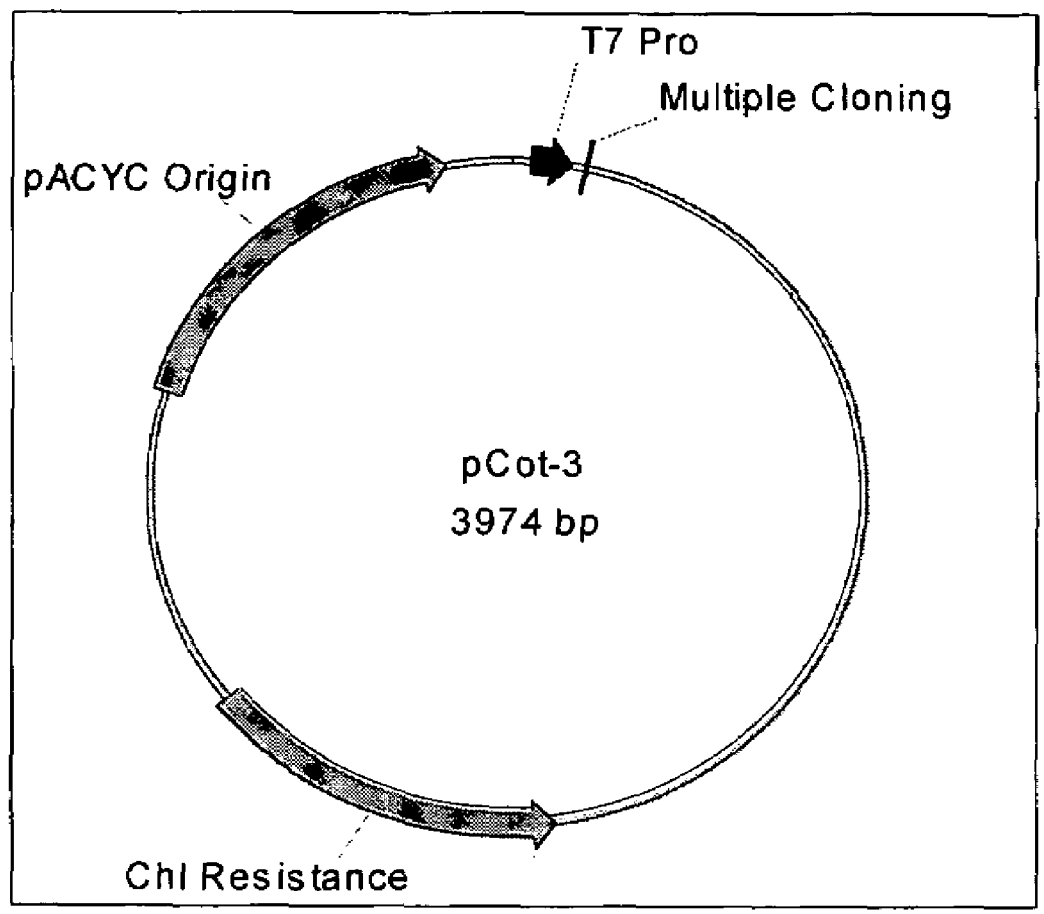

Figure 4. Expression Plasmid pCot-3

Figure 5:
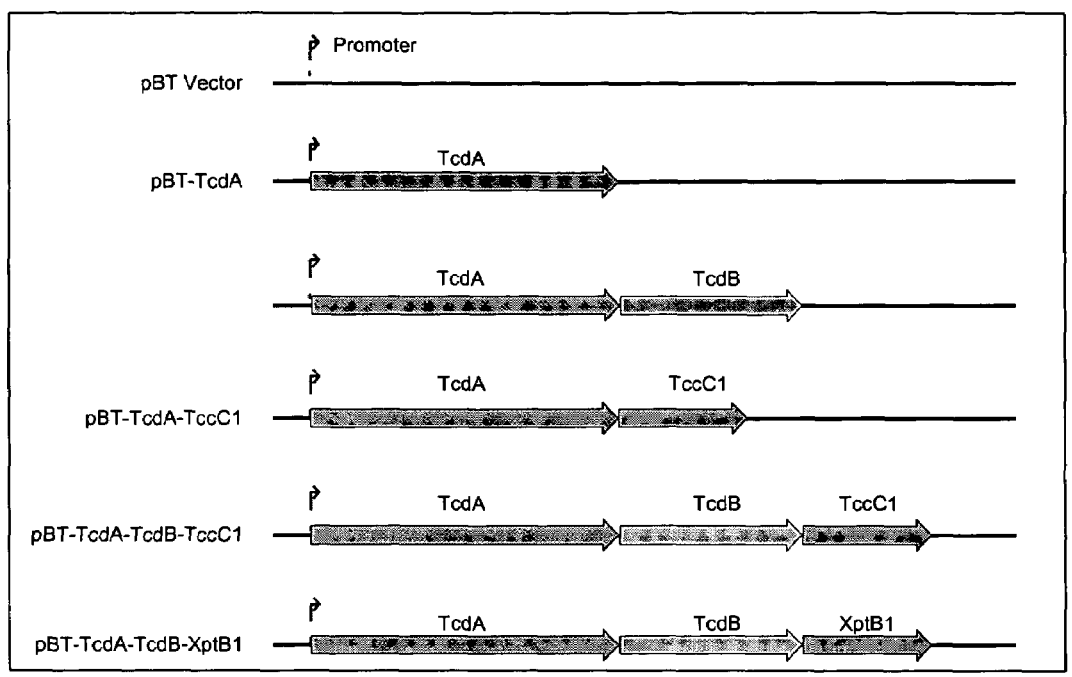

Figure 5. Schematic Diagram of pBT Constructions

Figure 6:
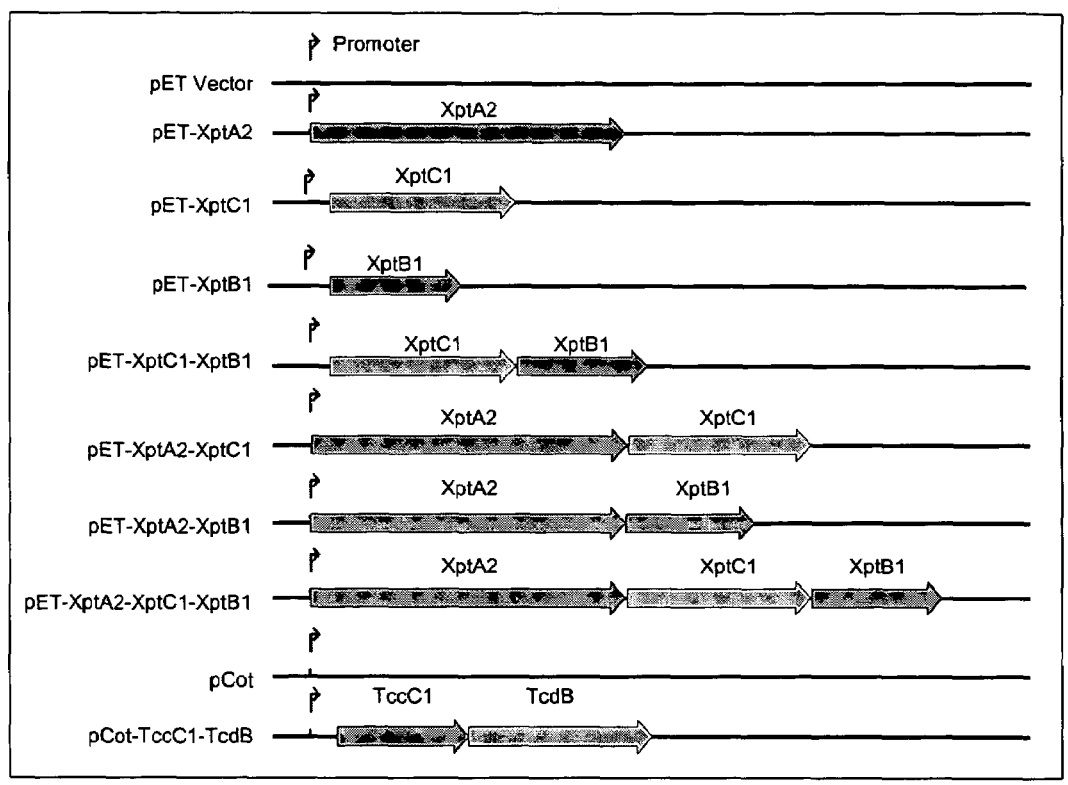

Figure 6. Schematic Diagram of pET/pCot Constructions

*Photorhabdus*
*tca*
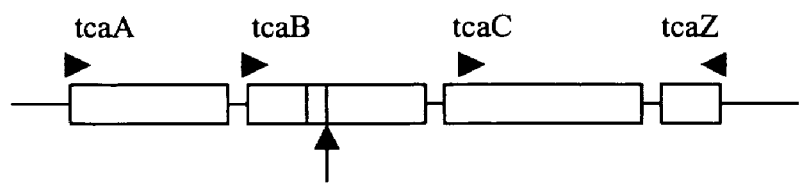
*tcb*
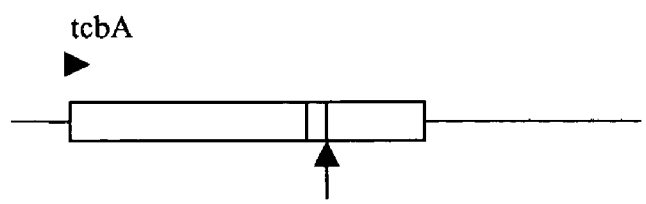
*tcc*
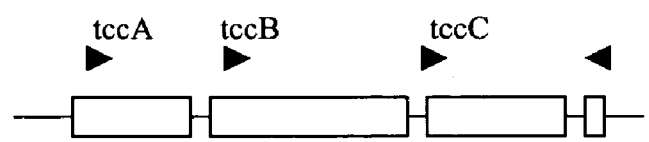
*tcd*
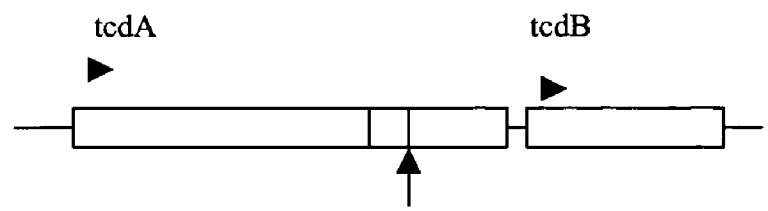
Fig. 7

MIXING AND MATCHING TC PROTEINS FOR PEST CONTROL

CROSS-REFERENCE TO A RELATED APPLICATION

This application claims the benefit of U.S. Provisional Application Ser. No. 60/441,723, filed Jan. 21, 2003.

BACKGROUND OF THE INVENTION

Insects and other pests cost farmers billions of dollars annually in crop losses and in the expense of keeping these pests under control. The losses caused by insect pests in agricultural production environments include decreases in crop yield, reduced crop quality, and increased harvesting costs. Insect pests are also a burden to vegetable and fruit growers, to producers of ornamental flowers, and to home gardeners and homeowners.

Cultivation methods, such as crop rotation and the application of high levels of nitrogen fertilizers, have partially addressed problems caused by agricultural pests. However, various demands on the utilization of farmland restrict the use of crop rotation. In addition, overwintering traits of some insects are disrupting crop rotations in some areas.

Thus, synthetic chemical insecticides are relied upon most heavily to achieve a sufficient level of control. However, the use of synthetic chemical insecticides has several drawbacks. For example, the use of these chemicals can adversely affect many beneficial insects. Target insects have also developed resistance to some chemical pesticides. Furthermore, rain and improper calibration of insecticide application equipment can result in poor control. The use of insecticides often raises environmental concerns such as contamination of soil and water supplies when not used properly, and residues can also remain on treated fruits and vegetables. Working with some insecticides can also pose hazards to the persons applying them. Stringent new restrictions on the use of pesticides and the elimination of some effective pesticides could limit effective options for controlling damaging and costly pests.

The replacement of synthetic chemical pesticides, or combination of these agents with biological pesticides, could reduce the levels of toxic chemicals in the environment. Some biological pesticidal agents that are now being used with some success are derived from the soil microbe *Bacillus thuringiensis* (B.t.). While most B.t. strains do not exhibit pesticidal activity, some B.t. strains produce proteins that are highly toxic to pests, such as insects, and are specific in their toxic activity. Genes that encode δ-endotoxin proteins have been isolated. Other species of *Bacillus* also produce pesticidal proteins.

Recombinant DNA-based B.t. products have been produced and approved for use. In addition, with the use of genetic engineering techniques, various approaches for delivering these toxins to agricultural environments are being perfected. These include the use of plants genetically engineered with toxin genes for insect resistance and the use of stabilized intact microbial cells as toxin delivery vehicles. Thus, isolated *Bacillus* toxin genes are becoming commercially valuable.

B.t. protein toxins were initially formulated as sprayable insect control agents. A relatively more recent application of B.t. technology has been to isolate and transform plants with genes that encode these toxins. Transgenic plants subsequently produce the toxins, thereby providing insect control. See U.S. Pat. Nos. 5,380,831; 5,567,600; and 5,567,862 to Mycogen Corporation. Transgenic B.t. plants are quite efficacious, and usage is predicted to be high in some crops and areas.

There are some obstacles to the successful agricultural use of *Bacillus* (and other biological) pesticidal proteins. Certain insects can be refractory to the effects of *Bacillus* toxins. Insects such as boll weevils, black cutworm, and *Helicoverpa zea*, as well as adult insects of most species, heretofore have demonstrated no significant sensitivity to many B.t. δ-endotoxins.

Another potential obstacle is the development of resistance to B.t. toxins by insects. The potential for wide-spread use of B.t. plants has caused some concern that resistance management issues may arise more quickly than with traditional sprayable applications. While a number of insects have been selected for resistance to B.t. toxins in the laboratory, only the diamondback moth (*Plutella xylostella*) has demonstrated resistance in a field setting (Ferre, J. and Van Rie, J., *Annu. Rev. Entomol.* 47:501-533, 2002).

Resistance management strategies in B.t. transgene plant technology have become of great interest. Several strategies have been suggested for preserving the ability to effectively use *B. thuringiensis* toxins. These strategies include high dose with refuge, and alternation with, or co-deployment of, different toxins (McGaughey et al. (1998), "B.t. Resistance Management," *Nature Biotechnol* 16:144-146), as in a natural bacterium, for example.

Thus, there remains a great need for developing additional genes that can be expressed in plants in order to effectively control various insects. In addition to continually trying to discover new B.t. toxins (which is becoming increasingly difficult due to the numerous B.t. toxins that have already been discovered), it would be quite desirable to discover other bacterial sources (distinct from B.t.) that produce toxins that could be used in transgenic plant strategies.

The relatively more recent efforts to clone insecticidal toxin genes from the *Photorhabdus/Xenorhabdus* group of bacteria present potential alternatives to toxins derived from *B. thuringiensis*. The genus *Xenorhabdus* is taxonomically defined as a member of the Family Enterobacteriaceae, although it has certain traits atypical of this family. For example, strains of this genus are typically nitrate reduction negative and catalase negative. *Xenorhabdus* has only recently been subdivided to create a second genus, *Photorhabdus*, which is comprised of three species, *Photorhabdus asymbiotica, Photorhabdus temperata,* and *P. luminescens. P. luminescens* has three recognized subspecies, *Photorhabdus luminescens* subsp. *akhurstii, Photorhabdus luminescens* subsp. *laumondii,* and *Photorhabdus luminescens* subsp. *luminescens* (Type species). (Fischer-Le Saux, M., Viallard, V., Brunel, B., Normand, P., Boemare, N. E. Title Polyphasic classification of the genus *Photorhabdus* and proposal of new taxa: *P. luminescens* subsp. *luminescens* subsp. nov., *P. luminescens* subsp. *akhurstii* subsp. nov., *P. luminescens* subsp. *laumondii* subsp. nov., *P. temperata* sp. nov., *P. temperata* subsp. *temperata* subsp. nov. and *P. asymbiotica* sp. nov. Int. J. Syst. Bacteriol. 49; 1645-1656, (1999)). This differentiation is based on several distinguishing characteristics easily identifiable by the skilled artisan. These differences include the following: DNA-DNA characterization studies; phenotypic presence (*Photorhabdus*) or absence (*Xenorhabdus*) of catalase activity; presence (*Photorhabdus*) or absence (*Xenorhabdus*) of bioluminescence; the Family of the nematode host in that *Xenorhabdus* is found in Steinernematidae and *Photorhabdus* is found in Heterorhabditidae); as well as comparative, cellular fatty-acid analyses (Janse et al. 1990, *Lett. Appl. Microbiol.* 10, 131-135; Suzuki et al. 1990, *J. Gen.*

*Appl. Microbiol.,* 36, 393-401). In addition, recent molecular studies focused on sequence (Rainey et al. 1995, *Int. J. Syst. Bacteriol.,* 45,379-381) and restriction analysis (Brunel et al., 1997, *App. Environ. Micro.,* 63, 574-580) of 16S rRNA genes also support the separation of these two genera.

The expected traits for *Xenorhabdus* are the following: Gram stain negative rods, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus *Xenorhabdus* is comprised of four recognized species, *Xenorhabdus nematophilus, Xenorhabdus poinarii, Xenorhabdus bovienii* and *Xenorhabdus beddingii* (Brunel et al., 1997, *App. Environ. Micro.,* 63, 574-580). A variety of related strains have been described in the literature (e.g., Akhurst and Boemare 1988 *J. Gen. Microbiol.,* 134, 1835-1845; Boemare et al. 1993 *Int. J. Syst. Bacteriol.* 43, pp. 249-255; Putz et al. 1990, *Appl. Environ. Microbiol.,* 56, 181-186, Brunel et al., 1997, *App. Environ. Micro.,* 63, 574-580, Rainey et al. 1995, *Int. J. Syst. Bacteriol.,* 45, 379-381).

*Photorhabdus* and *Xenorhabdus* spp. are Gram-negative bacteria that entomopathogenically and symbiotically associate with soil nematodes. These bacteria are found in the gut of entomopathogenic nematodes that invade and kill insects. When the nematode invades an insect host, the bacteria are released into the insect haemocoel (the open circulatory system), and both the bacteria and the nematode undergo multiple rounds of replication; the insect host typically dies. These bacteria can be cultured away from their nematode hosts. For a more detailed discussion of these bacteria, see Forst and Nealson, 60 *Microbiol. Rev.* 1 (1996), pp. 21-43. Unfortunately, as reported in a number of articles, the bacteria only had pesticidal activity when injected into insect larvae and did not exhibit biological activity when delivered orally.

*Xenorhabdus* and *Photorhabus* bacteria secrete a wide variety of substances into the culture medium. See R. H. ffrench-Constant et al. 66 *AEM* No. 8, pp. 3310-3329 (August 2000), for a review of various factors involved in *Photorhabdus* virulence of insects.

It has been difficult to effectively exploit the insecticidal properties of the nematode or its bacterial symbiont. Thus, proteinaceous agents from *Photorhabdus/Xenorhabdus* bacteria that have oral activity are desirable so that the products produced therefrom could be formulated as a sprayable insecticide, or the genes encoding said proteinaceous agents could be isolated and used in the production of transgenic plants.

There has been substantial progress in the cloning of genes encoding insecticidal toxins from both *Photorhabdus luminescens* and *Xenorhabdus nematophilus*. Toxin-complex encoding genes from *P. luminescens* were examined first. See WO 98/08932. Parallel genes were more recently cloned from *X. nematophilus*. See, e.g., Morgan et al, *Applied and Environmental Microbiology* 2001, 67:2062-69. The degree of "parallelism" is discussed in more detail below.

WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25-280 kDa. The ORFs that encode the typical TCs from *Photorhabdus*, together with protease cleavage sites (vertical arrows), are illustrated in FIG. 7. See also R. H. ffrench-Constant and Bowen, 57 *Cell. Mol. Life Sci.* 828-833 (2000).

Genomic libraries of *P. luminescens* were screened with DNA probes and with monoclonal and/or polyclonal antibodies raised against the toxins. Four tc loci were cloned: tca, tcb, tcc and tcd. The tca locus is a putative operon of three open reading frames (ORFs), tcaA, tcaB, and tcaC, transcribed from the same DNA strand, with a smaller terminal ORF (tcaZ) transcribed in the opposite direction. The tcc locus also is comprised of three ORFs putatively transcribed in the same direction (tccA, tccB, and tccC). The tcb locus is a single large ORF (tcbA), and the tcd locus is composed of two ORFs (tcdA and tcdB); tcbA and tcdA, each about 7.5 kb, encode large insect toxins. It was determined that many of these gene products were cleaved by proteases. For example, both TcbA and TcdA are cleaved into three fragments termed i, ii and iii (e.g. TcbAi, TcbAii and TcbAiii). Products of the tca and tcc ORFs are also cleaved. See FIG. 7. See also R. H. ffrench-Constant and D. J. Bowen, *Current Opinions in Microbiology,* 1999, 12:284-288.

As reported in WO 98/08932, protein toxins from the genus *Photorhabdus* have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO 98/08932 discloses nucleotide sequences for many of the native toxin genes.

Bioassays of the Tca toxin complexes revealed them to be highly toxic to first instar tomato hornworms (*Manduca sexta*) when given orally ($LD_{50}$ of 875 ng per square centimeter of artificial diet). R. H. ffrench-Constant and Bowen 1999. Feeding was inhibited at Tca doses as low as 40 ng/cm². Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Micriobiology,* 1999, 12:284-288.

None of the four loci showed overall similarity to any sequences of known function in GenBank. Regions of sequence similarity raised some suggestion that these proteins (TcaC and TccA) may overcome insect immunity by attacking insect hemocytes. R. H. ffrench-Constant and Bowen, *Current Opinions in Microbiology,* 1999, 12:284-288.

TcaB, TcbA, and TcdA all show amino acid conservation (~50% identity), compared with each other, immediately around their predicted protease cleavage sites. This conservation between three different Tc proteins suggests that they may all be processed by the same or similar proteases. TcbA and TcdA also share ~50% identity overall, as well as a similar predicted pattern of both carboxy- and amino-terminal cleavage. It was postulated that these proteins might thus be homologs (to some degree) of one another. Furthermore, the similar, large size of TcbA and TcdA, and also the fact that both toxins appear to act on the gut of the insect, may suggest similar modes of action. R. H. ffrench-Constant and Bowen, *Current Opinions in Microbiology,* 1999, 12:284-288.

Deletion/knock-out studies suggest that products of the tca and tcd loci account for the majority of oral toxicity to lepidopterans. Deletion of either of the tca or tcd genes greatly reduced oral activity against *Manduca sexta*. That is, products of the tca and tcd loci are oral lepidopteran toxins on their own; their combined effect contributed most of the secreted oral activity. R. H. ffrench-Constant and D. J. Bowen, 57 *Cell. Mol. Life. Sci.* 831 (2000). Interestingly, deletion of either of the tcb or tcc loci alone also reduces mortality, suggesting that there may be complex interactions among the different gene products. Thus, products of the tca locus may enhance the toxicity of tcd products. Alternatively, tcd products may modulate the toxicity of tca products and possibly other complexes. Noting that the above relates to oral activity against a single insect species, tcb or tcc loci may produce toxins that are more active against other groups of insects (or active via injection directly into the insect haemocoel—the normal route of delivery when secreted by the bacteria in vivo). R. H. ffrench-Constant and Bowen, *Current Opinions in Microbiology*, 1999, 12:284-288.

The insect midgut epithelium contains both columnar (structural) and goblet (secretory) cells. Ingestion of tca products by *M. sexta* leads to apical swelling and blebbing of large cytoplasmic vesicles by the columnar cells, leading to the eventual extrusion of cell nuclei in vesicles into the gut lumen. Goblet cells are also apparently affected in the same fashion. Products of tca act on the insect midgut following either oral delivery or injection. R. H. ffrench-Constant and D. J. Bowen, *Current Opinions in Microbiology*, 1999, 12:284-288. Purified tca products have shown oral toxicity against *Manduca sexta* ($LD_{50}$ of 875 ng/cm$^2$). R. H. ffrench-Constant and D. J. Bowen, 57 *Cell. Mol. Life Sci.* 828-833 (2000).

WO 99/42589 and U.S. Pat. No. 6,281,413 disclose TC-like ORFs from *Photorhabdus luminescens*. WO 00/30453 and WO 00/42855 disclose TC-like proteins from *Xenorhabdus*. WO 99/03328 and WO 99/54472 (and U.S. Pat. Nos. 6,174,860 and 6,277,823) relate to other toxins from *Xenorhabdus* and *Photorhabdus*.

WO 01/11029 and U.S. Pat. No. 6,590,142 B1 disclose nucleotide sequences that encode TcdA and TcbA and have base compositions that have been altered from that of the native genes to make them more similar to plant genes. Also disclosed are transgenic plants that express Toxin A and Toxin B. These references also disclose *Photorhabdus luminescens* strain W-14 (ATCC 55397; deposited Mar. 5, 1993) and many other strains.

Of the separate toxins isolated from *Photorhabdus luminescens* (W-14), those designated Toxin A and Toxin B have been the subject of focused investigation for their activity against target insect species of interest (e.g., corn rootworm). Toxin A is comprised of two different subunits. The native gene tcdA encodes protoxin TcdA. As determined by mass spectrometry, TcdA is processed by one or more proteases to provide Toxin A. More specifically, TcdA is an approximately 282.9 kDa protein (2516 aa) that is processed to provide TcdAi (the first 88 amino acids), TcdAii (the next 1849 aa; an approximately 208.2 kDa protein encoded by nucleotides 265-5811 of tcdA), and TcdAiii, an approximately 63.5 kDa (579 aa) protein (encoded by nucleotides 5812-7551 of tcdA). TcdAii and TcdAiii appear to assemble into a dimer (perhaps aided by TcdAi), and the dimers assemble into a tetramer of four dimers. Toxin B is similarly derived from TcbA.

While the exact molecular interactions of the TC proteins with each other, and their mechanism(s) of action, are not currently understood, it is known, for example, that the Tca toxin complex of *Photorhabdus* is toxic to *Manduca sexta*. In addition, some TC proteins are known to have "stand alone" insecticidal activity, while other TC proteins are known to potentiate or enhance the activity of the stand-alone toxins. It is known that the TcdA protein is active, alone, against *Manduca sexta;* but that TcdB and TccC, together, can be used to enhance the activity of TcdA. Waterfield, N. et al., *Appl. Environ. Microbiol.* 2001, 67:5017-5024. TcbA (there is only one Tcb protein) is another stand-alone toxin from *Photorhabdus.* The activity of this toxin (TcbA) can also be enhanced by TcdB together with TccC-like proteins.

U.S. Patent Application 20020078478 provides nucleotide sequences for two potentiator genes, tcdB2 and tccC2, from the tcd genomic region of *Photorhabdus luminescens* W-14. It is shown therein that coexpression of tcdB and tccC1 with tcdA in heterologous hosts results in enhanced levels of oral insect toxicity compared to that obtained when tcdA is expressed alone in such heterologous hosts. Coexpression of tcdB and tccC1 with tcdA or tcbA provide enhanced oral insect activity.

As indicated in the chart below, TccA has some level of homology with the N terminus of TcdA, and TccB has some level of homology with the C terminus of TcdA. TccA and TccB are much less active on certain test insects than is TcdA. TccA and TccB from Photorhabdus strain W-14 are called "Toxin D." "Toxin A" (TcdA), "Toxin B" (TcbA), and "Toxin C" (TcaA and TcaB) are also indicated below.

Furthermore, TcaA has some level of homology with TccA and likewise with the N terminus of TcdA. Still further, TcaB has some level of homology with TccB and likewise with the N terminus of TcdA.

TccA and TcaA are of a similar size, as are TccB and TcaB. TcdB has a significant level of similarity (both in sequence and size) to TcaC.

| Photorhabdus | Photorhabdus strain W-14 nomenclature | Some homology to: |
|---|---|---|
| TcaA | Toxin C | TccA |
| TcaB | | TccB |
| TcaC | | TcdB |
| TcbA | Toxin B | |
| TccA | Toxin D | TcdA N terminus |
| TccB | | TcdA C terminus |
| TccC | | |
| TcdA | Toxin A | TccA + TccB |
| TcdB | | TcaC |

Relatively more recent cloning efforts in *Xenorhabdus nematophilus* also appear to have identified novel insecticidal toxin genes with homology to the *P. luminescens* tc loci. See, e.g., WO 98/08388 and Morgan et al., *Applied and Environmental Microbiology* 2001, 67:2062-69. In R. H. ffrench-Constant and D. J. Bowen, *Current Opinions in Microbiology*, 1999, 12:284-288, cosmid clones were screened directly for oral toxicity to another lepidopteran, *Pieris brassicae.* One orally toxic cosmid clone was sequenced. Analysis of the sequence in that cosmid suggested that there are five different ORF's with similarity to *Photorhabdus* tc genes; orf2 and orf5 both have some level of sequence relatedness to both tcbA and tcdA, whereas orf1 is similar to tccB, orf3 is similar to tccC and orf4 is similar to tcaC. A number of these predicted ORFs also share the putative cleavage site documented in *P. luminescens,* suggesting that active toxins might also be proteolytically processed.

The finding of somewhat similar, toxin-encoding loci in these two different bacteria is interesting in terms of the possible origins of these virulence genes. The *X. nematophilus* cosmid also appears to contain transposase-like sequences, the presence of which might suggest the potential that these loci can be transferred horizontally between different strains or species of bacteria. A range of such transfer events may also explain the apparently different genomic organization of the tc operons in the two different bacteria. Further, only a subset of *X nematophilus* and *P. luminescens* strains appear to be toxic to *M. sexta,* suggesting either that different strains lack the tc genes or that they carry a different tc gene compliment. Detailed analysis of the phylogeny of strains and toxins within, and between, these bacterial species should help clarify the likely origin of the toxin genes and how they are maintained in different bacterial populations. R. H. ffrench-Constant and Bowen, *Current Opinions in Microbiology,* 1999, 12:284-288.

There are five typical *Xenorhabdus* TC proteins: XptA1, XptA2, XptB1, XptC1, and XptD1. XptA1 is a "stand-alone" toxin. XptA2 is another TC protein from *Xenorhabdus* that has stand-alone toxin activity. XptB1 and XptC1 are potentiators that can enhance the activity of either (or both) of the XptA toxins. XptD1 has some level of homology with TccB. XptC1 has some level of similarity to *Photorhabdus* TcaC. The XptA2 protein of *Xenorhabdus* has some degree of similarity to the *Photorhabdus* TcdA protein. XptB1 has some level of similarity to *Photorhabdus* TccC.

TC proteins and genes have more recently been described from other insect-associated bacteria such as *Serratia entomophila,* an insect pathogen. *Pseudomonas* species were found to have potentiators. Waterfield et al., *TRENDS in Microbiology,* Vol. 9, No. 4, April 2001.

Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus,*" *Antonie Van Leeuwenhoek* 64:253-260). Some species in this genus are known to be pathogenic to honeybees (*Paenibacillus larvae*) and to scarab beetle grubs (*P. popilliae* and *P. lentimorbus*). *P. larvae, P. popilliae,* and *P. lentimorbus* are considered obligate insect pathogens involved with milky disease of scarab beetles (D. P. Stahly et al. (1992), "The genus *Bacillus:* insect pathogens," pp. 1697-1745, In A. Balows et al., ed., *The Procaryotes,* 2$^{nd}$ Ed., Vol. 2, Springer-Verlag, New York, N.Y.).

A crystal protein, Cry18, has been identified in strains of *Paenibacillus popilliae* and *Paenibacillus lentimorbus.* Cry18 has scarab and grub toxicity, and has about 40% identity to Cry2 proteins (Zhang et al., 1997; Harrison et al., 2000). TC proteins and lepidopteran-toxic Cry proteins have very recently been discovered in *Paenibacillus.* See U.S. Ser. No. 60/392,633 (Bintrim et al.), filed Jun. 28, 2002. Six TC protein ORFs were found in that strain of *Paenibacillus.* ORF3 and ORF1 are shown there to each have some level of homology with TcaA. ORF4 and ORF2 are shown there to have some level of homology with TcaB. ORF5 appears to be a TcaC-like potentiator, and ORF6 has homology with the TccC potentiator.

Although some *Xenorhabdus* TC proteins were found to "correspond" (have a similar function and some level of sequence homology) to some of the *Photorhabdus* TC proteins, a given *Photorhabdus* protein shares only about 40% sequence identity with the "corresponding" *Xenorhabdus* protein. This is illustrated below for four "stand-alone" toxins:

|  | Identity to *P. l.* W-14 TcbA | Identity to *P. l.* W-14 TcdA |
|---|---|---|
| Xwi XptA1 | 44% | 46% |
| Xwi XptA2 | 41% | 41% |

(For a more complete review, see, e.g., Morgan et al., "Sequence Analysis of Insecticidal Genes from *Xenorhabdus nematophiles* PMFI296,"Vol. 67, *Applied and Environmental Microbiology,* May 2001, pp. 2062-2069.) This approximate degree of sequence relatedness is also observed when comparing the more recently discovered TC proteins from *Paenibacillus* (those proteins and that discovery are the subject of co-pending U.S. Ser. No. 60/392,633) to their *Xenorhabdus* and *Photorhabdus*"counterparts."

While *Photorhabdus* toxins have been used successfully, and *Xenorhabdus* toxins have been used successfully (apart from *Photorhabdus* toxins), enhancing the activity of a TC protein toxin from one of these source organisms (such as a *Photorhabdus*) with one or more TC protein potentiators from the other (a *Xenorhabdus,* for example) has not heretofore been proposed or demonstrated.

BRIEF SUMMARY OF THE INVENTION

The subject invention relates to the surprising discovery that toxin complex (TC) proteins, obtainable from organisms such as *Xenorhabdus, Photorhabdus,* and *Paenibacillus,* can be used interchangeably with each other. As one skilled in the art will recognize with the benefit of this disclosure, this has broad implications and expands the range of utility that individual types of TC proteins will now be recognized to have. This was not previously contemplated, and it would not have been thought possible, especially given the high level of divergence at the sequence level of the TC proteins from *Photorhabdus* compared to "corresponding" TC proteins of *Xenorhabdus* and *Paenibacillus,* for example.

In particularly preferred embodiments of the subject invention, the toxicity of a "stand-alone" TC protein (from *Photorhabdus, Xenorhabdus,* or *Paenibacillus,* for example) is enhanced by one or more TC protein "potentiators" derived from a different source organism. The subject invention provides one skilled in the art with many surprising advantages. One of the most important advantages is that one skilled in the art will now be able to use a single pair of potentiators to enhance the activity of a stand-alone *Xenorhabdus* protein toxin and a stand-alone *Photorhabdus* protein toxin. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes (and transformation events) needed to be co-expressed by individual transgenic plants and/or plant cells to achieve effective control of a wider spectrum of target pests.

Stated another way, the subject invention relates to the discovery that *Xenorhabdus* TC proteins could be used to enhance the activity of *Photorhabdus* TC proteins and vice versa. Similarly, and also surprisingly, it was discovered that TC proteins from *Paenibacillus* could be used in place of *Xenorhabdus/Photorhabdus* TC proteins, and vice versa. Again, there was no expectation that proteins from these divergent organisms would be compatible with each other; this was not previously proposed or demonstrated. The subject invention was surprising especially in light of the notable differences between *Xenorhabdus, Photorhabdus,* and

*Paenibacillus* TC proteins (as well as those from other genera) notwithstanding some characteristics they have in common.

Certain preferred combinations of heterologous TC proteins are also disclosed herein.

Many objects, advantages, and features of the subject invention will be apparent to one skilled in the art having the benefit of the subject disclosure.

BRIEF DESCRIPTION OF THE FIGURES

FIG. 1 shows the orientation of ORFs identified in pDAB2097.

FIG. 2 shows expression vector plasmid pBT-TcdA.

FIG. 3 shows expression vector plasmid pET280 vector.

FIG. 4 shows expression vector plasmid pCot-3.

FIG. 5 is a schematic diagram of pBT constructions.

FIG. 6 is a schematic diagram of pET/pCot constructions.

FIG. 7 shows the TC operons from *Photorhabdus.*

BRIEF DESCRIPTION OF THE SEQUENCES

SEQ ID NO:1 is the N-terminus of $Toxin_{XwiA}$ 220 kDa protein ($XptA2_{Wi}$).

SEQ ID NO:2 is an internal peptide of $Toxin_{XwiA}$ purified toxin ($XptA2_{Wi}$).

SEQ ID NO:3 is an internal peptide of $Toxin_{XwiA}$ purified toxin ($XptA2_{Wi}$).

SEQ ID NO:4 is an internal peptide of $Toxin_{XwiA}$ purified toxin ($XptA2_{Wi}$).

SEQ ID NO:5 is an internal peptide of $Toxin_{XwiA}$ purified toxin ($XptA2_{Wi}$).

SEQ ID NO:6 is the pDAB2097 cosmid insert: 39,005 bp.

SEQ ID NO:7 is the pDAB2097 cosmid ORF1: nucleotides 1-1,533 of SEQ ID NO:6.

SEQ ID NO:8 is the pDAB2097 cosmid ORF1 deduced protein: 511 aa.

SEQ ID NO:9 is the pDAB2097 cosmid ORF2 ($xptD1_{Wi}$): nucleotides 1,543-5,715 of SEQ ID NO:6.

SEQ ID NO:10 is the pDAB2097 cosmid ORF2 deduced protein: 1,391 aa.

SEQ ID NO:11 is the pDAB2097 cosmid ORF3: nucleotides 5,764-7,707 of SEQ ID NO:6.

SEQ ID NO:12 is the pDAB2097 cosmid ORF3 deduced protein: 648 aa.

SEQ ID NO:13 is the pDAB2097 cosmid ORF4 ($xptA1_{Wi}$): nucleotides 10,709-18,277 of SEQ ID NO:6.

SEQ ID NO:14 is the pDAB2097 cosmid ORF4 deduced protein: 2,523 aa.

SEQ ID NO:15 is the pDAB2097 cosmid ORF5 ($xptB1_{Wi}$): nucleotides 18,383-21,430 (C) of SEQ ID NO:6.

SEQ ID NO:16 is the pDAB2097 cosmid ORF5 deduced protein: 1,016 aa.

SEQ ID NO:17 is the pDAB2097 cosmid ORF6 ($xptC1_{Wi}$): nucleotides 21,487-25,965 (C) of SEQ ID NO:6.

SEQ ID NO:18 is the pDAB2097 cosmid ORF6 deduced protein: 1,493 aa.

SEQ ID NO:19 is the pDAB2097 cosmid ORF7 ($xptA2_{Wi}$): nucleotides 26,021-33,634 (C) of SEQ ID NO:6.

SEQ ID NO:20 is the pDAB2097 cosmid ORF7 deduced protein: 2,538 aa.

SEQ ID NO:21 is the TcdA gene and protein sequence from GENBANK Accession No. AF188483.

SEQ ID NO:22 is the TcdB1 gene and protein sequence from GENBANK Accession No. AF346500.

SEQ ID NO:23 is the forward primer used to amplify the TcdB1 sequence from plasmid pBC-AS4.

SEQ ID NO:24 is the reverse primer used to amplify the TcdB1 sequence from plasmid pBC-AS4.

SEQ ID NO:25 is the gene and protein sequence for TccC1 from GENBANK Accession No. AAC38630.1.

SEQ ID NO:26 is the forward primer used to amplify TccC1 from the pBC KS+ vector.

SEQ ID NO:27 is the reverse primer used to amplify TccC1 from the pBC KS+ vector.

SEQ ID NO:28 is the forward primer used to amplify $xptA2_{Wi}$.

SEQ ID NO:29 is the reverse primer used to amplify $xptA2_{Wi}$.

SEQ ID NO:30 is the forward primer used to amplify $xptC1_{Wi}$.

SEQ ID NO:31 is the reverse primer used to amplify $xptC1_{Wi}$.

SEQ ID NO:32 is the forward primer used to amplify $xptB1_{Wi}$.

SEQ ID NO:33 is the reverse primer used to amplify $xptB1_{Wi}$.

SEQ ID NO:34 is the amino acid sequence of the $XptA2_{Wi}$ protein from *Xenorhabdus nematophilus* Xwi.

SEQ ID NO:35 is the nucleic acid sequence of ORF3, of *Paenibacillus* strain DAS1529, which encodes a tcaA-like protein.

SEQ ID NO:36 is the amino acid sequence encoded by *Paenibacillus* ORF3.

SEQ ID NO:37 is the nucleic acid sequence of ORF4, of *Paenibacillus* strain DAS1529, which encodes a tcaB-like protein.

SEQ ID NO:38 is the amino acid sequence encoded by *Paenibacillus* ORF4.

SEQ ID NO:39 is the nucleic acid sequence of ORF5, of *Paenibacillus* strain DAS 1529, which encodes a tcaC-like protein ($pptB1_{1529}$).

SEQ ID NO:40 is the amino acid sequence encoded by *Paenibacillus* ORF5 ($PptB1_{1529}$).

SEQ ID NO:41 is the nucleic acid sequence of ORF6 (short), of *Paenibacillus* strain DAS1529, which encodes a tccC-like protein ($PptC1_{1529S}$).

SEQ ID NO:42 is a protein sequence encoded by *Paenibacillus* (short) ORF6 ($PptC1_{1529S}$).

SEQ ID NO:43 is an alternate (long) protein sequence ($PptC1_{1529L}$) encoded by *Paenibacillus* ORF6 (long) of SEQ ID NO:55.

SEQ ID NO:44 is the nucleotide sequence for TcdB2.

SEQ ID NO:45 is the amino acid sequence of the TcdB2 protein.

SEQ ID NO:46 is the nucleotide sequence of TccC3.

SEQ ID NO:47 is the amino acid sequence of the TccC3 protein.

SEQ ID NO:48 is the native $xptB1_{xb}$ coding region (4521 bases).

SEQ ID NO:49 is the native $xptB1_{xb}$ protein encoded by SEQ ID NO:48 (1506 amino acids).

SEQ ID NO:50 is the native $xptC1_{xb}$ coding region (2889 bases).

SEQ ID NO:51 is the native $XptC1_{xb}$ protein encoded by SEQ ID NO:50 (962 amino acids).

SEQ ID NO:52 is the Xba I to Xho I fragment of expression plasmid pDAB6031 comprising the native $xptB1_{xb}$ coding region, where bases 40 to 4557 encode the protein of SEQ ID NO:49 (4595 bases).

SEQ ID NO:53 is the Xba I to Xho I fragment of expression plasmid pDAB6032 comprising the native $xptC1_{xb}$ coding region, where bases 40 to 2925 encode the protein of SEQ ID NO:51 (2947 bases).

SEQ ID NO:54 is the Xba I to Xho I fragment of expression plasmid pDAB6033 comprising the native xptB1$_{xb}$ and native xptC1$_{xb}$ coding regions, where bases 40 to 4557 encode the protein of SEQ ID NO:49, and bases 4601 to 7486 encode the protein of SEQ ID NO:51 (7508 bases).

SEQ ID NO:55 is the nucleic acid sequence of ORF6 (long; pptC1$_{1529L}$), of *Paenibacillus* strain DAS1529, which encodes a tccC-like protein (PptC1$_{1529L}$) disclosed in SEQ ID NO:43.

SEQ ID NO:56 is the gene and protein sequence for TcaC from GENBANK Accession No. AF346497.1.

SEQ ID NO:57 is the gene and protein sequence for TccC5 from GENBANK Accession No. AF346500.2.

SEQ ID NO:58 is the protein sequence for TccC2 from GENBANK Accession No. AAL18492.

SEQ ID NO:59 shows the amino acid sequence for the TcbA$_{W-14}$ protein.

SEQ ID NO:60 shows the amino acid sequence for the SepB protein.

SEQ ID NO:61 shows the amino acid sequence for the SepC protein.

SEQ ID NO:62 shows the amino acid sequence for the TcdA2$_{W-14}$ protein.

SEQ ID NO:63 shows the amino acid sequence for the TcdA4$_{W-14}$ protein.

SEQ ID NO:64 shows the amino acid sequence for the TccC4$_{W-14}$ protein.

DETAILED DESCRIPTION OF THE INVENTION

The subject invention relates to the novel use of toxin complex (TC) proteins, obtainable from organisms such as *Xenorhabdus, Photorhabdus,* and *Paenibacillus.* As discussed below, one or more TC potentiators were used to enhance the activity of a TC toxin protein that is different from the TC toxin which one or both of the potentiators enhance in nature. As one skilled in the art will recognize with the benefit of this disclosure, this has broad implications and expands the range of utility that individual types of TC proteins will now be recognized to have.

It was known that some TC proteins have "stand alone" insecticidal activity, and other TC proteins were known to enhance the activity of the stand-alone toxins produced by the same given organism. In particularly preferred embodiments of the subject invention, the toxicity of a "stand-alone" TC protein (from *Photorhabdus, Xenorhabdus,* or *Paenibacillus,* for example) is enhanced by one or more TC protein "potentiators" derived from a source organism of a different genus.

There are three main types of TC proteins. As referred to herein, Class A proteins ("Protein A") are stand alone toxins. Native Class A proteins are approximately 280 kDa.

Class B proteins ("Protein B") and Class C proteins ("Protein C") enhance the toxicity of Class A proteins. As used referred to herein, native Class B proteins are approximately 170 kDa, and native Class C proteins are approximately 112 kDa.

Examples of Class A proteins are TcbA, TcdA, XptA1, and XptA2. Examples of Class B proteins are TcaC, TcdB, XptB1$_{Xb}$, and XptC1$_{Wi}$. Examples of Class C proteins are TccC, XptC1$_{Xb}$, and XptB1$_{Wi}$.

The exact mechanism of action for the toxicity and enhancement activities are not currently known, but the exact mechanism of action is not important. What is important is that the target insect eats or otherwise ingests the A, B, and C proteins.

It was known that the TcdA protein is active, alone, against *Manduca sexta.* It was also known that TcdB1 and TccC, together, can be used to enhance the activity of TcdA. TcbA is another stand-alone *Photorhabdus* toxin. One combination of TC proteins currently contemplated in the art is TcaC (or TcdB) and TccC (as potentiators) together with TcdA or TcbA. Similarly in *Xenorhabdus,* it was known that XptB1 and XptC1 enhanced the activity of XptA1 or XptA2, the latter of which are each "stand alone" toxins.

Although the complex of (TcbA or TcdA)+(TcaC+TccC) might appear to be a similar arrangement as the complex of (XptA1 or XptA2)+(XptC2+XptB1), each *Photorhabdus* component shares only about 40% (approximately) sequence identity with the "corresponding" *Xenorhabdus* component. The unique TC proteins from *Paenibacillus* also share only about 40% sequence identity with "corresponding" *Photorhabdus* and *Xenorhabdus* TC proteins (those proteins and that discovery are the subject of co-pending U.S. application Ser. No. 60/392,633, Bintrim et al., filed Jun. 28, 2002).

It is in this context that it was discovered, as described herein, that *Xenorhabdus* TC proteins could be used to enhance the activity of *Photorhabdus* TC proteins and vice versa. *Paenibacillus* TC proteins are also surprisingly demonstrated herein to potentiate the activity of *Xenorhabdus* (and *Photorhabdus*) TC toxins. This was not previously proposed or demonstrated, and was very surprising especially in light of the notable differences between *Xenorhabdus, Photorhabdus,* and *Paenibacillus* TC proteins. There was certainly no expectation that divergent proteins from these divergent organisms would be compatible with each other.

The subject invention can be performed in many different ways. A plant can be engineered to produce two types of Class A proteins and a single pair of potentiators (B and C proteins). Every cell of the plant, or every cell in a given type of tissue (such as roots or leaves) can have genes to encode the two A proteins and the B and C pair.

Alternatively, different cells of the plant can produce only one (or more) of each of these proteins. In this situation, when an insect bites and eats tissues of the plant, it could eat a cell that produces the first Protein A, another cell that produces the second Protein A, another cell that produces the B protein, and yet another cell that produces the C protein. Thus, what would be important is that the plant (not necessarily each plant cell) produces two A proteins, the B protein, and the C protein of the subject invention so that insect pests eat all four of these proteins when they eat tissue of the plant.

Aside from transgenic plants, there are many other ways of administering the proteins, in a combination of the subject invention, to the target pest. Spray-on applications are known in the art. Some or all of the A, B, and C proteins can be sprayed (the plant could produce one or more of the proteins and the others could be sprayed). Various types of bait granules for soil applications, for example, are also known in the art and can be used according to the subject invention.

Many combinations of various TC proteins are shown herein to function in surprising, new ways. One example set forth herein shows the use of TcdB1 and TccC1 to enhance the activity of XptA2 against corn earworm, for example. Another example set forth herein is the use of XptB1 together with TcdB1 to enhance the activity of TcdA against corn rootworm, for example. Similarly, and also surprisingly, it was further discovered that TC proteins from *Paenibacillus* could be used to enhance the activity of TcdA-like and XptA2$_{Xwi}$-like proteins. Some of the examples included herein are as follows:

| Protein A (Toxin) | Protein B (Potentiator 1) | Protein C (Potentiator 2) |
| --- | --- | --- |
| XptA2 | *Paenibacillus* ORF5 (TcaC-like) | *Paenibacillus* ORF 6 |
| XptA2 | *Photorhabdus* TcdB1 | *Photorhabdus* TccC1 |
| *Photorhabdus* TcdA | *Photorhabdus* TcdB1 | XptB1 |

The use of these and other combinations will now be apparent to those skilled in the art having the benefit of the subject disclosure.

Stand-alone toxins such as TcbA, TcdA, XptA1, and XptA2 are each in the approximate size range of 280 kDa. TcaC, TcdB1, TcdB2, and XptC1 are each approximately 170 kDa. TccC1, TccC3, and XptB1 are each approximately 112 kDa. Thus, preferred embodiments of the subject invention include the use of a 280-kDa type TC protein toxin (as described herein) with a 170-kDa class TC protein (as described herein) together with a 112-kDa class TC protein (as described herein), wherein at least one of said three proteins is derived from a source organism (such as *Photorhabdus*, *Xenorhabdus*, or *Paenibacillus*) that is of a different genus than the source organism from which one or more of the other TC proteins is/are derived.

The subject invention provides one skilled in the art with many surprising advantages. Among the most important advantages is that one skilled in the art will now be able to use a single pair of potentiators to enhance the activity of a stand-alone *Xenorhabdus* protein toxin, for example, as well as a stand-alone *Photorhabdus* protein toxin, for example. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes (and transformation events) needed to be expressed by a transgenic plant to achieve effective control of a wider spectrum of target pests. That is, rather than having to express six genes—two toxins and two pairs of potentiators—the subject invention allows for the expression of only four genes—two toxins and one pair of potentiator proteins.

Thus, the subject invention includes a transgenic plant and/or a transgenic plant cell that co-expresses a polynucleotide or polynucleotides encoding two (or more) different stand-alone TC protein toxins, and a polynucleotide or polynucleotides encoding a single pair of TC protein potentiators—a Class B protein and a Class C protein—wherein one or both of said potentiators is/are derived from a bacterium of a genus that is different from the genus from which one of the stand-alone TC protein toxins is derived. Accordingly, one can now obtain a cell having two (or more) TC protein toxins (Class A proteins) that are enhanced by a single pair of protein potentiators (a Class B and a Class C protein). There was no previous suggestion to produce such cells, and certainly no expectation that both (or all) such toxins produced by said cell would be active to adequate levels (due to the surprising enhancement as reported herein). TC proteins, as the term is used herein, are known in the art. Such proteins include stand-alone toxins and potentiators. Bacteria known to produce TC proteins include those of the following genera: *Photorhabdus*, *Xenorhabdus*, *Paenibacillus*, *Serratia*, and *Pseudomonas*. See, e.g., *Pseudomonas syringae* pv. *syringae* B728a (GenBank Accession Numbers gi:23470933 and gi:23472543). Any of such TC proteins can be used according to the subject invention.

Examples of stand-alone (Class A) toxins, as the term is used herein, include TcbA and TcdA from *Photorhabus*, and XptA1 and XptA2 from *Xenorhabdus*. Toxins in this class are about 280 kDa. Further examples of stand-alone toxins include SepA from *Serratia entomophila* (GenBank Accession No. AAG09642.1). Class A proteins can be ~230 kDa (especially if truncated), ~250-290 kDa, ~260-285 kDa, and ~270 kDa, for example.

There are two main types or classes of potentiators, as the term is used herein. Examples of the "Class B" of potentiators (sometimes referred to herein as Potentiator 1) include TcaC, TcdB1, and TcdB2 from *Photorhabus*, XptC1 from *Xenorhabdus*, and the protein product of ORF5 of *Paenibacillus* strain DAS 1529. Potentiators in this class are typically in the size range of about 170 kDa. Further examples of ~170 kDa class potentiators are SepB from *Serratia entomophila* (GenBank Accession No. AAG09643.1; reproduced here as SEQ ID NO:60), TcaC homologs from *Pseudomonas syringae* pv. *syringae* B728a (GenBank Accession Numbers gi23472544 and gi23059431), and *X. nematophilus* PO ORF268 (encoded by bases 258-1991 of FIG. 2 of WO 20/004855). A preferred ~170 kDa potentiator is TcdB2 (SEQ ID NOs:44-45). Class B proteins can be ~130-180 kDa, ~140-170 kDa, ~150-165 kDa, and ~155 kDa, for example.

Examples of the "Class C" potentiators (sometimes referred to herein as Potentiator 2) include TccC1 and TccC3 from *Photorhabus*, XptB1 from *Xenorhabdus*, and the protein product of ORF6 of *Paenibacillus* strain DAS 1529. Potentiators in this class are typically in the size range of about 112 kDa. Further examples of ~112 kDa class potentiators are SepC from *Serratia entomophila* (GenBank Accession No. AAG09644.1; reproduced here as SEQ ID NO:61), and TccC homologs from *Pseudomonas syringae* pv. *syringae* B728a (GenBank Accession Numbers gi:23470227, gi:23472546, gi:23472540, gi:23472541, gi:23468542, gi:23472545, gi:23058175, gi:23058176, gi:23059433, gi:23059435, and gi:23059432). A preferred ~112 kDa potentiator is TccC3 (SEQ ID NOs:46-47). Class C proteins can be ~90-120 kDa, ~95-115 kDa, ~100-110 kDa, and ~105-107 kDa, for example.

WO 02/94867, U.S. patent application 20020078478, and Waterfield et al. (*TRENDS in Microbiology* Vol. 10, No. 12, December 2002, pp. 541-545) disclose TC proteins that can be used according to the subject invention. For example, Waterfield et al. disclose tcdB2, tccC3, tccC5, tcdA2, tcdA3, and tcdA4 genes and proteins. Any of the relevant TC proteins disclosed by relevant references discussed above in the Background section (and any other references relating to TC proteins) can also be used according to the subject invention.

Thus, one embodiment of the subject invention includes a transgenic plant or plant cell that produces one, two, or more types of stand-alone TC protein toxins, and a single pair of potentiators: Potentiator 1 and Potentiator 2 (examples of each of these three components are given above and elsewhere herein) wherein at least one of said TC proteins is derived from an organism of a genus that is different from the genes from which one or more of the other TC proteins is derived.

It should be clear that examples of the subject invention include a transgenic plant or plant cell that produces/co-expresses one type of a *Photorhabdus* toxin (e.g., TcbA or TcdA), one type of a *Xenorhabdus* toxin (e.g., XptA1 or XptA2), and a single (one and only one) pair of potentiator proteins (e.g., TcaC and TccC, without XptC1 or XptB1; or XptC1 and XptB1, without TcaC or TccC; or TcaC and *Paenibacillus* ORF6 without any other potentiators; or TcdB and XptB1 without any other potentiators; these combinations are only exemplary; many other combinations would be clear to one skilled in the art having the benefit of the subject disclosure). Additional potentiators could be used according to the subject invention to enhance heterologous toxins, but multiple types of potentiator pairs are not essential. This is one very surprising aspect of the subject invention.

It should also be clear that the subject invention can be defined in many ways—other than in terms of what is coexpressed by a transgenic plant or plant cell. For example, the subject invention includes methods of potentiating the activity of one or more stand-alone TC protein toxin(s) by coexpressing/coproducing it (or them) with a single pair of potentiators, wherein one or both of the potentiators is/are derived from an organism of a genus that is different from the genus of the organism from which the TC protein toxin is derived. The subject invention also includes methods of controlling insect (and like) pests by feeding them one or more types of TC protein toxins together with one or more pairs of potentiators (e.g., TcbA and XptA1 and XptC1 and XptB1, possibly without TcaC and TccC), including cells that produced this combination of proteins, wherein one or both of the potentiators is/are derived from an organism of a genus that differs from one or both of the stand-alone toxins.

Such arrangements were not heretofore contemplated or expected to have activity. One way of understanding why the subject results were surprising is to consider the sequence relatedness of some of the protein components exemplified herein. For example, XptA2, a stand-alone toxin from *Xenorhabdus*, has about 43% sequence identity with TcdA and about 41% identity with TcbA. TcdA and TcbA are each stand-alone toxins from *Photorhabdus*. XptA1 (another stand-alone toxin from *Xenorhabdus*) has about 45% identity with TcdA and TcbA.

TcaC (a *Photorhabdus* ~170 kDa potentiator) has about 49% sequence identity with XptC1 (a ~170 kDa *Xenorhabdus* potentiator). TccC (a ~112 kDa *Photorhabdus* potentiator) has about 48% sequence identity with XptB1 (a ~112 kDa *Xenorhabdus* potentiator). Heretofore, TcaC+TccC, for example, would not have been expected to enhance the activity of a protein (XptA1 or XptA2) that has only 40-45% sequence identity with the native "target" of the TcaC+TccC association. (The scores reported above were obtained by using the program FASTA 6.0 and are from Morgan et al., "Sequence Analysis of Insecticidal Genes from *Xenorhabdus nematophiles* PMFI296," Vol. 67, *Applied and Environmental Microbiology*, May 2001, pp. 2062-2069).

Some examples of components for use according to the subject invention, and their relatedness to each other, include:

| | Class A Proteins | |
|---|---|---|
| | *Photorhabdus* TcdA toxin homologs | |
| Name | Reference | Sequence identity to W-14 TcdA (GenBank Accession NO. AAF05542.1) |
| *P. l.* Hph2 | SEQ ID NO: 13 of U.S. Pat. No. 6,281,413B1 | ~93% |
| *P. l.* Hph3 | Encoded by bases 2416 to 9909 of SEQ ID NO: 11 of U.S. Pat. No. 6,281,413B1 | ~57% |
| | *Photorhabdus* TcbA toxin homologs | |
| Name | Reference | Sequence identity to W-14 TcdA (GenBank Accession NO. AAF05542.1) |
| *P. l.* W-14 TcbA | GenBank Accession No. AAC38627.1 (reproduced here as SEQ ID NO: 59) | (~50% sequence identity to W-14 TcdA) |
| | *Xenorhabdus* XptA1 toxin homologs | |
| Name | Reference | Sequence identity to Xwi XptA1 (disclosed herein as SEQ ED NO: 14) |
| *X. n* XptA1 | GenBank Accession No. CAC38401.1 (AJ308438) | ~96% |
| | *Xenorhabdus* XptA2 toxin homologs | |
| Name | Reference | Sequence identity to Xwi XptA2 (disclosed herein as SEQ ID NO:20) |
| *X. n.* XptA2 | GenBank Accession No. CAC38404.1 (AJ308438) | ~95% |

Class B Proteins

Photorhabdus ~170 kDa Potentiators

| Name | Identifier | Sequence identity to P. l. W-14 TcdB (GenBank Accession No. AAL18487.1) |
|---|---|---|
| P. l. ORF2 | SEQ ID NO: 14 of U.S. Pat. No. 6,281,413B1 | ~93% |
| P. l. ORF4 | Encoded by bases 9966 to 14633 of SEQ ID NO: 11 Of U.S. Pat. No. 6,281,413B1 | ~71% |
| P. l. W-14 TcaC | GenBank Accession No. AF046867 | ~58% |

Xenorhabdus ~170 kDa Potentiators

| Name | Identifier | Sequence identity to Xwi XptC1 (disclosed herein as SEQ ID NO: 18) |
|---|---|---|
| X. n. XptC1 | GenBank Accession No. CAC38403.1 | ~90% |

Class C Proteins

Photorhabdus ~112 kDa Potentiators

| Name | Identifier | Sequence identity to P. l. W-14 TccC1 (GenBank Accession No. AAC38630.1) |
|---|---|---|
| P. l. ORF5 | SEQ ID NO: 12 of U.S. Pat. No. 6,281,413B1 | ~51% |
| P. l. TccC2 | GenBank Accession No. AAL18492 | ~48% |
| P. l. W-14 TccC3 | SEQ ID NO: 45 | ~53% |

Xenorhabdus ~112 kDa Potentiators

| Name | Identifier | Sequence identity to Xwi XptB1 (disclosed herein as SEQ ID NO: 16) |
|---|---|---|
| X. n. XptB1 | GenBank Accession No. CAC38402 | ~96% |
| X. nem. P2-ORF 2071 | Encoded by bases 2071 to 4929 of FIG. 2 of WO 20/004855 | ~48% |

Thus, referring to the genus of a bacterium from which a TC protein was derived is not simply a matter of arbitrary nomenclature. As illustrated above, doing so helps define a class of TC proteins that are relatively conserved amongst themselves (such as a given type of TC protein produced by Photorhabdus species and strains) but which are relatively quite divergent from other "corresponding" TC proteins derived from a different microbial genus (such as those produced by various Xenorhabdus species and strains).

Another way to define each TC protein component of the subject invention is by a given protein's degree of sequence identity to a given toxin or potentiator. Means for calculating identity scores are provided herein. Thus, one specific embodiment of the subject invention includes a transgenic plant or plant cell co-producing a toxin having at least 75% sequence identity with XptA2, a toxin having at least 75% identity with TcdA or TcbA, a potentiator having at least 75% sequence identity with TcdB1 or TcdB2, and a potentiator having at least 75% sequence identity with TccC1 or TccC3. Other TC proteins can be substituted into the above formula, in accordance with the teachings of the subject invention. Other, more specific ranges of identity scores are provided elsewhere herein.

Yet another way of defining a given type of TC protein component of the subject invention is by the hybridization characteristics of the polynucleotide that encodes it. Much more detailed information regarding such "tests" and hybridization (and wash) conditions is provided throughout the subject specification. Thus, TC proteins for use according to the subject invention can be defined by the ability of a polynucleotide that encodes the TC protein to hybridize with a given "tc" gene.

Applying that guidance to a particular example, an XptA2-type toxin of the subject invention could be defined as being encoded by a polynucleotide, wherein a nucleic acid sequence that codes for said ZptA2-type toxin hybridizes with the xptA2 gene of SEQ ID NO:19, wherein hybridization is maintained after hybridization and wash under any such conditions described or suggested herein (such as the examples of low, moderate, and high stringency hybridization/wash conditions mentioned herein). Any of the other exemplified or suggested TC proteins (including potentiators or other toxins) could be substituted for XptA2 in this definition, such as TcdB2, TccC3, TcdA, and TcbA.

Thus, the subject invention includes a transgenic plant, a transgenic plant cell, or a bacterial cell that co-expresses certain combinations of polynucleotides that encode TC proteins of the subject invention. It should be clear that the subject invention includes a transgenic plant or plant cell that co-expresses two toxin genes and only one pair of potentiators. Thus, the subject invention includes a trangenic plant or plant cell comprising one or more polynucleotides encoding a toxin in a class of a toxin indicated below as Toxin Pair 1, 2, 3, or 4 as follows, and wherein said plant or cell consists of DNA encoding one pair of potentiators selected from the group consisting of proteins in the class of potentiators shown in Potentiator Pair 1, 2, 3, 4, 5, or 6, as indicated below. Stated another way, said plant or cell consists of a polynucleotide segment encoding one potentiator of Potentiator Pair 1, 2, 3, 4, 5, or 6, and said plant or cell consists of another polynucleotide segment encoding the other potentiator of the selected Potentiator Pair.

| Toxin Pair # | |
|---|---|
| 1 | TcbA & XptA1 |
| 2 | TcbA & XptA2 |
| 3 | TcdA & XptA1 |
| 4 | TcdA & XptA2 |

| Potentiator Pair # | |
|---|---|
| 1 | TcdB1 & TccC |
| 2 | TcaC & TccC |
| 3 | XptC1 & TccC |
| 4 | TcdB1 & XptB1 |
| 5 | TcaC & XptB1 |
| 6 | XptC1 & XptB1 |

The plant or cell can comprise genes encoding additional TC protein toxins (e.g., so that the cell produces TcbA as well as TcdA, and/or XptA1 and XptA2), but only one pair of potentiators is used according to preferred embodiments of the subject invention. (Of course, the cell or plant will produce multiple copies of the potentiators; the key is that additional transformation events can be avoided.)

Further embodiments of the subject invention include a transgenic cell or plant that co-expresses a stand-alone protein toxin and a single (no more than one) potentiator pair comprising at least one "heterologous" (derived from a bacterium of a genus that is other than the genus of the organism from which the toxin is derived) TC protein. The subject invention also includes potentiating the insecticidal activity of a TC protein toxin with a pair of TC proteins that are potentiators, wherein at least one (one or both) of said TC protein potentiators is a heterologous TC protein, with respect to the TC protein toxin it helps to potentiate. Sets of toxins and the potentiators used to enhance the toxin include the following combinations:

| TcbA | XptC1 | XptB1 |
| TcbA | TcdB1 | XptB1 |
| TcbA | TcaC | XptB1 |
| TcbA | XptC1 | TccC1 |
| TcdA | XptC1 | XptB1 |
| TcdA | TcdB1 | XptB1 |
| TcdA | TcaC | XptB1 |
| TcdA | XptC1 | TccC1 |

-continued

| XptA1 | TcdB1 | TccC1 |
| XptA1 | TcdB1 | XptB1 |
| XptA1 | TcaC | TccC1 |
| XptA1 | TcaC | XptB1 |
| XptA1 | XptC1 | TccC1 |
| XptA2 | TcdB1 | TccC1 |
| XptA2 | TcdB1 | XptB1 |
| XptA2 | TcaC | TccC1 |
| XptA2 | TcaC | XptB1 |
| XptA2 | XptC1 | TccC1 |

It should be clear that the above matrices are intended to include, for example, TcdB2+TccC3 (a preferred pair of potentiators) with any of the toxins such as XptA1 and/or XptA2 (together with TcbA and/or TcdA).

Other embodiments and combinations will be apparent to one skilled in the art having the benefit of this disclosure.

The subject invention also provides "mixed pairs" of potentiators such as Potentiator Pairs 3, 4, and 5 as illustrated above. Such combinations were not heretofore expected (or suggested) to be active as TC protein toxin enhancers. Thus, such "heterologous" combinations of potentiators can now be selected to maximize their ability to enhance two (for example) insecticidal toxins. That is, one might now find that, for a given use, TcdB1 and XptB1 is a more desirable pair of potentiators than is XptC1 and XptB1, for example. Again, this is surprising given the relative degree of sequence divergence between a given *Photorhabdus* potentiator and a *Xenorhabdus* potentiator for which it is substituted, as well as the degree of difference between the natural "target" toxins which the potentiators would naturally enhance. Therefore, it should be clear that the subject invention also provides heterologous potentiator pairs (i.e., where the Class B (~170 kDa) potentiator is derived from a bacterial genus that is different from the bacterial genus from which the Class C (~112 kDa) potentiator is derived).

The subject invention is not limited to 280 kDa TC protein toxins and a heterologous 112 kDa and/or 170 kDa TC protein potentiator. As this is the first observation of the ability to "mix and match" *Xenorhabdus* and *Photorhabdus*, for example, TC proteins, the subject invention includes any substitution of a *Xenorhabdus* TC protein with a "corresponding" *Photorhabdus* TC protein, and vice versa. For example, one skilled in the art will also now seek to use various heterlogous combinations involving "Toxin C" components (as discussed above in the Background section) and "Toxin D" components (e.g., TccA+XptD1).

The subject invention also includes the use of a transgenic plant producing a subject TC protein combination together with one or more *Bacillus thuringiensis* Cry proteins, for example.

Proteins and toxins. The present invention provides easily administered, functional proteins. The present invention also provides a method for delivering insecticidal toxins that are functionally active and effective against many orders of insects, preferably lepidopteran insects. By "functional activity" (or "active against") it is meant herein that the protein toxins function as orally active insect control agents (alone or in combination with other proteins), that the proteins have a toxic effect (alone or in combination with other proteins), or are able to disrupt or deter insect growth and/or feeding which may or may not cause death of the insect. When an insect comes into contact with an effective amount of a "toxin" of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Functional proteins of the subject invention can also work together or alone to enhance or improve the activity of one or more other toxin proteins. The terms "toxic," "toxicity," or "toxin" as used herein are meant to convey that the subject "toxins" have "functional activity" as defined herein.

Complete lethality to feeding insects is preferred, but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

The subject invention provides classes of TC proteins having toxin activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins for use according to the subject invention. For example, antibodies to the pesticidal toxins disclosed herein can be used to identify and isolate other toxins from a mixture of proteins. Specifically, antibodies maybe raised to the portions of the toxins which are most constant and most distinct from other toxins. These antibodies can then be used to specifically identify equivalent toxins with the characteristic activity by immunoprecipitation, enzyme linked immunosorbent assay (ELISA), or immuno-blotting. Antibodies to the toxins disclosed herein, or to equivalent toxins, or to fragments of these toxins, can be readily prepared using standard procedures. Such antibodies are an aspect of the subject invention. Toxins of the subject invention can be obtained from a variety of sources/source microorganisms.

One skilled in the art would readily recognize that toxins (and genes) of the subject invention can be obtained from a variety of sources. A toxin "from" or "obtainable from" any of the subject isolates referred to or suggested herein means that the toxin (or a similar toxin) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources.

Polynucleotides and probes. The subject invention further provides nucleotide sequences that encode the TC proteins for use according to the subject invention. The subject invention further provides methods of identifying and characterizing genes that encode proteins having toxin activity. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Proteins and genes for use according to the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes,* Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1× SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a tcdA-like gene (and the protein it encodes), for example, is by its ability to hybridize (under any of the conditions specifically disclosed herein) with a previously known, including a specifically exemplified, tcdA gene. The same is true for xptA2-, tcaC-, tcaA-, tcaB-, tcdB-, tccC-, and xptB1-like genes and related proteins, for example. This also includes the tcdB2 and tccC3 genes.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}P$-labeled gene-specific probes was performed by standard methods (see, e.g., Maniatis, T., E. F. Fritsch, J. Sambrook [1982] *Molecular Cloning: A Laboratory Manual,* Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu, L. Grossman and K. Moldave [eds.] Academic Press, New York 100:266-285):

$$Tm=81.5° C.+16.6 Log [Na+]+0.41(\% G+C)-0.61(\% formamide)-600/length of duplex in base pairs.$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6× SSPE, 5× Denhardt's solution, 0.1% SDS, 0.1 mg/ml denatured DNA. Tm for oligonucleotide probes was determined by the following formula:

$$Tm(° C.)=2(number\ T/A\ base\ pairs)+4(number\ G/C\ base\ pairs)$$

(Suggs, S. V., T. Miyake, E. H. Kawashime, M. J. Johnson, K. Itakura, and R. B. Wallace [1981] *ICN-UCLA Symp. Dev. Biol. Using Purified Genes,* D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| | |
|---|---|
| Low: | 1 or 2 × SSPE, room temperature |
| Low: | 1 or 2 × SSPE, 42° C. |
| Moderate: | 0.2 × or 1 × SSPE, 65° C. |
| High: | 0.1 × SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230: 1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. Proteins of the subject invention can have substituted amino acids so long as they retain the characteristic pesticidal/functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," as a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other *Bacillus, Serratia, Paenibacillus, Photorhabdus,* and *Xenorhabdus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins (and TC proteins) may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as E. coli, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B.t. toxins can be used in a truncated (core toxin) form. See, e.g., Adang et al., Gene 36:289-300 (1985), "Characterized full-length and truncated plasmid clones of the crystal protein of Bacillus thuringiensis subsp kurstaki HD-73 and their toxicity to Manduca sexta." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations.

In some cases, especially for expression in plants, it can be advantageous to use truncated genes that express truncated proteins. Höfte et al. 1989, for example, discussed in the Background Section above, discussed protoxin and core toxin segments of B.t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein. The Background section also discusses protease processing and reassembly of the segments of TcdA and TcbA, for example.

Certain toxins/TC proteins of the subject invention have been specifically exemplified herein. As these toxins/TC proteins are merely exemplary of the proteins of the subject invention, it should be readily apparent that the subject invention comprises variant or equivalent proteins (and nucleotide sequences coding for equivalents thereof) having the same or similar toxin activity of the exemplified proteins. Equivalent proteins will have amino acid similarity (and/or homology) with an exemplified toxin/TC protein. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits. For example, a Class A protein can be defined as having 50-90% identity with a given TcdA protein. Thus, a TcdA-like protein (and/or a tcdA-like gene) can be defined by any numerical identity score provided or suggested herein, as compared to any previously known TcdA protein, including any TcdA protein (and likewise with XptA2 proteins) specifically exemplified herein. The same is true for any other protein or gene, to be used according to the subject invention, such as TcaC-, TcaA-, TcaB-, TcdB-, TccC-, and XptB2-like proteins and genes. Thus, this applies to potentiators (such as TcdB2 and TccC3) and stand-alone toxins.

Unless otherwise specified, as used herein, percent sequence identity and/or similarity of two nucleic acids is determined using the algorithm of Karlin and Altschul (1990), Proc. Natl. Acad. Sci. USA 87:2264-2268, modified as in Karlin and Altschul (1993), Proc. Natl. Acad. Sci. USA 90:5873-5877. Such an algorithm is incorporated into the NBLAST and XBLAST programs of Altschul et al. (1990), J. Mol. Biol. 215:402-410. BLAST nucleotide searches are performed with the NBLAST program, score=100, wordlength=12. Gapped BLAST can be used as described in Altschul et al. (1997), Nucl. Acids Res. 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

The amino acid homology/similarity/identity will be highest in critical regions of the protein that account for its toxin activity or that are involved in the determination of three-dimensional configurations that are ultimately responsible for the toxin activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |

TABLE 1-continued

| Class of Amino Acid | Examples of Amino Acids |
|---|---|
| Acidic | Asp, Glu |
| Basic | Lys, Arg, His |

In some instances, non-conservative substitutions can also be made. The critical factor is that these substitutions must not significantly detract from the functional/biological/toxin activity of the protein.

As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Paenibacillus* protein, exemplified herein, produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence for expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector™ program (Accelerys, San Diego, Calif.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined, as well as the second, third, and fourth choices of preferred codons when multiple choices exist. A new DNA sequence can then be designed which encodes the amino sequence of the bacterial toxin, but the new DNA sequence differs from the native bacterial DNA sequence (encoding the toxin) by the substitution of the plant (first preferred, second preferred, third preferred, or fourth preferred) codons to specify the amino acid at each position within the toxin amino acid sequence. The new sequence is then analyzed for restriction enzyme sites that might have been created by the modification. The identified sites are further modified by replacing the codons with first, second, third, or fourth choice preferred codons. Other sites in the sequence which could affect transcription or translation of the gene of interest are the exon: intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class[a] | Range % G + C | Mean % G + C[b] |
|---|---|---|
| Metabolic Enzymes (76) | 44.4-75.3 | 59.0 (.+-.8.0) |
| Structural Proteins (18) | 48.6-70.5 | 63.6 (.+-.6.7) |
| Regulatory Proteins (5) | 57.2-68.8 | 62.0 (.+-.4.9) |
| Uncharacterized Proteins (9) | 41.5-70.3 | 64.3 (.+-.7.2) |
| All Proteins (108) | 44.4-75.3 | 60.8 (.+-.5.2) |

[a]Number of genes in class given in parentheses.
[b]Standard deviations given in parentheses.
[c]Combined groups mean ignored in mean calculation It is preferred that the plant optimized gene(s) encoding a bacterial toxin contain about 63% of first choice codons, between about 22% to about 37% second choice codons, and between about 15% to about 0% third or fourth choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, a DNA sequence is designed to encode the amino acid sequence of said protein toxin utilizing a redundant genetic code established from a codon bias table compiled for the gene sequences for the particular plant, as shown in Table 2. The resulting DNA sequence has a higher degree of codon diversity, a desirable base composition, can contain strategically placed restriction enzyme recognition sites, and lacks sequences that might interfere with transcription of the gene, or translation of the product mRNA.

TABLE 3

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes;* fungi, particularly yeast, e.g., genera *Saccharomyces, Cryptococcus, Kluyveromyces, Sporobolomyces, Rhodotorula,* and *Aureobasidium.* Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters et al. [1978] *Mol. Gen. Genet.* 163: 181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC toxins produced by *Xenorhabdus, Photorhabdus,* and the like with toxins such as B.t. crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26-33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing cells and/or proteins of the subject invention (including recombinant microbes comprising the genes described herein) can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The effect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to engineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of bacterial isolates can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

TC Proteins and Genes Obtainable from *Xenorhabdus* Strain Xwi

It was shown previously (U.S. Pat. No. 6,048,838) that *Xenorhabdus nematophilus* strain Xwi (NRRL B-21733, deposited on Apr. 29, 1997) produced extracellular proteins with oral insecticidal activity against members of the insect orders Coleoptera, Lepidoptera, Diptera, and Acarina. Full-length gene and TC protein sequence from strain Xwi are disclosed below. The methods used to obtain them are more fully discussed in concurrently filed U.S. provisional application by Bintrim et al. (Ser. No. 60/441,717), entitled "*Xenorhabdus* TC Proteins and Genes for Pest Control." These sequences, including N-terminal and internal peptide sequences (SEQ ID NOs:1-5) are also summarized above in the Brief Description of the Sequences section.

In summary, a 39,005 bp fragment of genomic DNA was obtained from strain Xwi and was cloned as cosmid pDAB2097. The sequence of the cosmid insert (SEQ ID NO. 6) was analyzed using the Vector NTI™ Suite (Informax, Inc. North Bethesda, Md., USA) to identify encoded ORFs (Open Reading Frames). Six full length ORFs and one partial ORF were identified (FIG. 1 and Table 4).

TABLE 4

ORFs identified in the pDAB2097 cosmid insert

| ORF Designation | ORF Position in SEQ ID NO. 13 | SEQ ID NO. (Nucleotide) | No. of Deduced Amino Acids | SEQ ID NO. (Amino Acid) |
|---|---|---|---|---|
| ORF1 | 1-1,533 | 7 | 511 | 8 |
| ORF2 | 1,543-5,715 | 9 | 1,391 | 10 |
| ORF3 | 5,764-7,707 | 11 | 648 | 12 |
| ORF4 | 10,709-18,277 | 13 | 2,523 | 14 |
| ORF5 | 18,383-21,430 (C*) | 15 | 1,016 | 16 |
| ORF6 | 21,487-25,965 (C) | 17 | 1,493 | 18 |
| ORF7 | 26,021-33,634 (C) | 19 | 2,538 | 20 |

*(C) designates complementary strand of SEQ ID NO: 6

The nucleotide sequences of the identified ORFs and the deduced amino acid sequences encoded by these ORFs were used to search the databases at the National Center for Biotechnology Information by using BLASTn, BLASTp, and BLASTx, via the government (".gov") website of ncbi/nih for BLAST. These analyses showed that the ORFs identified in the pDAB2097 insert had significant amino acid sequence identity to genes previously identified in *Photorhabdus luminescens* and *Xenorhabdus nematophilus* (Table 5). It is noteworthy that the xpt gene sequences presented in GenBank accession number AJ308438 were obtained from a recombinant cosmid that expressed oral insecticidal activity.

TABLE 5

Similarity of Deduced Proteins encoded by pDAB2097 ORFs to Known Genes

| pDAB2097 ORF* (deduced amino acids) | Gene/ORF Designation (GenBank Accession) | % Amino Acid Sequence Identity to Database Match |
|---|---|---|
| ORF1 (1-511) | tccA (AF047028) | 21.4% |
| ORF2 (313-1,391) | xptD1 (AJ308438) | 96.6% |
| ORF3 (1-648) | chi (AJ308438) | 100% |
| ORF4 (1-2,523) | xptA1 (AJ308438) | 99.5% |
| ORF5 (1-1,016) | xptB1 (AJ308438) | 95.9% |
| ORF6 (1-1,402) | xptC1 (AJ308438) | 96.4% |
| ORF7 (1-2,538) | xptA2 (AJ308438) | 95.1% |

*Deduced Amino Acid Positions with Identity to Database Sequence

Since ORF2, ORF4, ORF5, ORF6, and ORF7 were shown to have at least 95% amino acid sequence identity to previously identified genes, the same gene nomenclature was adopted for further studies on the ORFs identified in the pDAB2097 insert sequence (Table 6).

As used throughout this application, XptA2, for example, signifies a protein and xptA2, for example, signifies a gene. Furthermore, the source isolate for the gene and protein is indicated with subscript. An illustration of this appears in Table 6.

TABLE 6

Nomenclature of ORFs identified in pDAB2097 insert sequence

| PDAB2097 ORF | Gene Designation |
|---|---|
| ORF2 | xptD1$_{Xwi}$ |
| ORF4 | xptA1$_{Xwi}$ |
| ORF5 | xptB1$_{Xwi}$ |
| ORF6 | xptC1$_{Xwi}$ |
| ORF7 | xptA2$_{Xwi}$ |

EXAMPLE 2

Heterologous Expression of Toxin Complex Genes from *Photorhabdus* and *Xenorhabdus*

A series of experiments was done in which *Photorhabdus* and *Xenorhabdus* genes were expressed in *E. coli*. It is shown that co-expression of either the tcdA or xptA2 genes with specific combinations of the tcdB1, tccC1, xptB1 and xptC1 genes, results in significant activity in bioassay against sensitive insects. It is also demonstrated here that expression of the *Photorhabdus* genes tcdA and tcdB with the *Xenorhabdus* gene xptB1 results in significant activity against Southern corn rootworm (*Diabrotica undecinipunctata howardii*). Likewise, expression of *Xenorhabdus* xptA2 with *Photorhabdus* tcdB1 and tccC1 produces activity against corn earworm (*Helicoverpa zea*).

Two *E. coli* expression systems were employed for testing *Photorhabdus* and *Xenorhabdus* genes. The first relied on an *E. coli* promoter present in the expression vector pBT-TcdA (FIG. 2). Several plasmids were constructed in which polycistronic arrangements of up to three genes were constructed. Each gene contained a separate ribosome binding site and start codon, a coding sequence and a stop codon. The second system was mediated by the strong T7 phage promoter and T7 RNA polymerase (FIG. 3, pET; FIG. 4, pCot). Similarly, in some constructions polycistronic arrangements of coding sequences were used. In other experiments, compatible plasmids were used for co-expression. Schematic diagrams describing all of the constructions used in the experiments are shown in FIGS. 5 and 6.

Construction of pBT-TcdA. The expression plasmid pBT-TcdA is composed of the replication and antibiotic selection components of plasmid pBC KS+ (Stratagene) and the expression components (i.e. a strong *E. coli* promoter, lac operon repressor and operator, upstream of a multiple cloning site) from plasmid pTrc99a (Amersham Biosciences Corp., Piscataway, N.J.). An Nco I site was removed from the chloramphenicol resistance gene of pBC KS+ using in vitro mutagenesis. The modification did not change the amino acid sequence of the chloramphenicol acetyl transferase protein. As previously described (Example 27 of WO 98/08932, Insecticidal Protein Toxins from *Photorhabdus*), the TcdA coding sequence (GenBank Accession No. AF188483; reproduced here as SEQ ID NO:21) was modified using PCR to engineer both the 5' and 3' ends. This modified coding sequence was subsequently cloned into pTrc99a. Plasmid pBT-TcdA was made by joining the blunted Sph I/Pvu I fragment of pTrc-TcdA with the blunted Asn I/Pvu I fragment of the pBC KS+. The result is plasmid pBT-TcdA (FIGS. 2 and 5).

Construction of pBT-TcdA-TcdB. The TcdB1 coding sequence (GenBank Accession No. AF346500; reproduced here as SEQ ID NO:22) was amplified from plasmid pBC-AS4 (R. ffrench-Constant University of Wisconsin) using the forward primer:

```
5'ATATAGTCGACGAATTTTAATCTACTAGTAA    (SEQ ID NO:23)
AAAGGAGATAACCATGCAGAATTCACAAACATT
CAGTGTTACC 3'.
```

This primer does not change the protein coding sequence and adds Sal I and Spe I sites in the 5' non coding region. The reverse primer used was:

```
5'ATAATACGATCGTTTCTCGAGTCATTACACC    (SEQ ID NO:24)
AGCGCATCAGCGGCCGTATCATTCTC 3'.
```

Again, no changes were made to the protein coding sequence but an Xho I site was added to the 3' non coding region. The amplified product was cloned into pCR2.1 (Invitrogen) and the DNA sequence was determined. Two changes from the predicted sequence were noted, a single A deletion in the Spe I site of the forward primer (eliminating the site) and an A-to-T substitution at corresponding amino acid position 1041 that resulted in the conservative substitution of Asp-to-Glu. Neither change was corrected. Plasmid pBT-TcdA was digested with Xho I and Pvu I (cutting at the 3' end of the TcdA coding sequence). Plasmid pCR2.1-TcdB1 was cut with Sal I and Pvu I. The fragments were ligated and pBT-TcdA-TcdB1 recombinants (FIG. 5) were isolated. The Xho I and Sal I ends are compatible, but both sites are eliminated upon ligation. The plasmid encodes a polycistronic TcdA-TcdB1 RNA. Each coding region carries separate stop and start codons, and each is preceded by separate ribosome binding sites.

Construction of pDAB3059. The coding sequence for the TccC1 protein (GenBank Accession No. AAC38630.1; reproduced here as SEQ ID NO:25) was amplified from a pBC KS+ vector (pTccC ch1; from R. ffrench-Constant, the University of Wisconsin) containing the three-gene Tcc operon. The forward primer was:

```
5'GTCGACGCACTACTAGTAAAAAGGAGATAA    (SEQ ID NO:26)
CCCCATGAGCCCGTCTGAGACTACTCTTTATAC
TCAAACCCCAACAG 3'
```

This primer did not change the coding sequence of the tccC1 gene, but provided 5' non coding Sal I and Spe I sites as well as a ribosome binding site and ATG initiation codon. The reverse primer was:

```
5'CGGCCGCAGTCCTCGAGTCAGATTAATTA    (SEQ ID NO:27)
CAAAGAAAAAACTCGTCGTGCGGCTCCC 3'
```

This primer also did not alter the tccC1 coding sequence, but provided 3' Not I and Xho I cloning sites. Following amplification with components of an EPICENTRE FailSafe PCR kit (EPICENTRE; Madison, Wis.) the engineered TccC1 coding sequence was cloned into pCR2.1-TOPO (Invitrogen). The coding sequence was cut from pCR2.1 and transferred to a modified pET vector (Novagen; Madison Wis.) via the 5' Sal I and 3' Not I sites. The pET vector contains a gene conferring resistance to spectinomycin/streptomycin, and has a modified multiple cloning site. A PCR-induced mutation found via DNA sequencing was corrected using the pTccC ch1 plasmid DNA as template, and the plasmid containing the corrected coding region was named pDAB3059. Double-stranded DNA sequencing confirmed that the mutation had been corrected.

Construction of pBT-TcdA-TccC1. Plasmid pBT-TcdA DNA was cut with Xho I, and ligated to pDAB3059 DNA cut with Sal I and Xho I. The tccC1 gene was subsequently ligated downstream of the tcdA gene to create pBT-TcdA-TccC1 (FIG. 5).

Construction of pBT-TcdA-TcdB1-TccC1. Plasmid pBT-TcdA-TcdB1 DNA was cut with Xho I and ligated to pDAB3059 DNA cut with Sal I and Xho I. Recombinants were screened for insertion of the tccC1 gene behind the tcdB gene to create plasmid pBT-TcdA-TcdB1-TccC1 (FIG. 5).

Construction of pBT-TcdA-TcdB1-XptB1. Plasmid pBT-TcdA-TcdB1 DNA was cut with Xho I and shotgun ligated with pET280-XptB1DNA which was cut with Sal I and Xho I. Recombinants representing insertion of the xptB1 coding region into the Xho I site of pBT-TcdA-TcdB1 where identified to create plasmid pBT-TcdA-TcdB1-XptB1 (FIG. 5).

Construction of pET28-TcdA. The description of this plasmid can be found elsewhere as Example 27 of WO 98/08932, Insecticidal Protein Toxins from *Photorhabdus.*

Construction of pCot-TcdB1. Plasmid pCR2. 1-TcdB1 was cut with Xho I and Sal I and ligated into the Sal I site of the T7 expression plasmid pCot-3 (FIG. 4). Plasmid pCot-3 has a pACYC origin of replication, making it compatible with plasmids bearing a ColE1 origin (pBR322 derivatives). In addition, it carries a chloramphenicol antibiotic resistance marker gene and a T7 RNA polymerase-specific promoter for expression of coding regions inserted into the multiple cloning site.

Construction of pCot-TccC1-TcdB1. The TccC1 coding region was cut from pDAB3059 DNA with Spe I and Not I and ligated into the multiple cloning site of plasmid pET280-K (a modified pET28 which has had the multiple cloning site replaced). This resulted in acquisition of a Swa I site upstream of the Spe I site and an Xho I site downstream of the Not I site. DNA of plasmid pET280-K-TccC1 was cut with Swa I and Xho I to release the TccC1 coding sequence, which was then ligated into the Swa I and Sal I sites of plasmid pCot-3-TcdB1 to create plasmid pCot-3-TccC1-TcdB (FIG. 6).

Construction of pET280-XptA2, pET280-XptC1, and pET280-XptB1. The coding sequences for the XptA2, XptC1, and XptB1 proteins were each PCR amplified from pDAB2097, a recombinant cosmid containing the three genes that encode these proteins. The PCR primer sets used to amplify these coding sequences are listed in Table 7. In all of these primer sets, the forward primer did not change the coding sequence of the gene but provided 5' non coding Sal I and Xba I sites as well as a ribosome binding site. The reverse primers also did not alter the corresponding coding sequences, but provided a 3' Xho I cloning site. Following amplification with components of the EPICENTRE Fail Safe PCR kit, the engineered XptA2, XptC1, and XptB1 coding sequences were each cloned into pCR2.1. The cloned amplified products were sequence confirmed to ensure that PCR-induced mutations did not alter the coding sequences. Recombinant plasmids that contained unaltered coding sequences for XptA2, XptC1, and XptB1 were identified and designated as pDAB3056, pDAB3064, and pDAB3055, respectively. The coding sequences were each cut from the pCR2.1 derivatives and transferred to a modified pET vector (pET280-SS is a pET28 derivative which has had the multiple cloning site replaced, and a streptomycin/spectinomycin resistance gene inserted into the backbone to provide a selectable marker [FIG. 3]), via the 5' Xba I and 3' Xho I sites to create plasmids pET280-XptA2, pET280-XptC1, and pET280-XptB1.

Construction of pET280-XptA2-XptC1. Plasmid pET280-XptA2 DNA was cut with Xho I and ligated into the unique Sal I site in pDAB3064. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). DNA of the recovered plasmids was digested with Xho I to check fragment orientation. A plasmid with the XptC1 coding region immediately downstream of the XptA2 coding region was obtained and the DNA was digested with Xho I to remove the pCR2.1 vector backbone. The resulting construct, which contains the pET280-SS vector backbone and the coding sequences for XptA2 and XptC1, was self-ligated to produce pET280-XptA2-XptC1.

Construction of pET280-XptC1-XptB1. Plasmid pET280-XptC1 DNA was cut with Xho I and ligated into the unique Sal I site in pDAB3055. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). DNA of the recovered plasmids was digested with Xho I to check fragment orientation. A plasmid with the XptB1 coding region immediately downstream of the XptC1 coding region was obtained and the DNA was digested with Xho I to remove the pCR2.1 vector backbone. The resulting construct, which contains the pET280-SS vector backbone and the coding sequences for XptC1 XptB1, was self-ligated to produce pET280-XptC1-XptB1.

Construction of pET280-XptA2-XptB1. Plasmid pET280-XptA2 DNA was cut with Xho I and ligated into the unique Sal I site in pDAB3055. The resulting ligated product contained both pCR2.1 and pET280-SS vector backbones and

TABLE 7

PCR Primers Used to Amplify XptA2, XptC1, and XptB1 Coding Sequences

| Coding Sequence Amplified | Forward Primer Sequence (5'-3') | | Reverse Primer Sequence (5'-3') | |
|---|---|---|---|---|
| XptA2 | GTCTAGACGTGCGTCGAC AAGAAGGAGATATACCAT GTATAGCACGGCTGTATTA CTCAATAAAATCAGTCCCA CTCGCGACGG* | (SEQ ID NO:28) | GCTCGAGATTAATTAAGAAC GAATGGTATAGCGGATATGC AGAATGATATCGCTCAGGCT CTCC | (SEQ ID NO:29) |
| XptC1 | GTCTAGACGTGCGTCGAC AAGAAGGAGATATACCAT GCAGGGTTCAACACCTTTG AAACTTGAAATACCGTCAT TGCCCTC | (SEQ ID NO:30) | GACTCGAGAGCATTAATTAT GCTGTCATTTCACCGGCAGT GTCATTTTCATCTTCATTCAC CAC | (SEQ ID NO:31) |
| XptB1 | GTCTAGACGTGCGTCGAC AAGAAGGAGATATACCAT GAAGAATTTCGTTCACAGC AATACGCCATCCGTCACCG TACTGGACAACC | (SEQ ID NO:32) | GCTCGAGCAGATTAATTATG CTTCGGATTCATTATGACGTG CAGAGGCGTTAAAGAAGAAG TTATT | (SEQ ID NO:33) |

*Underlined sequences in primers correspond to protein coding sequences could be recovered by antibiotic selection using a combination of streptomycin (25 µg/mL), spectinomycin (25 µg/mL), and ampicillin (100 µg/mL). DNA of the recovered plasmids was digested with Xho I to check fragment orientation. A plasmid with the XptB1 coding region immediately downstream of the XptA2 coding region was obtained and the DNA was digested with Xho I to remove the pCR2.1 vector backbone. The resulting construct, which contains the pET280-SS vector backbone and the coding sequences for XptA2 and XptB1, was self-ligated to produce pET280-XptA2-XptB1.

Construction of pET280-XptA2-XptC1-XptB1. Plasmid pET280-XptA2-XptC1 DNA was cut with Xho I and ligated into the unique Sal I site in pDAB3055. The resulting ligated product contained both pCR2.1 and pET280-SS vector backbones and could be recovered by antibiotic selection using a combination of streptomycin (25 µg/mL), spectinomycin (25 µg/mL), and ampicillin (100 µg/mL). The recovered plasmids were digested with Xho I to check fragment orientation. A plasmid with the XptB1 coding region immediately downstream of the XptC1 coding region was obtained and the DNA was digested with Xho I to remove the pCR2.1 vector backbone. The resulting construct, which contains the pET280-SS vector backbone and the XptA2,XptC1, and XptB1 coding sequences, was self-ligated to produce pET280-XptA2-XptC1-XptB1.

Expression of pBT-based constructions. The pBT expression plasmids were transformed into *E. coli* strain BL21 cells and plated on LB agar containing 50 µg/mL chloramphenicol and 50 mM glucose, and transformants were grown at 37° C. overnight. Approximately 10-100 well isolated colonies were used to inoculate 200 mL of sterile LB containing 50 µg/mL chloramphenicol plus 75 µM isopropyl-β-D-thiogalatopyranoside (IPTG) in 500 mL baffled flasks. The cultures were shaken at 200 rpm at 28° C. for 24 hours. Cells were collected by centrifugation (approximately 3000×g) and resuspended in phosphate buffer (30 mM, pH 7.4; NutraMax; Gloucester, Mass.) to a cell density of 30-120 $OD_{600}$ units/mL. Diluted cells were then used for insect bioassay.

Alternatively, the cells were chilled on ice after growth for 24 hours and adjusted to 20-30 $OD_{600}$ units/ml with phosphate buffer. The cells were lysed with a probe sonicator (Soniprep 150, MSE), using 2×45 second bursts at 20 microns amplitude with ⅓ volume 0.1 mm glass beads (Biospec; Bartletsville, Okla.). The lysates were cleared in an Eppendorf microfuge at 14,000 rpm for 10 minutes. Cleared lysates were concentrated in UltraFree 100 kDa units (Millipore; Bedford, Mass.), collected, adjusted to 10 mg/mL in phosphate buffer, and submitted for insect bioassay.

Expression of T7 Based Constructions. The T7 based expression plasmids were handled the same as the pBT expression plasmids described above, with the exception that they were transformed into the T7 expression strain BL21 (DE3) (Novagen, Madison, Wis.), and a combination of streptomycin (25 µg/mL) and spectinomycin (25 µg/mL) was used for the antibiotic selection.

EXAMPLE 3

Insect Bioassay Results of Heterologously Expressed Toxin Complex Genes

A series of expression experiments was performed using the pBT expression system as described above. *E. coli* cells were transformed, induced and grown overnight at 28° C. The cells were collected, washed, normalized to equal concentrations and applied to Southern corn rootworm diet and bioassayed. As shown in Table 8, only when all three *Photorhabdus* genes, tcdA, tcdB1 and tccC1 were expressed in the same cell was significant mortality observed. Other combinations of genes did not result in significant mortality. For example, the specific combination of tcdB1 and tccC1 genes, which showed no insect killing activity, is shown in Table 8. Mortality was observed routinely when the genes on plasmid pBT-TcdA-TcdB1-TccC1 were expressed, and storing the cells at 4° C. for 24 hours before application to insect diet did not decrease or increase mortality significantly in these experiments (Table 8). Southern corn rootworm mortality was also observed if the cells were lysed following co-expression of the genes on plasmid pBT-TcdA-TcdB1-TccC1. Activity did not appear to decrease if the lysate was stored frozen at −70° C. for one week (Table 9).

TABLE 8

Bioassay of pBT-Expressed *Photorhabdus* Toxin Complex Genes on Southern Corn Rootworm

| Plasmid | Day 1 | Day 2 |
|---|---|---|
| Experiment A. | | |
| | 68 units/ml | 68 units/ml |
| pBT | 0 | 0 |
| pBT-TcdA | 0 | 0 |
| pBT-TcdA-TcdB1 | 0 | 0 |
| pBT-TcdA-TccC1 | 0 | 0 |
| pBT-TcdA-TcdB1-TccC1 | ++++ | +++++ |
| Experiment B. | | |
| | 85 units/ml | 85 units/ml |
| PBT | 0 | 0 |
| pBT-TcdA | 0 | 0 |
| pBT-TcdA-TcdB1 | 0 | + |
| pBT-TcdA-TccC1 | 0 | 0 |
| pBT-TcdA-TcdB1-TccC1 | ++++ | +++++ |

Whole *E. coli* cells were washed with phosphate buffer, concentrated, adjusted to equal cell concentration, and applied to insect diet. Day 1 samples were assayed immediately. Day 2 samples were the same preparations of cells, but had been stored overnight at 4° C. before application to insect diet.
Grading Scale represents % mortality of Southern corn rootworm
(0 = 0-10%;
+ = 11-20%;
++ = 21-40%;
+++ = 41-60%;
++++ = 61-80%;
+++++ = 81-100%).

TABLE 9

Bioassay of pBT-Expressed *Photorhabdus* Toxin Complex Genes on Southern Corn Rootworm

| Plasmid | Cells 74 units/ml | Lysate 10 mg/ml | Frozen Lysate 10 mg/ml |
|---|---|---|---|
| pBT | 0 | 0 | 0 |
| pBT-TcdA-TcdB1-TccC1 | +++++ | +++++ | +++++ |

Whole *E. coli* cells were washed with phosphate buffer, concentrated, adjusted to equal cell concentrations, and applied to insect diet preparations. Alternatively, lysates were prepared by sonication and applied to diet either fresh or after being frozen at −70° C. for 7 days.
Grading Scale represents % mortality of Southern corn rootworm
(0 = 0-10%;
+ = 11-20%;
++ = 21-40%;
+++ = 41-60% = ++++, 61-80%;
+++++ = 81-100%).

In another series of experiments, the *Xenorhabdus* xptB1 gene was substituted for the *Photorhabdus* tccC1 gene and expressed as part of the polycistronic operon of plasmid pBT-TcdA-TcdB1-XptB1. These experiments demonstrated that the *Xenorhabdus* xptB1 gene was able to substitute for the *Photorhabdus* tccC1 gene, resulting in mortality of Southern corn root worm in bioassay of whole *E. coli* cells (Table 10).

TABLE 10

Bioassay of pBT Expressed *Photorhabdus* and *Xenorhabdus* Toxin Complex Genes on Southern Corn Rootworm

| Plasmid | Trial 1<br>110 units/ml | Trial 2<br>55 units/ml | Trial 3<br>111 units/ml |
|---|---|---|---|
| pBT | 0 | 0 | 0 |
| pBT-TcdA-TcdB1-TccC1 | +++ | +++ | +++ |
| pBT-TcdA-TcdB1-XptB1 | ++ | ++ | +++ |

Whole *E. coli* cells were washed with phosphate buffer, concentrated, adjusted to equal cell concentrations, and applied to insect diet preparations. Grading Scale represents % mortality of Southern corn rootworm
(0 = 0-10%;
+ = 11-20%;
++ = 21-40%;
+++ = 41-60% = ++++, 61-80%;
+++++ = 81-100%).

Expression of the various *Photorhabdus* genes from separate plasmids also resulted in Southern corn root worm mortality. When tcdA was present on the pET expression plasmid, and the tccC1 and tcdB1 genes were on the compatible expression vector pCot-3, significant activity was observed as compared to control combinations of these plasmids (Table 11). As noted above, the presence of the tcdB1 and tccC1 genes alone did not result in significant activity (Table 11).

TABLE 11

Bioassay of pCoT/pET (T7 promoter) Expressed *Photorhabdus* Toxin Complex Genes on Southern Corn Rootworm

| Plasmids | Trial 1<br>40 units/ml | Trial 2<br>60 units/ml |
|---|---|---|
| pCot/pET | 0 | 0 |
| pCot/pET-TcdA | 0 | 0 |
| pCot-TccC1-TcdB1/pET | 0 | 0 |
| pCot-TccC1-TcdB1/pET-TcdA | +++ | +++ |

Whole *E. coli* cells were washed with phosphate buffer, concentrated, adjusted to equal cell concentrations, and applied to insect diet preparations. Grading Scale represents % mortality of Southern corn rootworm
(0 = 0-10%;
+ = 11-20%;
++ = 21-40%;
+++ = 41-60% = ++++, 61-80%;
+++++ = 81-100%).

Bioassay Results of Heterologously Expressed *Xenorhabdus* Toxin Complex Genes. A series of expression experiments was performed using the pET expression system as described above. *E. coli* cells were transformed, induced and grown overnight at 28° C. The cells were collected, washed, normalized to equal concentrations, and tested for insecticidal activity against *Ostrinia nubilalis* European corn borer (ECB), corn earworm (CEW), and tobacco budworm (TBW). As shown in Table 12, the highest levels of insecticidal activity were observed when xptA2, xptC1, and xptB1 were present in the same construct.

TABLE 12

Bioassay of Heterologously Expressed *Xenorhabdus* Toxin Complex Genes on TBW, CEW, and ECB

| Plasmid Tested | TBW<br>Bioassay | CEW<br>Bioassay | ECB<br>Bioassay |
|---|---|---|---|
| pET-280 | 0* | 0 | 0 |
| pET-280-XptA2 | +++ | +++ | ++ |
| pET-280-XptC1 | 0 | 0 | 0 |
| pET-280-XptB1 | 0 | 0 | 0 |
| pET-280-XptA2-XptC1 | + | + | 0 |
| pET-280-XptA2-XptB1 | 0 | 0 | 0 |
| pET-280-XptC1-XptB1 | 0 | 0 | 0 |
| pET-280-XptA2-XptC1-XptB1 | +++++ | +++++ | +++++ |

*Whole *E. coli* cells were washed with phosphate buffer, concentrated, adjusted to equal cell concentrations, and applied to insect diet preparations. Grading Scale represents % growth inhibition relative to controls
(0 = 0-10%;
+ = 11-20%;
++ = 21-40%;
+++ = 41-60% = ++++, 61-80%;
+++++ = 81-100%).

Bioassay results of heterologously expressed xptA2, tcdB1, and tccC1. *E. coli* cells were co-transformed with the pET280 and pCoT constructs listed in Table 13. Transformants were induced, processed and bioassayed as described above. In these assays, co-transformants that contained either pCOT/pET280-XptA2-XptC1-XptB1 or pCoT-TcdB1-TccC1/pET280-XptA2 plasmid combinations exhibited the highest levels of insecticidal activity. These experiments show that the *Photorhabdus* tcdB1 and tccC1 genes, even in trans relative to xptA2, were able to substitute for the *Xenorhabdus* xptC1 and xptB1 genes, resulting in qualitatively similar levels of enhanced insecticidal activity.

TABLE 13

Bioassay of Heterologously Expressed xptA2, tcdB1, and tccC1 on CEW

| Plasmids Tested | CEW Bioassay |
|---|---|
| pET280/pCoT | 0* |
| pET280/pCoT-TcdB1-TccC1 | 0 |
| pCoT/pET280-XptA2 | +++ |
| pCoT/pET280-XptA2-XptC1-XptB1 | +++++ |
| pCoT-TcdB-TccC1/pET280-XptA2 | +++++ |

*Whole *E. coli* cells were washed with phosphate buffer, concentrated, adjusted to equal cell concentrations, and applied to insect diet preparations. Grading Scale represents % growth inhibition relative to controls
(0 = 0-10%;
+ = 11-20%;
++ = 21-40%;
+++ = 41-60% = ++++, 61-80%;
+++++ = 81-100%).

EXAMPLE 4

Complementation of *Xenorhabdus* XptA2 Toxin with *Paenibacillus* Strain DAS1529 TC Proteins This example provides additional data relating to co-pending U.S. provisional application Ser. No. 60/392,633, which is discussed in the Background section above. This data is relevant to the present application because it provides experimental evidence of the ability of *Paenibacillus* strain DAS1529 TC proteins (expressed here as a single operon) to complement, for example, the XptA2 toxin from *Xenorhabdus nematophilus* Xwi (see SEQ ID NO:34). Two independent experiments were carried out to express the DAS1529

TC operon and XptA2 independently, or to co-express the XptA2 gene and the TC operon in the same *E. coli* cells. Whole cells expressing different toxins/toxin combinations were tested for activity against two lepidopteran insects: corn earworm (*Heliothis zea*; CEW) and tobacco budworm (*Heliothis virescens*; TBW). The data from both experiments indicate that DAS1529 TC proteins are able to enhance *Xenorhabdus* XptA2 activity against both insect species tested.

A. Co-expression of DAS1529 TC Proteins and *Xenorhabdus* TC XptA2 Toxin

Expression of the DAS1529 TC operon was regulated by T7 promoter/lac operator in the pET101.D expression vector that carries a ColE1 replication origin and an ampicillin resistance selection marker (Invitrogen). A comprehensive description of cloning and expression of the *Paenibacillus* TC operon can be found in Example 8 of U.S. Ser. No. 60/392,633. The XptA2 gene was cloned in the pCot-3 expression vector, which carries a chloramphenicol resistance selection marker and a replication origin compatible with the ColE 1. The pCot-3 vector expression system is also regulated by the T7 promoter/lac operator. Hence, compatible replication origins and different selection markers form the basis for co-expression of the TC operon and XptA2 in the same *E. coli* cells. Plasmid DNAs carrying the TC operon and XptA2 were transformed into *E. coli,* BL21 Star™ (DE3) either independently or in combination. Transformants were selected on LB agar plates containing 50 μg/ml carbenicillin for pET101.D-TC operon, 50 μg/ml chloramphenicol for pCot-3-XptA2, and both antibiotics for pET101.D-TC operon/pCot-3-XptA2. To suppress basal toxin expression, glucose at a final concentration of 50 mM was included in both agar and liquid LB medium.

For toxin production, 5 mL and 50 mL of LB medium containing antibiotics and 50 mM glucose were inoculated with overnight cultures growing on the LB agar plates. Cultures were grown at 30° C. on a shaker at 300 rpm. Once the culture density reached an O.D. of ~0.4 at 600 nm, IPTG at a final concentration of 75 μM was added to the culture medium to induce gene expression. After 24 hours, *E. coli* cells were harvested for protein gel analysis by the NuPAGE system (Invitrogen). Cell pellets from 0.5 mL 1× culture broth was resuspended in 100 μL of 1× NuPAGE LDS sample buffer. Following brief sonication and boiling for 5 min, 5 μL of the sample was loaded onto 4 to 12% NuPAGE bis-tris gradient gel for total protein profile analysis. XptA2 expressed to detectable levels when expressed independently or in the presence of the TC operon. Based on gel scan analysis by a Personal Densitometer SI (Molecular Dynamics), XptA2 expressed nearly 8× as high by itself as when co-expressed with the TC operon. For the 5 mL induction experiment, there is a nearly equal expression of XptA2.

B. Bioassay for Insecticidal Activity

As described in Example 8 of U.S. Ser. No. 60/392,633, DAS1529 TC ORFs, when expressed independently or as an operon, did not appear to be active against TBW and CEW. The following bioassay experiments focused on determining whether *Paenibacillus* (DAS1529) TC proteins (of ORFs3-6; TcaA-, TcaB-, TcaC-, and TccC-like proteins; see SEQ ID NOs:35-43) could potentiate *Xenorhabdus* TC protein (XptA2 is exemplified) activity. Bioassay samples were prepared as whole *E. coli* cells in 4× cell concentrate for the 5 mL induction experiment, both the XptA2 and XptA2/TC operon cells contained very low but nearly equal amount of XptA2. Data in Table 14 showed that at the 4× cell concentration, the combination of the *Paenibacillius* TC proteins ("TCs" in Table 14) +XptA2 was active against CEW. This demonstrates a complementation effect of *Paenibacillus* DAS1529 TCs on *Xenorhabdus* XptA2.

TABLE 14

Bioassay of DAS1529 TC potentiation of *Xeno.* toxin on *H. zea*

| Insects: | CEW |
|---|---|
| Negative control | – |
| TCs (DAS1529) | – |
| XptA2 | – |
| TCs + XptA2 | ++ |

* –, ++, +++ = no, moderate and high activity, respectively

For the second bioassay experiment, the amount of XptA2 protein in the XptA2 cells and the XptA2+TC operon cells was normalized based on densitometer gel scan analysis. As shown in Table 15, XptA2 per se had moderate activity at 40× on TBW (*H. virescens*), but the activity dropped to a level undetectable at and below 20×. However, when co-expressed with the *Paenibacillus* TC proteins, high levels of activity were very apparent in the presence of 10× and 5× XptA2, and low activity was still noticeable at 1.25× XptA2. These observations indicate there is a significant potentiation effect of these DAS1529 TC proteins on XptA2 against *H. virescens.* At the highest doses tested, neither the negative control nor the TC operon per se had any activity against this pest.

TABLE 15

Bioassay of IDAS1529 TC complementation of XptA2 on *H. virescens*

| Normalized XptA2 | 40× | 20× | 10× | 5× | 2.5× | 1.25× |
|---|---|---|---|---|---|---|
| XptA2 | + | – | – | – | n.d. | n.d. |
| TCs + XptA2 | n.d. | n.d. | ++ | ++ | + | – |

* n.d.—not determined;
–, +, ++, +++ = no, low, moderate, and high activity, respectively

EXAMPLE 5

*Xenorhabdus bovienii* B and C Protein Mixed Complementation

EXAMPLE 5A

Overview

The identification and isolation of genes encoding factors that potentiate or synergize the activity of the insect active proteins *Photorhabdus* TcdA and *Xenorhabdus* $XptA2_{wi}$ were accomplished using a cosmid complementation screen. Individual *Escherichia coli* clones from a cosmid genomic library of *Xenorhabdus bovienii* (strain ILM104) were used to create crude cell extracts which were mixed with purified toxins and bioassayed. Lysates were assayed with purified *Photorhabdus* toxin TcdA against southern corn rootworm larvae (*Diabrotica undecimpunctata howardi*). Likewise, lysates were also mixed with purified *Xenorhabdus* XptA2$_{wi}$ protein and assayed against tobacco budworm (*Heliothis virescens*) or corn earworm (*Helicoverpa zea*) larvae. Cosmid lysates were scored as positive if the combination of lysate plus purified toxin had activity greater than either component alone.

The primary screen samples (in 96-well format) were tested in duplicate and scored compared to controls for insecticidal activity. Positive samples were re-grown and tested in the secondary screen. Cosmids identified as positive through primary and secondary screens were screened a third time. Larger culture volumes were utilized for tertiary screens (see below), tested for biological activity in a 128-well format bioassay.

DNA from one of the cosmids identified as having potentiating activity in this screen was subcloned. The DNA sequence of a single subclone which retained activity was determined and shown to contain two open reading frames, designated $xptB1_{xb}$ and $XptC1_{xb}$. These coding regions were subcloned into pET plasmids and expressed in *E. coli.* A dramatic increase in insect activity was seen when either TcdA or $XptA2_{wi}$ protein was mixed with lysates co-expressing both $XptB1_{xb}$ and $XptC1_{xb}$. Lysates containing only $XptB1_{xb}$ or only $XptC1_{xb}$ had minimal affects when mixed with purified TcdA or $XptA2_{wi}$.

EXAMPLE 5B

Insect Bioassay Methodology

Insect bioassays were conducted using artificial diets in either 96-well microtiter plates (Becton Dickinson and Company, Franklin Lakes, N.J.) or 128-well trays specifically designed for insect bioassays (C-D International, Pitman, N.J.). Eggs from 2 *lepidopteran* species were used for bioassays conducted in 96-well microtiter plates: the corn earworm (*Helicoverpa zea* (Boddie)) and the tobacco budworm (*Heliothis virescens* (F.)). Neonate larvae were used for bioassays conducted in 128-well trays. The lepidopteran species tested in this format included the corn earworm, the tobacco budworm, and the beet armyworm (*Spodoptera exigua* (Hübner)). A single coleopteran species, the southern corn rootworm (*Diabrotica undecimpunctata howardii* (Barber)) was also tested in this bioassay format.

The data recorded in these bioassays included the total number of insects in the treatment, number of dead insects, the number of insects whose growth was stunted, and the weight of surviving insects. In cases where growth inhibition is reported, this was calculated as follows:

% Growth Inhibition=[1−(Average Weight of Insects in Treatment/Average Weight of Insects in the Vector-Only Control)]*100

EXAMPLE 5C

Other Experimental Protocol

This is described in more detail in concurrently filed application by Apel-Birkhold et al., entitled "Toxin Complex Proteins and Genes from *Xenorhabdus bovienii,*" under attorney docket no. 60/534,893.

EXAMPLE 5D

Plasmid pDAB6026 was shown to encode activities which synergized the insect toxic activities of TcdA and $XptA2_{wi}$. *E. coli* cells containing plasmid pDAB6026 or the pBCKS+ vector control were inoculated into 200 mL of LB containing chloramphenicol (50 μg/mL) and 75 μM IPTG (isopropyl-β-D-thiogalactopyranoside) and grown for two days at 28° C. with shaking at 180 rpm. The cells were then centrifuged for 10 min at 3500×g. The pellets were resuspended in 5 mL of Butterfield's phosphate solution (Fisher Scientific) and transferred to 50 mL conical tubes containing 1.5 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~20, chilling completely between bursts. The supernatant was transferred to 2 mL microcentrifuge tubes and centrifuged for 5 min at 16,000.×g. The supernatants were then transferred to 15 mL tubes, and the protein concentration was measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The samples were then read on a spectrophotometer measuring the optical density at the wavelength of 595 in the Shimadzu UV160U spectrophotometer (Kyoto, JP). The amount of protein contained in each sample was then calculated against the BSA standard curve and adjusted to between 3-6 mg/mL with phosphate buffer. Six hundred nanograms of $XptA2_{wi}$ toxin protein were added to 500 μL of the *E. coli* lysate prior to testing in insect feeding bioassays. The combination of pDAB6026 and XptA2 was shown to have potent activity (Table 16).

TABLE 16

Response of 2 lepidopteran species to pDAB6026 lysates alone and with purified $XptA2_{wi}$ protein.

| | tobacco budworm | | | | corn earworm | | | |
|---|---|---|---|---|---|---|---|---|
| Treatment | Dead | Stunted | Total | Weight | Dead | Stunted | Total | Weight |
| 1 pBC | 0 | 0 | 8 | 674 | 0 | 0 | 8 | 352 |
| 2 pBC + $XptA2_{wi}$ | 0 | 0 | 8 | 538 | 0 | 0 | 8 | 423 |
| 3 pDAB6026 | 0 | 0 | 8 | 539 | 0 | 0 | 8 | 519 |
| 4 pDAB6026 + $XptA2_{wi}$ | 0 | 8 | 8 | 18 | 8 | — | 8 | — |

EXAMPLE 5E

Discovery, Engineering and Testing of xptB1$_{xb}$ and xptC1$_{xb}$ Genes

DNA of plasmid pDAB6026 was sent to Seq Wright DNA Sequencing (Houston, Tex.) for DNA sequence determination. Two complete open reading frames (ORFs) of substantial size were discovered. The first (disclosed as SEQ ID NO:48) has significant similarity to known toxin complex genes belonging to the "B" class. This ORF was therefore called $xptB1_{xb}$ and encodes the protein disclosed as SEQ ID NO:49. The second ORF (SEQ ID NO:50) encodes a protein (SEQ ID NO:51) with homology to toxin complex "C" proteins and therefore was named $XptC1_{xb}$.

The $xptB1_{xb}$ and $xptC1_{xb}$ genes were engineered (using the polymerase chain reaction; PCR) for high level recombinant expression by addition of restriction sites 5' and 3' to the coding regions, as well as provision of ribosome binding sequences and optimal translational stop signals. In addition, silent mutations (no change in amino acid sequence) were introduced into the 5' end of the coding regions to reduce potential secondary structure of the mRNA and hence increase translation. The strategy was to amplify/engineer segments at the 5' and 3' ends of the genes, join the distal fragments using 'Splice Overlap Extensions' reactions, then add the non-amplified center portion of the open reading frames via restriction sites. This approach minimized the potential of PCR-induced changes in the DNA sequence. The engineered coding regions were cloned into pET expression plasmids (Novagen, Madison, Wis.) as either separate coding regions (SEQ ID NO:52 and SEQ ID NO:53) or a dicistronic operon (SEQ ID NO:54). The names of the expression plasmids are shown in Table 17.

TABLE 17

Expression plasmids containing various coding regions cloned into the pET vector.

| Plasmid Name | Coding Region Engineered for Expression |
|---|---|
| pDAB6031 | $xptB1_{xb}$ as in SEQ ID NO: 52 |
| pDAB6032 | $xptC1_{xb}$ as in SEQ ID NO: 53 |
| pDAB6033 | $xptB1_{xb}$ + $xptC1_{xb}$ as in SEQ ID NO: 54 |

Competent cells of the *E. coli* T7 expression strain BL21 Star™ (DE3) (Stratagene, La Jolla, Calif.) were freshly transformed with DNA of either the pET (control) vector or plasmids pDAB6031, pDAB6032 or pDAB6033, and inoculated into 250 mL of LB containing 50 μg/mL chloramphenicol and 75 μM IPTG. After growth for 24 hrs at 28° C. with shaking at 180 rpm, the cells were centrifuged for 10 min at 5500×g. The pellets were resuspended in 5 mL of phosphate solution and transferred to 50 mL conical tubes containing 1.5 mL of 0.1 mm diameter glass beads, then were sonicated for two 45 sec bursts at "constant" and a setting of 30 as described above. The samples were centrifuged at 3000×g for 15 min, the supernatant was transferred to 2 mL microcentrifuge tubes, centrifuged for 5 min at 14,000 rpm, and the supernatants were then transferred to 15 mL tubes. The protein concentrations were measured as described above and the lysates were adjusted to 5 mg/mL with phosphate buffer. A set of three samples per lysate was submitted for insect bioassay. To the first sample, phosphate buffer was added in place of purified toxin; to the second sample, sufficient TcdA protein was added to provide a dose of 50 ng/cm$^2$ in the insect bioassay well, and to the third sample, sufficient $XptA2_{wi}$ protein was added to provide a dose of 250 ng/cm$^2$ in the insect bioassay well.

The results of the bioassay are shown in Table 18. Control samples, which were not supplemented with low levels of added TcdA or $XptA2_{wi}$ protein, (e.g. samples from vector, pDAB6031, pDAB6032 and pDAB6033), had little impact on the insects. Likewise, samples which contained low levels of TcdA or $XptA2_{wi}$, with either pDAB6031 or pDAB6032 lysates, had minimal effects. In contrast, significant activity was observed in the samples which included low levels of TcdA or $XptA2_{wi}$ with pDAB6033 lysates.

TABLE 18

Response of coleopteran and lepidopteran species to *E. coli* lysates and purified proteins. Responses are presented as percent mortality/percent growth inhibition.

| | | Insect Species | | | |
|---|---|---|---|---|---|
| Sample | Lysates Tested | southern corn rootworm | corn earworm | tobacco budworm | beet armyworm |
| vector | | 0/0 | 8/0 | 0/0 | 31/0 |
| pDAB6031 | $XptB1_{xb}$ | 0/0 | 0/0 | 0/0 | 31/33 |
| pDAB6032 | $XptC1_{xb}$ | 0/0 | 4/11 | 0/2 | 13/15 |
| pDAB6033 | $XptB1_{xb}$ + $XptC1_{xb}$ | 0/0 | 0/0 | 0/6 | 13/38 |
| Vector + TcdA | | 4/0 | 4/3 | 0/6 | 25/22 |
| pDAB6031 + TcdA | $XptB1_{xb}$ + TcdA | 0/0 | 0/0 | 0/5 | 13/34 |
| pDAB6032 + TcdA | $XptC1_{xb}$ + TcdA | 0/0 | 0/2 | 0/14 | 6/25 |
| pDAB6033 + TcdA | $XptB1_{xb}$ + $XptC1_{xb}$ + TcdA | 25/68 | 4/14 | 4/0 | 31/48 |
| Vector + $XptA2_{wi}$ | | 0/0 | 0/79 | 0/9 | 31/0 |
| pDAB6031 + $XptA2_{wi}$ | $XptB1_{xb}$ + $XptA2_{wi}$ | 0/0 | 4/75 | 8/22 | 25/36 |
| pDAB6032 + $XptA2_{wi}$ | $XptC1_{xb}$ + $XptA2_{wi}$ | 0/0 | 0/71 | 0/22 | 6/14 |
| pDAB6033 + $XptA2_{wi}$ | $XptB1_{xb}$ + $XptC1_{xb}$ + $XptA2_{wi}$ | 0/0 | 83/100 | 29/98 | 81/100 |

EXAMPLE 5F

Identification, Purification, and Characterization of XptB1$_{xb}$ and XptC1$_{xb}$ Proteins of *Xenorhabdus bovienii* Strain ILM104

Bioassay driven fractionation of a pDAB6033-containing *E. coli* lysate resulted in the identification by MALDI-TOF of two co-purifying proteins; XptB1$_{xb}$ and XptC1$_{xb}$. Peaks containing these 2 proteins effectively potentiated the activity of TcdA and XptA2wi.

Active fractions were identified based on their ability to synergize or potentiate the activity of TcdA against southern corn rootworm or XptA2$_{wi}$ against corn earworm. All bioassays were conducted in the 128-well format described above in Example 5A.

Two peaks of activity were detected from protein fractions eluting between 22-24 mS/cm conductance (Peak 1 and Peak 2). An example of the potentiating activity of Peaks 1 and 2 is shown in Table 19. Subsequent purification and analysis were performed on both Peak 1 and Peak 2

Gels from both Peak 1 and Peak 2 contained two predominant bands, one migrating at ~170 kDa and the other migrating at ~80 kDa. The gel from Peak 1 contained three additional proteins that migrated at approximately 18, 33 and 50 kDa. Retrospective analysis revealed that the ~170 kDa and ~80 kDa bands were abundant at the initial stages of purification and became progressively enriched at each step Extracted peptides were analyzed using MALDI-TOF mass spectrometry to produce peptide mass fingerprints (PMF) on a Voyager DE-STR MALDI-TOF mass spectrometer (PerSeptive Biosystems, Framingham, Mass.). Analysis of the samples extracted from the ~170 kDa band confirmed the identity as XptB1$_{xb}$. Analysis of the samples extracted from the ~80 kDa band confirmed the identity as XptC1$_{xb}$. Although the predicted molecular weight of the XptC1$_{xb}$ protein as calculated from the gene sequence (SEQ ID NO:50) is 108 kDa, the extracted protein ran significantly faster than expected in the SDS/PAGE. The presence of peptide fragments representing the entire peptide sequence indicated that the protein as extracted is full length.

TABLE 19

Biological activity of purified Peak 1 and Peak 2 from pDAB6033.

| Sample | corn earworm | | southern corn rootworm | |
|---|---|---|---|---|
| | Dead | Stunted | Dead | Stunted |
| Peak 1 | | | | |
| 0 | 0 | 0 | 0 | 0 |
| 125 | 2 | 6 | 4 | 2 |
| Peak 2 | | | | |
| 0 | 1 | 0 | 0 | 0 |
| 125 | 0 | 8 | 5 | 3 |

Values in column labeled Sample represent the concentration of Peak 1 or Peak 2 XptB1$_{xb}$/XptC1$_{xb}$ proteins applied to the diet (in ng/cm$^2$).
For bioassays against corn earworm, 250 ng/cm$^2$ of XptA2$_{xi}$ was included in the bioassay.
For bioassays against southern corn rootworm, 100 ng/cm$^2$ of TcdA was included in the bioassay.
A total of eight larvae were used per sample.

EXAMPLE 6

Additional Mix and Match Example

In this example, it is demonstrated that potent insect suppression is obtained with a combination of three toxin complex (TC) proteins. Compelling insect activity is observed when a Class A protein is mixed with a Class B and Class C protein. The present invention is surprising in that many combinations of a Class A, Class B and Class C protein result in powerful insect repression. The Toxin Complex proteins may be from widely divergent sources and may only share a limited amount of amino acid identity with other functional members of its class.

EXAMPLE 6A

Introduction

The insecticidal and growth inhibition activities encoded by fifteen different toxin complex genes were tested separately and in combination with one another. Several examples from each of the described classes, A, B or C, were tested. The genes were derived from three genera (*Photorhabdus, Xenorhabdus* and *Paenibacillus*; both gram negative and gram positive bacteria) and four different species. The results within this example are consistent with the observation that Toxin Complex Class A proteins (e.g. TcdA and XptA2$_{wi}$) have significant activity alone. This was recently shown in transgenic plants by Liu et al. (Liu, D., Burton, S., Glancy, T., Li, Z-S., Hampton, R., Meade, T. and Merlo, D. J. "Insect resistance conferred by 283-kDa *Photorhabdus luminescens* protein TcdA in *Arabidopsis thaliana.*" Nature Biotechnology October 2003. Volume 21, number 10 pages 1222-1228). The results also agree with the observation that co-expression of three toxin complex genes (Class A, Class B and Class C) from within the same operon, strain, or genus result in greater insect activity than the Class A gene alone, or any single or double combination of the three classes (Hurst, M., Glare, T., Jackson, T. and Ronson, C. "Plasmid-Located Pathogenicity Determinants of *Serratia entomophila*, the Causal Agent of Amber Disease of Grass Grub, Show Similarity to the Insecticidal Toxins of *Photorhabdus luminescens*". Journal of Bacteriology, September 2000, Volume 182, Number 18, pages 5127-5138; Morgan, J. A., Sergeant, M., Ellis, D., Ousley, M. and Jarrett, P. "Sequence Analysis of Insecticidal Genes from *Xenorhabdus nematophilus* PMFI296". Applied and Environmental Microbiology, May 2001, p. 2062-2069, Vol. 67, No. 5; Waterfield, N., Dowling, A., Sharma, S., Daborn, P., Potter, U. and Ffrench-Constant, R. "Oral Toxicity of *Photorhabdus luminescens* W-14 Toxin Complexes in *Escherichia coli*," Applied and Environmental Microbiology, November 2001, Volume 67, Number 11, pages 5017-5024).

Surprisingly, the data below document the discovery that toxin complex Class A proteins may be mixed and matched with, for example, lysates prepared from *E. coli* cells programmed to express Class B and Class C genes from widely divergent sources to produce stunning insecticidal and insect growth inhibition activity. For example, a Class A protein from *Xenorhabdus* may be mixed with a lysate programmed to express a Class B gene from *Photorhabdus* and a Class C gene from *Paenibacillus* to provide an insect active combination. Likewise, a Class A protein from *Photorhabdus* may be mixed with a lysate programmed to express a Class B and Class C gene from *Xenorhabdus*, and vice versa. Many combinations are possible; many are shown below to result in potent insect activity. It was an unexpected revelation that toxin complex Class A, B, and C components from strains noted for either coleopteran (*Photorhabdus luminescens* strain W-14) or lepidopteran activity (*Xenorhabdus nematophilus* strain Xwi) may be functionally mixed and matched. Additionally surprising was the discovery of the degree of divergence possible for individual A, B or C proteins. For example, individual Class A's (e.g. TcdA and XptA2$_{wi}$) which function with a Class B/Class C combination may only share 41% amino acid identity with each other. Likewise any individual Class B may only share 41% identity with another functional Class B protein. Similarly, any given Class C may share only 35% identity with another Class C protein.

EXAMPLE 6B

Protein Sources and Constructions

The Class A proteins TcdA and XptA2$_{wi}$ were utilized in a purified form prepared from cultures of *Pseudomonas fluorescens* heterologously expressing the proteins. Preparations of the TcdA and XptA2$_{wi}$ from other heterologous sources (plant; bacterial) were functionally equivalent in the assays. The Class B and Class C proteins were tested as components of *E. coli* lysates. The use of lysates was validated by comparison to purified preparations of several Class B and Class C combinations. Reading frames encoding Class B and Class C proteins were engineered for expression in *E. coli* by cloning into pET plasmids (Novagen, Madison Wis.). Each coding region contained an appropriately spaced ribosome binding site (relative to the start codon) and termination signal. The DNA sequences at the 5' end of some of the genes were modified to reduce predicted secondary structure of the RNA and hence increase translation. These base changes were silent and did not result in amino acid changes in the protein. In cases where a Class B gene was tested with a Class C gene, an operon was constructed in the pET expression plasmid with the Class B coding sequence being transcribed first, followed by the Class C coding sequence. The two coding regions were separated by a linker sequence which contained a ribosome binding site appropriately spaced relative to the start codon of the Class C protein coding region. The DNA sequence between the coding regions in the dicistronic constructions is shown in the 5' to 3'orientation. Tables 20-27 contain lists of the proteins encoded by the various expression plasmids, the source of the coding regions and the plasmid reference number. Tables 22B, 23B, and 28-31 show linker sequences used in expression plasmids.

TABLE 20

| Class B Proteins | Source | Plasmid Number |
|---|---|---|
| TcdB1 | *Photorhabdus luminescens* str W-14 | pDAB8907 |
| TcdB2 | *Photorhabdus luminescens* str W-14 | pDAB3089 |
| TcaC | *Photorhabdus luminescens* str W-14 | pDAB8905 |
| XptC1$_{wi}$ | *Xenorhabdus nematophilus* str Xwi | pDAB8908 |
| XptBl$_{xb}$ | *Xenorhabdus bovienii* str ILM104 | pDAB6031 |
| PptB1$_{1529}$ | *Paenibacillus* spp str 1529 | pDAB8722 |

TABLE 21

| Class C Proteins | Source | Plasmid Number |
|---|---|---|
| TccC1 | *Photorhabdus luminescens* str W-14 | pDAB8913 |
| TccC2 | *Photorhabdus luminescens* str W-14 | pDAB3118 |
| TccC3 | *Photorhabdus luminescens* str W-14 | pDAB3090 |
| TccC5 | *Photorhabdus luminescens* str W-14 | pDAB3119 |
| XptBl$_{wi}$ | *Xenorhabdus nematophilus* str Xwi | pDAB8909 |
| XptC1$_{xb}$ | *Xenorhabdus bovienii* str ILM104 | pDAB6032 |
| PptC1$_{1529}$ | *Paenibacillus* spp str 1529 | pDAB8723 |

TABLE 22A

| Protein Combination | Source | Plasmid Number |
|---|---|---|
| TcdB1 + TccC1 | *Photorhabdus luminescens* str W-14 | pDAB8912 |
| TcdB1 + TccC2 | *Photorhabdus luminescens* str W-14 | pDAB8712 |
| TcdB1 + TccC3 | *Photorhabdus luminescens* str W-14 | pDAB3104 |
| TcdB1 + TccC5 | *Photorhabdus luminescens* str W-14 | pDAB8718 |
| TcdB1 + XptB1$_{wi}$ | *Photorhabdus luminescens* str W-14 *Xenorhabdus nematophilus* str Xwi | pDAB8713 |

TABLE 22B

| Plasmid Number | Protein Combination | Linker Sequence |
|---|---|---|
| pDAB8912 | TcdB1 + TccC1 | tgactcgacgcactactagtaaaaaggagataacccc |
| pDAB8712 | TcdB1 + TccC2 | tgactcgaatttaaattatatatatatatactcgacgaattttaatctactagtaaaaaggagataacc |
| pDAB3104 | TcdB1 + TccC3 | tgactcgacgcactactagtaaacaagaaggagatatacc |
| pDAB8718 | TcdB1 + TccC5 | tgactcgaatttaaattatatatatatatactcgacgaattttaatctactagatttatttaaattttttactagttttgtcgacaaaaaggagataacccc |
| pDAB8713 | TcdB1 + XptB1$_{wi}$ | tgactcgaatttaaattatatatatatatactcgacaagaaggagatatacc |

TABLE 23A

| Protein Combination | Source | Plasmid Number |
|---|---|---|
| TcdB2 + TccC1 | *Photorhabdus luminescens* str W-14 | pDAB3114 |
| TcdB2 + TccC2 | *Photorhabdus luminescens* str W-14 | pDAB3115 |
| TcdB2 + TccC3 | *Photorhabdus luminescens* str W-14 | pDAB3093 |
| TcdB2 + TccC5 | *Photorhabdus luminescens* str W-14 | pDAB3106 |
| TcdB2 + XptB1$_{wi}$ | *Photorhabdus luminescens* str W-14<br>*Xenorhabdus nematophilus* str Xwi | pDAB3097 |
| TcdB2 + XptC1$_{xb}$ | *Photorhabdus luminescens* str W-14<br>*Xenorhabdus bovienii* str ILM104 | pDAB8910 |
| TcdB2 + PptC1$_{1529}$ | *Photorhabdus luminescens* str W-14<br>*Paenibacillus* spp str 1529 | pDAB8725 |

TABLE 25-continued

| Protein Combination | Source | Plasmid Number |
|---|---|---|
| XptC1$_{wi}$ + TccC3 | *Xenorhabdus nematophilus* str Xwi<br>*Photorhabdus luminescens* str W-14 | pDAB3103 |
| XptC1$_{wi}$ + TccC5 | *Xenorhabdus nematophilus* str Xwi<br>*Photorhabdus luminescens* str W-14 | pDAB3105 |
| XptC1$_{wi}$ + XptB1$_{wi}$ | *Xenorhabdus nematophilus* str Xwi | pDAB8916 |

TABLE 23B

| Plasmid Number | Protein Combination | Linker Sequence |
|---|---|---|
| pDAB3114 | TcdB2 + TccC1 | ttaatctgactcgacgcactactagtaaaaaggagataacccc |
| pDAB3115 | TcdB2 + TccC2 | ttaatctgactcgacgaattttaatctactagtaaaaaggagataacc |
| pDAB3093 | TcdB2 + TccC3 | ttaatctgactcgacgcactactagtaaacaagaaggagatatacc |
| pDAB3106 | TcdB2 + TccC5 | ttaatctgactcgacaaaaaggagataacccc |
| pDAB3097 | TcdB2 + XptB1$_{wi}$ | ttaatctgactcgacaagaaggagatatacc |
| pDAB8910 | TcdB2 + XptC1$_{xb}$ | ttaatctgactcgacaaaaaggagataaccccatgccttaaagaagagag<br>agatatacc |
| pDAB8725 | TcdB2 + PptC1$_{1529}$ | ttaatctgactcgactttactagtaaggagatatacc |

TABLE 24

| Protein Combination | Source | Plasmid Number |
|---|---|---|
| TcaC + TccC1 | *Photorhabdus luminescens* str W-14 | pDAB8901 |
| TcaC + TccC2 | *Photorhabdus luminescens* str W-14 | pDAB8902 |
| TcaC + TccC3 | *Photorhabdus luminescens* str W-14 | pDAB8903 |
| TcaC + TccC5 | *Photorhabdus luminescens* str W-14 | pDAB8904 |
| TcaC + XptB1$_{wi}$ | *Photorhabdus luminescens* str W-14<br>*Xenorhabdus nematophilus* str Xwi | pDAB8900 |
| TcaC + XptCl$_{xb}$ | *Photorhabdus luminescens* str W-14<br>*Xenorhabdus bovienii* str ILM104 | pDAB8906 |

TABLE 25

| Protein Combination | Source | Plasmid Number |
|---|---|---|
| XptC1$_{wi}$ + TccC1 | *Xenorhabdus nematophilus* str Xwi<br>*Photorhabdus luminescens* str W-14 | pDAB8914 |
| XptC1$_{wi}$ + TccC2 | *Xenorhabdus nematophilus* str Xwi<br>*Photorhabdus luminescens* str W-14 | pDAB8915 |

TABLE 26

| Protein Combination | Source | Plasmid Number |
|---|---|---|
| XptB1$_{xb}$ + TccC1 | *Xenorhabdus bovienii* str ILM104<br>*Photorhabdus luminescens* str W-14 | pDAB8918 |
| XptB1$_{xb}$ + TccC3 | *Xenorhabdus bovienii* str ILM104<br>*Photorhabdus luminescens* str W-14 | pDAB6039 |
| XptB1$_{xb}$ + XptC1$_{xb}$ | *Xenorhabdus bovienii* str ILM104 | pDAB6033 |
| XptB1$_{xb}$ + PptC1$_{1529}$ | *Xenorhabdus bovienii* str ILM104<br>*Paenibacillus* spp str 1529 | pDAB8732 |

TABLE 27

| Protein Combination | Source | Plasmid Number |
|---|---|---|
| PptB1$_{1529}$ + PptC1$_{1529}$ | *Paenibacillus* spp str 1529 | pDAB8724 |
| PptB1$_{1529}$ + TccC3 | *Paenibacillus* spp str 1529<br>*Photorhabdus luminescens* str W-14 | pDAB8726 |
| PptB1$_{1529}$ + TccC1 | *Paenibacillus* spp str 1529<br>*Photorhabdus luminescens* str W-14 | pDAB8733 |

TABLE 28

| Plasmid Number | Protein Combination | Linker Sequence |
| --- | --- | --- |
| pDAB8901 | TcaC + TccC1 | taactcgatatggctagcatgactggtggacagcaaatgggtcgcggatcgatccgaattcgcccttgtcgacgcactactagtaaaaaggagataacccc |
| pDAB8902 | TcaC + TccC2 | taactcgatatggctagcatgactggtggacagcaaatgggtcgcggatcaaattatatatatatatatactcgacgaattttaatctactagtaaaaaggagataacc |
| pDAB8903 | TcaC + TccC3 | taactcgatatggctagcatgactggtggacagcaaatgggtcgcggatccgaattcgagctccgtcgacgcactactagtaaacaagaaggagatatacc |
| pDAB8904 | TcaC + TccC5 | taactcgatatggctagcatgactggtggacagcaaatgggtcgcggatcaaattttttttactagttttgtcgacaaaaaggagataacccc |
| pDAB8900 | TcaC + XptB1$_{wi}$ | taactcgatatggctagcatgactggtggacagcaaatgggtcgcggatctcgatcccgcgaaattaatacgactcactatagggggaattgtgagcggataacaattccccctctagacgtgcgtcgacaagaaggagatatacc |
| pDAB8906 | TcaC + XptC1$_{xb}$ | taactcgatatggctagcatgactggtggacagcaaatgggtcgcggatcccttaaagaagagagagatatacc |

TABLE 29

| Plasmid Number | Protein Combination | Linker Sequence |
| --- | --- | --- |
| pDAB8914 | XptC1$_{wi}$ + TccC1 | ttaatgctctcgaatttgactagaaataattttgtttaactttaagaaggagatataccatgggcagcagccatcatcatcatcatcacagcagcggcctggtgccgcgcggcagccatatggctagcatgactggtggacagcaaatgggtcgcggatccgaattcgcccttgtcgacgcactactagtaaaaaggagataacccc |
| pDAB8915 | XptC1$_{wi}$ + TccC2 | ttaatgctctcgaatttgactagagtcgacgaattttaatctactagtaaaaaggagataacc |
| pDAB3103 | XptC1$_{wi}$ + TccC3 | ttaatgctctcgaatttgactagtcaaattatatatatatatatactcgacgcactactagtaaacaagaaggagatatacc |
| pDAB3105 | XptC1$_{wi}$ + TccC5 | ttaatgctctcgaatttgactagattttatttaaattttttttactagttttgtcgacaaaaaggagataacccc |
| pDAB8916 | XptC1$_{wi}$ + XptB1$_{wi}$ | ttaatgctctcgaatttgactagacgtgcgtcgacaagaaggagatatacc |

TABLE 30

| Plasmid Number | Protein Combination | Linker Sequence |
| --- | --- | --- |
| pDAB8918 | XptB1$_{xb}$ + TccC1 | ttaatgcggccgcaggaaatttttttgtcgactttactagtaaaaaggagataacccc |
| pDAB6039 | XptB1$_{xb}$ + TccC3 | ttaatgcggccgcaggctagtaaacaagaaggagatatacc |
| pDAB6033 | XptB1$_{xb}$ + XptC1$_{xb}$ | ttaatgcggccgcaggccttaaagaagagagagatatacc |
| pDAB8732 | XptB1$_{xb}$ + PptC1$_{1529}$ | ttaatgcggccgcaggcctctgtaagactctcgactttactagtaaggagatatacc |

TABLE 31

| Plasmid Number | Protein Combination | Linker Sequence |
|---|---|---|
| pDAB8724 | $PptB1_{1529}$ + $PptC1_{1529}$ | taatgtcgactttactagtaaggagatatacc |
| pDAB8726 | $PptB1_{1529}$ + TccC3 | taatgtcgactttactagtaaacaagaaggagatatacc |
| pDAB8733 | $PptB1_{1529}$ + TccC1 | taatgtcgactttactagtaaaaaggagataacccc |

EXAMPLE 6C

Expression Conditions and Lysate Preparations

The pET expression plasmids listed in Tables 20-27 were transformed into the *E. coli* T7 expression strains BL21 (DE3) (Novagen, Madison Wis.) or BL21 Star™ (DE3) (Stratagene, La Jolla, Calif.) using standard methods. Expression cultures were initiated with 10-200 freshly transformed colonies into 250 mL LB 50 μg/ml antibiotic and 75 μM IPTG. The cultures were grown at 28° C. for 24 hours at 180-200 rpm. The cells were collected by centrifugation in 250 ml Nalgene bottles at 3,400×g for 10 minutes at 4° C. The pellets were suspended in 4-4.5 mL Butterfield's Phosphate solution (Hardy Diagnostics, Santa Maria, Calif.; 0.3 mM potassium phosphate pH 7.2). The suspended cells were transferred to 50 mL polypropylene screw cap centrifuge tubes with 1 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~20, chilling completely between bursts. The lysates were transferred to 2 mL Eppendorf tubes and centrifuged 5 minutes at 16,000×g. The supernatants were collected and the protein concentration measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The samples were then read on a spectrophotometer measuring the optical density at the wavelength of 595 nm in the Shimadzu UV160U spectrophotometer (Kyoto, JP). The amount of protein contained in each sample was then calculated against the BSA standard curve and adjusted to between 3-6 mg/mL with phosphate buffer. The lysates were typically assayed fresh, however no loss in activity was observed when stored at −70° C.

EXAMPLE 6D

Bioassay Conditions

Insect bioassays were conducted with neonate larvae on artificial diets in 128-well trays specifically designed for insect bioassays (C-D International, Pitman, N.J.). The species assayed were the southern corn rootworm, *Diabrotica undecimpunctata howardii* (Barber), the corn earworm, *Helicoverpa zea* (Boddie), the tobacco budworm, *Heliothis virescens* (F.), and the beet armyworm, *Spodoptera exigua* (Hübner).

Bioassays were incubated under controlled environmental conditions (28° C., ~40% r.h., 16:8 [L:D]) for 5 days at which point the total number of insects in the treatment, the number of dead insects, and the weight of surviving insects were recorded. Percent mortality and percent growth inhibition were calculated for each treatment. Growth inhibition was calculated as follows:

% Growth Inhibition=[1−(Average Weight of Insects in Treatment/Average Weight of Insects in the Vector-Only Control)]*100

In cases where the average weight of insects in treatment was greater that of insects in the vector only control, growth inhibition was scored as 0%.

The biological activity of the crude lysates alone or with added TcdA or $XptA2_{wi}$ toxin proteins was assayed as follows. Crude *E. coli* lysates (40 μL) of either control cultures or those expressing potentiator proteins were applied to the surface of artificial diet in 8 wells of a bioassay tray. The average surface area of treated diet in each well was ~1.5 $cm^2$. The lysates were adjusted to between 2-5 mg/mL total protein and were applied with and without TcdA or $XptA2_{wi}$. The TcdA or $XptA2_{wi}$ added were highly purified fractions from bacterial cultures heterologously expressing the proteins. The final concentrations of $XptA2_{wi}$ and TcdA on the diet were 250 ng/$cm^2$ and 50 ng/$cm^2$, respectively.

The results of bioassays are summarized in Tables 32-39. Little to no effect on the survival or growth of the insect species tested was observed when larvae were fed lysates from *E. coli* clones engineered to express a Class B or Class C protein alone (Tables 32 and 33). Similarly, little to no effect was observed when larvae were fed combinations of Class B and Class C proteins in the absence of a purified toxin (Tables 34-39, "none" column). Significant effects on survival and/or growth were commonly observed when larvae were fed lysates from *E. coli* clones engineered to express a combination of a Class B and Class C protein with a purified toxin (Tables 2C-2H, "TcdA" and "$XptA2_{wi}$" columns). Class B and Class C combinations tested with purified TcdA most typically exerted an effect on southern corn rootworm while combinations tested with purified $XptA2_{wi}$ typically exerted an effect on one of the 3 lepidopteran species with corn earworm being the most consistently sensitive species. It is notable that many Class B and Class C combinations produced an observable effect of $XptA2_{wi}$ on southern corn rootworm. The converse, that these combinations would produce an observable effect of TcdA on lepidopteran species, did not hold true.

Tables 32-39 show biological activity of *E. coli* lysates fed to insect larvae alone and combined with *Photorhabdus* or *Xenorhabdus* toxin proteins. The gene contained in each *E. coli* clone corresponds to those contained in Tables 20-27. Biological activity is classified using the following scale: 0=average mortality<50% AND average weight>50% of the average weight of empty vector/no toxin treatment, +=average weight≦50% of the average weight of empty vector/no toxin treatment, ++=average mortality≧50% OR average weight≦20% of the average weight of empty vector/no toxin treatment, and +++=average mortality≧95% OR average weight≦5% of the average weight of empty vector/no toxin treatment.

TABLE 32

Biological activity of *E. coli* clones engineered to express Class B protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| Class B Genes | | | | | | | | | | | | |
| tcdB1 | 0 | + | + | 0 | 0 | 0 | 0 | 0 | 0 | 0 | 0 | 0 |
| tcdB2 | 0 | + | 0 | 0 | 0 | 0 | 0 | 0 | ++ | 0 | 0 | 0 |
| tcaC | 0 | 0 | 0 | 0 | 0 | 0 | 0 | 0 | 0 | 0 | 0 | 0 |
| xptC1$_{wi}$ | 0 | 0 | 0 | 0 | 0 | 0 | 0 | 0 | 0 | 0 | 0 | 0 |
| xptB1$_{xb}$ | 0 | 0 | 0 | 0 | 0 | 0 | 0 | 0 | + | 0 | 0 | 0 |
| pptB1$_{1529}$ | 0 | + | 0 | 0 | 0 | 0 | 0 | 0 | 0 | 0 | 0 | 0 |

TABLE 33

Biological activity of *E. coli* clones engineered to express Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| Class C Genes | | | | | | | | | | | | |
| tccC1 | 0 | 0 | 0 | 0 | 0 | 0 | 0 | 0 | 0 | 0 | 0 | 0 |
| tccC2 | 0 | 0 | 0 | 0 | 0 | 0 | 0 | 0 | 0 | 0 | 0 | 0 |
| tccC3 | 0 | 0 | 0 | 0 | 0 | 0 | 0 | 0 | + | 0 | 0 | 0 |
| tccC5 | 0 | 0 | 0 | 0 | 0 | 0 | 0 | 0 | 0 | 0 | 0 | 0 |
| xptB1$_{wi}$ | 0 | 0 | + | 0 | 0 | 0 | 0 | 0 | + | 0 | 0 | 0 |
| xptC1$_{xb}$ | 0 | 0 | 0 | 0 | 0 | 0 | 0 | 0 | + | 0 | 0 | 0 |
| pptC1$_{1529}$ | 0 | + | 0 | 0 | 0 | 0 | 0 | 0 | 0 | 0 | 0 | 0 |

TABLE 34

Biological activity of *E. coli* clones engineered to express the Class B protein gene tcdB1 in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| TcdB1 Combinations | | | | | | | | | | | | |
| tcdB1 + tccC1 | 0 | + | + | 0 | 0 | ++ | 0 | + | +++ | 0 | 0 | 0 |
| tcdB1 + tccC2 | 0 | 0 | 0 | 0 | 0 | 0 | 0 | 0 | + | 0 | 0 | 0 |
| tcdB1 + tccC3 | 0 | ++ | + | 0 | 0 | ++ | 0 | 0 | +++ | 0 | 0 | +++ |
| tcdB1 + tccC5 | 0 | + | + | 0 | 0 | ++ | 0 | 0 | +++ | 0 | 0 | ++ |
| tcdB1 + xptB1$_{wi}$ | 0 | 0 | 0 | 0 | 0 | ++ | 0 | 0 | ++ | 0 | 0 | ++ |

TABLE 35

Biological activity of *E. coli* clones engineered to express the Class B protein gene tcdB2 in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| tcdB2 Combinations | | | | | | | | | | | | |
| tcdB2 + tccC3 | 0 | +++ | + | 0 | 0 | +++ | 0 | 0 | +++ | 0 | 0 | +++ |
| tcdB2 + tccC5 | 0 | +++ | + | 0 | 0 | +++ | 0 | 0 | +++ | 0 | 0 | +++ |
| tcdB2 + xptB1$_{wi}$ | 0 | + | + | 0 | 0 | ++ | 0 | + | +++ | 0 | 0 | + |
| tcdB2 + xptC1$_{xb}$ | nt | nt | nt | 0 | 0 | + | 0 | 0 | +++ | 0 | 0 | + |
| tcdB2 + pptC1$_{1529}$ | 0 | +++ | + | 0 | 0 | + | 0 | 0 | ++ | 0 | 0 | + |

TABLE 36

Biological activity of *E. coli* clones engineered to express the Class B protein gene tcaC in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| tcaC Combinations | | | | | | | | | | | | |
| tcaC + tccC1 | 0 | ++ | + | 0 | 0 | ++ | 0 | 0 | +++ | 0 | 0 | +++ |
| tcaC + tccC2 | 0 | 0 | 0 | 0 | 0 | 0 | 0 | 0 | + | 0 | 0 | 0 |
| tcaC + tccC3 | 0 | + | + | 0 | 0 | ++ | 0 | 0 | +++ | 0 | 0 | ++ |
| tcaC + tccC5 | 0 | +++ | + | 0 | 0 | ++ | 0 | 0 | ++ | 0 | 0 | +++ |
| tcaC + xptB1$_{wi}$ | 0 | ++ | 0 | + | + | ++ | 0 | 0 | +++ | 0 | 0 | +++ |

TABLE 37

Biological activity of *E. coli* clones engineered to express the Class B protein gene xptC1$_{wi}$ in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| xptC1$_{wi}$ Combinations | | | | | | | | | | | | |
| xptC1$_{wi}$ + tccC1 | 0 | 0 | 0 | 0 | 0 | + | 0 | 0 | +++ | 0 | 0 | 0 |
| xptC1$_{wi}$ + tccC2 | 0 | 0 | 0 | 0 | 0 | 0 | 0 | 0 | + | 0 | 0 | 0 |
| xptC1$_{wi}$ + tccC3 | 0 | ++ | + | 0 | 0 | ++ | 0 | 0 | +++ | 0 | 0 | ++ |
| xptC1$_{wi}$ + tccC5 | 0 | ++ | + | 0 | 0 | + | 0 | 0 | +++ | 0 | 0 | ++ |
| xptC1$_{wi}$ + xptB1$_{wi}$ | 0 | 0 | 0 | 0 | 0 | + | 0 | 0 | ++ | 0 | 0 | 0 |

TABLE 38

Biological activity of E. coli clones engineered to express the Class B protein gene xptB1$_{xb}$, in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| xptB1$_{xb}$ Combinations | | | | | | | | | | | | |
| xptB1$_{xb}$ + tccC3 | nt | nt | nt | 0 | 0 | + | 0 | 0 | +++ | 0 | 0 | + |
| xptB1$_{xb}$ + xptC1$_{xb}$ | 0 | + | 0 | 0 | 0 | +++ | 0 | 0 | +++ | 0 | 0 | +++ |

TABLE 39

Biological activity of E. coli clones engineered to express the Class B protein gene pptB1$_{1529}$ in combination with various Class C protein genes. Lysates were tested alone and with purified TcdA or XptA2$_{wi}$.

| | Insect Species | | | | | | | | | | | |
|---|---|---|---|---|---|---|---|---|---|---|---|---|
| | southern corn rootworm | | | tobacco budworm | | | corn earworm | | | beet armyworm | | |
| Toxin Protein | none | TcdA | XptA2$_{wi}$ | none | TcdA | XptA2$_{wi}$ | none | TcdA | XptA2$_{wi}$ | none | TcdA | XptA2$_{wi}$ |
| pptB1$_{1529}$ Combinations | | | | | | | | | | | | |
| pptB1$_{1529}$ + pptC1$_{1529}$ | 0 | +++ | 0 | 0 | 0 | ++ | 0 | 0 | +++ | 0 | 0 | + |
| pptB1$_{1529}$ + tccC3 | 0 | +++ | + | 0 | 0 | ++ | 0 | 0 | +++ | 0 | 0 | +++ |

EXAMPLE 7

Additional Mixing and Matching of TC Proteins

To demonstrate the presently discovered versatility of TC proteins, additional E. coli expression experiments were done employing double plasmid expression systems. A T7 promoter based system utilized a pACYC derivative (called pCot-3 or 4, chloramphenicol resistant) to express either the TcdA or XptA2 proteins while a compatible T7 promoter pET280 plasmid (kanamycin resistant) expressed various combinations of the TcdB1 (SEQ ID NO:22), TcdB2 (SEQ ID NO:45), XptC1 (SEQ ID NO:18), TccC1 (SEQ ID NO:25), TccC3 (SEQ ID NO:47) and XptB1 (SEQ ID NO:16) proteins, all within the same cell. Likewise, in another series of experiments, an E. coli promoter system was used that utilized a different pACYC derivative (called pCTS, spectinomycin/streptomycin resistant) to express either TcdA (SEQ ID NO:21) or XptA2 (SEQ ID NO:34) proteins while a compatible pBT280 plasmid (chloramphenicol resistant) expressed various combinations of TcdB1, TcdB2, XptC1, TccC1, TccC3 and XptB1. Both systems produced proteins of similar activities when bioassayed.

The T7 promoter based experiments were done by first preparing stocks of competent BL21(DE3) cells containing either pCot-3, pCot-TcdA or pCot-XptA2. These cells were then transformed with either control pET280 plasmid or any of the combinations of TC genes noted above in the pET280 vector. Cells containing both plasmids were selected on media containing chloramphenicol and kanamycin. Similarly, for the E. coli promoted system, competent BL21 cells containing either pCTS, pCTS-TcdA or pCTS-XptA2 were prepared. The competent cells were then transformed with either pBT280 control plasmid or any of TC combinations noted above in the pBT280 vector. When more than one TC gene was present on a particular plasmid, they were arranged as a two gene operon with a single promoter at the 5' end. The first coding region was followed by translational termination signals; a separate ribosome binding site (Shine-Dalgarno sequence) and translational start signal were used to initiation translation of the second coding region. The methods described in Examples 2 and 3 were used to grow expression cultures, prepare lysates and assess insect activity. Some experiments utilized a modified assay method where enriched preparations of proteins TcdA and XptA2 were added to lysates containing either singly or in combination TcdB1, TcdB2, XptC1, TccC1, TccC3 and XptB1 (Tables 40 and 41).

TABLE 40

Bioassay Results of Heterologously Expressed Toxin Complex Genes on TBW, SCR, ECB and BAW

| Sample Tested | TBW Bioassay | SCR Bioassay | ECB Bioassay | BAW Bioassay |
|---|---|---|---|---|
| XptA2 | ++ | 0 | ++ | ++ |
| TcdB1 | 0 | 0 | + | +++ |
| XptC1 | 0 | 0 | 0 | +++ |
| TccC1 | + | 0 | + | +++ |
| XptB1 | 0 | 0 | 0 | +++ |
| TcdB1 + TccC1 | 0 | 0 | | |
| TcdB1 + XptB1 | 0 | 0 | | |
| XptC1 + TccC1 | 0 | 0 | | |
| XptC1 + XptB1 | + | 0 | | |

TABLE 40-continued

Bioassay Results of Heterologously Expressed
Toxin Complex Genes on TBW, SCR, ECB and BAW

| Sample Tested | TBW Bio-assay | SCR Bio-assay | ECB Bio-assay | BAW Bio-assay |
|---|---|---|---|---|
| XptA2 + TcdB1 | +++ | + | | ++ |
| XptA2 + XptC1 | ++ | 0 | 0 | ++ |
| XptA2 + TccC1 | +++ | + | + | +++ |
| XptA2 + XptB1 | +++ | + | 0 | ++++ |
| XptA2 + TcdB1 + TccC1 | +++++ | +++ | | +++++ |
| XptA2 + TcdB1 + XptB1 | +++++ | +++ | +++++ | ++++ |
| XptA2 + XptC1 + TccC1 | ++++ | 0 | ++++ | ++++ |
| XptA2 + XptC1 + XptB1 | ++++ | + | +++++ | ++++ |
| TcdA | 0 | +++ | ++ | 0 |
| TcdA + TcdB1 | 0 | +++ | ++ | 0 |
| TcdA + XptC1 | 0 | +++ | ++++ | 0 |
| TcdA + TccC1 | 0 | ++ | 0 | 0 |
| TcdA + XptB1 | 0 | +++ | ++ | 0 |
| TcdA + TcdB1 + TccC1 | 0 | ++++ | ++++ | 0 |
| TcdA + TcdB1 + XptB1 | 0 | ++++ | ++++ | 0 |
| TcdA + XptC1 + TccC1 | 0 | ++++ | ++ | 0 |
| TcdA + XptC1 + XptB1 | 0 | +++ | ++++ | 0 |

Whole *E. coli* cells were lysed and the soluble protein generally normalized within an experiment to between 5-10 mg/ml. The lysates were bioassayed as described by top loading onto insect diets. Grading Scale represents % growth inhibition relative to controls
(0 = 0-25%;
+ = 26-50%;
++ = 51-65%;
+++ = 66-80% = ++++, 81-95%;
+++++ = 96-100%).

TABLE 41

Bioassay of Heterologously Expressed Toxin Complex
Genes on SCR, TBW, CEW, and FAW with the addition
of purified TcdA Toxin Protein*

| Plasmid Tested | SCR Bioassay | TBW Bioassay | CEW Bioassay | FAW Bioassay |
|---|---|---|---|---|
| pET-280 | 0 | 0 | 0 | 0 |
| pET-280-TcdB1-XptB1 | ++++ | + | ++ | 0 |
| pET-280-TcdB2-TccC3 | +++++ | + | 0 | ++ |

Whole *E. coli* cells were lysed and the soluble protein was adjusted to equal sample concentrations of between 8-15 mg/ml.
*TcdA protein was added to the samples for a final concentration of 50 ng/cm$^2$ when applied on top of the insect diet preparations.
Grading Scale represents % growth inhibition of surviving insects fed the treatment plus TcdA Toxin Protein relative to surviving insects fed the treatment in the absence of TcdA Toxin Protein
(0 = 0-10%;
+ = 11-20%;
++ = 21-40%;
+++ = 41-60% = ++++, 61-80%;
+++++ >80%).

TABLE 42

Bioassay of Heterologously Expressed Toxin Complex
Genes on SCR, TBW, CEW, and FAW with the addition
of purified XptA2 Toxin Protein*

| Plasmid Tested | SCR Bioassay | TBW Bioassay | CEW Bioassay | FAW Bioassay |
|---|---|---|---|---|
| pET-280 | 0 | + | +++ | 0 |
| pET-280-TcdB1-XptB1 | ++++ | +++++ | +++++ | +++ |
| pET-280-TcdB2-TccC3 | ++++ | +++++ | +++++ | ++++ |

Whole *E. coli* cells were lysed and the soluble protein was adjusted to equal sample concentrations of between 8-15 mg/ml.
*XptA2 protein was added to the samples for a final concentration of 250 ng/cm$^2$ when applied on top of the insect diet preparations.
Grading Scale represents % growth inhibition of surviving insects fed the treatment plus XptA2 Toxin Protein relative to surviving insects fed the treatment in the absence of XptA2 Toxin Protein
(0 = 0-10%;
+ = 11-20%;
++ = 21-40%;
+++ = 41-60% = ++++, 61-80%;
+++++ >80%).

EXAMPLE 8

Summary of Mix & Match Assays and Sequence Relatedness

The following Tables summarize and compare proteins used in the assays described above. Tables 43-45 compare A, B, and C class proteins. Tables 46-48 compare A, B, and C class genes (bacterial). Any of the numbers in these tables can be used as upper and/or lower limits for defining proteins and polynucleotides for use according to the subject invention. Table 49 compares the sizes of various TC proteins. Again, any of the numbers in this table can be used to define the upper and/or lower size limits of proteins (and polynucleotides) for use according to the subject invention.

These tables help to show that even highly divergent proteins (in the ~40-75% identity range) can surprisingly be used and substituted for each other according to the subject invention. TcdA2$_{W-14}$ is reproduced here as SEQ ID NO:62, TcdA4$_{W-14}$ as SEQ ID NO:63, and TccC$_{W-14}$ as SEQ ID NO:64.

TABLE 43

| | TcdA | | TcdA2 | | TcdA4 | | TcbA | | XptA1$_{xwi}$ | | XptA2$_{xwi}$ | | SepA | |
|---|---|---|---|---|---|---|---|---|---|---|---|---|---|---|
| | % Similarity | % Identity | % Similarity | % Identity | % Similarity | % Identity | % Similarity | % Identity | % Similarity | % Identity | % Similarity | % Identity | % Similarity | % Identity |
| *Photorhabdus luminescens* A Class | | | | | | | | | | | | | | |
| TcdA | 100.0 | 100.0 | 61.3 | 55.0 | 74.3 | 68.0 | 61.4 | 50.1 | 57.3 | 46.3 | 53.8 | 40.6 | 52.6 | 40.7 |
| TcdA2 | | | 100.0 | 100.0 | 63.7 | 55.9 | 52.7 | 42.4 | 52.3 | 41.3 | 48.3 | 36.8 | 45.5 | 34.7 |
| TcdA4 | | | | | 100.0 | 100.0 | 59.0 | 49.4 | 54.8 | 44.4 | 51.7 | 38.7 | 50.6 | 38.7 |
| TcbA | | | | | | | 100.0 | 100.0 | 54.7 | 43.7 | 54.0 | 40.8 | 52.8 | 40.2 |

TABLE 43-continued

| | TcdA | | TcdA2 | | TcdA4 | | TcbA | | XptA1$_{xwi}$ | | XptA2$_{xwi}$ | | SepA | |
|---|---|---|---|---|---|---|---|---|---|---|---|---|---|---|
| | % Similarity | % Identity | % Similarity | % Identity | % Similarity | % Identity | % Similarity | % Identity | % Similarity | % Identity | % Similarity | % Identity | % Similarity | % Identity |
| *Xenorhabdus nematophilus* xwi A Class | | | | | | | | | | | | | | |
| XptA1$_{xwi}$ | | | | | | | | | 100.0 | 100.0 | 57.6 | 44.2 | 57.7 | 46.6 |
| XptA2$_{xwi}$ | | | | | | | | | | | 100.0 | 100.0 | 50.7 | 38.2 |
| *Serratia entomophila* A Class | | | | | | | | | | | | | | |
| SepA | | | | | | | | | | | | | 100.0 | 100.0 |
| Tested in Mix & Match Assays? | yes | | no | | no | | yes | | no | | yes | | no | |
| Does it work? | yes | | NA | | NA | | yes | | NA | | yes | | NA | |

NOTE:
tcdA3 is a pseudo gene (does not encode a full-length protein) so is left out of this analysis

TABLE 44

| | TcdB1 | | TcdB2 | | TcaC | | XptC1$_{xwi}$ | | XptB1$_{xb}$ | | PptB1 (Orf5) | | SepB | |
|---|---|---|---|---|---|---|---|---|---|---|---|---|---|---|
| | % Similarity | % Identity | % Similarity | % Identity | % Similarity | % Identity | % Similarity | % Identity | % Similarity | % Identity | % Similarity | % Identity | % Similarity | % Identity |
| *Photorhabdus luminescens* B Class | | | | | | | | | | | | | | |
| TcdB1 | 100.0 | 100.0 | 79.9 | 75.6 | 69.5 | 58.2 | 61.3 | 50.2 | 65.6 | 54.6 | 55.3 | 42.3 | 63.7 | 52.6 |
| TcdB2 | | | 100.0 | 100.0 | 68.1 | 57.2 | 60.7 | 49.8 | 65.6 | 53.3 | 54.2 | 42.0 | 61.7 | 51.4 |
| TcaC | | | | | 100.0 | 100.0 | 63.9 | 51.6 | 70.6 | 59.8 | 56.9 | 42.6 | 61.4 | 50.1 |
| *Xenorhabdus nematophilus* xwi B Class | | | | | | | | | | | | | | |
| XptC1$_{xwi}$ | | | | | | | 100.0 | 100.0 | 65.2 | 53.2 | 53.9 | 40.7 | 58.1 | 47.8 |
| *Xenorhabdus bovienii* B Class | | | | | | | | | | | | | | |
| XptB1$_{xb}$ | | | | | | | | | 100.0 | 100.0 | 54.2 | 40.6 | 57.4 | 46.0 |
| *Paenibacillus* spp str 1529 B Class | | | | | | | | | | | | | | |
| PptB1 (Orf5) | | | | | | | | | | | 100.0 | 100.0 | 51.5 | 38.7 |
| *Serratia entomophila* B Class | | | | | | | | | | | | | | |
| SepB | | | | | | | | | | | | | 100.0 | 100.0 |
| Tested in Mix & Match assays? | yes | | yes | | yes | | yes | | yes | | yes | | no | |
| Does it work? | yes | | yes | | yes | | yes | | yes | | yes | | NA | |

TABLE 45

| | TccC1 | | TccC2 | | TccC3 | | TccC4 | | TccC5 | |
|---|---|---|---|---|---|---|---|---|---|---|
| | % Sim. | % Id | % Sim. | % Id | % Sim. | % Id | % Sim. | % Id | % Sim. | % Id |
| *Photorhabdus luminescens* C Class | | | | | | | | | | |
| TccC1 | 100.0 | 100.0 | 57.8 | 48.1 | 62.0 | 52.8 | 62.5 | 52.9 | 59.7 | 51.3 |
| TccC2 | | | 100.0 | 100.0 | 60.3 | 52.5 | 62.2 | 53.7 | 67.9 | 61.4 |
| TccC3 | | | | | 100.0 | 100.0 | 65.4 | 59.5 | 66.0 | 58.4 |
| TccC4 | | | | | | | 100.0 | 100.0 | 64.8 | 57.2 |
| TccC5 | | | | | | | | | 100.0 | 100.0 |
| *Xenorhabdus nematophilus* xwi C Class | | | | | | | | | | |
| XptB1$_{xwi}$ | | | | | | | | | | |
| *Xenorhabdus bovienii* C Class | | | | | | | | | | |
| XptC1$_{xb}$ | | | | | | | | | | |
| *Paenibacillus* spp str 1529 C Class | | | | | | | | | | |
| PptC1 (Orf6 long) | | | | | | | | | | |
| PptC1 (Orf6 short) | | | | | | | | | | |

TABLE 45-continued

*Serratia entomophila* C Class

SepC
Tested in Mix & Match assays? yes  yes  yes  no  yes
Does it work? yes  no  yes  NA  yes

| | XptB1$_{xwi}$ | | XptC1$_{xb}$ | | PptC1 (Orf6 long) | | PptC1 (Orf6 short) | | SepC | |
|---|---|---|---|---|---|---|---|---|---|---|
| | % Sim. | % Id | % Sim. | % Id | % Sim. | % Id | % Sim. | % Id | % Sim. | % Id |
| *Photorhabdus luminescens* C Class | | | | | | | | | | |
| TccC1 | 59.0 | 45.5 | 55.8 | 46.5 | 45.0 | 35.0 | 45.9 | 35.7 | 56.0 | 44.1 |
| TccC2 | 54.0 | 44.1 | 56.4 | 47.2 | 46.5 | 35.3 | 45.7 | 36.1 | 55.8 | 46.1 |
| TccC3 | 54.8 | 46.0 | 56.5 | 48.1 | 45.1 | 35.4 | 46.1 | 36.1 | 56.4 | 46.6 |
| TccC4 | 53.6 | 44.8 | 58.8 | 49.1 | 46.3 | 36.9 | 47.3 | 37.7 | 56.6 | 45.3 |
| TccC5 | 55.1 | 45.6 | 57.6 | 48.7 | 45.3 | 35.2 | 46.3 | 36.0 | 54.8 | 44.9 |
| *Xenorhabdus nematophilus* xwi C Class | | | | | | | | | | |
| XptB1$_{xwi}$ | 100.0 | 100.0 | 52.6 | 41.4 | 43.3 | 32.7 | 44.3 | 33.5 | 55.2 | 46.3 |
| *Xenorhabdus bovienii* C Class | | | | | | | | | | |
| XptC1$_{xb}$ | | | 100.0 | 100.0 | 46.4 | 35.4 | 47.4 | 36.2 | 53.0 | 43.5 |
| *Paenibacillus* spp str 1529 C Class | | | | | | | | | | |
| PptC1 (Orf6 long) | | | | | 100.0 | 100.0 | 97.6 | 97.6 | 45.1 | 34.9 |
| PptC1 (Orf6 short) | | | | | | | 100.0 | 100.0 | 46.2 | 35.7 |
| *Serratia entomophila* C Class | | | | | | | | | | |
| SepC | | | | | | | | | 100.0 | 100.0 |
| Tested in Mix & Match assays? | yes | | yes | | yes | | current testing | | no | |
| Does it work? | yes | | yes | | yes | | ? | | NA | |

TABLE 46

| | tcdA % Identity | tcdA2 % Identity | tcdA4 % Identity | tcbA % Identity | xptA1$_{xwi}$ % Identity | xptA2$_{xwi}$ % Identity | sepA % Identity |
|---|---|---|---|---|---|---|---|
| *Photorhabdus luminescens* A Class | | | | | | | |
| tcdA | 100.0 | 65.3 | 70.6 | 58.2 | 56.8 | 54.4 | 53.1 |
| tcdA2 | | 100.0 | 64.5 | 56.2 | 55.9 | 53.3 | 51.9 |
| tcdA4 | | | 100.0 | 57.8 | 55.6 | 52.5 | 51.7 |
| tcbA | | | | 100.0 | 56.3 | 54.0 | 52.7 |
| *Xenorhabdus nematophilus* xwi A Class | | | | | | | |
| xptA1$_{xwi}$ | | | | | 100.0 | 55.8 | 55.4 |
| xptA2$_{xwi}$ | | | | | | 100.0 | 53.8 |
| *Serratia entomophila* A Class | | | | | | | |
| sepA | | | | | | | 100.0 |
| Tested in Mix & Match Assays? | yes | no | no | yes | no | yes | no |
| Does it work? | yes | NA | NA | yes | NA | yes | NA |

NOTE:
tcdA3 is a pseudo gene (does not encode a full-length protein) so is left out of this analysis

TABLE 47

| | tcdB1 % Identity | tcdB2 % Identity | tcaC % Identity | xptC1$_{xwi}$ % Identity | xptB1$_{xb}$ % Identity | pptB1 (Orf5) % Identity | sepB % Identity |
|---|---|---|---|---|---|---|---|
| *Photorhabdus luminescens* B Class | | | | | | | |
| tcdB1 | 100.0 | 74.1 | 62.3 | 44.7 | 59.7 | 52.3 | 57.6 |
| tcdB2 | | 100.0 | 61.5 | 44.7 | 59.6 | 52.6 | 57.1 |
| TcaC | | | 100.0 | 46.0 | 62.0 | 52.5 | 55.3 |

TABLE 47-continued

|  | tcdB1 % Identity | tcdB2 % Identity | tcaC % Identity | xptC1$_{xwi}$ % Identity | xptB1$_{xb}$ % Identity | pptB1 (Orf5) % Identity | sepB % Identity |
|---|---|---|---|---|---|---|---|
| *Xenorhabdus nematophilus* xwi B Class |  |  |  |  |  |  |  |
| xptC1$_{xwi}$ |  |  |  | 100.0 | 44.9 | 44.9 | 44.5 |
| *Xenorhabdus bovienii* B Class |  |  |  |  |  |  |  |
| xptB1$_{xwi}$ |  |  |  |  | 100.0 | 52.3 | 54.7 |
| *Paenibacillus* spp str 1529 B Class |  |  |  |  |  |  |  |
| pptB1 (Orf5) |  |  |  |  |  | 100.0 | 52.5 |
| *Serratia entomophila* B Class |  |  |  |  |  |  |  |
| sepB |  |  |  |  |  |  | 100.0 |
| Tested in Mix & Match assays? | yes | yes | yes | yes | yes | yes | no |
| Does it work? | yes | yes | yes | yes | yes | yes | NA |

TABLE 48

|  | TccC1 % Identity | TccC2 % Identity | TccC3 % Identity | TccC4 % Identity | TccC5 % Identity | XptB1$_{xwi}$ % Identity | XptC1$_{xb}$ % Identity | PptC1 (Orf6 long) % Identity | PptC1 (Orf6 short) % Identity | SepC % Identity |
|---|---|---|---|---|---|---|---|---|---|---|
| *Photorhabdus luminescens* C Class |  |  |  |  |  |  |  |  |  |  |
| TccC1 | 100.0 | 55.7 | 58.8 | 60.0 | 59.4 | 45.0 | 55.7 | 47.5 | 48.4 | 54.3 |
| TccC2 |  | 100.0 | 62.6 | 62.2 | 69.9 | 43.5 | 58.1 | 51.6 | 52.4 | 55.4 |
| TccC3 |  |  | 100.0 | 65.7 | 66.4 | 44.9 | 58.4 | 51.5 | 52.4 | 56.8 |
| TccC4 |  |  |  | 100.0 | 65.8 | 43.0 | 59.4 | 52.2 | 53.2 | 54.9 |
| TccC5 |  |  |  |  | 100.0 | 43.0 | 58.5 | 50.8 | 51.7 | 56.2 |
| *Xenorhabdus nematophilus* xwi C Class |  |  |  |  |  |  |  |  |  |  |
| XptB1$_{xwi}$ |  |  |  |  |  | 100.0 | 44.6 | 43.6 | 43.2 | 44.0 |
| *Xenorhabdus bovienii* C Class |  |  |  |  |  |  |  |  |  |  |
| XptC1$_{xb}$ |  |  |  |  |  |  | 100.0 | 49.7 | 50.6 | 54.5 |
| *Paenibacillus* spp str 1529 C Class |  |  |  |  |  |  |  |  |  |  |
| PptC1 (Orf6 long) |  |  |  |  |  |  |  | 100.0 | 97.6 | 50.6 |
| PptC1 (Orf6 short) |  |  |  |  |  |  |  |  | 100.0 | 51.8 |
| *Serratia entomophila* C Class |  |  |  |  |  |  |  |  |  |  |
| SepC |  |  |  |  |  |  |  |  |  | 100.0 |
| Tested in Mix & Match assays? | yes | yes | yes | no | yes | yes | yes | yes | in progress | no |
| Does it work? | yes | no | yes | NA | yes | yes | yes | yes | ? | NA |

TABLE 49

|  | DNA Bases | Protein Amino Acids | Protein Daltons | Functional? |
|---|---|---|---|---|
| *Photorhabdus luminescens* A Class |  |  |  |  |
| tcdA | 7548 | 2516 | 282,932 | yes |
| tcdA2 | 7497 | 2499 | 283,725 | ? |
| tcdA4 | 7143 | 2381 | 270,397 | ? |
| tcbA | 7512 | 2504 | 280,632 | yes |
| *Xenorhabdus nematophilus* xwi A Class |  |  |  |  |
| xptA1$_{xwi}$ | 7569 | 2523 | 286,799 | ? |
| xptA2$_{xwi}$ | 7614 | 2538 | 284,108 | yes |
| *Serratia entomophlla* A Class |  |  |  |  |
| SepA | 7128 | 2376 | 262,631 | ? |
| Range | 7128-7614 | 2376-2538 | 262,631-286,799 |  |
| *Photorhabdus luminescens* B Class |  |  |  |  |
| tcdB1 | 4428 | 1476 | 165,127 | yes |
| tcdB2 | 4422 | 1474 | 166,326 | yes |
| TcaC | 4455 | 1485 | 166,153 | yes |

TABLE 49-continued

| | DNA Bases | Protein Amino Acids | Protein Daltons | Functional? |
|---|---|---|---|---|
| *Xenorhabdus nematophilus* xwi B Class | | | | |
| $xptC1_{xwi}$ | 4479 | 1493 | 168,076 | yes |
| *Xenorhabdus bovienii* B Class | | | | |
| $xptB1_{xb}$ | 4518 | 1506 | 168,635 | yes |
| *Paenibacillus* spp str 1529 B Class | | | | |
| pptB1 (Orf5) | 4332 | 1444 | 161,708 | yes |
| *Serratia entomophila* B Class | | | | |
| SepB | 4284 | 1428 | 156,539 | ? |
| Range | 4284-4518 | 1428-1506 | 156,539-168,635 | |
| *Photorhabdus luminescens* C Class | | | | |
| TccC1 | 3129 | 1043 | 111,686 | yes |
| TccC2 | 2745 | 915 | 103,398 | no |
| TccC3 | 2880 | 960 | 107,054 | yes |
| TccC4 | 2847 | 949 | 106,563 | ? |
| TccC5 | 2814 | 938 | 105,106 | yes |
| *Xenorhabdus nematophilus* xwi C Class | | | | |
| $XptB1_{xwi}$ | 3048 | 1016 | 111,037 | yes |
| *Xenorhabdus bovienii* C Class | | | | |
| $XptC1_{xb}$ | 2886 | 962 | 107,960 | yes |
| *Paenibacillus* spp str 1529 C Class | | | | |
| PptC1 (Orf6 long) | 2859 | 953 | 109,130 | yes |
| PptC1 (Orf6 short) | 2790 | 930 | 106,244 | ? |
| *Serratia entomophila* C Class | | | | |
| SepC | 2919 | 973 | 107,020 | ? |
| Range | 2745-3129 | 915-1043 | 103,398-111,686 | |

The invention claimed is:

1. A method of controlling or inhibiting an insect wherein said method comprises contacting said insect with effective amounts of a Protein A, a Protein B, and a Protein C, wherein said Protein A is an approximately 230-290 kDa complex-forming protein having at least 99% sequence identity with SEQ ID NO:34 (XptA2$_{Xwi}$);

said Protein B is an approximately 130-180 kDa complex-forming protein comprising an amino acid sequence selected from the group consisting of SEQ ID NO:22 (TcdB1), SEQ ID NO:56 (TcaC), and an amino acid sequence having at least 99% sequence identity with SEQ ID NO:45 (TcdB2);

said Protein C is an approximately 90-120 kDa complex-forming protein comprising an amino acid sequence selected from the group consisting of SEQ ID NO:25 (TccC1), SEQ ID NO:57 (TccC5): and an amino acid sequence having at least 99% sequence identity with SEQ ID NO:47 (TccC3);

said Protein A has activity against an insect and said activity is potentiated by said Protein B and said Protein C; and said Protein B and said Protein C potentiate the activity of said Protein A.

2. The method of claim 1 wherein said Protein C comprises the polypeptide of SEQ ID NO:47 (TccC3).

3. The method of claim 1 wherein said Protein B comprises the polypeptide of SEQ ID NO:45 (TcdB2).

4. The method of claim 1 wherein said Protein C comprises the polypeptide of SEQ ID NO:57 (TccC5).

5. The method of claim 1 wherein said Protein B comprises the polypeptide of SEQ ID NO:47 (TcdB2) and said Protein C comprises the polypeptide of SEQ ID NO:47 (TccC3).

6. A method of inhibiting an insect wherein said method comprises contacting said insect with an A component and a B component, wherein said components form an insecticidal toxin complex, wherein said A component is a 230-290 kDa complex-forming protein having at least 99% sequence identity with SEQ ID NO:34 (XptA2$_{Xwi}$);

said B component is a 130-180 kDa complex-forming protein comprising a polypeptide selected from the group consisting of SEQ ID NO:22 (TcdB1), SEQ ID NO:56 (TcaC), and an amino acid sequence having at least 99% sequence identity with SEQ ID NO:45 (TcdB2); wherein said A component has activity against an insect, and wherein said B component is a potentiator of said A component.

7. The method of claim 6 wherein said A component is the polypeptide of SEQ ID NO:34 (XptA2$_{Xwi}$).

8. A method of inhibiting an insect wherein said method comprises contacting said insect with an A component and a C component, wherein said components form an insecticidal toxin complex, wherein said A component is a 230-290 kDa complex-forming protein having at least 99% sequence identity with SEQ ID NO:34 (XptA2$_{Xwi}$);

said C component is a 90-120 kDa complex-forming protein comprising an amino acid sequence selected from the group consisting of SEQ ID NO:25 (TccC1), SEQ ID NO:57 (TccC5), and an amino acid sequence having at least 99% sequence identity with SEQ ID NO:47

(TccC3); wherein said A component has activity against an insect, and wherein said C component is a potentiator of said A component.

9. The method of claim 8 wherein said C component comprises the polypeptide of SEQ ID NO:47 (TccC3).

10. The method of claim 7 wherein said B component is the polypeptide of SEQ ID NO:45 (TcdB2).

11. The method of claim 8 wherein said A component is the polypeptide of SEQ ID NO: 34 (XptA2$_{Xwi}$).

12. The method of claim 1 wherein said Protein A comprises the polypeptide of SEQ ID NO: 34 (XptA2$_{Xwi}$).

13. The method of claim 3 wherein said Protein A comprises the polypeptide of SEQ ID NO: 34 (XptA2$_{Xwi}$) and said Protein C comprises the polypeptide of SEQ ID NO:47 (TccC3).

14. The method of claim 5 wherein said Protein A comprises the polypeptide of SEQ ID NO: 34 (XptA2$_{Xwi}$).

15. The method of claim 6 wherein said B component is the polypeptide of SEQ ID NO:45 (TcdB2).

16. The method of claim 8 wherein said C component is the polypeptide of SEQ ID NO:57 (TccC5).

17. The method of claim 11 wherein said C component is the polypeptide of SEQ ID NO:47 (TccC3).

18. The method of claim 11 wherein said C component is the polypeptide of SEQ ID NO:57 (TccC5).

19. A method of inhibiting an insect wherein said method comprises contacting said insect with an A component, a B component, and a C component, wherein said components form an insecticidal toxin complex, wherein said A component is a 230-290 kDa complex-forming protein comprising the polypeptide of SEQ ID NO:34 (XptA2$_{Xwi}$);

said B component is a 130-180 kDa complex-forming protein comprising the polypeptide of SEQ ID NO:45 (TcdB2);

said C component is an approximately 90-120 kDa complex-forming protein comprising the polypeptide of SEQ ID NO:47 (TccC3); wherein said A component has activity against an insect, and wherein said B component and said C component are potentiators of said A component.

\* \* \* \* \*

SEQUENCE LISTING

```
<160> NUMBER OF SEQ ID NOS: 64

<210> SEQ ID NO 1
<211> LENGTH: 20
<212> TYPE: PRT
<213> ORGANISM: Xenorhabdus nematophilus

<400> SEQUENCE: 1

Met Tyr Ser Thr Ala Val Leu Leu Asn Lys Ile Ser Pro Thr Arg Asp
1               5                   10                  15

Gly Gln Thr Met
            20

<210> SEQ ID NO 2
<211> LENGTH: 5
<212> TYPE: PRT
<213> ORGANISM: Xenorhabdus nematophilus

<400> SEQUENCE: 2

Met Trp Tyr Val Arg
1               5

<210> SEQ ID NO 3
<211> LENGTH: 6
<212> TYPE: PRT
<213> ORGANISM: Xenorhabdus nematophilus

<400> SEQUENCE: 3
```

```
Leu Thr Gln Phe Leu Arg
1               5

<210> SEQ ID NO 4
<211> LENGTH: 10
<212> TYPE: PRT
<213> ORGANISM: Xenorhabdus nematophilus

<400> SEQUENCE: 4

Ala Asn Pro Gln Leu Ser Gly Ala Ile Arg
1               5                   10

<210> SEQ ID NO 5
<211> LENGTH: 8
<212> TYPE: PRT
<213> ORGANISM: Xenorhabdus nematophilus

<400> SEQUENCE: 5

Leu Leu Asp Gln Leu Ile Leu Arg
1               5

<210> SEQ ID NO 6
<211> LENGTH: 39005
<212> TYPE: DNA
<213> ORGANISM: Xenorhabdus nematophilus

<400> SEQUENCE: 6
gatcaggtat tcaatcaacc caaactgttt gatgaacctt tctttgttga taatcgtact      60
tttgattaca acgccattcg tgtaatgat gcacgaacaa ttaagcaact gtgcgccgga     120
ttgaaaatca ccgtagccac cttccaattg ttagctgagc aggtaaacac cgcctttcat     180
ctgccatccg gcaaattaac ctgttcactg cctgttattt cagcgcttta tcgtctggtg     240
actgttcctc ggttatttaa tttaaccgct gaacagggca tgatgctgat taacgcatta     300
aatgccagcg agaaattctc acctcatatt ctggctggtg agcctcgatt aagcctgtta     360
acaacagagg gttcagatac cacagaggtc gatttattgg atgttattct gatgttggaa     420
gaagttgctg tctggctgca acagagcaaa ctgaaaccgg aagaattctg cctgatgctg     480
caaagtgtta tgttgccggt ggttgccacg gacagcagtg tgacattctt cgacaacctg     540
ctgcaaggca ttcccaaaac cttactcaca gaagataact tcaacgcagg ggatatcccc     600
agactccctg aaggagaaac ctggtttgac aaactttcga tgctgataac cagcgatgga     660
ctcgtcaacg tttaccctct cagttggggc cagagtgatg aagattatct gaaatcagta     720
ttgacacctg tcgtcgaaaa aatcattagc gatccaaaca gtgtgattat cactgttttcc    780 gcattaacac aggtcattac tcaggcgaaa actgcgcagg aagatctggt ttccgccagc     840
gtgacacggg aatacggtac tggacgtgat atcgttcctt ggttattacg ctggattggc     900
agcagtgttc ccgatttcct tggcaaaatt tatatacaag gcgcaaccag aggcggacac     960
ttgcgcactc cgccggatat cagcgctgaa ttactgcata tcacctatca tctggcgatg    1020
aataacatgc tgattaagca gttacgactc aaagctcaaa tcatttcatt acgtatcatc    1080
atgcctgaat ggctcggatt accaacgata gatggcagtc cgctatccgt gcatgaaatt    1140
tgggcactga gccggttccg taactgggcg accagctcat tgttcagtga agacgagtta    1200
atcgagtatt ttgcttttgc caatcagccg gagcaggacg ttcgtaacga tgaagatttt    1260
aatcgggact gtgctgaaaa agcttgccga cgtactggaat gggatgccga tgaaattgag    1320
ctggcaaccc gacattttga tcctgcccca gcacgtgcca gaaatatggg acaaattgac    1380
```

-continued

```
tggctgcgtc gtgtcatggc gttgtcgcgt cagactggcc tgtcagtgac accgttaatg    1440
acagccgcaa cgttaccgcc tttcccgccc tatgaccaga taacccatgt cggtgaagcg    1500
gtgattgcgg caacccagta cccatcagag gagtaaggaa cgatgagttc agttacccaa    1560
cctattgaag agcgtttact ggaatcacag cgcgacgcac tgctggattt ctatctcgga    1620
caggtcgttg cctattcacc tgacatgaca agtcagcgcg acaaaattaa ggatattgac    1680
gatgcctgcg actacctcct gctggatctg ctgacttccg ccaaagtcaa agcgacacga    1740 cttttcacttg cgaccaattc attgcagcaa tttgtgaacc gcgtgtcact gaatattgaa    1800
cccggtttgt ttatgaccgc ggaagagagc gaaaattggc aggaatttgc gaatcgttat    1860
aattactggt ctgcggatcg cttattacgg acttatccgg aaagctatct ggaaccctg    1920 ttacgcctga ataaaacaga attcttcttc caactggaaa gtgcccttaa tcagggaaaa    1980
attaccgaag attccgtaca acaagcggtg ctcggttatc tgaataattt tgaagatgtc    2040
agtaacctga aagttatcgc aggttatgaa gatggtgtta acatcaaacg cgataagttc    2100
ttctttgtcg gacgtacccg tacacagcca taccaatatt actggcgttc actgaatctt    2160
tcgatacgcc atcctgatac cgatgcgtta tctcccaatg cctggagcga gtggaaacct    2220
attgacctgc cattgggcag cgtagacccc aatttgatac gccccatttt cctgaataat    2280
cgcctgtata ttgcctggac ggaagttgaa gaacagtctg aaactaaaga tacaactgcg    2340
ttatcactgc ataaccaaaa cgttgagcct agtgcgggtg attgggttcc tcccacaccg    2400
ttcctgaccc ggatcaaaat cgcttatgcc aaatatgatg gcagctggag tacacccacc    2460
attctgcgcg aagacaatct gcaataccgg atggcccaga tggttgctgt gatggatata    2520
cagcaagacc cgcataaccc gtttctggct ctggttccgt tgtccgtct tcaggggaca    2580 gataagaaag gtaaggatta tgattatgac gaagccttcg gttatgtctg cgatacactg    2640
ctggtagaaa ttactgattt gccggatgac gaatatgctg atggacgaaa aggaaaatat    2700
gtcggcaacc tggtctggta ttactcacgt gaacacaagg atgcagaagg caatcctatc    2760
gattaccgta ctatggtgct ctatccggca acccgggaag aacgctttcc tattgccgga    2820
gaagccaaac cggaaggaag ccctgatttt ggcaaagaca gtatcaaact gattgtcaat    2880
tttgttcatg gcactgatga cacactggag attgtcgctc aatctgactt taagtttggt    2940
gcgatagaag atcatcaata ttacaacggt tctttccggc tgatgcacga taatactgtc    3000
ttggatgaac aaccactggt actgaacgaa aaagttcctg atttaaccta tccatcaatc    3060
aagctggggt cggataatcg aatcaccctg aaagccgaac ttctctttaa gcccaaaggt    3120
ggtgttggca atgaaagtgc cagctgtact caagagttca gaatcggtat gcacattcgc    3180
gaactgatta aactcaatga acaggatcag gtgcaattcc tttccttccc cgcagatgaa    3240
actggtaacg cgccacaaaa cattcgcctt aatacactgt tgcaaaaaa actgatcgcc    3300 attgccagtc agggtatccc gcaggtactg agctggaata cacagcttat tactgaacaa    3360
cccatacccg gttcattccc tacgccgatt gatttaaatg gcgcaaatgg gatctatttc    3420
tgggaactgt ttttccatat gccatttctg gtcgcgtggc gactgaatat cgaacaacga    3480
ttaaaagagg ccaccgaatg gctgcactat atttttaatc cgctggaaga tgaacttgtt    3540
caggccagca accaaggtaa accgcgttac tggaattcac ggccaattat tgatcctcca    3600
cccaccgtgt accggatgtt aattgaacca accgatccgg atgccattgc agccagtgaa    3660
cccattcact accggaaagc aatattccgt ttctatgtca agaatctgtt agatcaggga    3720
gacatggaat accgtaagct gacatccagt gcacgtactg tcgccaagca gatctatgac    3780
```

```
tccgtcaata tgttactggg taccagccct gatattctgc tcgcggcaaa ctggcaaccc   3840
cgtacgctgc aagatgtggc tctgtatgaa acagtgaag cacgggcaca ggagttaatg    3900
cttactgtca gcagcgtgcc acttctgcct gtgacatatg atacatccgt ctctgccgca   3960
ccgtctgatt tatttgtcaa acctgttgat acggaatatc tcaaactgtg gcaaatgttg   4020
gatcagcgtc tatataactt acgtcataac ctgaccttgg atggtaaaga gtttccggcc   4080
ggattatacg atgaacccat cagcccgcaa gatctgctca ggcagcgtta ccagcgtgtt   4140
gtggctaatc gtatggcggg catgaaacgc cgggcaatcc cgaattatcg tttcaccccg   4200
atcatgagcc gggcaaaaga ggccgcagaa acgctgattc agtacggcag cacgttactg   4260
agtttgctgg agaaaaaaga caataccgat tttgaacact tccgtatgca gcagcaactg   4320
gggctgtaca gctttacccg caatctgcaa cagcaagcga ttgacatgca acaggcttca   4380
ttggatgcac tgaccatcag ccgacgggcc gctcaggagc gccagcaaca ctataaatcg   4440
ctctatgatg aaaacatctc catcaccgag caggaagtta tcgcattaca atcaagagcg   4500
gctgaaggtg tgatcgctgc ccagtcagcc gccactgcgg ccgctgtggc ggatatggtt   4560
cccaatattt tcggtctggc cgtcgggggg atggtctttg gcggtatgct tcgggcaatc   4620
ggtgaaggaa tacgcattga cgttgaaagt aaaaatgcca aagccaccag cctgagcgtg   4680
tcagaaaatt accgtcgccg tcagcaagaa tgggagctgc aatacaaaca ggcggatatc   4740
aacattgagg agatcgacgc acagattggt atccagcaac gccaactgaa tatcagcaca   4800
acccaactgg cacaattgga agcccagcat gagcaggatc aagtcctgct ggagtactat   4860
tcaaaccgtt ttaccaatga tgcgttatac atgtggatga tcagccaaat ctccgggctt   4920
tacctgcaag cctatgatgc ggttaattcc ctctgtttac tggccgaagc ctcctggcag   4980
tacgaaacag gtcagtatga tatgaatttc gtccaaagtg gtctctggaa tgatctttat   5040
caggggctgc tggtcggaga acatctgaaa ttagccttac aacggatgga tcaggcgtat   5100
ttgcaacata caccagacg tctggagatc ataaaaacca tatcggtaaa atcattactg   5160
acatcatcac agtgggaaat tggcaagagt acgggttcat tcactttctt actgagcgcc   5220
gaaatgttct tgcgcgatta tccgacccac gctgatcggc gtataaaaac cgtagcgctg   5280
tcattgcccg cattgctggg gccttatgaa gatgtacggg cttcactggt acaactcagc   5340
aatacgcttt acagtactgc tgacttaaaa actatcgatt atttgcttaa ccccttggaa   5400
tacaccaaac ccgaaaacgt tttgctgaac gtacaggcta atcaaggtgt ggtgatttca   5460
acggccatgg aagacagcgg catgttcagg ctcaattttg atgatgaact tttcctgcct   5520
tttgaaggga caggcgccat ttcacagtgg aagttggaat tcggttccga tcaggatcag   5580
ctgctggagt cgctgagcga tattatcctc catctgcgtt ataccgcgcg tgatgtgagt   5640
ggcggaagta atgagttcag ccagcaggtt cgtagccgtc tgaataaaca tcaattaaaa   5700
caagacaatt ctaactgata tcaggagccg gccccggaat ataacggggc cggaagtgaa   5760
attatgtctc aaaatgttta tcgatacccct tcaattaaag cgatgtctga cgccagcagc   5820
gaagtaggcg catctctggt tgcctggcag aatcaatctg gtggtcaaac ctggtatgtc   5880
atttatgata gcgcggtttt taaaaacatc ggctgggttg aacgctggca tattcccgac   5940
cgcaatattt cacctgattt accggtttat gagaatgcct ggcaatatgt ccgtgaggcg   6000
acaccggaag aaattgccga tcacggtaac cccaatacgc ctgatgtacc gccgggagaa   6060
aaaaccgagg tattgcaata tgatgcactc acagaagaaa cctatcagaa ggtgggatat   6120
```

```
aaacctgacg gcagcggaac tcctttgagt tattcttcag cacgtgttgc caagtccctg    6180
tacaacgaat atgaagttga tccggaaaat acagaaccgc tgcctaaagt ctctgcctat    6240
attactgact ggtgccagta tgatgcgcgt tgtcgccag aaacccagga taacactgcg     6300
ctgaccagcg acgatgcccc cggccgtggt tttgatctgg aaaaaatccc gcctaccgcc    6360
tacgaccgcc tgattttcag ttttatggcc gtcaacggtg ataaaggcaa gttatccgaa    6420
cggattaatg aggttgttga cgggtggaac cggcaagcag aagccagcag tggccagatt    6480
gcccctatta cattaggcca tattgtaccc gttgatcctt atggtgattt aggcaccaca    6540
cgcaatgtcg gtctggacgc ggatcagcgc cgtgatgcca gcccgaagaa tttcttgcaa    6600
tattacaatc aggatgcagc ctccggtttta ctgggggat tgcgtaatct gaaagcgcga    6660
gcaaaacagg cagggcacaa gctggaactc gcattcagta tcggcggctg gagtatgtca    6720
gggtatttct ctgtgatggc caagatcct gagcaacgtg ctacatttgt gagtagcatc     6780
gtcgacttct tccggcgttt tcccatgttt actgcggtgg atatcgactg gaatacccc     6840 ggcgccacag gtgaagaagg taatgaattc gacccggaac atgatggccc aaactatgtt    6900
ttgttagtga aagagctgcg tgaagcactg aacatcgcct ttggaacccg ggcccgtaaa    6960
gaaatcacga tagcctgtag cgccgtcgtt gccaaaatgg agaagtccag cttcaaagaa    7020
atcgcacctt atttagacaa tatctttgtg atgacctacg acttctttgg taccggttgg    7080
gcagaataca tcggtcacca tactaacctg tatcccccca gatatgaata tgacggcgat    7140
aaccctcctc cgcccaatcc tgatcgggac atggattact cggctgatga ggcgatccgc    7200
tttttactgt cacaaggtgt acaaccggag aaaattcacc tcggatttgc taactatgga    7260
cgttcatgtc tgggtgctga tctgacaact cgccgctata cagaacagg agagccactg    7320 ggcacgatgg aaaaaggtgc tccggaattc ttctgtctgc tgaataacca atacgatgcg    7380
gaatatgaaa ttgcacgcgg gaaaaatcag tttgaactgg tgacagacac ggaaaccgac    7440
gctgacgcac tctttaatgc tgacggtggt cactggattt cactggatac gccccgcact    7500
gtgctgcata agggaattta tgcaaccaaa atgaaattgg gcgggatctt ctcttggtca    7560
ggcgatcagg atgatggcct gttggcaaat gctgctcacg aaggtttggg ttacttacct    7620
gtacgcggaa aagagaagat tgatatggga ccgttatata caaaggacg tctcattcag    7680 cttcctaaag taacccgtcg taaatcgtag taaataaaat tttccggtgg cctcacaggg    7740
gtcaccatat cctgctgtga aaagcgtat ccatttaatg ctttaacgct tcaattttct     7800
cccggctcag gccggtactg gtgacaatga tgtccagact gacaccatgc cgtaataatg    7860
cgcgcgccgt ttccagcttg ccttcttccc gtccttcagc tctgccttct gttctgcctt    7920
cagccctgcc ttctgtccgg ccttgctcac gccctttttg ttcaagctgt tctgcaatag    7980
tcatcaacat ggtttcatgc tccggagatt gttcagtcag ttgatggaca aactgggcga    8040
gatccagcgt atgtccattc agtaaaatat agcttaacac aacatggcgc tgttcggcgc    8100
tattataacc ggcattcaac aacgccacta attgggaac ccactccagc atatcccggc     8160
aacggatatg ttttgtacc agctccatca aggcaatgct tttatgtgtc aggatctctt     8220
catcactgag cgcactgata tccaccaacg gcaggggctg attatacagg tgagccgcgt    8280
gttcagagag tgtaaaacaa tccagccatc gatttgagta agggtaaggc ctcacctcac    8340
catgataaaa cagcagggg acgaccaaag ggagttcagt atgtccttttt ttcagatgcg    8400 cagccatggc tgacagcgaa taatacatca gccgccaggc cattaacgga tcaggcgtgg    8460
actggtgttc aatcaggcaa taaatgtaac cgtccccgtg ggttgtctcg acagaataca    8520
```

```
gcacatcact gtgcaactga cgtaattgcc tgtccacaaa gctgccgggt tccagtttta   8580
gtgtggttaa atcacacact gaccggatcg cttccggcag ataaagggat aaaaattccc   8640
gggcggtttc tggttgggtt aaaaaatgtt tgaataacgc gtcatggtga ggcttttttg   8700
ctttcctggc cacaatccgt ctctctgttt tatcggttat taatcgcctt tactgccaaa   8760
gctatcatct cgctgaaaaa tccacagcca atatacaaca tattatctgc tgacccaaca   8820
ctcgtccggc taatcaatcc agtatcaatg cgagttctac agtaaataca gctcttcatg   8880
gtcaggaaac cggacaaaag ttgattgaat ttcctaacca tgaattttct gttatgttaa   8940
ttattaccgt ctcacaataa taatcacatc aacagaatt tatttactat ataaataaac    9000
tatcaattat tataagaaaa ataatatgat tggcattaaa tataaaacca taaaaaagta   9060
gaattaattt ttaaaactta attgcagaaa ccagatgaaa tataaactta atttcttatc   9120
cataaataat aatgaatcaa tatttattca ataccatcag tggaaggttc ccgtttgttt   9180
taatttcaag cttataatcc cctttgcctt tagctgaatc accagacata atttgcttat   9240
tgctaaattg tttactactg tctgtaaaat aaacataact gccatgttga acatgtagt    9300
tcacaatatc agcagcgtcc ttttactga aagtaacttt gatataatgg ccagagttaa    9360
tatctttctg actatcgcac caaggaatcc acataccacc ggtagatgaa tcatttcccg   9420
gagaaacaac cacatggtca ggtattatgg ggataactc atttgctgac tcctgattaa    9480
ataaatccgc tttatattca caaccaaaat tgttatcaac attaataata ttacgaacat   9540
ctgacataat aatttccccc gaatatagtt taaaggtttt tcaatttaa taacatatca    9600
aaggaactat aatactgtat atttacatcc gtcaacatta ttcacctaca gggtgacatt   9660
cctctattaa ataaaaata agtttgatt tttaactttt gataacttat gcaccaaatc     9720
agtgaccact gccgttaact tagttttgat cctcgtcact acggttaaac ttccgactcc   9780
cagaaagcaa aaaccccgc gagtgcgggg ctatattcaa agtgcttgag ttatttcact   9840
atgcggatag ttttgacatc aatttcaaca ctgttccagt ctttgtccac ttcaccttcg   9900
atacgaactt tgtcagttgg agtggccgtc agacccatcc agcgcttatc atcaatgtca   9960
acataaacag aaccactgtt atccctgaat tcatagagtt cgtgaccaac ctgtttaaca  10020
atgtttcctt ccagaacaac ccacgcatca tcacgaaaag attttgcttg agcaacgctg  10080
gtcaggttgg gagttggacc tttaaatcca ccctgagtat agtctgtgct gtctggggaa  10140
acgaagccac cctgctgtgc caaagcacca aagaaaggg tactgagaat aagagtaatc   10200
agtgtttttt tcatagcttt ctctttgatt atgcgaagaa aaaccccgca tttgcgaggt  10260
tcgggtattc aataaattat gtgacattac tatcactctt gtcacgatat atcaactttt  10320
gtaattacgc aactttatta aggatttctt tttgcacaca tttatctgac tccaacgtag  10380
ccccctgaaa ccagcaagac atcctcaata aataatcttt catagataaa tattagttat  10440
tcattttttca aacagcacaa acacaattaa aaatatttaa acaattgttg agttgaattt  10500
tttcatgaaa gtttgttaaa atttaatttt taacatacgg tattcattat ttaaatccat  10560
gtattatagg gaagttcttt attttttatt gaaagaatag agcgataaat cagtatcaat  10620
ttaattaacc ataatattcc tatcagatta taataatctc cacctaaaaa ccattaatca  10680
ttaaattgac aataacttaa ggattatat gataaaagtt aatgaactgt tagataagat   10740
aaatagaaaa aggtctggtg atactttatt attgacaaac atttcgttta tgtctttcag  10800
cgaatttcgt cataggacaa gtggaactct gacgtggcga gaaacagact ttttatatca  10860
```

```
acaggctcat caggaatcaa aacagaataa acttgaagaa ctgcgcattt tgtcccgtgc    10920
taatccacaa ctggctaata ccactaacct taatattaca ccgtcaaccc taaacaatag    10980
ttacaacagt tggttttatg gccgtgccca ccgttttgta aaaccgggat caattgcttc    11040
catattttca ccagcggctt atttaacaga attatatcgg gaagcgaaag attttcatcc    11100
tgacaattct caatatcacc tgaataaacg acgcccgac attgcttcac tggcactgac     11160
acagaataat atggatgaag aaatttccac attatcctta tctaatgaat tactgctgca    11220
taatattcag acgttagaga aaactgacta taacggtgta atgaaaatgt tgtccactta    11280
ccggcaaacc ggcatgacac cctatcatct gccgtatgag tcagcccgtc aggcaatttt    11340
attgcaagat aaaaacctca ccgcatttag ccgtaataca gacgtagcgg aattaatgga    11400
cccaacatcg ctactggcta ttaagactga tatatcgcct gaattgtatc aaatccttgt    11460
agaagaaatt acaccggaaa attcaacaga actgatgaag aaaaatttcg gtacagatga    11520
tgtactgatt tttaagagtt atgcttcttt ggctcgctac tacgatttgt cttatgatga    11580
actcagttta tttgtcaatc tctccttcgg taagaaaaat acaaatcaac agtataagaa    11640
tgagcaactg ataacattgg tcaatgacgg gaatgatacg gcaacggcaa gattgattaa    11700
gcgaacccgc aaagatttct acgattcaca tttaaactat gcagaactaa ttccaatcaa    11760
agaaaatgaa tacaaatata atttcagtgt aaaaaaaaca gaacctgacc acttggattt    11820
tcgtctccag aatggagata agaatatat ataccaagat aaaaatttcg tccccattgc      11880
taatacccat tacagtattc ccattaaatt gacgacagag caaatcacca acggtataac    11940
actccgctta tggcgagtta aaccaaatcc gtcggatgct atcaatgcca atgcatactt    12000
taaaatgatg gagttccccg gtgatatatt cctgttaaag ctgaataaag cgattcgttt    12060
gtataaagcc acaggcatat ctccagaaga tatctggcaa gtaatagaaa gtatttatga    12120
tgacttaacc attgacagca atgtgttggg taagctgttt tatgttcaat attatatgca    12180
gcactataat attagcgtca gcgatgcgct ggtattgtgt cattcagata tcagccaata    12240
ttccactaaa caacaaccca gtcattttac aatactgttc aatacaccgc tattaaatgg    12300
ccaagagttt tctgctgata ataccaaact ggatttaacc cccggtgaat caaaaaacca    12360
tttttatttg ggaataatga aacgtgcttt cagagtgaat gatactgaac tgtatacatt    12420
atggaagctg gctaatggcg gaacaaatcc agaatttatg tgttccatcg agaacctgtc    12480
tctgctttat cgcgttcgtc tgctggcaga cattcatcat ctgacagtga atgaattatc    12540
catgttgttg tcgttttctc cctatgtgaa cacgaaaatt gcccttttt ctgatacagc      12600
attaacgcaa ttaatcagct ttctgttcca atgcacccag tggctgacaa cacagaaatg    12660
gtctgtcagt gatgtgtttc tgatgaccac ggataattac agcactgtcc ttacgccgga    12720
tattgaaaac cttatcacga cactaagtaa tggattatca acactttcac tcggtgatga    12780
cgaactgatc cgtgcagctg ccccgctgat tgctgccagc attcaaatgg attcagccaa    12840
gacagcagaa actattttgc tgtggattaa tcagataaaa ccacaaggac tgacattcga    12900
tgatttcatg attattgcgg ctaaccgtga tcgctcagaa aatgaaacca gcaacatggt    12960
ggcttttttgt caggtactgg ggcaactttc tctgattgtg cgcaatattg gactcagcga    13020
aaacgaactg accctgttgg tgacaaaacc ggagaaattc caatcagaaa ccacagcact    13080
gcaacatgat ctccccactt tgcaagcgct gacccgcttc catgctgtga tcatgcgttg    13140
tggaagctac gcgacagaaa tcttaacagc attggaacta ggagcgctga ctgccgaaca    13200
attggcggtg gcgttaaaat ttgatgctca ggttgtgaca caagcattgc aacagaccgg    13260
```

```
tttgggagtg aatacccttta ccaactggag aactatagat gtcactctgc aatggctgga    13320
tgtcgctgct acattgggta ttaccccgga tggtgttgct gcactcataa aattaaaata    13380
tatcggtgaa ccagaaaccc cgatgccaac atttgatgat tggcaagccg ccagtacttt    13440
gttgcaggcg ggactgaaca gtcaacaatc cgaccagctt caggcatggc tggatgaagc    13500
cacgacgaca gcggccagtg cttactacat caaaaatagt gcacctcaac agattaagag    13560
ccgggatgag ttgtacagct atctgctgat tgataaccaa gtttctgccc aagtgaaaac    13620
cacccgtgtg gcagaagcca ttgccagcat tcagttatat gtcaaccggg cgttgaataa    13680
tgttgaagga aaagtatcaa agccagtgaa aacccgtcag ttcttctgcg actgggaaac    13740
ctacaatcga cggtatagca cctgggccgg cgtatctgaa ctggcctatt atccggaaaa    13800
ctatatcgac cccacgattc gtattggtca gacaggtatg atgaacaacc tgttacagca    13860
actttcccaa agtcagttaa atatcgatac cgttgaagat agctttaaaa attatctgac    13920
cgcatttgaa gatgtcgcta acttgcaggt gattagcgga tatcatgaca gtatcaatgt    13980
caatgaggga ctcacttatt taattggtta tagccagaca gaacccagaa tatattattg    14040
gcgcaatgtc gatcaccaaa agtgccagca cggtcaattt gctgccaatg cctggggaga    14100
atggaaaaaa attgaaatac ccatcaatgt atggcaggaa aatatcagac ctgttatttta    14160 caagtctcgt ttgtatttac tgtggctgga acaaaaagag ctgaaaaatg aaagtgaaga    14220
tggcaagata gatatcactg attatatatt aaaactgtca catattcgtt atgatggcag    14280
ctggagctca ccgtttaatt ttaatgtgac tgataaaata gaaaacctga tcaataaaaa    14340
agccagcatt ggtatgtatt gttcttctga ttatgaaaaa gacgtcatta ttgtttattt    14400
ccatgagaaa aaagacaatt attctttttaa tagtcttcct gcaagagaag ggatgaccat    14460
taaccctgat atgacattat ccattctcac agaaaatgat ttagacgcca ttgttaagag    14520
cacattatca gaacttgata ccaggacaga atacaaagtc aacaatcaat ttgctacaga    14580
ttatttggcc gaatataagg aatctataac cacaaaaaat aaattagcca gttttaccgg    14640
aaaatatttt gatctctcgt atatatcacc aggaaatggt catattaatt taacgttcaa    14700
tccttcaatg gaaattaatt tttcaaaagg caatatatat aatgatgagg ttaaatacct    14760
gttatcgatg gtagaagatg aaacggttat tttatttgat tatgatagac atgatgaaat    14820
gcttggaaaa gaagaagaag ttttttcatta tggaactttg gattttatta tttccatcga    14880
tcttaaaaat gccgaatatt ttagagtgtt aatgcatcta agaaccaagg aaaaaattcc    14940
tagaaaatca gaaattggag ttggtataaa ttatgattat gaatcaaatg atgctgaatt    15000
caaacttgat actaacatag tattagattg gaaagataac acaggagtat ggcatactat    15060
atgtgaatca tttactaatg atgtttcaat cattaataac atgggaaata ttgcggcact    15120
gttccttcgc gaggatccat gtgtgtattt atgttcaata gccacagata taaaaattgc    15180
ttcatctatg atcgaacaga tccaagataa aaacattagt tttttattaa aaaatggctc    15240
tgatattcta gtggagttaa atgctgaaga ccatgtggca tctaaacctt cacacgaatc    15300
tgaccctatg gtatatgatt ttaatcaagt aaaagttgat attgaaggct atgatattcc    15360
tctggtgagc gagtttatta ttaagcaacc cgacggcggt tataacgata ttgttattga    15420
atcgccaatt catataaaac taaatccaa agatacaagt aacgttatat cactgcataa    15480
aatgccatca ggcacacaat atatgcagat tggcccttac agaaccggt taaatacttt    15540 attttccaga aaattagctg aaagagccaa tattggtatt gataatgttt taagtatgga    15600
```

```
aacgcaaaat ttaccagagc cgcaattagg tgaagggttt tatgcgacat ttaagttgcc   15660
cccctacaat aaagaggagc atggtgatga acgttggttt aagatccata ttgggaatat   15720
tgatggcaat tctgccagac aaccttatta cgaaggaatg ttatctgata ttgaaaccac   15780
agtaacgctc tttgttccct atgctaaagg atattacata cgtgaaggtg tcagattagg   15840
ggttgggtac aaaaaaatta tctatgacaa atcctgggaa tctgctttct tttattttga   15900
tgagacgaaa aatcaattta tattcattaa tgatgccgat catgattcgg gaatgacaca   15960 acagggata gtaaaaaata tcaaaaaata taaagggttt attcatgtcg ttgtcatgaa   16020
aaataacact gaacccatgg atttcaacgg cgccaatgca atctatttct gggaattgtt   16080 ctattcacg cccatgatgg tattccagcg cttattgcaa gagcagaatt ttaccgaatc   16140
gacacgctgg ctgcgctata tctggaaccc ggccggatat tcggttcagg gtgaaatgca   16200
ggattattac tggaacgtcc gcccattgga ggaagatacg tcctggaatg ccaatccgct   16260
ggattcggtc gatcctgacg ccgttgccca gcatgatccg atgcactata aagtggctac   16320
ctttatgaaa atgctggatt tgttgattac ccgcggagat agcgcctatc gccagcttga   16380
acgtgatacc ttaaacgaag ctaaaatgtg gtatgtacag gcgctcactt tattgggtga   16440
tgagccttat ttttcattgg ataacgattg gtcagagcca cggctggaag aagctgccag   16500
ccaaacaatg cggcatcatt atcaacataa aatgctgcaa ctgcgtcagc gcgctgcatt   16560
acccacgaaa cgtacggcaa attcgttaac cgcattgttc ctccctcaaa ttaataaaaa   16620
actgcaaggt tactggcaga cattgacgca acgcctctat aacttacgcc ataacctgac   16680
aatcgacggt cagccactgt cattatctct ctatgccacg cccgcagatc cgtccatgtt   16740
actcagtgct gccatcactg cttcacaagg cggcggcgat ttacctcatg cagtgatgcc   16800
gatgtaccgt tttccggtga ttctggaaaa tgccaagtgg ggggtaagcc agttgataca   16860
atttggcaat accctgctca gcattactga acggcaggat gcagaagcct tggctgaaat   16920
actgcaaact caaggcagtg agttagccct gcaaagtatt aaaatgcagg ataaggtcat   16980
ggctgaaatt gatgctgata aattggcgct tcaagaaagc cgtcatggtg cacagtctcg   17040
ttttgacagt ttcaatacgc tgtacgacga agatgttaac gctggtgaaa aacaagcgat   17100
ggatctttac ctctcttcat cggtcttgag caccagcggc acagccctgc atatggccgc   17160
cgccgcggca gatctcgtcc ccaatattta cggttttgct gtgggaggtt cccgttttgg   17220
ggcgcttttc aatgccagtg cgattggtat cgaaatttct gcgtcagcaa cacgtattgc   17280
cgcagacaaa atcagccaat cagaaatata ccgtcgccgt cggcaagagt gggaaattca   17340
gcgcaataat gcggaagctg agataaaaca aattgatgct caattagcga cgctggctgt   17400
acgtcgtgaa gcggcagtat tacaaaaaaa ctatctggaa actcagcagg cacaaactca   17460
ggcgcagtta gccttttctgc aaagtaaatt cagtaatgca gcgctataca actggctccg   17520
tggaaggttg tccgctattt attatcagtt ttatgatttg gcggtctcac tctgtttaat   17580
ggcagagcaa acttatcagt atgaattgaa taatgcggca gcacacttta ttaaaccagg   17640
tgcctggcat gggacttatg cgggtttatt agcgggtgaa accctgatgc tgaatttagc   17700
acagatggaa aaaagctatt tggaaaaaga tgaacgggca ctggaggtca ccagaaccgt   17760
ttctctggct gaagtgtatg ctggtctgac agaaaatagt ttcatttaa aagataaagt   17820 gactgagtta gtcaatgcag gtgaaggcag tgcaggcaca acgcttaacg gtttgaacgt   17880
cgaagggaca caactgcaag ccagcctcaa attatcggga ctgaatattg ctaccgatta   17940
tcctgacggt ttaggtaata cacgccgtat caaacaaatc agtgtgacat tacctgccct   18000
```

```
tttagggcct tatcaggatg ttcgggcaat actaagttat ggcggcagca caatgatgcc   18060
acgtggctgc aaagcgattg cgatctcaca tggcatgaat gacagtggtc aattccagat   18120
ggatttcaat gatgccaagt acctgccatt tgaagggctt cctgtggccg atacaggcac   18180
attaaccctc agttttcccg gtatcagtgg taaacagaaa agcttattgc tcagcctgag   18240
cgatatcatt ctgcatatcc gttacaccat tcgttcttga tccaaaaatt aactggacag   18300
agaccctgta cgggtctctg tccacacatc cgaaaaccc accttgtcat ccatgacaaa    18360
gtgggaatga acatgattgt tatgcttcgg attcattatg acgtgcagag gcgttaaaga   18420
agaagttatt aaaagcccgc ttaaagccgc tccaggtaac ccggctagcg gcattggcaa   18480
cttcccctcc aacggcatga tgagcggccg cggctgtccc gccaatggct gcaccaaccc   18540
attcaccggg tgtacggcta aaggtaata atacttcaga atatttctc ccgacacttt     18600 ctcctatcat tcggccaaac cagctcctgg aactgacagc gtgggaaatg gcagagctaa   18660
tgcctcttct gagcagtaac ctgccgataa accgataagg gccatcccat agattaccaa   18720
tgatccttcc ccatcgagca ccatacatag caccaatcgc tgcccgttca cccagctcag   18780
aacttccctg atggcggcca agtaatatgc cgccaataat tgcgcctgat agtgcccta    18840 accgctctgg cgcgctgaca ttaccgggcc tgagcgtatc cagcgtacct tgtccggcgg   18900
gtgtggcaat actgatagcc atgcccgtgt tatgctctcc ggctaaagcc attaatcctc   18960
caacggtgac cgctgttgct gcggaaatgg cggtacctgt cgaagagctg ttaaatagtg   19020
cagacgtcac aagcgatgtg acaacaaaag cgccaacctg aacaggaaca gaacgtttac   19080
gcgtcagata acttaaaact tccccaattt tttctgagat gttgttcgcg aaaaacccca   19140
tcaccgcccc ggagacaaaa ccaccaatgg cagcccgac aatcccccaa ggcgacgctc     19200
ctgcaatcgt ggccgccttc acccccagac ttgctacccc cacacccaaa acaaacgttc   19260
gcaatcctcg gttaatttc aagaacgtat caaaggaagc gccttgttca agcaggtgtt    19320
ctgtcgtgat gttgactgcc tttcgatacg cttttttccc tatccaggca aggacaccct   19380
gaccggggaa acgaccatca gaatcagaaa aaacgatggg gttattcctg cacattcgga   19440
acaaattgag accatcgacc tcaccggcag gatctacact caaccatcgc cctgtccacg   19500
attgataata acgataaccg tagtaataca accctgttgc atcccgctct ttgccagaat   19560
aacgcacggt tttgtaatca gcttctgact gacttcgggc tgcccacacg gcggttcccc   19620 catagggta atattcttcc tgactaatga tctgcccgtc actgtccaat tccagcccgc    19680
tactgccaat caggttgcca taactgtagc gcagctgatc attgctgata tccgccggtt   19740
tgcctgtttc ccaatgcagc acccgcactt gtgcctgacc cgattcaccg acagtgatga   19800
cctgcaaaaa ctcttttaat gtattgccgc tatatgtcgt gcgccattcc agctctggca   19860
aatataatgt tcgctgtatt tgctcactgt tacctgtctt ctgaatatga gtcttaatga   19920
cacgctgact gtctgcatca taacggtaga attcctgatc aggcgtcgta ttttccctat   19980
tgaccaatat cacttgttgc aattcgtcac ggggtgtcca gaaaagatcc tgaccgggaa   20040
caagccgggt ctgatgcccg ccggggggtga acaacatatc cacctgagtg ggatcttgcg   20100
ccagctcttc cagtacagcc cggttgctgt gatctgaaac ggtcatgttc gttgtatagt   20160
tattaccggt gatcggtgaa ttatggcgaa ttctggtcag atttccccca cgatcatagt   20220
cgtaagtgcg agagtaattc gtataagtat tgttatcaat cagagcgggg atgggtaact   20280 ggttttttttg tcggccaata ttcgccattt cacgcccagt gacggaaacc agctggtaca   20340
```

```
ggctgtcata ggtgtaagta ttttccggta caattttctg gttgcgccaa aagcgggtaa    20400
tttcagcatc attagttgat ttcagcacat ttccgacagg atcatattca taacgcaggt    20460
tttgtaaaat tttctcccca gcggcatgac cggaaggacg ttctgttttt atgccaataa    20520
ctcgttgcgt ctcgggttca taggtatatg tagtcactat cccgttacca tgttcctccc    20580
gtagcttctg gctggcagcc gaataggtca gggatttcac gataacttgt tcttgtttcc    20640
ccttcagcgc caaccaactg ccttgaagca gaccggccac atcataggcg atacgttgct    20700
tgtttccggc agcatctgta ctcgttaata ccgtgccggt agcatccgtt gtgctgacag    20760
aagtgaagct ttccggcgcc agcgcgtttt tccagccaga ttcatccata ccgtgccaat    20820
cggcttcgct gtcatctttc agtaattgct gtgtgatgga caagggtatg ctggttaacg    20880
atatgctgtt ggtttgattc attccggtgg gatcataatg gaccacgcac tggccggcca    20940
gattattgcc tttttctgcc ggcgtatttc ctgaccagat caatcgctcc gtgatacagg    21000
cgttctctcc ttttacctgc tcggtaatcg ttagcaatcg tcccggaagg ttatcacttt    21060
catactgaaa cgttcggcta acgccattgg cgctgacagc taaaacggga cgcccggcaa    21120
catcatgcag ggcgacacgg gttccggcat ccacactttg cgtacgcaat gccttcttac    21180
tgagtgatga caagagaata agattgggtg taatggcgtt cttgtcactc gctgtctgct    21240
ggcgttcata aaatcgcgga tcaatactct gagtcagaga tccttgagca tcatattgat    21300
aaccggtgat gcgttcatcg gttacctgag gtgtatcggg gtgccgatac caggctatt    21360 cgcgtactgt ctgaccacgg ttgtccagta cggtgacgga tggcgtattg ctgtgaacga    21420
aattcttcat gattcattcc taaatggagt gatgtctgtt cagtgaacag gcatcactga    21480
gctttatgct gtcatttcac cggcagtgtc atttttcatct tcattcacca caaaccaggg    21540
agtgaataag gatcgacgaa acccgccttt ggccgtgata acctgatatt cacgccccaa    21600
cggatcatag taatgggtat cggcatatat atcctgccgg gcactgtcat cactgacgta    21660
ctgccaacta ttcaggaaat acggttgata cttacgcagg gcttggcctt ttccgtcata    21720
ttctgtacgt ccggaaactg cccaacggaa atctgtcatc gccgtttcag gcgcgccatg    21780 atttttcagcc acaatggctc catactcatc acgtacccag gcttcaccac tttcatggcg    21840
tacggctgtt tgtaaggttc gcccaaaacc atcactaaac gtaaacgttt gacgtaattg    21900
ttgttccgga tcggcatcat agcggtcggt gatcacactc agtacatggg gtgggttctg    21960
tgaattgact tgctttggca tggcagcggc agggttattt tgttgccagc ggcgaaaagc    22020
aagcgacagg agataaccat cttcagtgat gatcccagcc ggtttcagct ctccataaag    22080
ctccccatca ttagaaaagc tggcctgaac catccagctc agagggcat aaaccatcag    22140 ccctgcaaca ggtataccgg gtttcaatgc cagagcatca tccaccgttg tggggacaat    22200 aaagggggaca gtttcatttt ccgcagggggt atatccttgt ttttcaccgt tttcagtccc    22260
ccagaaacgg aagctggtta ccctccccag tgcatcaaac gtcacggtgt gatagttatc    22320
attgacatct gtggtgttat ccgcaaccat aaatcgataa tcgtaatgcg cttgcatacg    22380
caggccagcc gcatcctctg ttgcggtgat aacacagtaa tggctatccc acgtgactgt    22440
cgttttacct gtaagcttgg tttcccgttg caccaatggc cgatagaatc cgtctgcacc    22500
ggcatattct gtaaattcct tttgtcccac ccagacatgg aaatctgtct tttcactgaa    22560
cggcactttt gccgtattcc agcccgcatc attcagctgt tttgtcagct cctgctcatc    22620
catcacctcc tcaaaagccg ccaacgatcg ttcatcaaac tctgcggttt caatgtatgc    22680
caccagcgga ggaatagcgg gttgttcttc tggaccggta tatgctacac gctgatgtcc    22740
```

```
cagataatcg gctgcggcat caggcaacaa caatgctcct gcacctgtgg cagaaaacca    22800
ttcaagggaa aatccaccgt ccggcacttt atcggcttga taaatacgtg cgtcactgcg    22860
tgaggtatcc ataagccctg tgatccacgt attatcatca tgattcagat gatgataaga    22920
agaacgctgg cgtgtcagac gaaggaacat ctgctgttcg tcgaaactgc tggtgaaaag    22980
tgtttcgggc agggtatccg gataaggcga gaactcaggc tgtggacgtc tcgaataggc    23040
aatctcaaga ttgtcctgcg gaaatcctaa cgcatcagat ttaaggacga tcttttggct    23100
gcactgtgga tcggtagcaa cccgttcata tcggtattgg cgggattcgg ccaccgaaac    23160
cagtaccgca ggcacgtccg ataccatcac cggtaacaaa cgtacttggg tgcgggattc    23220
atccactgaa taaggcgtac cggccagtat agaatcatca tccccataca gctcactgcg    23280
taaacgttgt ccttttaagg ctcgatgtaa ccagtattct tcctgttcgc tcggcgtgac    23340
cgtcatatca ccaccggatt tttcgtcata acgggtaaag cgtggggtaa aatggggaaa    23400
tgcctgttga tcccctgcc aatattccgt gggcagaaga atatcgactt cccgtacgcc    23460
agtgccgtac caattaaccg tgcgcgaagg tgccggtggt tcagcatgtg tcccctgtgt    23520
cgcactcgcc cgtgaatcaa tatcagtttg tgtcacccgc ccaaaaccac gaaactcccg    23580
ttccagacca tcccaggcac catgtgagta atgataatgg ctggtcaatc ggttaccgga    23640
aatttcatcc agcacttccg tgcgccacaa cacatgcacc gggaacggta agtagctgac    23700
caccgtcatc ccggattcag aagcctgtaa tttctcatcc agccagaact gggcagagct    23760
gcgataatac agcgtggttt ctgttcccat attgttattg acggcattca gcagccaagg    23820
cttgaatatg gtcatatcca atcgccagtg ctgcaccttc atatggggga tcgtcaaaat    23880
aatgctggca gtccctaatc cttgtgtatc cgctatttgt aaccgacaag tatcatcaaa    23940 acgtaccca tccggcagat caatacgctg aggttcagca aaatgattgc cgctttcatt    24000
ggcatagagt tcaaggtaag tattgcgggc ataaataaaa tcggtggtgc ctgagccatc    24060
tatgtctacc atatacagtc tgtcgggggtt aaacgtttcc ccgctaatct ggaagcctgt    24120
catcatcaga ggctcaccaa attttccatg ccccaggttc ggccagtagc gcacgctatc    24180
tgccgttact tccaccagat gtgattgccc ggagcctgtc atatcactga atgcgacaag    24240
atgacgctca tttctgccgg gaaccggcag tggcatatct gacaaatgaa tcacatcctg    24300
agcgcgatcc catcctgccc gattatttga ccagacacgt acactatttg gcccgataag    24360
cgctaagtca ggcagcccag ccccatcaat atcagccagt tttgcctgcg gatggaaata    24420
ttccattggc acagcggata atggaataaa gggtgtccat tcaccttccg gtgacatggt    24480
gtggtagccc cgtaaccctg atgccgtaat cacccaatcc agacgcccgt caccattgat    24540
gtccaacaac atcgcgcttt cctgttgtgc cggaatatgt ggcagtggtt tggcctcctc    24600
ataggtaacc gcattcgttc cttcggcagt gatatcccgt accggagcac ggtaccacca    24660
ggctttctga gtatcctgat aaagtacgcc ggaaattcct tctccatata aatcaaccaa    24720
ttggtatggc tgcaacgtgt tcatttttc taactgcggc atggactgcc agttcagatt    24780
cacgccatga ttaacacgtt gataatccat ttccagcggg gacatcatca ctggcgtacc    24840
gtccgtttca tgggccagtc tgcgggccgt ttgcagcaag gaaaccttgt tgttcaggtc    24900
ataatccaga ataagacggg aaaccagcgc cggtgtttct tctgcaacct tttcccctgc    24960
cagcgctttc agctgatgaa acatcagaac ttggcgacac aagcgacggg ttcgaatttc    25020
aaacccatat tcatagcggg agaaactgtc cggacgacaa cgccattttt caggcacatt    25080
```

-continued

```
gttttcagac acattgtttt ctgacacatt gaattcgggt acagagttca gcgaagatga    25140
gcgctcaccg taatcaaata ccagatgaaa cagccagtca ttatcagcag gaatacctga    25200
ttttaccgcg aaaaagcgg tttccggctg agtattgcca tagctgactt ttgccagata     25260
acgctgggcc gtaacacctg aatgctgagc aagttcatgc tcatcacagt caagatcgtc    25320
ttctgcccga tagtgatagt aaatatgttc cccggtatgc gtgacggttt cctccatcag    25380
ccagcgggca attctggttt catcctgcgg gtcagcaata cgtgcatggt gatgcttacc    25440
gaataggtgc actaaaccat ccgcagtaaa aagtacccaa aaagacgtct cttcctcacg    25500
tctctgctgt ggctgccagt gttctaaacg aacgattttt tctgccacgc gggactgata    25560
gcgggtaaca gtatgcggct gtgtcagaac cgtccccaac agtgaggttg cggtgcgttg    25620
ctctggttgc ccttggctgt ccggcacaat actcaacact tccccatccg gcccgagata    25680
ctcatcttgt cccgtatagt gcggaacgcc cttggcggta cgcaggctga taaaaccaac    25740
cccacattgc caccccatcc cgaatgaccc attgccggca gtactgctgt aattcagtga    25800
tagcaccggc accagaccac gcccgacaga gatcggcaag ggcagtgaaa atgacgctcc    25860
cccttccgct ccgacggcat tgagtgcttc tcccattcct tttagtgatc cgcccccaga    25920
gggcaatgac ggtatttcaa gtttcaaagg tgttgaaccc tgcataaaaa ctccttaaac    25980
aggctccctc aggagcctgc ctatcacaat gttttaatta agaacgaatg gtatagcgga    26040
tatgcagaat gatatcgctc aggctctcca gcagcgcttt ctgccgatca gtcgcatccg    26100
ggaaactcaa cgtcaggctg ccgctgtcat tcacggaaat accttcaaac ggcagataac    26160
gggaatcgtt gaaatccagc ataaattgac cactgtcatt cacgccgtgg gagagagcaa    26220
tagcactgca accgcgtggc atgacgatgc tgccccgta attcagcacc gcccgaatat     26280
cttcatacgg cccaaccagc gccggcaagg tgacactcac ctgtttcaac tgacgggtat    26340
tgccaaggct ttcggggtag tcgctgaaaa ttttcaaatc agacaatcgc actgaggctt    26400
ctatctgacg gttactgagt tttaattcat tgccggaagc tcctacgttg ccttcccctt    26460
cacgcaggaa ttgcgtgagt ttttcggtca gattaaagtt gtctgatgat aaggcctgat    26520
agaactgtgc caacgagacg gtacgggtca cttccagtgc ccgctcatca cgctccagcc    26580
agactttttc catttctgcc agattcagca gcaacgtttc acccgccatc aaacccgcag    26640
tcgtaccgtt ccaggcccca ccccggataa aggtaacacc gttgtcggtc agctcgcggc    26700
gcagcgcttc ctgtgccatc aggcagaagg actgggtcag gtcaaagaac tggtaataga    26760
tagcactcag cttccgcgc atccaactgt aaagcgcttt gtttgtgaat ttacgctgta    26820
acagctctaa ctgagcctga gtatgggcct gctgggtctc ctgatattcc acctgcatct    26880
gtgctgcttc gcggcggatt ttcaggcttt ccaactgggc atccatttgt ttgacttcac    26940
cgtcagcatt atcacgctga atttcccact cctgacggcg gcggcggtag gcttccgaac    27000
ggctgatttt gtctgcggaa tattgggaag ctgtggcaga aagcgacatc acggaggcgg    27060
aagcacgcag tgctgccccc caacgactgc cgccacaagc taaaccgaac acgtttggca    27120
ctaaatcggc caccccttcc gctattgaaa gcacctgccc ggccagagac tgacctgccg    27180
ctgcatcaag cagtgacatt gcccgctgtt ctccgtggtt gatatcctcg tcatacagct    27240
gctggtatt ttccagacga ttttgtgcac tgcggcggct ctctgccaat acagcaatat   27300
cagcatccac ttcatcgaca gttcgttgct gaatacggat gctctgtgtc gccagttcca    27360
taccctgctg tagtagcagc gtggtgagtt catcggcatc atcatgctct gccatactga    27420
gcagagaggt gccgaactgg gttaattgcg ctaccagatt gcgggtccgc tccagcatca    27480
```

```
ccgggaagcg gtataacgac aatgtgccgg gcagcactgc actaccgccc tgagaggcct   27540
gtaccatact ggtgagcagc gctttcggat cggtaggctc ggcgtaaatc gccagcgata   27600
acggctgtcc gtcaatggaa agattatggc gcaggttaaa caggcgcaaa cgcagggttt   27660
gccagtaatc ggtgagcgcc gggttatatt ccggcaggaa caaacccacc aacgagttag   27720
cggtacggag attcttggaa accccaccac ggcccagcat cgtaagatcc tgctgataag   27780
ccgcctgcac ggtttgactc gccgccccgg aaagggacgg tgctgcccac tgttggctac   27840
cgtaatcctc cggctcatca ccgagcaatt ctaaagtacg cacataccac attttggctt   27900
cattcaacgc atcgcgggtc agttctcgat aggccatatc gccgcgcaga ataagttgat   27960
ccaacaggcg cataaaggtg gcaatcttgt agtgcattgg gtcattttgg gcgacggcat   28020
ccggatcgat ggcatccagc ggattggcat tccaggaggt ggtctcttcc agcggccggc   28080
agttccagat ccaggggcg atttctccgt taacgatata gccggcggga ttgtagacgt    28140
agtttatcca ttgtgtggct cgtcgaatt gttttcctg tagcaaacgc tggaagcaca     28200
tcatcggggt gtaatagaac aattcccagt aatagagggc gctggcacta ttgaaatcca   28260
tcggggcgga atagcccgtt gcgatagaaa cattcaaaaa tcctttgtat ttcttgatat   28320
ttttcacgat cccctgttgc gtcattcctg aatcatgatc agcatcgtta attaatacaa   28380
attgctgttt tgtctcatca aaataaaaga aagcagattc ccaagtgttg tcataggtaa   28440
ttttctggta tccaaccccc aatctgacac cttcatgcat gtaataccct tcggcataag   28500
ggacaaacag tgtcatactg gtttccgacg tatcggtaaa cattccgctg taataaggct   28560
gccttcccgt gttaccgcca acattcccaa tatggatttt aaaccaccgc tcatcgccat   28620
gttcagcagg tcatatttta ggcagaacaa agttggcaaa gaagccttct cccaacggag   28680
gttccggtaa ccgctgggtt tccattgtca ggatagtatc aatgcccgtg tttgctctgg   28740
ataccagttg agaagccagc agggtattaa gacgaatacg atacaccccg agctgcatat   28800
attgggcacc cgaatgagtt tcacgcagaa acagaatatc ttccggatta taatttaccc   28860
gtttcaccga taatgtttgc ttgatcttac ccagcactcg cccgtctttg ctttggtct    28920 caaaaacgat atccagagga gcaatattat tggtaaaggc caacgatgaa gcatcgattt   28980
ccagtggctt aaaggtgtac ggcatagcat caaaactgtt tgccggcaag gaagcaatat   29040
ggtcactggc cgtaaaggtg tgggttttac tgccagccat caccgtaatt tgatatcgg    29100 tattgttaat gcctgtatca atatccagcc agcggatga ttgataggaa ctaaatatct    29160
ggaagccctg agaattatta ccatcaacag cataactgca cttttttaaaa tcactggttt   29220 tattgctacc aaccgtgaaa acggtgttta aaattgtgtt tggagaaaat ggaaactcga   29280
acaatctggc ataataatta ttttcaactg gtgttagaat caaacgccta gtgtaatctg   29340
cgttcatcaa gtggccttga actgatgcaa tatagttttt cgttttatta taaacggtga   29400
tcggcccccc cagatcagag taaccgccat aatgtttaac ggtatttgcg atgataaatg   29460
cattgccgta ctgggacttt ccatccaccc ccgtcagttt catggcgctg atttgtttgt   29520
ttctgatgac attgccactg ccatcatatc tgacagtgaa agcggcgtta tgtagcgtaa   29580
tagcaaggtt atcgctggag tatttactgg ttatctgcgg aatattcccg ttctccatca   29640
ccgtcagact atcatcaccg atggcagaac ccatattcaa cgaggcaggc acttcaaaat   29700
cctgcgcgaa acgatagctg gccttttctta ccaagtcgtt gccttgagta tgaatgatat   29760
caaaggtatt tttcagttgg ctgtaacggc tgagtgctgt gttctccatc tttttgaagg   29820
```

```
agccatcgcc gtaaatggtc atgcctgcca cattttatt gctgccgcca aaatccgagt    29880
aactcttccc ggttttgtag acaaacacca gcagagtgtc ctcgccctga aagcctgatg    29940
cggccagcgc cagccgttca gtgtcaggtt ttttgtcagt gaccgcctcc acctgcgttg    30000
tgatatcgta agaccagggg gcactccaac tgccatcatg acgcagaaac gccagtttca    30060
gagtaaaacg gtcataggtt tccaccggat cagtaccatt tttcgccact tcctcttttt    30120
ctacccagat aaggtgcaaa cgttccctga atatgaccgg acgtattgca tccttgtagg    30180
ggttgaccgc tgtatcaatc ttcgtccact ctttccaggc attggcggcc agttcacccg    30240
cctgcatccg tgatatatcc acgttacgcc agtagtattc cggcaggttc tcccgcgttt    30300
ggccgacaaa ccaggtcagt ccggtgttgc tgttgacgtt gtcgtgatag gcgctgacaa    30360 cttttcagatc cgccacggtt tcaaagcggg tcaggtaagt tttaaaggca tcctccactg    30420
tgtcccggct aagtttactc tggctgatat tttccagcag ttcatccatc atccgggtct    30480
gcccgatacg ctgggttggg tcaatgtaat tttccggata ataaaccagc cgcgacaccc    30540
cgccccaggt gctgtaacgg ttattcaccg tccagtcggt aaaaaactgg cgggttgaca    30600
catcggcacg ggcattaggc tctatccgat tcagcgcccg gttgatgtag agctgaatac    30660
cggcaatggc ctctgccagt cgggtggttt ttatggcaga agagacctga ttatcaatca    30720
ggaaatagct gtacaggtca tcccggctgt gcagggacac cccttctggc tggatattcg    30780
ccagaaacca attgcacagc acgctactca ggcgctccgc ggtataatcc gccagcgtct    30840
gagcctgttg tgtactgagt ccggcttcca tattttctgc cagtgtctgc cactcatccc    30900
aggaaggcag attcgactcg gctttgttta atgcagtcac gtaacggata ttcaccagcg    30960 tacgataac cgacggcatc gtgtgcagtg ctgatgccac atctatccac tgcaacacgg    31020
tgttgatatc ctgccaacac tgaagctggt tcacgccggc ggaaaccatg gcctgcgtta    31080
ccatactgat gtccagcccc atcacggagg ccagtctgtc ggccgtgagt gtctgctggc    31140
gcagcatatc cagcgtgtca gagccgggat tgcccagccc attaatccac tggtggaatc    31200
ggtagagtga gaatagcgta tcaatattgt gctgtccggc aggttgattt tttgccccca    31260
gcacggcgaa tccggagatg accagcacgg atagctccgc ttcactgagg cgcagtgtct    31320
gtacggaaag cgataactgt gccatcacat ggcagaattg taccaattgg gtggtttcat    31380
tggcatttaa cgactctttc aataccagtg tcataaaccc ggcaatatct aagccacccg    31440
gccgcaggtt atcggtccac aacaggatat accgtgccat atccggtgac gccagatgca    31500
gcgttgcagc aataaacggc gcgagaattt cagcctgcag ctcccgattg tgactctgtg    31560
ccatatcttc actaatactc ggtcggaggt tattgagcag attactgatt ccggtgaaa    31620 tattcccgct aaactctggc gtacataata accagatcgc ttcagtggtg atttccgcct    31680
cagtcagcca ctgcgtcacc tgatacagcc agataaccag ccgtggcaac tccccggaag    31740
acaaagaagc cgttgttttg ccattgaacg gcgaaagacc ataaagcata cacagttcat    31800
tgaccgtcag ctgatggaca cgggccagta acgtgaggcg atacagtgaa gagataacga    31860
agacagaaag tgtgatggta ttttgggcgt ccagcacacc cgccagtttg cctaactgat    31920
acagttcacc actgttgacc cccagaccac gcatcagggc tgaacgggca aggtagatt    31980 gctcttcatc cggatcaatg ctgaccgtgt tgccgtcggc ttcaaagatt ttcccttca    32040 gcggcggtgt attaaagaga cggttaaaat gactgacact gtcatcgtcg gcatattgat    32100
taatgaccga tccgttcagt acctgtgcat catcaaagct cagtgcataa cggtgactgt    32160
agaacagagt atagaaaact ttggtcagaa cggagtcgtt gatgatgcct tgtgcattgt    32220
```

```
cactgcgtac gatagtttgc agttcattcg gtgaaagccc gctagtcagg cacaagcgaa   32280
tggctttatt cagtttgagc gcaaatatag tcaggggata agactcaaaa gtgaatattc   32340
cgccgccctg atttgtggcg ctggtggaag acgtatagcg ataggcgtat atctttacac   32400 cgttttgta ttcagaatca gatatgttac ttagataatt acttttaaaa ttcgtattgg    32460
ctattagagg accggaaagg ctgccgacaa tgccacttgg ccctgcgttt tttctaagag   32520
tagccccaaa ttctcttgat accttaaaat tagcacgtat aaagaactga ttatttcctt   32580
catacatcaa atcaaagtaa tttatatttt tatcataatc atctgttttt acacgtgtta   32640
ttttgtaagc ttcgagttta ctttcattat tgaccactaa acccgttgag atattatcca   32700
cataagcaga ggtgctgtca gaatagccat tctgcaacat cccgaggtat ttttgcacct   32760
cagaaagttc aagaccataa tacttggcta tccatgattg tgacgcgaaa ttttcgggcg   32820
tgatattttc actgaagttt tgcgcaaata aagcatcagc gttcttttcc gtaatctctt   32880
cggtcaaaat gttataaagc tccggagaaa tattggccag aatcgccagt aatgaagccc   32940
cttccgcctg ccccatcacc tcaggattac gggacagcgc tgacagtgta ctgtcatggg   33000
tcataatgac ctgacggata gtctcgtaag gctgatggta aggggtatca atggcctgac   33060
ggtaagttga caggctctcc atcaatgcgt ccgaatcacc tccggtcttg cgggtaatat   33120
gctccagcaa cagttcgtta gacagtgtca gggtggaaat ttctgtatcc atattactct   33180
ggctcagagt cagatcagcc agatccggac ggcgattatc aagatgataa gcagagcttg   33240
aaaaatgtaa gtccttcgct tcacgataca attcggtgag atagccagcc ggtgaaaaca   33300
tggaagccac tgaacccggt ttcacaaagg aagaagaacg ggcaccaaac atttcatcat   33360
aactgcgtga aacgctgtct cgttcaatac cgagtcggat agcaccggat aattgtgggt   33420
tggcacgggt aaaaatacgc gcttccagca agcgattatt tttttctgc tctatagttt    33480 catgatagag atggcgagcc tctccccaac tgagctggtc atcaaagatt tttctcagtt   33540
cactgaagga taaatattgc agatccgcaa gagtcatcgt ctgaccgtcg cgagtgggac   33600
tgattttatt gagtaataca gccgtgctat acataataac ctcaattatt ttataaaata   33660
gtgttgtcag ttaagagttc atctgaagat ttagtgctta ttttgtaagt cattattcta   33720
ttcacattgt aattatttgt tttatctgag attaatgata ttaaagagga tgctattgta   33780
aatggcggaa tagaatacga ttttctactg aaatttcatt ttaatcataa aatttataac   33840
tgactttaat gttacagtcg taatcgtatat tgtgtcatgt tggcatcctc ttcatctgcc   33900
ttaaaataaa gtagggtacc aaaaggaata catacttgaa tccaagattg agcacaaatc   33960
cacatattca gcttattaaa gataattaaa ttttatttat cataaataaa taggataacg   34020
gccctggatt ctgaccaggc gaggccaaaa gtcgatgaag ctaagttacg gttgaacaaa   34080 tttgttact ggttaaatgg gcacaaactc tttatataaa taaatagcat attgtaacga    34140
gtaattaaaa aatgaaaatc cagcttacct ggttattcat tcattaacaa acacaaaat    34200 atttatgcca acggcactta gaattaaata atttttcttta tcaacttttta cgttaacttc   34260 atttgataaa agtaagatcc catgattttt caagatcctt attcggttat aactgaccag   34320
attgggaaaa tcaaccttaa tgtctcatgt gaaataaaat attgtccaag tgatttattg   34380
ttttgtatta taattcagtc tctttttatca acatctaact taagtcctca agagaaatta   34440
attgcaaatc ggtcaccata accggctaat aatgtattga tctcatattc cattgtttcc   34500
tgagtccagg tgataaaacg tcgccagtgg tatttagcct ccctccagac gatttcaatc   34560
```

```
aaattcagtt ctgggctgta ggcgggaagg taaagtaaaa gcaggttgtg ctctcgtaac    34620
cagcgatttt taagttttc atcgatccca tgatggatag gcgcattatc taacacgaca     34680
aatgtcaggc gatgctcgcc ttgttgggcg acctgctcta aaaaatcaat gacattactt    34740
cgcgtgacac tgcttgatat tatctgataa aacagcctgt tatcagtgta atttagcgca    34800
cctagcactg accgtctgac agagctttgc ggctctgctt catggggctt acctcgtgga    34860
ctccatccat attggaccgg tgggcaggcg gaaaaacccg cctcatcaag atagagcagc    34920
cgataatgac ctgcccgtgc gcccgcctta attttattca gtaaggcggc ttttcagca     34980 aattccgttt tattgcgttt ttttaagcg acaggcgggg gcgttatag gggagtccct      35040 gttttttcag ggtattcgcc agcgtttcaa gcgtacaggg cagggaaccc tgcctggctt    35100
cgacgcacgt cagggactct gcgctggcgg cttcgagcgc agtggcaatc atgtcaggcg    35160
tcatggcgag ataccggcct ccggcatgac cccctaataa tcccgctatc cctgaatggt    35220
gccacatgtg aacccaatta tagataaccc ggagactgca tccgatttca gcggtgatct    35280
gggacggctt gatccctctg gcaagcatga gcaaacccgt tcctcgcgta cgaatgtccc    35340
ggtgtgggta ttcaaagcg agtggttgca atgtgattcg ttcaggctca gaaggatta     35400 tcttcgagtt cataagaaca ggcagaaagt caggttatcg tgttatcgat tataacagta    35460
atgcagataa tttatctgat taacttaatt tattttttgca ataaacgttt ttagcaccat   35520
gaaaaataat aagaaagaat cctgattatg ttgagagagt atacaaaagt ataaaaatgg   35580
cgaattaaat caccattctg atagtgacaa ttattcccctt actttatag tataattttt    35640 attgaactct ttccctgcgt acattgtacc caaagtaaat cctaccactt caattttat    35700 caattctgtc ttcttttgggg tacctgttat attttatatga tgataatctt ttcttatttc   35760 ttttttttcca ccctatagga aagaactatc ttttggattc catgttagtc ctgagccagt   35820
aggatgaatt tttacccaaa cgcttttttc attcaatgca cctcctgtga tggtaattga    35880
tgcctgatat ggttcattta tcactgcatc aggaagaaac tctgattttg gtaaaacttt   35940
tggcgttgga ttaccacaac cataaagtaa aaaaataaaa ataattaata ttttttttcat   36000 gttatttcat tggtttaaaa accaaccctc aaaaaatatg gttgagtaca taatctagtg   36060
atttgttttt tttaatttga tgttccactt taccccatga aaacagattt aaatttacat   36120
attgattcag atctgaatta tttgtgatat tttctttctc atagttttct actactcctt    36180
cccaaactat ccaatgattt tttcctgatg tttctatgtc accaaaatct gataacattc    36240
ctgctgaaat caaagtaaca acatgatatc ctttgtttata gtaatcacta agagttacta    36300
tgtcatttat attagaatgg gataagccga cattactaaa tacttttca taccctgatt      36360 tttcaaacca ttctgtcaat tttccccaca ttgtaatacc agctacttca tcatcaacct    36420
catcataact catcatcata ttttctgaat ctcttaggct tgccaatgtc agccaatcta    36480
acccagatat tctttcacca tattgattat aaaaagtacc tttaggatgt cggcaaccct    36540
cacccagctt aatttccagt tgaccaattt tagttcggcc atattgccat aattctcgtg    36600
cagcttgctc ataaatatct ggtctatcta ttggcaggca ataaaaaaaa gcggcagggc    36660
cacataaact tgctccattt tgatccggat aagttctttt cgatacccctg tcctgtattt   36720 atgattcaat tttactttt tcaaatggat cgtgtgggtg accaatggga tattctttgg    36780
caataaaagt ccgttcagga atggtgattt taattcgac ggtattatcc ccgtcgctga    36840
caggttttgt ttcaactgta ctttcaaaat aacaggcatt ttcccgtttt ttctccgaac   36900
aggctttacc ggaagttaat tcaccgaggg tatacatttt cttaaaatgg gtttgcagtg   36960
```

```
ccggaaatat atttgagcca tgtttgcggt gaagcataat ttgcataata taaatcacag   37020
aaagatcgtc gtctatttcc tgcgtgatat gctgttgtgt ttcataatta ctctgtagtt   37080
tctcctgaaa aacatcaagc aagatatgga aatttccttt tgcattctga cgataaatgg   37140
ttaagtcata aagcaggttt tcaacaggta cgttggattc tattttttgtc tgaacggtat   37200 aggctggcat ggtattaatc ctttaaaata tgaaattcaa gtttattttt gtcatccgta   37260
agatgccatt gggtgtaacc ttgtttatca gtctttcctt ctttttatctg accatccggc   37320 aggcaaaccc gatacttgcg ttcggttaaa agattgccgt catcatccac acaacgataa   37380
cgggcatgat gtttagcggg ttttaccggg gtttcttcaa ccagcggctt cttaagtggc   37440
ttaacattcg agaccccaga taaaagcggc ttgccttctt cacttccggc taattgcgta   37500
atgctgtagc ccgaagtccc tgcggcgatg tggttgcatg aaatggactt ataatcgagc   37560
atcaccactt catggggtat cgcaccatta tcattgattg aatgcggata attataggaa   37620
atatccacaa tcgtggcact ggtcagcttg atttcataaa agaactccag ttgtcccatc   37680
tggcttgtcc tgtaatgcac aaaactggca tccagcaaac aggggagagg atttatcaat   37740
gggtttcaca aaactgacgg gttgatgatt aacattctgg tcacggctca tcgaatgatt   37800
caggctcaat acctgtattt gatcacacag gccagctggt ttgcccgttc gttaagctgg   37860
cggtaggtca gtgttgcgcc ttcaaacacc agtgccccgt tatccggtgt cctttccacc   37920
tgagcttcaa acagttgtgg cagggttttg tcctgtggat aaggcgcatc ggtctggttc   37980
caggtatgca gcagggtatg cgctcctgt gcggacagaa tatccagcgc ggacagcggt   38040
tgtttctggt ctgccacaaa ggcttccagt acccgttgat agctctctgt cagcctgacg   38100
atggtggttt cattaaacag gctgactgcg taattcaggc aaccggtaat ctcggtttgt   38160
ccgtcggaca taaacaggct gaggtcaaac ttggcggggc tgtatagcgg ctcatccaga   38220
gtcaccggcc tgaatggcag gcggttgtct gacggatttt ctccaaagct ctgtaaacca   38280
aacatgatct gaaaaatcgg gtggcgggcg gtatcacgtt caatattcag ggcatcaagg   38340
agctgttcaa acggcatatc ctgataggcc ttggcttcgg caacctgttt atgggtctgc   38400
tcaatcaggg cttccacgct gacagtctgt tgcaactgtg cccttaagac cagtgaattg   38460
acaaacatcc caatcagggg ctgagtctgg gcatggtggc ggttatcggt tggcgtcccc   38520
agtacgatat cgttttgccc ggataatttt gccagcgtga cataaaaggc actgagcaac   38580
acggtataca gggtggtttc ctgtgttttt gccagactcc ttaactgttc agatagccgg   38640
gtattcagcc caaaactgaa attacatccc tgataattca cctgagccgg tctggggtaa   38700
tcggttggca aggccagtga ttcatagttg gctaaagcct gttgccagta agcgagttgg   38760
cgttcgcgcc ggtccccttg taaatagttg cgttgccatg cggcataatc gccataggtg   38820
atatccagcg ctgcaagctg gctgtcgcgg tttttcccgca aggactggta aatttccgcc   38880
agttcagcca taaagatatc aattgaccag ccatcaatgg cgatatggtg ccataacaat   38940
aataaatagt ggctgtcaga aaccggatag tgacacaggc gcagactggg ttctgtggtc   39000
agatc                                                                39005

<210> SEQ ID NO 7
<211> LENGTH: 1533
<212> TYPE: DNA
<213> ORGANISM: Xenorhabdus nematophilus

<400> SEQUENCE: 7
```

-continued

```
gatcaggtat tcaatcaacc caaactgttt gatgaacctt tctttgttga taatcgtact      60
tttgattaca acgccattcg tggtaatgat gcacgaacaa ttaagcaact gtgcgccgga     120
ttgaaaatca ccgtagccac cttccaattg ttagctgagc aggtaaacac cgcctttcat     180
ctgccatccg gcaaattaac ctgttcactg cctgttattt cagcgcttta tcgtctggtg     240
actgttcctc ggttatttaa tttaaccgct gaacagggca tgatgctgat taacgcatta     300
aatgccagcg agaaattctc acctcatatt ctggctggtg agcctcgatt aagcctgtta     360
acaacagagg gttcagatac cacagaggtc gatttattgg atgttattct gatgttggaa     420
gaagttgctg tctggctgca acagagcaaa ctgaaaccgg aagaattctg cctgatgctg     480
caaagtgtta tgttgccggt ggttgccacg gacagcagtg tgacattctt cgacaacctg     540
ctgcaaggca ttcccaaaac cttactcaca gaagataact caacgcagg ggatatcccc      600
agactccctg aaggagaaac ctggtttgac aaactttcga tgctgataac cagcgatgga     660
ctcgtcaacg tttaccctct cagttggggc cagagtgatg aagattatct gaaatcagta     720
ttgacacctg tcgtcgaaaa aatcattagc gatccaaaca gtgtgattat cactgtttcc     780
gcattaacac aggtcattac tcaggcgaaa actgcgcagg aagatctggt ttccgccagc     840
gtgacacggg aatacggtac tggacgtgat atcgttcctt ggttattacg ctggattggc     900
agcagtgttc ccgatttcct tggcaaaatt tatatacaag cgcaaccag aggcggacac      960
ttgcgcactc cgccggatat cagcgctgaa ttactgcata tcacctatca tctggcgatg    1020
aataacatgc tgattaagca gttacgactc aaagctcaaa tcatttcatt acgtatcatc    1080
atgcctgaat ggctcggatt accaacgata gatggcagtc cgctatccgt gcatgaaatt    1140
tgggcactga ccggttccg taactgggcg accagctcat tgttcagtga agacgagtta     1200
atcgagtatt ttgcttttgc caatcagccg gagcaggacg ttcgtaacga tgaagatttt    1260
aatcgggact gtgctgaaaa gcttgccgac atactggaat gggatgccga tgaaattgag    1320
ctggcaaccc gacattttga tcctgcccca gcacgtgcca gaaatatggg acaaattgac    1380
tggctgcgtc gtgtcatggc gttgtcgcgt cagactggcc tgtcagtgac accgttaatg    1440
acagccgcaa cgttaccgcc tttcccgccc tatgaccaga taacccatgt cggtgaagcg    1500
gtgattgcgg caacccagta cccatcagag gag                                 1533
```

<210> SEQ ID NO 8
<211> LENGTH: 511
<212> TYPE: PRT
<213> ORGANISM: Xenorhabdus nematophilus

<400> SEQUENCE: 8

```
Asp Gln Val Phe Asn Gln Pro Lys Leu Phe Asp Glu Pro Phe Val
1               5                   10                  15

Asp Asn Arg Thr Phe Asp Tyr Asn Ala Ile Arg Gly Asn Asp Ala Arg
            20                  25                  30

Thr Ile Lys Gln Leu Cys Ala Gly Leu Lys Ile Thr Val Ala Thr Phe
        35                  40                  45

Gln Leu Leu Ala Glu Gln Val Asn Thr Ala Phe His Leu Pro Ser Gly
    50                  55                  60

Lys Leu Thr Cys Ser Leu Pro Val Ile Ser Ala Leu Tyr Arg Leu Val
65                  70                  75                  80

Thr Val Pro Arg Leu Phe Asn Leu Thr Ala Glu Gln Gly Met Met Leu
                85                  90                  95

Ile Asn Ala Leu Asn Ala Ser Glu Lys Phe Ser Pro His Ile Leu Ala
```

```
                100                 105                 110
Gly Glu Pro Arg Leu Ser Leu Leu Thr Thr Glu Gly Ser Asp Thr Thr
            115                 120                 125

Glu Val Asp Leu Leu Asp Val Ile Leu Met Leu Glu Glu Val Ala Val
130                 135                 140

Trp Leu Gln Gln Ser Lys Leu Lys Pro Glu Glu Phe Cys Leu Met Leu
145                 150                 155                 160

Gln Ser Val Met Leu Pro Val Val Ala Thr Asp Ser Ser Val Thr Phe
                165                 170                 175

Phe Asp Asn Leu Leu Gln Gly Ile Pro Lys Thr Leu Leu Thr Glu Asp
            180                 185                 190

Asn Phe Asn Ala Gly Asp Ile Pro Arg Leu Pro Glu Gly Glu Thr Trp
        195                 200                 205

Phe Asp Lys Leu Ser Met Leu Ile Thr Ser Asp Gly Leu Val Asn Val
    210                 215                 220

Tyr Pro Leu Ser Trp Gly Gln Ser Asp Gly Asp Tyr Leu Lys Ser Val
225                 230                 235                 240

Leu Thr Pro Val Val Glu Lys Ile Ile Ser Asp Pro Asn Ser Val Ile
                245                 250                 255

Ile Thr Val Ser Ala Leu Thr Gln Val Ile Thr Gln Ala Lys Thr Ala
            260                 265                 270

Gln Glu Asp Leu Val Ser Ala Ser Val Thr Arg Glu Tyr Gly Thr Gly
        275                 280                 285

Arg Asp Ile Val Pro Trp Leu Leu Arg Trp Ile Gly Ser Ser Val Pro
    290                 295                 300

Asp Phe Leu Gly Lys Ile Tyr Ile Gln Gly Ala Thr Arg Gly Gly His
305                 310                 315                 320

Leu Arg Thr Pro Pro Asp Ile Ser Ala Glu Leu Leu His Ile Thr Tyr
                325                 330                 335

His Leu Ala Met Asn Asn Met Leu Ile Lys Gln Leu Arg Leu Lys Ala
            340                 345                 350

Gln Ile Ile Ser Leu Arg Ile Ile Met Pro Glu Trp Leu Gly Leu Pro
        355                 360                 365

Thr Ile Asp Gly Ser Pro Leu Ser Val His Glu Ile Trp Ala Leu Ser
    370                 375                 380

Arg Phe Arg Asn Trp Ala Thr Ser Ser Leu Phe Ser Glu Asp Glu Leu
385                 390                 395                 400

Ile Glu Tyr Phe Ala Phe Ala Asn Gln Pro Glu Gln Asp Val Arg Asn
                405                 410                 415

Asp Glu Asp Phe Asn Arg Asp Cys Ala Glu Lys Leu Ala Asp Ile Leu
            420                 425                 430

Glu Trp Asp Ala Asp Glu Ile Glu Leu Ala Thr Arg His Phe Asp Pro
        435                 440                 445

Ala Pro Ala Arg Ala Arg Asn Met Gly Gln Ile Asp Trp Leu Arg Arg
    450                 455                 460

Val Met Ala Leu Ser Arg Gln Thr Gly Leu Ser Val Thr Pro Leu Met
465                 470                 475                 480

Thr Ala Ala Thr Leu Pro Pro Phe Pro Pro Tyr Asp Gln Ile Thr His
                485                 490                 495

Val Gly Glu Ala Val Ile Ala Ala Thr Gln Tyr Pro Ser Glu Glu
            500                 505                 510

<210> SEQ ID NO 9
```

<211> LENGTH: 4173
<212> TYPE: DNA
<213> ORGANISM: Xenorhabdus nematophilus

<400> SEQUENCE: 9

```
atgagttcag ttacccaacc tattgaagag cgtttactgg aatcacagcg cgacgcactg      60
ctggatttct atctcggaca ggtcgttgcc tattcacctg acatgacaag tcagcgcgac     120
aaaattaagg atattgacga tgcctgcgac tacctcctgc tggatctgct gacttccgcc     180
aaagtcaaag cgacacgact ttcacttgcg accaattcat tgcagcaatt tgtgaaccgc     240
gtgtcactga atattgaacc cggttttgttt atgaccgcgg aagagagcga aaattggcag     300
gaatttgcga atcgttataa ttactggtct gcggatcgct tattacggac ttatccggaa     360
agctatctgg aaccctgtt acgcctgaat aaaacagaat tcttcttcca actgaaagt      420
gcccttaatc agggaaaaat taccgaagat tccgtacaac aagcggtgct cggttatctg     480
aataattttg aagatgtcag taacctgaaa gttatcgcag gttatgaaga tggtgttaac     540
atcaaacgcg ataagttctt ctttgtcgga cgtacccgta cacagccata ccaatattac     600
tggcgttcac tgaatctttc gatacgccat cctgataccg atgcgttatc tcccaatgcc     660
tggagcgagt ggaaacctat tgacctgcca ttgggcagcg tagaccccaa tttgatacgc     720
cccattttcc tgaataatcg cctgtatatt gcctggacgg aagttgaaga acagtctgaa     780
actaaagata caactgcgtt atcactgcat aaccaaaacg ttgagcctag tgcgggtgat     840
tgggttcctc ccacaccgtt cctgacccgg atcaaaatcg cttatgccaa atatgatggc     900
agctggagta cacccaccat tctgcgcgaa gacaatctgc aataccggat ggcccagatg     960
gttgctgtga tggatataca gcaagacccg cataacccgt ttctggctct ggttccgttt    1020
gtccgtcttc aggggacaga taagaaaggt aaggattatg attatgacga agccttcggt    1080
tatgtctgcg atacactgct ggtagaaatt actgatttgc cggatgacga atatgctgat    1140
ggacgaaaag gaaaatatgt cggcaacctg gtctggtatt actcacgtga acacaaggat    1200
gcagaaggca atcctatcga ttaccgtact atggtgctct atccggcaac ccggaagaa     1260
cgctttccta ttgccggaga agccaaaccg gaaggaagcc ctgattttgg caaagacagt    1320
atcaaactga ttgtcaattt tgttcatggc actgatgaca cactggagat tgtcgctcaa    1380
tctgacttta gtttggtgc gatagaagat catcaatatt acaacggttc tttccggctg    1440
atgcacgata atactgtctt ggatgaacaa ccactggtac tgaacgaaaa agttcctgat    1500
ttaacctatc catcaatcaa gctggggtcg gataatcgaa tcaccctgaa agccgaactt    1560
ctctttaagc ccaaaggtgg tgttggcaat gaaagtgcca gctgtactca agagttcaga    1620
atcggtatgc acattcgcga actgattaaa ctcaatgaac aggatcaggt gcaattcctt    1680
tccttccccg cagatgaaac tggtaacgcg ccacaaaaca ttcgccttaa tacactgttt    1740
gcaaaaaaac tgatcgccat tgccagtcag ggtatcccgc aggtactgag ctggaataca    1800
cagcttatta ctgaacaacc catacccggt tcattcccta cgccgattga tttaaatggc    1860
gcaaatggga tctatttctg ggaactgttt ttccatatgc catttctggt cgcgtggcga    1920
ctgaatatcg aacaacgatt aaaagaggcc accgaatggc tgcactatat tttaatccg     1980
ctggaagatg aacttgttca ggccagcaac caagtaaac cgcgttactg gaattcacgg     2040
ccaattattg atcctccacc caccgtgtac cggatgttaa ttgaaccaac cgatccggat    2100
gccattgcag ccagtgaacc cattcactac cggaaagcaa tattccgttt ctatgtcaag    2160
aatctgttag atcagggaga catggaatac cgtaagctga catccagtgc acgtactgtc    2220
```

```
gccaagcaga tctatgactc cgtcaatatg ttactgggta ccagccctga tattctgctc    2280
gcggcaaact ggcaaccccg tacgctgcaa gatgtggctc tgtatgaaaa cagtgaagca    2340
cgggcacagg agttaatgct tactgtcagc agcgtgccac ttctgcctgt gacatatgat    2400
acatccgtct ctgccgcacc gtctgattta tttgtcaaac ctgttgatac ggaatatctc    2460
aaactgtggc aaatgttgga tcagcgtcta tataacttac gtcataacct gaccttggat    2520
ggtaaagagt ttccggccgg attatacgat gaacccatca gcccgcaaga tctgctcagg    2580
cagcgttacc agcgtgttgt ggctaatcgt atggcgggca tgaaacgccg gcaatcccg    2640 aattatcgtt tcaccccgat catgagccgg gcaaaagagg ccgcagaaac gctgattcag    2700
tacggcagca cgttactgag tttgctggag aaaaaagaca ataccgattt tgaacacttc    2760
cgtatgcagc agcaactggg gctgtacagc tttacccgca atctgcaaca gcaagcgatt    2820
gacatgcaac aggcttcatt ggatgcactg accatcagcc gacgggccgc tcaggagcgc    2880
cagcaacact ataaatcgct ctatgatgaa acatctcca tcaccgagca ggaagttatc    2940
gcattacaat caagagcggc tgaaggtgtg atcgctgccc agtcagccgc cactgcggcc    3000
gctgtggcgg atatggttcc caatattttc ggtctggccg tcgggggat ggtctttggc    3060 ggtatgcttc gggcaatcgg tgaaggaata cgcattgacg ttgaaagtaa aaatgccaaa    3120
gccaccagcc tgagcgtgtc agaaaattac cgtcgccgtc agcaagaatg ggagctgcaa    3180
tacaaacagg cggatatcaa cattgaggag atcgacgcac agattggtat ccagcaacgc    3240
caactgaata tcagcacaac ccaactggca caattggaag cccagcatga gcaggatcaa    3300
gtcctgctgg agtactattc aaaccgtttt accaatgatg cgttatacat gtggatgatc    3360
agccaaatct ccgggcttta cctgcaagcc tatgatgcgg ttaattccct ctgtttactg    3420
gccgaagcct cctggcagta cgaaacaggt cagtatgata tgaatttcgt ccaaagtggt    3480
ctctggaatg atctttatca ggggctgctg gtcggagaac atctgaaatt agccttacaa    3540
cggatggatc aggcgtattt gcaacataac accagacgtc tggagatcat aaaaaaccata   3600 tcggtaaaat cattactgac atcatcacag tgggaaattg gcaagagtac gggttcattc    3660
actttcttac tgagcgccga aatgttcttg cgcgattatc cgacccacgc tgatcggcgt    3720 ataaaaccg tagcgctgtc attgcccgca ttgctggggc cttatgaaga tgtacgggct    3780
tcactggtac aactcagcaa tacgctttac agtactgctg acttaaaaac tatcgattat    3840
ttgcttaacc ccttggaata caccaaaccc gaaaacgttt tgctgaacgt acaggctaat    3900
caaggtgtgg tgatttcaac ggccatggaa gacagcggca tgttcaggct caattttgat    3960
gatgaacttt tcctgccttt tgaagggaca ggcgccattt cacagtggaa gttggaattc    4020
ggttccgatc aggatcagct gctggagtcg ctgagcgata ttatcctcca tctgcgttat    4080
accgcgcgtg atgtgagtgg cggaagtaat gagttcagcc agcaggttcg tagccgtctg    4140
aataaacatc aattaaaaca agacaattct aac                                 4173
```

<210> SEQ ID NO 10
<211> LENGTH: 1391
<212> TYPE: PRT
<213> ORGANISM: Xenorhabdus nematophilus

<400> SEQUENCE: 10

```
Met Ser Ser Val Thr Gln Pro Ile Glu Glu Arg Leu Leu Glu Ser Gln
1               5                   10                  15
```

-continued

```
Arg Asp Ala Leu Leu Asp Phe Tyr Leu Gly Gln Val Val Ala Tyr Ser
         20                  25                  30

Pro Asp Met Thr Ser Gln Arg Asp Lys Ile Lys Asp Ile Asp Asp Ala
             35                  40                  45

Cys Asp Tyr Leu Leu Asp Leu Leu Thr Ser Ala Lys Val Lys Ala
 50                  55                  60

Thr Arg Leu Ser Leu Ala Thr Asn Ser Leu Gln Gln Phe Val Asn Arg
 65                  70                  75                  80

Val Ser Leu Asn Ile Glu Pro Gly Leu Phe Met Thr Ala Glu Glu Ser
                 85                  90                  95

Glu Asn Trp Gln Glu Phe Ala Asn Arg Tyr Asn Tyr Trp Ser Ala Asp
             100                 105                 110

Arg Leu Leu Arg Thr Tyr Pro Glu Ser Tyr Leu Glu Pro Leu Leu Arg
             115                 120                 125

Leu Asn Lys Thr Glu Phe Phe Phe Gln Leu Glu Ser Ala Leu Asn Gln
130                 135                 140

Gly Lys Ile Thr Glu Asp Ser Val Gln Gln Ala Val Leu Gly Tyr Leu
145                 150                 155                 160

Asn Asn Phe Glu Asp Val Ser Asn Leu Lys Val Ile Ala Gly Tyr Glu
             165                 170                 175

Asp Gly Val Asn Ile Lys Arg Asp Lys Phe Phe Phe Val Gly Arg Thr
             180                 185                 190

Arg Thr Gln Pro Tyr Gln Tyr Tyr Trp Arg Ser Leu Asn Leu Ser Ile
             195                 200                 205

Arg His Pro Asp Thr Asp Ala Leu Ser Pro Asn Ala Trp Ser Glu Trp
             210                 215                 220

Lys Pro Ile Asp Leu Pro Leu Gly Ser Val Asp Pro Asn Leu Ile Arg
225                 230                 235                 240

Pro Ile Phe Leu Asn Asn Arg Leu Tyr Ile Ala Trp Thr Glu Val Glu
                 245                 250                 255

Glu Gln Ser Glu Thr Lys Asp Thr Thr Ala Leu Ser Leu His Asn Gln
             260                 265                 270

Asn Val Glu Pro Ser Ala Gly Asp Trp Val Pro Thr Pro Phe Leu
             275                 280                 285

Thr Arg Ile Lys Ile Ala Tyr Ala Lys Tyr Asp Gly Ser Trp Ser Thr
             290                 295                 300

Pro Thr Ile Leu Arg Glu Asp Asn Leu Gln Tyr Arg Met Ala Gln Met
305                 310                 315                 320

Val Ala Val Met Asp Ile Gln Gln Asp Pro His Asn Pro Phe Leu Ala
                 325                 330                 335

Leu Val Pro Phe Val Arg Leu Gln Gly Thr Lys Lys Gly Lys Asp
             340                 345                 350

Tyr Asp Tyr Asp Glu Ala Phe Gly Tyr Val Cys Asp Thr Leu Leu Val
             355                 360                 365

Glu Ile Thr Asp Leu Pro Asp Asp Glu Tyr Ala Asp Gly Arg Lys Gly
             370                 375                 380

Lys Tyr Val Gly Asn Leu Val Trp Tyr Tyr Ser Arg Glu His Lys Asp
385                 390                 395                 400

Ala Glu Gly Asn Pro Ile Asp Tyr Arg Thr Met Val Leu Tyr Pro Ala
                 405                 410                 415

Thr Arg Glu Glu Arg Phe Pro Ile Ala Gly Glu Ala Lys Pro Glu Gly
             420                 425                 430

Ser Pro Asp Phe Gly Lys Asp Ser Ile Lys Leu Ile Val Asn Phe Val
```

```
                435            440            445
His Gly Thr Asp Asp Thr Leu Glu Ile Val Ala Gln Ser Asp Phe Lys
    450                455                460

Phe Gly Ala Ile Glu Asp His Gln Tyr Tyr Asn Gly Ser Phe Arg Leu
465                470                475                480

Met His Asp Asn Thr Val Leu Asp Glu Gln Pro Leu Val Leu Asn Glu
                485                490                495

Lys Val Pro Asp Leu Thr Tyr Pro Ser Ile Lys Leu Gly Ser Asp Asn
            500                505                510

Arg Ile Thr Leu Lys Ala Glu Leu Leu Phe Lys Pro Lys Gly Gly Val
        515                520                525

Gly Asn Glu Ser Ala Ser Cys Thr Gln Glu Phe Arg Ile Gly Met His
    530                535                540

Ile Arg Glu Leu Ile Lys Leu Asn Glu Gln Asp Gln Val Gln Phe Leu
545                550                555                560

Ser Phe Pro Ala Asp Glu Thr Gly Asn Ala Pro Gln Asn Ile Arg Leu
                565                570                575

Asn Thr Leu Phe Ala Lys Lys Leu Ile Ala Ile Ala Ser Gln Gly Ile
            580                585                590

Pro Gln Val Leu Ser Trp Asn Thr Gln Leu Ile Thr Glu Gln Pro Ile
        595                600                605

Pro Gly Ser Phe Pro Thr Pro Ile Asp Leu Asn Gly Ala Asn Gly Ile
    610                615                620

Tyr Phe Trp Glu Leu Phe Phe His Met Pro Phe Leu Val Ala Trp Arg
625                630                635                640

Leu Asn Ile Glu Gln Arg Leu Lys Glu Ala Thr Glu Trp Leu His Tyr
                645                650                655

Ile Phe Asn Pro Leu Glu Asp Glu Leu Val Gln Ala Ser Asn Gln Gly
            660                665                670

Lys Pro Arg Tyr Trp Asn Ser Arg Pro Ile Ile Asp Pro Pro Thr
        675                680                685

Val Tyr Arg Met Leu Ile Glu Pro Thr Asp Pro Asp Ala Ile Ala Ala
    690                695                700

Ser Glu Pro Ile His Tyr Arg Lys Ala Ile Phe Arg Phe Tyr Val Lys
705                710                715                720

Asn Leu Leu Asp Gln Gly Asp Met Glu Tyr Arg Lys Leu Thr Ser Ser
                725                730                735

Ala Arg Thr Val Ala Lys Gln Ile Tyr Asp Ser Val Asn Met Leu Leu
            740                745                750

Gly Thr Ser Pro Asp Ile Leu Leu Ala Ala Asn Trp Gln Pro Arg Thr
        755                760                765

Leu Gln Asp Val Ala Leu Tyr Glu Asn Ser Glu Ala Arg Ala Gln Glu
    770                775                780

Leu Met Leu Thr Val Ser Val Pro Leu Leu Pro Val Thr Tyr Asp
785                790                795                800

Thr Ser Val Ser Ala Ala Pro Ser Asp Leu Phe Val Lys Pro Val Asp
                805                810                815

Thr Glu Tyr Leu Lys Leu Trp Gln Met Leu Asp Gln Arg Leu Tyr Asn
            820                825                830

Leu Arg His Asn Leu Thr Leu Asp Gly Lys Glu Phe Pro Ala Gly Leu
        835                840                845

Tyr Asp Glu Pro Ile Ser Pro Gln Asp Leu Leu Arg Gln Arg Tyr Gln
    850                855                860
```

```
Arg Val Val Ala Asn Arg Met Ala Gly Met Lys Arg Ala Ile Pro
865                 870                 875                 880

Asn Tyr Arg Phe Thr Pro Ile Met Ser Arg Ala Lys Glu Ala Glu
                885                 890                 895

Thr Leu Ile Gln Tyr Gly Ser Thr Leu Leu Ser Leu Leu Glu Lys Lys
                    900                 905                 910

Asp Asn Thr Asp Phe Glu His Phe Arg Met Gln Gln Gln Leu Gly Leu
                915                 920                 925

Tyr Ser Phe Thr Arg Asn Leu Gln Gln Gln Ala Ile Asp Met Gln Gln
930                 935                 940

Ala Ser Leu Asp Ala Leu Thr Ile Ser Arg Arg Ala Ala Gln Glu Arg
945                 950                 955                 960

Gln Gln His Tyr Lys Ser Leu Tyr Asp Glu Asn Ile Ser Ile Thr Glu
                965                 970                 975

Gln Glu Val Ile Ala Leu Gln Ser Arg Ala Ala Glu Gly Val Ile Ala
                980                 985                 990

Ala Gln Ser Ala Ala Thr Ala Ala  Ala Val Ala Asp Met  Val Pro Asn
                995                 1000                1005

Ile Phe  Gly Leu Ala Val Gly  Gly Met Val Phe  Gly  Gly Met Leu
1010                1015                1020

Arg Ala  Ile Gly Glu Gly Ile  Arg Ile Asp Val Glu  Ser Lys Asn
1025                1030                1035

Ala Lys  Ala Thr Ser Leu Ser  Val Ser Glu Asn Tyr  Arg Arg Arg
1040                1045                1050

Gln Gln  Glu Trp Glu Leu Gln  Tyr Lys Gln Ala Asp  Ile Asn Ile
1055                1060                1065

Glu Glu  Ile Asp Ala Gln Ile  Gly Ile Gln Gln Arg  Gln Leu Asn
1070                1075                1080

Ile Ser  Thr Thr Gln Leu Ala  Gln Leu Glu Ala Gln  His Glu Gln
1085                1090                1095

Asp Gln  Val Leu Leu Glu Tyr  Tyr Ser Asn Arg Phe  Thr Asn Asp
1100                1105                1110

Ala Leu  Tyr Met Trp Met Ile  Ser Gln Ile Ser Gly  Leu Tyr Leu
1115                1120                1125

Gln Ala  Tyr Asp Ala Val Asn  Ser Leu Cys Leu Leu  Ala Glu Ala
1130                1135                1140

Ser Trp  Gln Tyr Glu Thr Gly  Gln Tyr Asp Met Asn  Phe Val Gln
1145                1150                1155

Ser Gly  Leu Trp Asn Asp Leu  Tyr Gln Gly Leu Leu  Val Gly Glu
1160                1165                1170

His Leu  Lys Leu Ala Leu Gln  Arg Met Asp Gln Ala  Tyr Leu Gln
1175                1180                1185

His Asn  Thr Arg Arg Leu Glu  Ile Ile Lys Thr Ile  Ser Val Lys
1190                1195                1200

Ser Leu  Leu Thr Ser Ser Gln  Trp Glu Ile Gly Lys  Ser Thr Gly
1205                1210                1215

Ser Phe  Thr Phe Leu Leu Ser  Ala Glu Met Phe Leu  Arg Asp Tyr
1220                1225                1230

Pro Thr  His Ala Asp Arg Arg  Ile Lys Thr Val Ala  Leu Ser Leu
1235                1240                1245

Pro Ala  Leu Leu Gly Pro Tyr  Glu Asp Val Arg Ala  Ser Leu Val
1250                1255                1260
```

```
Gln Leu Ser Asn Thr Leu Tyr Ser Thr Ala Asp Leu Lys Thr Ile
    1265                1270                1275

Asp Tyr Leu Leu Asn Pro Leu Glu Tyr Thr Lys Pro Glu Asn Val
    1280                1285                1290

Leu Leu Asn Val Gln Ala Asn Gln Gly Val Val Ile Ser Thr Ala
    1295                1300                1305

Met Glu Asp Ser Gly Met Phe Arg Leu Asn Phe Asp Asp Glu Leu
    1310                1315                1320

Phe Leu Pro Phe Glu Gly Thr Gly Ala Ile Ser Gln Trp Lys Leu
    1325                1330                1335

Glu Phe Gly Ser Asp Gln Asp Gln Leu Leu Glu Ser Leu Ser Asp
    1340                1345                1350

Ile Ile Leu His Leu Arg Tyr Thr Ala Arg Asp Val Ser Gly Gly
    1355                1360                1365

Ser Asn Glu Phe Ser Gln Gln Val Arg Ser Arg Leu Asn Lys His
    1370                1375                1380

Gln Leu Lys Gln Asp Asn Ser Asn
    1385                1390

<210> SEQ ID NO 11
<211> LENGTH: 1944
<212> TYPE: DNA
<213> ORGANISM: Xenorhabdus nematophilus

<400> SEQUENCE: 11
atgtctcaaa atgtttatcg ataccctca attaaagcga tgtctgacgc cagcagcgaa      60
gtaggcgcat ctctggttgc ctggcagaat caatctggtg gtcaaacctg gtatgtcatt     120
tatgatagcg cggtttttaa aaacatcggc tgggttgaac gctggcatat tcccgaccgc     180
aatatttcac ctgatttacc ggtttatgag aatgcctggc aatatgtccg tgaggcgaca     240
ccggaagaaa ttgccgatca cggtaacccc aatacgcctg atgtaccgcc gggagaaaaa     300
accgaggtat tgcaatatga tgcactcaca gaagaaacct atcagaaggt gggatataaa     360
cctgacggca gcgaactcc tttgagttat tcttcagcac gtgttgccaa gtccctgtac     420
aacgaatatg aagttgatcc ggaaaataca gaaccgctgc ctaaagtctc tgcctatatt     480
actgactggt gccagtatga tgcgcgtttg tcgccagaaa cccaggataa cactgcgctg     540
accagcgacg atgcccccgg ccgtggtttt gatctggaaa aaatcccgcc taccgcctac     600
gaccgcctga ttttcagttt tatggccgtc aacggtgata aaggcaagtt atccgaacgg     660
attaatgagg ttgttgacgg gtggaaccgg caagcagaag ccagcagtgg ccagattgcc     720
cctattacat taggccatat tgtacccgtt gatccttatg gtgatttagg caccacacgc     780
aatgtcggtc tggacgcgga tcagcgccgt gatgccagcc gaagaatttt cttgcaatat     840
tacaatcagg atgcagcctc cggtttactg ggggattgc gtaatctgaa agcgcgagca     900
aaacaggcag ggcacaagct ggaactcgca ttcagtatcg gcggctggag tatgtcaggg     960
tatttctctg tgatggccaa agatcctgag caacgtgcta catttgtgag tagcatcgtc    1020
gacttcttcc ggcgttttcc catgtttact gcggtggata tcgactggga ataccccggc    1080
gccacaggtg aagaaggtaa tgaattcgac ccggaacatg atggcccaaa ctatgttttg    1140
ttagtgaaag agctgcgtga agcactgaac atcgcctttg gaacccgggc cgtaaagaa    1200 atcacgatag cctgtagcgc cgtcgttgcc aaaatggaga gtccagcttc aaagaaatc    1260 gcaccttatt tagacaatat ctttgtgatg acctacgact tctttggtac cggttgggca    1320
```

-continued

```
gaatacatcg gtcaccatac taacctgtat cccccagat atgaatatga cggcgataac     1380
cctcctccgc ccaatcctga tcgggacatg gattactcgg ctgatgaggc gatccgcttt     1440
ttactgtcac aaggtgtaca accggagaaa attcacctcg gatttgctaa ctatggacgt     1500
tcatgtctgg gtgctgatct gacaactcgc cgctataaca aacaggaga gccactgggc     1560 acgatggaaa aaggtgctcc ggaattcttc tgtctgctga ataaccaata cgatgcggaa     1620
tatgaaattg cacgcgggaa aaatcagttt gaactggtga cagacacgga aaccgacgct     1680
gacgcactct ttaatgctga cggtggtcac tggatttcac tggatacgcc ccgcactgtg     1740
ctgcataagg gaatttatgc aaccaaaatg aaattgggcg gatcttctc ttggtcaggc     1800 gatcaggatg atggcctgtt ggcaaatgct gctcacgaag gtttgggtta cttacctgta     1860
cgcggaaaag agaagattga tatgggaccg ttatataaca aaggacgtct cattcagctt     1920
cctaaagtaa cccgtcgtaa atcg                                            1944
```

<210> SEQ ID NO 12
<211> LENGTH: 648
<212> TYPE: PRT
<213> ORGANISM: Xenorhabdus nematophilus

<400> SEQUENCE: 12

```
Met Ser Gln Asn Val Tyr Arg Tyr Pro Ser Ile Lys Ala Met Ser Asp
1               5                   10                  15

Ala Ser Ser Glu Val Gly Ala Ser Leu Val Ala Trp Gln Asn Gln Ser
            20                  25                  30

Gly Gly Gln Thr Trp Tyr Val Ile Tyr Asp Ser Ala Val Phe Lys Asn
        35                  40                  45

Ile Gly Trp Val Glu Arg Trp His Ile Pro Asp Arg Asn Ile Ser Pro
    50                  55                  60

Asp Leu Pro Val Tyr Glu Asn Ala Trp Gln Tyr Val Arg Glu Ala Thr
65                  70                  75                  80

Pro Glu Glu Ile Ala Asp His Gly Asn Pro Asn Thr Pro Asp Val Pro
                85                  90                  95

Pro Gly Glu Lys Thr Glu Val Leu Gln Tyr Asp Ala Leu Thr Glu Glu
            100                 105                 110

Thr Tyr Gln Lys Val Gly Tyr Lys Pro Asp Gly Ser Gly Thr Pro Leu
        115                 120                 125

Ser Tyr Ser Ser Ala Arg Val Ala Lys Ser Leu Tyr Asn Glu Tyr Glu
    130                 135                 140

Val Asp Pro Glu Asn Thr Glu Pro Leu Pro Lys Val Ser Ala Tyr Ile
145                 150                 155                 160

Thr Asp Trp Cys Gln Tyr Asp Ala Arg Leu Ser Pro Glu Thr Gln Asp
                165                 170                 175

Asn Thr Ala Leu Thr Ser Asp Asp Ala Pro Gly Arg Gly Phe Asp Leu
            180                 185                 190

Glu Lys Ile Pro Pro Thr Ala Tyr Asp Arg Leu Ile Phe Ser Phe Met
        195                 200                 205

Ala Val Asn Gly Asp Lys Gly Lys Leu Ser Glu Arg Ile Asn Glu Val
    210                 215                 220

Val Asp Gly Trp Asn Arg Gln Ala Glu Ala Ser Ser Gly Gln Ile Ala
225                 230                 235                 240

Pro Ile Thr Leu Gly His Ile Val Pro Val Asp Pro Tyr Gly Asp Leu
                245                 250                 255

Gly Thr Thr Arg Asn Val Gly Leu Asp Ala Asp Gln Arg Arg Asp Ala
```

```
                260                 265                 270
Ser Pro Lys Asn Phe Leu Gln Tyr Tyr Asn Gln Asp Ala Ala Ser Gly
            275                 280                 285

Leu Leu Gly Gly Leu Arg Asn Leu Lys Ala Arg Ala Lys Gln Ala Gly
        290                 295                 300

His Lys Leu Glu Leu Ala Phe Ser Ile Gly Gly Trp Ser Met Ser Gly
305                 310                 315                 320

Tyr Phe Ser Val Met Ala Lys Asp Pro Glu Gln Arg Ala Thr Phe Val
                325                 330                 335

Ser Ser Ile Val Asp Phe Phe Arg Arg Phe Pro Met Phe Thr Ala Val
            340                 345                 350

Asp Ile Asp Trp Glu Tyr Pro Gly Ala Thr Gly Glu Glu Gly Asn Glu
        355                 360                 365

Phe Asp Pro Glu His Asp Gly Pro Asn Tyr Val Leu Leu Val Lys Glu
    370                 375                 380

Leu Arg Glu Ala Leu Asn Ile Ala Phe Gly Thr Arg Ala Arg Lys Glu
385                 390                 395                 400

Ile Thr Ile Ala Cys Ser Ala Val Val Ala Lys Met Glu Lys Ser Ser
                405                 410                 415

Phe Lys Glu Ile Ala Pro Tyr Leu Asp Asn Ile Phe Val Met Thr Tyr
            420                 425                 430

Asp Phe Phe Gly Thr Gly Trp Ala Glu Tyr Ile Gly His His Thr Asn
        435                 440                 445

Leu Tyr Pro Pro Arg Tyr Glu Tyr Asp Gly Asp Asn Pro Pro Pro
    450                 455                 460

Asn Pro Asp Arg Asp Met Asp Tyr Ser Ala Asp Glu Ala Ile Arg Phe
465                 470                 475                 480

Leu Leu Ser Gln Gly Val Gln Pro Glu Lys Ile His Leu Gly Phe Ala
                485                 490                 495

Asn Tyr Gly Arg Ser Cys Leu Gly Ala Asp Leu Thr Thr Arg Arg Tyr
            500                 505                 510

Asn Arg Thr Gly Glu Pro Leu Gly Thr Met Glu Lys Gly Ala Pro Glu
        515                 520                 525

Phe Phe Cys Leu Leu Asn Asn Gln Tyr Asp Ala Glu Tyr Glu Ile Ala
    530                 535                 540

Arg Gly Lys Asn Gln Phe Glu Leu Val Thr Asp Thr Glu Thr Asp Ala
545                 550                 555                 560

Asp Ala Leu Phe Asn Ala Asp Gly Gly His Trp Ile Ser Leu Asp Thr
                565                 570                 575

Pro Arg Thr Val Leu His Lys Gly Ile Tyr Ala Thr Lys Met Lys Leu
            580                 585                 590

Gly Gly Ile Phe Ser Trp Ser Gly Asp Gln Asp Gly Leu Leu Ala
        595                 600                 605

Asn Ala Ala His Glu Gly Leu Gly Tyr Leu Pro Val Arg Gly Lys Glu
    610                 615                 620

Lys Ile Asp Met Gly Pro Leu Tyr Asn Lys Gly Arg Leu Ile Gln Leu
625                 630                 635                 640

Pro Lys Val Thr Arg Arg Lys Ser
                645

<210> SEQ ID NO 13
<211> LENGTH: 7569
<212> TYPE: DNA
<213> ORGANISM: Xenorhabdus nematophilus
```

<400> SEQUENCE: 13

```
atgataaaag ttaatgaact gttagataag ataaatagaa aaaggtctgg tgatacttta      60
ttattgacaa acatttcgtt tatgtctttc agcgaatttc gtcataggac aagtggaact     120
ctgacgtggc gagaaacaga cttttatat caacaggctc atcaggaatc aaaacagaat     180
aaacttgaag aactgcgcat tttgtcccgt gctaatccac aactggctaa taccactaac     240
cttaatatta caccgtcaac cctaaacaat agttacaaca gttggtttta tggccgtgcc     300
caccgttttg taaaaccggg atcaattgct tccatatttt caccagcggc ttatttaaca     360
gaattatatc gggaagcgaa agattttcat cctgacaatt ctcaatatca cctgaataaa     420
cgacgccccg acattgcttc actggcactg acacagaata atatgatga agaaatttcc      480
acattatcct tatctaatga attactgctg cataatattc agacgttaga gaaaactgac     540
tataacggtg taatgaaaat gttgtccact taccggcaaa ccggcatgac accctatcat     600
ctgccgtatg agtcagcccg tcaggcaatt ttattgcaag ataaaaacct caccgcattt     660
agccgtaata cagacgtagc ggaattaatg gacccaacat cgctactggc tattaagact     720
gatatatcgc ctgaattgta tcaaatcctt gtagaagaaa ttacaccgga aaattcaaca     780
gaactgatga agaaaaattt cggtacagat gatgtactga ttttaagag ttatgcttct     840
ttggctcgct actacgattt gtcttatgat gaactcagtt tatttgtcaa tctctccttc     900
ggtaagaaaa atacaaatca acagtataag aatgagcaac tgataacatt ggtcaatgac     960
gggaatgata cggcaacggc aagattgatt aagcgaaccc gcaaagattt ctacgattca    1020
catttaaact atgcagaact aattccaatc aaagaaaatg aatacaaata taatttcagt    1080
gtaaaaaaaa cagaacctga ccacttggat tttcgtctcc agaatggaga taagaatat    1140
atataccaag ataaaaattt cgtccccatt gctaataccc attacagtat tcccattaaa    1200
ttgacgacag agcaaatcac caacggtata acactccgct tatggcgagt taaaccaaat    1260
ccgtcggatg ctatcaatgc caatgcatac tttaaaatga tggagttccc cggtgatata    1320
ttcctgttaa agctgaataa agcgattcgt ttgtataaag ccacaggcat atctccagaa    1380
gatatctggc aagtaataga agtatttat gatgacttaa ccattgacag caatgtgttg    1440
ggtaagctgt tttatgttca atattatatg cagcactata atattagcgt cagcgatgcg    1500
ctggtattgt gtcattcaga tatcagccaa tattccacta acaacaacc cagtcatttt    1560
acaatactgt tcaatacacc gctattaaat ggccaagagt tttctgctga taataccaaa    1620
ctggatttaa cccccggtga atcaaaaaac cattttttatt tgggaataat gaaacgtgct    1680
ttcagagtga atgatactga actgtataca ttatggaagc tggctaatgg cggaacaaat    1740
ccagaattta tgtgttccat cgagaacctg tctctgcttt atcgcgttcg tctgctggca    1800
gacattcatc atctgacagt gaatgaatta tccatgttgt tgtcggtttc tccctatgtg    1860
aacacgaaaa ttgccctttt ttctgataca gcattaacgc aattaatcag ctttctgttc    1920
caatgcaccc agtggctgac aacacagaaa tggtctgtca gtgatgtgtt tctgatgacc    1980
acggataatt acagcactgt ccttacgccg gatattgaaa accttatcac gacactaagt    2040
aatggattat caacactttc actcggtgat gacgaactga tccgtgcagc tgccccgctg    2100
attgctgcca gcattcaaat ggattcagcc aagacagcag aaactatttt gctgtggatt    2160
aatcagataa aaccacaagg actgacattc gatgatttca tgattattgc ggctaaccgt    2220
gatcgctcag agaatgaaac cagcaacatg gtggctttt gtcaggtact ggggcaactt    2280
```

```
tctctgattg tgcgcaatat tggactcagc gaaaacgaac tgaccctgtt ggtgacaaaa    2340
ccggagaaat tccaatcaga aaccacagca ctgcaacatg atctccccac tttgcaagcg    2400
ctgacccgct tccatgctgt gatcatgcgt tgtggaagct acgcgacaga aatcttaaca    2460
gcattggaac taggagcgct gactgccgaa caattggcgg tggcgttaaa atttgatgct    2520
caggttgtga cacaagcatt gcaacagacc ggtttgggag tgaataccct taccaactgg    2580
agaactatag atgtcactct gcaatggctg gatgtcgctg ctacattggg tattaccccg    2640
gatggtgttg ctgcactcat aaaattaaaa tatatcggtg aaccagaaac cccgatgcca    2700
acatttgatg attggcaagc cgccagtact ttgttgcagg cgggactgaa cagtcaacaa    2760
tccgaccagc ttcaggcatg gctggatgaa gccacgacga cagcggccag tgcttactac    2820
atcaaaaata gtgcacctca acagattaag agccgggatg agttgtacag ctatctgctg    2880
attgataacc aagtttctgc ccaagtgaaa accacccgtg tggcagaagc cattgccagc    2940
attcagttat atgtcaaccg ggcgttgaat aatgttgaag aaaagtatc aaagccagtg    3000 aaaacccgtc agttcttctg cgactgggaa acctacaatc gacggtatag cacctgggcc    3060
ggcgtatctg aactggccta ttatccggaa aactatatcg accccacgat tcgtattggt    3120
cagacaggta tgatgaacaa cctgttacag caactttccc aaagtcagtt aaatatcgat    3180
accgttgaag atagctttaa aaattatctg accgcatttg aagatgtcgc taacttgcag    3240
gtgattagcg gatatcatga cagtatcaat gtcaatgagg gactcactta tttaattggt    3300
tatagccaga cagaacccag aatatatatt ggcgcaatg tcgatcacca aaagtgccag    3360
cacggtcaat ttgctgccaa tgcctgggga gaatggaaaa aaattgaaat acccatcaat    3420
gtatggcagg aaaatatcag acctgttatt tacaagtctc gtttgtattt actgtggctg    3480
gaacaaaaag agctgaaaaa tgaaagtgaa gatggcaaga tagatatcac tgattatata    3540
ttaaaactgt cacatattcg ttatgatggc agctggagct caccgtttaa ttttaatgtg    3600
actgataaaa tagaaaacct gatcaataaa aaagccagca ttggtatgta ttgttcttct    3660
gattatgaaa aagacgtcat tattgtttat ttccatgaga aaaaagacaa ttattctttt    3720
aatagtcttc ctgcaagaga agggatgacc attaaccctg atatgacatt atccattctc    3780
acagaaaatg atttagacgc cattgttaag agcacattat cagaacttga taccaggaca    3840
gaatacaaag tcaacaatca atttgctaca gattatttgg ccgaatataa ggaatctata    3900
accacaaaaa ataaattagc cagttttacc ggaaatattt ttgatctctc gtatatatca    3960
ccaggaaatg gtcatattaa tttaacgttc aatccttcaa tggaaattaa ttttttcaaaa    4020 ggcaatatat ataatgatga ggttaaatac ctgttatcga tggtagaaga tgaaacggtt    4080
attttatttg attatgatag acatgatgaa atgcttggaa agaagaaga agttttttcat    4140 tatggaactt tggattttat tatttccatc gatcttaaaa atgccgaata ttttagagtg    4200
ttaatgcatc taagaaccaa ggaaaaaatt cctagaaaat cagaaattgg agttggtata    4260
aattatgatt atgaatcaaa tgatgctgaa ttcaaacttg atactaacat agtattagat    4320
tggaaagata acacaggagt atggcatact atatgtgaat catttactaa tgatgtttca    4380
atcattaata acatgggaaa tattgcggca ctgttccttc gcgaggatcc atgtgtgtat    4440
ttatgttcaa tagccacaga tataaaaatt gcttcatcta tgatcgaaca gatccaagat    4500
aaaaacatta gtttttatt aaaaaatggc tctgatattc tagtggagtt aaatgctgaa    4560
gaccatgtgg catctaaacc ttcacacgaa tctgaccca tggtatatga ttttaatcaa    4620
gtaaaagttg atattgaagg ctatgatatt cctctggtga gcgagtttat tattaagcaa    4680
```

```
cccgacggcg gttataacga tattgttatt gaatcgccaa ttcatataaa actaaaatcc    4740
aaagatacaa gtaacgttat atcactgcat aaaatgccat caggcacaca atatatgcag    4800
attggccctt acagaacccg gttaaatact ttattttcca gaaaattagc tgaaagagcc    4860
aatattggta ttgataatgt tttaagtatg gaaacgcaaa atttaccaga gccgcaatta    4920
ggtgaagggt tttatgcgac atttaagttg ccccccctaca ataaagagga gcatggtgat   4980
gaacgttggt ttaagatcca tattgggaat attgatggca attctgccag acaaccttat    5040
tacgaaggaa tgttatctga tattgaaacc acagtaacgc tctttgttcc ctatgctaaa    5100
ggatattaca tacgtgaagg tgtcagatta ggggttgggt acaaaaaaat tatctatgac    5160
aaatcctggg aatctgcttt cttttatttt gatgagacga aaaatcaatt tatattcatt    5220
aatgatgccg atcatgattc gggaatgaca caacagggga tagtaaaaaa tatcaaaaaa    5280
tataaagggt ttattcatgt cgttgtcatg aaaaataaca ctgaacccat ggatttcaac    5340
ggcgccaatg caatctattt ctgggaattg ttcattaca cgcccatgat ggtattccag     5400
cgcttattgc aagagcagaa ttttaccgaa tcgacacgct ggctgcgcta tatctggaac    5460
ccggccggat attcggttca gggtgaaatg caggattatt actggaacgt ccgcccattg    5520
gaggaagata cgtcctggaa tgccaatccg ctggattcgg tcgatcctga cgccgttgcc    5580
cagcatgatc cgatgcacta taaagtggct acctttatga aaatgctgga tttgttgatt    5640
acccgcggag atagcgccta tcgccagctt gaacgtgata ccttaaacga agctaaaatg    5700
tggtatgtac aggcgctcac tttattgggt gatgagcctt attttttcatt ggataacgat   5760
tggtcagagc cacggctgga agaagctgcc agccaaacaa tgcggcatca ttatcaacat    5820
aaaatgctgc aactgcgtca gcgcgctgca ttacccacga aacgtacggc aaattcgtta    5880
accgcattgt tcctccctca aattaataaa aaactgcaag ttactggca gacattgacg     5940
caacgcctct ataacttacg ccataacctg acaatcgacg tcagccact gtcattatct     6000
ctctatgcca cgcccgcaga tccgtccatg ttactcagtg ctgccatcac tgcttcacaa    6060
ggcggcggcg atttacctca tgcagtgatg ccgatgtacc gttttccggt gattctggaa    6120
aatgccaagt ggggggtaag ccagttgata caatttggca ataccctgct cagcattact    6180
gaacggcagg atgcagaagc cttggctgaa atactgcaaa ctcaaggcag tgagttagcc    6240
ctgcaaagta ttaaaatgca ggataaggtc atggctgaaa ttgatgctga taaattggcg    6300
cttcaagaaa gccgtcatgg tgcacagtct cgttttgaca gtttcaatac gctgtacgac    6360
gaagatgtta acgctggtga aaaacaagcg atggatcttt acctctcttc atcggtcttg    6420
agcaccagcg gcacagccct gcatatggcc gccgccgcgg cagatctcgt ccccaatatt    6480
tacggttttg ctgtgggagg ttcccgtttt ggggcgcttt tcaatgccag tgcgattggt    6540
atcgaaattt ctgcgtcagc aacacgtatt gccgcagaca aaatcagcca atcagaaata    6600
taccgtcgcc gtcggcaaga gtgggaaatt cagcgcaata atgcggaagc tgagataaaa    6660
caaattgatg ctcaattagc gacgctggct gtacgtcgtg aagcggcagt attacaaaaa    6720
aactatctgg aaactcagca ggcacaaact caggcgcagt tagcctttct gcaaagtaaa    6780
ttcagtaatg cagcgctata caactggctc cgtggaaggt tgtccgctat ttattatcag    6840
ttttatgatt tggcggtctc actctgttta atggcagagc aaacttatca gtatgaattg    6900
aataatgcgg cagcacactt tattaaacca ggtgcctggc atgggactta tgcgggttta    6960
ttagcgggtg aaaccctgat gctgaattta gcacagatgg aaaaaagcta tttggaaaaa    7020
```

-continued

```
gatgaacggg cactggaggt caccagaacc gtttctctgg ctgaagtgta tgctggtctg   7080
acagaaaata gtttcatttt aaaagataaa gtgactgagt tagtcaatgc aggtgaaggc   7140
agtgcaggca caacgcttaa cggtttgaac gtcgaaggga cacaactgca agccagcctc   7200
aaattatcgg atctgaatat tgctaccgat tatcctgacg gtttaggtaa tacacgccgt   7260
atcaaacaaa tcagtgtgac attacctgcc cttttagggc cttatcagga tgttcgggca   7320
atactaagtt atggcggcag cacaatgatg ccacgtggct gcaaagcgat tgcgatctca   7380
catggcatga atgacagtgg tcaattccag atggatttca atgatgccaa gtacctgcca   7440
tttgaagggc ttcctgtggc cgatacaggc acattaaccc tcagttttcc cggtatcagt   7500
ggtaaacaga aaagcttatt gctcagcctg agcgatatca ttctgcatat ccgttacacc   7560
attcgttct                                                           7569
```

```
<210> SEQ ID NO 14
<211> LENGTH: 2523
<212> TYPE: PRT
<213> ORGANISM: Xenorhabdus nematophilus

<400> SEQUENCE: 14

Met Ile Lys Val Asn Glu Leu Leu Asp Lys Ile Asn Arg Lys Arg Ser
1               5                   10                  15

Gly Asp Thr Leu Leu Thr Asn Ile Ser Phe Met Ser Phe Ser Glu
            20                  25                  30

Phe Arg His Arg Thr Ser Gly Thr Leu Thr Trp Arg Glu Thr Asp Phe
        35                  40                  45

Leu Tyr Gln Gln Ala His Gln Glu Ser Lys Gln Asn Lys Leu Glu Glu
    50                  55                  60

Leu Arg Ile Leu Ser Arg Ala Asn Pro Gln Leu Ala Asn Thr Thr Asn
65                  70                  75                  80

Leu Asn Ile Thr Pro Ser Thr Leu Asn Asn Ser Tyr Asn Ser Trp Phe
                85                  90                  95

Tyr Gly Arg Ala His Arg Phe Val Lys Pro Gly Ser Ile Ala Ser Ile
            100                 105                 110

Phe Ser Pro Ala Ala Tyr Leu Thr Glu Leu Tyr Arg Glu Ala Lys Asp
        115                 120                 125

Phe His Pro Asp Asn Ser Gln Tyr His Leu Asn Lys Arg Arg Pro Asp
    130                 135                 140

Ile Ala Ser Leu Ala Leu Thr Gln Asn Asn Met Asp Glu Glu Ile Ser
145                 150                 155                 160

Thr Leu Ser Leu Ser Asn Glu Leu Leu His Asn Ile Gln Thr Leu
                165                 170                 175

Glu Lys Thr Asp Tyr Asn Gly Val Met Lys Met Leu Ser Thr Tyr Arg
            180                 185                 190

Gln Thr Gly Met Thr Pro Tyr His Leu Pro Tyr Glu Ser Ala Arg Gln
        195                 200                 205

Ala Ile Leu Leu Gln Asp Lys Asn Leu Thr Ala Phe Ser Arg Asn Thr
    210                 215                 220

Asp Val Ala Glu Leu Met Asp Pro Thr Ser Leu Leu Ala Ile Lys Thr
225                 230                 235                 240

Asp Ile Ser Pro Glu Leu Tyr Gln Ile Leu Val Glu Glu Ile Thr Pro
                245                 250                 255

Glu Asn Ser Thr Glu Leu Met Lys Lys Asn Phe Gly Thr Asp Asp Val
            260                 265                 270
```

-continued

```
Leu Ile Phe Lys Ser Tyr Ala Ser Leu Ala Arg Tyr Tyr Asp Leu Ser
        275                 280                 285
Tyr Asp Glu Leu Ser Leu Phe Val Asn Leu Ser Phe Gly Lys Lys Asn
    290                 295                 300
Thr Asn Gln Gln Tyr Lys Asn Glu Gln Leu Ile Thr Leu Val Asn Asp
305                 310                 315                 320
Gly Asn Asp Thr Ala Thr Ala Arg Leu Ile Lys Arg Thr Arg Lys Asp
                325                 330                 335
Phe Tyr Asp Ser His Leu Asn Tyr Ala Glu Leu Ile Pro Ile Lys Glu
                340                 345                 350
Asn Glu Tyr Lys Tyr Asn Phe Ser Val Lys Lys Thr Glu Pro Asp His
            355                 360                 365
Leu Asp Phe Arg Leu Gln Asn Gly Asp Lys Glu Tyr Ile Tyr Gln Asp
        370                 375                 380
Lys Asn Phe Val Pro Ile Ala Asn Thr His Tyr Ser Ile Pro Ile Lys
385                 390                 395                 400
Leu Thr Thr Glu Gln Ile Thr Asn Gly Ile Thr Leu Arg Leu Trp Arg
                405                 410                 415
Val Lys Pro Asn Pro Ser Asp Ala Ile Asn Ala Asn Ala Tyr Phe Lys
            420                 425                 430
Met Met Glu Phe Pro Gly Asp Ile Phe Leu Leu Lys Leu Asn Lys Ala
        435                 440                 445
Ile Arg Leu Tyr Lys Ala Thr Gly Ile Ser Pro Glu Asp Ile Trp Gln
    450                 455                 460
Val Ile Glu Ser Ile Tyr Asp Asp Leu Thr Ile Asp Ser Asn Val Leu
465                 470                 475                 480
Gly Lys Leu Phe Tyr Val Gln Tyr Tyr Met Gln His Tyr Asn Ile Ser
                485                 490                 495
Val Ser Asp Ala Leu Val Leu Cys His Ser Asp Ile Ser Gln Tyr Ser
            500                 505                 510
Thr Lys Gln Gln Pro Ser His Phe Thr Ile Leu Phe Asn Thr Pro Leu
        515                 520                 525
Leu Asn Gly Gln Glu Phe Ser Ala Asp Asn Thr Lys Leu Asp Leu Thr
    530                 535                 540
Pro Gly Glu Ser Lys Asn His Phe Tyr Leu Gly Ile Met Lys Arg Ala
545                 550                 555                 560
Phe Arg Val Asn Asp Thr Glu Leu Tyr Thr Leu Trp Lys Leu Ala Asn
                565                 570                 575
Gly Gly Thr Asn Pro Glu Phe Met Cys Ser Ile Glu Asn Leu Ser Leu
            580                 585                 590
Leu Tyr Arg Val Arg Leu Leu Ala Asp Ile His His Leu Thr Val Asn
        595                 600                 605
Glu Leu Ser Met Leu Leu Ser Val Ser Pro Tyr Val Asn Thr Lys Ile
    610                 615                 620
Ala Leu Phe Ser Asp Thr Ala Leu Thr Gln Leu Ile Ser Phe Leu Phe
625                 630                 635                 640
Gln Cys Thr Gln Trp Leu Thr Thr Gln Lys Trp Ser Val Ser Asp Val
                645                 650                 655
Phe Leu Met Thr Thr Asp Asn Tyr Ser Thr Val Leu Thr Pro Asp Ile
            660                 665                 670
Glu Asn Leu Ile Thr Thr Leu Ser Asn Gly Leu Ser Thr Leu Ser Leu
        675                 680                 685
Gly Asp Asp Glu Leu Ile Arg Ala Ala Ala Pro Leu Ile Ala Ala Ser
```

```
              690             695             700
Ile Gln Met Asp Ser Ala Lys Thr Ala Glu Thr Ile Leu Leu Trp Ile
705                     710                     715             720

Asn Gln Ile Lys Pro Gln Gly Leu Thr Phe Asp Asp Phe Met Ile Ile
                725                     730                 735

Ala Ala Asn Arg Asp Arg Ser Glu Asn Glu Thr Ser Asn Met Val Ala
                740                     745                 750

Phe Cys Gln Val Leu Gly Gln Leu Ser Leu Ile Val Arg Asn Ile Gly
            755                     760                 765

Leu Ser Glu Asn Glu Leu Thr Leu Leu Val Thr Lys Pro Glu Lys Phe
770                     775                     780

Gln Ser Glu Thr Thr Ala Leu Gln His Asp Leu Pro Thr Leu Gln Ala
785                     790                     795             800

Leu Thr Arg Phe His Ala Val Ile Met Arg Cys Gly Ser Tyr Ala Thr
                805                     810                 815

Glu Ile Leu Thr Ala Leu Glu Leu Gly Ala Leu Thr Ala Glu Gln Leu
                820                     825                 830

Ala Val Ala Leu Lys Phe Asp Ala Gln Val Val Thr Gln Ala Leu Gln
            835                     840                 845

Gln Thr Gly Leu Gly Val Asn Thr Phe Thr Asn Trp Arg Thr Ile Asp
850                     855                     860

Val Thr Leu Gln Trp Leu Asp Val Ala Ala Thr Leu Gly Ile Thr Pro
865                     870                     875             880

Asp Gly Val Ala Ala Leu Ile Lys Leu Lys Tyr Ile Gly Glu Pro Glu
                885                     890                 895

Thr Pro Met Pro Thr Phe Asp Asp Trp Gln Ala Ala Ser Thr Leu Leu
                900                     905                 910

Gln Ala Gly Leu Asn Ser Gln Gln Ser Asp Gln Leu Gln Ala Trp Leu
            915                     920                 925

Asp Glu Ala Thr Thr Thr Ala Ala Ser Ala Tyr Tyr Ile Lys Asn Ser
            930                     935                 940

Ala Pro Gln Gln Ile Lys Ser Arg Asp Glu Leu Tyr Ser Tyr Leu Leu
945                     950                     955             960

Ile Asp Asn Gln Val Ser Ala Gln Val Lys Thr Thr Arg Val Ala Glu
                965                     970                 975

Ala Ile Ala Ser Ile Gln Leu Tyr Val Asn Arg Ala Leu Asn Asn Val
                980                     985                 990

Glu Gly Lys Val Ser Lys Pro Val  Lys Thr Arg Gln Phe  Phe Cys Asp
            995                 1000                1005

Trp Glu  Thr Tyr Asn Arg Arg  Tyr Ser Thr Trp Ala  Gly Val Ser
    1010                1015                1020

Glu Leu  Ala Tyr Tyr Pro Glu  Asn Tyr Ile Asp Pro  Thr Ile Arg
    1025                1030                1035

Ile Gly  Gln Thr Gly Met Met  Asn Asn Leu Leu Gln  Gln Leu Ser
    1040                1045                1050

Gln Ser  Gln Leu Asn Ile Asp  Thr Val Glu Asp Ser  Phe Lys Asn
    1055                1060                1065

Tyr Leu  Thr Ala Phe Glu Asp  Val Ala Asn Leu Gln  Val Ile Ser
    1070                1075                1080

Gly Tyr  His Asp Ser Ile Asn  Val Asn Glu Gly Leu  Thr Tyr Leu
    1085                1090                1095

Ile Gly  Tyr Ser Gln Thr Glu  Pro Arg Ile Tyr Tyr  Trp Arg Asn
    1100                1105                1110
```

-continued

Val Asp His Gln Lys Cys Gln His Gly Gln Phe Ala Ala Asn Ala
1115                1120                1125

Trp Gly Glu Trp Lys Lys Ile Glu Ile Pro Ile Asn Val Trp Gln
1130                1135                1140

Glu Asn Ile Arg Pro Val Ile Tyr Lys Ser Arg Leu Tyr Leu Leu
1145                1150                1155

Trp Leu Glu Gln Lys Glu Leu Lys Asn Glu Ser Glu Asp Gly Lys
1160                1165                1170

Ile Asp Ile Thr Asp Tyr Ile Leu Lys Leu Ser His Ile Arg Tyr
1175                1180                1185

Asp Gly Ser Trp Ser Ser Pro Phe Asn Phe Asn Val Thr Asp Lys
1190                1195                1200

Ile Glu Asn Leu Ile Asn Lys Lys Ala Ser Ile Gly Met Tyr Cys
1205                1210                1215

Ser Ser Asp Tyr Glu Lys Asp Val Ile Ile Val Tyr Phe His Glu
1220                1225                1230

Lys Lys Asp Asn Tyr Ser Phe Asn Ser Leu Pro Ala Arg Glu Gly
1235                1240                1245

Met Thr Ile Asn Pro Asp Met Thr Leu Ser Ile Leu Thr Glu Asn
1250                1255                1260

Asp Leu Asp Ala Ile Val Lys Ser Thr Leu Ser Glu Leu Asp Thr
1265                1270                1275

Arg Thr Glu Tyr Lys Val Asn Asn Gln Phe Ala Thr Asp Tyr Leu
1280                1285                1290

Ala Glu Tyr Lys Glu Ser Ile Thr Thr Lys Asn Lys Leu Ala Ser
1295                1300                1305

Phe Thr Gly Asn Ile Phe Asp Leu Ser Tyr Ile Ser Pro Gly Asn
1310                1315                1320

Gly His Ile Asn Leu Thr Phe Asn Pro Ser Met Glu Ile Asn Phe
1325                1330                1335

Ser Lys Gly Asn Ile Tyr Asn Asp Glu Val Lys Tyr Leu Leu Ser
1340                1345                1350

Met Val Glu Asp Glu Thr Val Ile Leu Phe Asp Tyr Asp Arg His
1355                1360                1365

Asp Glu Met Leu Gly Lys Glu Glu Val Phe His Tyr Gly Thr
1370                1375                1380

Leu Asp Phe Ile Ile Ser Ile Asp Leu Lys Asn Ala Glu Tyr Phe
1385                1390                1395

Arg Val Leu Met His Leu Arg Thr Lys Glu Lys Ile Pro Arg Lys
1400                1405                1410

Ser Glu Ile Gly Val Gly Ile Asn Tyr Asp Tyr Glu Ser Asn Asp
1415                1420                1425

Ala Glu Phe Lys Leu Asp Thr Asn Ile Val Leu Asp Trp Lys Asp
1430                1435                1440

Asn Thr Gly Val Trp His Thr Ile Cys Glu Ser Phe Thr Asn Asp
1445                1450                1455

Val Ser Ile Ile Asn Asn Met Gly Asn Ile Ala Ala Leu Phe Leu
1460                1465                1470

Arg Glu Asp Pro Cys Val Tyr Leu Cys Ser Ile Ala Thr Asp Ile
1475                1480                1485

Lys Ile Ala Ser Ser Met Ile Glu Gln Ile Gln Asp Lys Asn Ile
1490                1495                1500

```
Ser Phe Leu Leu Lys Asn Gly Ser Asp Ile Leu Val Glu Leu Asn
1505                1510                1515

Ala Glu Asp His Val Ala Ser Lys Pro Ser His Glu Ser Asp Pro
1520                1525                1530

Met Val Tyr Asp Phe Asn Gln Val Lys Val Asp Ile Glu Gly Tyr
1535                1540                1545

Asp Ile Pro Leu Val Ser Glu Phe Ile Ile Lys Gln Pro Asp Gly
1550                1555                1560

Gly Tyr Asn Asp Ile Val Ile Glu Ser Pro Ile His Ile Lys Leu
1565                1570                1575

Lys Ser Lys Asp Thr Ser Asn Val Ile Ser Leu His Lys Met Pro
1580                1585                1590

Ser Gly Thr Gln Tyr Met Gln Ile Gly Pro Tyr Arg Thr Arg Leu
1595                1600                1605

Asn Thr Leu Phe Ser Arg Lys Leu Ala Glu Arg Ala Asn Ile Gly
1610                1615                1620

Ile Asp Asn Val Leu Ser Met Glu Thr Gln Asn Leu Pro Glu Pro
1625                1630                1635

Gln Leu Gly Glu Gly Phe Tyr Ala Thr Phe Lys Leu Pro Pro Tyr
1640                1645                1650

Asn Lys Glu Glu His Gly Asp Glu Arg Trp Phe Lys Ile His Ile
1655                1660                1665

Gly Asn Ile Asp Gly Asn Ser Ala Arg Gln Pro Tyr Tyr Glu Gly
1670                1675                1680

Met Leu Ser Asp Ile Glu Thr Thr Val Thr Leu Phe Val Pro Tyr
1685                1690                1695

Ala Lys Gly Tyr Tyr Ile Arg Glu Gly Val Arg Leu Gly Val Gly
1700                1705                1710

Tyr Lys Lys Ile Ile Tyr Asp Lys Ser Trp Glu Ser Ala Phe Phe
1715                1720                1725

Tyr Phe Asp Glu Thr Lys Asn Gln Phe Ile Phe Ile Asn Asp Ala
1730                1735                1740

Asp His Asp Ser Gly Met Thr Gln Gln Gly Ile Val Lys Asn Ile
1745                1750                1755

Lys Lys Tyr Lys Gly Phe Ile His Val Val Met Lys Asn Asn
1760                1765                1770

Thr Glu Pro Met Asp Phe Asn Gly Ala Asn Ala Ile Tyr Phe Trp
1775                1780                1785

Glu Leu Phe Tyr Tyr Thr Pro Met Met Val Phe Gln Arg Leu Leu
1790                1795                1800

Gln Glu Gln Asn Phe Thr Glu Ser Thr Arg Trp Leu Arg Tyr Ile
1805                1810                1815

Trp Asn Pro Ala Gly Tyr Ser Val Gln Gly Glu Met Gln Asp Tyr
1820                1825                1830

Tyr Trp Asn Val Arg Pro Leu Glu Glu Asp Thr Ser Trp Asn Ala
1835                1840                1845

Asn Pro Leu Asp Ser Val Asp Pro Asp Ala Val Ala Gln His Asp
1850                1855                1860

Pro Met His Tyr Lys Val Ala Thr Phe Met Lys Met Leu Asp Leu
1865                1870                1875

Leu Ile Thr Arg Gly Asp Ser Ala Tyr Arg Gln Leu Glu Arg Asp
1880                1885                1890

Thr Leu Asn Glu Ala Lys Met Trp Tyr Val Gln Ala Leu Thr Leu
```

-continued

```
        1895                1900                1905

Leu Gly Asp Glu Pro Tyr Phe Ser Leu Asp Asn Asp Trp Ser Glu
        1910                1915                1920

Pro Arg Leu Glu Glu Ala Ala Ser Gln Thr Met Arg His His Tyr
        1925                1930                1935

Gln His Lys Met Leu Gln Leu Arg Gln Arg Ala Ala Leu Pro Thr
        1940                1945                1950

Lys Arg Thr Ala Asn Ser Leu Thr Ala Leu Phe Leu Pro Gln Ile
        1955                1960                1965

Asn Lys Lys Leu Gln Gly Tyr Trp Gln Thr Leu Thr Gln Arg Leu
        1970                1975                1980

Tyr Asn Leu Arg His Asn Leu Thr Ile Asp Gly Gln Pro Leu Ser
        1985                1990                1995

Leu Ser Leu Tyr Ala Thr Pro Ala Asp Pro Ser Met Leu Leu Ser
        2000                2005                2010

Ala Ala Ile Thr Ala Ser Gln Gly Gly Gly Asp Leu Pro His Ala
        2015                2020                2025

Val Met Pro Met Tyr Arg Phe Pro Val Ile Leu Glu Asn Ala Lys
        2030                2035                2040

Trp Gly Val Ser Gln Leu Ile Gln Phe Gly Asn Thr Leu Leu Ser
        2045                2050                2055

Ile Thr Glu Arg Gln Asp Ala Glu Ala Leu Ala Glu Ile Leu Gln
        2060                2065                2070

Thr Gln Gly Ser Glu Leu Ala Leu Gln Ser Ile Lys Met Gln Asp
        2075                2080                2085

Lys Val Met Ala Glu Ile Asp Ala Asp Lys Leu Ala Leu Gln Glu
        2090                2095                2100

Ser Arg His Gly Ala Gln Ser Arg Phe Asp Ser Phe Asn Thr Leu
        2105                2110                2115

Tyr Asp Glu Asp Val Asn Ala Gly Glu Lys Gln Ala Met Asp Leu
        2120                2125                2130

Tyr Leu Ser Ser Ser Val Leu Ser Thr Ser Gly Thr Ala Leu His
        2135                2140                2145

Met Ala Ala Ala Ala Asp Leu Val Pro Asn Ile Tyr Gly Phe
        2150                2155                2160

Ala Val Gly Gly Ser Arg Phe Gly Ala Leu Phe Asn Ala Ser Ala
        2165                2170                2175

Ile Gly Ile Glu Ile Ser Ala Ser Ala Thr Arg Ile Ala Ala Asp
        2180                2185                2190

Lys Ile Ser Gln Ser Glu Ile Tyr Arg Arg Arg Gln Glu Trp
        2195                2200                2205

Glu Ile Gln Arg Asn Asn Ala Glu Ala Glu Ile Lys Gln Ile Asp
        2210                2215                2220

Ala Gln Leu Ala Thr Leu Ala Val Arg Arg Glu Ala Ala Val Leu
        2225                2230                2235

Gln Lys Asn Tyr Leu Glu Thr Gln Gln Ala Gln Thr Gln Ala Gln
        2240                2245                2250

Leu Ala Phe Leu Gln Ser Lys Phe Ser Asn Ala Ala Leu Tyr Asn
        2255                2260                2265

Trp Leu Arg Gly Arg Leu Ser Ala Ile Tyr Tyr Gln Phe Tyr Asp
        2270                2275                2280

Leu Ala Val Ser Leu Cys Leu Met Ala Glu Gln Thr Tyr Gln Tyr
        2285                2290                2295
```

| | | | | | | | | | | | |
|---|---|---|---|---|---|---|---|---|---|---|---|
| Glu | Leu | Asn | Asn | Ala | Ala | His | Phe | Ile | Lys | Pro | Gly Ala Trp |
| | 2300 | | | | 2305 | | | | 2310 | | |
| His | Gly | Thr | Tyr | Ala | Gly | Leu | Leu | Ala | Gly | Glu | Thr Leu Met Leu |
| | 2315 | | | | 2320 | | | | 2325 | | |
| Asn | Leu | Ala | Gln | Met | Glu | Lys | Ser | Tyr | Leu | Glu | Lys Asp Glu Arg |
| | 2330 | | | | 2335 | | | | 2340 | | |
| Ala | Leu | Glu | Val | Thr | Arg | Thr | Val | Ser | Leu | Ala | Glu Val Tyr Ala |
| | 2345 | | | | 2350 | | | | 2355 | | |
| Gly | Leu | Thr | Glu | Asn | Ser | Phe | Ile | Leu | Lys | Asp | Lys Val Thr Glu |
| | 2360 | | | | 2365 | | | | 2370 | | |
| Leu | Val | Asn | Ala | Gly | Glu | Gly | Ser | Ala | Gly | Thr | Thr Leu Asn Gly |
| | 2375 | | | | 2380 | | | | 2385 | | |
| Leu | Asn | Val | Glu | Gly | Thr | Gln | Leu | Gln | Ala | Ser | Leu Lys Leu Ser |
| | 2390 | | | | 2395 | | | | 2400 | | |
| Asp | Leu | Asn | Ile | Ala | Thr | Asp | Tyr | Pro | Asp | Gly | Leu Gly Asn Thr |
| | 2405 | | | | 2410 | | | | 2415 | | |
| Arg | Arg | Ile | Lys | Gln | Ile | Ser | Val | Thr | Leu | Pro | Ala Leu Leu Gly |
| | 2420 | | | | 2425 | | | | 2430 | | |
| Pro | Tyr | Gln | Asp | Val | Arg | Ala | Ile | Leu | Ser | Tyr | Gly Gly Ser Thr |
| | 2435 | | | | 2440 | | | | 2445 | | |
| Met | Met | Pro | Arg | Gly | Cys | Lys | Ala | Ile | Ala | Ile | Ser His Gly Met |
| | 2450 | | | | 2455 | | | | 2460 | | |
| Asn | Asp | Ser | Gly | Gln | Phe | Gln | Met | Asp | Phe | Asn | Asp Ala Lys Tyr |
| | 2465 | | | | 2470 | | | | 2475 | | |
| Leu | Pro | Phe | Glu | Gly | Leu | Pro | Val | Ala | Asp | Thr | Gly Thr Leu Thr |
| | 2480 | | | | 2485 | | | | 2490 | | |
| Leu | Ser | Phe | Pro | Gly | Ile | Ser | Gly | Lys | Gln | Lys | Ser Leu Leu Leu |
| | 2495 | | | | 2500 | | | | 2505 | | |
| Ser | Leu | Ser | Asp | Ile | Ile | Leu | His | Ile | Arg | Tyr | Thr Ile Arg Ser |
| | 2510 | | | | 2515 | | | | 2520 | | |

<210> SEQ ID NO 15
<211> LENGTH: 3048
<212> TYPE: DNA
<213> ORGANISM: Xenorhabdus nematophilus

<400> SEQUENCE: 15

```
atgaagaatt tcgttcacag caatacgcca tccgtcaccg tactggacaa ccgtggtcag      60
acagtacgcg aaatagcctg gtatcggcac cccgatacac ctcaggtaac cgatgaacgc     120
atcaccggtt atcaatatga tgctcaagga tctctgactc agagtattga tccgcgattt     180
tatgaacgcc agcagacagc gagtgacaag aacgccatta cacccaatct tattctcttg     240
tcatcactca gtaagaaggc attgcgtacg caaagtgtgg atgccggaac ccgtgtcgcc     300
ctgcatgatg ttgccgggcg tcccgtttta gctgtcagcg ccaatggcgt tagccgaacg     360
tttcagtatg aaagtgataa ccttccggga cgattgctaa cgattaccga gcaggtaaaa     420
ggagagaacg cctgtatcac ggagcgattg atctggtcag gaaatacgcc ggcagaaaaa     480
ggcaataatc tggccggcca gtgcgtggtc cattatgatc ccaccggaat gaatcaaacc     540
aacagcatat cgttaaccag cataccccttg tccatcacac agcaattact gaaagatgac     600
agcgaagccg attggcacgg tatggatgaa tctggctgga aaaacgcgct ggcgccggaa     660
agcttcactt ctgtcagcac aacgatgct accggcacgg tattaacgag tacagatgct     720
gccggaaaca agcaacgtat cgcctatgat gtggccggtc tgcttcaagg cagttggttg     780
```

```
gcgctgaagg ggaaacaaga acaagttatc gtgaaatccc tgacctattc ggctgccagc    840
cagaagctac gggaggaaca tggtaacggg atagtgacta catataccta tgaacccgag    900
acgcaacgag ttattggcat aaaaacagaa cgtccttccg gtcatgccgc tggggagaaa    960 atttttacaaa acctgcgtta tgaatatgat cctgtcggaa atgtgctgaa atcaactaat   1020
gatgctgaaa ttacccgctt ttggcgcaac cagaaaattg taccggaaaa tacttacacc   1080
tatgacagcc tgtaccagct ggtttccgtc actgggcgtg aaatggcgaa tattggccga   1140
caaaaaaacc agttacccat ccccgctctg attgataaca atacttatac gaattactct   1200
cgcacttacg actatgatcg tgggggaaat ctgaccagaa ttcgccataa ttcaccgatc   1260
accggtaata actatacaac gaacatgacc gtttcagatc acagcaaccg ggctgtactg   1320
gaagagctgg cgcaagatcc cactcaggtg gatatgttgt tcacccccgg cgggcatcag   1380
acccggcttg ttcccggtca ggatcttttc tggacaccccc gtgacgaatt gcaacaagtg   1440
atattggtca atagggaaaa tacgacgcct gatcaggaat tctaccgtta tgatgcagac   1500
agtcagcgtg tcattaagac tcatattcag aagacaggta acagtgagca aatacagcga   1560
acattatatt tgccagagct ggaatggcgc acgacatata gcggcaatac attaaaagag   1620 ttttttgcagg tcatcactgt cggtgaatcg ggtcaggcac aagtgcgggt gctgcattgg   1680
gaaacaggca aaccggcgga tatcagcaat gatcagctgc gctacagtta tggcaacctg   1740
attggcagta gcgggctgga attggacagt gacgggcaga tcattagtca ggaagaatat   1800 taccccctatg ggggaaccgc cgtgtgggca gcccgaagtc agtcagaagc tgattacaaa   1860
accgtgcgtt attctggcaa agagcgggat gcaacagggt tgtattacta cggttatcgt   1920
tattatcaat cgtggacagg gcgatggttg agtgtagatc ctgccggtga ggtcgatggt   1980
ctcaatttgt tccgaatgtg caggaataac cccatcgttt tttctgattc tgatggtcgt   2040 ttcccccggtc agggtgtcct tgcctggata gggaaaaaag cgtatcgaaa ggcagtcaac   2100
atcacgacag aacacctgct tgaacaaggc gcttcctttg atacgttctt gaaattaaac   2160
cgaggattgc gaacgtttgt tttgggtgtg ggggtagcaa gtctgggggt gaaggcggcc   2220
acgattgcag gagcgtcgcc ttgggggatt gtcgggggctg ccattggtgg ttttgtctcc   2280
ggggcggtga tgggggtttt cgcgaacaac atctcagaaa aaattgggga agttttaagt   2340
tatctgacgc gtaaacgttc tgttcctgtt caggttggcg cttttgttgt cacatcgctt   2400
gtgacgtctg cactatttaa cagctcttcg acaggtaccg ccatttccgc agcaacagcg   2460
gtcaccgttg gaggattaat ggctttagcc ggagagcata acacgggcat ggctatcagt   2520
attgccacac ccgccggaca aggtacgctg gatacgctca ggcccggtaa tgtcagcgcg   2580
ccagagcggt taggggcact atcaggcgca attattggcg gcatattact tggccgccat   2640
cagggaagtt ctgagctggg tgaacgggca gcgattggtg ctatgtatgg tgctcgatgg   2700
ggaaggatca ttggtaatct atgggatggc ccttatcggt ttatcggcag gttactgctc   2760
agaagaggca ttagctctgc catttcccac gctgtcagtt ccaggagctg gtttggccga   2820
atgataggag aaagtgtcgg gagaaatatt tctgaagtat tattaccctta tagccgtaca   2880 cccggtgaat gggttggtgc agccattggc gggacagccg cggccgctca tcatgccgtt   2940 ggagggggaag ttgccaatgc cgctagccgg gttacctgga gcggctttaa gcgggctttt   3000
aataacttct tctttaacgc ctctgcacgt cataatgaat ccgaagca              3048
```

<210> SEQ ID NO 16

```
<211> LENGTH: 1016
<212> TYPE: PRT
<213> ORGANISM: Xenorhabdus nematophilus

<400> SEQUENCE: 16

Met Lys Asn Phe Val His Ser Asn Thr Pro Ser Val Thr Val Leu Asp
1               5                   10                  15

Asn Arg Gly Gln Thr Val Arg Glu Ile Ala Trp Tyr Arg His Pro Asp
            20                  25                  30

Thr Pro Gln Val Thr Asp Glu Arg Ile Thr Gly Tyr Gln Tyr Asp Ala
        35                  40                  45

Gln Gly Ser Leu Thr Gln Ser Ile Asp Pro Arg Phe Tyr Glu Arg Gln
    50                  55                  60

Gln Thr Ala Ser Asp Lys Asn Ala Ile Thr Pro Asn Leu Ile Leu Leu
65                  70                  75                  80

Ser Ser Leu Ser Lys Lys Ala Leu Arg Thr Gln Ser Val Asp Ala Gly
                85                  90                  95

Thr Arg Val Ala Leu His Asp Val Ala Gly Arg Pro Val Leu Ala Val
            100                 105                 110

Ser Ala Asn Gly Val Ser Arg Thr Phe Gln Tyr Glu Ser Asp Asn Leu
        115                 120                 125

Pro Gly Arg Leu Leu Thr Ile Thr Glu Gln Val Lys Gly Glu Asn Ala
    130                 135                 140

Cys Ile Thr Glu Arg Leu Ile Trp Ser Gly Asn Thr Pro Ala Glu Lys
145                 150                 155                 160

Gly Asn Asn Leu Ala Gly Gln Cys Val Val His Tyr Asp Pro Thr Gly
                165                 170                 175

Met Asn Gln Thr Asn Ser Ile Ser Leu Thr Ser Ile Pro Leu Ser Ile
            180                 185                 190

Thr Gln Gln Leu Leu Lys Asp Asp Ser Glu Ala Asp Trp His Gly Met
        195                 200                 205

Asp Glu Ser Gly Trp Lys Asn Ala Leu Ala Pro Glu Ser Phe Thr Ser
    210                 215                 220

Val Ser Thr Thr Asp Ala Thr Gly Thr Val Leu Thr Ser Thr Asp Ala
225                 230                 235                 240

Ala Gly Asn Lys Gln Arg Ile Ala Tyr Asp Val Ala Gly Leu Leu Gln
                245                 250                 255

Gly Ser Trp Leu Ala Leu Lys Gly Lys Gln Glu Gln Val Ile Val Lys
            260                 265                 270

Ser Leu Thr Tyr Ser Ala Ala Ser Gln Lys Leu Arg Glu Glu His Gly
        275                 280                 285

Asn Gly Ile Val Thr Thr Tyr Thr Tyr Glu Pro Glu Thr Gln Arg Val
    290                 295                 300

Ile Gly Ile Lys Thr Glu Arg Pro Ser Gly His Ala Ala Gly Glu Lys
305                 310                 315                 320

Ile Leu Gln Asn Leu Arg Tyr Glu Tyr Asp Pro Val Gly Asn Val Leu
                325                 330                 335

Lys Ser Thr Asn Asp Ala Glu Ile Thr Arg Phe Trp Arg Asn Gln Lys
            340                 345                 350

Ile Val Pro Glu Asn Thr Tyr Thr Tyr Asp Ser Leu Tyr Gln Leu Val
        355                 360                 365

Ser Val Thr Gly Arg Glu Met Ala Asn Ile Gly Arg Gln Lys Asn Gln
    370                 375                 380

Leu Pro Ile Pro Ala Leu Ile Asp Asn Asn Thr Tyr Thr Asn Tyr Ser
```

```
       385                 390                 395                 400
Arg Thr Tyr Asp Tyr Asp Arg Gly Gly Asn Leu Thr Arg Ile Arg His
                405                 410                 415

Asn Ser Pro Ile Thr Gly Asn Asn Tyr Thr Thr Asn Met Thr Val Ser
                420                 425                 430

Asp His Ser Asn Arg Ala Val Leu Glu Glu Leu Ala Gln Asp Pro Thr
                435                 440                 445

Gln Val Asp Met Leu Phe Thr Pro Gly Gly His Gln Thr Arg Leu Val
                450                 455                 460

Pro Gly Gln Asp Leu Phe Trp Thr Pro Arg Asp Glu Leu Gln Gln Val
465                 470                 475                 480

Ile Leu Val Asn Arg Glu Asn Thr Thr Pro Asp Gln Glu Phe Tyr Arg
                485                 490                 495

Tyr Asp Ala Asp Ser Gln Arg Val Ile Lys Thr His Ile Gln Lys Thr
                500                 505                 510

Gly Asn Ser Glu Gln Ile Gln Arg Thr Leu Tyr Leu Pro Glu Leu Glu
                515                 520                 525

Trp Arg Thr Thr Tyr Ser Gly Asn Thr Leu Lys Glu Phe Leu Gln Val
                530                 535                 540

Ile Thr Val Gly Glu Ser Gly Gln Ala Gln Val Arg Val Leu His Trp
545                 550                 555                 560

Glu Thr Gly Lys Pro Ala Asp Ile Ser Asn Asp Gln Leu Arg Tyr Ser
                565                 570                 575

Tyr Gly Asn Leu Ile Gly Ser Ser Gly Leu Glu Leu Asp Ser Asp Gly
                580                 585                 590

Gln Ile Ile Ser Gln Glu Glu Tyr Tyr Pro Tyr Gly Gly Thr Ala Val
                595                 600                 605

Trp Ala Ala Arg Ser Gln Ser Glu Ala Asp Tyr Lys Thr Val Arg Tyr
                610                 615                 620

Ser Gly Lys Glu Arg Asp Ala Thr Gly Leu Tyr Tyr Tyr Gly Tyr Arg
625                 630                 635                 640

Tyr Tyr Gln Ser Trp Thr Gly Arg Trp Leu Ser Val Asp Pro Ala Gly
                645                 650                 655

Glu Val Asp Gly Leu Asn Leu Phe Arg Met Cys Arg Asn Asn Pro Ile
                660                 665                 670

Val Phe Ser Asp Ser Asp Gly Arg Phe Pro Gly Gln Gly Val Leu Ala
                675                 680                 685

Trp Ile Gly Lys Lys Ala Tyr Arg Lys Ala Val Asn Ile Thr Thr Glu
                690                 695                 700

His Leu Leu Glu Gln Gly Ala Ser Phe Asp Thr Phe Leu Lys Leu Asn
705                 710                 715                 720

Arg Gly Leu Arg Thr Phe Val Leu Gly Val Gly Val Ala Ser Leu Gly
                725                 730                 735

Val Lys Ala Ala Thr Ile Ala Gly Ala Ser Pro Trp Gly Ile Val Gly
                740                 745                 750

Ala Ala Ile Gly Gly Phe Val Ser Gly Ala Val Met Gly Phe Phe Ala
                755                 760                 765

Asn Asn Ile Ser Glu Lys Ile Gly Glu Val Leu Ser Tyr Leu Thr Arg
                770                 775                 780

Lys Arg Ser Val Pro Val Gln Val Gly Ala Phe Val Val Thr Ser Leu
785                 790                 795                 800

Val Thr Ser Ala Leu Phe Asn Ser Ser Thr Gly Thr Ala Ile Ser
                805                 810                 815
```

```
Ala Ala Thr Ala Val Thr Val Gly Gly Leu Met Ala Leu Ala Gly Glu
            820                 825                 830

His Asn Thr Gly Met Ala Ile Ser Ile Ala Thr Pro Ala Gly Gln Gly
            835                 840                 845

Thr Leu Asp Thr Leu Arg Pro Gly Asn Val Ser Ala Pro Glu Arg Leu
        850                 855                 860

Gly Ala Leu Ser Gly Ala Ile Ile Gly Gly Ile Leu Gly Arg His
865                 870                 875                 880

Gln Gly Ser Ser Glu Leu Gly Glu Arg Ala Ile Gly Ala Met Tyr
                885                 890                 895

Gly Ala Arg Trp Gly Arg Ile Ile Gly Asn Leu Trp Asp Gly Pro Tyr
            900                 905                 910

Arg Phe Ile Gly Arg Leu Leu Leu Arg Arg Gly Ile Ser Ser Ala Ile
            915                 920                 925

Ser His Ala Val Ser Ser Arg Ser Trp Phe Gly Arg Met Ile Gly Glu
            930                 935                 940

Ser Val Gly Arg Asn Ile Ser Glu Val Leu Leu Pro Tyr Ser Arg Thr
945                 950                 955                 960

Pro Gly Glu Trp Val Gly Ala Ala Ile Gly Gly Thr Ala Ala Ala
                965                 970                 975

His His Ala Val Gly Gly Glu Val Ala Asn Ala Ala Ser Arg Val Thr
            980                 985                 990

Trp Ser Gly Phe Lys Arg Ala Phe  Asn Asn Phe Phe Phe  Asn Ala Ser
            995                 1000                1005

Ala Arg  His Asn Glu Ser Glu  Ala
    1010                1015

<210> SEQ ID NO 17
<211> LENGTH: 4479
<212> TYPE: DNA
<213> ORGANISM: Xenorhabdus nematophilus

<400> SEQUENCE: 17
atgcagggtt caacaccttt gaaacttgaa ataccgtcat gccctctgg gggcggatca    60 ctaaaaggaa tgggagaagc actcaatgcc gtcggagcgg aaggggagc gtcattttca   120 ctgcccttgc cgatctctgt cgggcgtggt ctggtgccgg tgctatcact gaattacagc   180
agtactgccg gcaatgggtc attcgggatg gggtggcaat gtggggttgg ttttatcagc   240
ctgcgtaccg ccaagggcgt tccgcactat acgggacaag atgagtatct cgggccggat   300
ggggaagtgt tgagtattgt gccggacagc caagggcaac cagagcaacg caccgcaacc   360
tcactgttgg ggacggttct gacacagccg catactgtta cccgctatca gtcccgcgtg   420
gcagaaaaaa tcgttcgttt agaacactgg cagccacagc agagacgtga ggaagagacg   480 tcttttggg tactttttac tgcggatggt ttagtgcacc tattcggtaa gcatcaccat   540
gcacgtattg ctgacccgca ggatgaaacc agaattgccc gctggctgat ggaggaaacc   600
gtcacgcata ccggggaaca tatttactat cactatcggg cagaagacga tcttgactgt   660
gatgagcatg aacttgctca gcattcaggt gttacggccc agcgttatct ggcaaaagtc   720
agctatggca atactcagcc ggaaaccgct tttttcgcgg taaatcagg tattcctgct   780 gataatgact ggctgtttca tctggtattt gattacggtg agcgctcatc ttcgctgaac   840
tctgtacccg aattcaatgt gtcagaaaac aatgtgtctg aaaacaatgt gcctgaaaaa   900
tggcgttgtc gtccggacag tttctcccgc tatgaatatg ggtttgaaat tcgaacccgt   960
```

```
cgcttgtgtc gccaagttct gatgtttcat cagctgaaag cgctggcagg ggaaaaggtt    1020
gcagaagaaa caccggcgct ggtttcccgt cttattctgg attatgacct gaacaacaag    1080
gtttccttgc tgcaaacggc ccgcagactg gcccatgaaa cggacggtac gccagtgatg    1140
atgtccccgc tggaaatgga ttatcaacgt gttaatcatg gcgtgaatct gaactggcag    1200
tccatgccgc agttagaaaa aatgaacacg ttgcagccat accaattggt tgatttatat    1260
ggagaaggaa tttccggcgt actttatcag gatactcaga aagcctggtg gtaccgtgct    1320
ccggtacggg atatcactgc cgaaggaacg aatgcggtta cctatgagga ggccaaacca    1380
ctgccacata ttccggcaca acaggaaagc gcgatgttgt tggacatcaa tggtgacggg    1440
cgtctggatt gggtgattac ggcatcaggg ttacggggct accacaccat gtcaccggaa    1500
ggtgaatgga cccctttat tccattatcc gctgtgccaa tggaatattt ccatccgcag    1560
gcaaaactgg ctgatattga tggggctggg ctgcctgact tagcgcttat cgggccaaat    1620
agtgtacgtg tctggtcaaa taatcgggca ggatgggatc gcgctcagga tgtgattcat    1680
ttgtcagata tgccactgcc ggttcccggc agaaatgagc gtcatcttgt cgcattcagt    1740
gatatgacag gctccgggca atcacatctg gtggaagtaa cggcagatag cgtgcgctac    1800
tggccgaacc tggggcatgg aaaatttggt gagcctctga tgatgacagg cttccagatt    1860
agcggggaaa cgtttaaccc cgacagactg tatatggtag acatagatgg ctcaggcacc    1920
accgatttta tttatgcccg caatacttac cttgaactct atgccaatga aagcggcaat    1980
cattttgctg aacctcagcg tattgatctg ccggatgggg tacgttttga tgatacttgt    2040
cggttacaaa tagcggatac acaaggatta gggactgcca gcattatttt gacgatcccc    2100
catatgaagg tgcagcactg gcgattggat atgaccatat tcaagccttg gctgctgaat    2160
gccgtcaata caatatggg aacagaaacc acgctgtatt atcgcagctc tgcccagttc    2220
tggctggatg agaaattaca ggcttctgaa tccgggatga cggtggtcag ctacttaccg    2280
ttcccggtgc atgtgttgtg gcgcacggaa gtgctggatg aaatttccgg taaccgattg    2340
accagccatt atcattactc acatggtgcc tgggatggtc tggaacggga gtttcgtggt    2400
tttgggcggg tgacacaaac tgatattgat tcacgggcga gtgcgacaca ggggacacat    2460
gctgaaccac cggcaccttc gcgcacggtt aattggtacg gcactggcgt acgggaagtc    2520
gatattcttc tgcccacgga atattggcag ggggatcaac aggcatttcc ccattttacc    2580
ccacgcttta cccgttatga cgaaaaatcc ggtggtgata tgacggtcac gccgagcgaa    2640
caggaagaat actggttaca tcgagcctta aaaggacaac gtttacgcag tgagctgtat    2700
ggggatgatg attctatact ggccggtacg ccttattcag tggatgaatc ccgcaccccaa    2760 gtacgtttgt taccggtgat ggtatcggac gtgcctgcgg tactggtttc ggtggccgaa    2820
tcccgccaat accgatatga acgggttgct accgatccac agtgcagcca aaagatcgtc    2880
cttaaatctg atgcgttagg atttccgcag gacaatcttg agattgccta ttcgagacgt    2940
ccacagcctg agttctcgcc ttatccggat accctgcccg aaacacttt caccagcagt    3000 ttcgacgaac agcagatgtt ccttcgtctg acacgccagc gttcttctta tcatcatctg    3060
aatcatgatg ataatacgtg gatcacaggg cttatggata cctcacgcag tgacgcacgt    3120
atttatcaag ccgataaagt gccggacggt ggattttccc ttgaatggtt ttctgccaca    3180
ggtgcaggag cattgttgtt gcctgatgcc cagccgatt atctgggaca tcagcgtgta    3240
gcatataccg gtccagaaga acaacccgct attcctccgc tggtggcata cattgaaacc    3300
```

-continued

```
gcagagtttg atgaacgatc gttggcggct tttgaggagg tgatggatga gcaggagctg    3360
acaaaacagc tgaatgatgc gggctggaat acggcaaaag tgccgttcag tgaaaagaca    3420
gatttccatg tctgggtggg acaaaaggaa tttacagaat atgccggtgc agacggattc    3480
tatcggccat tggtgcaacg ggaaaccaag cttacaggta aaacgacagt cacgtgggat    3540
agccattact gtgttatcac cgcaacagag gatgcggctg gcctgcgtat gcaagcgcat    3600
tacgattatc gatttatggt tgcggataac accacagatg tcaatgataa ctatcacacc    3660
gtgacgtttg atgcactggg gagggtaacc agcttccgtt tctgggggac tgaaaacggt    3720
gaaaaacaag gatataccce tgcggaaaat gaaactgtcc cctttattgt ccccacaacg    3780
gtggatgatg ctctggcatt gaaacccggt atacctgttg cagggctgat ggtttatgcc    3840
cctctgagct ggatggttca ggccagcttt tctaatgatg gggagcttta tggagagctg    3900
aaaccggctg ggatcatcac tgaagatggt tatctcctgt cgcttgcttt tcgccgctgg    3960
caacaaaata accctgccgc tgccatgcca aagcaagtca attcacagaa cccaccccat    4020
gtactgagtg tgatcaccga ccgctatgat gccgatccgg aacaacaatt acgtcaaacg    4080
tttacgttta gtgatggttt tgggcgaacc ttacaaacag ccgtacgcca tgaaagtggt    4140
gaagcctggg tacgtgatga gtatggagcc attgtggctg aaaatcatgg cgcgcctgaa    4200
acggcgatga cagatttccg ttgggcagtt tccggacgta cagaatatga cggaaaaggc    4260
caagccctgc gtaagtatca accgtatttc ctgaatagtt ggcagtacgt cagtgatgac    4320
agtgcccggc aggatatata tgccgatacc cattactatg atccgttggg gcgtgaatat    4380
caggttatca cggccaaagg cgggtttcgt cgatccttat tcactccctg gtttgtggtg    4440
aatgaagatg aaaatgacac tgccggtgaa atgacagca                          4479
```

<210> SEQ ID NO 18
<211> LENGTH: 1493
<212> TYPE: PRT
<213> ORGANISM: Xenorhabdus nematophilus

<400> SEQUENCE: 18

```
Met Gln Gly Ser Thr Pro Leu Lys Leu Glu Ile Pro Ser Leu Pro Ser
1               5                   10                  15

Gly Gly Gly Ser Leu Lys Gly Met Gly Glu Ala Leu Asn Ala Val Gly
            20                  25                  30

Ala Glu Gly Gly Ala Ser Phe Ser Leu Pro Leu Pro Ile Ser Val Gly
        35                  40                  45

Arg Gly Leu Val Pro Val Leu Ser Leu Asn Tyr Ser Ser Thr Ala Gly
    50                  55                  60

Asn Gly Ser Phe Gly Met Gly Trp Gln Cys Gly Val Gly Phe Ile Ser
65                  70                  75                  80

Leu Arg Thr Ala Lys Gly Val Pro His Tyr Thr Gly Gln Asp Glu Tyr
                85                  90                  95

Leu Gly Pro Asp Gly Glu Val Leu Ser Ile Val Pro Asp Ser Gln Gly
            100                 105                 110

Gln Pro Glu Gln Arg Thr Ala Thr Ser Leu Leu Gly Thr Val Leu Thr
        115                 120                 125

Gln Pro His Thr Val Thr Arg Tyr Gln Ser Arg Val Ala Glu Lys Ile
    130                 135                 140

Val Arg Leu Glu His Trp Gln Pro Gln Arg Arg Glu Glu Glu Thr
145                 150                 155                 160

Ser Phe Trp Val Leu Phe Thr Ala Asp Gly Leu Val His Leu Phe Gly
```

```
                165                 170                 175
Lys His His Ala Arg Ile Ala Asp Pro Gln Asp Glu Thr Arg Ile
            180                 185                 190
Ala Arg Trp Leu Met Glu Glu Thr Val Thr His Thr Gly Glu His Ile
                195                 200                 205
Tyr Tyr His Tyr Arg Ala Glu Asp Asp Leu Asp Cys Asp Glu His Glu
            210                 215                 220
Leu Ala Gln His Ser Gly Val Thr Ala Gln Arg Tyr Leu Ala Lys Val
225                 230                 235                 240
Ser Tyr Gly Asn Thr Gln Pro Glu Thr Ala Phe Phe Ala Val Lys Ser
                245                 250                 255
Gly Ile Pro Ala Asp Asn Asp Trp Leu Phe His Leu Val Phe Asp Tyr
            260                 265                 270
Gly Glu Arg Ser Ser Ser Leu Asn Ser Val Pro Glu Phe Asn Val Ser
        275                 280                 285
Glu Asn Asn Val Ser Glu Asn Val Pro Glu Lys Trp Arg Cys Arg
290                 295                 300
Pro Asp Ser Phe Ser Arg Tyr Glu Tyr Gly Phe Glu Ile Arg Thr Arg
305                 310                 315                 320
Arg Leu Cys Arg Gln Val Leu Met Phe His Gln Leu Lys Ala Leu Ala
                325                 330                 335
Gly Glu Lys Val Ala Glu Glu Thr Pro Ala Leu Val Ser Arg Leu Ile
            340                 345                 350
Leu Asp Tyr Asp Leu Asn Asn Lys Val Ser Leu Leu Gln Thr Ala Arg
            355                 360                 365
Arg Leu Ala His Glu Thr Asp Gly Thr Pro Val Met Met Ser Pro Leu
        370                 375                 380
Glu Met Asp Tyr Gln Arg Val Asn His Gly Val Asn Leu Asn Trp Gln
385                 390                 395                 400
Ser Met Pro Gln Leu Glu Lys Met Asn Thr Leu Gln Pro Tyr Gln Leu
                405                 410                 415
Val Asp Leu Tyr Gly Glu Gly Ile Ser Gly Val Leu Tyr Gln Asp Thr
            420                 425                 430
Gln Lys Ala Trp Trp Tyr Arg Ala Pro Val Arg Asp Ile Thr Ala Glu
        435                 440                 445
Gly Thr Asn Ala Val Thr Tyr Glu Glu Ala Lys Pro Leu Pro His Ile
        450                 455                 460
Pro Ala Gln Gln Glu Ser Ala Met Leu Leu Asp Ile Asn Gly Asp Gly
465                 470                 475                 480
Arg Leu Asp Trp Val Ile Thr Ala Ser Gly Leu Arg Gly Tyr His Thr
                485                 490                 495
Met Ser Pro Glu Gly Glu Trp Thr Pro Phe Ile Pro Leu Ser Ala Val
            500                 505                 510
Pro Met Glu Tyr Phe His Pro Gln Ala Lys Leu Ala Asp Ile Asp Gly
        515                 520                 525
Ala Gly Leu Pro Asp Leu Ala Leu Ile Gly Pro Asn Ser Val Arg Val
        530                 535                 540
Trp Ser Asn Asn Arg Ala Gly Trp Asp Arg Ala Gln Asp Val Ile His
545                 550                 555                 560
Leu Ser Asp Met Pro Leu Pro Val Pro Gly Arg Asn Glu Arg His Leu
                565                 570                 575
Val Ala Phe Ser Asp Met Thr Gly Ser Gly Gln Ser His Leu Val Glu
            580                 585                 590
```

-continued

```
Val Thr Ala Asp Ser Val Arg Tyr Trp Pro Asn Leu Gly His Gly Lys
        595                 600                 605
Phe Gly Glu Pro Leu Met Met Thr Gly Phe Gln Ile Ser Gly Glu Thr
    610                 615                 620
Phe Asn Pro Asp Arg Leu Tyr Met Val Asp Ile Asp Gly Ser Gly Thr
625                 630                 635                 640
Thr Asp Phe Ile Tyr Ala Arg Asn Thr Tyr Leu Glu Leu Tyr Ala Asn
                645                 650                 655
Glu Ser Gly Asn His Phe Ala Glu Pro Gln Arg Ile Asp Leu Pro Asp
            660                 665                 670
Gly Val Arg Phe Asp Asp Thr Cys Arg Leu Gln Ile Ala Asp Thr Gln
        675                 680                 685
Gly Leu Gly Thr Ala Ser Ile Ile Leu Thr Ile Pro His Met Lys Val
    690                 695                 700
Gln His Trp Arg Leu Asp Met Thr Ile Phe Lys Pro Trp Leu Leu Asn
705                 710                 715                 720
Ala Val Asn Asn Asn Met Gly Thr Glu Thr Thr Leu Tyr Tyr Arg Ser
                725                 730                 735
Ser Ala Gln Phe Trp Leu Asp Glu Lys Leu Gln Ala Ser Glu Ser Gly
            740                 745                 750
Met Thr Val Val Ser Tyr Leu Pro Phe Pro Val His Val Leu Trp Arg
        755                 760                 765
Thr Glu Val Leu Asp Glu Ile Ser Gly Asn Arg Leu Thr Ser His Tyr
    770                 775                 780
His Tyr Ser His Gly Ala Trp Asp Gly Leu Glu Arg Glu Phe Arg Gly
785                 790                 795                 800
Phe Gly Arg Val Thr Gln Thr Asp Ile Asp Ser Arg Ala Ser Ala Thr
                805                 810                 815
Gln Gly Thr His Ala Glu Pro Pro Ala Pro Ser Arg Thr Val Asn Trp
            820                 825                 830
Tyr Gly Thr Gly Val Arg Glu Val Asp Ile Leu Leu Pro Thr Glu Tyr
        835                 840                 845
Trp Gln Gly Asp Gln Gln Ala Phe Pro His Phe Thr Pro Arg Phe Thr
    850                 855                 860
Arg Tyr Asp Glu Lys Ser Gly Gly Asp Met Thr Val Thr Pro Ser Glu
865                 870                 875                 880
Gln Glu Glu Tyr Trp Leu His Arg Ala Leu Lys Gly Gln Arg Leu Arg
                885                 890                 895
Ser Glu Leu Tyr Gly Asp Asp Ser Ile Leu Ala Gly Thr Pro Tyr
            900                 905                 910
Ser Val Asp Glu Ser Arg Thr Gln Val Arg Leu Leu Pro Val Met Val
        915                 920                 925
Ser Asp Val Pro Ala Val Leu Val Ser Val Ala Glu Ser Arg Gln Tyr
    930                 935                 940
Arg Tyr Glu Arg Val Ala Thr Asp Pro Gln Cys Ser Gln Lys Ile Val
945                 950                 955                 960
Leu Lys Ser Asp Ala Leu Gly Phe Pro Gln Asp Asn Leu Glu Ile Ala
                965                 970                 975
Tyr Ser Arg Arg Pro Gln Pro Glu Phe Ser Pro Tyr Pro Asp Thr Leu
            980                 985                 990
Pro Glu Thr Leu Phe Thr Ser Ser  Phe Asp Glu Gln Gln  Met Phe Leu
        995                 1000                1005
```

-continued

```
Arg Leu Thr Arg Gln Arg Ser Ser Tyr His His Leu Asn His Asp
    1010                1015                1020

Asp Asn Thr Trp Ile Thr Gly Leu Met Asp Thr Ser Arg Ser Asp
    1025                1030                1035

Ala Arg Ile Tyr Gln Ala Asp Lys Val Pro Asp Gly Gly Phe Ser
    1040                1045                1050

Leu Glu Trp Phe Ser Ala Thr Gly Ala Gly Ala Leu Leu Leu Pro
    1055                1060                1065

Asp Ala Ala Ala Asp Tyr Leu Gly His Gln Arg Val Ala Tyr Thr
    1070                1075                1080

Gly Pro Glu Glu Gln Pro Ala Ile Pro Pro Leu Val Ala Tyr Ile
    1085                1090                1095

Glu Thr Ala Glu Phe Asp Glu Arg Ser Leu Ala Ala Phe Glu Glu
    1100                1105                1110

Val Met Asp Glu Gln Glu Leu Thr Lys Gln Leu Asn Asp Ala Gly
    1115                1120                1125

Trp Asn Thr Ala Lys Val Pro Phe Ser Glu Lys Thr Asp Phe His
    1130                1135                1140

Val Trp Val Gly Gln Lys Glu Phe Thr Glu Tyr Ala Gly Ala Asp
    1145                1150                1155

Gly Phe Tyr Arg Pro Leu Val Gln Arg Glu Thr Lys Leu Thr Gly
    1160                1165                1170

Lys Thr Thr Val Thr Trp Asp Ser His Tyr Cys Val Ile Thr Ala
    1175                1180                1185

Thr Glu Asp Ala Ala Gly Leu Arg Met Gln Ala His Tyr Asp Tyr
    1190                1195                1200

Arg Phe Met Val Ala Asp Asn Thr Thr Asp Val Asn Asp Asn Tyr
    1205                1210                1215

His Thr Val Thr Phe Asp Ala Leu Gly Arg Val Thr Ser Phe Arg
    1220                1225                1230

Phe Trp Gly Thr Glu Asn Gly Glu Lys Gln Gly Tyr Thr Pro Ala
    1235                1240                1245

Glu Asn Glu Thr Val Pro Phe Ile Val Pro Thr Thr Val Asp Asp
    1250                1255                1260

Ala Leu Ala Leu Lys Pro Gly Ile Pro Val Ala Gly Leu Met Val
    1265                1270                1275

Tyr Ala Pro Leu Ser Trp Met Val Gln Ala Ser Phe Ser Asn Asp
    1280                1285                1290

Gly Glu Leu Tyr Gly Glu Leu Lys Pro Ala Gly Ile Ile Thr Glu
    1295                1300                1305

Asp Gly Tyr Leu Leu Ser Leu Ala Phe Arg Arg Trp Gln Gln Asn
    1310                1315                1320

Asn Pro Ala Ala Ala Met Pro Lys Gln Val Asn Ser Gln Asn Pro
    1325                1330                1335

Pro His Val Leu Ser Val Ile Thr Asp Arg Tyr Asp Ala Asp Pro
    1340                1345                1350

Glu Gln Gln Leu Arg Gln Thr Phe Thr Phe Ser Asp Gly Phe Gly
    1355                1360                1365

Arg Thr Leu Gln Thr Ala Val Arg His Glu Ser Gly Glu Ala Trp
    1370                1375                1380

Val Arg Asp Glu Tyr Gly Ala Ile Val Ala Glu Asn His Gly Ala
    1385                1390                1395

Pro Glu Thr Ala Met Thr Asp Phe Arg Trp Ala Val Ser Gly Arg
```

-continued

```
          1400                1405                1410
Thr Glu  Tyr Asp Gly Lys Gly  Gln Ala Leu Arg Lys  Tyr Gln Pro
    1415                1420                1425

Tyr Phe  Leu Asn Ser Trp Gln  Tyr Val Ser Asp Ser  Ala Arg
    1430                1435                1440

Gln Asp  Ile Tyr Ala Asp Thr  His Tyr Tyr Asp Pro  Leu Gly Arg
    1445                1450                1455

Glu Tyr  Gln Val Ile Thr Ala  Lys Gly Gly Phe Arg  Arg Ser Leu
    1460                1465                1470

Phe Thr  Pro Trp Phe Val Val  Asn Glu Asp Glu Asn  Asp Thr Ala
    1475                1480                1485

Gly Glu  Met Thr Ala
    1490

<210> SEQ ID NO 19
<211> LENGTH: 7614
<212> TYPE: DNA
<213> ORGANISM: Xenorhabdus nematophilus

<400> SEQUENCE: 19
atgtatagca cggctgtatt actcaataaa atcagtccca ctcgcgacgg tcagacgatg    60
actcttgcgg atctgcaata tttatccttc agtgaactga aaaaatcttt gatgaccag    120
ctcagttggg gagaggctcg ccatctctat catgaaacta tagagcagaa aaaaaataat   180
cgcttgctgg aagcgcgtat ttttacccgt gccaacccac aattatccgg tgctatccga   240
ctcggtattg aacgagacag cgtttcacgc agttatgatg aaatgtttgg tgcccgttct   300
tcttcctttg tgaaaccggg ttcagtggct ccatgtttt caccggctgg ctatctcacc    360
gaattgtatc gtgaagcgaa ggacttacat ttttcaagct ctgcttatca tcttgataat   420
cgccgtccgg atctggctga tctgactctg agcagagta atatggatac agaaatttcc    480
acccctgacac tgtctaacga actgttgctg gagcatatta cccgcaagac cggaggtgat   540
tcggacgcat tgatggagag cctgtcaact taccgtcagg ccattgatac cccttaccat   600
cagccttacg agactatccg tcaggtcatt atgacccatg acagtacact gtcagcgctg   660
tcccgtaatc ctgaggtgat ggggcaggcg aaggggcctt cattactggc gattctggcc   720
aatatttctc cggagcttta taacattttg accgaagaga ttacggaaaa gaacgctgat   780
gctttatttg cgcaaaactt cagtgaaaat atcacgcccg aaaatttcgc gtcacaatca   840
tggatagcca agtattatgg tcttgaactt tctgaggtgc aaaaatacct cgggatgttg   900
cagaatggct attctgacag cacctctgct tatgtggata tatctcaacc gggtttagtg   960
gtcaataatg aaagtaaaact cgaagcttac aaaataacac gtgtaaaaac agatgattat  1020
gataaaaata taaattactt tgatttgatg tatgaaggaa ataatcagtt ctttatacgt  1080
gctaatttta aggtatcaag agaatttggg gctactctta aaaaaacgc agggccaagt  1140
ggcattgtcg gcagccttc cggtcctcta atagccaata cgaattttaa agtaattat   1200
ctaagtaaca tatctgattc tgaatacaaa acggtgtaa agatatacgc ctatcgctat  1260
acgtcttcca ccagcgccac aaatcagggc ggcggaatat tcacttttga gtcttatccc  1320
ctgactatat ttgcgctcaa actgaataaa gccattcgct tgtgcctgac tagcgggctt  1380
tcaccgaatg aactgcaaac tatcgtacgc agtgacaatg cacaaggcat catcaacgac  1440
tccgttctga ccaagttttt ctatactctg ttctacagtc accgttatgc actgagcttt  1500
gatgatgcac aggtactgaa cggatcggtc attaatcaat atgccgacga tgacagtgtc  1560
```

```
agtcatttta accgtctctt taatacaccg ccgctgaaag ggaaaatctt tgaagccgac    1620
ggcaacacgg tcagcattga tccggatgaa gagcaatcta cctttgcccg ttcagccctg    1680
atgcgtggtc tgggggtcaa cagtggtgaa ctgtatcagt taggcaaact ggcgggtgtg    1740
ctggacgccc aaaataccat cacactttct gtcttcgtta tctcttcact gtatcgcctc    1800
acgttactgg cccgtgtcca tcagctacgg gtcaatgaac tgtgtatgct ttatggtctt    1860
tcgccgttca atggcaaaac aacggcttct ttgtcttccg gggagttgcc acggctggtt    1920
atctggctgt atcaggtgac gcagtggctg actgaggcgg aaatcaccac tgaagcgatc    1980
tggttattat gtacgccaga gtttagcggg aatatttcac cggaaatcag taatctgctc    2040
aataacctcc gaccgagtat tagtgaagat atggcacaga gtcacaatcg ggagctgcag    2100
gctgaaattc tcgcgccgtt tattgctgca acgctgcatc tggcgtcacc ggatatggca    2160
cggtatatcc tgttgtggac cgataacctg cggccgggtg cttagatat tgccgggttt    2220 atgacactgg tattgaaaga gtcgttaaat gccaatgaaa ccacccaatt ggtacaattc    2280
tgccatgtga tggcacagtt atcgctttcc gtacagacac tgcgcctcag tgaagcggag    2340
ctatccgtgc tggtcatctc cggattcgcc gtgctggggg caaaaaatca acctgccgga    2400
cagcacaata ttgatacgct attctcactc taccgattcc accagtggat taatgggctg    2460
ggcaatcccg gctctgacac gctggatatg ctgcgccagc agacactcac ggccgacaga    2520
ctggcctccg tgatggggct ggacatcagt atggtaacgc aggccatggt ttccgccggc    2580
gtgaaccagc ttcagtgttg gcaggatatc aacaccgtgt tgcagtggat agatgtggca    2640
tcagcactgc acacgatgcc gtcggttatc cgtacgctgg tgaatatccg ttacgtgact    2700
gcattaaaca aagccgagtc gaatctgcct tcctgggatg agtggcagac actggcagaa    2760
aatatggaag ccggactcag tacacaacag gctcagacgc tggcggatta taccgcggag    2820
cgcctgagta gcgtgctgtg caattggttt ctggcgaata tccagccaga aggggtgtcc    2880
ctgcacagcc gggatgacct gtacagctat ttcctgattg ataatcaggt ctcttctgcc    2940
ataaaaacca cccgactggc agaggccatt gccggtattc agctctacat caaccgggcg    3000
ctgaatcgga tagagcctaa tgcccgtgcc gatgtgtcaa cccgccagtt ttttaccgac    3060
tggacggtga ataaccgtta cagcacctgg ggcggggtgt cgcggctggt ttattatccg    3120
gaaaattaca ttgacccaac ccagcgtatc gggcagaccc ggatgatgga tgaactgctg    3180
gaaaatatca gccagagtaa acttagccgg gacacagtgg aggatgcctt taaaacttac    3240
ctgacccgct ttgaaaccgt ggcggatctg aaagttgtca gcgcctatca cgacaacgtc    3300
aacagcaaca ccgactgac ctggtttgtc ggccaaacgc gggagaacct gccggaatac    3360
tactggcgta acgtggatat atcacggatg caggcgggtg aactggccgc caatgcctgg    3420
aaagagtgga cgaagattga tacagcggtc aaccccctaca aggatgcaat acgtccggtc    3480
atattcaggg aacgtttgca ccttatctgg gtagaaaaag aggaagtggc gaaaaatggt    3540
actgatccgg tggaaaccta tgaccgtttt actctgaaac tggcgtttct gcgtcatgat    3600
ggcagttgga gtgccccctg gtcttacgat atcacaacgc aggtggaggc ggtcactgac    3660
aaaaaacctg acactgaacg gctggcgctg ccgcatcag gctttcaggg cgaggacact    3720
ctgctggtgt ttgtctacaa aaccgggaag agttactcgg attttggcgg cagcaataaa    3780
aatgtggcag gcatgaccat ttacggcgat ggctccttca aaaagatgga gaacacagca    3840
ctcagccgtt acagccaact gaaaaatacc tttgatatca ttcatactca aggcaacgac    3900
```

-continued

```
ttggtaagaa aggccagcta tcgtttcgcg caggattttg aagtgcctgc ctcgttgaat    3960
atgggttctg ccatcggtga tgatagtctg acggtgatga gaacgggaa tattccgcag     4020
ataaccagta aatactccag cgataacctt gctattacgc tacataacgc cgctttcact    4080
gtcagatatg atggcagtgg caatgtcatc agaaacaaac aaatcagcgc catgaaactg    4140
acggggtgg atggaaagtc ccagtacggc aatgcattta tcatcgcaaa taccgttaaa     4200
cattatggcg gttactctga tctgggggg ccgatcaccg tttataataa aacgaaaaac     4260
tatattgcat cagttcaagg ccacttgatg aacgcagatt acactaggcg tttgattcta    4320
acaccagttg aaaataatta ttatgccaga ttgttcgagt ttccattttc tccaaacaca    4380
attttaaaca ccgttttcac ggttggtagc aataaaacca gtgattttaa aaagtgcagt    4440
tatgctgttg atggtaataa ttctcagggc ttccagatat ttagttccta tcaatcatcc    4500
ggctggctgg atattgatac aggcattaac aataccgata tcaaaattac ggtgatggct    4560
ggcagtaaaa cccacacctt tacgccagt gaccatattg cttccttgcc ggcaaacagt     4620
tttgatgcta tgccgtacac ctttaagcca ctggaaatcg atgcttcatc gttggccttt    4680
accaataata ttgctcctct ggatatcgtt tttgagacca agccaaaga cgggcgagtg     4740
ctgggtaaga tcaagcaaac attatcggtg aaacgggtaa attataatcc ggaagatatt    4800
ctgtttctgc gtgaaactca ttcgggtgcc caatatatgc agctcgggt gtatcgtatt     4860
cgtcttaata ccctgctggc ttctcaactg gtatccagag caaacacggg cattgatact    4920
atcctgacaa tggaaaccca gcggttaccg gaacctccgt tgggagaagg cttctttgcc    4980
aactttgttc tgcctaaata tgaccctgct gaacatggcg atgagcggtg gtttaaaatc    5040
catattggga atgttggcgg taacacggga aggcagcctt attacagcgg aatgttatcc    5100
gatacgtcgg aaaccagtat gacactgttt gtcccttatg ccgaagggta ttacatgcat    5160
gaaggtgtca gattgggggt tggataccag aaaattacct atgacaacac ttgggaatct    5220
gctttctttt attttgatga gacaaaacag caatttgtat taattaacga tgctgatcat    5280
gattcaggaa tgacgcaaca ggggatcgtg aaaaatatca agaaatacaa aggattttg    5340
aatgtttcta tcgcaacggg ctattccgcc ccgatggatt tcaatagtgc cagcgccctc    5400
tattactggg aattgttcta ttacaccccg atgatgtgct tccagcgttt gctacaggaa    5460
aaacaattcg acgaagccac acaatggata aactacgtct acaatcccgc cggctatatc    5520
gttaacggag aaatcgcccc ctggatctgg aactgccggc cgctggaaga gaccacctcc    5580
tggaatgcca atccgctgga tgccatcgat ccggatgccg tcgcccaaaa tgacccaatg    5640
cactacaaga ttgccacctt tatgcgcctg ttggatcaac ttattctgcg cggcgatatg    5700
gcctatcgag aactgacccg cgatgcgttg aatgaagcca aatgtggta tgtgcgtact    5760
ttagaattgc tcggtgatga gccggaggat tacggtagcc aacagtgggc agcaccgtcc    5820
cttttccgggg cggcgagtca aaccgtgcag gcggcttatc agcaggatct tacgatgctg    5880
ggccgtggtg gggtttccaa gaatctccgt accgctaact cgttggtggg tttgttcctg    5940
ccggaatata cccggcgct caccgattac tggcaaaccc tgcgtttgcg cctgtttaac    6000
ctgcgccata atctttccat tgacggacag ccgttatcgc tggcgattta cgccgagcct    6060
accgatccga aagcgctgct caccagtatg gtacaggcct ctcagggcgg tagtgcagtg    6120
ctgcccggca cattgtcgtt ataccgcttc ccggtgatgc tggagcggac ccgcaatctg    6180
gtagcgcaat taacccagtt cggcaccttc tctgctcagta tggcagagca tgatgatgcc    6240
gatgaactca ccacgctgct actacagcag ggtatggaac tggcgacaca gagcatccgt    6300
```

```
attcagcaac gaactgtcga tgaagtggat gctgatattg ctgtattggc agagagccgc    6360
cgcagtgcac aaaatcgtct ggaaaaatac cagcagctgt atgacgagga tatcaaccac    6420
ggagaacagc gggcaatgtc actgcttgat gcagcggcag gtcagtctct ggccgggcag    6480
gtgctttcaa tagcggaagg ggtggccgat ttagtgccaa acgtgttcgg tttagcttgt    6540
ggcggcagtc gttgggggc agcactgcgt gcttccgcct ccgtgatgtc gctttctgcc    6600
acagcttccc aatattccgc agacaaaatc agccgttcgg aagcctaccg ccgccgccgt    6660
caggagtggg aaattcagcg tgataatgct gacggtgaag tcaaacaaat ggatgcccag    6720
ttggaaagcc tgaaaatccg ccgcgaagca gcacagatgc aggtggaata tcaggagacc    6780
cagcaggccc atactcaggc tcagttagag ctgttacagc gtaaattcac aaacaaagcg    6840
ctttacagtt ggatgcgcgg caagctgagt gctatctatt accagttctt tgacctgacc    6900
cagtccttct gcctgatggc acaggaagcg ctgcgccgcg agctgaccga caacggtgtt    6960
acctttatcc ggggtggggc ctggaacggt acgactgcgg gtttgatggc gggtgaaacg    7020
ttgctgctga atctggcaga aatgggaaaaa gtctggctgg agcgtgatga gcgggcactg    7080
gaagtgaccc gtaccgtctc gttggcacag ttctatcagg ccttatcatc agacaacttt    7140
aatctgaccg aaaaactcac gcaattcctg cgtgaaggga aagcaacgt aggagcttcc    7200 ggcaatgaat taaaactcag taaccgtcag atagaagcct cagtgcgatt gtctgatttg    7260
aaaattttca gcgactaccc cgaaagcctt ggcaataccc gtcagttgaa acaggtgagt    7320
gtcaccttgc cggcgctggt tgggccgtat gaagatattc gggcggtgct gaattacggg    7380
ggcagcatcg tcatgccacg cggttgcagt gctattgctc tctcccacgg cgtgaatgac    7440
agtggtcaat ttatgctgga tttcaacgat tcccgttatc tgccgtttga aggtatttcc    7500
gtgaatgaca gcggcagcct gacgttgagt ttcccggatg cgactgatcg gcagaaagcg    7560
ctgctggaga gcctgagcga tatcattctg catatccgct ataccattcg ttct          7614
```

<210> SEQ ID NO 20
<211> LENGTH: 2538
<212> TYPE: PRT
<213> ORGANISM: Xenorhabdus nematophilus

<400> SEQUENCE: 20

```
Met Tyr Ser Thr Ala Val Leu Leu Asn Lys Ile Ser Pro Thr Arg Asp
1               5                   10                  15

Gly Gln Thr Met Thr Leu Ala Asp Leu Gln Tyr Leu Ser Phe Ser Glu
            20                  25                  30

Leu Arg Lys Ile Phe Asp Asp Gln Leu Ser Trp Gly Glu Ala Arg His
        35                  40                  45

Leu Tyr His Glu Thr Ile Glu Gln Lys Lys Asn Asn Arg Leu Leu Glu
    50                  55                  60

Ala Arg Ile Phe Thr Arg Ala Asn Pro Gln Leu Ser Gly Ala Ile Arg
65                  70                  75                  80

Leu Gly Ile Glu Arg Asp Ser Val Ser Arg Ser Tyr Asp Glu Met Phe
                85                  90                  95

Gly Ala Arg Ser Ser Ser Phe Val Lys Pro Gly Ser Val Ala Ser Met
            100                 105                 110

Phe Ser Pro Ala Gly Tyr Leu Thr Glu Leu Tyr Arg Glu Ala Lys Asp
        115                 120                 125

Leu His Phe Ser Ser Ala Tyr His Leu Asp Asn Arg Arg Pro Asp
    130                 135                 140
```

```
Leu Ala Asp Leu Thr Leu Ser Gln Ser Asn Met Asp Thr Glu Ile Ser
145                 150                 155                 160

Thr Leu Thr Leu Ser Asn Glu Leu Leu Leu Glu His Ile Thr Arg Lys
            165                 170                 175

Thr Gly Gly Asp Ser Asp Ala Leu Met Glu Ser Leu Ser Thr Tyr Arg
        180                 185                 190

Gln Ala Ile Asp Thr Pro Tyr His Gln Pro Tyr Glu Thr Ile Arg Gln
            195                 200                 205

Val Ile Met Thr His Asp Ser Thr Leu Ser Ala Leu Ser Arg Asn Pro
210                 215                 220

Glu Val Met Gly Gln Ala Glu Gly Ala Ser Leu Leu Ala Ile Leu Ala
225                 230                 235                 240

Asn Ile Ser Pro Glu Leu Tyr Asn Ile Leu Thr Glu Glu Ile Thr Glu
                245                 250                 255

Lys Asn Ala Asp Ala Leu Phe Ala Gln Asn Phe Ser Glu Asn Ile Thr
            260                 265                 270

Pro Glu Asn Phe Ala Ser Gln Ser Trp Ile Ala Lys Tyr Tyr Gly Leu
        275                 280                 285

Glu Leu Ser Glu Val Gln Lys Tyr Leu Gly Met Leu Gln Asn Gly Tyr
    290                 295                 300

Ser Asp Ser Thr Ser Ala Tyr Val Asp Asn Ile Ser Thr Gly Leu Val
305                 310                 315                 320

Val Asn Asn Glu Ser Lys Leu Glu Ala Tyr Lys Ile Thr Arg Val Lys
                325                 330                 335

Thr Asp Asp Tyr Asp Lys Asn Ile Asn Tyr Phe Asp Leu Met Tyr Glu
            340                 345                 350

Gly Asn Asn Gln Phe Phe Ile Arg Ala Asn Phe Lys Val Ser Arg Glu
        355                 360                 365

Phe Gly Ala Thr Leu Arg Lys Asn Ala Gly Pro Ser Gly Ile Val Gly
    370                 375                 380

Ser Leu Ser Gly Pro Leu Ile Ala Asn Thr Asn Phe Lys Ser Asn Tyr
385                 390                 395                 400

Leu Ser Asn Ile Ser Asp Ser Glu Tyr Lys Asn Gly Val Lys Ile Tyr
                405                 410                 415

Ala Tyr Arg Tyr Thr Ser Ser Thr Ser Ala Thr Asn Gln Gly Gly Gly
            420                 425                 430

Ile Phe Thr Phe Glu Ser Tyr Pro Leu Thr Ile Phe Ala Leu Lys Leu
        435                 440                 445

Asn Lys Ala Ile Arg Leu Cys Leu Thr Ser Gly Leu Ser Pro Asn Glu
    450                 455                 460

Leu Gln Thr Ile Val Arg Ser Asp Asn Ala Gln Gly Ile Ile Asn Asp
465                 470                 475                 480

Ser Val Leu Thr Lys Val Phe Tyr Thr Leu Phe Tyr Ser His Arg Tyr
                485                 490                 495

Ala Leu Ser Phe Asp Asp Ala Gln Val Leu Asn Gly Ser Val Ile Asn
            500                 505                 510

Gln Tyr Ala Asp Asp Asp Ser Val Ser His Phe Asn Arg Leu Phe Asn
        515                 520                 525

Thr Pro Pro Leu Lys Gly Lys Ile Phe Glu Ala Asp Gly Asn Thr Val
    530                 535                 540

Ser Ile Asp Pro Asp Glu Glu Gln Ser Thr Phe Ala Arg Ser Ala Leu
545                 550                 555                 560
```

-continued

```
Met Arg Gly Leu Gly Val Asn Ser Gly Glu Leu Tyr Gln Leu Gly Lys
                565                 570                 575
Leu Ala Gly Val Leu Asp Ala Gln Asn Thr Ile Thr Leu Ser Val Phe
            580                 585                 590
Val Ile Ser Ser Leu Tyr Arg Leu Thr Leu Leu Ala Arg Val His Gln
        595                 600                 605
Leu Thr Val Asn Glu Leu Cys Met Leu Tyr Gly Leu Ser Pro Phe Asn
    610                 615                 620
Gly Lys Thr Thr Ala Ser Leu Ser Ser Gly Glu Leu Pro Arg Leu Val
625                 630                 635                 640
Ile Trp Leu Tyr Gln Val Thr Gln Trp Leu Thr Glu Ala Glu Ile Thr
                645                 650                 655
Thr Glu Ala Ile Trp Leu Leu Cys Thr Pro Glu Phe Ser Gly Asn Ile
            660                 665                 670
Ser Pro Glu Ile Ser Asn Leu Leu Asn Asn Leu Arg Pro Ser Ile Ser
        675                 680                 685
Glu Asp Met Ala Gln Ser His Asn Arg Glu Leu Gln Ala Glu Ile Leu
    690                 695                 700
Ala Pro Phe Ile Ala Ala Thr Leu His Leu Ala Ser Pro Asp Met Ala
705                 710                 715                 720
Arg Tyr Ile Leu Leu Trp Thr Asp Asn Leu Arg Pro Gly Gly Leu Asp
                725                 730                 735
Ile Ala Gly Phe Met Thr Leu Val Leu Lys Glu Ser Leu Asn Ala Asn
            740                 745                 750
Glu Thr Thr Gln Leu Val Gln Phe Cys His Val Met Ala Gln Leu Ser
        755                 760                 765
Leu Ser Val Gln Thr Leu Arg Leu Ser Glu Ala Glu Leu Ser Val Leu
    770                 775                 780
Val Ile Ser Gly Phe Ala Val Leu Gly Ala Lys Asn Gln Pro Ala Gly
785                 790                 795                 800
Gln His Asn Ile Asp Thr Leu Phe Ser Leu Tyr Arg Phe His Gln Trp
                805                 810                 815
Ile Asn Gly Leu Gly Asn Pro Gly Ser Asp Thr Leu Asp Met Leu Arg
            820                 825                 830
Gln Gln Thr Leu Thr Ala Asp Arg Leu Ala Ser Val Met Gly Leu Asp
        835                 840                 845
Ile Ser Met Val Thr Gln Ala Met Val Ser Ala Gly Val Asn Gln Leu
    850                 855                 860
Gln Cys Trp Gln Asp Ile Asn Thr Val Leu Gln Trp Ile Asp Val Ala
865                 870                 875                 880
Ser Ala Leu His Thr Met Pro Ser Val Ile Arg Thr Leu Val Asn Ile
                885                 890                 895
Arg Tyr Val Thr Ala Leu Asn Lys Ala Glu Ser Asn Leu Pro Ser Trp
            900                 905                 910
Asp Glu Trp Gln Thr Leu Ala Glu Asn Met Glu Ala Gly Leu Ser Thr
        915                 920                 925
Gln Gln Ala Gln Thr Leu Ala Asp Tyr Thr Ala Glu Arg Leu Ser Ser
    930                 935                 940
Val Leu Cys Asn Trp Phe Leu Ala Asn Ile Gln Pro Glu Gly Val Ser
945                 950                 955                 960
Leu His Ser Arg Asp Asp Leu Tyr Ser Tyr Phe Leu Ile Asp Asn Gln
                965                 970                 975
Val Ser Ser Ala Ile Lys Thr Thr Arg Leu Ala Glu Ala Ile Ala Gly
```

-continued

```
                980             985             990
Ile Gln Leu Tyr Ile Asn Arg Ala Leu Asn Arg Ile Glu Pro Asn Ala
            995            1000            1005

Arg Ala Asp Val Ser Thr Arg Gln Phe Phe Thr Asp Trp Thr Val
    1010            1015            1020

Asn Asn Arg Tyr Ser Thr Trp Gly Gly Val Ser Arg Leu Val Tyr
    1025            1030            1035

Tyr Pro Glu Asn Tyr Ile Asp Pro Thr Gln Arg Ile Gly Gln Thr
    1040            1045            1050

Arg Met Met Asp Glu Leu Leu Glu Asn Ile Ser Gln Ser Lys Leu
    1055            1060            1065

Ser Arg Asp Thr Val Glu Asp Ala Phe Lys Thr Tyr Leu Thr Arg
    1070            1075            1080

Phe Glu Thr Val Ala Asp Leu Lys Val Val Ser Ala Tyr His Asp
    1085            1090            1095

Asn Val Asn Ser Asn Thr Gly Leu Thr Trp Phe Val Gly Gln Thr
    1100            1105            1110

Arg Glu Asn Leu Pro Glu Tyr Tyr Trp Arg Asn Val Asp Ile Ser
    1115            1120            1125

Arg Met Gln Ala Gly Glu Leu Ala Ala Asn Ala Trp Lys Glu Trp
    1130            1135            1140

Thr Lys Ile Asp Thr Ala Val Asn Pro Tyr Lys Asp Ala Ile Arg
    1145            1150            1155

Pro Val Ile Phe Arg Glu Arg Leu His Leu Ile Trp Val Glu Lys
    1160            1165            1170

Glu Glu Val Ala Lys Asn Gly Thr Asp Pro Val Glu Thr Tyr Asp
    1175            1180            1185

Arg Phe Thr Leu Lys Leu Ala Phe Leu Arg His Asp Gly Ser Trp
    1190            1195            1200

Ser Ala Pro Trp Ser Tyr Asp Ile Thr Thr Gln Val Glu Ala Val
    1205            1210            1215

Thr Asp Lys Lys Pro Asp Thr Glu Arg Leu Ala Leu Ala Ala Ser
    1220            1225            1230

Gly Phe Gln Gly Glu Asp Thr Leu Leu Val Phe Val Tyr Lys Thr
    1235            1240            1245

Gly Lys Ser Tyr Ser Asp Phe Gly Gly Ser Asn Lys Asn Val Ala
    1250            1255            1260

Gly Met Thr Ile Tyr Gly Asp Gly Ser Phe Lys Lys Met Glu Asn
    1265            1270            1275

Thr Ala Leu Ser Arg Tyr Ser Gln Leu Lys Asn Thr Phe Asp Ile
    1280            1285            1290

Ile His Thr Gln Gly Asn Asp Leu Val Arg Lys Ala Ser Tyr Arg
    1295            1300            1305

Phe Ala Gln Asp Phe Glu Val Pro Ala Ser Leu Asn Met Gly Ser
    1310            1315            1320

Ala Ile Gly Asp Asp Ser Leu Thr Val Met Glu Asn Gly Asn Ile
    1325            1330            1335

Pro Gln Ile Thr Ser Lys Tyr Ser Ser Asp Asn Leu Ala Ile Thr
    1340            1345            1350

Leu His Asn Ala Ala Phe Thr Val Arg Tyr Asp Gly Ser Gly Asn
    1355            1360            1365

Val Ile Arg Asn Lys Gln Ile Ser Ala Met Lys Leu Thr Gly Val
    1370            1375            1380
```

-continued

```
Asp Gly Lys Ser Gln Tyr Gly Asn Ala Phe Ile Ile Ala Asn Thr
    1385                1390                1395

Val Lys His Tyr Gly Gly Tyr Ser Asp Leu Gly Pro Ile Thr
    1400                1405                1410

Val Tyr Asn Lys Thr Lys Asn Tyr Ile Ala Ser Val Gln Gly His
    1415                1420                1425

Leu Met Asn Ala Asp Tyr Thr Arg Arg Leu Ile Leu Thr Pro Val
    1430                1435                1440

Glu Asn Asn Tyr Tyr Ala Arg Leu Phe Glu Phe Pro Phe Ser Pro
    1445                1450                1455

Asn Thr Ile Leu Asn Thr Val Phe Thr Val Gly Ser Asn Lys Thr
    1460                1465                1470

Ser Asp Phe Lys Lys Cys Ser Tyr Ala Val Asp Gly Asn Asn Ser
    1475                1480                1485

Gln Gly Phe Gln Ile Phe Ser Ser Tyr Gln Ser Ser Gly Trp Leu
    1490                1495                1500

Asp Ile Asp Thr Gly Ile Asn Asn Thr Asp Ile Lys Ile Thr Val
    1505                1510                1515

Met Ala Gly Ser Lys Thr His Thr Phe Thr Ala Ser Asp His Ile
    1520                1525                1530

Ala Ser Leu Pro Ala Asn Ser Phe Asp Ala Met Pro Tyr Thr Phe
    1535                1540                1545

Lys Pro Leu Glu Ile Asp Ala Ser Ser Leu Ala Phe Thr Asn Asn
    1550                1555                1560

Ile Ala Pro Leu Asp Ile Val Phe Glu Thr Lys Ala Lys Asp Gly
    1565                1570                1575

Arg Val Leu Gly Lys Ile Lys Gln Thr Leu Ser Val Lys Arg Val
    1580                1585                1590

Asn Tyr Asn Pro Glu Asp Ile Leu Phe Leu Arg Glu Thr His Ser
    1595                1600                1605

Gly Ala Gln Tyr Met Gln Leu Gly Val Tyr Arg Ile Arg Leu Asn
    1610                1615                1620

Thr Leu Leu Ala Ser Gln Leu Val Ser Arg Ala Asn Thr Gly Ile
    1625                1630                1635

Asp Thr Ile Leu Thr Met Glu Thr Gln Arg Leu Pro Glu Pro Pro
    1640                1645                1650

Leu Gly Glu Gly Phe Phe Ala Asn Phe Val Leu Pro Lys Tyr Asp
    1655                1660                1665

Pro Ala Glu His Gly Asp Glu Arg Trp Phe Lys Ile His Ile Gly
    1670                1675                1680

Asn Val Gly Gly Asn Thr Gly Arg Gln Pro Tyr Tyr Ser Gly Met
    1685                1690                1695

Leu Ser Asp Thr Ser Glu Thr Ser Met Thr Leu Phe Val Pro Tyr
    1700                1705                1710

Ala Glu Gly Tyr Tyr Met His Glu Gly Val Arg Leu Gly Val Gly
    1715                1720                1725

Tyr Gln Lys Ile Thr Tyr Asp Asn Thr Trp Glu Ser Ala Phe Phe
    1730                1735                1740

Tyr Phe Asp Glu Thr Lys Gln Gln Phe Val Leu Ile Asn Asp Ala
    1745                1750                1755

Asp His Asp Ser Gly Met Thr Gln Gln Gly Ile Val Lys Asn Ile
    1760                1765                1770
```

```
Lys Lys Tyr Lys Gly Phe Leu Asn Val Ser Ile Ala Thr Gly Tyr
1775                1780                1785

Ser Ala Pro Met Asp Phe Asn Ser Ala Ser Ala Leu Tyr Tyr Trp
1790                1795                1800

Glu Leu Phe Tyr Tyr Thr Pro Met Met Cys Phe Gln Arg Leu Leu
1805                1810                1815

Gln Glu Lys Gln Phe Asp Glu Ala Thr Gln Trp Ile Asn Tyr Val
1820                1825                1830

Tyr Asn Pro Ala Gly Tyr Ile Val Asn Gly Glu Ile Ala Pro Trp
1835                1840                1845

Ile Trp Asn Cys Arg Pro Leu Glu Glu Thr Thr Ser Trp Asn Ala
1850                1855                1860

Asn Pro Leu Asp Ala Ile Asp Pro Asp Ala Val Ala Gln Asn Asp
1865                1870                1875

Pro Met His Tyr Lys Ile Ala Thr Phe Met Arg Leu Leu Asp Gln
1880                1885                1890

Leu Ile Leu Arg Gly Asp Met Ala Tyr Arg Glu Leu Thr Arg Asp
1895                1900                1905

Ala Leu Asn Glu Ala Lys Met Trp Tyr Val Arg Thr Leu Glu Leu
1910                1915                1920

Leu Gly Asp Glu Pro Glu Asp Tyr Gly Ser Gln Gln Trp Ala Ala
1925                1930                1935

Pro Ser Leu Ser Gly Ala Ala Ser Gln Thr Val Gln Ala Ala Tyr
1940                1945                1950

Gln Gln Asp Leu Thr Met Leu Gly Arg Gly Gly Val Ser Lys Asn
1955                1960                1965

Leu Arg Thr Ala Asn Ser Leu Val Gly Leu Phe Leu Pro Glu Tyr
1970                1975                1980

Asn Pro Ala Leu Thr Asp Tyr Trp Gln Thr Leu Arg Leu Arg Leu
1985                1990                1995

Phe Asn Leu Arg His Asn Leu Ser Ile Asp Gly Gln Pro Leu Ser
2000                2005                2010

Leu Ala Ile Tyr Ala Glu Pro Thr Asp Pro Lys Ala Leu Leu Thr
2015                2020                2025

Ser Met Val Gln Ala Ser Gln Gly Gly Ser Ala Val Leu Pro Gly
2030                2035                2040

Thr Leu Ser Leu Tyr Arg Phe Pro Val Met Leu Glu Arg Thr Arg
2045                2050                2055

Asn Leu Val Ala Gln Leu Thr Gln Phe Gly Thr Ser Leu Leu Ser
2060                2065                2070

Met Ala Glu His Asp Asp Ala Asp Glu Leu Thr Thr Leu Leu Leu
2075                2080                2085

Gln Gln Gly Met Glu Leu Ala Thr Gln Ser Ile Arg Ile Gln Gln
2090                2095                2100

Arg Thr Val Asp Glu Val Asp Ala Asp Ile Ala Val Leu Ala Glu
2105                2110                2115

Ser Arg Arg Ser Ala Gln Asn Arg Leu Glu Lys Tyr Gln Gln Leu
2120                2125                2130

Tyr Asp Glu Asp Ile Asn His Gly Glu Gln Arg Ala Met Ser Leu
2135                2140                2145

Leu Asp Ala Ala Ala Gly Gln Ser Leu Ala Gly Gln Val Leu Ser
2150                2155                2160

Ile Ala Glu Gly Val Ala Asp Leu Val Pro Asn Val Phe Gly Leu
```

```
                2165                2170                2175

Ala Cys Gly Gly Ser Arg Trp Gly Ala Ala Leu Arg Ala Ser Ala
    2180                2185                2190

Ser Val Met Ser Leu Ser Ala Thr Ala Ser Gln Tyr Ser Ala Asp
    2195                2200                2205

Lys Ile Ser Arg Ser Glu Ala Tyr Arg Arg Arg Gln Glu Trp
    2210                2215                2220

Glu Ile Gln Arg Asp Asn Ala Asp Gly Glu Val Lys Gln Met Asp
    2225                2230                2235

Ala Gln Leu Glu Ser Leu Lys Ile Arg Arg Glu Ala Ala Gln Met
    2240                2245                2250

Gln Val Glu Tyr Gln Glu Thr Gln Gln Ala His Thr Gln Ala Gln
    2255                2260                2265

Leu Glu Leu Leu Gln Arg Lys Phe Thr Asn Lys Ala Leu Tyr Ser
    2270                2275                2280

Trp Met Arg Gly Lys Leu Ser Ala Ile Tyr Tyr Gln Phe Phe Asp
    2285                2290                2295

Leu Thr Gln Ser Phe Cys Leu Met Ala Gln Glu Ala Leu Arg Arg
    2300                2305                2310

Glu Leu Thr Asp Asn Gly Val Thr Phe Ile Arg Gly Gly Ala Trp
    2315                2320                2325

Asn Gly Thr Thr Ala Gly Leu Met Ala Gly Glu Thr Leu Leu Leu
    2330                2335                2340

Asn Leu Ala Glu Met Glu Lys Val Trp Leu Glu Arg Asp Glu Arg
    2345                2350                2355

Ala Leu Glu Val Thr Arg Thr Val Ser Leu Ala Gln Phe Tyr Gln
    2360                2365                2370

Ala Leu Ser Ser Asp Asn Phe Asn Leu Thr Glu Lys Leu Thr Gln
    2375                2380                2385

Phe Leu Arg Glu Gly Lys Gly Asn Val Gly Ala Ser Gly Asn Glu
    2390                2395                2400

Leu Lys Leu Ser Asn Arg Gln Ile Glu Ala Ser Val Arg Leu Ser
    2405                2410                2415

Asp Leu Lys Ile Phe Ser Asp Tyr Pro Glu Ser Leu Gly Asn Thr
    2420                2425                2430

Arg Gln Leu Lys Gln Val Ser Val Thr Leu Pro Ala Leu Val Gly
    2435                2440                2445

Pro Tyr Glu Asp Ile Arg Ala Val Leu Asn Tyr Gly Gly Ser Ile
    2450                2455                2460

Val Met Pro Arg Gly Cys Ser Ala Ile Ala Leu Ser His Gly Val
    2465                2470                2475

Asn Asp Ser Gly Gln Phe Met Leu Asp Phe Asn Asp Ser Arg Tyr
    2480                2485                2490

Leu Pro Phe Glu Gly Ile Ser Val Asn Asp Ser Gly Ser Leu Thr
    2495                2500                2505

Leu Ser Phe Pro Asp Ala Thr Asp Arg Gln Lys Ala Leu Leu Glu
    2510                2515                2520

Ser Leu Ser Asp Ile Ile Leu His Ile Arg Tyr Thr Ile Arg Ser
    2525                2530                2535

<210> SEQ ID NO 21
<211> LENGTH: 7551
<212> TYPE: DNA
<213> ORGANISM: Photorhabdus luminescens
```

```
<220> FEATURE:
<221> NAME/KEY: exon
<222> LOCATION: (1)..(7551)

<400> SEQUENCE: 21 atg aac gag tct gta aaa gag ata cct gat gta tta aaa agc cag tgt      48
Met Asn Glu Ser Val Lys Glu Ile Pro Asp Val Leu Lys Ser Gln Cys
1               5                   10                  15 ggt ttt aat tgt ctg aca gat att agc cac agc tct ttt aat gaa ttt      96
Gly Phe Asn Cys Leu Thr Asp Ile Ser His Ser Ser Phe Asn Glu Phe
            20                  25                  30 cgc cag caa gta tct gag cac ctc tcc tgg tcc gaa aca cac gac tta     144
Arg Gln Gln Val Ser Glu His Leu Ser Trp Ser Glu Thr His Asp Leu
        35                  40                  45 tat cat gat gca caa cag gca caa aag gat aat cgc ctg tat gaa gcg     192
Tyr His Asp Ala Gln Gln Ala Gln Lys Asp Asn Arg Leu Tyr Glu Ala
    50                  55                  60 cgt att ctc aaa cgc gcc aat ccc caa tta caa aat gcg gtg cat ctt     240
Arg Ile Leu Lys Arg Ala Asn Pro Gln Leu Gln Asn Ala Val His Leu
65                  70                  75                  80 gcc att ctc gct ccc aat gct gaa ctg ata ggc tat aac aat caa ttt     288
Ala Ile Leu Ala Pro Asn Ala Glu Leu Ile Gly Tyr Asn Asn Gln Phe
                85                  90                  95 agc ggt aga gcc agt caa tat gtt gcg ccg ggt acc gtt tct tcc atg     336
Ser Gly Arg Ala Ser Gln Tyr Val Ala Pro Gly Thr Val Ser Ser Met
            100                 105                 110 ttc tcc ccc gcc gct tat ttg act gaa ctt tat cgt gaa gca cgc aat     384
Phe Ser Pro Ala Ala Tyr Leu Thr Glu Leu Tyr Arg Glu Ala Arg Asn
        115                 120                 125 tta cac gca agt gac tcc gtt tat tat ctg gat acc cgc cgc cca gat     432
Leu His Ala Ser Asp Ser Val Tyr Tyr Leu Asp Thr Arg Arg Pro Asp
    130                 135                 140 ctc aaa tca atg gcg ctc agt cag caa aat atg gat ata gaa tta tcc     480
Leu Lys Ser Met Ala Leu Ser Gln Gln Asn Met Asp Ile Glu Leu Ser
145                 150                 155                 160 aca ctc tct ttg tcc aat gag ctg tta ttg gaa agc att aaa act gaa     528
Thr Leu Ser Leu Ser Asn Glu Leu Leu Leu Glu Ser Ile Lys Thr Glu
                165                 170                 175 tct aaa ctg gaa aac tat act aaa gtg atg gaa atg ctc tcc act ttc     576
Ser Lys Leu Glu Asn Tyr Thr Lys Val Met Glu Met Leu Ser Thr Phe
            180                 185                 190 cgt cct tcc ggc gca acg cct tat cat gat gct tat gaa aat gtg cgt     624
Arg Pro Ser Gly Ala Thr Pro Tyr His Asp Ala Tyr Glu Asn Val Arg
        195                 200                 205 gaa gtt atc cag cta caa gat cct gga ctt gag caa ctc aat gca tca     672
Glu Val Ile Gln Leu Gln Asp Pro Gly Leu Glu Gln Leu Asn Ala Ser
    210                 215                 220 ccg gca att gcc ggg ttg atg cat caa gcc tcc cta ttg ggt att aac     720
Pro Ala Ile Ala Gly Leu Met His Gln Ala Ser Leu Leu Gly Ile Asn
225                 230                 235                 240 gct tca atc tcg cct gag cta ttt aat att ctg acg gag gag att acc     768
Ala Ser Ile Ser Pro Glu Leu Phe Asn Ile Leu Thr Glu Glu Ile Thr
                245                 250                 255 gaa ggt aat gct gag gaa ctt tat aag aaa aat ttt ggt aat atc gaa     816
Glu Gly Asn Ala Glu Glu Leu Tyr Lys Lys Asn Phe Gly Asn Ile Glu
            260                 265                 270 ccg gcc tca ttg gct atg ccg gaa tac ctt aaa cgt tat tat aat tta     864
Pro Ala Ser Leu Ala Met Pro Glu Tyr Leu Lys Arg Tyr Tyr Asn Leu
        275                 280                 285 agc gat gaa gaa ctt agt cag ttt att ggt aaa gcc agc aat ttt ggt     912
```

```
Ser Asp Glu Glu Leu Ser Gln Phe Ile Gly Lys Ala Ser Asn Phe Gly
    290                 295                 300 caa cag gaa tat agt aat aac caa ctt att act ccg gta gtc aac agc     960
Gln Gln Glu Tyr Ser Asn Asn Gln Leu Ile Thr Pro Val Val Asn Ser
305                 310                 315                 320 agt gat ggc acg gtt aag gta tat cgg atc acc cgc gaa tat aca acc    1008
Ser Asp Gly Thr Val Lys Val Tyr Arg Ile Thr Arg Glu Tyr Thr Thr
                325                 330                 335 aat gct tat caa atg gat gtg gag cta ttt ccc ttc ggt ggt gag aat    1056
Asn Ala Tyr Gln Met Asp Val Glu Leu Phe Pro Phe Gly Gly Glu Asn
            340                 345                 350 tat cgg tta gat tat aaa ttc aaa aat ttt tat aat gcc tct tat tta    1104
Tyr Arg Leu Asp Tyr Lys Phe Lys Asn Phe Tyr Asn Ala Ser Tyr Leu
        355                 360                 365 tcc atc aag tta aat gat aaa aga gaa ctt gtt cga act gaa ggc gct    1152
Ser Ile Lys Leu Asn Asp Lys Arg Glu Leu Val Arg Thr Glu Gly Ala
    370                 375                 380 cct caa gtc aat ata gaa tac tcc gca aat atc aca tta aat acc gct    1200
Pro Gln Val Asn Ile Glu Tyr Ser Ala Asn Ile Thr Leu Asn Thr Ala
385                 390                 395                 400 gat atc agt caa cct ttt gaa att ggc ctg aca cga gta ctt cct tcc    1248
Asp Ile Ser Gln Pro Phe Glu Ile Gly Leu Thr Arg Val Leu Pro Ser
                405                 410                 415 ggt tct tgg gca tat gcc gcc gca aaa ttt acc gtt gaa gag tat aac    1296
Gly Ser Trp Ala Tyr Ala Ala Ala Lys Phe Thr Val Glu Glu Tyr Asn
            420                 425                 430 caa tac tct ttt ctg cta aaa ctt aac aag gct att cgt cta tca cgt    1344
Gln Tyr Ser Phe Leu Leu Lys Leu Asn Lys Ala Ile Arg Leu Ser Arg
        435                 440                 445 gcg aca gaa ttg tca ccc acg att ctg gaa ggc att gtg cgc agt gtt    1392
Ala Thr Glu Leu Ser Pro Thr Ile Leu Glu Gly Ile Val Arg Ser Val
    450                 455                 460 aat cta caa ctg gat atc aac aca gac gta tta ggt aaa gtt ttt ctg    1440
Asn Leu Gln Leu Asp Ile Asn Thr Asp Val Leu Gly Lys Val Phe Leu
465                 470                 475                 480 act aaa tat tat atg cag cgt tat gct att cat gct gaa act gcc ctg    1488
Thr Lys Tyr Tyr Met Gln Arg Tyr Ala Ile His Ala Glu Thr Ala Leu
                485                 490                 495 ata cta tgc aac gcg cct att tca caa cgt tca tat gat aat caa cct    1536
Ile Leu Cys Asn Ala Pro Ile Ser Gln Arg Ser Tyr Asp Asn Gln Pro
            500                 505                 510 agc caa ttt gat cgc ctg ttt aat acg cca tta ctg aac gga caa tat    1584
Ser Gln Phe Asp Arg Leu Phe Asn Thr Pro Leu Leu Asn Gly Gln Tyr
        515                 520                 525 ttt tct acc ggc gat gag gag att gat tta aat tca ggt agc acc ggc    1632
Phe Ser Thr Gly Asp Glu Glu Ile Asp Leu Asn Ser Gly Ser Thr Gly
    530                 535                 540 gat tgg cga aaa acc ata ctt aag cgt gca ttt aat att gat gat gtc    1680
Asp Trp Arg Lys Thr Ile Leu Lys Arg Ala Phe Asn Ile Asp Asp Val
545                 550                 555                 560 tcg ctc ttc cgc ctg ctt aaa att acc gac cat gat aat aaa gat gga    1728
Ser Leu Phe Arg Leu Leu Lys Ile Thr Asp His Asp Asn Lys Asp Gly
                565                 570                 575 aaa att aaa aat aac cta aag aat ctt tcc aat tta tat att gga aaa    1776
Lys Ile Lys Asn Asn Leu Lys Asn Leu Ser Asn Leu Tyr Ile Gly Lys
            580                 585                 590 tta ctg gca gat att cat caa tta acc att gat gaa ctg gat tta tta    1824
Leu Leu Ala Asp Ile His Gln Leu Thr Ile Asp Glu Leu Asp Leu Leu
        595                 600                 605
```

```
ctg att gcc gta ggt gaa gga aaa act aat tta tcc gct atc agt gat      1872
Leu Ile Ala Val Gly Glu Gly Lys Thr Asn Leu Ser Ala Ile Ser Asp
    610             615                 620 aag caa ttg gct acc ctg atc aga aaa ctc aat act att acc agc tgg      1920
Lys Gln Leu Ala Thr Leu Ile Arg Lys Leu Asn Thr Ile Thr Ser Trp
625             630                 635                 640 cta cat aca cag aag tgg agt gta ttc cag cta ttt atc atg acc tcc      1968
Leu His Thr Gln Lys Trp Ser Val Phe Gln Leu Phe Ile Met Thr Ser
            645                 650                 655 acc agc tat aac aaa acg cta acg cct gaa att aag aat ttg ctg gat      2016
Thr Ser Tyr Asn Lys Thr Leu Thr Pro Glu Ile Lys Asn Leu Leu Asp
        660                 665                 670 acc gtc tac cac ggt tta caa ggt ttt gat aaa gac aaa gca gat ttg      2064
Thr Val Tyr His Gly Leu Gln Gly Phe Asp Lys Asp Lys Ala Asp Leu
    675                 680                 685 cta cat gtc atg gcg ccc tat att gcg gcc acc ttg caa tta tca tcg      2112
Leu His Val Met Ala Pro Tyr Ile Ala Ala Thr Leu Gln Leu Ser Ser
690                 695                 700 gaa aat gtc gcc cac tcg gta ctc ctt tgg gca gat aag tta cag ccc      2160
Glu Asn Val Ala His Ser Val Leu Leu Trp Ala Asp Lys Leu Gln Pro
705             710                 715                 720 ggc gac ggc gca atg aca gca gaa aaa ttc tgg gac tgg ttg aat act      2208
Gly Asp Gly Ala Met Thr Ala Glu Lys Phe Trp Asp Trp Leu Asn Thr
            725                 730                 735 aag tat acg ccg ggt tca tcg gaa gcc gta gaa acg cag gaa cat atc      2256
Lys Tyr Thr Pro Gly Ser Ser Glu Ala Val Glu Thr Gln Glu His Ile
        740                 745                 750 gtt cag tat tgt cag gct ctg gca caa ttg gaa atg gtt tac cat tcc      2304
Val Gln Tyr Cys Gln Ala Leu Ala Gln Leu Glu Met Val Tyr His Ser
    755                 760                 765 acc ggc atc aac gaa aac gcc ttc cgt cta ttt gtg aca aaa cca gag      2352
Thr Gly Ile Asn Glu Asn Ala Phe Arg Leu Phe Val Thr Lys Pro Glu
770                 775                 780 atg ttt ggc gct gca act gga gca gcg ccc gcg cat gat gcc ctt tca      2400
Met Phe Gly Ala Ala Thr Gly Ala Ala Pro Ala His Asp Ala Leu Ser
785             790                 795                 800 ctg att atg ctg aca cgt ttt gcg gat tgg gtg aac gca cta ggc gaa      2448
Leu Ile Met Leu Thr Arg Phe Ala Asp Trp Val Asn Ala Leu Gly Glu
            805                 810                 815 aaa gcg tcc tcg gtg cta gcg gca ttt gaa gct aac tcg tta acg gca      2496
Lys Ala Ser Ser Val Leu Ala Ala Phe Glu Ala Asn Ser Leu Thr Ala
        820                 825                 830 gaa caa ctg gct gat gcc atg aat ctt gat gct aat ttg ctg ttg caa      2544
Glu Gln Leu Ala Asp Ala Met Asn Leu Asp Ala Asn Leu Leu Leu Gln
    835                 840                 845 gcc agt att caa gca caa aat cat caa cat ctt ccc cca gta act cca      2592
Ala Ser Ile Gln Ala Gln Asn His Gln His Leu Pro Pro Val Thr Pro
850                 855                 860 gaa aat gcg ttc tcc tgt tgg aca tct atc aat act atc ctg caa tgg      2640
Glu Asn Ala Phe Ser Cys Trp Thr Ser Ile Asn Thr Ile Leu Gln Trp
865             870                 875                 880 gtt aat gtc gca caa caa ttg aat gtc gcc cca cag ggc gtt tcc gct      2688
Val Asn Val Ala Gln Gln Leu Asn Val Ala Pro Gln Gly Val Ser Ala
            885                 890                 895 ttg gtc ggg ctg gat tat att caa tca atg aaa gag aca ccg acc tat      2736
Leu Val Gly Leu Asp Tyr Ile Gln Ser Met Lys Glu Thr Pro Thr Tyr
        900                 905                 910 gcc cag tgg gaa aac gcg gca ggc gta tta acc gcc ggg ttg aat tca      2784
Ala Gln Trp Glu Asn Ala Ala Gly Val Leu Thr Ala Gly Leu Asn Ser
    915                 920                 925
```

| | | |
|---|---|---|
| caa cag gct aat aca tta cac gct ttt ctg gat gaa tct cgc agt gcc<br>Gln Gln Ala Asn Thr Leu His Ala Phe Leu Asp Glu Ser Arg Ser Ala<br>930                   935                 940 | | 2832 |
| gca tta agc acc tac tat atc cgt caa gtc gcc aag gca gcg gcg gct<br>Ala Leu Ser Thr Tyr Tyr Ile Arg Gln Val Ala Lys Ala Ala Ala Ala<br>945                 950              955                 960 | | 2880 |
| att aaa agc cgt gat gac ttg tat caa tac tta ctg att gat aat cag<br>Ile Lys Ser Arg Asp Asp Leu Tyr Gln Tyr Leu Leu Ile Asp Asn Gln<br>                965                 970                 975 | | 2928 |
| gtt tct gcg gca ata aaa acc acc cgg atc gcc gaa gcc att gcc agt<br>Val Ser Ala Ala Ile Lys Thr Thr Arg Ile Ala Glu Ala Ile Ala Ser<br>980                 985              990 | | 2976 |
| att caa ctg tac gtc aac cgg gca ttg gaa aat gtg gaa gaa aat gcc<br>Ile Gln Leu Tyr Val Asn Arg Ala Leu Glu Asn Val Glu Glu Asn Ala<br>                995               1000              1005 | | 3024 |
| aat tcg ggg gtt atc agc cgc caa ttc ttt atc gac tgg gac aaa<br>Asn Ser Gly Val Ile Ser Arg Gln Phe Phe Ile Asp Trp Asp Lys<br>1010                1015                1020 | | 3069 |
| tac aat aaa cgc tac agc act tgg gcg ggt gtt tct caa tta gtt<br>Tyr Asn Lys Arg Tyr Ser Thr Trp Ala Gly Val Ser Gln Leu Val<br>1025                1030                1035 | | 3114 |
| tac tac ccg gaa aac tat att gat ccg acc atg cgt atc gga caa<br>Tyr Tyr Pro Glu Asn Tyr Ile Asp Pro Thr Met Arg Ile Gly Gln<br>1040                1045                1050 | | 3159 |
| acc aaa atg atg gac gca tta ctg caa tcc gtc agc caa agc caa<br>Thr Lys Met Met Asp Ala Leu Leu Gln Ser Val Ser Gln Ser Gln<br>1055                1060                1065 | | 3204 |
| tta aac gcc gat acc gtc gaa gat gcc ttt atg tct tat ctg aca<br>Leu Asn Ala Asp Thr Val Glu Asp Ala Phe Met Ser Tyr Leu Thr<br>1070                1075                1080 | | 3249 |
| tcg ttt gaa caa gtg gct aat ctt aaa gtt att agc gca tat cac<br>Ser Phe Glu Gln Val Ala Asn Leu Lys Val Ile Ser Ala Tyr His<br>1085                1090                1095 | | 3294 |
| gat aat att aat aac gat caa ggg ctg acc tat ttt atc gga ctc<br>Asp Asn Ile Asn Asn Asp Gln Gly Leu Thr Tyr Phe Ile Gly Leu<br>1100                1105                1110 | | 3339 |
| agt gaa act gat gcc ggt gaa tat tat tgg cgc agt gtc gat cac<br>Ser Glu Thr Asp Ala Gly Glu Tyr Tyr Trp Arg Ser Val Asp His<br>1115                1120                1125 | | 3384 |
| agt aaa ttc aac gac ggt aaa ttc gcg gct aat gcc tgg agt gaa<br>Ser Lys Phe Asn Asp Gly Lys Phe Ala Ala Asn Ala Trp Ser Glu<br>1130                1135                1140 | | 3429 |
| tgg cat aaa att gat tgt cca att aac cct tat aaa agc act atc<br>Trp His Lys Ile Asp Cys Pro Ile Asn Pro Tyr Lys Ser Thr Ile<br>1145                1150                1155 | | 3474 |
| cgt cca gtg ata tat aaa tcc cgc ctg tat ctg ctc tgg ttg gaa<br>Arg Pro Val Ile Tyr Lys Ser Arg Leu Tyr Leu Leu Trp Leu Glu<br>1160                1165                1170 | | 3519 |
| caa aag gag atc acc aaa cag aca gga aat agt aaa gat ggc tat<br>Gln Lys Glu Ile Thr Lys Gln Thr Gly Asn Ser Lys Asp Gly Tyr<br>1175                1180                1185 | | 3564 |
| caa act gaa acg gat tat cgt tat gaa cta aaa ttg gcg cat atc<br>Gln Thr Glu Thr Asp Tyr Arg Tyr Glu Leu Lys Leu Ala His Ile<br>1190                1195                1200 | | 3609 |
| cgc tat gat ggc act tgg aat acg cca atc acc ttt gat gtc aat<br>Arg Tyr Asp Gly Thr Trp Asn Thr Pro Ile Thr Phe Asp Val Asn<br>1205                1210                1215 | | 3654 |
| aaa aaa ata tcc gag cta aaa ctg gaa aaa aat aga gcg ccc gga<br>Lys Lys Ile Ser Glu Leu Lys Leu Glu Lys Asn Arg Ala Pro Gly | | 3699 |

```
                                 1220               1225               1230
              ctc tat tgt gcc ggt tat caa ggt gaa gat acg ttg ctg gtg atg       3744
              Leu Tyr Cys Ala Gly Tyr Gln Gly Glu Asp Thr Leu Leu Val Met
                  1235                1240                1245 ttt tat aac caa caa gac aca cta gat agt tat aaa aac gct tca       3789
              Phe Tyr Asn Gln Gln Asp Thr Leu Asp Ser Tyr Lys Asn Ala Ser
                  1250                1255                1260 atg caa gga cta tat atc ttt gct gat atg gca tcc aaa gat atg       3834
              Met Gln Gly Leu Tyr Ile Phe Ala Asp Met Ala Ser Lys Asp Met
                  1265                1270                1275 acc cca gaa cag agc aat gtt tat cgg gat aat agc tat caa caa       3879
              Thr Pro Glu Gln Ser Asn Val Tyr Arg Asp Asn Ser Tyr Gln Gln
                  1280                1285                1290 ttt gat acc aat aat gtc aga aga gtg aat aac cgc tat gca gag       3924
              Phe Asp Thr Asn Asn Val Arg Arg Val Asn Asn Arg Tyr Ala Glu
                  1295                1300                1305 gat tat gag att cct tcc tcg gta agt agc cgt aaa gac tat ggt       3969
              Asp Tyr Glu Ile Pro Ser Ser Val Ser Ser Arg Lys Asp Tyr Gly
                  1310                1315                1320 tgg gga gat tat tac ctc agc atg gta tat aac gga gat att cca       4014
              Trp Gly Asp Tyr Tyr Leu Ser Met Val Tyr Asn Gly Asp Ile Pro
                  1325                1330                1335 act atc aat tac aaa gcc gca tca agt gat tta aaa atc tat atc       4059
              Thr Ile Asn Tyr Lys Ala Ala Ser Ser Asp Leu Lys Ile Tyr Ile
                  1340                1345                1350 tca cca aaa tta aga att att cat aat gga tat gaa gga cag aag       4104
              Ser Pro Lys Leu Arg Ile Ile His Asn Gly Tyr Glu Gly Gln Lys
                  1355                1360                1365 cgc aat caa tgc aat ctg atg aat aaa tat ggc aaa cta ggt gat       4149
              Arg Asn Gln Cys Asn Leu Met Asn Lys Tyr Gly Lys Leu Gly Asp
                  1370                1375                1380 aaa ttt att gtt tat act agc ttg ggg gtc aat cca aat aac tcg       4194
              Lys Phe Ile Val Tyr Thr Ser Leu Gly Val Asn Pro Asn Asn Ser
                  1385                1390                1395 tca aat aag ctc atg ttt tac ccc gtc tat caa tat agc gga aac       4239
              Ser Asn Lys Leu Met Phe Tyr Pro Val Tyr Gln Tyr Ser Gly Asn
                  1400                1405                1410 acc agt gga ctc aat caa ggg aga cta cta ttc cac cgt gac acc       4284
              Thr Ser Gly Leu Asn Gln Gly Arg Leu Leu Phe His Arg Asp Thr
                  1415                1420                1425 act tat cca tct aaa gta gaa gct tgg att cct gga gca aaa cgt       4329
              Thr Tyr Pro Ser Lys Val Glu Ala Trp Ile Pro Gly Ala Lys Arg
                  1430                1435                1440 tct cta acc aac caa aat gcc gcc att ggt gat gat tat gct aca       4374
              Ser Leu Thr Asn Gln Asn Ala Ala Ile Gly Asp Asp Tyr Ala Thr
                  1445                1450                1455 gac tct ctg aat aaa ccg gat gat ctt aag caa tat atc ttt atg       4419
              Asp Ser Leu Asn Lys Pro Asp Asp Leu Lys Gln Tyr Ile Phe Met
                  1460                1465                1470 act gac agt aaa ggg act gct act gat gtc tca ggc cca gta gag       4464
              Thr Asp Ser Lys Gly Thr Ala Thr Asp Val Ser Gly Pro Val Glu
                  1475                1480                1485 att aat act gca att tct cca gca aaa gtt cag ata ata gtc aaa       4509
              Ile Asn Thr Ala Ile Ser Pro Ala Lys Val Gln Ile Ile Val Lys
                  1490                1495                1500 gcg ggt ggc aag gag caa act ttt acc gca gat aaa gat gtc tcc       4554
              Ala Gly Gly Lys Glu Gln Thr Phe Thr Ala Asp Lys Asp Val Ser
                  1505                1510                1515 att cag cca tca cct agc ttt gat gaa atg aat tat caa ttt aat       4599
              Ile Gln Pro Ser Pro Ser Phe Asp Glu Met Asn Tyr Gln Phe Asn
```

-continued

| | |
|---|---|
| Ile Gln Pro Ser Pro Ser Phe Asp Glu Met Asn Tyr Gln Phe Asn<br>1520                                1525                            1530 | |
| gcc ctt gaa ata gac ggt tct ggt ctg aat ttt att aac aac tca<br>Ala Leu Glu Ile Asp Gly Ser Gly Leu Asn Phe Ile Asn Asn Ser<br>1535                                1540                            1545 | 4644 |
| gcc agt att gat gtt act ttt acc gca ttt gcg gag gat ggc cgc<br>Ala Ser Ile Asp Val Thr Phe Thr Ala Phe Ala Glu Asp Gly Arg<br>1550                                1555                            1560 | 4689 |
| aaa ctg ggt tat gaa agt ttc agt att cct gtt acc ctc aag gta<br>Lys Leu Gly Tyr Glu Ser Phe Ser Ile Pro Val Thr Leu Lys Val<br>1565                                1570                            1575 | 4734 |
| agt acc gat aat gcc ctg acc ctg cac cat aat gaa aat ggt gcg<br>Ser Thr Asp Asn Ala Leu Thr Leu His His Asn Glu Asn Gly Ala<br>1580                                1585                            1590 | 4779 |
| caa tat atg caa tgg caa tcc tat cgt acc cgc ctg aat act cta<br>Gln Tyr Met Gln Trp Gln Ser Tyr Arg Thr Arg Leu Asn Thr Leu<br>1595                                1600                            1605 | 4824 |
| ttt gcc cgc cag ttg gtt gca cgc gcc acc acc gga atc gat aca<br>Phe Ala Arg Gln Leu Val Ala Arg Ala Thr Thr Gly Ile Asp Thr<br>1610                                1615                            1620 | 4869 |
| att ctg agt atg gaa act cag aat att cag gaa ccg cag tta ggc<br>Ile Leu Ser Met Glu Thr Gln Asn Ile Gln Glu Pro Gln Leu Gly<br>1625                                1630                            1635 | 4914 |
| aaa ggt ttc tat gct acg ttc gtg ata cct ccc tat aac cta tca<br>Lys Gly Phe Tyr Ala Thr Phe Val Ile Pro Pro Tyr Asn Leu Ser<br>1640                                1645                            1650 | 4959 |
| act cat ggt gat gaa cgt tgg ttt aag ctt tat atc aaa cat gtt<br>Thr His Gly Asp Glu Arg Trp Phe Lys Leu Tyr Ile Lys His Val<br>1655                                1660                            1665 | 5004 |
| gtt gat aat aat tca cat att atc tat tca ggc cag cta aca gat<br>Val Asp Asn Asn Ser His Ile Ile Tyr Ser Gly Gln Leu Thr Asp<br>1670                                1675                            1680 | 5049 |
| aca aat ata aac atc aca tta ttt att cct ctt gat gat gtc cca<br>Thr Asn Ile Asn Ile Thr Leu Phe Ile Pro Leu Asp Asp Val Pro<br>1685                                1690                            1695 | 5094 |
| ttg aat caa gat tat cac gcc aag gtt tat atg acc ttc aag aaa<br>Leu Asn Gln Asp Tyr His Ala Lys Val Tyr Met Thr Phe Lys Lys<br>1700                                1705                            1710 | 5139 |
| tca cca tca gat ggt acc tgg tgg ggc cct cac ttt gtt aga gat<br>Ser Pro Ser Asp Gly Thr Trp Trp Gly Pro His Phe Val Arg Asp<br>1715                                1720                            1725 | 5184 |
| gat aaa gga ata gta aca ata aac cct aaa tcc att ttg acc cat<br>Asp Lys Gly Ile Val Thr Ile Asn Pro Lys Ser Ile Leu Thr His<br>1730                                1735                            1740 | 5229 |
| ttt gag agc gtc aat gtc ctg aat aat att agt agc gaa cca atg<br>Phe Glu Ser Val Asn Val Leu Asn Asn Ile Ser Ser Glu Pro Met<br>1745                                1750                            1755 | 5274 |
| gat ttc agc ggc gct aac agc ctc tat ttc tgg gaa ctg ttc tac<br>Asp Phe Ser Gly Ala Asn Ser Leu Tyr Phe Trp Glu Leu Phe Tyr<br>1760                                1765                            1770 | 5319 |
| tat acc ccg atg ctg gtt gct caa cgt ttg ctg cat gaa cag aac<br>Tyr Thr Pro Met Leu Val Ala Gln Arg Leu Leu His Glu Gln Asn<br>1775                                1780                            1785 | 5364 |
| ttc gat gaa gcc aac cgt tgg ctg aaa tat gtc tgg agt cca tcc<br>Phe Asp Glu Ala Asn Arg Trp Leu Lys Tyr Val Trp Ser Pro Ser<br>1790                                1795                            1800 | 5409 |
| ggt tat att gtc cac ggc cag att cag aac tac cag tgg aac gtc<br>Gly Tyr Ile Val His Gly Gln Ile Gln Asn Tyr Gln Trp Asn Val<br>1805                                1810                            1815 | 5454 |

```
cgc ccg tta ctg gaa gac acc agt tgg aac agt gat cct ttg gat       5499
Arg Pro Leu Leu Glu Asp Thr Ser Trp Asn Ser Asp Pro Leu Asp
    1820                1825                1830 tcc gtc gat cct gac gcg gta gca cag cac gat cca atg cac tac       5544
Ser Val Asp Pro Asp Ala Val Ala Gln His Asp Pro Met His Tyr
1835                1840                1845 aaa gtt tca act ttt atg cgt acc ttg gat cta ttg ata gca cgc       5589
Lys Val Ser Thr Phe Met Arg Thr Leu Asp Leu Leu Ile Ala Arg
    1850                1855                1860 ggc gac cat gct tat cgc caa ctg gaa cga gat aca ctc aac gaa       5634
Gly Asp His Ala Tyr Arg Gln Leu Glu Arg Asp Thr Leu Asn Glu
1865                1870                1875 gcg aag atg tgg tat atg caa gcg ctg cat cta tta ggt gac aaa       5679
Ala Lys Met Trp Tyr Met Gln Ala Leu His Leu Leu Gly Asp Lys
    1880                1885                1890 cct tat cta ccg ctg agt acg aca tgg agt gat cca cga cta gac       5724
Pro Tyr Leu Pro Leu Ser Thr Thr Trp Ser Asp Pro Arg Leu Asp
1895                1900                1905 aga gcc gcg gat atc act acc caa aat gct cac gac agc gca ata       5769
Arg Ala Ala Asp Ile Thr Thr Gln Asn Ala His Asp Ser Ala Ile
    1910                1915                1920 gtc gct ctg cgg cag aat ata cct aca ccg gca cct tta tca ttg       5814
Val Ala Leu Arg Gln Asn Ile Pro Thr Pro Ala Pro Leu Ser Leu
1925                1930                1935 cgc agc gct aat acc ctg act gat ctc ttc ctg ccg caa atc aat       5859
Arg Ser Ala Asn Thr Leu Thr Asp Leu Phe Leu Pro Gln Ile Asn
    1940                1945                1950 gaa gtg atg atg aat tac tgg cag aca tta gct cag aga gta tac       5904
Glu Val Met Met Asn Tyr Trp Gln Thr Leu Ala Gln Arg Val Tyr
1955                1960                1965 aat ctg cgt cat aac ctc tct atc gac ggc cag ccg tta tat ctg       5949
Asn Leu Arg His Asn Leu Ser Ile Asp Gly Gln Pro Leu Tyr Leu
    1970                1975                1980 cca atc tat gcc aca ccg gcc gat ccg aaa gcg tta ctc agc gcc       5994
Pro Ile Tyr Ala Thr Pro Ala Asp Pro Lys Ala Leu Leu Ser Ala
1985                1990                1995 gcc gtt gcc act tct caa ggt gga ggc aag cta ccg gaa tca ttt       6039
Ala Val Ala Thr Ser Gln Gly Gly Gly Lys Leu Pro Glu Ser Phe
    2000                2005                2010 atg tcc ctg tgg cgt ttc ccg cac atg ctg gaa aat gcg cgc ggc       6084
Met Ser Leu Trp Arg Phe Pro His Met Leu Glu Asn Ala Arg Gly
2015                2020                2025 atg gtt agc cag ctc acc cag ttc ggc tcc acg tta caa aat att       6129
Met Val Ser Gln Leu Thr Gln Phe Gly Ser Thr Leu Gln Asn Ile
    2030                2035                2040 atc gaa cgt cag gac gcg gaa gcg ctc aat gcg tta tta caa aat       6174
Ile Glu Arg Gln Asp Ala Glu Ala Leu Asn Ala Leu Leu Gln Asn
2045                2050                2055 cag gcc gcc gag ctg ata ttg act aac ctg agc att cag gac aaa       6219
Gln Ala Ala Glu Leu Ile Leu Thr Asn Leu Ser Ile Gln Asp Lys
    2060                2065                2070 acc att gaa gaa ttg gat gcc gag aaa acg gtg ttg gaa aaa tcc       6264
Thr Ile Glu Glu Leu Asp Ala Glu Lys Thr Val Leu Glu Lys Ser
2075                2080                2085 aaa gcg gga gca caa tcg cgc ttt gat agc tac ggc aaa ctg tac       6309
Lys Ala Gly Ala Gln Ser Arg Phe Asp Ser Tyr Gly Lys Leu Tyr
    2090                2095                2100 gat gag aat atc aac gcc ggt gaa aac caa gcc atg acg cta cga       6354
Asp Glu Asn Ile Asn Ala Gly Glu Asn Gln Ala Met Thr Leu Arg
2105                2110                2115
```

| | |
|---|---:|
| gcg tcc gcc gcc ggg ctt acc acg gca gtt cag gca tcc cgt ctg<br>Ala Ser Ala Ala Gly Leu Thr Thr Ala Val Gln Ala Ser Arg Leu<br>2120                        2125                       2130 | 6399 |
| gcc ggt gcg gcg gct gat ctg gtg cct aac atc ttc ggc ttt gcc<br>Ala Gly Ala Ala Ala Asp Leu Val Pro Asn Ile Phe Gly Phe Ala<br>2135                        2140                       2145 | 6444 |
| ggt ggc ggc agc cgt tgg ggg gct atc gct gag gcg aca ggt tat<br>Gly Gly Gly Ser Arg Trp Gly Ala Ile Ala Glu Ala Thr Gly Tyr<br>2150                        2155                       2160 | 6489 |
| gtg atg gaa ttc tcc gcg aat gtt atg aac acc gaa gcg gat aaa<br>Val Met Glu Phe Ser Ala Asn Val Met Asn Thr Glu Ala Asp Lys<br>2165                        2170                       2175 | 6534 |
| att agc caa tct gaa acc tac cgt cgt cgc cgt cag gag tgg gag<br>Ile Ser Gln Ser Glu Thr Tyr Arg Arg Arg Arg Gln Glu Trp Glu<br>2180                        2185                       2190 | 6579 |
| atc cag cgg aat aat gcc gaa gcg gaa ttg aag caa atc gat gct<br>Ile Gln Arg Asn Asn Ala Glu Ala Glu Leu Lys Gln Ile Asp Ala<br>2195                        2200                       2205 | 6624 |
| cag ctc aaa tca ctc gct gta cgc cgc gaa gcc gcc gta ttg cag<br>Gln Leu Lys Ser Leu Ala Val Arg Arg Glu Ala Ala Val Leu Gln<br>2210                        2215                       2220 | 6669 |
| aaa acc agt ctg aaa acc caa caa gaa cag acc caa tct caa ttg<br>Lys Thr Ser Leu Lys Thr Gln Gln Glu Gln Thr Gln Ser Gln Leu<br>2225                        2230                       2235 | 6714 |
| gcc ttc ctg caa cgt aag ttc agc aat cag gcg tta tac aac tgg<br>Ala Phe Leu Gln Arg Lys Phe Ser Asn Gln Ala Leu Tyr Asn Trp<br>2240                        2245                       2250 | 6759 |
| ctg cgt ggt cga ctg gcg gcg att tac ttc cag ttc tac gat ttg<br>Leu Arg Gly Arg Leu Ala Ala Ile Tyr Phe Gln Phe Tyr Asp Leu<br>2255                        2260                       2265 | 6804 |
| gcc gtc gcg cgt tgc ctg atg gca gaa caa gct tac cgt tgg gaa<br>Ala Val Ala Arg Cys Leu Met Ala Glu Gln Ala Tyr Arg Trp Glu<br>2270                        2275                       2280 | 6849 |
| ctc aat gat gac tct gcc cgc ttc att aaa ccg ggc gcc tgg cag<br>Leu Asn Asp Asp Ser Ala Arg Phe Ile Lys Pro Gly Ala Trp Gln<br>2285                        2290                       2295 | 6894 |
| gga acc tat gcc ggt ctg ctt gca ggt gaa acc ttg atg ctg agt<br>Gly Thr Tyr Ala Gly Leu Leu Ala Gly Glu Thr Leu Met Leu Ser<br>2300                        2305                       2310 | 6939 |
| ctg gca caa atg gaa gac gct cat ctg aaa cgc gat aaa cgc gca<br>Leu Ala Gln Met Glu Asp Ala His Leu Lys Arg Asp Lys Arg Ala<br>2315                        2320                       2325 | 6984 |
| tta gag gtt gaa cgc aca gta tcg ctg gcc gaa gtt tat gca gga<br>Leu Glu Val Glu Arg Thr Val Ser Leu Ala Glu Val Tyr Ala Gly<br>2330                        2335                       2340 | 7029 |
| tta cca aaa gat aac ggt cca ttt tcc ctg gct cag gaa att gac<br>Leu Pro Lys Asp Asn Gly Pro Phe Ser Leu Ala Gln Glu Ile Asp<br>2345                        2350                       2355 | 7074 |
| aag ctg gtg agt caa ggt tca ggc agt gcc ggc agt ggt aat aat<br>Lys Leu Val Ser Gln Gly Ser Gly Ser Ala Gly Ser Gly Asn Asn<br>2360                        2365                       2370 | 7119 |
| aat ttg gcg ttc ggc gcc ggc acg gac act aaa acc tct ttg cag<br>Asn Leu Ala Phe Gly Ala Gly Thr Asp Thr Lys Thr Ser Leu Gln<br>2375                        2380                       2385 | 7164 |
| gca tca gtt tca ttc gct gat ttg aaa att cgt gaa gat tac ccg<br>Ala Ser Val Ser Phe Ala Asp Leu Lys Ile Arg Glu Asp Tyr Pro<br>2390                        2395                       2400 | 7209 |
| gca tcg ctt ggc aaa att cga cgt atc aaa cag atc agc gtc act<br>Ala Ser Leu Gly Lys Ile Arg Arg Ile Lys Gln Ile Ser Val Thr | 7254 |

-continued

```
            2405                2410                2415
ttg  ccc  gcg  cta  ctg  gga  ccg  tat  cag  gat  gta  cag  gca  ata  ttg           7299
Leu  Pro  Ala  Leu  Leu  Gly  Pro  Tyr  Gln  Asp  Val  Gln  Ala  Ile  Leu
     2420                2425                2430 tct  tac  ggc  gat  aaa  gcc  gga  tta  gct  aac  ggc  tgt  gaa  gcg  ctg           7344
Ser  Tyr  Gly  Asp  Lys  Ala  Gly  Leu  Ala  Asn  Gly  Cys  Glu  Ala  Leu
     2435                2440                2445 gca  gtt  tct  cac  ggt  atg  aat  gac  agc  ggc  caa  ttc  cag  ctc  gat           7389
Ala  Val  Ser  His  Gly  Met  Asn  Asp  Ser  Gly  Gln  Phe  Gln  Leu  Asp
     2450                2455                2460 ttc  aac  gat  ggc  aaa  ttc  ctg  cca  ttc  gaa  ggc  atc  gcc  att  gat           7434
Phe  Asn  Asp  Gly  Lys  Phe  Leu  Pro  Phe  Glu  Gly  Ile  Ala  Ile  Asp
     2465                2470                2475 caa  ggc  acg  ctg  aca  ctg  agc  ttc  cca  aat  gca  tct  atg  ccg  gag           7479
Gln  Gly  Thr  Leu  Thr  Leu  Ser  Phe  Pro  Asn  Ala  Ser  Met  Pro  Glu
     2480                2485                2490 aaa  ggt  aaa  caa  gcc  act  atg  tta  aaa  acc  ctg  aac  gat  atc  att           7524
Lys  Gly  Lys  Gln  Ala  Thr  Met  Leu  Lys  Thr  Leu  Asn  Asp  Ile  Ile
     2495                2500                2505 ttg  cat  att  cgc  tac  acc  att  aaa  taa                                         7551
Leu  His  Ile  Arg  Tyr  Thr  Ile  Lys
     2510                2515

<210> SEQ ID NO 22
<211> LENGTH: 4431
<212> TYPE: DNA
<213> ORGANISM: Photorhabdus luminescens
<220> FEATURE:
<221> NAME/KEY: exon
<222> LOCATION: (1)..(4431)

<400> SEQUENCE: 22 atg  cag  aat  tca  caa  aca  ttc  agt  gtt  acc  gag  ctg  tca  tta  ccc  aaa        48
Met  Gln  Asn  Ser  Gln  Thr  Phe  Ser  Val  Thr  Glu  Leu  Ser  Leu  Pro  Lys
1                 5                   10                  15 ggc  ggc  ggc  gct  att  acc  ggt  atg  ggt  gaa  gca  tta  aca  cca  gcc  ggg        96
Gly  Gly  Gly  Ala  Ile  Thr  Gly  Met  Gly  Glu  Ala  Leu  Thr  Pro  Ala  Gly
                  20                  25                  30 ccg  gat  ggt  atg  gcc  gcc  tta  tcc  ctg  cca  tta  ccc  att  tcc  gcc  ggg       144
Pro  Asp  Gly  Met  Ala  Ala  Leu  Ser  Leu  Pro  Leu  Pro  Ile  Ser  Ala  Gly
             35                  40                  45 cgt  ggt  tac  gca  ccc  tcg  ctc  act  ctg  aat  tac  aac  agt  gga  acc  ggt       192
Arg  Gly  Tyr  Ala  Pro  Ser  Leu  Thr  Leu  Asn  Tyr  Asn  Ser  Gly  Thr  Gly
         50                  55                  60 aac  agc  cca  ttt  ggt  ctc  ggt  tgg  gac  tgc  ggc  gtc  atg  gca  att  cgt       240
Asn  Ser  Pro  Phe  Gly  Leu  Gly  Trp  Asp  Cys  Gly  Val  Met  Ala  Ile  Arg
65                  70                  75                  80 cgt  cgc  acc  agt  acc  ggc  gta  ccg  aat  tac  gat  gaa  acc  gat  act  ttt       288
Arg  Arg  Thr  Ser  Thr  Gly  Val  Pro  Asn  Tyr  Asp  Glu  Thr  Asp  Thr  Phe
                 85                  90                  95 ctg  ggg  ccg  gaa  ggt  gaa  gtg  ttg  gtc  gta  gca  tta  aat  gag  gca  ggt       336
Leu  Gly  Pro  Glu  Gly  Glu  Val  Leu  Val  Val  Ala  Leu  Asn  Glu  Ala  Gly
            100                 105                 110 caa  gct  gat  atc  cgc  agt  gaa  tcc  tca  ttg  cag  ggc  atc  aat  ttg  ggt       384
Gln  Ala  Asp  Ile  Arg  Ser  Glu  Ser  Ser  Leu  Gln  Gly  Ile  Asn  Leu  Gly
        115                 120                 125 gcg  acc  ttc  acc  gtt  acc  tgt  tat  cgc  tcc  cgc  cta  gaa  agc  cac  ttt       432
Ala  Thr  Phe  Thr  Val  Thr  Cys  Tyr  Arg  Ser  Arg  Leu  Glu  Ser  His  Phe
        130                 135                 140 aac  cgg  ttg  gaa  tac  tgg  caa  ccc  caa  aca  acc  ggc  gca  acc  gat  ttc       480
Asn  Arg  Leu  Glu  Tyr  Trp  Gln  Pro  Gln  Thr  Thr  Gly  Ala  Thr  Asp  Phe
```

```
                 145                 150                 155                 160
tgg ctg ata tac agc ccc gac gga cag gtc cat tta ctg ggc aaa aat     528
Trp Leu Ile Tyr Ser Pro Asp Gly Gln Val His Leu Leu Gly Lys Asn
                165                 170                 175 cct cag gca cgt atc agc aat cca ctc aat gtt aac caa aca gcg caa     576
Pro Gln Ala Arg Ile Ser Asn Pro Leu Asn Val Asn Gln Thr Ala Gln
            180                 185                 190 tgg ctg ttg gaa gcc tcg ata tca tcc cac agc gaa cag att tat tat     624
Trp Leu Leu Glu Ala Ser Ile Ser Ser His Ser Glu Gln Ile Tyr Tyr
        195                 200                 205 caa tat cgc gct gaa gat gaa gca ggt tgt gaa acc gac gag cta gca     672
Gln Tyr Arg Ala Glu Asp Glu Ala Gly Cys Glu Thr Asp Glu Leu Ala
    210                 215                 220 gcc cac ccc agc gca acc gtt cag cgc tac ctg caa aca gta cat tac     720
Ala His Pro Ser Ala Thr Val Gln Arg Tyr Leu Gln Thr Val His Tyr
225                 230                 235                 240 ggg aac ctg acc gcc agc gac gtt ttt cct aca cta aac gga gat gac     768
Gly Asn Leu Thr Ala Ser Asp Val Phe Pro Thr Leu Asn Gly Asp Asp
                245                 250                 255 cca ctt aaa tct ggc tgg atg ttc tgt tta gta ttt gac tac ggt gag     816
Pro Leu Lys Ser Gly Trp Met Phe Cys Leu Val Phe Asp Tyr Gly Glu
            260                 265                 270 cgc aaa aac agc tta tct gaa atg ccg ctg ttt aaa gcc aca ggc aat     864
Arg Lys Asn Ser Leu Ser Glu Met Pro Leu Phe Lys Ala Thr Gly Asn
        275                 280                 285 tgg ctt tgc cga aaa gac cgt ttt tcc cgt tat gag tac ggt ttt gaa     912
Trp Leu Cys Arg Lys Asp Arg Phe Ser Arg Tyr Glu Tyr Gly Phe Glu
    290                 295                 300 ttg cgt act cgc cgc tta tgc cgc caa ata ctg atg ttt cac cgt cta     960
Leu Arg Thr Arg Arg Leu Cys Arg Gln Ile Leu Met Phe His Arg Leu
305                 310                 315                 320 caa acc cta tct ggt cag gca aag ggg gat gat gaa cct gcg cta gtg    1008
Gln Thr Leu Ser Gly Gln Ala Lys Gly Asp Asp Glu Pro Ala Leu Val
                325                 330                 335 tcg cgt ctg ata ctg gat tat gac gaa aac gcg atg gtc agt acg ctc    1056
Ser Arg Leu Ile Leu Asp Tyr Asp Glu Asn Ala Met Val Ser Thr Leu
            340                 345                 350 gtt tct gtc cgc cgg gta ggc cat gag gac aac aac acg gtt acc gcg    1104
Val Ser Val Arg Arg Val Gly His Glu Asp Asn Asn Thr Val Thr Ala
        355                 360                 365 ctg cca cca ctg gaa ctg gcc tat cag cct ttt gag cca gaa caa acc    1152
Leu Pro Pro Leu Glu Leu Ala Tyr Gln Pro Phe Glu Pro Glu Gln Thr
    370                 375                 380 gca ctc tgg caa tca atg gat gta ctg gca aat ttc aac acc att cag    1200
Ala Leu Trp Gln Ser Met Asp Val Leu Ala Asn Phe Asn Thr Ile Gln
385                 390                 395                 400 cgc tgg caa ctg ctt gac ctg aaa gga gaa ggc gtg ccc ggc att ctc    1248
Arg Trp Gln Leu Leu Asp Leu Lys Gly Glu Gly Val Pro Gly Ile Leu
                405                 410                 415 tat cag gat aga aat ggc tgg tgg tat cga tct gcc caa cgt cag gcc    1296
Tyr Gln Asp Arg Asn Gly Trp Trp Tyr Arg Ser Ala Gln Arg Gln Ala
            420                 425                 430 ggg gaa gag atg aat gcg gtc acc tgg ggg aaa atg caa ctc ctt ccc    1344
Gly Glu Glu Met Asn Ala Val Thr Trp Gly Lys Met Gln Leu Leu Pro
        435                 440                 445 atc aca cca gct gtg cag gat aac gcc tca ctg atg gat att aac ggt    1392
Ile Thr Pro Ala Val Gln Asp Asn Ala Ser Leu Met Asp Ile Asn Gly
    450                 455                 460 gac ggg caa ctg gac tgg gtg att acc ggg ccg ggg cta agg ggc tat    1440
```

```
Asp Gly Gln Leu Asp Trp Val Ile Thr Gly Pro Gly Leu Arg Gly Tyr
465                 470                 475                 480 cac agc caa cac ccg gat ggc agt tgg acg cgt ttt acg cca tta cat      1488
His Ser Gln His Pro Asp Gly Ser Trp Thr Arg Phe Thr Pro Leu His
                485                 490                 495 gcc ctg ccg ata gaa tat tct cat cct cgc gct caa ctt gcc gat tta      1536
Ala Leu Pro Ile Glu Tyr Ser His Pro Arg Ala Gln Leu Ala Asp Leu
            500                 505                 510 atg gga gcc ggg ctg tcc gat tta gtg cta att ggt ccc aaa agt gtg      1584
Met Gly Ala Gly Leu Ser Asp Leu Val Leu Ile Gly Pro Lys Ser Val
                515                 520                 525 cgc tta tat gtc aat aac cgt gat ggt ttt acc gaa ggg cgg gat gtg      1632
Arg Leu Tyr Val Asn Asn Arg Asp Gly Phe Thr Glu Gly Arg Asp Val
        530                 535                 540 gtg caa tcc ggt gat atc acc ctg ccg cta ccg ggc gcc gat gcc cgt      1680
Val Gln Ser Gly Asp Ile Thr Leu Pro Leu Pro Gly Ala Asp Ala Arg
545                 550                 555                 560 aag tta gtg gca ttt agt gac gta ctg ggt tca ggc caa gca cat ctg      1728
Lys Leu Val Ala Phe Ser Asp Val Leu Gly Ser Gly Gln Ala His Leu
                565                 570                 575 gtt gaa gtt agt gca act caa gtc acc tgc tgg ccg aat ctg ggg cat      1776
Val Glu Val Ser Ala Thr Gln Val Thr Cys Trp Pro Asn Leu Gly His
            580                 585                 590 ggc cgt ttt ggt cag cca atc gta ttg ccg gga ttc agc caa tct gcc      1824
Gly Arg Phe Gly Gln Pro Ile Val Leu Pro Gly Phe Ser Gln Ser Ala
                595                 600                 605 gcc agt ttt aat cct gat cga gtt cat ctg gcc gat ttg gat ggg agc      1872
Ala Ser Phe Asn Pro Asp Arg Val His Leu Ala Asp Leu Asp Gly Ser
610                 615                 620 ggc cct gcc gat ttg att tat gtt cat gct gac cgt ctg gat att ttc      1920
Gly Pro Ala Asp Leu Ile Tyr Val His Ala Asp Arg Leu Asp Ile Phe
625                 630                 635                 640 agc aat gaa agt ggc aac ggt ttt gca aaa cca ttc aca ctc tct ttt      1968
Ser Asn Glu Ser Gly Asn Gly Phe Ala Lys Pro Phe Thr Leu Ser Phe
                645                 650                 655 cct gac ggc ctg cgt ttt gat gat acc tgc cag ttg caa gta gcc gat      2016
Pro Asp Gly Leu Arg Phe Asp Asp Thr Cys Gln Leu Gln Val Ala Asp
            660                 665                 670 gta caa ggg tta ggc gtt gtc agc ctg atc cta agc gta ccg cat atg      2064
Val Gln Gly Leu Gly Val Val Ser Leu Ile Leu Ser Val Pro His Met
                675                 680                 685 gcg cca cat cat tgg cgc tgc gat ctg acc aac gcg aaa ccg tgg tta      2112
Ala Pro His His Trp Arg Cys Asp Leu Thr Asn Ala Lys Pro Trp Leu
690                 695                 700 ctc agt gaa acg aac aac aat atg ggg gcc aat cac acc ttg cat tac      2160
Leu Ser Glu Thr Asn Asn Asn Met Gly Ala Asn His Thr Leu His Tyr
705                 710                 715                 720 cgt agc tct gtc cag ttc tgg ctg gat gaa aaa gct gcg gca ttg gct      2208
Arg Ser Ser Val Gln Phe Trp Leu Asp Glu Lys Ala Ala Ala Leu Ala
                725                 730                 735 acc gga caa aca ccg gtc tgt tac ctg ccc ttc ccg gtc cat acc ctt      2256
Thr Gly Gln Thr Pro Val Cys Tyr Leu Pro Phe Pro Val His Thr Leu
            740                 745                 750 tgg caa aca gaa acc gag gat gaa atc agc ggc aat aag tta gtg acc      2304
Trp Gln Thr Glu Thr Glu Asp Glu Ile Ser Gly Asn Lys Leu Val Thr
                755                 760                 765 acg tta cgt tat gct cac ggc gct tgg gat gga cgt gaa cgg gaa ttt      2352
Thr Leu Arg Tyr Ala His Gly Ala Trp Asp Gly Arg Glu Arg Glu Phe
770                 775                 780
```

| | |
|---|---|
| cgt ggc ttt ggt tat gtt gag cag aca gac agc cat caa ctc gct caa<br>Arg Gly Phe Gly Tyr Val Glu Gln Thr Asp Ser His Gln Leu Ala Gln<br>785                      790                    795                    800 | 2400 |
| ggc aat gcg ccg gaa cgt aca cca ccg gca ctc acc aaa agc tgg tat<br>Gly Asn Ala Pro Glu Arg Thr Pro Pro Ala Leu Thr Lys Ser Trp Tyr<br>                 805                    810                    815 | 2448 |
| gcc acc gga tta cct gcg gta gat aat gcg tta tcc gcc ggg tat tgg<br>Ala Thr Gly Leu Pro Ala Val Asp Asn Ala Leu Ser Ala Gly Tyr Trp<br>              820                    825                    830 | 2496 |
| cgt ggc gat aag caa gct ttc gcc ggt ttt acg cca cgt ttt act ctc<br>Arg Gly Asp Lys Gln Ala Phe Ala Gly Phe Thr Pro Arg Phe Thr Leu<br>835                      840                    845 | 2544 |
| tgg aaa gag ggc aaa gat gtt cca ctg aca ccg gaa gat gac cat aat<br>Trp Lys Glu Gly Lys Asp Val Pro Leu Thr Pro Glu Asp Asp His Asn<br>850                      855                    860 | 2592 |
| cta tac tgg tta aac cgg gcg cta aaa ggt cag cca ctg cgt agt gaa<br>Leu Tyr Trp Leu Asn Arg Ala Leu Lys Gly Gln Pro Leu Arg Ser Glu<br>865                      870                    875                    880 | 2640 |
| ctc tac ggg ctg gat ggc agc gca cag caa cag atc ccc tat aca gtg<br>Leu Tyr Gly Leu Asp Gly Ser Ala Gln Gln Gln Ile Pro Tyr Thr Val<br>                 885                    890                    895 | 2688 |
| act gaa tcc cgt cca cag gtg cgc caa tta caa gat ggc gcc acc gtt<br>Thr Glu Ser Arg Pro Gln Val Arg Gln Leu Gln Asp Gly Ala Thr Val<br>                 900                    905                    910 | 2736 |
| tcc ccg gtg ctc tgg gcc tca gtc gtg gaa agc cgt agt tat cac tac<br>Ser Pro Val Leu Trp Ala Ser Val Val Glu Ser Arg Ser Tyr His Tyr<br>              915                    920                    925 | 2784 |
| gaa cgt att atc agt gat ccc cag tgc aat cag gat atc acg ttg tcc<br>Glu Arg Ile Ile Ser Asp Pro Gln Cys Asn Gln Asp Ile Thr Leu Ser<br>930                      935                    940 | 2832 |
| agt gac cta ttc ggg caa cca ctg aaa cag gtt tcc gta caa tat ccc<br>Ser Asp Leu Phe Gly Gln Pro Leu Lys Gln Val Ser Val Gln Tyr Pro<br>945                      950                    955                    960 | 2880 |
| cgc cgc aac aaa cca aca acc aat ccg tat ccc gat acc cta ccg gat<br>Arg Arg Asn Lys Pro Thr Thr Asn Pro Tyr Pro Asp Thr Leu Pro Asp<br>                 965                    970                    975 | 2928 |
| acg ctg ttt gcc agc agt tat gac gat caa caa cag cta ttg cga tta<br>Thr Leu Phe Ala Ser Ser Tyr Asp Asp Gln Gln Gln Leu Leu Arg Leu<br>              980                    985                    990 | 2976 |
| acc tgc cga caa tcc agt tgg cac cat ctt att ggt aat gag cta aga<br>Thr Cys Arg Gln Ser Ser Trp His His Leu Ile Gly Asn Glu Leu Arg<br>             995                    1000               1005 | 3024 |
| gtg ttg gga tta ccg gat ggc aca cgc agt gat gcc ttt act tac<br>Val Leu Gly Leu Pro Asp Gly Thr Arg Ser Asp Ala Phe Thr Tyr<br>1010                      1015                  1020 | 3069 |
| gat gcc aaa cag gta cct gtc gat ggc tta aat ctg gaa acc ctg<br>Asp Ala Lys Gln Val Pro Val Asp Gly Leu Asn Leu Glu Thr Leu<br>1025                      1030                  1035 | 3114 |
| tgt gct gaa aat agc ctg att gcc gat gat aaa cct cgc gaa tac<br>Cys Ala Glu Asn Ser Leu Ile Ala Asp Asp Lys Pro Arg Glu Tyr<br>1040                      1045                  1050 | 3159 |
| ctc aat cag caa cga acg ttc tat acc gac ggg aaa aac caa aca<br>Leu Asn Gln Gln Arg Thr Phe Tyr Thr Asp Gly Lys Asn Gln Thr<br>1055                      1060                  1065 | 3204 |
| ccg ctg aaa aca ccg aca cga caa gcg tta atc gcc ttt acc gaa<br>Pro Leu Lys Thr Pro Thr Arg Gln Ala Leu Ile Ala Phe Thr Glu<br>1070                      1075                  1080 | 3249 |
| acg gcg gta tta acg gaa tct ctg tta tcc gcg ttt gat ggc ggt<br>Thr Ala Val Leu Thr Glu Ser Leu Leu Ser Ala Phe Asp Gly Gly<br>1085                      1090                  1095 | 3294 |

-continued

```
att acg cca gac gaa tta ccg gga ata ctg aca cag gcc gga tac      3339
Ile Thr Pro Asp Glu Leu Pro Gly Ile Leu Thr Gln Ala Gly Tyr
    1100                1105                1110 caa caa gag cct tat ctg ttt cca cgc acc ggc gaa aac aaa gtt      3384
Gln Gln Glu Pro Tyr Leu Phe Pro Arg Thr Gly Glu Asn Lys Val
    1115                1120                1125 tgg gta gcg cgt caa ggc tat acc gat tac ggg acg gaa gca caa      3429
Trp Val Ala Arg Gln Gly Tyr Thr Asp Tyr Gly Thr Glu Ala Gln
    1130                1135                1140 ttt tgg cgt cct gtc gca caa cgt aac agc ctg tta acc ggg aaa      3474
Phe Trp Arg Pro Val Ala Gln Arg Asn Ser Leu Leu Thr Gly Lys
    1145                1150                1155 atg acg tta aaa tgg gat act cac tat tgt gtc atc acc caa acc      3519
Met Thr Leu Lys Trp Asp Thr His Tyr Cys Val Ile Thr Gln Thr
    1160                1165                1170 caa gat gct gcc ggc ctc acc gtc tca gcc aat tat gac tgg cgt      3564
Gln Asp Ala Ala Gly Leu Thr Val Ser Ala Asn Tyr Asp Trp Arg
    1175                1180                1185 ttt ctc aca cca acg caa ctg act gac atc aac gat aat gtg cat      3609
Phe Leu Thr Pro Thr Gln Leu Thr Asp Ile Asn Asp Asn Val His
    1190                1195                1200 ctc atc acc ttg gat gct ctg gga cgc cct gtc acg caa cgt ttc      3654
Leu Ile Thr Leu Asp Ala Leu Gly Arg Pro Val Thr Gln Arg Phe
    1205                1210                1215 tgg ggg atc gaa agc ggt gtg gca aca ggt tac tct tca tca gaa      3699
Trp Gly Ile Glu Ser Gly Val Ala Thr Gly Tyr Ser Ser Ser Glu
    1220                1225                1230 gaa aaa cca ttc tct cca cca aac gat atc gat acc gct att aat      3744
Glu Lys Pro Phe Ser Pro Pro Asn Asp Ile Asp Thr Ala Ile Asn
    1235                1240                1245 cta acc gga cca ctc cct gtc gca cag tgt ctg gtc tat gca ccg      3789
Leu Thr Gly Pro Leu Pro Val Ala Gln Cys Leu Val Tyr Ala Pro
    1250                1255                1260 gac agt tgg atg cca cta ttc agt caa gaa acc ttc aac aca tta      3834
Asp Ser Trp Met Pro Leu Phe Ser Gln Glu Thr Phe Asn Thr Leu
    1265                1270                1275 acg cag gaa gag cag gag acg ctg cgt gat tca cgt att atc acg      3879
Thr Gln Glu Glu Gln Glu Thr Leu Arg Asp Ser Arg Ile Ile Thr
    1280                1285                1290 gaa gat tgg cgt att tgc gca ctg act cgc cgc gt tgg cta caa      3924
Glu Asp Trp Arg Ile Cys Ala Leu Thr Arg Arg Arg Trp Leu Gln
    1295                1300                1305 agt caa aag atc agt aca cca tta gtt aaa ctg tta acc aac agc      3969
Ser Gln Lys Ile Ser Thr Pro Leu Val Lys Leu Leu Thr Asn Ser
    1310                1315                1320 att ggt tta cct ccc cat aac ctt acg ctg acc aca gac cgt tat      4014
Ile Gly Leu Pro Pro His Asn Leu Thr Leu Thr Thr Asp Arg Tyr
    1325                1330                1335 gac cgc gac tct gag cag caa att cgc caa caa gtc gca ttt agt      4059
Asp Arg Asp Ser Glu Gln Gln Ile Arg Gln Gln Val Ala Phe Ser
    1340                1345                1350 gat ggt ttt ggc cgt ctg cta caa gcg tct gta cga cat gag gca      4104
Asp Gly Phe Gly Arg Leu Leu Gln Ala Ser Val Arg His Glu Ala
    1355                1360                1365 ggc gaa gcc tgg caa cgt aac caa gac ggt tct ctg gtg aca aaa      4149
Gly Glu Ala Trp Gln Arg Asn Gln Asp Gly Ser Leu Val Thr Lys
    1370                1375                1380 gtg gag aat acc aaa acg cgt tgg gcg gtc acg gga cgc acc gaa      4194
Val Glu Asn Thr Lys Thr Arg Trp Ala Val Thr Gly Arg Thr Glu
```

|  |  |  |  |  |  |  |  |  |  |  |  |  |  |  |  |
|---|---|---|---|---|---|---|---|---|---|---|---|---|---|---|---|
|  |  | 1385 |  |  |  | 1390 |  |  |  | 1395 |  |  |  |  |  |
| tat<br>Tyr | gat<br>Asp | aat<br>Asn<br>1400 | aaa<br>Lys | ggg<br>Gly | caa<br>Gln | acg<br>Thr<br>1405 | ata<br>Ile | cgc<br>Arg | act<br>Thr | tat<br>Tyr<br>1410 | cag<br>Gln | ccc<br>Pro | tat<br>Tyr | ttc<br>Phe | 4239 |
| ctc<br>Leu | aac<br>Asn | gac<br>Asp<br>1415 | tgg<br>Trp | cga<br>Arg | tat<br>Tyr | gtc<br>Val<br>1420 | agt<br>Ser | gat<br>Asp | gac<br>Asp | agc<br>Ser<br>1425 | gcc<br>Ala | aga<br>Arg | aaa<br>Lys | gaa<br>Glu | 4284 |
| gcc<br>Ala | tat<br>Tyr | gcg<br>Ala<br>1430 | gat<br>Asp | act<br>Thr | cat<br>His | att<br>Ile<br>1435 | tat<br>Tyr | gat<br>Asp | cca<br>Pro | att<br>Ile<br>1440 | ggg<br>Gly | cga<br>Arg | gaa<br>Glu | atc<br>Ile | 4329 |
| cgg<br>Arg | gtt<br>Val | att<br>Ile<br>1445 | act<br>Thr | gca<br>Ala | aaa<br>Lys | ggc<br>Gly<br>1450 | tgg<br>Trp | ctg<br>Leu | cgc<br>Arg | caa<br>Gln<br>1455 | agc<br>Ser | caa<br>Gln | tat<br>Tyr | ttc<br>Phe | 4374 |
| ccg<br>Pro | tgg<br>Trp | ttt<br>Phe<br>1460 | acc<br>Thr | gtg<br>Val | agt<br>Ser | gag<br>Glu<br>1465 | gat<br>Asp | gag<br>Glu | aat<br>Asn | gat<br>Asp<br>1470 | acg<br>Thr | gcc<br>Ala | gct<br>Ala | gat<br>Asp | 4419 |
| gcg<br>Ala | ctg<br>Leu | gtg<br>Val<br>1475 | taa |  |  |  |  |  |  |  |  |  |  |  | 4431 |

<210> SEQ ID NO 23
<211> LENGTH: 74
<212> TYPE: DNA
<213> ORGANISM: Artificial Sequence
<220> FEATURE:
<223> OTHER INFORMATION: Forward primer used to amplify the TcdB1
      sequence from plasmid
      pBC-AS4.

<400> SEQUENCE: 23
atatagtcga cgaattttaa tctactagta aaaggagat aaccatgcag aattcacaaa      60 cattc

```
gat gcc cgt gga cac ctg aac tac agt att gac cca cgc ttg tat gat      192
Asp Ala Arg Gly His Leu Asn Tyr Ser Ile Asp Pro Arg Leu Tyr Asp
 50                  55                  60 gca aag cag gct gat aac tca gta aag cct aat ttt gtc tgg cag cat      240
Ala Lys Gln Ala Asp Asn Ser Val Lys Pro Asn Phe Val Trp Gln His
 65                  70                  75                  80 gat ctg gcc ggt cat gcc ctg cgg aca gag agt gtc gat gct ggt cgt      288
Asp Leu Ala Gly His Ala Leu Arg Thr Glu Ser Val Asp Ala Gly Arg
                 85                  90                  95 act gtt gca ttg aat gat att gaa ggt cgt tcg gta atg aca atg aat      336
Thr Val Ala Leu Asn Asp Ile Glu Gly Arg Ser Val Met Thr Met Asn
            100                 105                 110 gcg acc ggt gtt cgt cag acc cgt cgc tat gaa ggc aac acc ttg ccc      384
Ala Thr Gly Val Arg Gln Thr Arg Arg Tyr Glu Gly Asn Thr Leu Pro
        115                 120                 125 ggt cgc ttg tta tct gtg agc gag caa gtt ttc aac caa gag agt gct      432
Gly Arg Leu Leu Ser Val Ser Glu Gln Val Phe Asn Gln Glu Ser Ala
130                 135                 140 aaa gtg aca gag cgc ttt atc tgg gct ggg aat aca acc tcg gag aaa      480
Lys Val Thr Glu Arg Phe Ile Trp Ala Gly Asn Thr Thr Ser Glu Lys
145                 150                 155                 160 gag tat aac ctc tcc ggt ctg tgt ata cgc cac tac gac aca gcg gga      528
Glu Tyr Asn Leu Ser Gly Leu Cys Ile Arg His Tyr Asp Thr Ala Gly
                165                 170                 175 gtg acc cgg ttg atg agt cag tca ctg gcg ggc gcc atg cta tcc caa      576
Val Thr Arg Leu Met Ser Gln Ser Leu Ala Gly Ala Met Leu Ser Gln
            180                 185                 190 tct cac caa ttg ctg gcg gaa ggg cag gag gct aac tgg agc ggt gac      624
Ser His Gln Leu Leu Ala Glu Gly Gln Glu Ala Asn Trp Ser Gly Asp
        195                 200                 205 gac gaa act gtc tgg cag gga atg ctg gca agt gag gtc tat acg aca      672
Asp Glu Thr Val Trp Gln Gly Met Leu Ala Ser Glu Val Tyr Thr Thr
210                 215                 220 caa agt acc act aat gcc atc ggg gct tta ctg acc caa acc gat gcg      720
Gln Ser Thr Thr Asn Ala Ile Gly Ala Leu Leu Thr Gln Thr Asp Ala
225                 230                 235                 240 aaa ggc aat att cag cgt ctg gct tat gac att gcc ggt cag tta aaa      768
Lys Gly Asn Ile Gln Arg Leu Ala Tyr Asp Ile Ala Gly Gln Leu Lys
                245                 250                 255 ggg agt tgg ttg acg gtg aaa ggc cag agt gaa cag gtg att gtt aag      816
Gly Ser Trp Leu Thr Val Lys Gly Gln Ser Glu Gln Val Ile Val Lys
            260                 265                 270 tcc ctg agc tgg tca gcc gca ggt cat aaa ttg cgt gaa gag cac ggt      864
Ser Leu Ser Trp Ser Ala Ala Gly His Lys Leu Arg Glu Glu His Gly
        275                 280                 285 aac ggc gtg gtt acg gag tac agt tat gag ccg gaa act caa cgt ctg      912
Asn Gly Val Val Thr Glu Tyr Ser Tyr Glu Pro Glu Thr Gln Arg Leu
290                 295                 300 ata ggt atc acc acc cgg cgt gcc gaa ggg agt caa tca gga gcc aga      960
Ile Gly Ile Thr Thr Arg Arg Ala Glu Gly Ser Gln Ser Gly Ala Arg
305                 310                 315                 320 gta ttg cag gat cta cgc tat aag tat gat ccg gtg ggg aat gtt atc     1008
Val Leu Gln Asp Leu Arg Tyr Lys Tyr Asp Pro Val Gly Asn Val Ile
                325                 330                 335 agt atc cat aat gat gcc gaa gct acc cgc ttt tgg cgt aat cag aaa     1056
Ser Ile His Asn Asp Ala Glu Ala Thr Arg Phe Trp Arg Asn Gln Lys
            340                 345                 350 gtg gag ccg gag aat cgc tat gtt tat gat tct ctg tat cag ctt atg     1104
Val Glu Pro Glu Asn Arg Tyr Val Tyr Asp Ser Leu Tyr Gln Leu Met
        355                 360                 365
```

```
agt gcg aca ggg cgt gaa atg gct aat atc ggt cag caa agc aac caa    1152
Ser Ala Thr Gly Arg Glu Met Ala Asn Ile Gly Gln Gln Ser Asn Gln
        370                 375                 380 ctt ccc tca ccc gtt ata cct gtt cct act gac gac agc act tat acc    1200
Leu Pro Ser Pro Val Ile Pro Val Pro Thr Asp Asp Ser Thr Tyr Thr
385                 390                 395                 400 aat tac ctt cgt acc tat act tat gac cgt ggc ggt aat ttg gtt caa    1248
Asn Tyr Leu Arg Thr Tyr Thr Tyr Asp Arg Gly Gly Asn Leu Val Gln
            405                 410                 415 atc cga cac agt tca ccc gcg act caa aat agt tac acc aca gat atc    1296
Ile Arg His Ser Ser Pro Ala Thr Gln Asn Ser Tyr Thr Thr Asp Ile
                420                 425                 430 acc gtt tca agc cgc agt aac cgg gcg gta ttg agt aca tta acg aca    1344
Thr Val Ser Ser Arg Ser Asn Arg Ala Val Leu Ser Thr Leu Thr Thr
            435                 440                 445 gat cca acc cga gtg gat gcg cta ttt gat tcc ggc ggt cat cag aag    1392
Asp Pro Thr Arg Val Asp Ala Leu Phe Asp Ser Gly Gly His Gln Lys
450                 455                 460 atg tta ata ccg ggg caa aat ctg gat tgg aat att cgg ggt gaa ttg    1440
Met Leu Ile Pro Gly Gln Asn Leu Asp Trp Asn Ile Arg Gly Glu Leu
465                 470                 475                 480 caa cga gtc aca ccg gtg agc cgt gaa aat agc agt gac agt gaa tgg    1488
Gln Arg Val Thr Pro Val Ser Arg Glu Asn Ser Ser Asp Ser Glu Trp
            485                 490                 495 tat cgc tat agc agt gat ggc atg cgg ctg cta aaa gtg agt gaa cag    1536
Tyr Arg Tyr Ser Ser Asp Gly Met Arg Leu Leu Lys Val Ser Glu Gln
                500                 505                 510 cag acg ggc aac agt act caa gta caa cgg gtg act tat ctg ccg gga    1584
Gln Thr Gly Asn Ser Thr Gln Val Gln Arg Val Thr Tyr Leu Pro Gly
            515                 520                 525 tta gag cta cgg aca act ggg gtt gca gat aaa aca acc gaa gat ttg    1632
Leu Glu Leu Arg Thr Thr Gly Val Ala Asp Lys Thr Thr Glu Asp Leu
530                 535                 540 cag gtg att acg gta ggt gaa gcg ggt cgc gca cag gta agg gta ttg    1680
Gln Val Ile Thr Val Gly Glu Ala Gly Arg Ala Gln Val Arg Val Leu
545                 550                 555                 560 cac tgg gaa agt ggt aag ccg aca gat att gac aac aat cag gtg cgc    1728
His Trp Glu Ser Gly Lys Pro Thr Asp Ile Asp Asn Asn Gln Val Arg
            565                 570                 575 tac agc tac gat aat ctg ctt ggc tcc agc cag ctt gaa ctg gat agc    1776
Tyr Ser Tyr Asp Asn Leu Leu Gly Ser Ser Gln Leu Glu Leu Asp Ser
                580                 585                 590 gaa ggg cag att ctc agt cag gaa gag tat tat ccg tat ggc ggt acg    1824
Glu Gly Gln Ile Leu Ser Gln Glu Glu Tyr Tyr Pro Tyr Gly Gly Thr
            595                 600                 605 gcg ata tgg gcg gcg aga aat cag aca gaa gcc agc tac aaa ttt att    1872
Ala Ile Trp Ala Ala Arg Asn Gln Thr Glu Ala Ser Tyr Lys Phe Ile
610                 615                 620 cgt tac tcc ggt aaa gag cgg gat gcc act gga ttg tat tat tac ggc    1920
Arg Tyr Ser Gly Lys Glu Arg Asp Ala Thr Gly Leu Tyr Tyr Tyr Gly
625                 630                 635                 640 tac cgt tat tat caa cct tgg gtg ggt cga tgg ttg agt gct gat ccg    1968
Tyr Arg Tyr Tyr Gln Pro Trp Val Gly Arg Trp Leu Ser Ala Asp Pro
            645                 650                 655 gcg gga acc gtg gat ggg ctg aat ttg tac cga atg gtg agg aat aac    2016
Ala Gly Thr Val Asp Gly Leu Asn Leu Tyr Arg Met Val Arg Asn Asn
                660                 665                 670 ccc atc aca ttg act gac cat gac gga tta gca ccg tct cca aat aga    2064
Pro Ile Thr Leu Thr Asp His Asp Gly Leu Ala Pro Ser Pro Asn Arg
```

-continued

```
           675                 680                 685
aat cga aat aca ttt tgg ttt gct tca ttt ttg ttt cgt aaa cct gat    2112
Asn Arg Asn Thr Phe Trp Phe Ala Ser Phe Leu Phe Arg Lys Pro Asp
        690                 695                 700 gag gga atg tcc gcg tca atg aga cgg gga caa aaa att ggc aga gcc    2160
Glu Gly Met Ser Ala Ser Met Arg Arg Gly Gln Lys Ile Gly Arg Ala
705                 710                 715                 720 att gcc ggc ggg att gcg att ggc ggt ctt gcg gct acc att gcc gct    2208
Ile Ala Gly Gly Ile Ala Ile Gly Gly Leu Ala Ala Thr Ile Ala Ala
                725                 730                 735 acg gct ggc gcg gct atc ccc gtc att ctg ggg gtt gcg gcc gta ggc    2256
Thr Ala Gly Ala Ala Ile Pro Val Ile Leu Gly Val Ala Ala Val Gly
            740                 745                 750 gcg ggg att ggc gcg ttg atg gga tat aac gtc ggt agc ctg ctg gaa    2304
Ala Gly Ile Gly Ala Leu Met Gly Tyr Asn Val Gly Ser Leu Leu Glu
        755                 760                 765 aaa ggc ggg gca tta ctt gct cga ctc gta cag ggg aaa tcg acg tta    2352
Lys Gly Gly Ala Leu Leu Ala Arg Leu Val Gln Gly Lys Ser Thr Leu
770                 775                 780 gta cag tcg gcg gct ggc gcg gct gcc gga gcg agt tca gcc gcg gct    2400
Val Gln Ser Ala Ala Gly Ala Ala Gly Ala Ser Ser Ala Ala Ala
785                 790                 795                 800 tat ggc gca cgg gca caa ggt gtc ggt gtt gca tca gcc gcc ggg gcg    2448
Tyr Gly Ala Arg Ala Gln Gly Val Gly Val Ala Ser Ala Ala Gly Ala
                805                 810                 815 gta aca ggg gct gtg gga tca tgg ata aat aat gct gat cgg ggg att    2496
Val Thr Gly Ala Val Gly Ser Trp Ile Asn Asn Ala Asp Arg Gly Ile
            820                 825                 830 ggc ggc gct att ggg gcc ggg agt gcg gta ggc acc att gat act atg    2544
Gly Gly Ala Ile Gly Ala Gly Ser Ala Val Gly Thr Ile Asp Thr Met
        835                 840                 845 tta ggg act gcc tct acc ctt acc cat gaa gtc ggg gca gcg gcg ggt    2592
Leu Gly Thr Ala Ser Thr Leu Thr His Glu Val Gly Ala Ala Ala Gly
850                 855                 860 ggg gcg gcg ggt ggg atg atc acc ggt acg caa ggg agt act cgg gca    2640
Gly Ala Ala Gly Gly Met Ile Thr Gly Thr Gln Gly Ser Thr Arg Ala
865                 870                 875                 880 ggt atc cat gcc ggt att ggc acc tat tat ggc tcc tgg att ggt ttt    2688
Gly Ile His Ala Gly Ile Gly Thr Tyr Tyr Gly Ser Trp Ile Gly Phe
                885                 890                 895 ggt tta gat gtc gct agt aac ccc gcc gga cat tta gcg aat tac gca    2736
Gly Leu Asp Val Ala Ser Asn Pro Ala Gly His Leu Ala Asn Tyr Ala
            900                 905                 910 gtg ggt tat gcc gct ggt ttg ggt gct gaa atg gct gtc aac aga ata    2784
Val Gly Tyr Ala Ala Gly Leu Gly Ala Glu Met Ala Val Asn Arg Ile
        915                 920                 925 atg ggt ggt gga ttt ttg agt agg ctc tta ggc cgg gtt gtc agc cca    2832
Met Gly Gly Gly Phe Leu Ser Arg Leu Leu Gly Arg Val Val Ser Pro
930                 935                 940 tat gcc gcc ggt tta gcc aga caa tta gta cat ttc agt gtc gcc aga    2880
Tyr Ala Ala Gly Leu Ala Arg Gln Leu Val His Phe Ser Val Ala Arg
945                 950                 955                 960 cct gtc ttt gag ccg ata ttt agt gtt ctc ggc ggg ctt gtc ggt ggt    2928
Pro Val Phe Glu Pro Ile Phe Ser Val Leu Gly Gly Leu Val Gly Gly
                965                 970                 975 att gga act ggc ctg cac aga gtg atg gga aga gag agt tgg att tcc    2976
Ile Gly Thr Gly Leu His Arg Val Met Gly Arg Glu Ser Trp Ile Ser
            980                 985                 990 aga gcg tta agt gct gcc ggt agt  ggt ata gat cat gtc  gct ggc atg   3024
```

```
Arg Ala Leu Ser Ala Ala Gly Ser  Gly Ile Asp His Val  Ala Gly Met
        995                 1000                 1005 att ggt  aat cag atc aga ggc  agg gtc ttg acc aca  acc ggg atc          3069
Ile Gly  Asn Gln Ile Arg Gly  Arg Val Leu Thr Thr  Thr Gly Ile
   1010                 1015                 1020 gct aat  gcg ata gac tat ggc  acc agt gct gtg gga  gcc gca cga          3114
Ala Asn  Ala Ile Asp Tyr Gly  Thr Ser Ala Val Gly  Ala Ala Arg
   1025                 1030                 1035 cga gtt  ttt tct ttg taa                                                3132
Arg Val  Phe Ser Leu
   1040
```

<210> SEQ ID NO 26
<211> LENGTH: 77
<212> TYPE: DNA
<213> ORGANISM: Artificial Sequence
<220> FEATURE:
<223> OTHER INFORMATION: Forward primer used to amplify TccC1 from the
      pBC KS+ vector.

<400> SEQUENCE: 26
gtcgacgcac tactagtaaa aaggagataa ccccatgagc ccgtctgaga ctactcttta     60
tactcaaacc ccaacag                                                    77

<210> SEQ ID NO 27
<211> LENGTH: 57
<212> TYPE: DNA
<213> ORGANISM: Artificial Sequence
<220> FEATURE:
<223> OTHER INFORMATION: Reverse primer used to amplify TccC1 from the
      pBC KS+ vector.

<400> SEQUENCE: 27
cggccgcagt cctcgagtca gattaattac aaagaaaaaa ctcgtcgtgc ggctccc        57

<210> SEQ ID NO 28
<211> LENGTH: 84
<212> TYPE: DNA
<213> ORGANISM: Artificial Sequence
<220> FEATURE:
<223> OTHER INFORMATION: Forward primer used to amplify XptA2.

<400> SEQUENCE: 28
gtctagacgt gcgtcgacaa gaaggagata taccatgtat agcacggctg tattactcaa     60
taaaatcagt cccactcgcg acgg                                            84

<210> SEQ ID NO 29
<211> LENGTH: 64
<212> TYPE: DNA
<213> ORGANISM: Artificial Sequence
<220> FEATURE:
<223> OTHER INFORMATION: Reverse primer used to amplify XptA2.

<400> SEQUENCE: 29
gctcgagatt aattaagaac gaatggtata gcggatatgc agaatgatat cgctcaggct     60
ctcc                                                                  64

<210> SEQ ID NO 30
<211> LENGTH: 81
<212> TYPE: DNA
<213> ORGANISM: Artificial Sequence
<220> FEATURE:
<223> OTHER INFORMATION: Forward primer used to amplify XptC1.

-continued

<400> SEQUENCE: 30

```
gtctagacgt gcgtcgacaa gaaggagata taccatgcag ggttcaacac ctttgaaact    60
tgaaataccg tcattgccct c                                              81
```

<210> SEQ ID NO 31
<211> LENGTH: 64
<212> TYPE: DNA
<213> ORGANISM: Artificial Sequence
<220> FEATURE:
<223> OTHER INFORMATION: Reverse primer used to amplify XptC1.

<400> SEQUENCE: 31

```
gactcgagag cattaattat gctgtcattt caccggcagt gtcattttca tcttcattca    60
ccac                                                                 64
```

<210> SEQ ID NO 32
<211> LENGTH: 86
<212> TYPE: DNA
<213> ORGANISM: Artificial Sequence
<220> FEATURE:
<223> OTHER INFORMATION: Forward primer used to amplify XptB1.

<400> SEQUENCE: 32

```
gtctagacgt gcgtcgacaa gaaggagata taccatgaag aatttcgttc acagcaatac    60
gccatccgtc accgtactgg acaacc                                         86
```

<210> SEQ ID NO 33
<211> LENGTH: 66
<212> TYPE: DNA
<213> ORGANISM: Artificial Sequence
<220> FEATURE:
<223> OTHER INFORMATION: Reverse primer used to amplify XptB1.

<400> SEQUENCE: 33

```
gctcgagcag attaattatg cttcggattc attatgacgt gcagaggcgt taaagaagaa    60
gttatt                                                               66
```

<210> SEQ ID NO 34
<211> LENGTH: 2538
<212> TYPE: PRT
<213> ORGANISM: Xenorhabdus nematophilus

<400> SEQUENCE: 34

```
Met Tyr Ser Thr Ala Val Leu Leu Asn Lys Ile Ser Pro Thr Arg Asp
1               5                   10                  15

Gly Gln Thr Met Thr Leu Ala Asp Leu Gln Tyr Leu Ser Phe Ser Glu
            20                  25                  30

Leu Arg Lys Ile Phe Asp Asp Gln Leu Ser Trp Gly Glu Ala Arg His
        35                  40                  45

Leu Tyr His Glu Thr Ile Glu Gln Lys Lys Asn Asn Arg Leu Leu Glu
    50                  55                  60

Ala Arg Ile Phe Thr Arg Ala Asn Pro Gln Leu Ser Gly Ala Ile Arg
65                  70                  75                  80

Leu Gly Ile Glu Arg Asp Ser Val Ser Arg Ser Tyr Asp Glu Met Phe
                85                  90                  95

Gly Ala Arg Ser Ser Ser Phe Val Lys Pro Gly Ser Val Ala Ser Met
            100                 105                 110

Phe Ser Pro Ala Gly Tyr Leu Thr Glu Leu Tyr Arg Glu Ala Lys Asp
        115                 120                 125
```

-continued

```
Leu His Phe Ser Ser Ser Ala Tyr His Leu Asp Asn Arg Pro Asp
    130                 135                 140
Leu Ala Asp Leu Thr Leu Ser Gln Ser Asn Met Asp Thr Glu Ile Ser
145                 150                 155                 160
Thr Leu Thr Leu Ser Asn Glu Leu Leu Glu His Ile Thr Arg Lys
                165                 170                 175
Thr Gly Gly Asp Ser Asp Ala Leu Met Glu Ser Leu Ser Thr Tyr Arg
                180                 185                 190
Gln Ala Ile Asp Thr Pro Tyr His Gln Pro Tyr Glu Thr Ile Arg Gln
                195                 200                 205
Val Ile Met Thr His Asp Ser Thr Leu Ser Ala Leu Ser Arg Asn Pro
    210                 215                 220
Glu Val Met Gly Gln Ala Glu Gly Ala Ser Leu Leu Ala Ile Leu Ala
225                 230                 235                 240
Asn Ile Ser Pro Glu Leu Tyr Asn Ile Leu Thr Glu Glu Ile Thr Glu
                245                 250                 255
Lys Asn Ala Asp Ala Leu Phe Ala Gln Asn Phe Ser Glu Asn Ile Thr
                260                 265                 270
Pro Glu Asn Phe Ala Ser Gln Ser Trp Ile Ala Lys Tyr Tyr Gly Leu
                275                 280                 285
Glu Leu Ser Glu Val Gln Lys Tyr Leu Gly Met Leu Gln Asn Gly Tyr
    290                 295                 300
Ser Asp Ser Thr Ser Ala Tyr Val Asp Asn Ile Ser Thr Gly Leu Val
305                 310                 315                 320
Val Asn Asn Glu Ser Lys Leu Glu Ala Tyr Lys Ile Thr Arg Val Lys
                325                 330                 335
Thr Asp Asp Tyr Asp Lys Asn Ile Asn Tyr Phe Asp Leu Met Tyr Glu
                340                 345                 350
Gly Asn Asn Gln Phe Phe Ile Arg Ala Asn Phe Lys Val Ser Arg Glu
                355                 360                 365
Phe Gly Ala Thr Leu Arg Lys Asn Ala Gly Pro Ser Gly Ile Val Gly
    370                 375                 380
Ser Leu Ser Gly Pro Leu Ile Ala Asn Thr Asn Phe Lys Ser Asn Tyr
385                 390                 395                 400
Leu Ser Asn Ile Ser Asp Ser Glu Tyr Lys Asn Gly Val Lys Ile Tyr
                405                 410                 415
Ala Tyr Arg Tyr Thr Ser Ser Thr Ser Ala Thr Asn Gln Gly Gly Gly
                420                 425                 430
Ile Phe Thr Phe Glu Ser Tyr Pro Leu Thr Ile Phe Ala Leu Lys Leu
                435                 440                 445
Asn Lys Ala Ile Arg Leu Cys Leu Thr Ser Gly Leu Ser Pro Asn Glu
    450                 455                 460
Leu Gln Thr Ile Val Arg Ser Asp Asn Ala Gln Gly Ile Ile Asn Asp
465                 470                 475                 480
Ser Val Leu Thr Lys Val Phe Tyr Thr Leu Phe Tyr Ser His Arg Tyr
                485                 490                 495
Ala Leu Ser Phe Asp Asp Ala Gln Val Leu Asn Gly Ser Val Ile Asn
                500                 505                 510
Gln Tyr Ala Asp Asp Ser Val Ser His Phe Asn Arg Leu Phe Asn
                515                 520                 525
Thr Pro Pro Leu Lys Gly Lys Ile Phe Glu Ala Asp Gly Asn Thr Val
    530                 535                 540
```

-continued

```
Ser Ile Asp Pro Asp Glu Glu Gln Ser Thr Phe Ala Arg Ser Ala Leu
545                 550                 555                 560

Met Arg Gly Leu Gly Val Asn Ser Gly Glu Leu Tyr Gln Leu Gly Lys
                565                 570                 575

Leu Ala Gly Val Leu Asp Ala Gln Asn Thr Ile Thr Leu Ser Val Phe
            580                 585                 590

Val Ile Ser Ser Leu Tyr Arg Leu Thr Leu Leu Ala Arg Val His Gln
        595                 600                 605

Leu Thr Val Asn Glu Leu Cys Met Leu Tyr Gly Leu Ser Pro Phe Asn
    610                 615                 620

Gly Lys Thr Thr Ala Ser Leu Ser Ser Gly Glu Leu Pro Arg Leu Val
625                 630                 635                 640

Ile Trp Leu Tyr Gln Val Thr Gln Trp Leu Thr Glu Ala Glu Ile Thr
                645                 650                 655

Thr Glu Ala Ile Trp Leu Leu Cys Thr Pro Glu Phe Ser Gly Asn Ile
            660                 665                 670

Ser Pro Glu Ile Ser Asn Leu Leu Asn Asn Leu Arg Pro Ser Ile Ser
        675                 680                 685

Glu Asp Met Ala Gln Ser His Asn Arg Glu Leu Gln Ala Glu Ile Leu
    690                 695                 700

Ala Pro Phe Ile Ala Ala Thr Leu His Leu Ala Ser Pro Asp Met Ala
705                 710                 715                 720

Arg Tyr Ile Leu Leu Trp Thr Asp Asn Leu Arg Pro Gly Gly Leu Asp
                725                 730                 735

Ile Ala Gly Phe Met Thr Leu Val Leu Lys Glu Ser Leu Asn Ala Asn
            740                 745                 750

Glu Thr Thr Gln Leu Val Gln Phe Cys His Val Met Ala Gln Leu Ser
        755                 760                 765

Leu Ser Val Gln Thr Leu Arg Leu Ser Glu Ala Glu Leu Ser Val Leu
    770                 775                 780

Val Ile Ser Gly Phe Ala Val Leu Gly Ala Lys Asn Gln Pro Ala Gly
785                 790                 795                 800

Gln His Asn Ile Asp Thr Leu Phe Ser Leu Tyr Arg Phe His Gln Trp
                805                 810                 815

Ile Asn Gly Leu Gly Asn Pro Gly Ser Asp Thr Leu Asp Met Leu Arg
            820                 825                 830

Gln Gln Thr Leu Thr Ala Asp Arg Leu Ala Ser Val Met Gly Leu Asp
        835                 840                 845

Ile Ser Met Val Thr Gln Ala Met Val Ser Ala Gly Val Asn Gln Leu
    850                 855                 860

Gln Cys Trp Gln Asp Ile Asn Thr Val Leu Gln Trp Ile Asp Val Ala
865                 870                 875                 880

Ser Ala Leu His Thr Met Pro Ser Val Ile Arg Thr Leu Val Asn Ile
                885                 890                 895

Arg Tyr Val Thr Ala Leu Asn Lys Ala Glu Ser Asn Leu Pro Ser Trp
            900                 905                 910

Asp Glu Trp Gln Thr Leu Ala Glu Asn Met Glu Ala Gly Leu Ser Thr
        915                 920                 925

Gln Gln Ala Gln Thr Leu Ala Asp Tyr Thr Ala Glu Arg Leu Ser Ser
    930                 935                 940

Val Leu Cys Asn Trp Phe Leu Ala Asn Ile Gln Pro Glu Gly Val Ser
945                 950                 955                 960

Leu His Ser Arg Asp Asp Leu Tyr Ser Tyr Phe Leu Ile Asp Asn Gln
```

-continued

```
                 965                 970                 975
Val Ser Ser Ala Ile Lys Thr Thr Arg Leu Ala Glu Ala Ile Ala Gly
            980                 985                 990
Ile Gln Leu Tyr Ile Asn Arg Ala Leu Asn Arg Ile Glu Pro Asn Ala
            995                1000                1005
Arg Ala Asp Val Ser Thr Arg Gln Phe Phe Thr Asp Trp Thr Val
       1010                1015                1020
Asn Asn Arg Tyr Ser Thr Trp Gly Gly Val Ser Arg Leu Val Tyr
       1025                1030                1035
Tyr Pro Glu Asn Tyr Ile Asp Pro Thr Gln Arg Ile Gly Gln Thr
       1040                1045                1050
Arg Met Met Asp Glu Leu Leu Glu Asn Ile Ser Gln Ser Lys Leu
       1055                1060                1065
Ser Arg Asp Thr Val Glu Asp Ala Phe Lys Thr Tyr Leu Thr Arg
       1070                1075                1080
Phe Glu Thr Val Ala Asp Leu Lys Val Val Ser Ala Tyr His Asp
       1085                1090                1095
Asn Val Asn Ser Asn Thr Gly Leu Thr Trp Phe Val Gly Gln Thr
       1100                1105                1110
Arg Glu Asn Leu Pro Glu Tyr Tyr Trp Arg Asn Val Asp Ile Ser
       1115                1120                1125
Arg Met Gln Ala Gly Glu Leu Ala Ala Asn Ala Trp Lys Glu Trp
       1130                1135                1140
Thr Lys Ile Asp Thr Ala Val Asn Pro Tyr Lys Asp Ala Ile Arg
       1145                1150                1155
Pro Val Ile Phe Arg Glu Arg Leu His Leu Ile Trp Val Glu Lys
       1160                1165                1170
Glu Glu Val Ala Lys Asn Gly Thr Asp Pro Val Glu Thr Tyr Asp
       1175                1180                1185
Arg Phe Thr Leu Lys Leu Ala Phe Leu Arg His Asp Gly Ser Trp
       1190                1195                1200
Ser Ala Pro Trp Ser Tyr Asp Ile Thr Thr Gln Val Glu Ala Val
       1205                1210                1215
Thr Asp Lys Lys Pro Asp Thr Glu Arg Leu Ala Leu Ala Ala Ser
       1220                1225                1230
Gly Phe Gln Gly Glu Asp Thr Leu Leu Val Phe Val Tyr Lys Thr
       1235                1240                1245
Gly Lys Ser Tyr Ser Asp Phe Gly Gly Ser Asn Lys Asn Val Ala
       1250                1255                1260
Gly Met Thr Ile Tyr Gly Asp Gly Ser Phe Lys Lys Met Glu Asn
       1265                1270                1275
Thr Ala Leu Ser Arg Tyr Ser Gln Leu Lys Asn Thr Phe Asp Ile
       1280                1285                1290
Ile His Thr Gln Gly Asn Asp Leu Val Arg Lys Ala Ser Tyr Arg
       1295                1300                1305
Phe Ala Gln Asp Phe Glu Val Pro Ala Ser Leu Asn Met Gly Ser
       1310                1315                1320
Ala Ile Gly Asp Asp Ser Leu Thr Val Met Glu Asn Gly Asn Ile
       1325                1330                1335
Pro Gln Ile Thr Ser Lys Tyr Ser Ser Asp Asn Leu Ala Ile Thr
       1340                1345                1350
Leu His Asn Ala Ala Phe Thr Val Arg Tyr Asp Gly Ser Gly Asn
       1355                1360                1365
```

-continued

```
Val Ile Arg Asn Lys Gln Ile Ser Ala Met Lys Leu Thr Gly Val
    1370                1375                1380
Asp Gly Lys Ser Gln Tyr Gly Asn Ala Phe Ile Ile Ala Asn Thr
1385                1390                1395
Val Lys His Tyr Gly Gly Tyr Ser Asp Leu Gly Gly Pro Ile Thr
    1400                1405                1410
Val Tyr Asn Lys Thr Lys Asn Tyr Ile Ala Ser Val Gln Gly His
1415                1420                1425
Leu Met Asn Ala Asp Tyr Thr Arg Arg Leu Ile Leu Thr Pro Val
    1430                1435                1440
Glu Asn Asn Tyr Tyr Ala Arg Leu Phe Glu Phe Pro Phe Ser Pro
1445                1450                1455
Asn Thr Ile Leu Asn Thr Val Phe Thr Val Gly Ser Asn Lys Thr
    1460                1465                1470
Ser Asp Phe Lys Lys Cys Ser Tyr Ala Val Asp Gly Asn Asn Ser
1475                1480                1485
Gln Gly Phe Gln Ile Phe Ser Ser Tyr Gln Ser Ser Gly Trp Leu
    1490                1495                1500
Asp Ile Asp Thr Gly Ile Asn Asn Thr Asp Ile Lys Ile Thr Val
1505                1510                1515
Met Ala Gly Ser Lys Thr His Thr Phe Thr Ala Ser Asp His Ile
    1520                1525                1530
Ala Ser Leu Pro Ala Asn Ser Phe Asp Ala Met Pro Tyr Thr Phe
1535                1540                1545
Lys Pro Leu Glu Ile Asp Ala Ser Ser Leu Ala Phe Thr Asn Asn
    1550                1555                1560
Ile Ala Pro Leu Asp Ile Val Phe Glu Thr Lys Ala Lys Asp Gly
1565                1570                1575
Arg Val Leu Gly Lys Ile Lys Gln Thr Leu Ser Val Lys Arg Val
    1580                1585                1590
Asn Tyr Asn Pro Glu Asp Ile Leu Phe Leu Arg Glu Thr His Ser
1595                1600                1605
Gly Ala Gln Tyr Met Gln Leu Gly Val Tyr Arg Ile Arg Leu Asn
    1610                1615                1620
Thr Leu Leu Ala Ser Gln Leu Val Ser Arg Ala Asn Thr Gly Ile
1625                1630                1635
Asp Thr Ile Leu Thr Met Glu Thr Gln Arg Leu Pro Glu Pro Pro
    1640                1645                1650
Leu Gly Glu Gly Phe Phe Ala Asn Phe Val Leu Pro Lys Tyr Asp
1655                1660                1665
Pro Ala Glu His Gly Asp Glu Arg Trp Phe Lys Ile His Ile Gly
    1670                1675                1680
Asn Val Gly Gly Asn Thr Gly Arg Gln Pro Tyr Tyr Ser Gly Met
1685                1690                1695
Leu Ser Asp Thr Ser Glu Thr Ser Met Thr Leu Phe Val Pro Tyr
    1700                1705                1710
Ala Glu Gly Tyr Tyr Met His Glu Gly Val Arg Leu Gly Val Gly
1715                1720                1725
Tyr Gln Lys Ile Thr Tyr Asp Asn Thr Trp Glu Ser Ala Phe Phe
    1730                1735                1740
Tyr Phe Asp Glu Thr Lys Gln Gln Phe Val Leu Ile Asn Asp Ala
1745                1750                1755
```

-continued

```
Asp His Asp Ser Gly Met Thr Gln Gln Gly Ile Val Lys Asn Ile
1760                1765                1770

Lys Lys Tyr Lys Gly Phe Leu Asn Val Ser Ile Ala Thr Gly Tyr
1775                1780                1785

Ser Ala Pro Met Asp Phe Asn Ser Ala Ser Ala Leu Tyr Tyr Trp
1790                1795                1800

Glu Leu Phe Tyr Tyr Thr Pro Met Met Cys Phe Gln Arg Leu Leu
1805                1810                1815

Gln Glu Lys Gln Phe Asp Glu Ala Thr Gln Trp Ile Asn Tyr Val
1820                1825                1830

Tyr Asn Pro Ala Gly Tyr Ile Val Asn Gly Glu Ile Ala Pro Trp
1835                1840                1845

Ile Trp Asn Cys Arg Pro Leu Glu Glu Thr Thr Ser Trp Asn Ala
1850                1855                1860

Asn Pro Leu Asp Ala Ile Asp Pro Asp Ala Val Ala Gln Asn Asp
1865                1870                1875

Pro Met His Tyr Lys Ile Ala Thr Phe Met Arg Leu Leu Asp Gln
1880                1885                1890

Leu Ile Leu Arg Gly Asp Met Ala Tyr Arg Glu Leu Thr Arg Asp
1895                1900                1905

Ala Leu Asn Glu Ala Lys Met Trp Tyr Val Arg Thr Leu Glu Leu
1910                1915                1920

Leu Gly Asp Glu Pro Glu Asp Tyr Gly Ser Gln Trp Ala Ala
1925                1930                1935

Pro Ser Leu Ser Gly Ala Ala Ser Gln Thr Val Gln Ala Ala Tyr
1940                1945                1950

Gln Gln Asp Leu Thr Met Leu Gly Arg Gly Gly Val Ser Lys Asn
1955                1960                1965

Leu Arg Thr Ala Asn Ser Leu Val Gly Leu Phe Leu Pro Glu Tyr
1970                1975                1980

Asn Pro Ala Leu Thr Asp Tyr Trp Gln Thr Leu Arg Leu Arg Leu
1985                1990                1995

Phe Asn Leu Arg His Asn Leu Ser Ile Asp Gly Gln Pro Leu Ser
2000                2005                2010

Leu Ala Ile Tyr Ala Glu Pro Thr Asp Pro Lys Ala Leu Leu Thr
2015                2020                2025

Ser Met Val Gln Ala Ser Gln Gly Gly Ser Ala Val Leu Pro Gly
2030                2035                2040

Thr Leu Ser Leu Tyr Arg Phe Pro Val Met Leu Glu Arg Thr Arg
2045                2050                2055

Asn Leu Val Ala Gln Leu Thr Gln Phe Gly Thr Ser Leu Leu Ser
2060                2065                2070

Met Ala Glu His Asp Asp Ala Asp Glu Leu Thr Thr Leu Leu Leu
2075                2080                2085

Gln Gln Gly Met Glu Leu Ala Thr Gln Ser Ile Arg Ile Gln Gln
2090                2095                2100

Arg Thr Val Asp Glu Val Asp Ala Asp Ile Ala Val Leu Ala Glu
2105                2110                2115

Ser Arg Arg Ser Ala Gln Asn Arg Leu Glu Lys Tyr Gln Gln Leu
2120                2125                2130

Tyr Asp Glu Asp Ile Asn His Gly Glu Gln Arg Ala Met Ser Leu
2135                2140                2145

Leu Asp Ala Ala Ala Gly Gln Ser Leu Ala Gly Gln Val Leu Ser
```

```
                2150                 2155                 2160

Ile Ala Glu Gly Val Ala Asp Leu Val Pro Asn Val Phe Gly Leu
    2165                 2170                 2175

Ala Cys Gly Gly Ser Arg Trp Gly Ala Ala Leu Arg Ala Ser Ala
    2180                 2185                 2190

Ser Val Met Ser Leu Ser Ala Thr Ala Ser Gln Tyr Ser Ala Asp
    2195                 2200                 2205

Lys Ile Ser Arg Ser Glu Ala Tyr Arg Arg Arg Gln Glu Trp
    2210                 2215                 2220

Glu Ile Gln Arg Asp Asn Ala Asp Gly Glu Val Lys Gln Met Asp
    2225                 2230                 2235

Ala Gln Leu Glu Ser Leu Lys Ile Arg Arg Glu Ala Ala Gln Met
    2240                 2245                 2250

Gln Val Glu Tyr Gln Glu Thr Gln Gln Ala His Thr Gln Ala Gln
    2255                 2260                 2265

Leu Glu Leu Leu Gln Arg Lys Phe Thr Asn Lys Ala Leu Tyr Ser
    2270                 2275                 2280

Trp Met Arg Gly Lys Leu Ser Ala Ile Tyr Tyr Gln Phe Phe Asp
    2285                 2290                 2295

Leu Thr Gln Ser Phe Cys Leu Met Ala Gln Glu Ala Leu Arg Arg
    2300                 2305                 2310

Glu Leu Thr Asp Asn Gly Val Thr Phe Ile Arg Gly Gly Ala Trp
    2315                 2320                 2325

Asn Gly Thr Thr Ala Gly Leu Met Ala Gly Glu Thr Leu Leu Leu
    2330                 2335                 2340

Asn Leu Ala Glu Met Glu Lys Val Trp Leu Glu Arg Asp Glu Arg
    2345                 2350                 2355

Ala Leu Glu Val Thr Arg Thr Val Ser Leu Ala Gln Phe Tyr Gln
    2360                 2365                 2370

Ala Leu Ser Ser Asp Asn Phe Asn Leu Thr Glu Lys Leu Thr Gln
    2375                 2380                 2385

Phe Leu Arg Glu Gly Lys Gly Asn Val Gly Ala Ser Gly Asn Glu
    2390                 2395                 2400

Leu Lys Leu Ser Asn Arg Gln Ile Glu Ala Ser Val Arg Leu Ser
    2405                 2410                 2415

Asp Leu Lys Ile Phe Ser Asp Tyr Pro Glu Ser Leu Gly Asn Thr
    2420                 2425                 2430

Arg Gln Leu Lys Gln Val Ser Val Thr Leu Pro Ala Leu Val Gly
    2435                 2440                 2445

Pro Tyr Glu Asp Ile Arg Ala Val Leu Asn Tyr Gly Gly Ser Ile
    2450                 2455                 2460

Val Met Pro Arg Gly Cys Ser Ala Ile Ala Leu Ser His Gly Val
    2465                 2470                 2475

Asn Asp Ser Gly Gln Phe Met Leu Asp Phe Asn Asp Ser Arg Tyr
    2480                 2485                 2490

Leu Pro Phe Glu Gly Ile Ser Val Asn Asp Ser Gly Ser Leu Thr
    2495                 2500                 2505

Leu Ser Phe Pro Asp Ala Thr Asp Arg Gln Lys Ala Leu Leu Glu
    2510                 2515                 2520

Ser Leu Ser Asp Ile Ile Leu His Ile Arg Tyr Thr Ile Arg Ser
    2525                 2530                 2535

<210> SEQ ID NO 35
```

<211> LENGTH: 3300
<212> TYPE: DNA
<213> ORGANISM: Paenibacillus strain DAS1529

<400> SEQUENCE: 35

```
atggtgtcaa caacagacaa cacggccggc gtattccggc tcggaaccga agaattaaca      60
gaagcgctta agcagtccgg ttatcggacc gtctttgata ttgtatctga caatcttgcg     120
gaatttcaga aaacaatcc ggagattccc tcttctgacg cgaaggagat tcatcaatta     180
gccgtccaga ggacagaaaa cttatgcatg ctttataagg cctggcagct gcacaatgat     240
ccggttgtcc agagccttcc caattatcc gcggataccg gcctgcaagg catgcgtgcc     300
gcgttggagc ggagtcttgg aggcggagcc gattttggag acttgttccc ggagcgatcg     360
ccagagggct atgcggaagc ctcctctata cagtcgcttt tctcgccggg acgttacctg     420
acggtgctgt ataaaattgc gcgggatctc cacgacccaa agataaaact gcatattgac     480
aaccgccgtc cagatttgaa gtcgctgatc ctcaataatg acaatatgaa ccgagaggta     540
tcttctctgg atatccttct ggatgtgctg cagcccgaag ctctgacac gctgacatcc     600
ttgaaggata cctaccatcc gatgacccct ccctatgatg acgaccttgc gcaaatcaat     660
gccgtggcgg aggcgcgttc atctaatttg ctggggattt gggatacct gctggacacg     720
cagcggactt ccatcctgca gaattccgcc gctgcccgcc ggataagcaa ggcgcggcac     780
tcggcatacg ccaatcagaa agcctccaat gatgagccgg tattcatcac gggagaggaa     840
atctacctgg aaaccggagg taaacggctt tttctggcgc ataaactcga dataggttca     900
actattagcg ctaaaatcaa cattggaccg ccgcaagcgg ccgatatcgc gccggcaaag     960
ttgcaactcg tatattacgg cagaggcggc agagggaact acttcctgcg cgtggcagac    1020
gatgtgtccc tcggtggaaa gctgctgacc aattgttatc tgaccagcga tgacggacag    1080
agcaacaata ttagcgggcc atactgccta atgatcaacc gaggcaccgg cagcatgcct    1140
agcgggactc accttccagt tcagattgaa agagtgaccg atacatccat ccgcattttt    1200
gtgccggatc acggctattt ggggctaggc gaaagccttg ccagcaactg gaatgaaccg    1260
ttggcgctga atctgggctt ggatgaagcg ttgacctta ccttgagaaa gaaggagacg    1320
ggaaatgaca ccatttccat aatcgacatg ctgccgccgg tagcgaacac gactccgtct    1380
ccgccgacga gggaaacgct ttccttgacg ccaaacagct tccgtctgct ggtcaaccct    1440
gagccgacag cggaggacat cgccaagcac tacaacgtca cgacggtaac ccgggctcct    1500
gccgatctgg cctccgcctt aaatgttgtc gatgatttct gcttgaaaac cggtttgagc    1560
tttaacgaat tgctggattt aaccatgcag aaggattatc agtcaaaaag cagtgagtac    1620
aaaagccgat ttgtaaaatt cggcggcggg gagaatgttc cggtatcaag ctatggcgca    1680
gcctttctga caggagcgga agatactcct tgtgggtga aacagtataa cagcgtgggg    1740
actgcaacaa gcaccctgt tttaaacttt acgccagata tgttgtggc tttggcagga    1800
agggcggaaa agcttgtccg gctgatgcgc agcacgggtc tttcctttga gcagttggat    1860
tggctgattg ccaatgccag ccgtgccgtt atcgaacacg gtggagagct tttctctggat    1920
aagccggtac tggaagctgt ggccgaattc acaaggctca ataagcgtta tggcgtcaca    1980
tcggatatgt tcgccgcgtt tatcggcgaa gtcaatacgt atacagaagc gggcaaggac    2040
agcttttatc aggcgagttt cagcacggcc gaccattcgg ctaccttacc tttgggcgct    2100
tctttgcaac ttgaggtgag caagcaggat cgatatgaag cgatttgctg cggggctatg    2160
ggggtgaccg ccgatgagtt ctcccgtatc ggcaaatact gctttgggga taaagcacag    2220
```

-continued

```
caaatcacgg ccaatgaaac aaccgttgcc cagctttatc gtttaggccg aattcctcat    2280
atgctaggct tgcgttttac cgaggcagag ctgttgtgga aattgatggc tgggggcgag    2340
gataccttgc tccgcacgat tggcgcgaac cctcgcagtt tagaagcgtt agagattatt    2400
cgccggacgg aggtcctttt ggactggatg gatgcccatc agctggatgt tgtctccctg    2460
caagccatgg ttaccaatcg gtacagcggc acagccacgc cggagctgta caattttttg    2520
gcacaggtgc atcaatccgc aagcagtgcc gcgaacgtgg ccagagcgga tggtcaggat    2580
acgttgcctg cggacaagct gctccgggca ttggcggcgg gcttcaaact gaaagccaac    2640
gtgatggcgc gagtaatcga ctggatggac aaaaccaata aagcgtttac gctgcgggct    2700
ttctgggaca gcttcaagc gtatttcagc gccgatcatg aagaagaact gaccgccctg    2760
gaaggagaag ccgcaatgct gcagtggtgc cagcagatca gccagtatgc gctcattgtc    2820
cgctggtgcg ggttaagcga gcaggatctg gcgctgctga ccgggaatcc ggagcagctt    2880
ctggacggac aacatacggt gcccgtaccc tcgctgcatc tcctgctggt gctgacccgc    2940
ctgaaggaat ggcagcagcg cgtccaggtt tccagcgagg aggctatgcg ctattttgcc    3000
caggccgatt cgccaaccgt cacgcgcgac gatgcggtta atctgcttgc ccgtatccat    3060
ggctggaatg aagcggatac cgtctcgatg aatgactacc tgctgggaga gaacgaatat    3120
cctaagaact ttgatcagat ctttgcactg gaaagctggg tcaacctggg ccgtcaactg    3180
aacgtgggca gcagaacgct gggagagctg gttgacatgg ctgaagagga taaaaccgcg    3240
gaaaacatgg atctgattac ttcggtggcc catagcctga tggctgcagc gaaagcctga    3300
```

<210> SEQ ID NO 36
<211> LENGTH: 1080
<212> TYPE: PRT
<213> ORGANISM: Paenibacillus strain DAS1529

<400> SEQUENCE: 36

```
Met Val Ser Thr Thr Asp Asn Thr Ala Gly Val Phe Arg Leu Gly Thr
1               5                   10                  15

Glu Glu Leu Thr Glu Ala Leu Lys Gln Ser Gly Tyr Arg Thr Val Phe
            20                  25                  30

Asp Ile Val Ser Asp Asn Leu Ala Glu Phe Gln Lys Asn Asn Pro Glu
        35                  40                  45

Ile Pro Ser Ser Asp Ala Lys Glu Ile His Gln Leu Ala Val Gln Arg
    50                  55                  60

Thr Glu Asn Leu Cys Met Leu Tyr Lys Ala Trp Gln Leu His Asn Asp
65                  70                  75                  80

Pro Val Val Gln Ser Leu Pro Lys Leu Ser Ala Asp Thr Gly Leu Gln
                85                  90                  95

Gly Met Arg Ala Ala Leu Glu Arg Ser Leu Gly Gly Gly Ala Asp Phe
            100                 105                 110

Gly Asp Leu Phe Pro Glu Arg Ser Pro Glu Gly Tyr Ala Glu Ala Ser
        115                 120                 125

Ser Ile Gln Ser Leu Phe Ser Pro Gly Arg Tyr Leu Thr Val Leu Tyr
    130                 135                 140

Lys Ile Ala Arg Asp Leu His Asp Pro Lys Asp Lys Leu His Ile Asp
145                 150                 155                 160

Asn Arg Arg Pro Asp Leu Lys Ser Leu Ile Leu Asn Asn Asp Asn Met
                165                 170                 175

Asn Arg Glu Val Ser Ser Leu Asp Ile Leu Leu Asp Val Leu Gln Pro
```

-continued

```
              180                 185                 190
    Glu Gly Ser Asp Thr Leu Thr Ser Leu Lys Asp Thr Tyr His Pro Met
            195                 200                 205

Thr Leu Pro Tyr Asp Asp Leu Ala Gln Ile Asn Ala Val Ala Glu
    210                 215                 220

Ala Arg Ser Ser Asn Leu Leu Gly Ile Trp Asp Thr Leu Leu Asp Thr
    225                 230                 235                 240

Gln Arg Thr Ser Ile Leu Gln Asn Ser Ala Ala Arg Arg Ile Ser
                    245                 250                 255

Lys Ala Arg His Ser Ala Tyr Ala Asn Gln Lys Ala Ser Asn Asp Glu
                260                 265                 270

Pro Val Phe Ile Thr Gly Glu Glu Ile Tyr Leu Glu Thr Gly Gly Lys
                275                 280                 285

Arg Leu Phe Leu Ala His Lys Leu Glu Ile Gly Ser Thr Ile Ser Ala
    290                 295                 300

Lys Ile Asn Ile Gly Pro Pro Gln Ala Ala Asp Ile Ala Pro Ala Lys
    305                 310                 315                 320

Leu Gln Leu Val Tyr Tyr Gly Arg Gly Gly Arg Gly Asn Tyr Phe Leu
                    325                 330                 335

Arg Val Ala Asp Asp Val Ser Leu Gly Gly Lys Leu Leu Thr Asn Cys
                340                 345                 350

Tyr Leu Thr Ser Asp Asp Gly Gln Ser Asn Asn Ile Ser Gly Pro Tyr
                355                 360                 365

Cys Leu Met Ile Asn Arg Gly Thr Gly Ser Met Pro Ser Gly Thr His
    370                 375                 380

Leu Pro Val Gln Ile Glu Arg Val Thr Asp Thr Ser Ile Arg Ile Phe
    385                 390                 395                 400

Val Pro Asp His Gly Tyr Leu Gly Leu Gly Glu Ser Leu Ala Ser Asn
                    405                 410                 415

Trp Asn Glu Pro Leu Ala Leu Asn Leu Gly Leu Asp Glu Ala Leu Thr
                420                 425                 430

Phe Thr Leu Arg Lys Lys Glu Thr Gly Asn Asp Thr Ile Ser Ile Ile
                435                 440                 445

Asp Met Leu Pro Pro Val Ala Asn Thr Thr Pro Ser Pro Pro Thr Arg
    450                 455                 460

Glu Thr Leu Ser Leu Thr Pro Asn Ser Phe Arg Leu Leu Val Asn Pro
    465                 470                 475                 480

Glu Pro Thr Ala Glu Asp Ile Ala Lys His Tyr Asn Val Thr Thr Val
                    485                 490                 495

Thr Arg Ala Pro Ala Asp Leu Ala Ser Ala Leu Asn Val Val Asp Asp
                500                 505                 510

Phe Cys Leu Lys Thr Gly Leu Ser Phe Asn Glu Leu Leu Asp Leu Thr
                515                 520                 525

Met Gln Lys Asp Tyr Gln Ser Lys Ser Ser Glu Tyr Lys Ser Arg Phe
                530                 535                 540

Val Lys Phe Gly Gly Glu Asn Val Pro Val Ser Ser Tyr Gly Ala
    545                 550                 555                 560

Ala Phe Leu Thr Gly Ala Glu Asp Thr Pro Leu Trp Val Lys Gln Tyr
                    565                 570                 575

Asn Ser Val Gly Thr Ala Thr Ser Thr Pro Val Leu Asn Phe Thr Pro
                580                 585                 590

Asp Asn Val Val Ala Leu Ala Gly Arg Ala Glu Lys Leu Val Arg Leu
                595                 600                 605
```

Met Arg Ser Thr Gly Leu Ser Phe Glu Gln Leu Asp Trp Leu Ile Ala
610                 615                 620

Asn Ala Ser Arg Ala Val Ile Glu His Gly Gly Glu Leu Phe Leu Asp
625                 630                 635                 640

Lys Pro Val Leu Glu Ala Val Ala Glu Phe Thr Arg Leu Asn Lys Arg
                645                 650                 655

Tyr Gly Val Thr Ser Asp Met Phe Ala Phe Ile Gly Glu Val Asn
                660                 665                 670

Thr Tyr Thr Glu Ala Gly Lys Asp Ser Phe Tyr Gln Ala Ser Phe Ser
                675                 680                 685

Thr Ala Asp His Ser Ala Thr Leu Pro Leu Gly Ala Ser Leu Gln Leu
690                 695                 700

Glu Val Ser Lys Gln Asp Arg Tyr Glu Ala Ile Cys Cys Gly Ala Met
705                 710                 715                 720

Gly Val Thr Ala Asp Glu Phe Ser Arg Ile Gly Lys Tyr Cys Phe Gly
                725                 730                 735

Asp Lys Ala Gln Gln Ile Thr Ala Asn Glu Thr Thr Val Ala Gln Leu
                740                 745                 750

Tyr Arg Leu Gly Arg Ile Pro His Met Leu Gly Leu Arg Phe Thr Glu
                755                 760                 765

Ala Glu Leu Leu Trp Lys Leu Met Ala Gly Gly Glu Asp Thr Leu Leu
770                 775                 780

Arg Thr Ile Gly Ala Asn Pro Arg Ser Leu Glu Ala Leu Glu Ile Ile
785                 790                 795                 800

Arg Arg Thr Glu Val Leu Leu Asp Trp Met Asp Ala His Gln Leu Asp
                805                 810                 815

Val Val Ser Leu Gln Ala Met Val Thr Asn Arg Tyr Ser Gly Thr Ala
                820                 825                 830

Thr Pro Glu Leu Tyr Asn Phe Leu Ala Gln Val His Gln Ser Ala Ser
                835                 840                 845

Ser Ala Ala Asn Val Ala Arg Ala Asp Gly Gln Asp Thr Leu Pro Ala
850                 855                 860

Asp Lys Leu Leu Arg Ala Leu Ala Gly Phe Lys Leu Lys Ala Asn
865                 870                 875                 880

Val Met Ala Arg Val Ile Asp Trp Met Asp Lys Thr Asn Lys Ala Phe
                885                 890                 895

Thr Leu Arg Ala Phe Trp Asp Lys Leu Gln Ala Tyr Phe Ser Ala Asp
                900                 905                 910

His Glu Glu Glu Leu Thr Ala Leu Glu Gly Glu Ala Ala Met Leu Gln
                915                 920                 925

Trp Cys Gln Gln Ile Ser Gln Tyr Ala Leu Ile Val Arg Trp Cys Gly
930                 935                 940

Leu Ser Glu Gln Asp Leu Ala Leu Leu Thr Gly Asn Pro Glu Gln Leu
945                 950                 955                 960

Leu Asp Gly Gln His Thr Val Pro Val Pro Ser Leu His Leu Leu
                965                 970                 975

Val Leu Thr Arg Leu Lys Glu Trp Gln Gln Arg Val Gln Val Ser Ser
                980                 985                 990

Glu Glu Ala Met Arg Tyr Phe Ala  Gln Ala Asp Ser Pro  Thr Val Thr
                995                 1000                1005

Arg Asp Asp Ala Val Asn Leu  Leu Ala Arg Ile His  Gly Trp Asn
   1010                1015                1020

```
Glu Ala Asp Thr Val Ser Met Asn Asp Tyr Leu Leu Gly Glu Asn
    1025                1030                1035

Glu Tyr Pro Lys Asn Phe Asp Gln Ile Phe Ala Leu Glu Ser Trp
    1040                1045                1050

Val Asn Leu Gly Arg Gln Leu Asn Val Gly Ser Arg Thr Leu Gly
    1055                1060                1065

Glu Leu Val Asp Met Ala Glu Glu Asp Lys Thr Ala
    1070                1075                1080

<210> SEQ ID NO 37
<211> LENGTH: 3627
<212> TYPE: DNA
<213> ORGANISM: Paenibacillus strain DAS1529

<400> SEQUENCE: 37
atgaccaagg aaggtgataa gcatatgtct acttcaaccc tgttgcaatc gattaaagaa      60
gcccgccggg atgcgctggt caaccattat attgctaatc aggttccgac agcgcttgcg     120
gacaagatta cggacgcgga cagcctgtat gagtacttgc tgctggatac caagatcagt     180
gaactcgtaa aacatcgcc gatagcggag gccatcagca gcgtgcagtt atacatgaac     240
cgctgcgtcg aaggctatga aggcaagttg actccggaaa gtaatactca ttttggccca     300
ggtaaatttc tatataactg gatacgtac aacaaacgtt tttccacctg gcaggaaaa      360 gaacgcttga atattatgc aggcagctat attgagccgt ccttgcgcta caacaaaacc     420
gatccattcc tgaacctgga acagagcatc agccagggaa gaattactga tgataccgta     480
aagaacgcgc tgcaacacta cctgactgaa tatgaagtgt tggcggatct ggattatatc     540
agcgttaata aaggcggcga cgaaagtgtt ttactctttg ttggacgcac caaaaccgta     600
ccgtatgaat actactggcg ccgtttgctt ttaaaaaggg acaataataa taagctagta     660
ccagcagtct ggtctcagtg gaaaaaaatc agtgccaata tcggtgaagc ggttgatagt     720
tatgtggtgc ctcggtggca taaaaaccgg ctacatgtgc aatggtgttc tatagagaaa     780
agtgaaaatg atgccggtga acccattgag aaacgatatt tgaatgactg gttcatggat     840
agttccggag tctggtcttc atttcgaaag attccggttg tggaaaagag tttcgaatat     900
ttggacggaa gcctcgatcc ccgatttgtc gctcttgtta gaaatcaaat attaattgat     960
gagccagaaa tattcagaat tacagtatca gcccctaatc gatagatgc aaatggaaga     1020 gtagaggtac attttgaaga aaactatgca aacagatata atattaccat taaatatggg     1080
acaacgagtc ttgctattcc tgcagggcag gtagggcatc aaatatctc tattaatgaa     1140 acattaaggg ttgaattcgg caccaggccg gattggtatt tactttcag atatttagga     1200 aatacaatcc aaaactcata cggttcaatt gtcaataatc aattttcacc tccatcagga     1260
agcaatatta aggtcctat cgaccttacc ctgaaaaata acatcgacct gtcggccttg     1320
ttggatgaga gccttgacgc actgttcgac tataccattc agggcgataa ccaattgggc     1380
ggcttagctg cctttaacgg gccttacgga ctttacttgt gggaaatctt cttccatgtt     1440 cctttttttaa tggcggttcg cttccacacc gagcagcggt atgagttggc ggaacgttgg     1500
tttaaattca tcttcaacag cgcaggatac cgtgatgatt acggcagtct gctgacggat     1560
gacaaaggca acgtgcgtta ctggaacgtg ataccgctgc aagaggacac ggagtgggat     1620
gacacgttgt ccctggcaac gaccgacccg gacgagattg cgatggccga cccgatgcaa     1680
tacaagctgg ctatatttat tcacaccatg gacttcctga tcagccgcgg cgatagcttg     1740
taccggatgc tggagcggga taccctggcc gaagccaaga tgtattacat tcaggccagc     1800
```

-continued

```
caactgcttg ggccccgccc cgacatccgg ctcaatcaca gttggcctaa tccgaccttg    1860
caaagcgaag cggacgcggt aaccgccgtg ccgacgcgaa gcgattcgcc ggcagcgcca    1920
attttggcct tgcgagcgct tctgacaggc gaaaacggtc atttcctgcc gccttataat    1980
gatgaactgt tcgctttctg gacaaaatc gatctgcgtt tatacaattt gcgccacaat    2040
ttgagtctgg acggtcagcc gcttcatttg ccgctctttg ccgaaccggt caatccgcgt    2100
gaattgcagg ttcagcatgg cccgggcgat ggcttggggg aagcgcggg ttccgcccaa     2160 agccgtcaga gtgtctatcg ttttcctctg gtcatcgata aggcgcgcaa tgcggccaac    2220
agtgtcatcc aattcggcaa tgccctggaa aacgcactga ccaagcaaga cagcgaagca    2280
atgaccatgc tgttgcagtc ccagcagcag attgtcctgc agcaaacccg cgatattcag    2340
gagaagaacc tggccgcgct gcaagcaagt ctggaagcaa cgatgacagc gaaagcgggg    2400
gcggagtccc ggaagaccca ttttgccggc ttggcggaca ctggatgtc ggacaatgaa     2460 accgcctcac tcgcactgcg taccaccgcg ggaatcatca ataccagctc aaccgtgccg    2520
atcgccatca ccggcggctt ggatatggct ccgaacattt ttggtttcgc agttggaggt    2580
tcccgctggg gagcagccag cgcggctgta gcccaaggat tgcaaatcgc cgccggcgta    2640
atggaacaga cggccaatat tatcgatatt agcgaaagct accgccggcg ccggaggat     2700 tggctgctgc agcgggatgt tgccgaaaat gaagcggcgc agttggattc gcagattgcg    2760
gccctgcggg aacagatgga tatggcgcgc aagcaacttg cgctggcgga cacggaacag    2820
gcgcacgcgc aagcggtcta cgagctgcaa agcacccgct ttacgaatca gcttttgtat    2880
aactggatgg ctggacgtct gtcgtctcta tactatcaaa tgtatgacgc cgcattgccg    2940
ctctgcttga tggcgaagca ggcttttagag aaagaaatcg gttcgataa aacggtcgga    3000 gtcttgtccc tcccggcctg gaatgatcta tatcagggat tattggcggg cgaggcgctg    3060
ctgctcgagc ttcagaagct ggagaatctg tggctggagg aagacaagcg cggaatggaa    3120
gccgtaaaaa cagtctctct ggatactctt ctccgcaaaa caaatccgaa ctccgggttt    3180
gcggatctcg tcaaggaggc actggacgaa acggaaaga cgcctgaccc ggtgagcgga     3240
gtcggcgtac agctgcaaaa caatattttc agcgcaaccc ttgacctctc cgttcttggc    3300
ctggatcgct cttacaatca gcggaaaag tcccgcagga tcaaaaatat gtcgttacc      3360 ttacctgcgc tattggggcc ttaccaggat atagaggcaa ccttatcgct aggcggcgag    3420
accgttgcgc tgtcccatgg cgtggatgac agcggcttgt tcatcactga tctcaacgac    3480
agccggttcc tgcctttcga gggcatggat ccgttatccg gcacactcgt cctgtcgata    3540
ttccatgccg ggcaagacgg cgaccagcgc ctcctgctgg aaagtctcaa tgacgtcatc    3600
ttccacattc gatatgttat gaaatag                                       3627
```

<210> SEQ ID NO 38
<211> LENGTH: 1208
<212> TYPE: PRT
<213> ORGANISM: Paenibacillus strain DAS1529

<400> SEQUENCE: 38

```
Met Thr Lys Glu Gly Asp Lys His Met Ser Thr Ser Thr Leu Leu Gln
1               5                   10                  15

Ser Ile Lys Glu Ala Arg Arg Asp Ala Leu Val Asn His Tyr Ile Ala
            20                  25                  30

Asn Gln Val Pro Thr Ala Leu Ala Asp Lys Ile Thr Asp Ala Asp Ser
        35                  40                  45
```

```
Leu Tyr Glu Tyr Leu Leu Leu Asp Thr Lys Ile Ser Glu Leu Val Lys
         50                  55                  60

Thr Ser Pro Ile Ala Glu Ala Ile Ser Ser Val Gln Leu Tyr Met Asn
 65                  70                  75                  80

Arg Cys Val Glu Gly Tyr Gly Lys Leu Thr Pro Glu Ser Asn Thr
                 85                  90                  95

His Phe Gly Pro Gly Lys Phe Leu Tyr Asn Trp Asp Thr Tyr Asn Lys
                100                 105                 110

Arg Phe Ser Thr Trp Ala Gly Lys Glu Arg Leu Lys Tyr Tyr Ala Gly
                115                 120                 125

Ser Tyr Ile Glu Pro Ser Leu Arg Tyr Asn Lys Thr Asp Pro Phe Leu
        130                 135                 140

Asn Leu Glu Gln Ser Ile Ser Gln Gly Arg Ile Thr Asp Asp Thr Val
145                 150                 155                 160

Lys Asn Ala Leu Gln His Tyr Leu Thr Glu Tyr Glu Val Leu Ala Asp
                165                 170                 175

Leu Asp Tyr Ile Ser Val Asn Lys Gly Gly Asp Glu Ser Val Leu Leu
                180                 185                 190

Phe Val Gly Arg Thr Lys Thr Val Pro Tyr Glu Tyr Tyr Trp Arg Arg
        195                 200                 205

Leu Leu Leu Lys Arg Asp Asn Asn Lys Leu Val Pro Ala Val Trp
210                 215                 220

Ser Gln Trp Lys Lys Ile Ser Ala Asn Ile Gly Glu Ala Val Asp Ser
225                 230                 235                 240

Tyr Val Val Pro Arg Trp His Lys Asn Arg Leu His Val Gln Trp Cys
                245                 250                 255

Ser Ile Glu Lys Ser Glu Asn Asp Ala Gly Glu Pro Ile Glu Lys Arg
                260                 265                 270

Tyr Leu Asn Asp Trp Phe Met Asp Ser Ser Gly Val Trp Ser Ser Phe
        275                 280                 285

Arg Lys Ile Pro Val Val Glu Lys Ser Phe Glu Tyr Leu Asp Gly Ser
290                 295                 300

Leu Asp Pro Arg Phe Val Ala Leu Val Arg Asn Gln Ile Leu Ile Asp
305                 310                 315                 320

Glu Pro Glu Ile Phe Arg Ile Thr Val Ser Ala Pro Asn Pro Ile Asp
                325                 330                 335

Ala Asn Gly Arg Val Glu Val His Phe Glu Glu Asn Tyr Ala Asn Arg
                340                 345                 350

Tyr Asn Ile Thr Ile Lys Tyr Gly Thr Thr Ser Leu Ala Ile Pro Ala
        355                 360                 365

Gly Gln Val Gly His Pro Asn Ile Ser Ile Asn Glu Thr Leu Arg Val
        370                 375                 380

Glu Phe Gly Thr Arg Pro Asp Trp Tyr Tyr Thr Phe Arg Tyr Leu Gly
385                 390                 395                 400

Asn Thr Ile Gln Asn Ser Tyr Gly Ser Ile Val Asn Asn Gln Phe Ser
                405                 410                 415

Pro Pro Ser Gly Ser Asn Ile Lys Gly Pro Ile Asp Leu Thr Leu Lys
                420                 425                 430

Asn Asn Ile Asp Leu Ser Ala Leu Leu Asp Glu Ser Leu Asp Ala Leu
        435                 440                 445

Phe Asp Tyr Thr Ile Gln Gly Asp Asn Gln Leu Gly Gly Leu Ala Ala
        450                 455                 460
```

-continued

Phe Asn Gly Pro Tyr Gly Leu Tyr Leu Trp Glu Ile Phe His Val
465                 470                 475                 480

Pro Phe Leu Met Ala Val Arg Phe His Thr Glu Gln Arg Tyr Glu Leu
            485                 490                 495

Ala Glu Arg Trp Phe Lys Phe Ile Phe Asn Ser Ala Gly Tyr Arg Asp
            500                 505                 510

Asp Tyr Gly Ser Leu Leu Thr Asp Asp Lys Gly Asn Val Arg Tyr Trp
            515                 520                 525

Asn Val Ile Pro Leu Gln Glu Asp Thr Glu Trp Asp Asp Thr Leu Ser
530                 535                 540

Leu Ala Thr Thr Asp Pro Asp Glu Ile Ala Met Ala Asp Pro Met Gln
545                 550                 555                 560

Tyr Lys Leu Ala Ile Phe Ile His Thr Met Asp Phe Leu Ile Ser Arg
                565                 570                 575

Gly Asp Ser Leu Tyr Arg Met Leu Glu Arg Asp Thr Leu Ala Glu Ala
                580                 585                 590

Lys Met Tyr Tyr Ile Gln Ala Ser Gln Leu Leu Gly Pro Arg Pro Asp
            595                 600                 605

Ile Arg Leu Asn His Ser Trp Pro Asn Pro Thr Leu Gln Ser Glu Ala
            610                 615                 620

Asp Ala Val Thr Ala Val Pro Thr Arg Ser Asp Ser Pro Ala Ala Pro
625                 630                 635                 640

Ile Leu Ala Leu Arg Ala Leu Leu Thr Gly Glu Asn Gly His Phe Leu
                645                 650                 655

Pro Pro Tyr Asn Asp Glu Leu Phe Ala Phe Trp Asp Lys Ile Asp Leu
            660                 665                 670

Arg Leu Tyr Asn Leu Arg His Asn Leu Ser Leu Asp Gly Gln Pro Leu
            675                 680                 685

His Leu Pro Leu Phe Ala Glu Pro Val Asn Pro Arg Glu Leu Gln Val
            690                 695                 700

Gln His Gly Pro Gly Asp Gly Leu Gly Gly Ser Ala Gly Ser Ala Gln
705                 710                 715                 720

Ser Arg Gln Ser Val Tyr Arg Phe Pro Leu Val Ile Asp Lys Ala Arg
                725                 730                 735

Asn Ala Ala Asn Ser Val Ile Gln Phe Gly Asn Ala Leu Glu Asn Ala
                740                 745                 750

Leu Thr Lys Gln Asp Ser Glu Ala Met Thr Met Leu Leu Gln Ser Gln
            755                 760                 765

Gln Gln Ile Val Leu Gln Gln Thr Arg Asp Ile Gln Glu Lys Asn Leu
            770                 775                 780

Ala Ala Leu Gln Ala Ser Leu Glu Ala Thr Met Thr Ala Lys Ala Gly
785                 790                 795                 800

Ala Glu Ser Arg Lys Thr His Phe Ala Gly Leu Ala Asp Asn Trp Met
            805                 810                 815

Ser Asp Asn Glu Thr Ala Ser Leu Ala Leu Arg Thr Thr Ala Gly Ile
            820                 825                 830

Ile Asn Thr Ser Ser Thr Val Pro Ile Ala Ile Thr Gly Gly Leu Asp
            835                 840                 845

Met Ala Pro Asn Ile Phe Gly Phe Ala Val Gly Gly Ser Arg Trp Gly
850                 855                 860

Ala Ala Ser Ala Ala Val Ala Gln Gly Leu Gln Ile Ala Ala Gly Val
865                 870                 875                 880

Met Glu Gln Thr Ala Asn Ile Ile Asp Ile Ser Glu Ser Tyr Arg Arg

```
                 885              890              895
Arg Arg Glu Asp Trp Leu Leu Gln Arg Asp Val Ala Glu Asn Glu Ala
            900              905              910

Ala Gln Leu Asp Ser Gln Ile Ala Ala Leu Arg Glu Gln Met Asp Met
        915              920              925

Ala Arg Lys Gln Leu Ala Leu Ala Glu Thr Glu Gln Ala His Ala Gln
        930              935              940

Ala Val Tyr Glu Leu Gln Ser Thr Arg Phe Thr Asn Gln Ala Leu Tyr
945              950              955              960

Asn Trp Met Ala Gly Arg Leu Ser Ser Leu Tyr Tyr Gln Met Tyr Asp
                965              970              975

Ala Ala Leu Pro Leu Cys Leu Met Ala Lys Gln Ala Leu Glu Lys Glu
            980              985              990

Ile Gly Ser Asp Lys Thr Val Gly Val Leu Ser Leu Pro Ala Trp Asn
            995              1000             1005

Asp Leu Tyr Gln Gly Leu Leu Ala Gly Glu Ala Leu Leu Leu Glu
    1010             1015             1020

Leu Gln Lys Leu Glu Asn Leu Trp Leu Glu Glu Asp Lys Arg Gly
    1025             1030             1035

Met Glu Ala Val Lys Thr Val Ser Leu Asp Thr Leu Leu Arg Lys
    1040             1045             1050

Thr Asn Pro Asn Ser Gly Phe Ala Asp Leu Val Lys Glu Ala Leu
    1055             1060             1065

Asp Glu Asn Gly Lys Thr Pro Asp Pro Val Ser Gly Val Gly Val
    1070             1075             1080

Gln Leu Gln Asn Asn Ile Phe Ser Ala Thr Leu Asp Leu Ser Val
    1085             1090             1095

Leu Gly Leu Asp Arg Ser Tyr Asn Gln Ala Glu Lys Ser Arg Arg
    1100             1105             1110

Ile Lys Asn Met Ser Val Thr Leu Pro Ala Leu Leu Gly Pro Tyr
    1115             1120             1125

Gln Asp Ile Glu Ala Thr Leu Ser Leu Gly Gly Glu Thr Val Ala
    1130             1135             1140

Leu Ser His Gly Val Asp Asp Ser Gly Leu Phe Ile Thr Asp Leu
    1145             1150             1155

Asn Asp Ser Arg Phe Leu Pro Phe Glu Gly Met Asp Pro Leu Ser
    1160             1165             1170

Gly Thr Leu Val Leu Ser Ile Phe His Ala Gly Gln Asp Gly Asp
    1175             1180             1185

Gln Arg Leu Leu Leu Glu Ser Leu Asn Asp Val Ile Phe His Ile
    1190             1195             1200

Arg Tyr Val Met Lys
    1205

<210> SEQ ID NO 39
<211> LENGTH: 4335
<212> TYPE: DNA
<213> ORGANISM: Paenibacillus strain DAS1529

<400> SEQUENCE: 39
atgccacaat ctagcaatgc cgatatcaag ctattgtcgc catcgctgcc aaagggcggc      60
ggttccatga agggaatcga agaaaacatc gcggctcccg gctccgacgg catggcacgt     120
tgtaatgtgc cgctgccggt aacctccggc cgctatatta ctcctgatat aagcctgtcc     180
```

```
tatgcgagcg gccacggcaa cggcgcttat ggaatgggct ggacgatggg agtgatgagc       240
attagccgga gaacaagccg agggaccccc agttatacat ccgaagacca gttccttggt       300
ccggatgggg aggtgcttgt tccggaaagc aacgaacaag gggagatcat acccgccac        360 accgatacgg cccaagggat accgttaggc gagacgttta cggttacacg ctattttccc       420
cggatcgaga gcgcttttca tttgctggaa tactgggaag cgcaagcagg aagcgcaaca       480
gcgtcgtttt ggcttattca ctctgccgat ggagtgctgc actgtctggg taaaactgct       540
caggcgagga tagccgcccc tgacgattcc gccaagatcg cagaatggct agtggaggag       600
tccgtctccc ccttcggaga gcatatttat taccaataca agaagaaga caatcaaggc        660 gtgaatctgg aggaagacaa tcatcaatat ggggcgaacc gctatctgaa atcgattcgc       720
tatgaaaata aggttgcctc tccttctctc tatgtctgga aggggaaat tccggcagac        780 ggccaatggc tgtattccgt tatcctggat tatgcgagaa cgatacctc agcggatgtt        840 cctcccctat acacgcccca aggggagtgg ctggtgcgcc cggaccgttt ttcccgctat       900
gactacggat ttgaggtccg gacttgccgc ttgtgccgcc aggtcttgat gttccacgtc       960
tttaaggagc ttggcgggga ccggcgctg gtgtggcgga tgcagttgga atacgacgag       1020
aacccggcgg cgtccatgct gagcgcggtc cggcaattgg cttatgaagc agatggggcc       1080
attcgaagct gccgccgct ggaattcgat tatactccat ttggcatcga  caacggcc        1140 gattggcagc cttttctgcc tgtgcctgaa tgggcggatg aagaacatta tcagttggtc       1200
gatttgtacg gagaaggcat accgggctta ttatatcaga acaatgacca ctggcattat       1260
cgttcgcccg cccggggcga cacaccggac gggatcgcct ataacagctg gcggccgctt       1320
cctcatatcc ccgtgaactc ccggaacggg atgctgatgg atctgaatgg agacgggtat       1380
ctggaatggt tgcttgcgga acccgggtt gcggggcgct atagcatgaa cccggataag        1440
agctggtccg gttttgtgcc gctccaggca ctgccaacgg aattcttcca tccgcaggca       1500
cagcttgcca atgttaccgg atcgggttta accgacttgg ttatgatcgg tccgaagagc       1560
gtccggtttt atgccggaga agaagcgggc ttcaagcgcg catgtgaagt gtggcagcaa       1620
gtgggcatta ctttgcctgt ggaacgcgtg gataaaagg aactggtggc attcagcgat       1680
atgctgggat cggtcagtc tcatctggtg cgcatccggc atgatggcgt tacatgctgg       1740
cctaatctgg ggaacggcgt gttcggggcg ccgttggccc ttcacgggtt tacggcatcg       1800
gagcgggaat tcaatccgga acgtgtatat cttgtggacc ttgatggatc cggcgcttcc       1860
gatatcattt atgcttctcg tgacgctcta ctcatttacc gaaatctttc cggcaatggc       1920
tttgctgatc cggtgcgggt tccgctgcct gacggcgtgc ggtttgataa tctgtgccgg       1980
ctgctgcctg ccgatatccg cgggttaggt gtggccagtc tggtgctgca tgtaccttac       2040
atggcccccc gcagttggaa attagatttc tttgcggcga agccgtattt attgcaaacg       2100
gtcagcaaca atcttggagc ttccagctcg ttttggtacc gaagctccac ccagtattgg       2160
ctggatgaga aacaggcggc ctcatcggct gtctccgctt tgcccttccc gataaacgtg       2220
gtatcggata tgcacacggt ggacgaaatc agcggccgca ccaggactca gaagtatact       2280
taccgccatg gcgtgtatga ccggaccgaa aaggaatttg ccggattcgg ccgcattgac       2340
acatgggaag aggagcggga ttccgaagga accctgagcg tcagcactcc gcccgtgctg       2400
acgcggacct ggtatcatac cggcaaaag caggatgagg agcgtgccgt gcagcaatat       2460
tggcaaggcg accctgcggc ttttcaggtt aaacccgtcc ggcttactcg attcgatgcg       2520
gcagcggccc aggatctgcc gctagattct aataatgggc agcaagaata ctggctgtac       2580
```

```
cgatcattac aagggatgcc gctgcggact gagattttg cgggagatgt tggcgggtcg      2640
cctccttatc aggtagagag cttccgttat caagtgcgct tggtgcagag catcgattcg      2700
gaatgtgttg ccttgcccat gcagttggag cagcttacgt acaactatga gcaaatcgcc      2760
tctgatccgc agtgttcaca gcagatacag caatggttcg acgaatacgg cgtggcggca      2820
cagagtgtaa caatccaata tccgcgccgg gcacagccgg aggacaatcc gtaccctcgc      2880
acgctgccgg ataccagctg gagcagcagt tatgattcgc agcaaatgct gctgcggttg      2940
accaggcaaa ggcaaaaagc gtaccacctt gcagatcctg aaggctggcg cttgaatatt      3000
ccccatcaga cacgcctgga tgccttcatt tattctgctg acagcgtgcc cgccgaagga      3060
ataagcgccg agctgctgga ggtggacggc acgttacgat cttcggcgct ggaacaggct      3120 tatgcggcc agtcagagat catctatgcg ggcgggggcg aaccggattt gcgagccctg      3180
gtccattaca ccagaagcgc ggttcttgat gaagactgtt acaagcctta tgaaggcgta      3240
ctgagcgata gccaattgaa ctcgcttctt gcctcttccg gctatcaacg aagcgcaaga      3300
atattgggtt cgggcgatga agtggatatt tttgtcgcgg aacaaggatt tacccgttat      3360
gcggatgaac cgaattttt ccgtattctg gggcaacaat cctctctctt gtccggggaa      3420
caagtattaa catgggatga taatttctgt gcggttacat ccatcgaaga cgcgcttggc      3480
aatcaaattc agattgcata tgattaccgc tttgtggagg ccatccagat taccgatacg      3540
aataataatg tgaatcaggt cgccctggat gctctcggcc gggtcgtata cagccggacc      3600
tggggcacgg aggaagggat aaagaccggc ttccgcccgg aggtggaatt cgcgacgccc      3660
gagacaatgg agcaggcgct tgccctggca tctcccttgc cggttgcatc ctgctgtgta      3720
tatgatgcgc atagctggat gggaacgata actcttgcac aactgtcaga gcttgttcca      3780
gatagtgaaa agcaatggtc gttcttgata gacaatcgct tgattatgcc ggacggcaga      3840
atcagatccc gcggtcggga tccatggtcg cttaccggc tattgccgcc tgctgtgggc      3900
gaattgctga gcgaggcgga ccgtaaaccg ccgcatacgg taattttggc agcagatcgt      3960
tacccggatg acccatccca gcaaattcag gcgagcatcg tgtttagcga tggctttggg      4020
cgtacgatac aaactgctaa agagaagat acccgatggg cgattgcgga acgggtggac      4080
tatgacggaa ccggagccgt aatccgcagc tttcagcctt tttatcttga cgactggaat      4140
tatgtgggcg aagaggctgt cagcagctct atgtacgcaa cgatctatta ttatgatgct      4200
ctggcacgac aattaaggat ggtcaacgct aaaggatatg agaggagaac tgcttttac      4260 ccatggttta cagtaaacga agatgaaaat gataccatgg actcatcatt atttgcttca      4320
ccgcctgcgc ggtga                                                      4335
```

<210> SEQ ID NO 40
<211> LENGTH: 1444
<212> TYPE: PRT
<213> ORGANISM: Paenibacillus strain DAS1529

<400> SEQUENCE: 40

```
Met Pro Gln Ser Ser Asn Ala Asp Ile Lys Leu Leu Ser Pro Ser Leu
1               5                   10                  15

Pro Lys Gly Gly Gly Ser Met Lys Gly Ile Glu Glu Asn Ile Ala Ala
            20                  25                  30

Pro Gly Ser Asp Gly Met Ala Arg Cys Asn Val Pro Leu Pro Val Thr
        35                  40                  45

Ser Gly Arg Tyr Ile Thr Pro Asp Ile Ser Leu Ser Tyr Ala Ser Gly
```

-continued

```
              50                  55                  60
His Gly Asn Gly Ala Tyr Gly Met Gly Trp Thr Met Gly Val Met Ser
 65                  70                  75                  80

Ile Ser Arg Arg Thr Ser Arg Gly Thr Pro Ser Tyr Thr Ser Glu Asp
                 85                  90                  95

Gln Phe Leu Gly Pro Asp Gly Glu Val Leu Val Pro Glu Ser Asn Glu
            100                 105                 110

Gln Gly Glu Ile Ile Thr Arg His Thr Asp Thr Ala Gln Gly Ile Pro
            115                 120                 125

Leu Gly Glu Thr Phe Thr Val Thr Arg Tyr Phe Pro Arg Ile Glu Ser
            130                 135                 140

Ala Phe His Leu Leu Glu Tyr Trp Glu Ala Gln Ala Gly Ser Ala Thr
145                 150                 155                 160

Ala Ser Phe Trp Leu Ile His Ser Ala Asp Gly Val Leu His Cys Leu
                165                 170                 175

Gly Lys Thr Ala Gln Ala Arg Ile Ala Ala Pro Asp Asp Ser Ala Lys
            180                 185                 190

Ile Ala Glu Trp Leu Val Glu Glu Ser Val Ser Pro Phe Gly Glu His
            195                 200                 205

Ile Tyr Tyr Gln Tyr Lys Glu Glu Asp Asn Gln Gly Val Asn Leu Glu
            210                 215                 220

Glu Asp Asn His Gln Tyr Gly Ala Asn Arg Tyr Leu Lys Ser Ile Arg
225                 230                 235                 240

Tyr Gly Asn Lys Val Ala Ser Pro Ser Leu Tyr Val Trp Lys Gly Glu
                245                 250                 255

Ile Pro Ala Asp Gly Gln Trp Leu Tyr Ser Val Ile Leu Asp Tyr Gly
            260                 265                 270

Glu Asn Asp Thr Ser Ala Asp Val Pro Pro Leu Tyr Thr Pro Gln Gly
            275                 280                 285

Glu Trp Leu Val Arg Pro Asp Arg Phe Ser Arg Tyr Asp Tyr Gly Phe
            290                 295                 300

Glu Val Arg Thr Cys Arg Leu Cys Arg Gln Val Leu Met Phe His Val
305                 310                 315                 320

Phe Lys Glu Leu Gly Gly Glu Pro Ala Leu Val Trp Arg Met Gln Leu
                325                 330                 335

Glu Tyr Asp Glu Asn Pro Ala Ala Ser Met Leu Ser Ala Val Arg Gln
            340                 345                 350

Leu Ala Tyr Glu Ala Asp Gly Ala Ile Arg Ser Leu Pro Pro Leu Glu
            355                 360                 365

Phe Asp Tyr Thr Pro Phe Gly Ile Glu Thr Thr Ala Asp Trp Gln Pro
            370                 375                 380

Phe Leu Pro Val Pro Glu Trp Ala Asp Glu His Tyr Gln Leu Val
385                 390                 395                 400

Asp Leu Tyr Gly Glu Gly Ile Pro Gly Leu Leu Tyr Gln Asn Asn Asp
                405                 410                 415

His Trp His Tyr Arg Ser Pro Ala Arg Gly Asp Thr Pro Asp Gly Ile
            420                 425                 430

Ala Tyr Asn Ser Trp Arg Pro Leu Pro His Ile Pro Val Asn Ser Arg
            435                 440                 445

Asn Gly Met Leu Met Asp Leu Asn Gly Asp Gly Tyr Leu Glu Trp Leu
            450                 455                 460

Leu Ala Glu Pro Gly Val Ala Gly Arg Tyr Ser Met Asn Pro Asp Lys
465                 470                 475                 480
```

```
Ser Trp Ser Gly Phe Val Pro Leu Gln Ala Leu Pro Thr Glu Phe Phe
            485                 490                 495

His Pro Gln Ala Gln Leu Ala Asn Val Thr Gly Ser Gly Leu Thr Asp
            500                 505                 510

Leu Val Met Ile Gly Pro Lys Ser Val Arg Phe Tyr Ala Gly Glu Glu
            515                 520                 525

Ala Gly Phe Lys Arg Ala Cys Glu Val Trp Gln Val Gly Ile Thr
            530                 535                 540

Leu Pro Val Glu Arg Val Asp Lys Lys Glu Leu Val Ala Phe Ser Asp
545                 550                 555                 560

Met Leu Gly Ser Gly Gln Ser His Leu Val Arg Ile Arg His Asp Gly
            565                 570                 575

Val Thr Cys Trp Pro Asn Leu Gly Asn Gly Val Phe Gly Ala Pro Leu
            580                 585                 590

Ala Leu His Gly Phe Thr Ala Ser Glu Arg Glu Phe Asn Pro Glu Arg
            595                 600                 605

Val Tyr Leu Val Asp Leu Asp Gly Ser Gly Ala Ser Asp Ile Ile Tyr
            610                 615                 620

Ala Ser Arg Asp Ala Leu Leu Ile Tyr Arg Asn Leu Ser Gly Asn Gly
625                 630                 635                 640

Phe Ala Asp Pro Val Arg Val Pro Leu Pro Asp Gly Val Arg Phe Asp
            645                 650                 655

Asn Leu Cys Arg Leu Leu Pro Ala Asp Ile Arg Gly Leu Gly Val Ala
            660                 665                 670

Ser Leu Val Leu His Val Pro Tyr Met Ala Pro Arg Ser Trp Lys Leu
            675                 680                 685

Asp Phe Phe Ala Ala Lys Pro Tyr Leu Leu Gln Thr Val Ser Asn Asn
            690                 695                 700

Leu Gly Ala Ser Ser Phe Trp Tyr Arg Ser Ser Thr Gln Tyr Trp
705                 710                 715                 720

Leu Asp Glu Lys Gln Ala Ala Ser Ser Ala Val Ser Ala Leu Pro Phe
            725                 730                 735

Pro Ile Asn Val Val Ser Asp Met His Thr Val Asp Glu Ile Ser Gly
            740                 745                 750

Arg Thr Arg Thr Gln Lys Tyr Thr Tyr Arg His Gly Val Tyr Asp Arg
            755                 760                 765

Thr Glu Lys Glu Phe Ala Gly Phe Gly Arg Ile Asp Thr Trp Glu Glu
            770                 775                 780

Glu Arg Asp Ser Glu Gly Thr Leu Ser Val Ser Thr Pro Pro Val Leu
785                 790                 795                 800

Thr Arg Thr Trp Tyr His Thr Gly Gln Lys Gln Asp Glu Glu Arg Ala
            805                 810                 815

Val Gln Gln Tyr Trp Gln Gly Asp Pro Ala Ala Phe Gln Val Lys Pro
            820                 825                 830

Val Arg Leu Thr Arg Phe Asp Ala Ala Ala Gln Asp Leu Pro Leu
            835                 840                 845

Asp Ser Asn Asn Gly Gln Gln Glu Tyr Trp Leu Tyr Arg Ser Leu Gln
            850                 855                 860

Gly Met Pro Leu Arg Thr Glu Ile Phe Ala Gly Asp Val Gly Gly Ser
865                 870                 875                 880

Pro Pro Tyr Gln Val Glu Ser Phe Arg Tyr Gln Val Arg Leu Val Gln
            885                 890                 895
```

-continued

```
Ser Ile Asp Ser Glu Cys Val Ala Leu Pro Met Gln Leu Glu Gln Leu
            900                 905                 910

Thr Tyr Asn Tyr Glu Gln Ile Ala Ser Asp Pro Gln Cys Ser Gln Gln
            915                 920                 925

Ile Gln Gln Trp Phe Asp Glu Tyr Gly Val Ala Gln Ser Val Thr
            930                 935                 940

Ile Gln Tyr Pro Arg Arg Ala Gln Pro Glu Asp Asn Pro Tyr Pro Arg
945                 950                 955                 960

Thr Leu Pro Asp Thr Ser Trp Ser Ser Tyr Asp Ser Gln Gln Met
            965                 970                 975

Leu Leu Arg Leu Thr Arg Gln Arg Gln Lys Ala Tyr His Leu Ala Asp
            980                 985                 990

Pro Glu Gly Trp Arg Leu Asn Ile Pro His Gln Thr Arg Leu Asp Ala
            995                 1000                1005

Phe Ile Tyr Ser Ala Asp Ser Val Pro Ala Glu Gly Ile Ser Ala
            1010                1015                1020

Glu Leu Leu Glu Val Asp Gly Thr Leu Arg Ser Ser Ala Leu Glu
            1025                1030                1035

Gln Ala Tyr Gly Gly Gln Ser Glu Ile Ile Tyr Ala Gly Gly Gly
            1040                1045                1050

Glu Pro Asp Leu Arg Ala Leu Val His Tyr Thr Arg Ser Ala Val
            1055                1060                1065

Leu Asp Glu Asp Cys Leu Gln Ala Tyr Glu Gly Val Leu Ser Asp
            1070                1075                1080

Ser Gln Leu Asn Ser Leu Leu Ala Ser Ser Gly Tyr Gln Arg Ser
            1085                1090                1095

Ala Arg Ile Leu Gly Ser Gly Asp Glu Val Asp Ile Phe Val Ala
            1100                1105                1110

Glu Gln Gly Phe Thr Arg Tyr Ala Asp Glu Pro Asn Phe Phe Arg
            1115                1120                1125

Ile Leu Gly Gln Gln Ser Ser Leu Leu Ser Gly Glu Gln Val Leu
            1130                1135                1140

Thr Trp Asp Asp Asn Phe Cys Ala Val Thr Ser Ile Glu Asp Ala
            1145                1150                1155

Leu Gly Asn Gln Ile Gln Ile Ala Tyr Asp Tyr Arg Phe Val Glu
            1160                1165                1170

Ala Ile Gln Ile Thr Asp Thr Asn Asn Asn Val Asn Gln Val Ala
            1175                1180                1185

Leu Asp Ala Leu Gly Arg Val Val Tyr Ser Arg Thr Trp Gly Thr
            1190                1195                1200

Glu Glu Gly Ile Lys Thr Gly Phe Arg Pro Glu Val Glu Phe Ala
            1205                1210                1215

Thr Pro Glu Thr Met Glu Gln Ala Leu Ala Leu Ala Ser Pro Leu
            1220                1225                1230

Pro Val Ala Ser Cys Cys Val Tyr Asp Ala His Ser Trp Met Gly
            1235                1240                1245

Thr Ile Thr Leu Ala Gln Leu Ser Glu Leu Val Pro Asp Ser Glu
            1250                1255                1260

Lys Gln Trp Ser Phe Leu Ile Asp Asn Arg Leu Ile Met Pro Asp
            1265                1270                1275

Gly Arg Ile Arg Ser Arg Gly Arg Asp Pro Trp Ser Leu His Arg
            1280                1285                1290

Leu Leu Pro Pro Ala Val Gly Glu Leu Leu Ser Glu Ala Asp Arg
```

```
                1295                1300                1305
Lys Pro Pro His Thr Val Ile Leu Ala Ala Asp Arg Tyr Pro Asp
    1310                1315                1320

Asp Pro Ser Gln Gln Ile Gln Ala Ser Ile Val Phe Ser Asp Gly
    1325                1330                1335

Phe Gly Arg Thr Ile Gln Thr Ala Lys Arg Glu Asp Thr Arg Trp
    1340                1345                1350

Ala Ile Ala Glu Arg Val Asp Tyr Asp Gly Thr Gly Ala Val Ile
    1355                1360                1365

Arg Ser Phe Gln Pro Phe Tyr Leu Asp Asp Trp Asn Tyr Val Gly
    1370                1375                1380

Glu Glu Ala Val Ser Ser Ser Met Tyr Ala Thr Ile Tyr Tyr Tyr
    1385                1390                1395

Asp Ala Leu Ala Arg Gln Leu Arg Met Val Asn Ala Lys Gly Tyr
    1400                1405                1410

Glu Arg Arg Thr Ala Phe Tyr Pro Trp Phe Thr Val Asn Glu Asp
    1415                1420                1425

Glu Asn Asp Thr Met Asp Ser Ser Leu Phe Ala Ser Pro Pro Ala
    1430                1435                1440

Arg

<210> SEQ ID NO 41
<211> LENGTH: 2793
<212> TYPE: DNA
<213> ORGANISM: Paenibacillus strain DAS1529

<400> SEQUENCE: 41
atgaacacaa cgtccatata taggggcacg cctacgattt cagttgtgga taaccggaac     60
ttggagattc gcattcttca gtataaccgt atcgcggctg aagatccggc agatgagtgt    120
atcctgcgga cacgtatac gccgttaagc tatcttggca gcagcatgga tccccgtttg    180
ttctcgcaat atcaggatga tcgcggaaca ccgccgaata tacgaaccat ggcttccctg    240
agaggcgaag cgctgtgttc ggaaagtgtg gatgccggcc gcaaggcgga gcttttttgat    300
atcgagggc ggcccgtctg gcttatcgat gccaacggca cagagacgac tctcgaatat    360
gatgtcttag gcaggccaac agccgtattc gagcaacagg aaggtacgga ctccccccag    420
tgcagggagc ggtttatta tggtgagaag gaggcggatg cccaggccaa caatttgcgc    480
ggacaactgg ttcgccacta cgataccgcg ggcggatac agaccgacag catctccttg    540
gctggactgc cgttgcgcca aagccgtcaa ctgctgaaaa attgggatga acctggcgac    600
tggagtatgg atgaggaaag cgcctgggcc tcgttgctgg ctgccgaagc ttatgatacg    660
agctggcggt atgacgcgca ggacagggtg ctcgcccaaa ccgacgccaa agggaatctc    720
cagcaactga cttacaatga cgccggccag ccgcaggcgg tcagcctcaa gctgcaaggc    780
caagcggagc aacggatttg gaaccggatc gagtacaacg cggcgggtca gtggatctc    840
gccgaagccg ggaatggaat cgtaacggaa tatacttacg aggaaagcac gcagcggtta    900
atccgaaaaa aagattcccg cggactgtcc tccggggaaa gagaagtgct gcaggattat    960
cgttatgaat atgatccggt aggcaatatc ctttctattt acaatgaagc ggagccggtt   1020
cgttatttcc gcaatcaggc cgttgctccg aaaaggcaat atgcctacga tgccttgtat   1080
cagcttgtat ctagttcggg gcgggaatcc gacgcgcttc ggcagcagac gtcgcttcct   1140
cccttgatca cgcctatccc tctggacgat agccaatacg tcaattacgc tgaaaaatac   1200
```

```
agctatgatc aggcgggcaa tttaatcaag cttagccata acggggcaag tcaatataca    1260
acgaatgtgt atgtggacaa aagctcaaac cgggggattt ggcggcaagg ggaagacatc    1320
ccggatatcg cggcttcctt tgacagagca ggcaatcaac aagctttatt cccggggaga    1380
ccgttggaat gggatacacg caatcaatta agccgtgtcc atatggtcgt gcgcgaaggc    1440
ggagacaacg actgggaagg ctatctctat gacagctcgg gaatgcgtat cgtaaaacga    1500
tctacccgca aaacacagac aacgacgcaa acggatacga ccctctattt gccgggcctg    1560
gagctgcgaa tccgccagac cggggaccgg tcacggaag  cattgcaggt cattaccgtg    1620 gatgaggag  cgggacaagt gagggtgctg cactgggagg atggaaccga ccgggcggc     1680 atcgccaatg atcagtaccg gtacagcctg aacgatcatc ttacctcctc tttattggaa    1740
gttgacgggc aaggtcagat cattagtaag gaagaatttt atccctatgg cggcacagcc    1800
ctgtggacag cccggtcaga ggtagaggca agctacaaga ccatccgcta ttcaggcaaa    1860
gagcgggatg ccacaggcct gtattattac ggacaccgct actatatgcc atggttgggt    1920
cgctggctga atccggaccc ggccggaatg gtagatggac taaacctgta ccgtatggtc    1980
aggaacaatc ctataggact gatggatccg aatgggaatg cgccaatcaa cgtggcggat    2040
tatagcttcg tgcatggtga tttagtttat ggtcttagta aggaaagagg aagatatcta    2100
aagctattta atccaaactt taatatggaa aaatcagact ctcctgctat ggttatagat    2160
caatataata ataatgttgc attgagtata actaaccaat ataaagtaga agaattgatg    2220
aaatttcaaa aagacccaca aaaagccgca cggaaaataa aggttccaga agggaatcgt    2280
ttatcgagga acgaaaatta tcctttgtgg cacgattata ttaacattgg agaagctaaa    2340
gctgcattta aggcctctca tattttccaa gaagtgaagg ggaattatgg gaaagattat    2400
tatcataaat tattattaga cagaatgata gaatcgccgt tgctgtggaa acgaggcagc    2460
aaactcgggc tagaaatcgc cgctaccaat cagagaacaa aaatacactt tgttcttgac    2520
aatttaaata tcgagcaggt ggttacgaaa gagggtagcg gcggtcagtc aatcacagct    2580
tcggagctcc gttatattta tcgaaatcgc gaaagattga acgggcgtgt cattttctat    2640
agaaataatg aaaggctaga tcaggctcca tgcaagaaa  atccggactt atggagcaaa    2700
tatcaaccgg gtcttagaca aagcagcagt tcaagagtca agaacgagg  gattgggaac    2760 tttttccgcc ggttttcaat gaagagaaag tag                                 2793
```

<210> SEQ ID NO 42
<211> LENGTH: 930
<212> TYPE: PRT
<213> ORGANISM: Paenibacillus strain DAS1529

<400> SEQUENCE: 42

```
Met Asn Thr Thr Ser Ile Tyr Arg Gly Thr Pro Thr Ile Ser Val Val
1               5                   10                  15

Asp Asn Arg Asn Leu Glu Ile Arg Ile Leu Gln Tyr Asn Arg Ile Ala
            20                  25                  30

Ala Glu Asp Pro Ala Asp Glu Cys Ile Leu Arg Asn Thr Tyr Thr Pro
        35                  40                  45

Leu Ser Tyr Leu Gly Ser Ser Met Asp Pro Arg Leu Phe Ser Gln Tyr
    50                  55                  60

Gln Asp Asp Arg Gly Thr Pro Pro Asn Ile Arg Thr Met Ala Ser Leu
65                  70                  75                  80

Arg Gly Glu Ala Leu Cys Ser Glu Ser Val Asp Ala Gly Arg Lys Ala
                85                  90                  95
```

-continued

Glu Leu Phe Asp Ile Glu Gly Arg Pro Val Trp Leu Ile Asp Ala Asn
            100                 105                 110

Gly Thr Glu Thr Thr Leu Glu Tyr Asp Val Leu Gly Arg Pro Thr Ala
            115                 120                 125

Val Phe Glu Gln Gln Glu Gly Thr Asp Ser Pro Gln Cys Arg Glu Arg
            130                 135                 140

Phe Ile Tyr Gly Lys Glu Ala Asp Ala Gln Ala Asn Asn Leu Arg
145                 150                 155                 160

Gly Gln Leu Val Arg His Tyr Asp Thr Ala Gly Arg Ile Gln Thr Asp
            165                 170                 175

Ser Ile Ser Leu Ala Gly Leu Pro Leu Arg Gln Ser Arg Gln Leu Leu
            180                 185                 190

Lys Asn Trp Asp Glu Pro Gly Asp Trp Ser Met Asp Glu Glu Ser Ala
            195                 200                 205

Trp Ala Ser Leu Leu Ala Ala Glu Ala Tyr Asp Thr Ser Trp Arg Tyr
            210                 215                 220

Asp Ala Gln Asp Arg Val Leu Ala Gln Thr Asp Ala Lys Gly Asn Leu
225                 230                 235                 240

Gln Gln Leu Thr Tyr Asn Asp Ala Gly Gln Pro Gln Ala Val Ser Leu
            245                 250                 255

Lys Leu Gln Gly Gln Ala Glu Gln Arg Ile Trp Asn Arg Ile Glu Tyr
            260                 265                 270

Asn Ala Ala Gly Gln Val Asp Leu Ala Glu Ala Gly Asn Gly Ile Val
            275                 280                 285

Thr Glu Tyr Thr Tyr Glu Glu Ser Thr Gln Arg Leu Ile Arg Lys Lys
            290                 295                 300

Asp Ser Arg Gly Leu Ser Ser Gly Glu Arg Glu Val Leu Gln Asp Tyr
305                 310                 315                 320

Arg Tyr Glu Tyr Asp Pro Val Gly Asn Ile Leu Ser Ile Tyr Asn Glu
            325                 330                 335

Ala Glu Pro Val Arg Tyr Phe Arg Asn Gln Ala Val Ala Pro Lys Arg
            340                 345                 350

Gln Tyr Ala Tyr Asp Ala Leu Tyr Gln Leu Val Ser Ser Ser Gly Arg
            355                 360                 365

Glu Ser Asp Ala Leu Arg Gln Gln Thr Ser Leu Pro Pro Leu Ile Thr
            370                 375                 380

Pro Ile Pro Leu Asp Asp Ser Gln Tyr Val Asn Tyr Ala Glu Lys Tyr
385                 390                 395                 400

Ser Tyr Asp Gln Ala Gly Asn Leu Ile Lys Leu Ser His Asn Gly Ala
            405                 410                 415

Ser Gln Tyr Thr Thr Asn Val Tyr Val Asp Lys Ser Ser Asn Arg Gly
            420                 425                 430

Ile Trp Arg Gln Gly Glu Asp Ile Pro Asp Ile Ala Ala Ser Phe Asp
            435                 440                 445

Arg Ala Gly Asn Gln Gln Ala Leu Phe Pro Gly Arg Pro Leu Glu Trp
450                 455                 460

Asp Thr Arg Asn Gln Leu Ser Arg Val His Met Val Val Arg Glu Gly
465                 470                 475                 480

Gly Asp Asn Asp Trp Glu Gly Tyr Leu Tyr Asp Ser Ser Gly Met Arg
            485                 490                 495

Ile Val Lys Arg Ser Thr Arg Lys Thr Gln Thr Thr Gln Thr Asp
            500                 505                 510

-continued

```
Thr Thr Leu Tyr Leu Pro Gly Leu Glu Leu Arg Ile Arg Gln Thr Gly
        515                 520                 525
Asp Arg Val Thr Glu Ala Leu Gln Val Ile Thr Val Asp Glu Gly Ala
    530                 535                 540
Gly Gln Val Arg Val Leu His Trp Glu Asp Gly Thr Glu Pro Gly Gly
545                 550                 555                 560
Ile Ala Asn Asp Gln Tyr Arg Tyr Ser Leu Asn Asp His Leu Thr Ser
                565                 570                 575
Ser Leu Leu Glu Val Asp Gly Gln Gly Gln Ile Ile Ser Lys Glu Glu
            580                 585                 590
Phe Tyr Pro Tyr Gly Gly Thr Ala Leu Trp Thr Ala Arg Ser Glu Val
        595                 600                 605
Glu Ala Ser Tyr Lys Thr Ile Arg Tyr Ser Gly Lys Glu Arg Asp Ala
    610                 615                 620
Thr Gly Leu Tyr Tyr Gly His Arg Tyr Tyr Met Pro Trp Leu Gly
625                 630                 635                 640
Arg Trp Leu Asn Pro Asp Pro Ala Gly Met Val Asp Gly Leu Asn Leu
                645                 650                 655
Tyr Arg Met Val Arg Asn Asn Pro Ile Gly Leu Met Asp Pro Asn Gly
            660                 665                 670
Asn Ala Pro Ile Asn Val Ala Asp Tyr Ser Phe Val His Gly Asp Leu
        675                 680                 685
Val Tyr Gly Leu Ser Lys Glu Arg Gly Arg Tyr Leu Lys Leu Phe Asn
    690                 695                 700
Pro Asn Phe Asn Met Glu Lys Ser Asp Ser Pro Ala Met Val Ile Asp
705                 710                 715                 720
Gln Tyr Asn Asn Asn Val Ala Leu Ser Ile Thr Asn Gln Tyr Lys Val
                725                 730                 735
Glu Glu Leu Met Lys Phe Gln Lys Asp Pro Gln Lys Ala Ala Arg Lys
            740                 745                 750
Ile Lys Val Pro Glu Gly Asn Arg Leu Ser Arg Asn Glu Asn Tyr Pro
        755                 760                 765
Leu Trp His Asp Tyr Ile Asn Ile Gly Glu Ala Lys Ala Ala Phe Lys
    770                 775                 780
Ala Ser His Ile Phe Gln Glu Val Lys Gly Asn Tyr Gly Lys Asp Tyr
785                 790                 795                 800
Tyr His Lys Leu Leu Leu Asp Arg Met Ile Glu Ser Pro Leu Leu Trp
                805                 810                 815
Lys Arg Gly Ser Lys Leu Gly Leu Glu Ile Ala Ala Thr Asn Gln Arg
            820                 825                 830
Thr Lys Ile His Phe Val Leu Asp Asn Leu Asn Ile Glu Gln Val Val
        835                 840                 845
Thr Lys Glu Gly Ser Gly Gly Gln Ser Ile Thr Ala Ser Glu Leu Arg
    850                 855                 860
Tyr Ile Tyr Arg Asn Arg Glu Arg Leu Asn Gly Arg Val Ile Phe Tyr
865                 870                 875                 880
Arg Asn Asn Glu Arg Leu Asp Gln Ala Pro Trp Gln Glu Asn Pro Asp
                885                 890                 895
Leu Trp Ser Lys Tyr Gln Pro Gly Leu Arg Gln Ser Ser Ser Arg
            900                 905                 910
Val Lys Glu Arg Gly Ile Gly Asn Phe Phe Arg Arg Phe Ser Met Lys
        915                 920                 925
Arg Lys
```

930

<210> SEQ ID NO 43
<211> LENGTH: 953
<212> TYPE: PRT
<213> ORGANISM: Paenibacillus strain DAS1529

<400> SEQUENCE: 43

```
Met Lys Met Ile Pro Trp Thr His His Tyr Leu Leu His Arg Leu Arg
1               5                   10                  15

Gly Glu Met Glu Val Lys Pro Met Asn Thr Thr Ser Ile Tyr Arg Gly
            20                  25                  30

Thr Pro Thr Ile Ser Val Val Asp Asn Arg Asn Leu Glu Ile Arg Ile
        35                  40                  45

Leu Gln Tyr Asn Arg Ile Ala Ala Glu Asp Pro Ala Asp Glu Cys Ile
    50                  55                  60

Leu Arg Asn Thr Tyr Thr Pro Leu Ser Tyr Leu Gly Ser Ser Met Asp
65                  70                  75                  80

Pro Arg Leu Phe Ser Gln Tyr Gln Asp Asp Arg Gly Thr Pro Pro Asn
                85                  90                  95

Ile Arg Thr Met Ala Ser Leu Arg Gly Glu Ala Leu Cys Ser Glu Ser
            100                 105                 110

Val Asp Ala Gly Arg Lys Ala Glu Leu Phe Asp Ile Glu Gly Arg Pro
        115                 120                 125

Val Trp Leu Ile Asp Ala Asn Gly Thr Glu Thr Thr Leu Glu Tyr Asp
    130                 135                 140

Val Leu Gly Arg Pro Thr Ala Val Phe Glu Gln Gln Glu Gly Thr Asp
145                 150                 155                 160

Ser Pro Gln Cys Arg Glu Arg Phe Ile Tyr Gly Glu Lys Glu Ala Asp
                165                 170                 175

Ala Gln Ala Asn Asn Leu Arg Gly Gln Leu Val Arg His Tyr Asp Thr
            180                 185                 190

Ala Gly Arg Ile Gln Thr Asp Ser Ile Ser Leu Ala Gly Leu Pro Leu
        195                 200                 205

Arg Gln Ser Arg Gln Leu Leu Lys Asn Trp Asp Glu Pro Gly Asp Trp
    210                 215                 220

Ser Met Asp Glu Glu Ser Ala Trp Ala Ser Leu Leu Ala Ala Glu Ala
225                 230                 235                 240

Tyr Asp Thr Ser Trp Arg Tyr Asp Ala Gln Asp Arg Val Leu Ala Gln
                245                 250                 255

Thr Asp Ala Lys Gly Asn Leu Gln Gln Leu Thr Tyr Asn Asp Ala Gly
            260                 265                 270

Gln Pro Gln Ala Val Ser Leu Lys Leu Gln Gly Gln Ala Glu Gln Arg
        275                 280                 285

Ile Trp Asn Arg Ile Glu Tyr Asn Ala Ala Gly Gln Val Asp Leu Ala
    290                 295                 300

Glu Ala Gly Asn Gly Ile Val Thr Glu Tyr Thr Tyr Glu Glu Ser Thr
305                 310                 315                 320

Gln Arg Leu Ile Arg Lys Lys Asp Ser Arg Gly Leu Ser Ser Gly Glu
                325                 330                 335

Arg Glu Val Leu Gln Asp Tyr Arg Tyr Glu Tyr Asp Pro Val Gly Asn
            340                 345                 350

Ile Leu Ser Ile Tyr Asn Glu Ala Glu Pro Val Arg Tyr Phe Arg Asn
        355                 360                 365
```

-continued

```
Gln Ala Val Ala Pro Lys Arg Gln Tyr Ala Tyr Asp Ala Leu Tyr Gln
    370                 375                 380
Leu Val Ser Ser Ser Gly Arg Glu Ser Asp Ala Leu Arg Gln Gln Thr
385                 390                 395                 400
Ser Leu Pro Pro Leu Ile Thr Pro Ile Pro Leu Asp Asp Ser Gln Tyr
                405                 410                 415
Val Asn Tyr Ala Glu Lys Tyr Ser Tyr Asp Gln Ala Gly Asn Leu Ile
            420                 425                 430
Lys Leu Ser His Asn Gly Ala Ser Gln Tyr Thr Thr Asn Val Tyr Val
        435                 440                 445
Asp Lys Ser Ser Asn Arg Gly Ile Trp Arg Gln Gly Glu Asp Ile Pro
    450                 455                 460
Asp Ile Ala Ala Ser Phe Asp Arg Ala Gly Asn Gln Gln Ala Leu Phe
465                 470                 475                 480
Pro Gly Arg Pro Leu Glu Trp Asp Thr Arg Asn Gln Leu Ser Arg Val
                485                 490                 495
His Met Val Val Arg Glu Gly Gly Asp Asn Asp Trp Glu Gly Tyr Leu
            500                 505                 510
Tyr Asp Ser Ser Gly Met Arg Ile Val Lys Arg Ser Thr Arg Lys Thr
        515                 520                 525
Gln Thr Thr Thr Gln Thr Asp Thr Thr Leu Tyr Leu Pro Gly Leu Glu
    530                 535                 540
Leu Arg Ile Arg Gln Thr Gly Asp Arg Val Thr Glu Ala Leu Gln Val
545                 550                 555                 560
Ile Thr Val Asp Glu Gly Ala Gly Gln Val Arg Val Leu His Trp Glu
                565                 570                 575
Asp Gly Thr Glu Pro Gly Gly Ile Ala Asn Asp Gln Tyr Arg Tyr Ser
            580                 585                 590
Leu Asn Asp His Leu Thr Ser Ser Leu Leu Glu Val Asp Gly Gln Gly
        595                 600                 605
Gln Ile Ile Ser Lys Glu Glu Phe Tyr Pro Tyr Gly Gly Thr Ala Leu
    610                 615                 620
Trp Thr Ala Arg Ser Glu Val Glu Ala Ser Tyr Lys Thr Ile Arg Tyr
625                 630                 635                 640
Ser Gly Lys Glu Arg Asp Ala Thr Gly Leu Tyr Tyr Tyr Gly His Arg
                645                 650                 655
Tyr Tyr Met Pro Trp Leu Gly Arg Trp Leu Asn Pro Asp Pro Ala Gly
            660                 665                 670
Met Val Asp Gly Leu Asn Leu Tyr Arg Met Val Arg Asn Asn Pro Ile
        675                 680                 685
Gly Leu Met Asp Pro Asn Gly Asn Ala Pro Ile Asn Val Ala Asp Tyr
    690                 695                 700
Ser Phe Val His Gly Asp Leu Val Tyr Gly Leu Ser Lys Glu Arg Gly
705                 710                 715                 720
Arg Tyr Leu Lys Leu Phe Asn Pro Asn Phe Asn Met Glu Lys Ser Asp
                725                 730                 735
Ser Pro Ala Met Val Ile Asp Gln Tyr Asn Asn Val Ala Leu Ser
            740                 745                 750
Ile Thr Asn Gln Tyr Lys Val Glu Glu Leu Met Lys Phe Gln Lys Asp
        755                 760                 765
Pro Gln Lys Ala Ala Arg Lys Ile Lys Val Pro Glu Gly Asn Arg Leu
    770                 775                 780
Ser Arg Asn Glu Asn Tyr Pro Leu Trp His Asp Tyr Ile Asn Ile Gly
```

```
                785                 790                 795                 800
Glu Ala Lys Ala Ala Phe Lys Ala Ser His Ile Phe Gln Glu Val Lys
                805                 810                 815
Gly Asn Tyr Gly Lys Asp Tyr Tyr His Lys Leu Leu Leu Asp Arg Met
                820                 825                 830
Ile Glu Ser Pro Leu Leu Trp Lys Arg Gly Ser Lys Leu Gly Leu Glu
                835                 840                 845
Ile Ala Ala Thr Asn Gln Arg Thr Lys Ile His Phe Val Leu Asp Asn
                850                 855                 860
Leu Asn Ile Glu Gln Val Val Thr Lys Glu Gly Ser Gly Gly Gln Ser
865                 870                 875                 880
Ile Thr Ala Ser Glu Leu Arg Tyr Ile Tyr Arg Asn Arg Glu Arg Leu
                885                 890                 895
Asn Gly Arg Val Ile Phe Tyr Arg Asn Asn Glu Arg Leu Asp Gln Ala
                900                 905                 910
Pro Trp Gln Glu Asn Pro Asp Leu Trp Ser Lys Tyr Gln Pro Gly Leu
                915                 920                 925
Arg Gln Ser Ser Ser Arg Val Lys Glu Arg Gly Ile Gly Asn Phe
                930                 935                 940
Phe Arg Arg Phe Ser Met Lys Arg Lys
945                 950

<210> SEQ ID NO 44
<211> LENGTH: 4425
<212> TYPE: DNA
<213> ORGANISM: Photorhabdus luminescens
<220> FEATURE:
<221> NAME/KEY: CDS
<222> LOCATION: (1)..(4422)

<400> SEQUENCE: 44 atg caa aat tca caa gat ttt agt att acg gaa ctg tca ctg ccc aaa      48
Met Gln Asn Ser Gln Asp Phe Ser Ile Thr Glu Leu Ser Leu Pro Lys
1               5                   10                  15 ggg ggg ggc gct atc acg gga atg ggt gaa gca tta acc ccc act gga      96
Gly Gly Gly Ala Ile Thr Gly Met Gly Glu Ala Leu Thr Pro Thr Gly
                20                  25                  30 ccg gat ggt atg gcc gcg cta tct cta cca ttg cct att tct gcc ggg     144
Pro Asp Gly Met Ala Ala Leu Ser Leu Pro Leu Pro Ile Ser Ala Gly
            35                  40                  45 cgc ggt tat gct ccc gca ttc act ctg aat tac aac agc ggc gcc ggt     192
Arg Gly Tyr Ala Pro Ala Phe Thr Leu Asn Tyr Asn Ser Gly Ala Gly
        50                  55                  60 aac agt cca ttt ggt ctg ggt tgg gat tgc aac gtt atg act atc cgc     240
Asn Ser Pro Phe Gly Leu Gly Trp Asp Cys Asn Val Met Thr Ile Arg
65                  70                  75                  80 cgc cgc acc cat ttt ggc gtc ccc cat tat gac gaa acc gat acc ttt     288
Arg Arg Thr His Phe Gly Val Pro His Tyr Asp Glu Thr Asp Thr Phe
                85                  90                  95 ttg ggg cca gaa ggc gaa gtg ctg gtg gta gcg gat caa cct cgc gac     336
Leu Gly Pro Glu Gly Glu Val Leu Val Val Ala Asp Gln Pro Arg Asp
                100                 105                 110 gaa tcc aca tta cag ggt atc aat tta ggc gcc acc ttt acc gtt acc     384
Glu Ser Thr Leu Gln Gly Ile Asn Leu Gly Ala Thr Phe Thr Val Thr
            115                 120                 125 ggc tac cgt tcc cgt ctg gaa agc cat ttc agc cga ttg gaa tat tgg     432
Gly Tyr Arg Ser Arg Leu Glu Ser His Phe Ser Arg Leu Glu Tyr Trp
        130                 135                 140
```

-continued

| | | |
|---|---|---|
| caa ccc aaa aca aca ggt aaa aca gat ttt tgg ttg ata tat agc cca<br>Gln Pro Lys Thr Thr Gly Lys Thr Asp Phe Trp Leu Ile Tyr Ser Pro<br>145                     150                     155                     160 | 480 |
| gat ggg cag gtg cat cta ctg ggt aaa tca ccg caa gcg cgg atc agc<br>Asp Gly Gln Val His Leu Leu Gly Lys Ser Pro Gln Ala Arg Ile Ser<br>                 165                     170                     175 | 528 |
| aac cca tcc caa acg aca caa aca gca caa tgg ctg ctg gaa gcc tct<br>Asn Pro Ser Gln Thr Thr Gln Thr Ala Gln Trp Leu Leu Glu Ala Ser<br>        180                     185                     190 | 576 |
| gta tca tca cgt ggc gaa caa att tat tat caa tat cgc gcc gaa gat<br>Val Ser Ser Arg Gly Glu Gln Ile Tyr Tyr Gln Tyr Arg Ala Glu Asp<br>195                     200                     205 | 624 |
| gac aca ggt tgc gaa gca gat gaa att acg cac cat tta cag gct aca<br>Asp Thr Gly Cys Glu Ala Asp Glu Ile Thr His His Leu Gln Ala Thr<br>        210                     215                     220 | 672 |
| gcg caa cgt tat tta cac atc gtg tat tac ggc aac cgt aca gcc agc<br>Ala Gln Arg Tyr Leu His Ile Val Tyr Tyr Gly Asn Arg Thr Ala Ser<br>225                     230                     235                     240 | 720 |
| gaa aca tta ccc ggt ctg gat ggc agc gcc cca tca caa gca gac tgg<br>Glu Thr Leu Pro Gly Leu Asp Gly Ser Ala Pro Ser Gln Ala Asp Trp<br>                     245                     250                     255 | 768 |
| ttg ttc tat ctg gta ttt gat tac ggc gaa cgc agt aac aac ctg aaa<br>Leu Phe Tyr Leu Val Phe Asp Tyr Gly Glu Arg Ser Asn Asn Leu Lys<br>                 260                     265                     270 | 816 |
| acg cca cca gca ttt tcg act aca ggt agc tgg ctt tgc cgt cag gac<br>Thr Pro Pro Ala Phe Ser Thr Thr Gly Ser Trp Leu Cys Arg Gln Asp<br>        275                     280                     285 | 864 |
| cgt ttt tcc cgt tat gaa tat ggc ttt gag att cgt acc cgc cgc tta<br>Arg Phe Ser Arg Tyr Glu Tyr Gly Phe Glu Ile Arg Thr Arg Arg Leu<br>290                     295                     300 | 912 |
| tgc cgt cag gta ttg atg tac cat cac ctg caa gca ctg gat agt aag<br>Cys Arg Gln Val Leu Met Tyr His His Leu Gln Ala Leu Asp Ser Lys<br>305                     310                     315                     320 | 960 |
| ata aca gaa cac aac gga cca acg ctg gtt tca cgc ctg ata ctc aat<br>Ile Thr Glu His Asn Gly Pro Thr Leu Val Ser Arg Leu Ile Leu Asn<br>                 325                     330                     335 | 1008 |
| tac gac gaa agc gcg ata gcc agc acg cta gta ttc gtt cgc cga gtg<br>Tyr Asp Glu Ser Ala Ile Ala Ser Thr Leu Val Phe Val Arg Arg Val<br>        340                     345                     350 | 1056 |
| gga cac gag caa gat ggt aat gtc gtc acc ctg ccg cca tta gaa ttg<br>Gly His Glu Gln Asp Gly Asn Val Val Thr Leu Pro Pro Leu Glu Leu<br>355                     360                     365 | 1104 |
| gca tat cag gat ttt tca ccg cga cat cac gct cac tgg caa cca atg<br>Ala Tyr Gln Asp Phe Ser Pro Arg His His Ala His Trp Gln Pro Met<br>370                     375                     380 | 1152 |
| gat gta ctg gca aac ttc aat gcc att cag cgc tgg cag cta gtc gat<br>Asp Val Leu Ala Asn Phe Asn Ala Ile Gln Arg Trp Gln Leu Val Asp<br>385                     390                     395                     400 | 1200 |
| cta aaa ggc gaa gga tta ccc ggc ctg tta tat cag gat aaa ggc gct<br>Leu Lys Gly Glu Gly Leu Pro Gly Leu Leu Tyr Gln Asp Lys Gly Ala<br>                 405                     410                     415 | 1248 |
| tgg tgg tac cgc tcc gca cag cgt ctg ggc gaa att ggc tca gat gcc<br>Trp Trp Tyr Arg Ser Ala Gln Arg Leu Gly Glu Ile Gly Ser Asp Ala<br>        420                     425                     430 | 1296 |
| gtc act tgg gaa aag atg caa cct tta tcg gtt att cct tct ttg caa<br>Val Thr Trp Glu Lys Met Gln Pro Leu Ser Val Ile Pro Ser Leu Gln<br>                 435                     440                     445 | 1344 |
| agt aat gcc tcg ttg gtg gat atc aat gga gac ggc caa ctt gac tgg<br>Ser Asn Ala Ser Leu Val Asp Ile Asn Gly Asp Gly Gln Leu Asp Trp<br>450                     455                     460 | 1392 |

```
gtt atc acc gga ccg gga tta cgg gga tat cat agt caa cgc ccg gat    1440
Val Ile Thr Gly Pro Gly Leu Arg Gly Tyr His Ser Gln Arg Pro Asp
465                 470                 475                 480 ggc agt tgg aca cgt ttt acc cca ctc aac gct ctg ccg gtg gaa tac    1488
Gly Ser Trp Thr Arg Phe Thr Pro Leu Asn Ala Leu Pro Val Glu Tyr
                485                 490                 495 acc cat cca cgc gcg caa ctc gca gat tta atg gga gcc ggg cta tcc    1536
Thr His Pro Arg Ala Gln Leu Ala Asp Leu Met Gly Ala Gly Leu Ser
            500                 505                 510 gat ttg gtg ctg atc ggc cct aag agc gtg cgt tta tat gcc aat acc    1584
Asp Leu Val Leu Ile Gly Pro Lys Ser Val Arg Leu Tyr Ala Asn Thr
        515                 520                 525 cgc gac ggc ttt gcc aaa gga aaa gat gtg gtg caa tcc ggt gat atc    1632
Arg Asp Gly Phe Ala Lys Gly Lys Asp Val Val Gln Ser Gly Asp Ile
    530                 535                 540 aca ctg ccg gtg ccg ggc gcc gat cca cgt aag ttg gtg gcc ttt agt    1680
Thr Leu Pro Val Pro Gly Ala Asp Pro Arg Lys Leu Val Ala Phe Ser
545                 550                 555                 560 gat gta ttg ggt tca ggt caa gcc cat ctg gtt gaa gta agc gcg act    1728
Asp Val Leu Gly Ser Gly Gln Ala His Leu Val Glu Val Ser Ala Thr
                565                 570                 575 aaa gtc acc tgc tgg cct aat ctg ggg cgc gga cgt ttt ggt caa ccc    1776
Lys Val Thr Cys Trp Pro Asn Leu Gly Arg Gly Arg Phe Gly Gln Pro
            580                 585                 590 att acc tta ccg gga ttc agc cag cca gca acc gag ttt aac ccg gct    1824
Ile Thr Leu Pro Gly Phe Ser Gln Pro Ala Thr Glu Phe Asn Pro Ala
        595                 600                 605 caa gtt tat ctg gcc gat ctg gat ggc agc ggt cca acg gat ctg att    1872
Gln Val Tyr Leu Ala Asp Leu Asp Gly Ser Gly Pro Thr Asp Leu Ile
    610                 615                 620 tat gtt cat aca aac cgt ctg gat atc ttc ctg aac aaa agt ggc aat    1920
Tyr Val His Thr Asn Arg Leu Asp Ile Phe Leu Asn Lys Ser Gly Asn
625                 630                 635                 640 ggc ttt gct gaa cca gtg aca tta cgc ttc ccg gaa ggt ctg cgt ttt    1968
Gly Phe Ala Glu Pro Val Thr Leu Arg Phe Pro Glu Gly Leu Arg Phe
                645                 650                 655 gat cat acc tgt cag tta caa atg gcc gat gta caa gga tta ggc gtc    2016
Asp His Thr Cys Gln Leu Gln Met Ala Asp Val Gln Gly Leu Gly Val
            660                 665                 670 gcc agc ctg ata ctg agc gtg ccg cat atg tct ccc cat cac tgg cgc    2064
Ala Ser Leu Ile Leu Ser Val Pro His Met Ser Pro His His Trp Arg
        675                 680                 685 tgc gat ctg acc aac atg aag ccg tgg tta ctc aat gaa atg aac aac    2112
Cys Asp Leu Thr Asn Met Lys Pro Trp Leu Leu Asn Glu Met Asn Asn
    690                 695                 700 aat atg ggg gtc cat cac acc ttg cgt tac cgc agt tcc tcc caa ttc    2160
Asn Met Gly Val His His Thr Leu Arg Tyr Arg Ser Ser Ser Gln Phe
705                 710                 715                 720 tgg ctg gat gaa aaa gcc gcg gcg ctg act acc gga caa aca ccg gtt    2208
Trp Leu Asp Glu Lys Ala Ala Ala Leu Thr Thr Gly Gln Thr Pro Val
                725                 730                 735 tgc tat ctc ccc ttc ccg atc cac acc cta tgg caa acg gaa aca gaa    2256
Cys Tyr Leu Pro Phe Pro Ile His Thr Leu Trp Gln Thr Glu Thr Glu
            740                 745                 750 gat gaa atc agc ggc aac aaa tta gtc aca aca ctt cgt tat gct cgt    2304
Asp Glu Ile Ser Gly Asn Lys Leu Val Thr Thr Leu Arg Tyr Ala Arg
        755                 760                 765 ggc gca tgg gac gga cgc gag cgg gaa ttt cgc gga ttt ggt tat gta    2352
Gly Ala Trp Asp Gly Arg Glu Arg Glu Phe Arg Gly Phe Gly Tyr Val
```

-continued

```
     770                 775                 780
gag cag aca gac agc cat caa ctg gct caa ggc aac gcg cca gaa cgt    2400
Glu Gln Thr Asp Ser His Gln Leu Ala Gln Gly Asn Ala Pro Glu Arg
785                 790                 795                 800 acg cca ccg gcg ctg acc aaa aac tgg tat gcc acc gga ctg ccg gtg    2448
Thr Pro Pro Ala Leu Thr Lys Asn Trp Tyr Ala Thr Gly Leu Pro Val
                805                 810                 815 ata gat aac gca tta tca acc gag tat tgg cgt gat gat cag gct ttt    2496
Ile Asp Asn Ala Leu Ser Thr Glu Tyr Trp Arg Asp Asp Gln Ala Phe
            820                 825                 830 gcc ggt ttc tca ccg cgc ttt acg act tgg caa gat aac aaa gat gtc    2544
Ala Gly Phe Ser Pro Arg Phe Thr Thr Trp Gln Asp Asn Lys Asp Val
        835                 840                 845 ccg tta aca ccg gaa gat gat aac agt cgt tac tgg ttc aac cgc gcg    2592
Pro Leu Thr Pro Glu Asp Asp Asn Ser Arg Tyr Trp Phe Asn Arg Ala
    850                 855                 860 ttg aaa ggt caa ctg cta cgt agt gaa ctg tac gga ttg gac gat agt    2640
Leu Lys Gly Gln Leu Leu Arg Ser Glu Leu Tyr Gly Leu Asp Asp Ser
865                 870                 875                 880 aca aat aaa cac gtt ccc tat act gtc act gaa ttt cgt tca cag gta    2688
Thr Asn Lys His Val Pro Tyr Thr Val Thr Glu Phe Arg Ser Gln Val
                885                 890                 895 cgt cga tta cag cat acc gac agc cga tac cct gta ctt tgg tca tct    2736
Arg Arg Leu Gln His Thr Asp Ser Arg Tyr Pro Val Leu Trp Ser Ser
            900                 905                 910 gta gtt gaa agc cgc aac tat cac tac gaa cgt atc gcc agc gac ccg    2784
Val Val Glu Ser Arg Asn Tyr His Tyr Glu Arg Ile Ala Ser Asp Pro
        915                 920                 925 caa tgc agt caa aat att acg cta tcc agt gat cga ttt ggt cag ccg    2832
Gln Cys Ser Gln Asn Ile Thr Leu Ser Ser Asp Arg Phe Gly Gln Pro
    930                 935                 940 cta aaa cag ctt tcg gta cag tac ccg cgc cgc cag cag cca gca atc    2880
Leu Lys Gln Leu Ser Val Gln Tyr Pro Arg Arg Gln Gln Pro Ala Ile
945                 950                 955                 960 aat ctg tat cct gat aca ttg cct gat aag ttg tta gcc aac agc tat    2928
Asn Leu Tyr Pro Asp Thr Leu Pro Asp Lys Leu Leu Ala Asn Ser Tyr
                965                 970                 975 gat gac caa caa cgc caa tta cgg ctc acc tat caa caa tcc agt tgg    2976
Asp Asp Gln Gln Arg Gln Leu Arg Leu Thr Tyr Gln Gln Ser Ser Trp
            980                 985                 990 cat cac ctg acc aac aat acc gtt  cga gta ttg gga tta  ccg gat agt   3024
His His Leu Thr Asn Asn Thr Val  Arg Val Leu Gly Leu  Pro Asp Ser
        995                  1000                 1005 acc cgc agt gat atc ttt act  tat ggc gct gaa aat  gtg cct gct       3069
Thr Arg Ser Asp Ile Phe Tyr  Gly Ala Glu Asn  Val Pro Ala
    1010                 1015                 1020 ggt ggt tta aat ctg gaa ctt  ctg agt gat aaa aat  agc ctg atc       3114
Gly Gly Leu Asn Leu Glu Leu  Leu Ser Asp Lys Asn  Ser Leu Ile
1025                 1030                 1035 gcg gac gat aaa cca cgt gaa  tac ctc ggt cag caa  aaa acc gct       3159
Ala Asp Asp Lys Pro Arg Glu  Tyr Leu Gly Gln Gln  Lys Thr Ala
    1040                 1045                 1050 tat acc gat gga caa aat aca  acg ccg ttg caa aca  cca aca cgg       3204
Tyr Thr Asp Gly Gln Asn Thr  Thr Pro Leu Gln Thr  Pro Thr Arg
    1055                 1060                 1065 caa gcc ctg att gcc ttt acc  gaa aca acg gta ttc  aac cag tcc       3249
Gln Ala Leu Ile Ala Phe Thr  Glu Thr Thr Val Phe  Asn Gln Ser
    1070                 1075                 1080 aca tta tca gcg ttt aac gga  agc atc ccg tcc gat  aaa tta tca       3294
```

```
                Thr Leu Ser Ala Phe Asn Gly Ser Ile Pro Ser Asp Lys Leu Ser
                1085                1090                1095 acg acg ctg gag caa gct gga tat cag caa aca aat tat cta ttc          3339
Thr Thr Leu Glu Gln Ala Gly Tyr Gln Gln Thr Asn Tyr Leu Phe
1100                1105                1110 cct cgc act gga gaa gat aaa gtt tgg gta gcc cat cac ggc tat          3384
Pro Arg Thr Gly Glu Asp Lys Val Trp Val Ala His His Gly Tyr
1115                1120                1125 acc gat tat ggt aca gcg gca cag ttc tgg cgc ccg caa aaa cag          3429
Thr Asp Tyr Gly Thr Ala Ala Gln Phe Trp Arg Pro Gln Lys Gln
1130                1135                1140 agc aac acc caa ctc acc ggt aaa atc acc ctc atc tgg gat gca          3474
Ser Asn Thr Gln Leu Thr Gly Lys Ile Thr Leu Ile Trp Asp Ala
1145                1150                1155 aac tat tgc gtt gtg gta caa acc cgg gat gct gct gga ctg aca          3519
Asn Tyr Cys Val Val Val Gln Thr Arg Asp Ala Ala Gly Leu Thr
1160                1165                1170 acc tca gcc aaa tat gac tgg cgt ttt ctg acc ccg gtg caa ctc          3564
Thr Ser Ala Lys Tyr Asp Trp Arg Phe Leu Thr Pro Val Gln Leu
1175                1180                1185 acc gat atc aat gac aat cag cac ctt atc aca ctg gat gca ttg          3609
Thr Asp Ile Asn Asp Asn Gln His Leu Ile Thr Leu Asp Ala Leu
1190                1195                1200 ggc cga cca atc aca ttg cgc ttt tgg gga act gaa aac ggc aag          3654
Gly Arg Pro Ile Thr Leu Arg Phe Trp Gly Thr Glu Asn Gly Lys
1205                1210                1215 atg aca ggt tat tcc tca ccg gaa aaa gca tca ttt tct cca cca          3699
Met Thr Gly Tyr Ser Ser Pro Glu Lys Ala Ser Phe Ser Pro Pro
1220                1225                1230 tcc gat gtt aat gcc gct att gag tta aaa aaa ccg ctc cct gta          3744
Ser Asp Val Asn Ala Ala Ile Glu Leu Lys Lys Pro Leu Pro Val
1235                1240                1245 gca cag tgt cag gtc tac gca cca gaa agc tgg atg cca gta tta          3789
Ala Gln Cys Gln Val Tyr Ala Pro Glu Ser Trp Met Pro Val Leu
1250                1255                1260 agt cag aaa acc ttc aat cga ctg gca gaa caa gat tgg caa aag          3834
Ser Gln Lys Thr Phe Asn Arg Leu Ala Glu Gln Asp Trp Gln Lys
1265                1270                1275 tta tat aac gcc cga atc atc acc gaa gat gga cgt atc tgc aca          3879
Leu Tyr Asn Ala Arg Ile Ile Thr Glu Asp Gly Arg Ile Cys Thr
1280                1285                1290 ctg gct tat cgc cgc tgg gta caa agc caa aag gca atc cct caa          3924
Leu Ala Tyr Arg Arg Trp Val Gln Ser Gln Lys Ala Ile Pro Gln
1295                1300                1305 ctc att agc ctg tta aac aac gga ccc cgt tta cct cct cac agc          3969
Leu Ile Ser Leu Leu Asn Asn Gly Pro Arg Leu Pro Pro His Ser
1310                1315                1320 ctg aca ttg acg acg gat cgt tat gat cac gat cct gag caa cag          4014
Leu Thr Leu Thr Thr Asp Arg Tyr Asp His Asp Pro Glu Gln Gln
1325                1330                1335 atc cgt caa cag gtg gta ttc agt gat ggc ttt ggc cgc ttg ctg          4059
Ile Arg Gln Gln Val Val Phe Ser Asp Gly Phe Gly Arg Leu Leu
1340                1345                1350 caa gcc gct gcc cga cat gag gca ggc atg gcc cgg caa cgc aat          4104
Gln Ala Ala Ala Arg His Glu Ala Gly Met Ala Arg Gln Arg Asn
1355                1360                1365 gaa gac ggc tct ttg att ata aat gtc cag cat act gag aac cgt          4149
Glu Asp Gly Ser Leu Ile Ile Asn Val Gln His Thr Glu Asn Arg
1370                1375                1380
```

```
tgg gca gtg act gga cga acg gaa tat gac aat aag ggg caa ccg    4194
Trp Ala Val Thr Gly Arg Thr Glu Tyr Asp Asn Lys Gly Gln Pro
    1385            1390                1395 ata cgt acc tat cag ccc tat ttc ctc aat gac tgg cga tac gtc    4239
Ile Arg Thr Tyr Gln Pro Tyr Phe Leu Asn Asp Trp Arg Tyr Val
1400            1405                1410 agc aat gat agt gcc cgg cag gaa aaa gaa gct tat gca gat acc    4284
Ser Asn Asp Ser Ala Arg Gln Glu Lys Glu Ala Tyr Ala Asp Thr
    1415            1420                1425 cat gtc tat gat ccc ata ggt cga gaa atc aag gtt atc acc gca    4329
His Val Tyr Asp Pro Ile Gly Arg Glu Ile Lys Val Ile Thr Ala
    1430            1435                1440 aaa ggt tgg ttc cgt cga acc ttg ttc act ccc tgg ttt act gtc    4374
Lys Gly Trp Phe Arg Arg Thr Leu Phe Thr Pro Trp Phe Thr Val
1445            1450                1455 aat gaa gat gaa aat gac aca gcc gct gag gtg aag aag gta aag    4419
Asn Glu Asp Glu Asn Asp Thr Ala Ala Glu Val Lys Lys Val Lys
    1460            1465                1470 atg taa                                                        4425
Met

<210> SEQ ID NO 45
<211> LENGTH: 1474
<212> TYPE: PRT
<213> ORGANISM: Photorhabdus luminescens

<400> SEQUENCE: 45

Met Gln Asn Ser Gln Asp Phe Ser Ile Thr Glu Leu Ser Leu Pro Lys
1               5                   10                  15

Gly Gly Gly Ala Ile Thr Gly Met Gly Glu Ala Leu Thr Pro Thr Gly
            20                  25                  30

Pro Asp Gly Met Ala Ala Leu Ser Leu Pro Leu Pro Ile Ser Ala Gly
        35                  40                  45

Arg Gly Tyr Ala Pro Ala Phe Thr Leu Asn Tyr Asn Ser Gly Ala Gly
    50                  55                  60

Asn Ser Pro Phe Gly Leu Gly Trp Asp Cys Asn Val Met Thr Ile Arg
65                  70                  75                  80

Arg Arg Thr His Phe Gly Val Pro His Tyr Asp Glu Thr Asp Thr Phe
                85                  90                  95

Leu Gly Pro Glu Gly Glu Val Leu Val Val Ala Asp Gln Pro Arg Asp
            100                 105                 110

Glu Ser Thr Leu Gln Gly Ile Asn Leu Gly Ala Thr Phe Thr Val Thr
        115                 120                 125

Gly Tyr Arg Ser Arg Leu Glu Ser His Phe Ser Arg Leu Glu Tyr Trp
    130                 135                 140

Gln Pro Lys Thr Thr Gly Lys Thr Asp Phe Trp Leu Ile Tyr Ser Pro
145                 150                 155                 160

Asp Gly Gln Val His Leu Leu Gly Lys Ser Pro Gln Ala Arg Ile Ser
                165                 170                 175

Asn Pro Ser Gln Thr Thr Gln Thr Ala Gln Trp Leu Leu Glu Ala Ser
            180                 185                 190

Val Ser Ser Arg Gly Glu Gln Ile Tyr Tyr Gln Tyr Arg Ala Glu Asp
        195                 200                 205

Asp Thr Gly Cys Glu Ala Asp Glu Ile Thr His His Leu Gln Ala Thr
    210                 215                 220

Ala Gln Arg Tyr Leu His Ile Val Tyr Tyr Gly Asn Arg Thr Ala Ser
225                 230                 235                 240
```

```
Glu Thr Leu Pro Gly Leu Asp Gly Ser Ala Pro Ser Gln Ala Asp Trp
            245                 250                 255

Leu Phe Tyr Leu Val Phe Asp Tyr Gly Glu Arg Ser Asn Asn Leu Lys
        260                 265                 270

Thr Pro Pro Ala Phe Ser Thr Thr Gly Ser Trp Leu Cys Arg Gln Asp
    275                 280                 285

Arg Phe Ser Arg Tyr Glu Tyr Gly Phe Glu Ile Arg Thr Arg Arg Leu
290                 295                 300

Cys Arg Gln Val Leu Met Tyr His Leu Gln Ala Leu Asp Ser Lys
305                 310                 315                 320

Ile Thr Glu His Asn Gly Pro Thr Leu Val Ser Arg Leu Ile Leu Asn
                325                 330                 335

Tyr Asp Glu Ser Ala Ile Ala Ser Thr Leu Val Phe Val Arg Arg Val
            340                 345                 350

Gly His Glu Gln Asp Gly Asn Val Val Thr Leu Pro Pro Leu Glu Leu
        355                 360                 365

Ala Tyr Gln Asp Phe Ser Pro Arg His His Ala His Trp Gln Pro Met
    370                 375                 380

Asp Val Leu Ala Asn Phe Asn Ala Ile Gln Arg Trp Gln Leu Val Asp
385                 390                 395                 400

Leu Lys Gly Glu Gly Leu Pro Gly Leu Leu Tyr Gln Asp Lys Gly Ala
                405                 410                 415

Trp Trp Tyr Arg Ser Ala Gln Arg Leu Gly Glu Ile Gly Ser Asp Ala
            420                 425                 430

Val Thr Trp Glu Lys Met Gln Pro Leu Ser Val Ile Pro Ser Leu Gln
        435                 440                 445

Ser Asn Ala Ser Leu Val Asp Ile Asn Gly Asp Gly Gln Leu Asp Trp
    450                 455                 460

Val Ile Thr Gly Pro Gly Leu Arg Gly Tyr His Ser Gln Arg Pro Asp
465                 470                 475                 480

Gly Ser Trp Thr Arg Phe Thr Pro Leu Asn Ala Leu Pro Val Glu Tyr
                485                 490                 495

Thr His Pro Arg Ala Gln Leu Ala Asp Leu Met Gly Ala Gly Leu Ser
            500                 505                 510

Asp Leu Val Leu Ile Gly Pro Lys Ser Val Arg Leu Tyr Ala Asn Thr
        515                 520                 525

Arg Asp Gly Phe Ala Lys Gly Lys Asp Val Val Gln Ser Gly Asp Ile
    530                 535                 540

Thr Leu Pro Val Pro Gly Ala Asp Pro Arg Lys Leu Val Ala Phe Ser
545                 550                 555                 560

Asp Val Leu Gly Ser Gly Gln Ala His Leu Val Glu Val Ser Ala Thr
                565                 570                 575

Lys Val Thr Cys Trp Pro Asn Leu Gly Arg Gly Arg Phe Gly Gln Pro
            580                 585                 590

Ile Thr Leu Pro Gly Phe Ser Gln Pro Ala Thr Glu Phe Asn Pro Ala
        595                 600                 605

Gln Val Tyr Leu Ala Asp Leu Asp Gly Ser Gly Pro Thr Asp Leu Ile
    610                 615                 620

Tyr Val His Thr Asn Arg Leu Asp Ile Phe Leu Asn Lys Ser Gly Asn
625                 630                 635                 640

Gly Phe Ala Glu Pro Val Thr Leu Arg Phe Pro Glu Gly Leu Arg Phe
                645                 650                 655
```

-continued

```
Asp His Thr Cys Gln Leu Gln Met Ala Asp Val Gln Gly Leu Gly Val
        660                 665                 670

Ala Ser Leu Ile Leu Ser Val Pro His Met Ser Pro His His Trp Arg
        675                 680                 685

Cys Asp Leu Thr Asn Met Lys Pro Trp Leu Leu Asn Glu Met Asn Asn
        690                 695                 700

Asn Met Gly Val His His Thr Leu Arg Tyr Arg Ser Ser Ser Gln Phe
705                 710                 715                 720

Trp Leu Asp Glu Lys Ala Ala Ala Leu Thr Thr Gly Gln Thr Pro Val
                725                 730                 735

Cys Tyr Leu Pro Phe Pro Ile His Thr Leu Trp Gln Thr Glu Thr Glu
                740                 745                 750

Asp Glu Ile Ser Gly Asn Lys Leu Val Thr Thr Leu Arg Tyr Ala Arg
                755                 760                 765

Gly Ala Trp Asp Gly Arg Glu Arg Glu Phe Arg Gly Phe Gly Tyr Val
        770                 775                 780

Glu Gln Thr Asp Ser His Gln Leu Ala Gln Gly Asn Ala Pro Glu Arg
785                 790                 795                 800

Thr Pro Pro Ala Leu Thr Lys Asn Trp Tyr Ala Thr Gly Leu Pro Val
                805                 810                 815

Ile Asp Asn Ala Leu Ser Thr Glu Tyr Trp Arg Asp Gln Ala Phe
                820                 825                 830

Ala Gly Phe Ser Pro Arg Phe Thr Thr Trp Gln Asp Asn Lys Asp Val
                835                 840                 845

Pro Leu Thr Pro Glu Asp Asp Asn Ser Arg Tyr Trp Phe Asn Arg Ala
850                 855                 860

Leu Lys Gly Gln Leu Leu Arg Ser Glu Leu Tyr Gly Leu Asp Asp Ser
865                 870                 875                 880

Thr Asn Lys His Val Pro Tyr Thr Val Thr Glu Phe Arg Ser Gln Val
                885                 890                 895

Arg Arg Leu Gln His Thr Asp Ser Arg Tyr Pro Val Leu Trp Ser Ser
                900                 905                 910

Val Val Glu Ser Arg Asn Tyr His Tyr Glu Arg Ile Ala Ser Asp Pro
                915                 920                 925

Gln Cys Ser Gln Asn Ile Thr Leu Ser Ser Asp Arg Phe Gly Gln Pro
            930                 935                 940

Leu Lys Gln Leu Ser Val Gln Tyr Pro Arg Arg Gln Pro Ala Ile
945                 950                 955                 960

Asn Leu Tyr Pro Asp Thr Leu Pro Asp Lys Leu Leu Ala Asn Ser Tyr
                965                 970                 975

Asp Asp Gln Gln Arg Gln Leu Arg Leu Thr Tyr Gln Ser Ser Trp
                980                 985                 990

His His Leu Thr Asn Asn Thr Val  Arg Val Leu Gly Leu  Pro Asp Ser
            995                 1000                1005

Thr Arg  Ser Asp Ile Phe Thr  Tyr Gly Ala Glu Asn  Val Pro Ala
    1010                1015                1020

Gly Gly  Leu Asn Leu Glu Leu  Leu Ser Asp Lys Asn  Ser Leu Ile
    1025                1030                1035

Ala Asp  Asp Lys Pro Arg Glu  Tyr Leu Gly Gln Gln  Lys Thr Ala
    1040                1045                1050

Tyr Thr  Asp Gly Gln Asn Thr  Thr Pro Leu Gln Thr  Pro Thr Arg
    1055                1060                1065

Gln Ala  Leu Ile Ala Phe Thr  Glu Thr Thr Val Phe  Asn Gln Ser
```

-continued

```
                     1070                1075              1080
Thr Leu Ser Ala Phe Asn Gly Ser Ile Pro Ser Asp Lys Leu Ser
    1085                1090              1095

Thr Thr Leu Glu Gln Ala Gly Tyr Gln Gln Thr Asn Tyr Leu Phe
    1100                1105              1110

Pro Arg Thr Gly Glu Asp Lys Val Trp Val Ala His His Gly Tyr
    1115                1120              1125

Thr Asp Tyr Gly Thr Ala Ala Gln Phe Trp Arg Pro Gln Lys Gln
    1130                1135              1140

Ser Asn Thr Gln Leu Thr Gly Lys Ile Thr Leu Ile Trp Asp Ala
    1145                1150              1155

Asn Tyr Cys Val Val Val Gln Thr Arg Asp Ala Ala Gly Leu Thr
    1160                1165              1170

Thr Ser Ala Lys Tyr Asp Trp Arg Phe Leu Thr Pro Val Gln Leu
    1175                1180              1185

Thr Asp Ile Asn Asp Asn Gln His Leu Ile Thr Leu Asp Ala Leu
    1190                1195              1200

Gly Arg Pro Ile Thr Leu Arg Phe Trp Gly Thr Glu Asn Gly Lys
    1205                1210              1215

Met Thr Gly Tyr Ser Ser Pro Glu Lys Ala Ser Phe Ser Pro Pro
    1220                1225              1230

Ser Asp Val Asn Ala Ala Ile Glu Leu Lys Lys Pro Leu Pro Val
    1235                1240              1245

Ala Gln Cys Gln Val Tyr Ala Pro Glu Ser Trp Met Pro Val Leu
    1250                1255              1260

Ser Gln Lys Thr Phe Asn Arg Leu Ala Glu Gln Asp Trp Gln Lys
    1265                1270              1275

Leu Tyr Asn Ala Arg Ile Ile Thr Glu Asp Gly Arg Ile Cys Thr
    1280                1285              1290

Leu Ala Tyr Arg Arg Trp Val Gln Ser Gln Lys Ala Ile Pro Gln
    1295                1300              1305

Leu Ile Ser Leu Leu Asn Asn Gly Pro Arg Leu Pro Pro His Ser
    1310                1315              1320

Leu Thr Leu Thr Thr Asp Arg Tyr Asp His Asp Pro Glu Gln Gln
    1325                1330              1335

Ile Arg Gln Gln Val Val Phe Ser Asp Gly Phe Gly Arg Leu Leu
    1340                1345              1350

Gln Ala Ala Ala Arg His Glu Ala Gly Met Ala Arg Gln Arg Asn
    1355                1360              1365

Glu Asp Gly Ser Leu Ile Ile Asn Val Gln His Thr Glu Asn Arg
    1370                1375              1380

Trp Ala Val Thr Gly Arg Thr Glu Tyr Asp Asn Lys Gly Gln Pro
    1385                1390              1395

Ile Arg Thr Tyr Gln Pro Tyr Phe Leu Asn Asp Trp Arg Tyr Val
    1400                1405              1410

Ser Asn Asp Ser Ala Arg Gln Glu Lys Glu Ala Tyr Ala Asp Thr
    1415                1420              1425

His Val Tyr Asp Pro Ile Gly Arg Glu Ile Lys Val Ile Thr Ala
    1430                1435              1440

Lys Gly Trp Phe Arg Arg Thr Leu Phe Thr Pro Trp Phe Thr Val
    1445                1450              1455

Asn Glu Asp Glu Asn Asp Thr Ala Ala Glu Val Lys Lys Val Lys
    1460                1465              1470
```

Met

<210> SEQ ID NO 46
<211> LENGTH: 2883
<212> TYPE: DNA
<213> ORGANISM: Photorhabdus luminescens
<220> FEATURE:
<221> NAME/KEY: CDS
<222> LOCATION: (1)..(2880)

<400> SEQUENCE: 46

| atg aaa aac att gat ccc aaa ctt tat caa aaa acc cct act gtc agc | 48 |
|---|---|
| Met Lys Asn Ile Asp Pro Lys Leu Tyr Gln Lys Thr Pro Thr Val Ser | |
| 1               5                   10                  15 | |

| gtt tac gat aac cgt ggt ctg ata atc cgt aac atc gat ttt cat cgt | 96 |
|---|---|
| Val Tyr Asp Asn Arg Gly Leu Ile Ile Arg Asn Ile Asp Phe His Arg | |
|                 20                  25                  30 | |

| act acc gca aat ggt gat ccc gat acc cgt att acc cgc cat caa tac | 144 |
|---|---|
| Thr Thr Ala Asn Gly Asp Pro Asp Thr Arg Ile Thr Arg His Gln Tyr | |
|             35                  40                  45 | |

| gat att cac gga cac cta aat caa agc atc gat ccg cgc cta tat gaa | 192 |
|---|---|
| Asp Ile His Gly His Leu Asn Gln Ser Ile Asp Pro Arg Leu Tyr Glu | |
|         50                  55                  60 | |

| gcc aag caa acc aac aat acg atc aaa ccc aat ttt ctt tgg cag tat | 240 |
|---|---|
| Ala Lys Gln Thr Asn Asn Thr Ile Lys Pro Asn Phe Leu Trp Gln Tyr | |
| 65                  70                  75                  80 | |

| gat ttg acc ggt aat ccc cta tgt aca gag agc att gat gca ggt cgc | 288 |
|---|---|
| Asp Leu Thr Gly Asn Pro Leu Cys Thr Glu Ser Ile Asp Ala Gly Arg | |
|                 85                  90                  95 | |

| act gtc acc ttg aat gat att gaa ggc cgt ccg cta cta acg gtg act | 336 |
|---|---|
| Thr Val Thr Leu Asn Asp Ile Glu Gly Arg Pro Leu Leu Thr Val Thr | |
|             100                 105                 110 | |

| gca aca ggg gtt ata caa act cga caa tat gaa act tct tcc ctg ccc | 384 |
|---|---|
| Ala Thr Gly Val Ile Gln Thr Arg Gln Tyr Glu Thr Ser Ser Leu Pro | |
|         115                 120                 125 | |

| ggt cgt ctg tta tct gtt gcc gaa caa aca ccc gag gaa aaa aca tcc | 432 |
|---|---|
| Gly Arg Leu Leu Ser Val Ala Glu Gln Thr Pro Glu Glu Lys Thr Ser | |
| 130                 135                 140 | |

| cgt atc acc gaa cgc ctg att tgg gct ggc aat acc gaa gca gag aaa | 480 |
|---|---|
| Arg Ile Thr Glu Arg Leu Ile Trp Ala Gly Asn Thr Glu Ala Glu Lys | |
| 145                 150                 155                 160 | |

| gac cat aac ctt gcc ggc cag tgc gtg cgt cac tat gac acg gcg gga | 528 |
|---|---|
| Asp His Asn Leu Ala Gly Gln Cys Val Arg His Tyr Asp Thr Ala Gly | |
|                 165                 170                 175 | |

| gtt acc cgg tta gag agt tta tca ctg acc ggt act gtt tta tct caa | 576 |
|---|---|
| Val Thr Arg Leu Glu Ser Leu Ser Leu Thr Gly Thr Val Leu Ser Gln | |
|             180                 185                 190 | |

| tcc agc caa cta ttg atc gac act caa gag gca aac tgg aca ggt gat | 624 |
|---|---|
| Ser Ser Gln Leu Leu Ile Asp Thr Gln Glu Ala Asn Trp Thr Gly Asp | |
|         195                 200                 205 | |

| aac gaa acc gtc tgg caa aac atg ctg gct gat gac atc tac aca acc | 672 |
|---|---|
| Asn Glu Thr Val Trp Gln Asn Met Leu Ala Asp Asp Ile Tyr Thr Thr | |
| 210                 215                 220 | |

| ctg agc acc ttc gat gcc acc ggt gct tta ctg act cag acc gat gcg | 720 |
|---|---|
| Leu Ser Thr Phe Asp Ala Thr Gly Ala Leu Leu Thr Gln Thr Asp Ala | |
| 225                 230                 235                 240 | |

| aaa ggg aac att cag aga ctg gct tat gat gtg gcc ggg cag cta aac | 768 |
|---|---|
| Lys Gly Asn Ile Gln Arg Leu Ala Tyr Asp Val Ala Gly Gln Leu Asn | |
|                 245                 250                 255 | |

| ggg agc tgg cta aca ctc aaa ggc cag acg gaa caa gtg att atc aaa | 816 |

```
            Gly Ser Trp Leu Thr Leu Lys Gly Gln Thr Glu Gln Val Ile Ile Lys
                        260                 265                 270 tcc ctg acc tac tcc gcc gcc gga caa aaa tta cgt gag gaa cac ggc        864
Ser Leu Thr Tyr Ser Ala Ala Gly Gln Lys Leu Arg Glu Glu His Gly
            275                 280                 285 aat gat gtt atc acc gaa tac agt tat gaa ccg gaa acc caa cgg ctg        912
Asn Asp Val Ile Thr Glu Tyr Ser Tyr Glu Pro Glu Thr Gln Arg Leu
        290                 295                 300 atc ggt atc aaa acc cgc cgt ccg tca gac act aaa gtg cta caa gac        960
Ile Gly Ile Lys Thr Arg Arg Pro Ser Asp Thr Lys Val Leu Gln Asp
305                 310                 315                 320 ctg cgc tat gaa tat gac ccg gta ggc aat gtc atc agc atc cgt aat       1008
Leu Arg Tyr Glu Tyr Asp Pro Val Gly Asn Val Ile Ser Ile Arg Asn
                325                 330                 335 gac gcg gaa gcc acc cgc ttt tgg cac aat cag aaa gtg atg ccg gaa       1056
Asp Ala Glu Ala Thr Arg Phe Trp His Asn Gln Lys Val Met Pro Glu
            340                 345                 350 aac act tat acc tac gat tcc ctg tat cag ctt atc agc gcc acc ggg       1104
Asn Thr Tyr Thr Tyr Asp Ser Leu Tyr Gln Leu Ile Ser Ala Thr Gly
        355                 360                 365 cgc gaa atg gcg aat ata ggt caa caa agt cac caa ttt ccc tca ccc       1152
Arg Glu Met Ala Asn Ile Gly Gln Gln Ser His Gln Phe Pro Ser Pro
370                 375                 380 gct cta cct tct gat aac aac acc tat acc aac tat acc cgt act tat       1200
Ala Leu Pro Ser Asp Asn Asn Thr Tyr Thr Asn Tyr Thr Arg Thr Tyr
                385                 390                 395                 400 act tat gac cgt ggc ggc aat ctg acc aaa atc cag cac agt tca ccg       1248
Thr Tyr Asp Arg Gly Gly Asn Leu Thr Lys Ile Gln His Ser Ser Pro
            405                 410                 415 gcg acg caa aac aac tac acc acc aat atc acg gtt tca aat cgc agc       1296
Ala Thr Gln Asn Asn Tyr Thr Thr Asn Ile Thr Val Ser Asn Arg Ser
        420                 425                 430 aac cgc gca gta ctc agc aca ttg acc gaa gat ccg gcg caa gta gat       1344
Asn Arg Ala Val Leu Ser Thr Leu Thr Glu Asp Pro Ala Gln Val Asp
                435                 440                 445 gct ttg ttt gat gca ggc gga cat cag aac acc ttg ata tca gga caa       1392
Ala Leu Phe Asp Ala Gly Gly His Gln Asn Thr Leu Ile Ser Gly Gln
        450                 455                 460 aac ctg aac tgg aat act cgt ggt gaa ctg caa caa gta aca ctg gtt       1440
Asn Leu Asn Trp Asn Thr Arg Gly Glu Leu Gln Gln Val Thr Leu Val
465                 470                 475                 480 aaa cgg gac aag ggc gcc aat gat gat cgg gaa tgg tat cgt tat agc       1488
Lys Arg Asp Lys Gly Ala Asn Asp Asp Arg Glu Trp Tyr Arg Tyr Ser
                485                 490                 495 ggt gac gga aga agg atg tta aaa atc aat gaa cag cag gcc agc aac       1536
Gly Asp Gly Arg Arg Met Leu Lys Ile Asn Glu Gln Gln Ala Ser Asn
            500                 505                 510 aac gct caa aca caa cgt gtg act tat ttg ccg aac tta gaa ctt cgt       1584
Asn Ala Gln Thr Gln Arg Val Thr Tyr Leu Pro Asn Leu Glu Leu Arg
        515                 520                 525 cta aca caa aac agc acg gcc aca acc gaa gat ttg caa gtt atc acc       1632
Leu Thr Gln Asn Ser Thr Ala Thr Thr Glu Asp Leu Gln Val Ile Thr
    530                 535                 540 gta ggc gaa gcg ggc cgg gca cag gta cga gta tta cat tgg gag agc       1680
Val Gly Glu Ala Gly Arg Ala Gln Val Arg Val Leu His Trp Glu Ser
545                 550                 555                 560 ggt aaa ccg gaa gat atc gac aat aat cag ttg cgt tat agt tac gat       1728
Gly Lys Pro Glu Asp Ile Asp Asn Asn Gln Leu Arg Tyr Ser Tyr Asp
            565                 570                 575
```

```
-continued aat ctt atc ggt tcc agt caa ctt gaa tta gat agc gaa gga caa att     1776
Asn Leu Ile Gly Ser Ser Gln Leu Glu Leu Asp Ser Glu Gly Gln Ile
            580                 585                 590 atc agt gaa gaa gaa tat tat ccc tat ggt gga aca gca tta tgg gcc     1824
Ile Ser Glu Glu Glu Tyr Tyr Pro Tyr Gly Gly Thr Ala Leu Trp Ala
        595                 600                 605 gcc agg aat cag aca gaa gcc agt tat aaa act atc cgt tat tca ggc     1872
Ala Arg Asn Gln Thr Glu Ala Ser Tyr Lys Thr Ile Arg Tyr Ser Gly
610                 615                 620 aaa gag cgg gat gcc acc ggg cta tat tac tac ggc tat cgg tat tac     1920
Lys Glu Arg Asp Ala Thr Gly Leu Tyr Tyr Tyr Gly Tyr Arg Tyr Tyr
625                 630                 635                 640 caa ccg tgg ata gga cgg tgg tta agc tcc gat ccg gca gga aca atc     1968
Gln Pro Trp Ile Gly Arg Trp Leu Ser Ser Asp Pro Ala Gly Thr Ile
            645                 650                 655 gat ggg ctg aat tta tat cgg atg gtg agg aat aat cca gtt acc ctc     2016
Asp Gly Leu Asn Leu Tyr Arg Met Val Arg Asn Asn Pro Val Thr Leu
        660                 665                 670 ctt gat cct gat gga tta atg cca aca att gca gaa cgc ata gca gca     2064
Leu Asp Pro Asp Gly Leu Met Pro Thr Ile Ala Glu Arg Ile Ala Ala
    675                 680                 685 cta aaa aaa aat aaa gta aca gac tca gcg cct tcg cca gca aat gcc     2112
Leu Lys Lys Asn Lys Val Thr Asp Ser Ala Pro Ser Pro Ala Asn Ala
690                 695                 700 aca aac gta gcg ata aac atc cgc ccg cct gta gca cca aaa cct agc     2160
Thr Asn Val Ala Ile Asn Ile Arg Pro Pro Val Ala Pro Lys Pro Ser
705                 710                 715                 720 tta ccg aaa gca tca acg agt agc caa cca acc aca cac cct atc gga     2208
Leu Pro Lys Ala Ser Thr Ser Ser Gln Pro Thr Thr His Pro Ile Gly
            725                 730                 735 gct gca aac ata aaa cca acg acg tct ggg tca tct att gtt gct cca     2256
Ala Ala Asn Ile Lys Pro Thr Thr Ser Gly Ser Ser Ile Val Ala Pro
        740                 745                 750 ttg agt cca gta gga aat aaa tct act tct gaa atc tct ctg cca gaa     2304
Leu Ser Pro Val Gly Asn Lys Ser Thr Ser Glu Ile Ser Leu Pro Glu
    755                 760                 765 agc gct caa agc agt tct tca agc act acc tcg aca aat cta cag aaa     2352
Ser Ala Gln Ser Ser Ser Ser Ser Thr Thr Ser Thr Asn Leu Gln Lys
770                 775                 780 aaa tca ttt act tta tat aga gca gat aac aga tcc ttt gaa gaa atg     2400
Lys Ser Phe Thr Leu Tyr Arg Ala Asp Asn Arg Ser Phe Glu Glu Met
785                 790                 795                 800 caa agt aaa ttc cct gaa gga ttt aaa gcc tgg act cct cta gac act     2448
Gln Ser Lys Phe Pro Glu Gly Phe Lys Ala Trp Thr Pro Leu Asp Thr
            805                 810                 815 aag atg gca agg caa ttt gct agt atc ttt att ggt cag aaa gat aca     2496
Lys Met Ala Arg Gln Phe Ala Ser Ile Phe Ile Gly Gln Lys Asp Thr
        820                 825                 830 tct aat tta cct aaa gaa aca gtc aag aac ata agc aca tgg gga gca     2544
Ser Asn Leu Pro Lys Glu Thr Val Lys Asn Ile Ser Thr Trp Gly Ala
    835                 840                 845 aag cca aaa cta aaa gat ctc tca aat tac ata aaa tat acc aag gac     2592
Lys Pro Lys Leu Lys Asp Leu Ser Asn Tyr Ile Lys Tyr Thr Lys Asp
850                 855                 860 aaa tct aca gta tgg gtt tct act gca att aat act gaa gca ggt gga     2640
Lys Ser Thr Val Trp Val Ser Thr Ala Ile Asn Thr Glu Ala Gly Gly
865                 870                 875                 880 caa agc tca ggg gct cca ctc cat aaa att gat atg gat ctc tac gag     2688
Gln Ser Ser Gly Ala Pro Leu His Lys Ile Asp Met Asp Leu Tyr Glu
            885                 890                 895
```

| | | | | | | | | | | | | |
|---|---|---|---|---|---|---|---|---|---|---|---|---|
| ttt | gcc | att | gat | gga | caa | aaa | cta | aat | cca | cta | ccg | gag | ggt | aga | act | 2736 |
| Phe | Ala | Ile | Asp | Gly | Gln | Lys | Leu | Asn | Pro | Leu | Pro | Glu | Gly | Arg | Thr | |
|     |     | 900 |     |     |     | 905 |     |     |     |     | 910 |     |     |     |     | |
| aaa | aac | atg | gta | cct | tcc | ctt | tta | ctc | gac | acc | cca | caa | ata | gag | aca | 2784 |
| Lys | Asn | Met | Val | Pro | Ser | Leu | Leu | Leu | Asp | Thr | Pro | Gln | Ile | Glu | Thr | |
|     |     | 915 |     |     |     | 920 |     |     |     |     | 925 |     |     |     |     | |
| tca | tcc | atc | att | gca | ctt | aat | cat | gga | ccg | gta | aat | gat | gca | gaa | att | 2832 |
| Ser | Ser | Ile | Ile | Ala | Leu | Asn | His | Gly | Pro | Val | Asn | Asp | Ala | Glu | Ile | |
|     |     | 930 |     |     |     | 935 |     |     |     |     | 940 |     |     |     |     | |
| tca | ttt | ctg | aca | aca | att | ccg | ctt | aaa | aat | gta | aaa | cct | cat | aag | aga | 2880 |
| Ser | Phe | Leu | Thr | Thr | Ile | Pro | Leu | Lys | Asn | Val | Lys | Pro | His | Lys | Arg | |
| 945 |     |     |     |     | 950 |     |     |     |     | 955 |     |     |     |     | 960 | |
| taa | | | | | | | | | | | | | | | | 2883 |

<210> SEQ ID NO 47
<211> LENGTH: 960
<212> TYPE: PRT
<213> ORGANISM: Photorhabdus luminescens

<400> SEQUENCE: 47

```
Met Lys Asn Ile Asp Pro Lys Leu Tyr Gln Lys Thr Pro Thr Val Ser
1               5                   10                  15

Val Tyr Asp Asn Arg Gly Leu Ile Ile Arg Asn Ile Asp Phe His Arg
            20                  25                  30

Thr Thr Ala Asn Gly Asp Pro Asp Thr Arg Ile Thr Arg His Gln Tyr
        35                  40                  45

Asp Ile His Gly His Leu Asn Gln Ser Ile Asp Pro Arg Leu Tyr Glu
    50                  55                  60

Ala Lys Gln Thr Asn Asn Thr Ile Lys Pro Asn Phe Leu Trp Gln Tyr
65                  70                  75                  80

Asp Leu Thr Gly Asn Pro Leu Cys Thr Glu Ser Ile Asp Ala Gly Arg
                85                  90                  95

Thr Val Thr Leu Asn Asp Ile Glu Gly Arg Pro Leu Leu Thr Val Thr
            100                 105                 110

Ala Thr Gly Val Ile Gln Thr Arg Gln Tyr Glu Thr Ser Ser Leu Pro
        115                 120                 125

Gly Arg Leu Leu Ser Val Ala Glu Gln Thr Pro Glu Glu Lys Thr Ser
    130                 135                 140

Arg Ile Thr Glu Arg Leu Ile Trp Ala Gly Asn Thr Glu Ala Glu Lys
145                 150                 155                 160

Asp His Asn Leu Ala Gly Gln Cys Val Arg His Tyr Asp Thr Ala Gly
                165                 170                 175

Val Thr Arg Leu Glu Ser Leu Ser Leu Thr Gly Thr Val Leu Ser Gln
            180                 185                 190

Ser Ser Gln Leu Leu Ile Asp Thr Gln Glu Ala Asn Trp Thr Gly Asp
        195                 200                 205

Asn Glu Thr Val Trp Gln Asn Met Leu Ala Asp Ile Tyr Thr Thr
    210                 215                 220

Leu Ser Thr Phe Asp Ala Thr Gly Ala Leu Leu Thr Gln Thr Asp Ala
225                 230                 235                 240

Lys Gly Asn Ile Gln Arg Leu Ala Tyr Asp Val Ala Gly Gln Leu Asn
                245                 250                 255

Gly Ser Trp Leu Thr Leu Lys Gly Gln Thr Glu Gln Val Ile Ile Lys
            260                 265                 270

Ser Leu Thr Tyr Ser Ala Ala Gly Gln Lys Leu Arg Glu Glu His Gly
```

-continued

```
              275                 280                 285
Asn Asp Val Ile Thr Glu Tyr Ser Tyr Glu Pro Glu Thr Gln Arg Leu
            290                 295                 300
Ile Gly Ile Lys Thr Arg Arg Pro Ser Asp Thr Lys Val Leu Gln Asp
305                 310                 315                 320
Leu Arg Tyr Glu Tyr Asp Pro Val Gly Asn Val Ile Ser Ile Arg Asn
                325                 330                 335
Asp Ala Glu Ala Thr Arg Phe Trp His Asn Gln Lys Val Met Pro Glu
            340                 345                 350
Asn Thr Tyr Thr Tyr Asp Ser Leu Tyr Gln Leu Ile Ser Ala Thr Gly
                355                 360                 365
Arg Glu Met Ala Asn Ile Gly Gln Gln Ser His Gln Phe Pro Ser Pro
            370                 375                 380
Ala Leu Pro Ser Asp Asn Asn Thr Tyr Thr Asn Tyr Thr Arg Thr Tyr
385                 390                 395                 400
Thr Tyr Asp Arg Gly Gly Asn Leu Thr Lys Ile Gln His Ser Ser Pro
                405                 410                 415
Ala Thr Gln Asn Asn Tyr Thr Thr Asn Ile Thr Val Ser Asn Arg Ser
            420                 425                 430
Asn Arg Ala Val Leu Ser Thr Leu Thr Glu Asp Pro Ala Gln Val Asp
            435                 440                 445
Ala Leu Phe Asp Ala Gly Gly His Gln Asn Thr Leu Ile Ser Gly Gln
            450                 455                 460
Asn Leu Asn Trp Asn Thr Arg Gly Glu Leu Gln Gln Val Thr Leu Val
465                 470                 475                 480
Lys Arg Asp Lys Gly Ala Asn Asp Asp Arg Glu Trp Tyr Arg Tyr Ser
                485                 490                 495
Gly Asp Gly Arg Arg Met Leu Lys Ile Asn Glu Gln Gln Ala Ser Asn
                500                 505                 510
Asn Ala Gln Thr Gln Arg Val Thr Tyr Leu Pro Asn Leu Glu Leu Arg
            515                 520                 525
Leu Thr Gln Asn Ser Thr Ala Thr Thr Glu Asp Leu Gln Val Ile Thr
            530                 535                 540
Val Gly Glu Ala Gly Arg Ala Gln Val Arg Val Leu His Trp Glu Ser
545                 550                 555                 560
Gly Lys Pro Glu Asp Ile Asp Asn Asn Gln Leu Arg Tyr Ser Tyr Asp
                565                 570                 575
Asn Leu Ile Gly Ser Ser Gln Leu Glu Leu Asp Ser Glu Gly Gln Ile
            580                 585                 590
Ile Ser Glu Glu Glu Tyr Tyr Pro Tyr Gly Gly Thr Ala Leu Trp Ala
            595                 600                 605
Ala Arg Asn Gln Thr Glu Ala Ser Tyr Lys Thr Ile Arg Tyr Ser Gly
            610                 615                 620
Lys Glu Arg Asp Ala Thr Gly Leu Tyr Tyr Gly Tyr Arg Tyr Tyr
625                 630                 635                 640
Gln Pro Trp Ile Gly Arg Trp Leu Ser Ser Asp Pro Ala Gly Thr Ile
                645                 650                 655
Asp Gly Leu Asn Leu Tyr Arg Met Val Arg Asn Asn Pro Val Thr Leu
            660                 665                 670
Leu Asp Pro Asp Gly Leu Met Pro Thr Ile Ala Glu Arg Ile Ala Ala
            675                 680                 685
Leu Lys Lys Asn Lys Val Thr Asp Ser Ala Pro Ser Pro Ala Asn Ala
            690                 695                 700
```

| | | | | | | | | | | |
|---|---|---|---|---|---|---|---|---|---|---|
|Thr|Asn|Val|Ala|Ile|Asn|Ile|Arg|Pro|Pro|Val|Ala|Pro|Lys|Pro|Ser|
|705| | | |710| | | |715| | | |720| | | |

Leu Pro Lys Ala Ser Thr Ser Ser Gln Pro Thr Thr His Pro Ile Gly
            725                 730                 735

Ala Ala Asn Ile Lys Pro Thr Thr Ser Gly Ser Ser Ile Val Ala Pro
            740                 745                 750

Leu Ser Pro Val Gly Asn Lys Ser Thr Ser Glu Ile Ser Leu Pro Glu
            755                 760                 765

Ser Ala Gln Ser Ser Ser Ser Thr Thr Ser Thr Asn Leu Gln Lys
770                 775                 780

Lys Ser Phe Thr Leu Tyr Arg Ala Asp Asn Arg Ser Phe Glu Glu Met
785                 790                 795                 800

Gln Ser Lys Phe Pro Glu Gly Phe Lys Ala Trp Thr Pro Leu Asp Thr
            805                 810                 815

Lys Met Ala Arg Gln Phe Ala Ser Ile Phe Ile Gly Gln Lys Asp Thr
            820                 825                 830

Ser Asn Leu Pro Lys Glu Thr Val Lys Asn Ile Ser Thr Trp Gly Ala
            835                 840                 845

Lys Pro Lys Leu Lys Asp Leu Ser Asn Tyr Ile Lys Tyr Thr Lys Asp
            850                 855                 860

Lys Ser Thr Val Trp Val Ser Thr Ala Ile Asn Thr Glu Ala Gly Gly
865                 870                 875                 880

Gln Ser Ser Gly Ala Pro Leu His Lys Ile Asp Met Asp Leu Tyr Glu
            885                 890                 895

Phe Ala Ile Asp Gly Gln Lys Leu Asn Pro Leu Pro Glu Gly Arg Thr
            900                 905                 910

Lys Asn Met Val Pro Ser Leu Leu Leu Asp Thr Pro Gln Ile Glu Thr
            915                 920                 925

Ser Ser Ile Ile Ala Leu Asn His Gly Pro Val Asn Asp Ala Glu Ile
            930                 935                 940

Ser Phe Leu Thr Thr Ile Pro Leu Lys Asn Val Lys Pro His Lys Arg
945                 950                 955                 960

<210> SEQ ID NO 48
<211> LENGTH: 4521
<212> TYPE: DNA
<213> ORGANISM: Xenorhabdus bovienii

<400> SEQUENCE: 48

```
atgaaacaag attcacagga catgacagta acacagctgt ccctgcccaa agggggcggt    60
gcgatcagtg gcatgggtga cactatcagc aatgcaggac cggatgggat ggcttcgctt   120
tccgtgcctt tgcctatctc tgccggtcgg gggggcgcac cgaatttatc cctgaactac   180
agtagcggag caggaaacgg gtcatttggt attggctggc aatccagtac catggctatc   240
agccgtcgta ctcaacatgg cgtaccgcaa tatcacggcg aagatacttt tttatgtccg   300
atgggagaag tgatggcggt tgccgtcaat cagagcgggc aacccgatgt gcgtaaaacc   360
gataaactat taggcgggca actgcctgtt acttataccg ttacgcgtca tcagcccaga   420
aatattcagc acttcagcaa acttgaatac tggcagcccc caacggatgt ggaaaccacg   480
ccttttggt taatgtattc acccgatgga caaattcaca ttttcggaaa aactgagcag   540
gctcagatcg ctaaccccgg cagaggtttca cagattgccc aatggctttt ggaagaaacc   600
gtaacaccag cgggagaaca catttattac cagtatcggg cagaagacga tatcggttgt   660
```

-continued

```
gatgacagcg aaaaaaatgc ccaccctaat gccagtgctc aacgttattt gactcaggtg      720
aactacggca atattacacc tgaatccagc ctgcttgtgc tgaagaatac gccaccggcg      780
gataacgaat ggctattcca tttggttttt gattatggtg aacgagcgca ggaaataaac      840
acggttcctc ctttcaaagc accttcaaac aactggaaaa tacggccaga ccgtttctcc      900
cgctttgaat atggttttga ggtgcgaacc cgccgcctgt gtcaacaaat tctgatgttc      960
catcgcctga aatcccttgc aggagaacag attgacggag aagaaatccc tgccttggtt     1020
gcccgtctgc ttctcagtta tgacctgaac gacagcgtga caaccccttac cgccattcgg    1080 caaatggcgt atgaaactga cgcaaccttta atcgctttac cgccactgga gtttgactat    1140
cagccctttg aggcaaaagt cacgcagaaa tggcaggaaa tgcctcaatt ggccggattg     1200
aatgcccaac aaccttacca actcgtcgat ctctatggtg aaggtatctc cggcatcttg     1260
tatcaggaca gacccggagc atggtggtat caggcaccga tccgtcagaa aaacgttgaa     1320
gatattaacg ctgtcaccta tagcccaata aaccccttac ctaagatccc cagccagcag    1380
gacagagcaa cgttgatgga tatcgacggt gatggacatc tggattgggt gatcgctggc    1440
gcaggtattc aggggcggta cagtatgcag ccgaatggag agtggacaca ctttattccc    1500
atttctgcac tgccaacaga atattttcat ccacaggcac aactggcgga tctggtgggg    1560
gccgggttat ctgatttagc gctgattggc cccagaagtg tgcgtttata tgccaacgac    1620
cgaggaaact ggaaagcggg tattaatgtt atgccacctg atggtgtgaa tttgccgata    1680
tttggtggtg atgccagcag tctgtcgca ttttctgaca tgttgggatc gggacagcag    1740
catttggtgg aaattgccgc tcagagcgtc aaatgctggc cgaatctagg acatggccgt    1800
tttggtgcgg ctattttgct gccgggggttt agccagccga atggaacatt caatgctaac    1860 caagttttc tggcagatat cgatggttcc ggcaccgccg acatcatcta tgcacacagt    1920
acgtatctgg atatttacct gaacgaaagc ggcaaccgtt tcagtgcacc cgttcggctt    1980
aatttgccgg aaggggtgat gtttgacaat acctgtcagt tacaggtgtc ggatattcaa    2040
ggattgggcg ctgccagcat tgtactgacc gtacctcata tgacaccgcg ccattggcgt    2100
tatgatttta ctcacaataa accttggctg ctcaatgtca tcaacaacaa tcgtggcgca    2160
gaaaccacgt tgttttaccg tagttctgcc caattctggc tggatgaaaa aagtcagatc    2220
gaagagctgg gaaaatttgc agcgagttat ctgccttttcc ccatacattt gttgtggcgc    2280
aatgaggcgc tggatgaaat tactggtaat cgactgacta aggtcatgaa ttatgcccac    2340
ggtgcatggg atggcagaga gagagaattt tgcggatttg gccgtgtaac gcaaattgat    2400
accgacgaat ttgccaaggg aaccacagag aaagcgccgg atgaaaatat ctatccttcc    2460
cgtagcataa gctggtttgc cacgggttta ccagaagtgg attctcaact tccggcagaa    2520
tactggcgtg gtgacgatca ggcatttgcc ggctttacac cgcgcttcac tcgttatgaa    2580
aaaggtaatg cggggcaaga ggggcaggat accccgatta agaaccgac cgaaacagaa    2640 gcgtattggc ttaaccgcgc catgaaaggc caattactgc gcagtgaagt ctatggtgac    2700
gacaaaacag aaaaagctaa aattccgtac accgtcacag aagctcgctg tcaggtcaga    2760
ttaattccca gcaatgacga agccgcgccg tcgtcttgga cgtcgatcat tgaaaaccgc    2820
agttatcact atgagcgtat cgtcgtcgat ccgagttgca acaacaggt cgtgctcaag    2880 gcggatgaat atggcttccc actggcaaaa gtagatatcg cctatccacg gcgcaataaa    2940
ccggcacaga acccttatcc ggattcgtta ccggatactc tgttcgccga tagctatgac    3000
gaccagcaaa aacagttata tctgacaaaa cagcagcaga gctattacca cctgacccag    3060
```

```
caggatgatt gggttctggg tttgacggat agccgataca gcgaagttta tcattatgcg    3120
caaactgacg ctcaaagtga catccccaag gcagggctga tattggaaga cctgctgaaa    3180
gttgacggcc tgataggtaa agacaagact tttatctatt tagggcagca gcgagtggct    3240
tatgtgggag gagatgcaga aaaaccgaca cgtcaggtgc gggtggctta tacagaaacc    3300
gctgcttttg atgacaatgc gctgcacgcc tttgatggcg tgattgcccc tgatgaactg    3360
acgcaacagt tgctggcggg tggataccta ctcgtgccgc agatttctga tgtggcaggc    3420
agtagtgaaa aggtatgggt agctcggcag ggatacaccg aatacggcag tgctgctcaa    3480
ttctaccggc cactcatcca gcgcaaaagc ttgctgaccg aaaatatac ccttagttgg     3540 gatacgcact attgtgtggt ggtaaaaacc gaagatggtg cgggaatgac cacgcaagcg    3600
aagtacgatt accgcttcct gcttccggcg caattgacag atatcaatga caaccagcac    3660
atcgtgacat ttaatgcatt ggggcaggtg acttccagcc gtttctgggg cacagaaaat    3720
ggcaaaataa gcggttactc gacgccggag agtaaaccgt tcacagtacc cgataccgtc    3780
gaaaaagccc ttgccttgca accgacgatc ccggtttcac agtgcaacat ttatgtgccg    3840
gatagttgga tgcggcttct gccccaacag tctctgactg gccagctaaa agaggggaa    3900 actttgtgga acgcattaca ccgggcgggt gtagtaacgg aagacggttt gatctgtgaa    3960
ctggcctatc gtcgttggat caaacgtcag gcaacgtctt caatgatggc cgtgacatta    4020
cagcaaatct tggctcagac tccacgacaa cctccgcatg ccatgacgat cacgacagat    4080
cgttatgaca cgcgattctca gcagcaactt cggcagtcga tagtattgag tgatggtttt    4140
ggtcgcgtat tgcaaagcgc ccagcgtcat gaagcaggag aggcatggca gcgtgcagaa    4200
gatggttctt tggttgtcga taataccggt aaacccgttg ttgctaatac cacaacgcgc    4260
tgggcagtat ccggtcgcac agaatacgac ggcaaagggc aggcgatcag agcttacctg    4320
ccttattatc tcaatgattg cgcctatgtc agtgatgaca cgcccgggga tgacctgtac    4380
gccgataccc atttttacga tcctctgggg cgtgaatatc aggtaaaaac cgcgaaagga    4440
ttttggcgtg aaaacatgtt tatgccgtgg tttgtcgtca atgaagatga aaatgacaca    4500
gcagcacgtt taacatctta a                                              4521
```

<210> SEQ ID NO 49
<211> LENGTH: 1506
<212> TYPE: PRT
<213> ORGANISM: Xenorhabdus bovienii

<400> SEQUENCE: 49

```
Met Lys Gln Asp Ser Gln Asp Met Thr Val Thr Gln Leu Ser Leu Pro
1               5                   10                  15

Lys Gly Gly Gly Ala Ile Ser Gly Met Gly Asp Thr Ile Ser Asn Ala
            20                  25                  30

Gly Pro Asp Gly Met Ala Ser Leu Ser Val Pro Leu Pro Ile Ser Ala
        35                  40                  45

Gly Arg Gly Gly Ala Pro Asn Leu Ser Leu Asn Tyr Ser Ser Gly Ala
    50                  55                  60

Gly Asn Gly Ser Phe Gly Ile Gly Trp Gln Ser Ser Thr Met Ala Ile
65                  70                  75                  80

Ser Arg Arg Thr Gln His Gly Val Pro Gln Tyr His Gly Glu Asp Thr
                85                  90                  95

Phe Leu Cys Pro Met Gly Glu Val Met Ala Val Ala Val Asn Gln Ser
            100                 105                 110
```

-continued

```
Gly Gln Pro Asp Val Arg Lys Thr Asp Lys Leu Leu Gly Gln Leu
            115                 120                 125

Pro Val Thr Tyr Thr Val Thr Arg His Gln Pro Arg Asn Ile Gln His
        130                 135                 140

Phe Ser Lys Leu Glu Tyr Trp Gln Pro Thr Asp Val Glu Thr Thr
145                 150                 155                 160

Pro Phe Trp Leu Met Tyr Ser Pro Asp Gly Gln Ile His Ile Phe Gly
                165                 170                 175

Lys Thr Glu Gln Ala Gln Ile Ala Asn Pro Ala Glu Val Ser Gln Ile
            180                 185                 190

Ala Gln Trp Leu Leu Glu Glu Thr Val Thr Pro Ala Gly Glu His Ile
        195                 200                 205

Tyr Tyr Gln Tyr Arg Ala Glu Asp Asp Ile Gly Cys Asp Asp Ser Glu
    210                 215                 220

Lys Asn Ala His Pro Asn Ala Ser Ala Gln Arg Tyr Leu Thr Gln Val
225                 230                 235                 240

Asn Tyr Gly Asn Ile Thr Pro Glu Ser Ser Leu Val Leu Lys Asn
                245                 250                 255

Thr Pro Pro Ala Asp Asn Glu Trp Leu Phe His Leu Val Phe Asp Tyr
            260                 265                 270

Gly Glu Arg Ala Gln Glu Ile Asn Thr Val Pro Pro Phe Lys Ala Pro
        275                 280                 285

Ser Asn Asn Trp Lys Ile Arg Pro Asp Arg Phe Ser Arg Phe Glu Tyr
    290                 295                 300

Gly Phe Glu Val Arg Thr Arg Arg Leu Cys Gln Gln Ile Leu Met Phe
305                 310                 315                 320

His Arg Leu Lys Ser Leu Ala Gly Glu Gln Ile Asp Gly Glu Glu Ile
                325                 330                 335

Pro Ala Leu Val Ala Arg Leu Leu Leu Ser Tyr Asp Leu Asn Asp Ser
            340                 345                 350

Val Thr Thr Leu Thr Ala Ile Arg Gln Met Ala Tyr Glu Thr Asp Ala
        355                 360                 365

Thr Leu Ile Ala Leu Pro Pro Leu Glu Phe Asp Tyr Gln Pro Phe Glu
    370                 375                 380

Ala Lys Val Thr Gln Lys Trp Gln Glu Met Pro Gln Leu Ala Gly Leu
385                 390                 395                 400

Asn Ala Gln Gln Pro Tyr Gln Leu Val Asp Leu Tyr Gly Glu Gly Ile
                405                 410                 415

Ser Gly Ile Leu Tyr Gln Asp Arg Pro Gly Ala Trp Trp Tyr Gln Ala
            420                 425                 430

Pro Ile Arg Gln Lys Asn Val Glu Asp Ile Asn Ala Val Thr Tyr Ser
        435                 440                 445

Pro Ile Asn Pro Leu Pro Lys Ile Pro Ser Gln Asp Arg Ala Thr
    450                 455                 460

Leu Met Asp Ile Asp Gly Asp Gly His Leu Asp Trp Val Ile Ala Gly
465                 470                 475                 480

Ala Gly Ile Gln Gly Arg Tyr Ser Met Gln Pro Asn Gly Glu Trp Thr
                485                 490                 495

His Phe Ile Pro Ile Ser Ala Leu Pro Thr Glu Tyr Phe His Pro Gln
            500                 505                 510

Ala Gln Leu Ala Asp Leu Val Gly Ala Gly Leu Ser Asp Leu Ala Leu
        515                 520                 525
```

```
Ile Gly Pro Arg Ser Val Arg Leu Tyr Ala Asn Asp Arg Gly Asn Trp
    530                 535                 540
Lys Ala Gly Ile Asn Val Met Pro Pro Asp Gly Val Asn Leu Pro Ile
545                 550                 555                 560
Phe Gly Gly Asp Ala Ser Ser Leu Val Ala Phe Ser Asp Met Leu Gly
                565                 570                 575
Ser Gly Gln Gln His Leu Val Glu Ile Ala Ala Gln Ser Val Lys Cys
            580                 585                 590
Trp Pro Asn Leu Gly His Gly Arg Phe Gly Ala Ala Ile Leu Leu Pro
    595                 600                 605
Gly Phe Ser Gln Pro Asn Gly Thr Phe Asn Ala Asn Gln Val Phe Leu
    610                 615                 620
Ala Asp Ile Asp Gly Ser Gly Thr Ala Asp Ile Ile Tyr Ala His Ser
625                 630                 635                 640
Thr Tyr Leu Asp Ile Tyr Leu Asn Glu Ser Gly Asn Arg Phe Ser Ala
                645                 650                 655
Pro Val Arg Leu Asn Leu Pro Glu Gly Val Met Phe Asp Asn Thr Cys
            660                 665                 670
Gln Leu Gln Val Ser Asp Ile Gln Gly Leu Gly Ala Ala Ser Ile Val
    675                 680                 685
Leu Thr Val Pro His Met Thr Pro Arg His Trp Arg Tyr Asp Phe Thr
690                 695                 700
His Asn Lys Pro Trp Leu Leu Asn Val Ile Asn Asn Asn Arg Gly Ala
705                 710                 715                 720
Glu Thr Thr Leu Phe Tyr Arg Ser Ser Ala Gln Phe Trp Leu Asp Glu
                725                 730                 735
Lys Ser Gln Ile Glu Glu Leu Gly Lys Phe Ala Ala Ser Tyr Leu Pro
            740                 745                 750
Phe Pro Ile His Leu Leu Trp Arg Asn Glu Ala Leu Asp Glu Ile Thr
    755                 760                 765
Gly Asn Arg Leu Thr Lys Val Met Asn Tyr Ala His Gly Ala Trp Asp
    770                 775                 780
Gly Arg Glu Arg Glu Phe Cys Gly Phe Gly Arg Val Thr Gln Ile Asp
785                 790                 795                 800
Thr Asp Glu Phe Ala Lys Gly Thr Thr Glu Lys Ala Pro Asp Glu Asn
                805                 810                 815
Ile Tyr Pro Ser Arg Ser Ile Ser Trp Phe Ala Thr Gly Leu Pro Glu
            820                 825                 830
Val Asp Ser Gln Leu Pro Ala Glu Tyr Trp Arg Gly Asp Asp Gln Ala
    835                 840                 845
Phe Ala Gly Phe Thr Pro Arg Phe Thr Arg Tyr Glu Lys Gly Asn Ala
    850                 855                 860
Gly Gln Glu Gly Gln Asp Thr Pro Ile Lys Glu Pro Thr Glu Thr Glu
865                 870                 875                 880
Ala Tyr Trp Leu Asn Arg Ala Met Lys Gly Gln Leu Leu Arg Ser Glu
                885                 890                 895
Val Tyr Gly Asp Asp Lys Thr Glu Lys Ala Lys Ile Pro Tyr Thr Val
            900                 905                 910
Thr Glu Ala Arg Cys Gln Val Arg Leu Ile Pro Ser Asn Asp Glu Ala
    915                 920                 925
Ala Pro Ser Ser Trp Thr Ser Ile Ile Glu Asn Arg Ser Tyr His Tyr
    930                 935                 940
Glu Arg Ile Val Val Asp Pro Ser Cys Lys Gln Gln Val Val Leu Lys
```

-continued

```
             945                 950                 955                 960
Ala Asp Glu Tyr Gly Phe Pro Leu Ala Lys Val Asp Ile Ala Tyr Pro
                 965                 970                 975
Arg Arg Asn Lys Pro Ala Gln Asn Pro Tyr Pro Asp Ser Leu Pro Asp
                 980                 985                 990
Thr Leu Phe Ala Asp Ser Tyr Asp Asp Gln Gln Lys Gln Leu Tyr Leu
             995                 1000                1005
Thr Lys Gln Gln Gln Ser Tyr Tyr His Leu Thr Gln Gln Asp Asp
        1010                1015                1020
Trp Val Leu Gly Leu Thr Asp Ser Arg Tyr Ser Glu Val Tyr His
        1025                1030                1035
Tyr Ala Gln Thr Asp Ala Gln Ser Asp Ile Pro Lys Ala Gly Leu
        1040                1045                1050
Ile Leu Glu Asp Leu Leu Lys Val Asp Gly Leu Ile Gly Lys Asp
        1055                1060                1065
Lys Thr Phe Ile Tyr Leu Gly Gln Gln Arg Val Ala Tyr Val Gly
        1070                1075                1080
Gly Asp Ala Glu Lys Pro Thr Arg Gln Val Arg Val Ala Tyr Thr
        1085                1090                1095
Glu Thr Ala Ala Phe Asp Asp Asn Ala Leu His Ala Phe Asp Gly
        1100                1105                1110
Val Ile Ala Pro Asp Glu Leu Thr Gln Gln Leu Leu Ala Gly Gly
        1115                1120                1125
Tyr Leu Leu Val Pro Gln Ile Ser Asp Val Ala Gly Ser Ser Glu
        1130                1135                1140
Lys Val Trp Val Ala Arg Gln Gly Tyr Thr Glu Tyr Gly Ser Ala
        1145                1150                1155
Ala Gln Phe Tyr Arg Pro Leu Ile Gln Arg Lys Ser Leu Leu Thr
        1160                1165                1170
Gly Lys Tyr Thr Leu Ser Trp Asp Thr His Tyr Cys Val Val Val
        1175                1180                1185
Lys Thr Glu Asp Gly Ala Gly Met Thr Thr Gln Ala Lys Tyr Asp
        1190                1195                1200
Tyr Arg Phe Leu Leu Pro Ala Gln Leu Thr Asp Ile Asn Asp Asn
        1205                1210                1215
Gln His Ile Val Thr Phe Asn Ala Leu Gly Gln Val Thr Ser Ser
        1220                1225                1230
Arg Phe Trp Gly Thr Glu Asn Gly Lys Ile Ser Gly Tyr Ser Thr
        1235                1240                1245
Pro Glu Ser Lys Pro Phe Thr Val Pro Asp Thr Val Glu Lys Ala
        1250                1255                1260
Leu Ala Leu Gln Pro Thr Ile Pro Val Ser Gln Cys Asn Ile Tyr
        1265                1270                1275
Val Pro Asp Ser Trp Met Arg Leu Leu Pro Gln Gln Ser Leu Thr
        1280                1285                1290
Gly Gln Leu Lys Glu Gly Glu Thr Leu Trp Asn Ala Leu His Arg
        1295                1300                1305
Ala Gly Val Val Thr Glu Asp Gly Leu Ile Cys Glu Leu Ala Tyr
        1310                1315                1320
Arg Arg Trp Ile Lys Arg Gln Ala Thr Ser Ser Met Met Ala Val
        1325                1330                1335
Thr Leu Gln Gln Ile Leu Ala Gln Thr Pro Arg Gln Pro Pro His
        1340                1345                1350
```

| Ala | Met | Thr | Ile | Thr | Thr | Asp | Arg | Tyr | Asp | Ser | Asp | Ser | Gln | Gln |
|     | 1355|     |     |     | 1360|     |     |     |     | 1365|     |     |     |     |

| Gln | Leu | Arg | Gln | Ser | Ile | Val | Leu | Ser | Asp | Gly | Phe | Gly | Arg | Val |
|     | 1370|     |     |     | 1375|     |     |     |     | 1380|     |     |     |     |

| Leu | Gln | Ser | Ala | Gln | Arg | His | Glu | Ala | Gly | Glu | Ala | Trp | Gln | Arg |
|     | 1385|     |     |     | 1390|     |     |     |     | 1395|     |     |     |     |

| Ala | Glu | Asp | Gly | Ser | Leu | Val | Val | Asp | Asn | Thr | Gly | Lys | Pro | Val |
|     | 1400|     |     |     | 1405|     |     |     |     | 1410|     |     |     |     |

| Val | Ala | Asn | Thr | Thr | Thr | Arg | Trp | Ala | Val | Ser | Gly | Arg | Thr | Glu |
|     | 1415|     |     |     | 1420|     |     |     |     | 1425|     |     |     |     |

| Tyr | Asp | Gly | Lys | Gly | Gln | Ala | Ile | Arg | Ala | Tyr | Leu | Pro | Tyr | Tyr |
|     | 1430|     |     |     | 1435|     |     |     |     | 1440|     |     |     |     |

| Leu | Asn | Asp | Trp | Arg | Tyr | Val | Ser | Asp | Ser | Ala | Arg | Asp | Asp |     |
|     | 1445|     |     |     | 1450|     |     |     |     | 1455|     |     |     |     |

| Leu | Tyr | Ala | Asp | Thr | His | Phe | Tyr | Asp | Pro | Leu | Gly | Arg | Glu | Tyr |
|     | 1460|     |     |     | 1465|     |     |     |     | 1470|     |     |     |     |

| Gln | Val | Lys | Thr | Ala | Lys | Gly | Phe | Trp | Arg | Glu | Asn | Met | Phe | Met |
|     | 1475|     |     |     | 1480|     |     |     |     | 1485|     |     |     |     |

| Pro | Trp | Phe | Val | Val | Asn | Glu | Asp | Glu | Asn | Asp | Thr | Ala | Ala | Arg |
|     | 1490|     |     |     | 1495|     |     |     |     | 1500|     |     |     |     |

| Leu | Thr | Ser |
|     | 1505|     |

```
<210> SEQ ID NO 50
<211> LENGTH: 2889
<212> TYPE: DNA
<213> ORGANISM: Xenorhabdus bovienii

<400> SEQUENCE: 50
atgaatgttt ttaatccaac tttatatgcc ggtacaccga ctgtcaccgt catggacaat       60
cgagggctgt cagtgcggga tattgcttat caccgtacaa cagcaggaga gcaggctgac      120
actcgcatca cccgccatca atacagtccc cataatttt  taatcgagag cattgatcca      180
cgccttttg  atttgcaatc tcagagcacc ataaaccta  atttcaccta ctgtcctgcc      240
ttgaagggtg atgtcctacg gacagagagt gtggatgccg acaaactgt  catttttgagt    300
gacatcgaag tcgtccgtt  actgaatatc agtgcgatgg gtgtcgtcaa acactggcaa     360
tatgaagaga gtacattgcc ggggcgcttg ctcgctgtca gtgaacggaa gaatgaggct     420
tcaacacccc aaattattga acggtttatt tggtcgggaa atagcccatc agaaaaagat     480
cacaatttgg cgggaaaata tcttcgtcat tatgataccg ccggattaaa ccagcttaat    540
gctgtgtctc tgaccagcgt ggatctctca caatcccgtc agttattgca ggatgatgtc    600
acagcagatt ggagcggaag tgacgaatcc cagtggaaga cgcgactgag taacgacata    660
ttcacaaccg aaatcaccgc tgatgcggtt ggcaatttct tgactcagaa tgatgccaaa    720
agcaaccagc aacgattgtc ctatgatgtg gcagggcagt taaaggcaag ctggctgacg    780
ataaaaggcc agaatgagca ggtgatagtt aactccctga cttactccgc cgcagggcag    840
aaactgcgtg aagagcaggg taacggcgtt gtcactgaat actcctatga gcacaaacc     900
tggcgtttga taggtgtaac ggcttaccgt cagtcagata aaaaaagatt gcaggatctt    960
gtctataact atgatccggt cggtaatctc ctgaatattc gcaataatgc agaggcaacc   1020
cgttctctggc gtaatcagat agtagaacca gagaaccact atgcttatga ctcgctttat  1080
caactcatca gtgctagtgg tcgagaaatc gccagtatcg gtcagcaggg cagccggctg   1140
```

-continued

```
cctgtaccga ttattcctct tcctgccaat gacgatgttt atactcgcta cacccgcaca    1200
tatcactatg atcgcggtgg aaatctctgc cagatccggc attgcgctcc tgctacagat    1260
aataagtaca ccacaaagat caccgtatcg aatcgtagta atcgtgcagt atgggatacc    1320
ttgaccacag atcccgccaa agtggatacc ctgtttgatc atggagggca tcaacttcaa    1380
ctccagtcag gccagacttt atgttggaac tatcggggtg aactacagca ataacaaag    1440 atacagcgtg acgaaaaacc cgcagataaa gagcggtatc gctatggtgt tgggctgcg    1500 cgggtcgtga aaatcagcac acagcaggcg ggggaagca gccatgtgca gcgtgttgtt    1560
tatctgccgg ggttggaact acgcacaact cagcatgatg cgacattaat cgaagactta    1620
caggtgatta tcatgggtga agcaggacgt gctcaggtac gcgtacttca ttgggaaata    1680
ccaccaccgg ataatcttaa caatgactca ctgcgttaca gctacgatag tttgatgggt    1740
tccagtcagc ttgaattgga tggagcaggg cagattatta cgcaggaaga atactacccc    1800
tatggaggta cagcaatatg gcggcaaga aaccagaccg aagccaatta caaaaccatt    1860
cgctactccg gcaaagagcg tgatgcgacg gggctttatt actacgggca ccgttattat    1920
cagccgtggc tagggcgctg gttgagcgca gatcccgccg gaaccgtgga cggactgaat    1980
ctatatcgaa tggtgaggaa taacccgatt acttaccggg atgcagatgg gcttgcgccg    2040
ataggcgata agatcagcga agggatttat gagcctgagt tgcgagttgg tcttgaacga    2100
gatgacccaa atgtcagaga ttatgaccgg gtttatcctg atacggccaa gacagagatg    2160
atcgaagcaa ctgcgaccac aattgctccc agtcaaatgt tatcggcgca tgcttttgca    2220
tctgtaccta tattgacaga tttgtttaat cctcaaacag caaggctttc tcaaaagaca    2280
acggatattg tattaaacac acaaggtgga ggcgatttaa tctttactgg catgaatatt    2340
aaaggtaagg gaaaagaatt taatgcatta aaaatcgttg atacttatgg cggagaaatg    2400
cctgatagca aaaccgctat ttcagcatat tggcttccgc aaggtgggta tactgatatt    2460
ccgatacatc cgactggaat acaaaagtat ttgtttacgc ctgcgtttag tggttgcact    2520
ctggcagtag ataagcttaa cgaaaataca ttacgggcgt atcacgtcga aggaagtaag    2580
gaagatgctc aatataataa tttagcagtt gcagcgcacg gagagggttt ggtcatggct    2640
atggaatttc ctgactatgg atttcataca gacaaaacag gcaaagact aaggaacaca    2700 cagggatttg cgtttatgtc ctacaatcaa tcccagaaaa aatgggaaat tcattatcaa    2760
aggcaagcat tgacatcaaa caccggtatc atgaatgtta gtgctaaaaa caagattcga    2820
ttgaatgccc ccagtcatgt aaaaaatagc tcaatcaaag gaactgaaat aatgacgaca    2880
catttttaa                                                           2889
```

<210> SEQ ID NO 51
<211> LENGTH: 962
<212> TYPE: PRT
<213> ORGANISM: Xenorhabdus bovienii

<400> SEQUENCE: 51

```
Met Asn Val Phe Asn Pro Thr Leu Tyr Ala Gly Thr Pro Thr Val Thr
1               5                   10                  15

Val Met Asp Asn Arg Gly Leu Ser Val Arg Asp Ile Ala Tyr His Arg
            20                  25                  30

Thr Thr Ala Gly Glu Gln Ala Asp Thr Arg Ile Thr Arg His Gln Tyr
        35                  40                  45

Ser Pro His Asn Phe Leu Ile Glu Ser Ile Asp Pro Arg Leu Phe Asp
```

```
                50                    55                    60
Leu Gln Ser Gln Ser Thr Ile Lys Pro Asn Phe Thr Tyr Cys Pro Ala
 65                      70                      75                      80

Leu Lys Gly Asp Val Leu Arg Thr Glu Ser Val Asp Ala Gly Gln Thr
                         85                      90                      95

Val Ile Leu Ser Asp Ile Glu Gly Arg Pro Leu Leu Asn Ile Ser Ala
                    100                     105                     110

Met Gly Val Val Lys His Trp Gln Tyr Glu Glu Ser Thr Leu Pro Gly
                    115                     120                     125

Arg Leu Leu Ala Val Ser Glu Arg Lys Asn Glu Ala Ser Thr Pro Gln
130                     135                     140

Ile Ile Glu Arg Phe Ile Trp Ser Gly Asn Ser Pro Ser Glu Lys Asp
145                     150                     155                     160

His Asn Leu Ala Gly Lys Tyr Leu Arg His Tyr Asp Thr Ala Gly Leu
                    165                     170                     175

Asn Gln Leu Asn Ala Val Ser Leu Thr Ser Val Asp Leu Ser Gln Ser
                    180                     185                     190

Arg Gln Leu Leu Gln Asp Asp Val Thr Ala Asp Trp Ser Gly Ser Asp
                    195                     200                     205

Glu Ser Gln Trp Lys Thr Arg Leu Ser Asn Asp Ile Phe Thr Thr Glu
                    210                     215                     220

Ile Thr Ala Asp Ala Val Gly Asn Phe Leu Thr Gln Asn Asp Ala Lys
225                     230                     235                     240

Ser Asn Gln Gln Arg Leu Ser Tyr Asp Val Ala Gly Gln Leu Lys Ala
                    245                     250                     255

Ser Trp Leu Thr Ile Lys Gly Gln Asn Glu Gln Val Ile Val Asn Ser
                    260                     265                     270

Leu Thr Tyr Ser Ala Ala Gly Gln Lys Leu Arg Glu Glu Gln Gly Asn
                    275                     280                     285

Gly Val Val Thr Glu Tyr Ser Tyr Glu Ala Gln Thr Trp Arg Leu Ile
                    290                     295                     300

Gly Val Thr Ala Tyr Arg Gln Ser Asp Lys Lys Arg Leu Gln Asp Leu
305                     310                     315                     320

Val Tyr Asn Tyr Asp Pro Val Gly Asn Leu Leu Asn Ile Arg Asn Asn
                    325                     330                     335

Ala Glu Ala Thr Arg Phe Trp Arg Asn Gln Ile Val Glu Pro Glu Asn
                    340                     345                     350

His Tyr Ala Tyr Asp Ser Leu Tyr Gln Leu Ile Ser Ala Ser Gly Arg
                    355                     360                     365

Glu Ile Ala Ser Ile Gly Gln Gln Gly Ser Arg Leu Pro Val Pro Ile
                    370                     375                     380

Ile Pro Leu Pro Ala Asn Asp Val Tyr Thr Arg Tyr Thr Arg Thr
385                     390                     395                     400

Tyr His Tyr Asp Arg Gly Gly Asn Leu Cys Gln Ile Arg His Cys Ala
                    405                     410                     415

Pro Ala Thr Asp Asn Lys Tyr Thr Thr Lys Ile Thr Val Ser Asn Arg
                    420                     425                     430

Ser Asn Arg Ala Val Trp Asp Thr Leu Thr Thr Asp Pro Ala Lys Val
                    435                     440                     445

Asp Thr Leu Phe Asp His Gly His Gln Leu Gln Leu Gln Ser Gly
                    450                     455                     460

Gln Thr Leu Cys Trp Asn Tyr Arg Gly Glu Leu Gln Gln Ile Thr Lys
465                     470                     475                     480
```

```
Ile Gln Arg Asp Glu Lys Pro Ala Asp Lys Glu Arg Tyr Arg Tyr Gly
                485                 490                 495

Val Gly Ala Ala Arg Val Val Lys Ile Ser Thr Gln Ala Gly Gly
            500                 505                 510

Ser Ser His Val Gln Arg Val Val Tyr Leu Pro Gly Leu Glu Leu Arg
            515                 520                 525

Thr Thr Gln His Asp Ala Thr Leu Ile Glu Asp Leu Gln Val Ile Ile
            530                 535                 540

Met Gly Glu Ala Gly Arg Ala Gln Val Arg Val Leu His Trp Glu Ile
545                 550                 555                 560

Pro Pro Pro Asp Asn Leu Asn Asn Asp Ser Leu Arg Tyr Ser Tyr Asp
                565                 570                 575

Ser Leu Met Gly Ser Ser Gln Leu Glu Leu Asp Gly Ala Gly Gln Ile
            580                 585                 590

Ile Thr Gln Glu Glu Tyr Tyr Pro Tyr Gly Gly Thr Ala Ile Trp Ala
            595                 600                 605

Ala Arg Asn Gln Thr Glu Ala Asn Tyr Lys Thr Ile Arg Tyr Ser Gly
            610                 615                 620

Lys Glu Arg Asp Ala Thr Gly Leu Tyr Tyr Gly His Arg Tyr Tyr
625                 630                 635                 640

Gln Pro Trp Leu Gly Arg Trp Leu Ser Ala Asp Pro Ala Gly Thr Val
                645                 650                 655

Asp Gly Leu Asn Leu Tyr Arg Met Val Arg Asn Asn Pro Ile Thr Tyr
                660                 665                 670

Arg Asp Ala Asp Gly Leu Ala Pro Ile Gly Asp Lys Ile Ser Glu Gly
                675                 680                 685

Ile Tyr Glu Pro Glu Leu Arg Val Gly Leu Glu Arg Asp Asp Pro Asn
            690                 695                 700

Val Arg Asp Tyr Asp Arg Val Tyr Pro Asp Thr Ala Lys Thr Glu Met
705                 710                 715                 720

Ile Glu Ala Thr Ala Thr Thr Ile Ala Pro Ser Gln Met Leu Ser Ala
                725                 730                 735

His Ala Phe Ala Ser Val Pro Ile Leu Thr Asp Leu Phe Asn Pro Gln
                740                 745                 750

Thr Ala Arg Leu Ser Gln Lys Thr Thr Asp Ile Val Leu Asn Thr Gln
                755                 760                 765

Gly Gly Gly Asp Leu Ile Phe Thr Gly Met Asn Ile Lys Gly Lys Gly
            770                 775                 780

Lys Glu Phe Asn Ala Leu Lys Ile Val Asp Thr Tyr Gly Gly Glu Met
785                 790                 795                 800

Pro Asp Ser Lys Thr Ala Ile Ser Ala Tyr Trp Leu Pro Gln Gly Gly
                805                 810                 815

Tyr Thr Asp Ile Pro Ile His Pro Thr Gly Ile Gln Lys Tyr Leu Phe
                820                 825                 830

Thr Pro Ala Phe Ser Gly Cys Thr Leu Ala Val Asp Lys Leu Asn Glu
                835                 840                 845

Asn Thr Leu Arg Ala Tyr His Val Glu Gly Ser Lys Glu Asp Ala Gln
            850                 855                 860

Tyr Asn Asn Leu Ala Val Ala Ala His Gly Glu Gly Leu Val Met Ala
865                 870                 875                 880

Met Glu Phe Pro Asp Tyr Gly Phe His Thr Asp Lys Thr Gly Gln Arg
                885                 890                 895
```

```
Leu Arg Asn Thr Gln Gly Phe Ala Phe Met Ser Tyr Asn Gln Ser Gln
                900                 905                 910

Lys Lys Trp Glu Ile His Tyr Gln Arg Gln Ala Leu Thr Ser Asn Thr
            915                 920                 925

Gly Ile Met Asn Val Ser Ala Lys Asn Lys Ile Arg Leu Asn Ala Pro
        930                 935                 940

Ser His Val Lys Asn Ser Ser Ile Lys Gly Thr Glu Ile Met Thr Thr
945                 950                 955                 960

His Phe

<210> SEQ ID NO 52
<211> LENGTH: 4595
<212> TYPE: DNA
<213> ORGANISM: Xenorhabdus bovienii

<400> SEQUENCE: 52
```

| | | | | | |
|---|---|---|---|---|---|
| tctagaacta | gtgtcgacta | aagaagaagg | agatatacca | tgaaacaaga | cagccaggac | 60 |
| atgacagtaa | cacagctgtc | cctgcccaaa | gggggcggtg | cgatcagtgg | catgggtgac | 120 |
| actatcagca | atgcagggcc | ggatgggatg | gcttcgcttt | ccgtgccttt | gcctatctct | 180 |
| gccggtcggg | gggcgcaccg | aatttatccc | tgaactaca | gtagcggagc | aggaaacggg | 240 |
| tcatttggta | ttggctggca | atccagtacc | atggctatca | gccgtcgtac | tcaacatggc | 300 |
| gtaccgcaat | atcacggcga | agatactttt | ttatgtccga | tgggagaagt | gatggcggtt | 360 |
| gccgtcaatc | agagcgggca | acccgatgtg | cgtaaaaccg | ataaactatt | aggcgggcaa | 420 |
| ctgcctgtta | cttataccgt | tacgcgtcat | cagcccagaa | atattcagca | cttcagcaaa | 480 |
| cttgaatact | ggcagccccc | aacgatgtg | gaaaccacgc | cttttggtt | aatgtattca | 540 |
| cccgatggac | aaattcacat | tttcggaaaa | actgagcagg | ctcagatcgc | taacccggca | 600 |
| gaggtttcac | agattgccca | atggcttttg | gaagaaaccg | taacaccagc | gggagaacac | 660 |
| atttattacc | agtatcgggc | agaagacgat | atcggttgtg | atgacagcga | aaaaaatgcc | 720 |
| caccctaatg | ccagtgctca | acgttatttg | actcaggtga | actacggcaa | tattacacct | 780 |
| gaatccagcc | tgcttgtgct | gaagaatacg | ccaccggcgg | ataacgaatg | gctattccat | 840 |
| ttggttttg | attatggtga | acgagcgcag | gaaataaaca | cggttcctcc | tttcaaagca | 900 |
| ccttcaaaca | actggaaaat | acggccagac | cgtttctccc | gctttgaata | tggttttgag | 960 |
| gtgcgaaccc | gccgcctgtg | tcaacaaatt | ctgatgttcc | atcgcctgaa | atcccttgca | 1020 |
| ggagaacaga | ttgacggaga | agaaatccct | gccttggttg | cccgtctgct | tctcagttat | 1080 |
| gacctgaacg | acagcgtgac | aaccccttacc | gccattcggc | aaatggcgta | tgaaactgac | 1140 |
| gcaaccttaa | tcgctttacc | gccactggag | tttgactatc | agcccttga | ggcaaaagtc | 1200 |
| acgcagaaat | ggcaggaaat | gcctcaattg | gccggattga | atgcccaaca | accttaccaa | 1260 |
| ctcgtcgatc | tctatggtga | aggtatctcc | ggcatcttgt | atcaggacag | acccggagca | 1320 |
| tggtggtatc | aggcaccgat | ccgtcagaaa | aacgttgaag | atattaacgc | tgtcacctat | 1380 |
| agcccaataa | acccccttacc | taagatcccc | agccagcagg | acagagcaac | gttgatggat | 1440 |
| atcgacggtg | atggacatct | ggattgggtg | atcgctggcg | caggtattca | ggggcggtac | 1500 |
| agtatgcagc | cgaatggaga | gtggacacac | tttattccca | tttctgcact | gccaacagaa | 1560 |
| tattttcatc | cacaggcaca | actggcggat | ctggtggggg | ccgggttatc | tgatttagcg | 1620 |
| ctgattggcc | ccagagtgt | gcgtttatat | gccaacgacc | gaggaaactg | gaaagcgggt | 1680 |
| attaatgtta | tgccacctga | tggtgtgaat | ttgccgatat | ttggtggtga | tgccagcagt | 1740 |

```
ctggtcgcat tttctgacat gttgggatcg ggacagcagc atttggtgga aattgccgct    1800
cagagcgtca aatgctggcc gaatctagga catggccgtt ttggtgcggc tattttgctg    1860
ccggggttta gccagccgaa tggaacattc aatgctaacc aagttttcct ggcagatatc    1920
gatggttccg gcaccgccga catcatctat gcacacagta cgtatctgga tatttacctg    1980
aacgaaagcg gcaaccgttt cagtgcaccc gttcggctta atttgccgga aggggtgatg    2040
tttgacaata cctgtcagtt acaggtgtcg atattcaag gattgggcgc tgccagcatt      2100
gtactgaccg tacctcatat gacaccgcgc cattggcgtt atgattttac tcacaataaa    2160
ccttggctgc tcaatgtcat caacaacaat cgtggcgcag aaaccacgtt gttttaccgt    2220
agttctgccc aattctggct ggatgaaaaa agtcagatcg aagagctggg aaaatttgca    2280
gcgagttatc tgccttttcc catacatttg ttgtggcgca atgaggcgct ggatgaaatt    2340
actggtaatc gactgactaa ggtcatgaat tatgcccacg gtgcatggga tggcagagag    2400
agagaatttt gcggatttgg ccgtgtaacg caaattgata ccgacgaatt tgccaaggga    2460
accacagaga aagcgccgga tgaaaatatc tatccttccc gtagcataag ctggtttgcc    2520
acgggtttac cagaagtgga ttctcaactt ccggcagaat actggcgtgg tgacgatcag    2580
gcatttgccg gctttacacc gcgcttcact cgttatgaaa aaggtaatgc ggggcaagag    2640
gggcaggata ccccgattaa agaaccgacc gaaacagaag cgtattggct taaccgcgcc    2700
atgaaaggcc aattactgcg cagtgaagtc tatggtgacg acaaaacaga aaaagctaaa    2760
attccgtaca ccgtcacaga agctcgctgt caggtcagat taattcccag caatgacgaa    2820
gccgcgccgt cgtcttggac gtcgatcatt gaaaaccgca gttatcacta tgagcgtatc    2880
gtcgtcgatc cgagttgcaa acaacaggtc gtgctcaagg cggatgaata tggcttccca    2940
ctggcaaaag tagatatcgc ctatccacgg cgcaataaac cggcacagaa cccttatccg    3000
gattcgttac cggatactct gttcgccgat agctatgacg accagcaaaa acagttatat    3060
ctgacaaaac agcagcagag ctattaccac ctgacccagc aggatgattg ggttctgggt    3120
ttgacggata gccgatacag cgaagtttat cattatgcgc aaactgacgc tcaaagtgac    3180
atccccaagg cagggctgat attggaagac ctgctgaaag ttgacggcct gataggtaaa    3240
gacaagactt ttatctattt agggcagcag cgagtggctt atgtgggagg agatgcagaa    3300
aaaccgacac gtcaggtgcg ggtggcttat acagaaaccg ctgcttttga tgacaatgcg    3360
ctgcacgcct ttgatggcgt gattgcccct gatgaactga cgcaacagtt gctggcgggt    3420
ggatacctgc tcgtgccgca gatttctgat gtggcaggca gtagtgaaaa ggtatgggta    3480
gctcggcagg gatacaccga atacggcagt gctgctcaat tctaccggcc actcatccag    3540
cgcaaaagct tgctgaccgg aaaatatacc cttagttggg atacgcacta ttgtgtggtg    3600
gtaaaaaccg aagatggtgc gggaatgacc acgcaagcga agtacgatta ccgcttcctg    3660
cttccggcgc aattgacaga tatcaatgac aaccagcaca tcgtgacatt taatgcattg    3720
gggcaggtga cttccagccg tttctggggc acagaaaatg gcaaaataag cggttactcg    3780
acgccggaga gtaaaccgtt cacagtaccc gataccgtcg aaaaagccct tgccttgcaa    3840
ccgacgatcc cggtttcaca gtgcaacatt tatgtgccgg atagttggat gcggcttctg    3900
ccccaacagt ctctgactgg ccagctaaaa gaggggaaa ctttgtggaa cgcattacac      3960
cgggcgggtg tagtaacgga agacggtttg atctgtgaac tggcctatcg tcgttggatc    4020
aaacgtcagg caacgtcttc aatgatggcc gtgacattac agcaaatctt ggctcagact    4080
```

```
ccacgacaac ctccgcatgc catgacgatc acgacagatc gttatgacag cgattctcag    4140
cagcaacttc ggcagtcgat agtattgagt gatggttttg gtcgcgtatt gcaaagcgcc    4200
cagcgtcatg aagcaggaga ggcatggcag cgtgcagaag atggttcttt ggttgtcgat    4260
aataccggta aacccgttgt tgctaatacc acaacgcgct gggcagtatc cggtcgcaca    4320
gaatacgacg gcaaagggca ggcgatcaga gcttacctgc cttattatct caatgattgg    4380
cgctatgtca gtgatgacag cgcccgggat gacctgtacg ccgataccca tttttacgat    4440 cctctgggc gtgaatatca ggtaaaaacc gcgaaggat tttggcgtga aaacatgttt      4500
atgccgtggt ttgtcgtcaa tgaagatgaa atgacacag cagcacgttt aacatcttaa    4560
ttaatgcggc cgcaggcctc tgtaagactc tcgag                               4595

<210> SEQ ID NO 53
<211> LENGTH: 2947
<212> TYPE: DNA
<213> ORGANISM: Xenorhabdus bovienii

<400> SEQUENCE: 53
tctagaacta gtaggcctta agaagagag agatatacca tgaatgtttt taatccaact     60
ttatatgccg gtacaccgac tgtcaccgtc atggacaatc gagggctgtc agtgcgggat    120
attgcttatc accgtacaac agcaggagag caggctgaca ctcgcatcac ccgccatcaa    180
tacagtcccc ataattttt aatcgagagc attgatccac gcctttttga tttgcaatct    240
cagagcacca taaacctaa tttcacctac tgtcctgcct tgaagggtga gtcctacgg     300 acagagagtg tggatgccgg acaaactgtc attttgagtg acatcgaagg tcgtccgtta    360
ctgaatatca gtgcgatggg tgtcgtcaaa cactggcaat atgaagagag tacattgccg    420
gggcgcttgc tcgctgtcag tgaacggaag aatgaggctt caacacccca attattgaa     480 cggtttattt ggtcgggaaa tagcccatca gaaaaagatc acaatttggc gggaaaatat    540
cttcgtcatt atgataccgc cggattaaac cagcttaatg ctgtgtctct gaccagcgtg    600
gatctctcac aatcccgtca gttattgcag gatgatgtca cagcagattg gagcggaagt    660
gacgaatccc agtggaagac gcgactgagt aacgacatat tcacaaccga aatcaccgct    720
gatgcggttg gcaattctt gactcagaat gatgccaaaa gcaaccagca acgattgtcc    780
tatgatgtgg cagggcagtt aaaggcaagc tggctgacga taaaaggcca gaatgagcag    840
gtgatagtta actccctgac ttactccgcc gcagggcaga aactgcgtga agagcagggt    900
aacggcgttg tcactgaata ctcctatgaa gcacaaacct ggcgtttgat aggtgtaacg    960
gcttaccgtc agtcagataa aaaaagattg caggatcttg tctataacta tgatccggtc    1020
ggtaatctcc tgaatattcg caataatgca gaggcaaccc gtttctggcg taatcagata    1080
gtagaaccag agaaccacta tgcttatgac tcgctttatc aactcatcag tgctagtggt    1140
cgagaaatcg ccagtatcgg tcagcagggc agccggctgc ctgtaccgat tattcctctt    1200
cctgccaatg acgatgttta tactcgctac acccgcacat atcactatga tcgcggtgga    1260
aatctctgcc agatccggca ttgcgctcct gctacagata taagtacac cacaaagatc    1320 accgtatcga atcgtagtaa tcgtgcagta tgggatacct tgaccacaga tcccgccaaa    1380 gtggatacccc tgtttgatca tggagggcat caacttcaac tccagtcagg ccagacttta    1440
tgttggaact atcggggtga actacagcaa ataacaaaga tacagcgtga cgaaaaaccc    1500
gcagataaag agcggtatcg ctatggtgtt gggctgcgc gggtcgtgaa atcagcaca     1560 cagcaggcgg ggggaagcag ccatgtgcag cgtgttgttt atctgccggg gttggaacta    1620
```

| | |
|---|---|
| cgcacaactc agcatgatgc gacattaatc gaagacttac aggtgattat catgggtgaa | 1680 |
| gcaggacgtg ctcaggtacg cgtacttcat tgggaaatac caccaccgga taatcttaac | 1740 |
| aatgactcac tgcgttacag ctacgatagt ttgatgggtt ccagtcagct tgaattggat | 1800 |
| ggagcagggc agattattac gcaggaagaa tactacccct atggaggtac agcaatatgg | 1860 |
| gcggcaagaa accagaccga agccaattac aaaaccattc gctactccgg caaagagcgt | 1920 |
| gatgcgacgg ggctttatta ctacgggcac cgttattatc agccgtggct agggcgctgg | 1980 |
| ttgagcgcag atcccgccgg aaccgtggac ggactgaatc tatatcgaat ggtgaggaat | 2040 |
| aacccgatta cttaccggga tgcagatggg cttgcgccga taggcgataa gatcagcgaa | 2100 |
| gggatttatg agcctgagtt gcgagttggt cttgaacgag atgacccaaa tgtcagagat | 2160 |
| tatgaccggg tttatcctga tacggccaag acagagatga tcgaagcaac tgcgaccaca | 2220 |
| attgctccca gtcaaatgtt atcggcgcat gcttttgcat ctgtacctat attgacagat | 2280 |
| ttgtttaatc ctcaaacagc aaggctttct caaaagacaa cggatattgt attaaacaca | 2340 |
| caaggtggag gcgatttaat ctttactggc atgaatatta aggtaaggg aaaagaattt | 2400 |
| aatgcattaa aaatcgttga tacttatggc ggagaaatgc ctgatagcaa aaccgctatt | 2460 |
| tcagcatatt ggcttccgca aggtgggtat actgatattc cgatacatcc gactggaata | 2520 |
| caaaagtatt tgtttacgcc tgcgtttagt ggttgcactc tggcagtaga taagcttaac | 2580 |
| gaaaatacat tacgggcgta tcacgtcgaa ggaagtaagg aagatgctca atataataat | 2640 |
| ttagcagttg cagcgcacgg agagggtttg gtcatggcta tggaatttcc tgactatgga | 2700 |
| tttcatacag acaaaacagg gcaaagacta aggaacacac agggatttgc gtttatgtcc | 2760 |
| tacaatcaat cccagaaaaa atgggaaatt cattatcaaa ggcaagcatt gacatcaaac | 2820 |
| accggtatca tgaatgttag tgctaaaaac aagattcgat tgaatgcccc cagtcatgta | 2880 |
| aaaaatagct caatcaaagg aactgaaata atgacgacac attttaatt aatgcggccg | 2940 |
| cctcgag | 2947 |

<210> SEQ ID NO 54
<211> LENGTH: 7508
<212> TYPE: DNA
<213> ORGANISM: Xenorhabdus bovienii

<400> SEQUENCE: 54

| | |
|---|---|
| tctagaacta gtgtcgacta aagaagaagg agatatacca tgaaacaaga cagccaggac | 60 |
| atgacagtaa cacagctgtc cctgcccaaa ggggcggtg cgatcagtgg catgggtgac | 120 |
| actatcagca atgcagggcc ggatgggatg gcttcgcttt ccgtgccttt gcctatctct | 180 |
| gccggtcggg ggggcgcacc gaatttatcc ctgaactaca gtagcggagc aggaaacggg | 240 |
| tcatttggta ttggctggca atccagtacc atggctatca gccgtcgtac tcaacatggc | 300 |
| gtaccgcaat atcacggcga agatactttt ttatgtccga tgggagaagt gatggcggtt | 360 |
| gccgtcaatc agagcgggca acccgatgtg cgtaaaaccg ataaactatt aggcgggcaa | 420 |
| ctgcctgtta cttataccgt tacgcgtcat cagcccagaa atattcagca cttcagcaaa | 480 |
| cttgaatact ggcagccccc aacgatgtg gaaaccacgc cttttggtt aatgtattca | 540 |
| cccgatggac aaattcacat tttcggaaaa actgagcagg ctcagatcgc taacccggca | 600 |
| gaggtttcac agattgccca atggcttttg gaagaaaccg taacaccagc gggagaaacac | 660 |
| atttattacc agtatcgggc agaagacgat atcggttgtg atgacagcga aaaaaatgcc | 720 |

```
caccctaatg ccagtgctca acgttatttg actcaggtga actacggcaa tattacacct      780
gaatccagcc tgcttgtgct gaagaatacg ccaccggcgg ataacgaatg gctattccat      840
ttggttttg attatggtga acgagcgcag gaaataaaca cggttcctcc tttcaaagca       900
ccttcaaaca actggaaaat acggccagac cgtttctccc gctttgaata tggttttgag      960
gtgcgaaccc gccgcctgtg tcaacaaatt ctgatgttcc atcgcctgaa atcccttgca     1020
ggagaacaga ttgacggaga agaaatccct gccttggttg cccgtctgct tctcagttat     1080
gacctgaacg acagcgtgac aacccttacc gccattcggc aaatggcgta tgaaactgac     1140
gcaaccttaa tcgctttacc gccactggag tttgactatc agccctttga ggcaaaagtc     1200
acgcagaaat ggcaggaaat gcctcaattg gccggattga atgcccaaca accttaccaa     1260
ctcgtcgatc tctatggtga aggtatctcc ggcatcttgt atcaggacag acccggagca     1320
tggtggtatc aggcaccgat ccgtcagaaa aacgttgaag atattaacgc tgtcacctat     1380
agcccaataa accccttacc taagatcccc agccagcagg acagagcaac gttgatggat     1440
atcgacggtg atggacatct ggattgggtg atcgctggcg caggtattca ggggcggtac     1500
agtatgcagc cgaatggaga gtggacacac tttattccca tttctgcact gccaacagaa     1560
tattttcatc cacaggcaca actggcggat ctggtggggg ccgggttatc tgatttagcg     1620
ctgattggcc ccagaagtgt gcgtttatat gccaacgacc gaggaaactg aaagcgggt      1680
attaatgtta tgccacctga tggtgtgaat ttgccgatat ttggtggtga tgccagcagt     1740
ctggtcgcat tttctgacat gttgggatcg ggacagcagc atttggtgga aattgccgct     1800
cagagcgtca aatgctggcc gaatctagga catggccgtt ttggtgcggc tattttgctg     1860
ccggggttta gccagccgaa tggaacattc aatgctaacc aagttttctct ggcagatatc    1920
gatggttccg gcaccgccga catcatctat gcacacagta cgtatctgga tatttacctg     1980
aacgaaagcg gcaaccgttt cagtgcaccc gttcggctta atttgccgga aggggtgatg     2040
tttgacaata cctgtcagtt acaggtgtcg gatattcaag gattgggcgc tgccagcatt     2100
gtactgaccg tacctcatat gacaccgcgc cattggcgtt atgatttac tcacaataaa      2160
ccttggctgc tcaatgtcat caacaacaat cgtggcgcag aaaccacgtt gttttaccgt     2220
agttctgccc aattctggct ggatgaaaaa agtcagatcg aagagctggg aaaatttgca     2280
gcgagttatc tgccttttccc catacatttg ttgtggcgca atgaggcgct ggatgaaatt    2340
actggtaatc gactgactaa ggtcatgaat tatgcccacg gtgcatggga tggcagagag    2400
agagaatttt gcggatttgg ccgtgtaacg caaattgata ccgacgaatt tgccaaggga     2460
accacagaga aagcgccgga tgaaaatatc tatccttccc gtagcataag ctggtttgcc     2520
acgggtttac cagaagtgga ttctcaactt ccggcagaat actggcgtgg tgacgatcag     2580
gcatttgccg gctttacacc gcgcttcact cgttatgaaa aggtaatgc ggggcaagag      2640
gggcaggata ccccgattaa agaaccgacc gaaacagaag cgtattggct taaccgcgcc     2700
atgaaaggcc aattactgcg cagtgaagtc tatggtgacg acaaaacaga aaaagctaaa     2760
attccgtaca ccgtcacaga agctcgctgt caggtcagat taattcccag caatgacgaa     2820
gccgcgccgt cgtcttggac gtcgatcatt gaaaaccgca gttatcacta tgagcgtatc     2880
gtcgtcgatc cgagttgcaa acaacaggtc gtgctcaagg cggatgaata tggcttccca     2940
ctggcaaaag tagatatcgc ctatccacgg cgcaataaac cggcacagaa cccttatccg     3000
gattcgttac cggatactct gttcgccgat agctatgacg accagcaaaa acagttatat     3060
ctgacaaaac agcagcagag ctattaccac ctgacccagc aggatgattg ggttctgggt     3120
```

```
ttgacggata gccgatacag cgaagtttat cattatgcgc aaactgacgc tcaaagtgac   3180
atccccaagg cagggctgat attggaagac ctgctgaaag ttgacggcct gataggtaaa   3240
gacaagactt ttatctattt agggcagcag cgagtggctt atgtgggagg agatgcagaa   3300
aaaccgacac gtcaggtgcg ggtggcttat acagaaaccg ctgcttttga tgacaatgcg   3360
ctgcacgcct tgatggcgt gattgcccct gatgaactga cgcaacagtt gctggcgggt   3420
ggatacctgc tcgtgccgca gatttctgat gtggcaggca gtagtgaaaa ggtatgggta   3480
gctcggcagg gatacaccga ataccggcagt gctgctcaat tctaccggcc actcatccag   3540
cgcaaaagct tgctgaccgg aaaatatacc cttagttggg atacgcacta ttgtgtggtg   3600
gtaaaaaccg aagatggtgc gggaatgacc acgcaagcga agtacgatta ccgcttcctg   3660
cttccggcgc aattgacaga tatcaatgac aaccagcaca tcgtgacatt taatgcattg   3720
gggcaggtga cttccagccg tttctggggc acagaaaatg gcaaaataag cggttactcg   3780
acgccggaga gtaaaccgtt cacagtaccc gataccgtcg aaaaagccct tgccttgcaa   3840
ccgacgatcc cggttttcaca gtgcaacatt tatgtgccgg atagttggat gcggcttctg   3900
ccccaacagt ctctgactgg ccagctaaaa gagggggaaa ctttgtggaa cgcattacac   3960
cgggcgggtg tagtaacgga agacggtttg atctgtgaac tggcctatcg tcgttggatc   4020
aaacgtcagg caacgtcttc aatgatggcc gtgacattac agcaaatctt ggctcagact   4080
ccacgacaac ctccgcatgc catgacgatc acgacagatc gttatgacag cgattctcag   4140
cagcaacttc ggcagtcgat agtattgagt gatggttttg gtcgcgtatt gcaaagcgcc   4200
cagcgtcatg aagcaggaga ggcatggcag cgtgcagaag atggttcttt ggttgtcgat   4260
aataccggta aacccgttgt tgctaatacc acaacgcgct gggcagtatc cggtcgcaca   4320
gaatacgacg gcaaagggca ggcgatcaga gcttacctgc cttattatct caatgattgg   4380
cgctatgtca gtgatgacag cgcccgggat gacctgtacg ccgataccca ttttttacgat   4440 cctctggggc gtgaatatca ggtaaaaacc gcgaaaggat tttggcgtga aaacatgttt   4500
atgccgtggt ttgtcgtcaa tgaagatgaa atgacacag cagcacgttt aacatcttaa   4560
ttaatgcggc cgcaggcctt aaagaagaga gagatatacc atgaatgttt ttaatccaac   4620
tttatatgcc ggtacaccga ctgtcaccgt catggacaat cgagggctgt cagtgcggga   4680
tattgcttat caccgtacaa cagcaggaga gcaggctgac actcgcatca cccgccatca   4740
atacagtccc cataattttt taatcgagag cattgatcca cgccttttg atttgcaatc   4800 tcagagcacc ataaaaccta atttcaccta ctgtcctgcc ttgaagggtg atgtcctacg   4860
gacagagagt gtggatgccg gacaaactgt cattttgagt gacatcgaag gtcgtccgtt   4920
actgaatatc agtgcgatgg gtgtcgtcaa acactggcaa tatgaagaga gtacattgcc   4980
ggggcgcttg ctcgctgtca gtgaacggaa gaatgaggct tcaacacccc aaattattga   5040
acggtttatt tggtcgggaa atagcccatc agaaaaagat cacaatttgg cgggaaaata   5100
tcttcgtcat tatgataccg ccggattaaa ccagcttaat gctgtgtctc tgaccagcgt   5160
ggatctctca caatcccgtc agttattgca ggatgatgtc acagcagatt ggagcggaag   5220
tgacgaatcc cagtggaaga cgcgactgag taacgacata ttcacaaccg aaatcaccgc   5280
tgatgcggtt ggcaatttct tgactcagaa tgatgccaaa agcaaccagc aacgattgtc   5340
ctatgatgtg gcagggcagt taaaggcaag ctggctgacg ataaaaggcc agaatgagca   5400
ggtgatagtt aactccctga cttactccgc cgcagggcag aaactgcgtg aagagcaggg   5460
```

-continued

```
taacggcgtt gtcactgaat actcctatga agcacaaacc tggcgtttga taggtgtaac      5520
ggcttaccgt cagtcagata aaaaagatt gcaggatctt gtctataact atgatccggt      5580
cggtaatctc ctgaatattc gcaataatgc agaggcaacc cgtttctggc gtaatcagat      5640
agtagaacca gagaaccact atgcttatga ctcgctttat caactcatca gtgctagtgg      5700
tcgagaaatc gccagtatcg gtcagcaggg cagccggctg cctgtaccga ttattcctct      5760
tcctgccaat gacgatgttt atactcgcta cacccgcaca tatcactatg atcgcggtgg      5820
aaatctctgc cagatccggc attgcgctcc tgctacagat aataagtaca ccacaaagat      5880
caccgtatcg aatcgtagta atcgtgcagt atgggatacc ttgaccacag atcccgccaa      5940
agtggatacc ctgtttgatc atggagggca tcaacttcaa ctccagtcag gccagacttt      6000
atgttggaac tatcggggtg aactacagca ataacaaag atacagcgtg acgaaaaacc       6060
cgcagataaa gagcggtatc gctatggtgt tggggctgcg cgggtcgtga aaatcagcac      6120
acagcaggcg gggggaagca gccatgtgca gcgtgttgtt tatctgccgg ggttggaact      6180
acgcacaact cagcatgatg cgacattaat cgaagactta caggtgatta tcatgggtga      6240
agcaggacgt gctcaggtac gcgtacttca ttgggaaata ccaccaccgg ataatcttaa      6300
caatgactca ctgcgttaca gctacgatag tttgatgggt tccagtcagc ttgaattgga      6360
tggagcaggg cagattatta cgcaggaaga atactacccc tatggaggta cagcaatatg      6420
ggcggcaaga aaccagaccg aagccaatta caaaaccatt cgctactccg gcaaagagcg      6480
tgatgcgacg gggctttatt actacgggca ccgttattat cagccgtggc tagggcgctg      6540
gttgagcgca gatcccgccg gaaccgtgga cggactgaat ctatatcgaa tggtgaggaa      6600
taacccgatt acttaccggg atgcagatgg gcttgcgccg ataggcgata agatcagcga      6660
agggatttat gagcctgagt tgcgagttgg tcttgaacga gatgacccaa atgtcagaga      6720
ttatgaccgg gttatcctg atacggccaa gacagagatg atcgaagcaa ctgcgaccac       6780
aattgctccc agtcaaatgt tatcggcgca tgcttttgca tctgtaccta tattgacaga      6840 tttgttttaat cctcaaacag caaggctttc tcaaaagaca acggatattg tattaaacac     6900
acaaggtgga ggcgatttaa tctttactgg catgaatatt aaaggtaagg gaaaagaatt      6960
taatgcatta aaaatcgttg atacttatgg cggagaaatg cctgatagca aaaccgctat      7020
ttcagcatat tggcttccgc aaggtgggta tactgatatt ccgatacatc cgactggaat      7080 acaaagtat ttgtttacgc ctgcgtttag tggttgcact ctggcagtag ataagcttaa       7140
cgaaaataca ttacgggcgt atcacgtcga aggaagtaag gaagatgctc aatataataa      7200
tttagcagtt gcagcgcacg gagagggttt ggtcatggct atggaatttc ctgactatgg      7260
atttcataca gacaaaacag ggcaaagact aaggaacaca cagggatttg cgtttatgtc      7320
ctacaatcaa tcccagaaaa aatgggaaat tcattatcaa aggcaagcat tgacatcaaa      7380
caccggtatc atgaatgtta gtgctaaaaa caagattcga ttgaatgccc ccagtcatgt      7440
aaaaaatagc tcaatcaaag gaactgaaat aatgacgaca cattttttaat taatgcggcc    7500 gcctcgag                                                                7508
```

<210> SEQ ID NO 55
<211> LENGTH: 2862
<212> TYPE: DNA
<213> ORGANISM: Paenibacillus strain DAS1529

<400> SEQUENCE: 55

```
atgaaaatga taccgtggac tcaccattat ttgcttcacc gcctgcgcgg tgagatggag       60
```

-continued

```
gttaaaccta tgaacacaac gtccatatat aggggcacgc ctacgatttc agttgtggat      120
aaccggaact tggagattcg cattcttcag tataaccgta tcgcggctga agatccggca      180
gatgagtgta tcctgcggaa cacgtatacg ccgttaagct atcttggcag cagcatggat      240
ccccgtttgt tctcgcaata tcaggatgat cgcggaacac cgccgaatat acgaaccatg      300
gcttccctga gaggcgaagc gctgtgttcg gaaagtgtgg atgccggccg caaggcggag      360
cttttgata tcgaggggcg gcccgtctgg cttatcgatg ccaacggcac agagacgact      420
ctcgaatatg atgtcttagg caggccaaca gccgtattcg agcaacagga aggtacggac      480
tcccccagt gcagggagcg gtttatttat ggtgagaagg aggcggatgc ccaggccaac       540
aatttgcgcg acaactggt tcgccactac gataccgcgg gccggataca gaccgacagc       600
atctccttgg ctggactgcc gttgcgccaa agccgtcaac tgctgaaaaa ttgggatgaa      660
cctggcgact ggagtatgga tgaggaaagc gcctgggcct cgttgctggc tgccgaagct      720
tatgatacga gctggcggta tgacgcgcag gacagggtgc tcgcccaaac cgacgccaaa      780
gggaatctcc agcaactgac ttacaatgac gccggccagc cgcaggcggt cagcctcaag      840
ctgcaaggcc aagcggagca acggatttgg aaccggatcg agtacaacgc ggcgggtcaa      900
gtggatctcg ccgaagccgg gaatggaatc gtaacggaat atacttacga ggaaagcacg      960
cagcggttaa tccgaaaaaa agattcccgc ggactgtcct ccggggaaag agaagtgctg     1020
caggattatc gttatgaata tgatccggta ggcaatatcc tttctattta caatgaagcg     1080
gagccggttc gttatttccg caatcaggcc gttgctccga aaaggcaata tgcctacgat     1140
gccttgtatc agcttgtatc tagttcgggg cgggaatccg acgcgcttcg gcagcagacg     1200
tcgcttcctc ccttgatcac gcctatccct ctggacgata gccaatacgt caattacgct     1260
gaaaaataca gctatgatca ggcgggcaat ttaatcaagc ttagccataa cggggcaagt     1320
caatatacaa cgaatgtgta tgtggacaaa agctcaaacc gggggatttg gcggcaaggg     1380
gaagacatcc cggatatcgc ggcttccttt gacagagcag gcaatcaaca agctttattc     1440
ccggggagac cgttgaatg gatacacgc aatcaattaa gccgtgtcca tatggtcgtg       1500
cgcgaaggcg gagacaacga ctgggaaggc tatctctatg acagctcggg aatgcgtatc     1560
gtaaaacgat ctacccgcaa aacacagaca acgacgcaaa cggatacgac cctctatttg     1620
ccgggcctgg agctgcgaat ccgccagacc ggggaccggg tcacggaagc attgcaggtc     1680
attaccgtgg atgagggagc gggacaagtg agggtgctgc actgggagga tggaaccgag     1740
ccgggcggca tcgccaatga tcagtaccgg tacagcctga cgatcatct tacctcctct      1800
ttattggaag ttgacgggca aggtcagatc attagtaagg aagaatttta tccctatggc     1860
ggcacagccc tgtggacagc ccggtcagag gtagaggcaa gctacaagac catccgctat     1920
tcaggcaaag agcgggatgc cacaggcctg tattattacg acaccgcta ctatatgcca      1980
tggttgggtc gctggctgaa tccggacccg gccggaatgg tagatggact aaacctgtac     2040
cgtatggtca ggaacaatcc tataggactg atggatccga atgggaatgc gccaatcaac     2100
gtggcggatt atagcttcgt gcatggtgat ttagtttatg gtcttagtaa ggaaagagga     2160
agatatctaa agctatttaa tccaaacttt aatatggaaa aatcagactc tcctgctatg     2220
gttatagatc aatataataa taatgttgca ttgagtataa ctaaccaata taagtagaa      2280
gaattgatga aatttcaaaa agaccccacaa aaagccgcac ggaaaataaa ggttccagaa    2340
gggaatcgtt tatcgaggaa cgaaaattat cctttgtggc acgattatat taacattgga    2400
```

-continued

```
gaagctaaag ctgcatttaa ggcctctcat attttccaag aagtgaaggg gaattatggg    2460
aaagattatt atcataaatt attattagac agaatgatag aatcgccgtt gctgtggaaa    2520
cgaggcagca aactcgggct agaaatcgcc gctaccaatc agagaacaaa aatacacttt    2580
gttcttgaca atttaaatat cgagcaggtg gttacgaaag agggtagcgg cggtcagtca    2640
atcacagctt cggagctccg ttatatttat cgaaatcgcg aaagattgaa cgggcgtgtc    2700
attttctata gaaataatga aaggctagat caggctccat ggcaagaaaa tccggactta    2760
tggagcaaat atcaaccggg tcttagacaa agcagcagtt caagagtcaa agaacgaggg    2820
attgggaact ttttccgccg gttttcaatg aagagaaagt aa                      2862
```

<210> SEQ ID NO 56
<211> LENGTH: 4458
<212> TYPE: DNA
<213> ORGANISM: Photorhabdus luminescens strain W14
<220> FEATURE:
<221> NAME/KEY: exon
<222> LOCATION: (1)..(4458)

<400> SEQUENCE: 56

| | | |
|---|---|---|
| atg cag gat tca cca gaa gta tcg att aca acg ctg tca ctt ccc aaa<br>Met Gln Asp Ser Pro Glu Val Ser Ile Thr Thr Leu Ser Leu Pro Lys<br>1               5                   10                  15 | | 48 |
| ggt ggc ggt gct atc aat ggc atg gga gaa gca ctg aat gct gcc ggc<br>Gly Gly Gly Ala Ile Asn Gly Met Gly Glu Ala Leu Asn Ala Ala Gly<br>            20                  25                  30 | | 96 |
| cct gat gga atg gcc tcc cta tct ctg cca tta ccc ctt tcg acc ggc<br>Pro Asp Gly Met Ala Ser Leu Ser Leu Pro Leu Pro Leu Ser Thr Gly<br>        35                  40                  45 | | 144 |
| aga ggg acg gct cct gga tta tcg ctg att tac agc aac agt gca ggt<br>Arg Gly Thr Ala Pro Gly Leu Ser Leu Ile Tyr Ser Asn Ser Ala Gly<br>    50                  55                  60 | | 192 |
| aat ggg cct ttc ggc atc ggc tgg caa tgc ggt gtt atg tcc att agc<br>Asn Gly Pro Phe Gly Ile Gly Trp Gln Cys Gly Val Met Ser Ile Ser<br>65                  70                  75                  80 | | 240 |
| cga cgc acc caa cat ggc att cca caa tac ggt aat gac gac acg ttc<br>Arg Arg Thr Gln His Gly Ile Pro Gln Tyr Gly Asn Asp Asp Thr Phe<br>                85                  90                  95 | | 288 |
| cta tcc cca caa ggc gag gtc atg aat atc gcc ctg aat gac caa ggg<br>Leu Ser Pro Gln Gly Glu Val Met Asn Ile Ala Leu Asn Asp Gln Gly<br>            100                 105                 110 | | 336 |
| caa cct gat atc cgt caa gac gtt aaa acg ctg caa ggc gtt acc ttg<br>Gln Pro Asp Ile Arg Gln Asp Val Lys Thr Leu Gln Gly Val Thr Leu<br>        115                 120                 125 | | 384 |
| cca att tcc tat acc gtg acc cgc tat caa gcc cgc cag atc ctg gat<br>Pro Ile Ser Tyr Thr Val Thr Arg Tyr Gln Ala Arg Gln Ile Leu Asp<br>    130                 135                 140 | | 432 |
| ttc agt aaa atc gaa tac tgg caa cct gcc tcc ggt caa gaa gga cgc<br>Phe Ser Lys Ile Glu Tyr Trp Gln Pro Ala Ser Gly Gln Glu Gly Arg<br>145                 150                 155                 160 | | 480 |
| gct ttc tgg ctg ata tcg tca ccg gac ggc caa cta cac atc tta ggg<br>Ala Phe Trp Leu Ile Ser Ser Pro Asp Gly Gln Leu His Ile Leu Gly<br>                165                 170                 175 | | 528 |
| aaa acc gcg cag gct tgt ctg gca aat ccg caa aat gac caa caa atc<br>Lys Thr Ala Gln Ala Cys Leu Ala Asn Pro Gln Asn Asp Gln Gln Ile<br>            180                 185                 190 | | 576 |
| gcc cag tgg ttg ctg gaa gaa act gtg acg cca gcc ggt gaa cat gtc<br>Ala Gln Trp Leu Leu Glu Glu Thr Val Thr Pro Ala Gly Glu His Val<br>        195                 200                 205 | | 624 |

-continued

| | | |
|---|---|---|
| agc tat caa tat cga gcc gaa gat gaa gcc cat tgt gac gac aat gaa<br>Ser Tyr Gln Tyr Arg Ala Glu Asp Glu Ala His Cys Asp Asp Asn Glu<br>210                         215                    220 | 672 |
| aaa acc gct cat ccc aat gtt acc gca cag cgc tat ctg gta cag gtg<br>Lys Thr Ala His Pro Asn Val Thr Ala Gln Arg Tyr Leu Val Gln Val<br>225                         230                    235                    240 | 720 |
| aac tac ggc aac atc aaa cca caa gcc agc ctg ttc gta ctg gat aac<br>Asn Tyr Gly Asn Ile Lys Pro Gln Ala Ser Leu Phe Val Leu Asp Asn<br>                    245                    250                    255 | 768 |
| gca cct ccc gca ccg gaa gag tgg ctg ttt cat ctg gtc ttt gac cac<br>Ala Pro Pro Ala Pro Glu Glu Trp Leu Phe His Leu Val Phe Asp His<br>              260                    265                    270 | 816 |
| ggt gag cgc gat acc tca ctt cat acc gtg cca aca tgg gat gca ggt<br>Gly Glu Arg Asp Thr Ser Leu His Thr Val Pro Thr Trp Asp Ala Gly<br>275                         280                    285 | 864 |
| aca gcg caa tgg tct gta cgc ccg gat atc ttc tct cgc tat gaa tat<br>Thr Ala Gln Trp Ser Val Arg Pro Asp Ile Phe Ser Arg Tyr Glu Tyr<br>290                         295                    300 | 912 |
| ggt ttt gaa gtg cgt act cgc cgc tta tgt caa caa gtg ctg atg ttt<br>Gly Phe Glu Val Arg Thr Arg Arg Leu Cys Gln Gln Val Leu Met Phe<br>305                         310                    315                    320 | 960 |
| cac cgc acc gcg ctc atg gcc gga gaa gcc agt acc aat gac gcc ccg<br>His Arg Thr Ala Leu Met Ala Gly Glu Ala Ser Thr Asn Asp Ala Pro<br>              325                    330                    335 | 1008 |
| gaa ctg gtt gga cgc tta ata ctg gaa tat gac aaa aac gcc agc gtc<br>Glu Leu Val Gly Arg Leu Ile Leu Glu Tyr Asp Lys Asn Ala Ser Val<br>                    340                    345                    350 | 1056 |
| acc acg ttg att acc atc cgt caa tta agc cat gaa tcg gac ggc agc<br>Thr Thr Leu Ile Thr Ile Arg Gln Leu Ser His Glu Ser Asp Gly Ser<br>              355                    360                    365 | 1104 |
| cca gtc acc cag cca cca cta gaa cta gcc tgg caa cgg ttt gat ctg<br>Pro Val Thr Gln Pro Pro Leu Glu Leu Ala Trp Gln Arg Phe Asp Leu<br>370                         375                    380 | 1152 |
| gag aaa atg ccg aca tgg caa cgc ttt gac gca cta gat aat ttt aac<br>Glu Lys Met Pro Thr Trp Gln Arg Phe Asp Ala Leu Asp Asn Phe Asn<br>385                         390                    395                    400 | 1200 |
| tcg cag caa cgt tat caa ctg gtt gat ctg cgg gga gaa ggg ttg cca<br>Ser Gln Gln Arg Tyr Gln Leu Val Asp Leu Arg Gly Glu Gly Leu Pro<br>                    405                    410                    415 | 1248 |
| ggt atg ctg tat caa gat cga ggc gct tgg tgg tat aaa gct ccg caa<br>Gly Met Leu Tyr Gln Asp Arg Gly Ala Trp Trp Tyr Lys Ala Pro Gln<br>              420                    425                    430 | 1296 |
| cgt cag gaa gac gga gac agc aat gcc gtc act tac gac aaa atc gcc<br>Arg Gln Glu Asp Gly Asp Ser Asn Ala Val Thr Tyr Asp Lys Ile Ala<br>                    435                    440                    445 | 1344 |
| cca ctg cct acc cta ccc aat ttg cag gat aat gcc tca ttg atg gat<br>Pro Leu Pro Thr Leu Pro Asn Leu Gln Asp Asn Ala Ser Leu Met Asp<br>450                         455                    460 | 1392 |
| atc aac gga gac ggc caa ctg gat tgg gtt gtt acc gcc tcc ggt att<br>Ile Asn Gly Asp Gly Gln Leu Asp Trp Val Val Thr Ala Ser Gly Ile<br>465                         470                    475                    480 | 1440 |
| cgc gga tac cat agt cag caa ccc gat gga aag tgg acg cac ttt acg<br>Arg Gly Tyr His Ser Gln Gln Pro Asp Gly Lys Trp Thr His Phe Thr<br>                    485                    490                    495 | 1488 |
| cca atc aat gcc ttg ccc gtg gaa tat ttt cat cca agc atc cag ttc<br>Pro Ile Asn Ala Leu Pro Val Glu Tyr Phe His Pro Ser Ile Gln Phe<br>              500                    505                    510 | 1536 |
| gct gac ctt acc ggg gca ggc tta tct gat tta gtg ttg atc ggg ccg<br>Ala Asp Leu Thr Gly Ala Gly Leu Ser Asp Leu Val Leu Ile Gly Pro<br>              515                    520                    525 | 1584 |

-continued

```
aaa agc gtg cgt cta tat gcc aac cag cga aac ggc tgg cgt aaa gga     1632
Lys Ser Val Arg Leu Tyr Ala Asn Gln Arg Asn Gly Trp Arg Lys Gly
    530                 535                 540 gaa gat gtc ccc caa tcc aca ggt atc acc ctg cct gtc aca ggg acc     1680
Glu Asp Val Pro Gln Ser Thr Gly Ile Thr Leu Pro Val Thr Gly Thr
545                 550                 555                 560 gat gcc cgc aaa ctg gtg gct ttc agt gat atg ctc ggt tcc ggt caa     1728
Asp Ala Arg Lys Leu Val Ala Phe Ser Asp Met Leu Gly Ser Gly Gln
                565                 570                 575 caa cat ctg gtg gaa atc aag gct aat cgc gtc acc tgt tgg ccg aat     1776
Gln His Leu Val Glu Ile Lys Ala Asn Arg Val Thr Cys Trp Pro Asn
            580                 585                 590 cta ggg cat ggc cgt ttc ggt caa cca cta act ctg tca gga ttt agc     1824
Leu Gly His Gly Arg Phe Gly Gln Pro Leu Thr Leu Ser Gly Phe Ser
        595                 600                 605 cag ccc gaa aat agc ttc aat ccc gaa cgg ctg ttt ctg gcg gat atc     1872
Gln Pro Glu Asn Ser Phe Asn Pro Glu Arg Leu Phe Leu Ala Asp Ile
    610                 615                 620 gac ggc tcc ggc acc acc gac ctt atc tat gcg caa tcc ggc tct ttg     1920
Asp Gly Ser Gly Thr Thr Asp Leu Ile Tyr Ala Gln Ser Gly Ser Leu
625                 630                 635                 640 ctc att tat ctc aac caa agt ggt aat cag ttt gat gcc ccg ttg aca     1968
Leu Ile Tyr Leu Asn Gln Ser Gly Asn Gln Phe Asp Ala Pro Leu Thr
                645                 650                 655 tta gcg ttg cca gaa ggc gta caa ttt gac aac act tgc caa ctt caa     2016
Leu Ala Leu Pro Glu Gly Val Gln Phe Asp Asn Thr Cys Gln Leu Gln
            660                 665                 670 gtc gcc gat att cag gga tta ggg ata gcc agc ttg att ctg act gtg     2064
Val Ala Asp Ile Gln Gly Leu Gly Ile Ala Ser Leu Ile Leu Thr Val
        675                 680                 685 cca cat atc gcg cca cat cac tgg cgt tgt gac ctg tca ctg acc aaa     2112
Pro His Ile Ala Pro His His Trp Arg Cys Asp Leu Ser Leu Thr Lys
    690                 695                 700 ccc tgg ttg ttg aat gta atg aac aat aac cgg ggc gca cat cac acg     2160
Pro Trp Leu Leu Asn Val Met Asn Asn Asn Arg Gly Ala His His Thr
705                 710                 715                 720 cta cat tat cgt agt tcc gcg caa ttc tgg ttg gat gaa aaa tta cag     2208
Leu His Tyr Arg Ser Ser Ala Gln Phe Trp Leu Asp Glu Lys Leu Gln
                725                 730                 735 ctc acc aaa gca ggc aaa tct ccg gct tgt tat ctg ccg ttt cca atg     2256
Leu Thr Lys Ala Gly Lys Ser Pro Ala Cys Tyr Leu Pro Phe Pro Met
            740                 745                 750 cat ttg cta tgg tat acc gaa att cag gat gaa atc agc ggc aac cgg     2304
His Leu Leu Trp Tyr Thr Glu Ile Gln Asp Glu Ile Ser Gly Asn Arg
        755                 760                 765 ctc acc agt gaa gtc aac tac agc cac ggc gtc tgg gat ggt aaa gag     2352
Leu Thr Ser Glu Val Asn Tyr Ser His Gly Val Trp Asp Gly Lys Glu
    770                 775                 780 cgg gaa ttc aga gga ttt ggc tgc atc aaa cag aca gat acc aca acg     2400
Arg Glu Phe Arg Gly Phe Gly Cys Ile Lys Gln Thr Asp Thr Thr Thr
785                 790                 795                 800 ttt tct cac ggc acc gcc ccc gaa cag gcg gca ccg tcg ctg agt att     2448
Phe Ser His Gly Thr Ala Pro Glu Gln Ala Ala Pro Ser Leu Ser Ile
                805                 810                 815 agc tgg ttt gcc acc ggc atg gat gaa gta gac agc caa tta gct acg     2496
Ser Trp Phe Ala Thr Gly Met Asp Glu Val Asp Ser Gln Leu Ala Thr
            820                 825                 830 gaa tat tgg cag gca gac acg caa gct tat agc gga ttt gaa acc cgt     2544
Glu Tyr Trp Gln Ala Asp Thr Gln Ala Tyr Ser Gly Phe Glu Thr Arg
```

-continued

|     |     | 835 |     |     |     | 840 |     |     |     | 845 |     |     |     |     |      |
|---|---|---|---|---|---|---|---|---|---|---|---|---|---|---|---|
| tat | acc | gtc | tgg | gat | cac | acc | aac | cag | aca | gac | caa | gca | ttt | acc | ccc | 2592 |
| Tyr | Thr | Val | Trp | Asp | His | Thr | Asn | Gln | Thr | Asp | Gln | Ala | Phe | Thr | Pro |
|     | 850 |     |     |     |     | 855 |     |     |     |     | 860 |     |     |     |     |

| aat | gag | aca | caa | cgt | aac | tgg | ctg | acg | cga | gcg | ctt | aaa | ggc | caa | ctg | 2640 |
|---|---|---|---|---|---|---|---|---|---|---|---|---|---|---|---|---|
| Asn | Glu | Thr | Gln | Arg | Asn | Trp | Leu | Thr | Arg | Ala | Leu | Lys | Gly | Gln | Leu |
| 865 |     |     |     |     | 870 |     |     |     |     | 875 |     |     |     |     | 880 |

| cta | cgc | act | gag | ctc | tac | ggt | ctg | gac | gga | aca | gat | aag | caa | aca | gtg | 2688 |
|---|---|---|---|---|---|---|---|---|---|---|---|---|---|---|---|---|
| Leu | Arg | Thr | Glu | Leu | Tyr | Gly | Leu | Asp | Gly | Thr | Asp | Lys | Gln | Thr | Val |
|     |     |     |     |     | 885 |     |     |     |     | 890 |     |     |     |     | 895 |

| cct | tat | acc | gtc | agt | gaa | tcg | cgc | tat | cag | gta | cgc | tct | att | ccc | gta | 2736 |
|---|---|---|---|---|---|---|---|---|---|---|---|---|---|---|---|---|
| Pro | Tyr | Thr | Val | Ser | Glu | Ser | Arg | Tyr | Gln | Val | Arg | Ser | Ile | Pro | Val |
|     |     |     | 900 |     |     |     |     | 905 |     |     |     |     | 910 |     |     |

| aat | aaa | gaa | act | gaa | tta | tct | gcc | tgg | gtg | act | gct | att | gaa | aat | cgc | 2784 |
|---|---|---|---|---|---|---|---|---|---|---|---|---|---|---|---|---|
| Asn | Lys | Glu | Thr | Glu | Leu | Ser | Ala | Trp | Val | Thr | Ala | Ile | Glu | Asn | Arg |
|     |     | 915 |     |     |     |     | 920 |     |     |     |     | 925 |     |     |     |

| agc | tac | cac | tat | gaa | cgt | atc | atc | act | gac | cca | cag | ttc | agc | cag | agt | 2832 |
|---|---|---|---|---|---|---|---|---|---|---|---|---|---|---|---|---|
| Ser | Tyr | His | Tyr | Glu | Arg | Ile | Ile | Thr | Asp | Pro | Gln | Phe | Ser | Gln | Ser |
|     | 930 |     |     |     |     | 935 |     |     |     |     | 940 |     |     |     |     |

| atc | aag | ttg | caa | cac | gat | atc | ttt | ggt | caa | tca | ctg | caa | agt | gtc | gat | 2880 |
|---|---|---|---|---|---|---|---|---|---|---|---|---|---|---|---|---|
| Ile | Lys | Leu | Gln | His | Asp | Ile | Phe | Gly | Gln | Ser | Leu | Gln | Ser | Val | Asp |
| 945 |     |     |     |     | 950 |     |     |     |     | 955 |     |     |     |     | 960 |

| att | gcc | tgg | ccg | cgc | cgc | gaa | aaa | cca | gca | gtg | aat | ccc | tac | ccg | cct | 2928 |
|---|---|---|---|---|---|---|---|---|---|---|---|---|---|---|---|---|
| Ile | Ala | Trp | Pro | Arg | Arg | Glu | Lys | Pro | Ala | Val | Asn | Pro | Tyr | Pro | Pro |
|     |     |     |     | 965 |     |     |     |     | 970 |     |     |     |     | 975 |     |

| acc | ctg | ccg | gaa | acg | cta | ttt | gac | agc | agc | tat | gat | gat | caa | caa | caa | 2976 |
|---|---|---|---|---|---|---|---|---|---|---|---|---|---|---|---|---|
| Thr | Leu | Pro | Glu | Thr | Leu | Phe | Asp | Ser | Ser | Tyr | Asp | Asp | Gln | Gln | Gln |
|     |     |     | 980 |     |     |     |     | 985 |     |     |     |     | 990 |     |     |

| cta | tta | cgt | ctg | gtg | aga | caa | aaa | aat | agc | tgg | cat | cac | ctg | act | gat | 3024 |
|---|---|---|---|---|---|---|---|---|---|---|---|---|---|---|---|---|
| Leu | Leu | Arg | Leu | Val | Arg | Gln | Lys | Asn | Ser | Trp | His | His | Leu | Thr | Asp |
|     |     | 995 |     |     |     |     | 1000 |     |     |     |     | 1005 |     |     |     |

| ggg | gaa | aac | tgg | cga | tta | ggt | tta | ccg | aat | gca | caa | cgc | cgt | gat | 3069 |
|---|---|---|---|---|---|---|---|---|---|---|---|---|---|---|---|
| Gly | Glu | Asn | Trp | Arg | Leu | Gly | Leu | Pro | Asn | Ala | Gln | Arg | Arg | Asp |
|     |     | 1010 |     |     |     | 1015 |     |     |     |     | 1020 |     |     |     |

| gtt | tat | act | tat | gac | cgg | agc | aaa | att | cca | acc | gaa | ggg | att | tcc | 3114 |
|---|---|---|---|---|---|---|---|---|---|---|---|---|---|---|---|
| Val | Tyr | Thr | Tyr | Asp | Arg | Ser | Lys | Ile | Pro | Thr | Glu | Gly | Ile | Ser |
|     | 1025 |     |     |     |     | 1030 |     |     |     |     | 1035 |     |     |     |

| ctt | gaa | atc | ttg | ctg | aaa | gat | gat | ggc | ctg | cta | gca | gat | gaa | aaa | 3159 |
|---|---|---|---|---|---|---|---|---|---|---|---|---|---|---|---|
| Leu | Glu | Ile | Leu | Leu | Lys | Asp | Asp | Gly | Leu | Leu | Ala | Asp | Glu | Lys |
|     | 1040 |     |     |     |     | 1045 |     |     |     |     | 1050 |     |     |     |

| gcg | gcc | gtt | tat | ctg | gga | caa | caa | cag | acg | ttt | tac | acc | gcc | ggt | 3204 |
|---|---|---|---|---|---|---|---|---|---|---|---|---|---|---|---|
| Ala | Ala | Val | Tyr | Leu | Gly | Gln | Gln | Gln | Thr | Phe | Tyr | Thr | Ala | Gly |
|     | 1055 |     |     |     |     | 1060 |     |     |     |     | 1065 |     |     |     |

| caa | gcg | gaa | gtc | act | cta | gaa | aaa | ccc | acg | tta | caa | gca | ctg | gtc | 3249 |
|---|---|---|---|---|---|---|---|---|---|---|---|---|---|---|---|
| Gln | Ala | Glu | Val | Thr | Leu | Glu | Lys | Pro | Thr | Leu | Gln | Ala | Leu | Val |
|     | 1070 |     |     |     |     | 1075 |     |     |     |     | 1080 |     |     |     |

| gcg | ttc | caa | gaa | acc | gcc | atg | atg | gac | gat | acc | tca | tta | cag | gcg | 3294 |
|---|---|---|---|---|---|---|---|---|---|---|---|---|---|---|---|
| Ala | Phe | Gln | Glu | Thr | Ala | Met | Met | Asp | Asp | Thr | Ser | Leu | Gln | Ala |
|     | 1085 |     |     |     |     | 1090 |     |     |     |     | 1095 |     |     |     |

| tat | gaa | ggc | gtg | att | gaa | gag | caa | gag | ttg | aat | acc | gcg | ctg | aca | 3339 |
|---|---|---|---|---|---|---|---|---|---|---|---|---|---|---|---|
| Tyr | Glu | Gly | Val | Ile | Glu | Glu | Gln | Glu | Leu | Asn | Thr | Ala | Leu | Thr |
|     | 1100 |     |     |     |     | 1105 |     |     |     |     | 1110 |     |     |     |

| cag | gcc | ggt | tat | cag | caa | gtc | gcg | cgg | ttg | ttt | aat | acc | aga | tca | 3384 |
|---|---|---|---|---|---|---|---|---|---|---|---|---|---|---|---|
| Gln | Ala | Gly | Tyr | Gln | Gln | Val | Ala | Arg | Leu | Phe | Asn | Thr | Arg | Ser |
|     | 1115 |     |     |     |     | 1120 |     |     |     |     | 1125 |     |     |     |

| gaa | agc | ccg | gta | tgg | gcg | gca | cgg | caa | ggt | tat | acc | gat | tac | ggt | 3429 |
|---|---|---|---|---|---|---|---|---|---|---|---|---|---|---|---|
| Glu | Ser | Pro | Val | Trp | Ala | Ala | Arg | Gln | Gly | Tyr | Thr | Asp | Tyr | Gly |
|     | 1130 |     |     |     |     | 1135 |     |     |     |     | 1140 |     |     |     |

| gac | gcc | gca | cag | ttc | tgg | cgg | cct | cag | gct | cag | cgt | aac | tcg | ttg | 3474 |
|---|---|---|---|---|---|---|---|---|---|---|---|---|---|---|---|

```
                                        -continued

Asp Ala Ala Gln Phe Trp Arg Pro Gln Ala Gln Arg Asn Ser Leu
1145                1150                1155 ctg aca ggg aaa acc aca ctg acc tgg gat acc cat cat tgt gta      3519
Leu Thr Gly Lys Thr Thr Leu Thr Trp Asp Thr His His Cys Val
    1160                1165                1170 ata ata cag act caa gat gcc gct gga tta acg acg caa gcc cat      3564
Ile Ile Gln Thr Gln Asp Ala Ala Gly Leu Thr Thr Gln Ala His
1175                1180                1185 tac gat tat cgt ttc ctt aca ccg gta caa ctg aca gat att aat      3609
Tyr Asp Tyr Arg Phe Leu Thr Pro Val Gln Leu Thr Asp Ile Asn
    1190                1195                1200 gat aat caa cat att gtg act ctg gac gcg cta ggt cgc gta acc      3654
Asp Asn Gln His Ile Val Thr Leu Asp Ala Leu Gly Arg Val Thr
1205                1210                1215 acc agc cgg ttc tgg gga aca gag gca gga caa gcc gca ggc tat      3699
Thr Ser Arg Phe Trp Gly Thr Glu Ala Gly Gln Ala Ala Gly Tyr
    1220                1225                1230 tcc aac cag ccc ttc aca cca ccg gac tcc gta gat aaa gcg ctg      3744
Ser Asn Gln Pro Phe Thr Pro Pro Asp Ser Val Asp Lys Ala Leu
1235                1240                1245 gca tta acc ggc gca ctc cct gtt gcc caa tgt tta gtc tat gcc      3789
Ala Leu Thr Gly Ala Leu Pro Val Ala Gln Cys Leu Val Tyr Ala
    1250                1255                1260 gtt gat agc tgg atg ccg tcg tta tct ttg tct cag ctt tct cag      3834
Val Asp Ser Trp Met Pro Ser Leu Ser Leu Ser Gln Leu Ser Gln
1265                1270                1275 tca caa gaa gag gca gaa gcg cta tgg gcg caa ctg cgt gcc gct      3879
Ser Gln Glu Glu Ala Glu Ala Leu Trp Ala Gln Leu Arg Ala Ala
    1280                1285                1290 cat atg att acc gaa gat ggg aaa gtg tgt gcg tta agc ggg aaa      3924
His Met Ile Thr Glu Asp Gly Lys Val Cys Ala Leu Ser Gly Lys
1295                1300                1305 cga gga aca agc cat cag aac ctg acg att caa ctt att tcg cta      3969
Arg Gly Thr Ser His Gln Asn Leu Thr Ile Gln Leu Ile Ser Leu
    1310                1315                1320 ttg gca agt att ccc cgt tta ccg cca cat gta ctg ggg atc acc      4014
Leu Ala Ser Ile Pro Arg Leu Pro Pro His Val Leu Gly Ile Thr
1325                1330                1335 act gat cgc tat gat agc gat ccg caa cag cag cac caa cag acg      4059
Thr Asp Arg Tyr Asp Ser Asp Pro Gln Gln Gln His Gln Gln Thr
    1340                1345                1350 gtg agc ttt agt gac ggt ttt ggc cgg tta ctc cag agt tca gct      4104
Val Ser Phe Ser Asp Gly Phe Gly Arg Leu Leu Gln Ser Ser Ala
1355                1360                1365 cgt cat gag tca ggt gat gcc tgg caa cgt aaa gag gat ggc ggg      4149
Arg His Glu Ser Gly Asp Ala Trp Gln Arg Lys Glu Asp Gly Gly
    1370                1375                1380 ctg gtc gtg gat gca aat ggc gtt ctg gtc agt gcc cct aca gac      4194
Leu Val Val Asp Ala Asn Gly Val Leu Val Ser Ala Pro Thr Asp
1385                1390                1395 acc cga tgg gcc gtt tcc ggt cgc aca gaa tat gac gac aaa ggc      4239
Thr Arg Trp Ala Val Ser Gly Arg Thr Glu Tyr Asp Asp Lys Gly
    1400                1405                1410 caa cct gtg cgt act tat caa ccc tat ttt cta aat gac tgg cgt      4284
Gln Pro Val Arg Thr Tyr Gln Pro Tyr Phe Leu Asn Asp Trp Arg
1415                1420                1425 tac gtt agt gat gac agc gca cga gat gac ctg ttt gcc gat acc      4329
Tyr Val Ser Asp Asp Ser Ala Arg Asp Asp Leu Phe Ala Asp Thr
    1430                1435                1440
```

-continued

```
cac ctt tat gat cca ttg gga cgg gaa tac aaa gtc atc act gct      4374
His Leu Tyr Asp Pro Leu Gly Arg Glu Tyr Lys Val Ile Thr Ala
    1445            1450                1455 aag aaa tat ttg cga gaa aag ctg tac acc ccg tgg ttt att gtc      4419
Lys Lys Tyr Leu Arg Glu Lys Leu Tyr Thr Pro Trp Phe Ile Val
1460                1465                1470 agt gag gat gaa aac gat aca gca tca aga acc cca tag              4458
Ser Glu Asp Glu Asn Asp Thr Ala Ser Arg Thr Pro
    1475            1480                1485

<210> SEQ ID NO 57
<211> LENGTH: 2817
<212> TYPE: DNA
<213> ORGANISM: Photorhabdus luminescens strain W14
<220> FEATURE:
<221> NAME/KEY: exon
<222> LOCATION: (1)..(2817)

<400> SEQUENCE: 57 atg gaa aac att gac cca aaa ctt tat cac cat acg cct acc gtc agt   48
Met Glu Asn Ile Asp Pro Lys Leu Tyr His His Thr Pro Thr Val Ser
1               5                   10                  15 gtt cac gat aac cgt gga cta gct atc cgt aat att agt ttt cac cgc   96
Val His Asp Asn Arg Gly Leu Ala Ile Arg Asn Ile Ser Phe His Arg
                20                  25                  30 act acc gca gaa gca aat acc gat acc cgt att acc cgc cat caa tat  144
Thr Thr Ala Glu Ala Asn Thr Asp Thr Arg Ile Thr Arg His Gln Tyr
            35                  40                  45 aat gcc ggc gga tat ttg aac caa agc att gat cct cgc ctg tat gac  192
Asn Ala Gly Gly Tyr Leu Asn Gln Ser Ile Asp Pro Arg Leu Tyr Asp
        50                  55                  60 gcc aaa cag act aac aac gct gta caa ccg aat ttt atc tgg cga cat  240
Ala Lys Gln Thr Asn Asn Ala Val Gln Pro Asn Phe Ile Trp Arg His
65                  70                  75                  80 aat ttg acc ggc aat atc ctg cga aca gag agc gtc gat gcc ggt cgg  288
Asn Leu Thr Gly Asn Ile Leu Arg Thr Glu Ser Val Asp Ala Gly Arg
                85                  90                  95 acg att acc ctc aac gat att gaa ggc cgc ccg gtg ttg acc atc aat  336
Thr Ile Thr Leu Asn Asp Ile Glu Gly Arg Pro Val Leu Thr Ile Asn
                100                 105                 110 gca gcc ggt gtc cgg caa aac cat cgc tac gaa gat aac acc ctg ccc  384
Ala Ala Gly Val Arg Gln Asn His Arg Tyr Glu Asp Asn Thr Leu Pro
            115                 120                 125 ggt cgc ctg ctc gct atc agc gaa caa gga cag gca gaa gag aaa acg  432
Gly Arg Leu Leu Ala Ile Ser Glu Gln Gly Gln Ala Glu Glu Lys Thr
        130                 135                 140 acc gag cgc ctt atc tgg gcc ggc aat acg ccg caa gaa aaa gac cac  480
Thr Glu Arg Leu Ile Trp Ala Gly Asn Thr Pro Gln Glu Lys Asp His
145                 150                 155                 160 aac ctt gcc ggt cag tgc gtc cgc cat tac gat acc gca gga ctc act  528
Asn Leu Ala Gly Gln Cys Val Arg His Tyr Asp Thr Ala Gly Leu Thr
                165                 170                 175 caa ctc aac agc ctt gcc ctg acc ggc gcc gtt cta tca caa tct caa  576
Gln Leu Asn Ser Leu Ala Leu Thr Gly Ala Val Leu Ser Gln Ser Gln
                180                 185                 190 caa ctg ctt acc gat aac cag gat gcc gac tgg aca ggt gaa gac cag  624
Gln Leu Leu Thr Asp Asn Gln Asp Ala Asp Trp Thr Gly Glu Asp Gln
            195                 200                 205 agc ctc tgg caa caa aaa ctg agt agt gat gtc tat atc acc caa agt  672
Ser Leu Trp Gln Gln Lys Leu Ser Ser Asp Val Tyr Ile Thr Gln Ser
        210                 215                 220
```

```
                                         -continued aac act gat gcc acc ggg gct tta ctg acc cag acc gat gcc aaa ggc      720
Asn Thr Asp Ala Thr Gly Ala Leu Leu Thr Gln Thr Asp Ala Lys Gly
225                 230                 235                 240 aac att cag cgg ctg gcc tat gat gtg gcc ggg cag cta aaa ggg agt      768
Asn Ile Gln Arg Leu Ala Tyr Asp Val Ala Gly Gln Leu Lys Gly Ser
            245                 250                 255 tgg tta aca ctc aaa ggt cag gcg gaa cag gtg att atc aaa tcg cta      816
Trp Leu Thr Leu Lys Gly Gln Ala Glu Gln Val Ile Ile Lys Ser Leu
        260                 265                 270 acc tac tcc gcc gcc ggg caa aaa tta cgt gaa gag cac ggt aac ggg      864
Thr Tyr Ser Ala Ala Gly Gln Lys Leu Arg Glu Glu His Gly Asn Gly
    275                 280                 285 att gtc act gaa tac agc tac gaa ccg gaa acc caa cgg ctt atc ggc      912
Ile Val Thr Glu Tyr Ser Tyr Glu Pro Glu Thr Gln Arg Leu Ile Gly
290                 295                 300 att acc act cgc cgt cca tca gac gcc aag gtg ttg caa gac cta cgc      960
Ile Thr Thr Arg Arg Pro Ser Asp Ala Lys Val Leu Gln Asp Leu Arg
305                 310                 315                 320 tat caa tat gac cca gta ggc aat gtc att agt atc cgt aat gat gcg     1008
Tyr Gln Tyr Asp Pro Val Gly Asn Val Ile Ser Ile Arg Asn Asp Ala
            325                 330                 335 gaa gcc act cgc ttt tgg cgc aat cag aaa gta gcc ccg gag aat agc     1056
Glu Ala Thr Arg Phe Trp Arg Asn Gln Lys Val Ala Pro Glu Asn Ser
        340                 345                 350 tat acc tac gat tcc ctg tat cag ctt atc agc gcc acc ggg cgc gag     1104
Tyr Thr Tyr Asp Ser Leu Tyr Gln Leu Ile Ser Ala Thr Gly Arg Glu
    355                 360                 365 atg gcc aat atc ggt cag caa agc aac caa ctt ccc tct ccg gcg cta     1152
Met Ala Asn Ile Gly Gln Gln Ser Asn Gln Leu Pro Ser Pro Ala Leu
370                 375                 380 cct tct gat aac aat acc tac acc aac tat act cgc act tat act tat     1200
Pro Ser Asp Asn Asn Thr Tyr Thr Asn Tyr Thr Arg Thr Tyr Thr Tyr
385                 390                 395                 400 gac cgt ggc ggc aat ttg acg aaa att cag cat agt tca cca gcc gcg     1248
Asp Arg Gly Gly Asn Leu Thr Lys Ile Gln His Ser Ser Pro Ala Ala
            405                 410                 415 caa aat aac tac acg acg gat ata acg gtt tca aat cgc agc aac cgc     1296
Gln Asn Asn Tyr Thr Thr Asp Ile Thr Val Ser Asn Arg Ser Asn Arg
        420                 425                 430 gcg gta ctc agc aca ttg acc gca gat cca act caa gtc gat gcc tta     1344
Ala Val Leu Ser Thr Leu Thr Ala Asp Pro Thr Gln Val Asp Ala Leu
    435                 440                 445 ttt gat gcg gga ggc cat caa acc agc ttg tta tcc ggc caa gtt cta     1392
Phe Asp Ala Gly Gly His Gln Thr Ser Leu Leu Ser Gly Gln Val Leu
450                 455                 460 act tgg aca ccg cga ggc gaa ttg aaa caa gcc aac aat agc gca gga     1440
Thr Trp Thr Pro Arg Gly Glu Leu Lys Gln Ala Asn Asn Ser Ala Gly
465                 470                 475                 480 aat gag tgg tat cgc tac gat agc aac ggc ata cgc cag cta aaa gtg     1488
Asn Glu Trp Tyr Arg Tyr Asp Ser Asn Gly Ile Arg Gln Leu Lys Val
            485                 490                 495 aat gaa caa caa act cag aat atc ccg caa caa caa agg gta act tat     1536
Asn Glu Gln Gln Thr Gln Asn Ile Pro Gln Gln Gln Arg Val Thr Tyr
        500                 505                 510 cta ccg ggg ctg gaa ata cgt aca acc cag aac aac gcc aca aca aca     1584
Leu Pro Gly Leu Glu Ile Arg Thr Thr Gln Asn Asn Ala Thr Thr Thr
    515                 520                 525 gaa gag tta cac gtt atc aca ctc ggt aaa gcc ggc cgc gcg caa gtc     1632
Glu Glu Leu His Val Ile Thr Leu Gly Lys Ala Gly Arg Ala Gln Val
530                 535                 540
```

-continued

```
cga gta ttg cat tgg gag agc ggt aaa cca gaa gat att aat aac aat     1680
Arg Val Leu His Trp Glu Ser Gly Lys Pro Glu Asp Ile Asn Asn Asn
545                 550                 555                 560 cag ctt cgt tac agc tac gat aat ctt att ggc tcc agc caa ctt caa     1728
Gln Leu Arg Tyr Ser Tyr Asp Asn Leu Ile Gly Ser Ser Gln Leu Gln
                565                 570                 575 tta gat agc gac gga caa att atc agt gaa gaa gaa tat tat cca ttt     1776
Leu Asp Ser Asp Gly Gln Ile Ile Ser Glu Glu Glu Tyr Tyr Pro Phe
            580                 585                 590 ggt ggt aca gcg ctg tgg gcg gca agg aat caa acc gaa gcc agc tat     1824
Gly Gly Thr Ala Leu Trp Ala Ala Arg Asn Gln Thr Glu Ala Ser Tyr
        595                 600                 605 aaa acc att cgt tat tct ggt aaa gag cgg gat gtt acc ggg ctg tat     1872
Lys Thr Ile Arg Tyr Ser Gly Lys Glu Arg Asp Val Thr Gly Leu Tyr
610                 615                 620 tat tat ggc tac cgt tat tac caa ccg tgg gcg ggc aga tgg tta ggt     1920
Tyr Tyr Gly Tyr Arg Tyr Tyr Gln Pro Trp Ala Gly Arg Trp Leu Gly
625                 630                 635                 640 gca gac ccg gca gga acc att gat gga ctg aat tta tat cgc atg gtg     1968
Ala Asp Pro Ala Gly Thr Ile Asp Gly Leu Asn Leu Tyr Arg Met Val
                645                 650                 655 aga aat aac ccg gtg acg caa ttt gat gtt cag gga tta tca ccg gcc     2016
Arg Asn Asn Pro Val Thr Gln Phe Asp Val Gln Gly Leu Ser Pro Ala
            660                 665                 670 aac aga aca gaa gaa gcg ata ata aaa cag ggt tcc ttt acg gga atg     2064
Asn Arg Thr Glu Glu Ala Ile Ile Lys Gln Gly Ser Phe Thr Gly Met
        675                 680                 685 gaa gaa gct gtt tat aaa aaa atg gct aaa cct caa act ttc aaa cgc     2112
Glu Glu Ala Val Tyr Lys Lys Met Ala Lys Pro Gln Thr Phe Lys Arg
690                 695                 700 caa aga gct atc gct gcc caa aca gag caa gaa gcc cat gaa tca ttg     2160
Gln Arg Ala Ile Ala Ala Gln Thr Glu Gln Glu Ala His Glu Ser Leu
705                 710                 715                 720 acc aac aac cct agt gta gat att agc cca att aaa aac tac acc aca     2208
Thr Asn Asn Pro Ser Val Asp Ile Ser Pro Ile Lys Asn Tyr Thr Thr
                725                 730                 735 gat agc tca caa att aat gcc gcg ata agg gaa aat cgt att acg cca     2256
Asp Ser Ser Gln Ile Asn Ala Ala Ile Arg Glu Asn Arg Ile Thr Pro
            740                 745                 750 gca gtg gaa agt tta gac gcc aca tta tct tcc cta caa gat aga caa     2304
Ala Val Glu Ser Leu Asp Ala Thr Leu Ser Ser Leu Gln Asp Arg Gln
        755                 760                 765 atg agg gta act tat cgg gtg atg acc tat gta gat aat tcc acg cca     2352
Met Arg Val Thr Tyr Arg Val Met Thr Tyr Val Asp Asn Ser Thr Pro
770                 775                 780 tcg cct tgg cac tcg cca cag gaa gga aat agt att aat gtt ggt gat     2400
Ser Pro Trp His Ser Pro Gln Glu Gly Asn Ser Ile Asn Val Gly Asp
785                 790                 795                 800 atc gtt tcg gat aac gct tat tta tca aca tcg gcc cat cgt ggt ttt     2448
Ile Val Ser Asp Asn Ala Tyr Leu Ser Thr Ser Ala His Arg Gly Phe
                805                 810                 815 ctg aat ttt gtt cac aaa aaa gaa acc agt gaa act cga tac gtc aag     2496
Leu Asn Phe Val His Lys Lys Glu Thr Ser Glu Thr Arg Tyr Val Lys
            820                 825                 830 atg gca ttt tta acg aat gcg ggt gtc aat gtc cca gca gca tct atg     2544
Met Ala Phe Leu Thr Asn Ala Gly Val Asn Val Pro Ala Ala Ser Met
        835                 840                 845 tat aat aat gct ggc gag gag caa gta ttt aaa atg gat tta aac gat     2592
Tyr Asn Asn Ala Gly Glu Glu Gln Val Phe Lys Met Asp Leu Asn Asp
```

```
                850                 855                 860
tca aga aaa agc ctt gct gaa aaa tta aaa cta aga gtc agt gga cca    2640
Ser Arg Lys Ser Leu Ala Glu Lys Leu Lys Leu Arg Val Ser Gly Pro
865                 870                 875                 880 caa tcg gga caa gcg gaa ata tta cta cct agg gaa aca cag ttc gaa    2688
Gln Ser Gly Gln Ala Glu Ile Leu Leu Pro Arg Glu Thr Gln Phe Glu
            885                 890                 895 gtt gtt tca atg aaa cat caa ggc aga gat acc tat gta tta ttg caa    2736
Val Val Ser Met Lys His Gln Gly Arg Asp Thr Tyr Val Leu Leu Gln
        900                 905                 910 gat att aac caa tcc gca gcc act cat aga aat gta cgt aac act tac    2784
Asp Ile Asn Gln Ser Ala Ala Thr His Arg Asn Val Arg Asn Thr Tyr
    915                 920                 925 acc ggt aat ttc aaa tca tcc agt gca aat taa                        2817
Thr Gly Asn Phe Lys Ser Ser Ser Ala Asn
            930                 935

<210> SEQ ID NO 58
<211> LENGTH: 915
<212> TYPE: PRT
<213> ORGANISM: Photorhabdus luminescens

<400> SEQUENCE: 58

Met Ser Ser Tyr Asn Ser Ala Ile Asp Gln Lys Thr Pro Ser Ile Lys
1               5                   10                  15

Val Leu Asp Asn Arg Lys Leu Asn Val Arg Thr Leu Glu Tyr Leu Arg
            20                  25                  30

Thr Gln Ala Asp Glu Asn Ser Asp Glu Leu Ile Thr Phe Tyr Glu Phe
        35                  40                  45

Asn Ile Pro Gly Phe Gln Val Lys Ser Thr Asp Pro Arg Lys Asn Lys
    50                  55                  60

Asn Gln Ser Gly Pro Asn Phe Ile Arg Val Phe Asn Leu Ala Gly Gln
65                  70                  75                  80

Val Leu Arg Glu Glu Ser Val Asp Ala Gly Arg Thr Ile Thr Leu Asn
                85                  90                  95

Asp Ile Glu Ser Arg Pro Val Leu Ile Ile Asn Ala Thr Gly Val Arg
            100                 105                 110

Gln Asn His Arg Tyr Glu Asp Asn Thr Leu Pro Gly Arg Leu Leu Ala
        115                 120                 125

Ile Thr Glu Gln Val Gln Ala Gly Glu Lys Thr Thr Glu Arg Leu Ile
    130                 135                 140

Trp Ala Gly Asn Thr Pro Gln Glu Lys Asp Tyr Asn Leu Ala Gly Gln
145                 150                 155                 160

Cys Val Arg His Tyr Asp Thr Ala Gly Leu Thr Gln Leu Asn Ser Leu
                165                 170                 175

Ser Leu Ala Gly Val Val Leu Ser Gln Ser Gln Gln Leu Leu Val Asp
            180                 185                 190

Asp Lys Asn Ala Asp Trp Thr Gly Glu Asp Gln Ser Leu Trp Gln Gln
        195                 200                 205

Lys Leu Ser Ser Asp Val Tyr Thr Thr Gln Asn Lys Ala Asp Ala Thr
    210                 215                 220

Gly Ala Leu Leu Thr Gln Thr Asp Ala Lys Gly Asn Ile Gln Arg Leu
225                 230                 235                 240

Ala Tyr Asp Val Ala Gly Gln Leu Lys Gly Cys Trp Leu Thr Leu Lys
                245                 250                 255

Gly Gln Ala Glu Gln Val Ile Ile Lys Ser Leu Thr Tyr Ser Ala Ala
```

-continued

```
                260                 265                 270
Gly Gln Lys Leu Arg Glu Glu His Gly Asn Gly Val Ile Thr Glu Tyr
            275                 280                 285
Ser Tyr Glu Pro Glu Thr Gln Arg Leu Ile Gly Ile Ala Thr Arg Arg
        290                 295                 300
Pro Ser Asp Ala Lys Val Leu Gln Asp Leu Arg Tyr Gln Tyr Asp Pro
305                 310                 315                 320
Val Gly Asn Val Ile Asn Ile Arg Asn Asp Ala Glu Ala Thr Arg Phe
                325                 330                 335
Trp Arg Asn Gln Lys Val Val Pro Glu Asn Ser Tyr Thr Tyr Asp Ser
            340                 345                 350
Leu Tyr Gln Leu Ile Ser Ala Thr Gly Arg Glu Met Ala Asn Ile Gly
        355                 360                 365
Gln Gln Asn Asn Gln Leu Pro Ser Pro Ala Leu Pro Ser Asp Asn Asn
    370                 375                 380
Thr Tyr Thr Asn Tyr Thr Arg Ser Tyr Ser Tyr Asp His Ser Gly Asn
385                 390                 395                 400
Leu Thr Gln Ile Arg His Ser Ser Pro Ala Thr Gln Asn Asn Tyr Thr
                405                 410                 415
Val Ala Ile Thr Leu Ser Asn Arg Ser Asn Arg Gly Val Leu Ser Thr
            420                 425                 430
Leu Thr Thr Asp Pro Asn Gln Val Asp Thr Leu Phe Asp Ala Gly Gly
        435                 440                 445
His Gln Thr Ser Leu Leu Pro Gly Gln Thr Leu Ile Trp Thr Pro Arg
    450                 455                 460
Gly Glu Leu Lys Gln Val Asn Asn Gly Pro Gly Asn Glu Trp Tyr Arg
465                 470                 475                 480
Tyr Asp Ser Asn Gly Met Arg Gln Leu Lys Val Ser Glu Gln Pro Thr
                485                 490                 495
Gln Asn Thr Thr Gln Gln Arg Val Ile Tyr Leu Pro Gly Leu Glu
            500                 505                 510
Leu Arg Thr Thr Gln Ser Asn Ala Thr Thr Thr Glu Glu Leu His Val
        515                 520                 525
Ile Thr Leu Gly Glu Ala Gly Arg Ala Gln Val Arg Val Leu His Trp
    530                 535                 540
Glu Ser Gly Lys Pro Glu Asp Val Asn Asn Asn Gln Leu Arg Tyr Ser
545                 550                 555                 560
Tyr Asp Asn Leu Ile Gly Ser Ser Gln Leu Glu Leu Asp Asn Gln Gly
                565                 570                 575
Gln Ile Ile Ser Glu Glu Glu Tyr Tyr Pro Phe Gly Gly Thr Ala Leu
            580                 585                 590
Trp Ala Ala Asn Ser Gln Thr Glu Ala Ser Tyr Lys Thr Ile Arg Tyr
        595                 600                 605
Ser Gly Lys Glu Arg Asp Ala Thr Gly Leu Tyr Tyr Tyr Gly Tyr Arg
    610                 615                 620
Tyr Tyr Gln Pro Trp Ala Gly Arg Trp Leu Ser Ala Asp Pro Ala Gly
625                 630                 635                 640
Thr Ile Asp Gly Leu Asn Leu Tyr Arg Met Val Arg Asn Asn Pro Val
                645                 650                 655
Ser Leu Gln Asp Glu Asn Gly Leu Ala Pro Glu Lys Gly Lys Tyr Thr
            660                 665                 670
Lys Glu Val Asn Phe Phe Asp Glu Leu Lys Phe Lys Leu Ala Ala Lys
        675                 680                 685
```

```
Ser Ser His Val Val Lys Trp Asn Glu Lys Glu Ser Ser Tyr Thr Lys
    690                 695                 700

Asn Lys Ser Leu Lys Val Val Arg Val Gly Asp Ser Asp Pro Ser Gly
705                 710                 715                 720

Tyr Leu Leu Ser His Glu Glu Leu Leu Lys Gly Ile Glu Lys Ser Gln
                725                 730                 735

Ile Ile Tyr Ser Arg Leu Glu Glu Asn Ser Ser Leu Ser Glu Lys Ser
            740                 745                 750

Lys Thr Asn Leu Ser Leu Gly Ser Glu Ile Ser Gly Tyr Met Ala Arg
        755                 760                 765

Thr Ile Gln Asp Thr Ile Ser Glu Tyr Ala Glu His Lys Tyr Arg
    770                 775                 780

Ser Asn His Pro Asp Phe Tyr Ser Glu Thr Asp Phe Phe Ala Leu Met
785                 790                 795                 800

Asp Lys Ser Glu Lys Asn Asp Tyr Ser Gly Glu Arg Lys Ile Tyr Ala
                805                 810                 815

Ala Met Glu Val Lys Val Tyr His Asp Leu Lys Asn Lys Gln Ser Glu
            820                 825                 830

Leu His Val Asn Tyr Ala Leu Ala His Pro Tyr Thr Gln Leu Ser Asn
        835                 840                 845

Glu Glu Arg Ala Leu Leu Gln Glu Thr Glu Pro Ala Ile Ala Ile Asp
    850                 855                 860

Arg Glu Tyr Asn Phe Lys Gly Val Gly Lys Phe Leu Thr Met Lys Ala
865                 870                 875                 880

Ile Lys Lys Ser Leu Lys Gly His Lys Ile Asn Arg Ile Ser Thr Glu
                885                 890                 895

Ala Ile Asn Ile Arg Ser Ala Ala Ile Ala Glu Asn Leu Gly Met Arg
            900                 905                 910

Arg Thr Ser
        915

<210> SEQ ID NO 59
<211> LENGTH: 2504
<212> TYPE: PRT
<213> ORGANISM: Photorhabdus luminescens

<400> SEQUENCE: 59

Met Gln Asn Ser Leu Ser Ser Thr Ile Asp Thr Ile Cys Gln Lys Leu
1               5                   10                  15

Gln Leu Thr Cys Pro Ala Glu Ile Ala Leu Tyr Pro Phe Asp Thr Phe
            20                  25                  30

Arg Glu Lys Thr Arg Gly Met Val Asn Trp Gly Glu Ala Lys Arg Ile
        35                  40                  45

Tyr Glu Ile Ala Gln Ala Glu Gln Asp Arg Asn Leu Leu His Glu Lys
    50                  55                  60

Arg Ile Phe Ala Tyr Ala Asn Pro Leu Leu Lys Asn Ala Val Arg Leu
65                  70                  75                  80

Gly Thr Arg Gln Met Leu Gly Phe Ile Gln Gly Tyr Ser Asp Leu Phe
                85                  90                  95

Gly Asn Arg Ala Asp Asn Tyr Ala Ala Pro Gly Ser Val Ala Ser Met
            100                 105                 110

Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
```

```
              130                 135                 140
Leu Ala Ser Leu Met Leu Ser Gln Lys Asn Met Asp Glu Glu Ile Ser
145                 150                 155                 160
Thr Leu Ala Leu Ser Asn Glu Leu Cys Leu Ala Gly Ile Glu Thr Lys
                    165                 170                 175
Thr Gly Lys Ser Gln Asp Glu Val Met Asp Met Leu Ser Thr Tyr Arg
                180                 185                 190
Leu Ser Gly Glu Thr Pro Tyr His His Ala Tyr Glu Thr Val Arg Glu
            195                 200                 205
Ile Val His Glu Arg Asp Pro Gly Phe Arg His Leu Ser Gln Ala Pro
210                 215                 220
Ile Val Ala Ala Lys Leu Asp Pro Val Thr Leu Leu Gly Ile Ser Ser
225                 230                 235                 240
His Ile Ser Pro Glu Leu Tyr Asn Leu Leu Ile Glu Glu Ile Pro Glu
                245                 250                 255
Lys Asp Glu Ala Ala Leu Asp Thr Leu Tyr Lys Thr Asn Phe Gly Asp
                260                 265                 270
Ile Thr Thr Ala Gln Leu Met Ser Pro Ser Tyr Leu Ala Arg Tyr Tyr
            275                 280                 285
Gly Val Ser Pro Glu Asp Ile Ala Tyr Val Thr Thr Ser Leu Ser His
        290                 295                 300
Val Gly Tyr Ser Ser Asp Ile Leu Val Ile Pro Leu Val Asp Gly Val
305                 310                 315                 320
Gly Lys Met Glu Val Val Arg Val Thr Arg Thr Pro Ser Asp Asn Tyr
                325                 330                 335
Thr Ser Gln Thr Asn Tyr Ile Glu Leu Tyr Pro Gln Gly Gly Asp Asn
                340                 345                 350
Tyr Leu Ile Lys Tyr Asn Leu Ser Asn Ser Phe Gly Leu Asp Asp Phe
            355                 360                 365
Tyr Leu Gln Tyr Lys Asp Gly Ser Ala Asp Trp Thr Glu Ile Ala His
        370                 375                 380
Asn Pro Tyr Pro Asp Met Val Ile Asn Gln Lys Tyr Glu Ser Gln Ala
385                 390                 395                 400
Thr Ile Lys Arg Ser Asp Ser Asp Asn Ile Leu Ser Ile Gly Leu Gln
                405                 410                 415
Arg Trp His Ser Gly Ser Tyr Asn Phe Ala Ala Asn Phe Lys Ile
                420                 425                 430
Asp Gln Tyr Ser Pro Lys Ala Phe Leu Leu Lys Met Asn Lys Ala Ile
            435                 440                 445
Arg Leu Leu Lys Ala Thr Gly Leu Ser Phe Ala Thr Leu Glu Arg Ile
        450                 455                 460
Val Asp Ser Val Asn Ser Thr Lys Ser Ile Thr Val Glu Val Leu Asn
465                 470                 475                 480
Lys Val Tyr Arg Val Lys Phe Tyr Ile Asp Arg Tyr Gly Ile Ser Glu
                485                 490                 495
Glu Thr Ala Ala Ile Leu Ala Asn Ile Asn Ile Ser Gln Gln Ala Val
                500                 505                 510
Gly Asn Gln Leu Ser Gln Phe Glu Gln Leu Phe Asn His Pro Pro Leu
            515                 520                 525
Asn Gly Ile Arg Tyr Glu Ile Ser Glu Asp Asn Ser Lys His Leu Pro
        530                 535                 540
Asn Pro Asp Leu Asn Leu Lys Pro Asp Ser Thr Gly Asp Asp Gln Arg
545                 550                 555                 560
```

```
Lys Ala Val Leu Lys Arg Ala Phe Gln Val Asn Ala Ser Glu Leu Tyr
            565                 570                 575

Gln Met Leu Leu Ile Thr Asp Arg Lys Glu Asp Gly Val Ile Lys Asn
            580                 585                 590

Asn Leu Glu Asn Leu Ser Asp Leu Tyr Leu Val Ser Leu Leu Ala Gln
            595                 600                 605

Ile His Asn Leu Thr Ile Ala Glu Leu Asn Ile Leu Leu Val Ile Cys
            610                 615                 620

Gly Tyr Gly Asp Thr Asn Ile Tyr Gln Ile Thr Asp Asp Asn Leu Ala
625                 630                 635                 640

Lys Ile Val Glu Thr Leu Leu Trp Ile Thr Gln Trp Leu Lys Thr Gln
            645                 650                 655

Lys Trp Thr Val Thr Asp Leu Phe Leu Met Thr Thr Ala Thr Tyr Ser
            660                 665                 670

Thr Thr Leu Thr Pro Glu Ile Ser Asn Leu Thr Ala Thr Leu Ser Ser
            675                 680                 685

Thr Leu His Gly Lys Glu Ser Leu Ile Gly Glu Asp Leu Lys Arg Ala
            690                 695                 700

Met Ala Pro Cys Phe Thr Ser Ala Leu His Leu Thr Ser Gln Glu Val
705                 710                 715                 720

Ala Tyr Asp Leu Leu Trp Ile Asp Gln Ile Gln Pro Ala Gln Ile
            725                 730                 735

Thr Val Asp Gly Phe Trp Glu Glu Val Gln Thr Thr Pro Thr Ser Leu
            740                 745                 750

Lys Val Ile Thr Phe Ala Gln Val Leu Ala Gln Leu Ser Leu Ile Tyr
            755                 760                 765

Arg Arg Ile Gly Leu Ser Glu Thr Glu Leu Ser Leu Ile Val Thr Gln
            770                 775                 780

Ser Ser Leu Leu Val Ala Gly Lys Ser Ile Leu Asp His Gly Leu Leu
785                 790                 795                 800

Thr Leu Met Ala Leu Glu Gly Phe His Thr Trp Val Asn Gly Leu Gly
            805                 810                 815

Gln His Ala Ser Leu Ile Leu Ala Ala Leu Lys Asp Gly Ala Leu Thr
            820                 825                 830

Val Thr Asp Val Ala Gln Ala Met Asn Lys Glu Glu Ser Leu Leu Gln
            835                 840                 845

Met Ala Ala Asn Gln Val Glu Lys Asp Leu Thr Lys Leu Thr Ser Trp
850                 855                 860

Thr Gln Ile Asp Ala Ile Leu Gln Trp Leu Gln Met Ser Ser Ala Leu
865                 870                 875                 880

Ala Val Ser Pro Leu Asp Leu Ala Gly Met Met Ala Leu Lys Tyr Gly
            885                 890                 895

Ile Asp His Asn Tyr Ala Ala Trp Gln Ala Ala Ala Ala Leu Met
            900                 905                 910

Ala Asp His Ala Asn Gln Ala Gln Lys Lys Leu Asp Glu Thr Phe Ser
            915                 920                 925

Lys Ala Leu Cys Asn Tyr Tyr Ile Asn Ala Val Val Asp Ser Ala Ala
            930                 935                 940

Gly Val Arg Asp Arg Asn Gly Leu Tyr Thr Tyr Leu Leu Ile Asp Asn
945                 950                 955                 960

Gln Val Ser Ala Asp Val Ile Thr Ser Arg Ile Ala Glu Ala Ile Ala
            965                 970                 975
```

-continued

Gly Ile Gln Leu Tyr Val Asn Arg Ala Leu Asn Arg Asp Glu Gly Gln
              980                 985                 990

Leu Ala Ser Asp Val Ser Thr Arg Gln Phe Phe Thr Asp Trp Glu Arg
              995                 1000                1005

Tyr Asn Lys Arg Tyr Ser Thr Trp Ala Gly Val Ser Glu Leu Val
    1010                1015                1020

Tyr Tyr Pro Glu Asn Tyr Val Asp Pro Thr Gln Arg Ile Gly Gln
    1025                1030                1035

Thr Lys Met Met Asp Ala Leu Leu Gln Ser Ile Asn Gln Ser Gln
    1040                1045                1050

Leu Asn Ala Asp Thr Val Glu Asp Ala Phe Lys Thr Tyr Leu Thr
    1055                1060                1065

Ser Phe Glu Gln Val Ala Asn Leu Lys Val Ile Ser Ala Tyr His
    1070                1075                1080

Asp Asn Val Asn Val Asp Gln Gly Leu Thr Tyr Phe Ile Gly Ile
    1085                1090                1095

Asp Gln Ala Ala Pro Gly Thr Tyr Tyr Trp Arg Ser Val Asp His
    1100                1105                1110

Ser Lys Cys Glu Asn Gly Lys Phe Ala Ala Asn Ala Trp Gly Glu
    1115                1120                1125

Trp Asn Lys Ile Thr Cys Ala Val Asn Pro Trp Lys Asn Ile Ile
    1130                1135                1140

Arg Pro Val Val Tyr Met Ser Arg Leu Tyr Leu Leu Trp Leu Glu
    1145                1150                1155

Gln Gln Ser Lys Lys Ser Asp Asp Gly Lys Thr Thr Ile Tyr Gln
    1160                1165                1170

Tyr Asn Leu Lys Leu Ala His Ile Arg Tyr Asp Gly Ser Trp Asn
    1175                1180                1185

Thr Pro Phe Thr Phe Asp Val Thr Glu Lys Val Lys Asn Tyr Thr
    1190                1195                1200

Ser Ser Thr Asp Ala Ala Glu Ser Leu Gly Leu Tyr Cys Thr Gly
    1205                1210                1215

Tyr Gln Gly Glu Asp Thr Leu Leu Val Met Phe Tyr Ser Met Gln
    1220                1225                1230

Ser Ser Tyr Ser Ser Tyr Thr Asp Asn Asn Ala Pro Val Thr Gly
    1235                1240                1245

Leu Tyr Ile Phe Ala Asp Met Ser Ser Asp Asn Met Thr Asn Ala
    1250                1255                1260

Gln Ala Thr Asn Tyr Trp Asn Asn Ser Tyr Pro Gln Phe Asp Thr
    1265                1270                1275

Val Met Ala Asp Pro Asp Ser Asp Asn Lys Lys Val Ile Thr Arg
    1280                1285                1290

Arg Val Asn Asn Arg Tyr Ala Glu Asp Tyr Glu Ile Pro Ser Ser
    1295                1300                1305

Val Thr Ser Asn Ser Asn Tyr Ser Trp Gly Asp His Ser Leu Thr
    1310                1315                1320

Met Leu Tyr Gly Gly Ser Val Pro Asn Ile Thr Phe Glu Ser Ala
    1325                1330                1335

Ala Glu Asp Leu Arg Leu Ser Thr Asn Met Ala Leu Ser Ile Ile
    1340                1345                1350

His Asn Gly Tyr Ala Gly Thr Arg Arg Ile Gln Cys Asn Leu Met
    1355                1360                1365

Lys Gln Tyr Ala Ser Leu Gly Asp Lys Phe Ile Ile Tyr Asp Ser

-continued

```
            1370                1375                1380

Ser Phe Asp Asp Ala Asn Arg Phe Asn Leu Val Pro Leu Phe Lys
    1385                1390                1395

Phe Gly Lys Asp Glu Asn Ser Asp Asp Ser Ile Cys Ile Tyr Asn
    1400                1405                1410

Glu Asn Pro Ser Ser Glu Asp Lys Lys Trp Tyr Phe Ser Ser Lys
    1415                1420                1425

Asp Asp Asn Lys Thr Ala Asp Tyr Asn Gly Gly Thr Gln Cys Ile
    1430                1435                1440

Asp Ala Gly Thr Ser Asn Lys Asp Phe Tyr Tyr Asn Leu Gln Glu
    1445                1450                1455

Ile Glu Val Ile Ser Val Thr Gly Gly Tyr Trp Ser Ser Tyr Lys
    1460                1465                1470

Ile Ser Asn Pro Ile Asn Ile Asn Thr Gly Ile Asp Ser Ala Lys
    1475                1480                1485

Val Lys Val Thr Val Lys Ala Gly Gly Asp Asp Gln Ile Phe Thr
    1490                1495                1500

Ala Asp Asn Ser Thr Tyr Val Pro Gln Gln Pro Ala Pro Ser Phe
    1505                1510                1515

Glu Glu Met Ile Tyr Gln Phe Asn Asn Leu Thr Ile Asp Cys Lys
    1520                1525                1530

Asn Leu Asn Phe Ile Asp Asn Gln Ala His Ile Glu Ile Asp Phe
    1535                1540                1545

Thr Ala Thr Ala Gln Asp Gly Arg Phe Leu Gly Ala Glu Thr Phe
    1550                1555                1560

Ile Ile Pro Val Thr Lys Lys Val Leu Gly Thr Glu Asn Val Ile
    1565                1570                1575

Ala Leu Tyr Ser Glu Asn Asn Gly Val Gln Tyr Met Gln Ile Gly
    1580                1585                1590

Ala Tyr Arg Thr Arg Leu Asn Thr Leu Phe Ala Gln Gln Leu Val
    1595                1600                1605

Ser Arg Ala Asn Arg Gly Ile Asp Ala Val Leu Ser Met Glu Thr
    1610                1615                1620

Gln Asn Ile Gln Glu Pro Gln Leu Gly Ala Gly Thr Tyr Val Gln
    1625                1630                1635

Leu Val Leu Asp Lys Tyr Asp Glu Ser Ile His Gly Thr Asn Lys
    1640                1645                1650

Ser Phe Ala Ile Glu Tyr Val Asp Ile Phe Lys Glu Asn Asp Ser
    1655                1660                1665

Phe Val Ile Tyr Gln Gly Glu Leu Ser Glu Thr Ser Gln Thr Val
    1670                1675                1680

Val Lys Val Phe Leu Ser Tyr Phe Ile Glu Ala Thr Gly Asn Lys
    1685                1690                1695

Asn His Leu Trp Val Arg Ala Lys Tyr Gln Lys Glu Thr Thr Asp
    1700                1705                1710

Lys Ile Leu Phe Asp Arg Thr Asp Glu Lys Asp Pro His Gly Trp
    1715                1720                1725

Phe Leu Ser Asp Asp His Lys Thr Phe Ser Gly Leu Ser Ser Ala
    1730                1735                1740

Gln Ala Leu Lys Asn Asp Ser Glu Pro Met Asp Phe Ser Gly Ala
    1745                1750                1755

Asn Ala Leu Tyr Phe Trp Glu Leu Phe Tyr Tyr Thr Pro Met Met
    1760                1765                1770
```

-continued

```
Met Ala His Arg Leu Leu Gln Glu Gln Asn Phe Asp Ala Ala Asn
    1775                1780                1785

His Trp Phe Arg Tyr Val Trp Ser Pro Ser Gly Tyr Ile Val Asp
    1790                1795                1800

Gly Lys Ile Ala Ile Tyr His Trp Asn Val Arg Pro Leu Glu Glu
    1805                1810                1815

Asp Thr Ser Trp Asn Ala Gln Gln Leu Asp Ser Thr Asp Pro Asp
    1820                1825                1830

Ala Val Ala Gln Asp Asp Pro Met His Tyr Lys Val Ala Thr Phe
    1835                1840                1845

Met Ala Thr Leu Asp Leu Leu Met Ala Arg Gly Asp Ala Ala Tyr
    1850                1855                1860

Arg Gln Leu Glu Arg Asp Thr Leu Ala Glu Ala Lys Met Trp Tyr
    1865                1870                1875

Thr Gln Ala Leu Asn Leu Leu Gly Asp Glu Pro Gln Val Met Leu
    1880                1885                1890

Ser Thr Thr Trp Ala Asn Pro Thr Leu Gly Asn Ala Ala Ser Lys
    1895                1900                1905

Thr Thr Gln Gln Val Arg Gln Val Leu Thr Gln Leu Arg Leu
    1910                1915                1920

Asn Ser Arg Val Lys Thr Pro Leu Leu Gly Thr Ala Asn Ser Leu
    1925                1930                1935

Thr Ala Leu Phe Leu Pro Gln Glu Asn Ser Lys Leu Lys Gly Tyr
    1940                1945                1950

Trp Arg Thr Leu Ala Gln Arg Met Phe Asn Leu Arg His Asn Leu
    1955                1960                1965

Ser Ile Asp Gly Gln Pro Leu Ser Leu Pro Leu Tyr Ala Lys Pro
    1970                1975                1980

Ala Asp Pro Lys Ala Leu Leu Ser Ala Ala Val Ser Ala Ser Gln
    1985                1990                1995

Gly Gly Ala Asp Leu Pro Lys Ala Pro Leu Thr Ile His Arg Phe
    2000                2005                2010

Pro Gln Met Leu Glu Gly Ala Arg Gly Leu Val Asn Gln Leu Ile
    2015                2020                2025

Gln Phe Gly Ser Ser Leu Leu Gly Tyr Ser Glu Arg Gln Asp Ala
    2030                2035                2040

Glu Ala Met Ser Gln Leu Leu Gln Thr Gln Ala Ser Glu Leu Ile
    2045                2050                2055

Leu Thr Ser Ile Arg Met Gln Asp Asn Gln Leu Ala Glu Leu Asp
    2060                2065                2070

Ser Glu Lys Thr Ala Leu Gln Val Ser Leu Ala Gly Val Gln Gln
    2075                2080                2085

Arg Phe Asp Ser Tyr Ser Gln Leu Tyr Glu Glu Asn Ile Asn Ala
    2090                2095                2100

Gly Glu Gln Arg Ala Leu Ala Leu Arg Ser Glu Ser Ala Ile Glu
    2105                2110                2115

Ser Gln Gly Ala Gln Ile Ser Arg Met Ala Gly Ala Gly Val Asp
    2120                2125                2130

Met Ala Pro Asn Ile Phe Gly Leu Ala Asp Gly Gly Met His Tyr
    2135                2140                2145

Gly Ala Ile Ala Tyr Ala Ile Ala Asp Gly Ile Glu Leu Ser Ala
    2150                2155                2160
```

```
Ser Ala Lys Met Val Asp Ala Glu Lys Val Ala Gln Ser Glu Ile
2165                2170                2175

Tyr Arg Arg Arg Gln Glu Trp Lys Ile Gln Arg Asp Asn Ala
    2180                2185                2190

Gln Ala Glu Ile Asn Gln Leu Asn Ala Gln Leu Glu Ser Leu Ser
    2195                2200                2205

Ile Arg Arg Glu Ala Ala Glu Met Gln Lys Glu Tyr Leu Lys Thr
    2210                2215                2220

Gln Gln Ala Gln Ala Gln Ala Gln Leu Thr Phe Leu Arg Ser Lys
    2225                2230                2235

Phe Ser Asn Gln Ala Leu Tyr Ser Trp Leu Arg Gly Arg Leu Ser
    2240                2245                2250

Gly Ile Tyr Phe Gln Phe Tyr Asp Leu Ala Val Ser Arg Cys Leu
    2255                2260                2265

Met Ala Glu Gln Ser Tyr Gln Trp Glu Ala Asn Asp Asn Ser Ile
    2270                2275                2280

Ser Phe Val Lys Pro Gly Ala Trp Gln Gly Thr Tyr Ala Gly Leu
    2285                2290                2295

Leu Cys Gly Glu Ala Leu Ile Gln Asn Leu Ala Gln Met Glu Glu
    2300                2305                2310

Ala Tyr Leu Lys Trp Glu Ser Arg Ala Leu Glu Val Glu Arg Thr
    2315                2320                2325

Val Ser Leu Ala Val Val Tyr Asp Ser Leu Glu Gly Asn Asp Arg
    2330                2335                2340

Phe Asn Leu Ala Glu Gln Ile Pro Ala Leu Leu Asp Lys Gly Glu
    2345                2350                2355

Gly Thr Ala Gly Thr Lys Glu Asn Gly Leu Ser Leu Ala Asn Ala
    2360                2365                2370

Ile Leu Ser Ala Ser Val Lys Leu Ser Asp Leu Lys Leu Gly Thr
    2375                2380                2385

Asp Tyr Pro Asp Ser Ile Val Gly Ser Asn Lys Val Arg Arg Ile
    2390                2395                2400

Lys Gln Ile Ser Val Ser Leu Pro Ala Leu Val Gly Pro Tyr Gln
    2405                2410                2415

Asp Val Gln Ala Met Leu Ser Tyr Gly Gly Ser Thr Gln Leu Pro
    2420                2425                2430

Lys Gly Cys Ser Ala Leu Ala Val Ser His Gly Thr Asn Asp Ser
    2435                2440                2445

Gly Gln Phe Gln Leu Asp Phe Asn Asp Gly Lys Tyr Leu Pro Phe
    2450                2455                2460

Glu Gly Ile Ala Leu Asp Asp Gln Gly Thr Leu Asn Leu Gln Phe
    2465                2470                2475

Pro Asn Ala Thr Asp Lys Gln Lys Ala Ile Leu Gln Thr Met Ser
    2480                2485                2490

Asp Ile Ile Leu His Ile Arg Tyr Thr Ile Arg
    2495                2500

<210> SEQ ID NO 60
<211> LENGTH: 1428
<212> TYPE: PRT
<213> ORGANISM: Serratia entomophila

<400> SEQUENCE: 60

Met Gln Asn His Gln Asp Met Ala Ile Thr Ala Pro Thr Leu Pro Ser
1               5                   10                  15
```

-continued

```
Gly Gly Gly Ala Val Thr Gly Leu Lys Gly Asp Ile Ala Ala Gly
             20                  25                  30

Pro Asp Gly Ala Ala Thr Leu Ser Ile Pro Leu Pro Val Ser Pro Gly
             35                  40                  45

Arg Gly Tyr Ala Pro Thr Gly Ala Leu Asn Tyr His Ser Arg Ser Gly
             50                  55                  60

Asn Gly Pro Phe Gly Ile Gly Trp Gly Ile Gly Gly Ala Ala Val Gln
 65                  70                  75                  80

Arg Arg Thr Arg Asn Gly Ala Pro Thr Tyr Asp Asp Thr Asp Glu Phe
                 85                  90                  95

Thr Gly Pro Asp Gly Glu Val Leu Val Pro Ala Leu Thr Ala Ala Gly
            100                 105                 110

Thr Gln Glu Ala Arg Gln Ala Thr Ser Leu Leu Gly Ile Asn Pro Gly
            115                 120                 125

Gly Ser Phe Asn Val Gln Val Tyr Arg Ser Arg Thr Glu Gly Ser Leu
            130                 135                 140

Ser Arg Leu Glu Arg Trp Leu Pro Ala Asp Glu Thr Glu Thr Glu Phe
145                 150                 155                 160

Trp Val Leu Tyr Thr Pro Asp Gly Gln Val Ala Leu Leu Gly Arg Asn
                165                 170                 175

Ala Gln Ala Arg Ile Ser Asn Pro Thr Ala Pro Thr Gln Thr Ala Val
            180                 185                 190

Trp Leu Met Glu Ser Ser Val Ser Leu Thr Gly Glu Gln Met Tyr Tyr
            195                 200                 205

Gln Tyr Arg Ala Glu Asp Asp Gly Cys Asp Glu Ala Glu Arg Asp
            210                 215                 220

Ala His Pro Gln Ala Gly Ala Gln Arg Tyr Pro Val Ala Val Trp Tyr
225                 230                 235                 240

Gly Asn Arg Gln Ala Ala Arg Thr Leu Pro Ala Leu Val Ser Thr Pro
                245                 250                 255

Ser Met Asp Ser Trp Leu Phe Ile Leu Val Phe Asp Tyr Gly Glu Arg
            260                 265                 270

Ser Ser Val Leu Ser Glu Ala Pro Ala Trp Gln Thr Pro Gly Ser Gly
            275                 280                 285

Glu Trp Leu Cys Arg Gln Asp Cys Phe Ser Gly Tyr Glu Phe Gly Phe
            290                 295                 300

Asn Leu Arg Thr Arg Arg Leu Cys Arg Gln Val Leu Met Phe His Tyr
305                 310                 315                 320

Leu Gly Val Leu Ala Gly Ser Ser Gly Ala Asn Asp Ala Pro Ala Leu
                325                 330                 335

Ile Ser Arg Leu Leu Asp Tyr Arg Glu Ser Pro Ser Leu Ser Leu
            340                 345                 350

Leu Glu Asn Val His Gln Val Ala Tyr Glu Ser Asp Gly Thr Ser Cys
            355                 360                 365

Ala Leu Pro Ala Leu Ala Leu Gly Trp Gln Thr Phe Thr Pro Pro Thr
            370                 375                 380

Leu Ser Ala Trp Gln Thr Arg Asp Asp Met Gly Lys Leu Ser Leu Leu
385                 390                 395                 400

Gln Pro Tyr Gln Leu Val Asp Leu Asn Gly Glu Gly Val Val Gly Ile
                405                 410                 415

Leu Tyr Gln Asp Ser Gly Ala Trp Trp Tyr Arg Glu Pro Val Arg Gln
            420                 425                 430
```

-continued

```
Ser Gly Asp Asp Pro Asp Ala Val Thr Trp Gly Ala Ala Ala Leu
        435                 440                 445
Pro Thr Met Pro Ala Leu His Asn Ser Gly Ile Leu Ala Asp Leu Asn
    450                 455                 460
Gly Asp Gly Arg Leu Glu Trp Val Val Thr Ala Pro Gly Val Ala Gly
465                 470                 475                 480
Met Tyr Asp Arg Thr Pro Gly Arg Asp Trp Leu His Phe Thr Pro Leu
            485                 490                 495
Ser Ala Leu Pro Val Glu Tyr Ala His Pro Lys Ala Val Leu Ala Asp
            500                 505                 510
Ile Leu Gly Ala Gly Leu Thr Asp Met Val Leu Ile Gly Pro Arg Ser
        515                 520                 525
Val Arg Leu Tyr Ser Gly Lys Asn Asp Gly Trp Asn Lys Gly Glu Thr
    530                 535                 540
Val Gln Gln Thr Glu Arg Leu Thr Leu Pro Val Pro Gly Val Asp Pro
545                 550                 555                 560
Arg Thr Leu Val Ala Phe Ser Asp Met Ala Gly Ser Gly Gln Gln His
                565                 570                 575
Leu Thr Glu Val Arg Ala Asn Gly Val Arg Tyr Trp Pro Asn Leu Gly
            580                 585                 590
His Gly Arg Phe Gly Gln Pro Val Asn Ile Pro Gly Phe Ser Gln Ser
        595                 600                 605
Val Thr Thr Phe Asn Pro Asp Gln Ile Leu Leu Ala Asp Thr Asp Gly
    610                 615                 620
Ser Gly Thr Thr Asp Leu Ile Tyr Ala Met Ser Asp Arg Leu Val Ile
625                 630                 635                 640
Tyr Phe Asn Gln Ser Gly Asn Tyr Phe Ala Glu Pro His Thr Leu Leu
                645                 650                 655
Leu Pro Lys Gly Val Arg Tyr Asp Arg Thr Cys Ser Leu Gln Val Ala
            660                 665                 670
Asp Ile Gln Gly Leu Gly Val Pro Ser Leu Leu Thr Val Pro His
        675                 680                 685
Val Ala Pro His His Trp Val Cys His Leu Ser Ala Asp Lys Pro Trp
    690                 695                 700
Leu Leu Asn Gly Met Asn Asn Asn Met Gly Ala Arg His Ala Leu His
705                 710                 715                 720
Tyr Arg Ser Ser Val Gln Phe Trp Leu Asp Glu Lys Ala Glu Ala Leu
                725                 730                 735
Ala Ala Gly Ser Ser Pro Ala Cys Tyr Leu Pro Phe Thr Leu His Thr
            740                 745                 750
Leu Trp Arg Ser Val Val Gln Asp Glu Ile Thr Gly Asn Arg Leu Val
        755                 760                 765
Ser Asp Val Leu Tyr Arg His Gly Val Trp Asp Gly Gln Glu Arg Glu
    770                 775                 780
Phe Arg Gly Phe Gly Phe Val Glu Ile Arg Asp Thr Asp Thr Leu Ala
785                 790                 795                 800
Ser Gln Gly Thr Ala Thr Glu Leu Ser Met Pro Ser Val Ser Arg Asn
                805                 810                 815
Trp Tyr Ala Thr Gly Val Pro Ala Val Asp Glu Arg Leu Pro Glu Thr
            820                 825                 830
Tyr Trp Gln Asn Asp Ala Ala Ala Phe Ala Asp Phe Ala Thr Arg Phe
        835                 840                 845
Thr Val Gly Ser Gly Glu Asp Glu Gln Thr Tyr Thr Pro Asp Asp Ser
```

-continued

```
            850                 855                 860
Lys Thr Phe Trp Leu Gln Arg Ala Leu Lys Gly Ile Leu Leu Arg Ser
865                 870                 875                 880

Glu Leu Tyr Gly Ala Asp Gly Ser Ser Gln Ala Asp Ile Pro Tyr Ser
                885                 890                 895

Val Thr Glu Ser Arg Pro Gln Val Arg Leu Val Glu Ala Asn Gly Asp
                900                 905                 910

Tyr Pro Val Val Trp Pro Met Gly Ala Glu Ser Arg Thr Ser Val Tyr
                915                 920                 925

Glu Arg Tyr His Asn Asp Pro Gln Cys Gln Gln Ala Val Leu Leu
930                 935                 940

Ser Asp Glu Tyr Gly Phe Pro Leu Arg Gln Val Ser Val Asn Tyr Pro
945                 950                 955                 960

Arg Arg Pro Pro Ser Ala Asp Asn Pro Tyr Pro Ala Ser Leu Pro Ala
                965                 970                 975

Thr Leu Phe Ala Asn Ser Tyr Asp Glu Gln Gln Ile Leu Arg Leu
                980                 985                 990

Gly Leu Gln Gln Ser Ser Ala His His Leu Val Ser Leu Ser Glu Gly
            995                 1000                1005

His Trp Leu Leu Gly Leu Ala Glu Ala Ser Arg Asp Asp Val Phe
    1010                1015                1020

Thr Tyr Ser Ala Asp Asn Val Pro Glu Gly Gly Leu Thr Leu Glu
    1025                1030                1035

His Leu Leu Ala Pro Glu Ser Leu Val Ser Asp Ser Gln Val Gly
    1040                1045                1050

Thr Leu Ala Gly Gln Gln Gln Val Trp Tyr Leu Asp Ser Gln Asp
    1055                1060                1065

Val Ala Thr Val Ala Ala Pro Pro Leu Pro Pro Lys Val Ala Phe
    1070                1075                1080

Ile Glu Thr Ala Val Leu Asp Glu Gly Met Val Ser Ser Leu Ala
    1085                1090                1095

Ala Tyr Ile Val Asp Glu His Leu Glu Gln Ala Gly Tyr Arg Gln
    1100                1105                1110

Ser Gly Tyr Leu Phe Pro Arg Gly Arg Glu Ala Glu Gln Ala Leu
    1115                1120                1125

Trp Thr Gln Cys Gln Gly Tyr Val Thr Tyr Ala Gly Ala Glu His
    1130                1135                1140

Phe Trp Leu Pro Leu Ser Phe Arg Asp Ser Met Leu Thr Gly Pro
    1145                1150                1155

Val Thr Val Thr Arg Asp Ala Tyr Asp Cys Val Ile Thr Gln Trp
    1160                1165                1170

Gln Asp Ala Ala Gly Ile Val Thr Thr Ala Asp Tyr Asp Trp Arg
    1175                1180                1185

Phe Leu Thr Pro Val Arg Val Thr Asp Pro Asn Asp Asn Leu Gln
    1190                1195                1200

Ser Val Thr Leu Asp Ala Leu Gly Arg Val Thr Thr Leu Arg Phe
    1205                1210                1215

Trp Gly Thr Glu Asn Gly Ile Ala Thr Gly Tyr Ser Asp Ala Thr
    1220                1225                1230

Leu Ser Val Pro Asp Gly Ala Ala Ala Ala Leu Ala Leu Thr Ala
    1235                1240                1245

Pro Leu Pro Val Ala Gln Cys Leu Val Tyr Val Thr Asp Ser Trp
    1250                1255                1260
```

-continued

Gly Asp Asp Asp Asn Glu Lys Met Pro Pro His Val Val Val Leu
    1265                1270                1275

Ala Thr Asp Arg Tyr Asp Ser Asp Thr Gly Gln Gln Val Arg Gln
    1280                1285                1290

Gln Val Thr Phe Ser Asp Gly Phe Gly Arg Glu Leu Gln Ser Ala
    1295                1300                1305

Thr Arg Gln Ala Glu Gly Asn Ala Trp Gln Arg Gly Arg Asp Gly
    1310                1315                1320

Lys Leu Val Thr Ala Ser Asp Gly Leu Pro Val Thr Val Ala Thr
    1325                1330                1335

Asn Phe Arg Trp Ala Val Thr Gly Arg Ala Glu Tyr Asp Asn Lys
    1340                1345                1350

Gly Leu Pro Val Arg Val Tyr Gln Pro Tyr Phe Leu Asp Ser Trp
    1355                1360                1365

Gln Tyr Val Ser Asp Asp Ser Ala Arg Gln Asp Leu Tyr Ala Asp
    1370                1375                1380

Thr His Phe Tyr Asp Pro Thr Ala Arg Glu Trp Gln Val Ile Thr
    1385                1390                1395

Ala Lys Gly Glu Arg Arg Gln Val Leu Tyr Thr Pro Trp Phe Val
    1400                1405                1410

Val Ser Glu Asp Glu Asn Asp Thr Val Gly Leu Asn Asp Ala Ser
    1415                1420                1425

<210> SEQ ID NO 61
<211> LENGTH: 973
<212> TYPE: PRT
<213> ORGANISM: Serratia entomophila

<400> SEQUENCE: 61

Met Ser Thr Ser Leu Phe Ser Ser Thr Pro Ser Val Ala Val Leu Asp
1               5                   10                  15

Asn Arg Gly Leu Leu Val Arg Glu Leu Gln Tyr Tyr Arg His Pro Asp
            20                  25                  30

Thr Pro Glu Glu Thr Asp Glu Arg Ile Thr Cys His Gln His Asp Glu
        35                  40                  45

Arg Gly Ser Leu Ser Gln Ser Ala Asp Pro Arg Leu His Ala Ala Gly
    50                  55                  60

Leu Thr Asn Phe Thr Tyr Leu Asn Ser Leu Thr Gly Thr Val Leu Gln
65                  70                  75                  80

Ser Val Ser Ala Asp Ala Gly Thr Ser Leu Glu Leu Ser Asp Ala Ala
                85                  90                  95

Gly Arg Ala Phe Leu Ala Val Thr Gly Ala Gly Thr Glu Asp Ala Val
            100                 105                 110

Thr Arg Thr Trp Gln Tyr Glu Asp Asp Thr Leu Pro Gly Arg Pro Leu
        115                 120                 125

Ser Ile Thr Glu Gln Val Thr Gly Glu Ala Ala Gln Ile Thr Glu Arg
    130                 135                 140

Phe Val Tyr Ala Gly Asn Thr Asp Ala Glu Lys Ile Leu Asn Leu Ala
145                 150                 155                 160

Gly Gln Cys Val Ser His Tyr Asp Thr Ala Gly Leu Val Gln Thr Asp
                165                 170                 175

Ser Ile Ala Leu Ser Gly Val Pro Leu Ala Val Thr Arg Gln Leu Leu
            180                 185                 190

Pro Asp Ala Ala Gly Ala Asn Trp Met Gly Glu Asp Ala Ser Ala Trp

-continued

```
                195                 200                 205
Asn Asp Leu Leu Asp Gly Glu Thr Phe Phe Thr Gln Thr His Ala Asp
    210                 215                 220

Ala Thr Gly Ala Val Leu Ser Ile Thr Asp Ala Lys Gly Asn Leu Gln
225                 230                 235                 240

Arg Val Ala Tyr Asp Val Ala Gly Leu Leu Ser Gly Ser Trp Leu Thr
                245                 250                 255

Leu Lys Asp Gly Thr Glu Gln Val Ile Val Ala Ser Leu Thr Tyr Ser
                260                 265                 270

Ala Ala Gly Lys Lys Leu Arg Glu Glu His Gly Asn Gly Val Val Thr
                275                 280                 285

Ser Tyr Ile Tyr Glu Pro Glu Thr Gln Arg Leu Thr Gly Ile Lys Thr
                290                 295                 300

Glu Arg Pro Ser Gly His Val Ala Gly Ala Lys Val Leu Gln Asp Leu
305                 310                 315                 320

Arg Tyr Thr Tyr Asp Pro Val Gly Asn Val Leu Ser Val Asn Asn Asp
                325                 330                 335

Ala Glu Glu Thr Arg Phe Trp Arg Asn Gln Lys Val Val Pro Glu Asn
                340                 345                 350

Thr Tyr Ile Tyr Asp Ser Leu Tyr Gln Leu Val Ser Ala Thr Gly Arg
                355                 360                 365

Glu Met Ala Asn Ala Gly Gln Gln Gly Asn Asp Leu Pro Ser Ala Thr
                370                 375                 380

Ala Pro Leu Pro Thr Asp Ser Ser Ala Tyr Thr Asn Tyr Thr Arg Thr
385                 390                 395                 400

Tyr Arg Tyr Asp Arg Gly Gly Asn Leu Thr Gln Met Arg His Ser Ala
                405                 410                 415

Pro Ala Thr Asn Asn Asn Tyr Thr Thr Asp Ile Thr Val Ser Asp Arg
                420                 425                 430

Ser Asn Arg Ala Val Leu Ser Thr Leu Ala Glu Val Pro Ser Asp Val
                435                 440                 445

Asp Met Leu Phe Ser Ala Gly Gly His Gln Lys His Leu Gln Pro Gly
                450                 455                 460

Gln Ala Leu Val Trp Thr Pro Arg Gly Glu Leu Gln Lys Val Thr Pro
465                 470                 475                 480

Val Val Arg Asp Gly Gly Ala Asp Asp Ser Glu Ser Tyr Arg Tyr Asp
                485                 490                 495

Ala Gly Ser Gln Arg Ile Ile Lys Thr Gly Thr Arg Gln Thr Gly Asn
                500                 505                 510

Asn Val Gln Thr Gln Arg Val Val Tyr Leu Pro Gly Leu Glu Leu Arg
                515                 520                 525

Ile Met Ala Asn Gly Val Thr Glu Lys Glu Ser Leu Gln Val Ile Thr
                530                 535                 540

Val Gly Glu Ala Gly Arg Ala Gln Val Arg Val Leu His Trp Glu Ile
545                 550                 555                 560

Gly Lys Pro Asp Asp Leu Asp Glu Asp Ser Val Arg Tyr Ser Tyr Asp
                565                 570                 575

Asn Leu Val Gly Ser Ser Gln Leu Glu Leu Asp Arg Glu Gly Tyr Leu
                580                 585                 590

Ile Ser Glu Glu Glu Phe Tyr Pro Tyr Gly Gly Thr Ala Val Leu Thr
                595                 600                 605

Ala Arg Ser Glu Val Glu Ala Asp Tyr Lys Thr Ile Arg Tyr Ser Gly
610                 615                 620
```

```
Lys Glu Arg Asp Ala Thr Gly Leu Asp Tyr Tyr Gly Tyr Arg Tyr Tyr
625                 630                 635                 640

Gln Pro Trp Ala Gly Arg Trp Leu Ser Thr Asp Pro Ala Gly Thr Val
                645                 650                 655

Asp Gly Leu Asn Leu Phe Arg Met Val Arg Asn Asn Pro Val Thr Leu
                660                 665                 670

Phe Asp Ser Asn Gly Arg Ile Ser Thr Gly Gln Glu Ala Arg Arg Leu
                675                 680                 685

Val Gly Glu Ala Phe Val His Pro Leu His Met Pro Val Phe Glu Arg
690                 695                 700

Ile Ser Val Glu Arg Lys Ile Ser Met Ser Val Arg Glu Ala Gly Ile
705                 710                 715                 720

Tyr Thr Ile Ser Ala Leu Gly Glu Gly Ala Ala Lys Gly His Asn
                725                 730                 735

Ile Leu Glu Lys Thr Ile Lys Pro Gly Ser Leu Lys Ala Ile Tyr Gly
                740                 745                 750

Asp Lys Ala Glu Ser Ile Leu Gly Leu Ala Lys Arg Ser Gly Leu Val
                755                 760                 765

Gly Arg Val Gly Gln Trp Asp Ala Ser Gly Val Arg Gly Ile Tyr Ala
770                 775                 780

His Asn Arg Pro Gly Gly Glu Asp Leu Val Tyr Pro Val Ser Leu Gln
785                 790                 795                 800

Asn Thr Ser Ala Asn Glu Ile Val Asn Ala Trp Ile Lys Phe Lys Ile
                805                 810                 815

Ile Thr Pro Tyr Thr Gly Asp Tyr Asp Met His Asp Ile Ile Lys Phe
                820                 825                 830

Ser Asp Gly Lys Gly His Val Pro Thr Ala Glu Ser Ser Glu Glu Arg
                835                 840                 845

Gly Val Lys Asp Leu Ile Asn Lys Gly Val Ala Glu Val Asp Pro Ser
850                 855                 860

Arg Pro Phe Glu Tyr Thr Ala Met Asn Val Ile Arg His Gly Pro Gln
865                 870                 875                 880

Val Asn Phe Val Pro Tyr Met Trp Glu His Glu His Asp Lys Val Val
                885                 890                 895

Asn Asp Asn Gly Tyr Leu Gly Val Val Ala Ser Pro Gly Pro Phe Pro
                900                 905                 910

Val Ala Met Val His Gln Gly Glu Trp Thr Val Phe Asp Asn Ser Glu
                915                 920                 925

Glu Leu Phe Asn Phe Tyr Lys Ser Thr Asn Thr Pro Leu Pro Glu His
                930                 935                 940

Trp Ser Gln Asp Phe Met Asp Arg Gly Lys Gly Ile Val Ala Thr Pro
945                 950                 955                 960

Arg His Ala Glu Leu Leu Asp Lys Arg Arg Val Met Tyr
                965                 970

<210> SEQ ID NO 62
<211> LENGTH: 2499
<212> TYPE: PRT
<213> ORGANISM: Photorhabdus luminescens

<400> SEQUENCE: 62

Met Asn Thr Leu Lys Ser Glu Tyr Gln Gln Ala Leu Gly Ala Gly Phe
1               5                   10                  15

Asn Asn Leu Thr Asp Ile Cys His Leu Ser Phe Asp Glu Leu Arg Lys
```

-continued

```
              20                  25                  30
Lys Val Lys Asp Lys Leu Ser Trp Ser Gln Thr Gln Ser Leu Tyr Leu
            35                  40                  45
Glu Ala Gln Gln Val Gln Lys Asp Asn Leu Leu His Glu Ala Arg Ile
        50                  55                  60
Leu Lys Arg Ala Asn Pro His Leu Gln Ser Ala Val His Leu Ala Leu
65                  70                  75                  80
Thr Ala Pro His Ala Asp Gln Gln Gly Tyr Asn Ser Arg Phe Gly Asn
                85                  90                  95
Arg Ala Ser Lys Tyr Ala Ala Pro Gly Ala Ile Ser Ser Met Phe Ser
                100                 105                 110
Leu Ala Ala Tyr Leu Thr Glu Leu Tyr Arg Gln Ala Arg Asn Leu His
                115                 120                 125
Ala Glu Gly Ser Ile Tyr His Leu Asp Thr Arg Arg Pro Asp Leu Lys
            130                 135                 140
Ser Leu Val Leu Ser Gln Lys Asn Met Asn Thr Glu Ile Ser Thr Leu
145                 150                 155                 160
Ser Leu Ser Asn Asn Met Leu Leu Asn Ser Ile Lys Thr Gln Pro Asn
                165                 170                 175
Leu Asn Ser His Ala Lys Val Met Glu Lys Leu Ser Thr Phe Arg Thr
                180                 185                 190
Ser Gly Ser Met Pro Tyr His Asp Ala Tyr Glu Ser Val Arg Lys Ile
            195                 200                 205
Ile Gln Leu Gln Ala Pro Val Phe Glu Gln Ser Ser Thr Leu Thr Asp
        210                 215                 220
Thr Pro Ile Thr Lys Leu Met Tyr Gln Ile Ser Leu Leu Gly Ile Asn
225                 230                 235                 240
Ala Ser Val Ser Pro Glu Leu Phe Thr Ile Leu Thr Gln Lys Ile Lys
                245                 250                 255
Pro Ala Thr Asn Ala Asp Asn Thr Asn Glu Leu Lys Lys Leu Tyr Lys
                260                 265                 270
Lys Asn Phe Gly Glu Ile Lys Ser Ile Gln Met Ala Arg Ala Glu Tyr
            275                 280                 285
Leu Lys Ser Tyr Tyr Asn Leu Thr Asp Lys Glu Leu Asn Gln Phe Ser
        290                 295                 300
Lys Lys Ile Lys Gln Ile Asp Ser Leu Trp Asn Ile Gly Asp Glu Ile
305                 310                 315                 320
Thr Gln Tyr His Leu Leu Lys Phe Asn Lys Ala Ile Asn Leu Ser Arg
                325                 330                 335
Ser Thr Glu Leu Ser Pro Ile Ile Leu Asn Ser Ile Ala Ile Asp Ile
            340                 345                 350
Leu Lys Lys Thr Pro Pro Glu Asp Asp Ser Asp Asn Pro Phe Arg Asp
        355                 360                 365
Asp Pro Asp Tyr Leu Glu Ser Phe Gln Asp Leu Leu Ser Asp Glu
        370                 375                 380
Pro Asp Ile Asp Glu Asp Val Leu Arg Glu Ala Leu Arg Val Lys Asp
385                 390                 395                 400
Tyr Met Gln Arg Tyr Gly Ile Asp Ala Glu Thr Ala Leu Ile Leu Cys
                405                 410                 415
Lys Ala Pro Ile Ser Glu Asn Pro Ser His Pro Asp Leu Ser Lys Leu
                420                 425                 430
Leu Ala Asp Ile His Gln Leu Thr Ile Asp Glu Leu Gly Val Leu Leu
            435                 440                 445
```

```
Val Ala Ile Asp Glu Gly Lys Thr Asp Leu Ser Gln Ile Thr His Asp
    450             455                 460

Asn Leu Ala Val Leu Ile Ser Lys Leu Tyr Ser Val Thr Asn Trp Leu
465                 470                 475                 480

Arg Thr Arg Lys Trp Ser Val Tyr Gln Leu Phe Val Met Thr Thr Asp
                485                 490                 495

Lys Tyr Asn Lys Thr Leu Thr Pro Glu Ile Asn Asn Leu Leu Asp Thr
            500                 505                 510

Val Tyr Asn Gly Leu Gln Asn Phe Tyr Lys Asp Asn Leu Leu Lys Ile
            515                 520                 525

Lys Asp Asn Leu Leu Lys Ala Lys Glu Ser Leu Pro Glu Asp Lys Asp
    530                 535                 540

Asn Leu Pro Lys Ala Glu Gln Tyr Leu Leu Glu Ala Glu Lys Tyr Leu
545                 550                 555                 560

Leu Ala Ala Glu Lys Tyr Leu Leu Ala Ala Glu Lys Tyr Leu Leu Glu
                565                 570                 575

Ala Asn Lys Asn Pro Leu Glu Ala Lys Lys Ala Leu Lys Glu Tyr Glu
                580                 585                 590

Lys Asn Gln Glu Ala Tyr Glu Lys Asn Leu Lys Glu His Glu Lys Tyr
            595                 600                 605

Leu Leu Lys Ala Gly Glu Asn Leu Pro Ala Ile Lys Glu Asn Leu Leu
    610                 615                 620

Lys Ile Lys Glu Asn Leu Pro Lys Ala Ile Ser Pro Tyr Ile Ala Ala
625                 630                 635                 640

Ala Leu Gln Leu Pro Ser Glu Asn Val Ala Leu Ser Val Leu Ala Trp
                645                 650                 655

Ala Asp Lys Leu Asn Ser Gly Lys Glu Asn Lys Met Thr Ala Asp Ser
            660                 665                 670

Phe Trp Asn Trp Leu Arg Lys Lys Pro Ile Glu Thr Gln Ser Lys Thr
            675                 680                 685

Thr Glu Ala Thr Glu Ala Thr Glu Ala Thr Glu Ala Thr Glu Ala Thr
    690                 695                 700

Glu Ala Thr Glu Lys Thr Thr Leu Ile Gln Gln Ala Val Gln Tyr Cys
705                 710                 715                 720

Gln Cys Leu Ala Gln Leu Ala Leu Ile Tyr Arg Ser Thr Gly Leu Ser
                725                 730                 735

Glu Ser Thr Leu Arg Leu Phe Val Thr Asn Pro Gln Ile Phe Gly Leu
            740                 745                 750

Thr Ala Lys Thr Thr Ser Thr His Asn Val Leu Ser Leu Ile Met Leu
            755                 760                 765

Thr Arg Phe Thr Asp Trp Val Asn Ser Leu Gly Glu Asn Ala Ser Ser
    770                 775                 780

Val Leu Thr Glu Phe Glu Lys Gly Thr Leu Thr Ala Glu Leu Leu Ala
785                 790                 795                 800

Asn Ala Met Asn Leu Asp Lys Asn Leu Leu Glu Gln Ala Ser Thr Gln
                805                 810                 815

Ala Gln Ala Asp Phe Ser Asn Trp Pro Ser Ile Asp Asn Leu Leu Gln
            820                 825                 830

Trp Ile Asn Ile Ser Arg Gln Leu Asn Ile Ser Pro Gln Gly Val Ser
            835                 840                 845

Glu Leu Ala Lys Ile Leu Asp Ile Glu Ser Ser Thr Asn Tyr Ala Gln
    850                 855                 860
```

-continued

```
Trp Glu Asn Val Ala Ser Ile Leu Thr Ala Gly Leu Asp Thr Gln Lys
865                 870                 875                 880

Ala Asn Thr Leu His Ala Phe Leu Gly Glu Ser Arg Ser Thr Ala Leu
                885                 890                 895

Ser Thr Tyr Tyr Ile Tyr Ser His Asn Gln Lys Asp Arg Glu Arg
            900                 905                 910

Lys His Thr Val Ile Lys Asp Arg Asp Leu Tyr Gln Tyr Leu Leu
            915                 920                 925

Ile Asp Asn Gln Val Ser Ala Ala Ile Lys Thr Thr Glu Ile Ala Glu
    930                 935                 940

Ala Ile Ala Ser Ile Gln Leu Tyr Ile Asn Arg Ala Leu Lys Asn Met
945                 950                 955                 960

Glu Gly Asp Thr Asp Thr Ser Val Thr Ser Arg Leu Phe Phe Thr Asn
                965                 970                 975

Trp Asp Lys Tyr Asn Lys Arg Tyr Ser Thr Trp Ala Gly Ile Thr Lys
                980                 985                 990

Leu Leu Tyr Tyr Pro Glu Asn Tyr  Ile Asp Pro Thr Leu Arg Ile Gly
            995                 1000                1005

Gln Thr  Lys Met Met Asp Thr  Leu Leu Gln Ser Ile  Ser Gln Ser
    1010                1015                1020

Gln Leu Asn Thr Asp Thr Val  Glu Asp Ala Phe Lys  Ser Tyr Leu
    1025                1030                1035

Thr Ser  Phe Glu Gln Val Ala  Asn Leu Glu Val Ile  Ser Ala Tyr
    1040                1045                1050

His Asp  Asn Ile Asn Asn Asp  Gln Gly Leu Thr Tyr  Phe Ile Gly
    1055                1060                1065

Arg Ser  Lys Thr Glu Val Asn  Gln Tyr Tyr Trp Arg  Ser Val Asp
    1070                1075                1080

His Asn  Lys Phe Ser Glu Gly  Lys Phe Pro Ala Asn  Ala Trp Ser
    1085                1090                1095

Glu Trp  His Lys Ile Asp Cys  Pro Ile Asn Pro Tyr  Glu Asp Thr
    1100                1105                1110

Ile Arg  Pro Val Val Tyr Gln  Ser Arg Leu Tyr Ile  Ile Trp Leu
    1115                1120                1125

Glu Gln  Lys Lys Val Thr Asn  Arg Ala Glu Gly Glu  Ala Ile Lys
    1130                1135                1140

Gln Gly  Ser Lys Thr Thr  Ser Tyr His Tyr Glu  Leu Lys Leu
    1145                1150                1155

Ala His  Ile Arg Tyr Asp Gly  Thr Trp Asn Thr Pro  Ile Thr Phe
    1160                1165                1170

Asp Val  Asp Glu Lys Ile Ser  Gly Leu Asn Leu Glu  Leu Asn Lys
    1175                1180                1185

Ala Leu  Gly Leu Tyr Cys Ala  Ser Tyr Gln Gly Lys  Asp Lys Leu
    1190                1195                1200

Leu Val  Met Phe Tyr Lys Lys  Gln Glu Gln Leu Asn  Asn Tyr Thr
    1205                1210                1215

Glu Lys  Thr Gly Asn Thr Tyr  Thr Ala Pro Ile Lys  Gly Leu Tyr
    1220                1225                1230

Ile Thr  Ser Asn Met Ser Pro  Glu Glu Met Thr Pro  Glu Ser Tyr
    1235                1240                1245

Arg Leu  Asn Ala His Lys Gln  Phe Asp Thr Asn Asn  Val Val Arg
    1250                1255                1260

Val Asn  Asn Arg Tyr Ala Glu  Ser Tyr Glu Ile Pro  Ser Ser Val
```

```
                1265                1270                1275
Asn Ser Asn Asn Gly Tyr Asp Trp Gly Glu Gly Tyr Leu Ser Met
    1280                1285                1290
Val Tyr Gly Gly Ser Ile Leu Ile Thr Arg Asp Pro Ser Asp Asn
    1295                1300                1305
Ser Lys Ile Gln Ile Ser Pro Lys Leu Arg Ile Ile His Asn Gly
    1310                1315                1320
Tyr Glu Gly Arg Gln Arg Asn Gln Cys Asn Leu Met Lys Lys Tyr
    1325                1330                1335
Gly Lys Leu Gly Asp Lys Phe Ile Ile Tyr Thr Thr Leu Gly Ile
    1340                1345                1350
Asn Pro Asn Asn Leu Ser Asn Lys Lys Leu Ile Tyr Pro Val Tyr
    1355                1360                1365
Gln Tyr Glu Gly Asn Glu Ser Lys Leu Ser Gln Gly Arg Leu Leu
    1370                1375                1380
Phe Tyr Arg Asp Ser Thr Thr Asn Phe Thr Arg Ala Trp Phe Pro
    1385                1390                1395
Asn Leu Ser Ser Asp Ser Lys Glu Met Ser Ile Thr Thr Gly Gly
    1400                1405                1410
Asn Ile Ser Gly Asn Tyr Gly Tyr Ile Asp Asn Lys His Ser Asp
    1415                1420                1425
Asn Lys Pro Phe Glu Glu Tyr Phe Tyr Met Asp Asp His Gly Gly
    1430                1435                1440
Ile Asp Thr Asp Val Ser Glu Pro Ile Phe Ile Asn Thr Lys Ile
    1445                1450                1455
Gln Pro Ser Asn Val Lys Ile Ile Val Lys Thr Val Lys Asp Asp
    1460                1465                1470
Gly Lys Leu Asp Ser Lys Pro Tyr Ile Ala Glu Asp Lys Val Ser
    1475                1480                1485
Val Lys Pro Thr Pro Asn Phe Glu Glu Met Cys Tyr Gln Phe Asn
    1490                1495                1500
Asn Leu Asp Gln Ile Asp Val Ser Thr Leu Val Phe Lys Asn Asn
    1505                1510                1515
Glu Ala Ser Ile Asp Ile Thr Phe Thr Ala Ser Ala Asp Ala Phe
    1520                1525                1530
Glu Ser Gly Lys Glu Gln Arg Asn Leu Gly Glu Glu His Phe Ser
    1535                1540                1545
Ile Arg Ile Ile Lys Lys Ala Asn Val Asn Asp Val Leu Thr Leu
    1550                1555                1560
His His Asp Pro Ser Gly Ala Gln Tyr Met Gln Trp Gly Ala Tyr
    1565                1570                1575
Arg Thr Arg Leu Asn Thr Leu Phe Ala Arg Lys Leu Ile Ser Arg
    1580                1585                1590
Ala Asn Ala Gly Ile Asp Thr Ile Leu Ser Met Glu Thr Gln Asn
    1595                1600                1605
Ile Gln Glu Pro Gln Leu Gly Lys Gly Phe Tyr Val Asn Phe Thr
    1610                1615                1620
Leu Pro Lys Tyr Asp Gln Asn Thr His Gly Asn Glu Arg Gln Phe
    1625                1630                1635
Lys Ile His Ile Gly Asn Ile Ala Gly Asp Asn Thr Met Arg Pro
    1640                1645                1650
Tyr Tyr Gln Gly Ile Leu Ala Asp Thr Glu Thr Ser Val Val Leu
    1655                1660                1665
```

-continued

```
Phe Val Pro Tyr Glu Lys Gln Ser Tyr Thr Asn Glu Gly Val Arg
    1670            1675                1680

Leu Gly Val Glu Tyr Lys Lys Val Ser Tyr Leu Gly Val Trp Glu
    1685            1690                1695

Pro Ala Phe Phe Tyr Phe Asn Glu Ile Gln Gln Lys Phe Ile Leu
    1700            1705                1710

Ile Asn Asp Ala Asp His Asn Ser Ala Met Thr Gln Ser Gly Glu
    1715            1720                1725

Lys Thr Gly Ile Lys Lys Tyr Lys Gly Phe Leu Asp Val Ser Ile
    1730            1735                1740

Leu Ile Asp His Gln His Thr Glu Pro Met Asp Phe Asn Gly Ala
    1745            1750                1755

Asn Ser Leu Tyr Phe Trp Glu Leu Phe Tyr Tyr Thr Pro Met Leu
    1760            1765                1770

Ile Ala Gln Arg Leu Leu His Glu Gln Asn Phe Asp Glu Ala Asn
    1775            1780                1785

Arg Trp Leu Lys Tyr Val Trp Asn Pro Ser Gly His Ile Ala Asn
    1790            1795                1800

Gly Gln Lys Gln His Pro His Asn Trp Asn Val Arg Pro Leu Gln
    1805            1810                1815

Glu Asp Thr Ser Trp Asn Asp Asp Pro Leu Asp Thr Phe Asp Pro
    1820            1825                1830

Asp Ala Ile Ala Gln His Asp Pro Met His Tyr Lys Val Ala Thr
    1835            1840                1845

Phe Met Cys Ala Leu Asp Leu Leu Ile Glu Gln Gly Asp Tyr Ala
    1850            1855                1860

Tyr Arg Gln Leu Glu Arg Asp Thr Leu Ala Glu Ala Lys Met Trp
    1865            1870                1875

Tyr Met Gln Ala Leu His Leu Leu Gly Asp Lys Pro His Leu Leu
    1880            1885                1890

Leu Ser Ser Thr Trp Ser Asp Pro Glu Leu Lys Glu Ala Ala Asp
    1895            1900                1905

Leu Glu Lys Gln Gln Ala His Ala Lys Ala Ile Ala Asp Leu Arg
    1910            1915                1920

Gln Gly Gln Pro Lys Asp Gly Ser Asn Thr Asp Leu Phe Leu Pro
    1925            1930                1935

Gln Val Asn Glu Val Met Leu Ser Tyr Trp Gln Lys Leu Glu Gln
    1940            1945                1950

Arg Leu Tyr Asn Leu Arg His Asn Leu Ser Ile Asp Gly Gln Pro
    1955            1960                1965

Leu His Leu Pro Ile Phe Ala Thr Pro Ala Asp Pro Lys Ala Leu
    1970            1975                1980

Leu Ser Ala Ala Val Ala Ser Ser Gln Gly Gly Ser Asn Leu Pro
    1985            1990                1995

Ser Glu Phe Ile Ser Val Trp Arg Phe Pro His Met Leu Glu Asn
    2000            2005                2010

Ala Arg Ser Met Val Ser Gln Leu Thr Gln Phe Gly Ser Thr Leu
    2015            2020                2025

Gln Asn Ile Ile Glu Arg Gln Asp Ala Glu Ala Leu Asn Thr Leu
    2030            2035                2040

Leu Gln Asn Gln Ala Ala Glu Leu Ile Leu Thr Asn Leu Ser Ile
    2045            2050                2055
```

-continued

```
Gln Asp Lys Thr Ile Glu Glu Leu Asp Val Glu Lys Thr Val Leu
    2060            2065            2070

Glu Lys Thr Arg Ala Gly Ala Lys Ser Arg Phe Asp Ser Tyr Ser
    2075            2080            2085

Lys Phe Tyr Asp Glu Asp Ile Asn Ala Gly Glu Lys Gln Ala Met
    2090            2095            2100

Ala Leu Arg Ala Ser Val Ala Gly Ile Ser Thr Ala Leu Gln Ala
    2105            2110            2115

Ser His Leu Ala Gly Ala Ala Leu Asp Leu Ala Pro Asn Ile Phe
    2120            2125            2130

Gly Phe Ala Asp Gly Gly Ser His Trp Gly Ala Ile Ala Gln Ala
    2135            2140            2145

Thr Ser Asn Val Met Glu Phe Ser Ala Ser Val Met Ser Thr Glu
    2150            2155            2160

Ala Asp Lys Ile Ser Gln Ser Glu Ala Tyr Arg Arg Arg Arg Gln
    2165            2170            2175

Glu Trp Lys Ile Gln Arg Asn Asn Ala Asp Ala Glu Leu Lys Gln
    2180            2185            2190

Ile Asp Ala Gln Leu Gln Ser Leu Val Val Arg Arg Glu Ala Ala
    2195            2200            2205

Val Leu Gln Lys Thr Ser Leu Lys Thr Gln Gln Glu Gln Thr His
    2210            2215            2220

Ala Gln Leu Thr Phe Leu Gln His Lys Phe Ser Asn Gln Ala Leu
    2225            2230            2235

Tyr Asn Trp Leu Arg Gly Arg Leu Ser Ala Ile Tyr Phe Gln Phe
    2240            2245            2250

Tyr Asp Leu Ala Val Ala Arg Cys Leu Met Ala Glu Met Ala Tyr
    2255            2260            2265

Arg Trp Glu Thr Asn Asp Ala Ala Ala Arg Phe Ile Lys Pro Gly
    2270            2275            2280

Ala Trp Gln Gly Thr His Ala Gly Leu Leu Ala Gly Glu Thr Leu
    2285            2290            2295

Met Leu Asn Leu Ala Gln Met Glu Asp Ala His Leu Lys Gln Glu
    2300            2305            2310

Gln Arg Val Leu Glu Val Glu Arg Thr Val Ser Leu Ala Glu Val
    2315            2320            2325

Tyr Lys Glu Lys Gly Gln Phe Ser Leu Thr Lys Lys Ile Ala Glu
    2330            2335            2340

Leu Val Asn Lys Lys Pro Asp Thr Thr Ser Ser Arg Asn Asn Thr
    2345            2350            2355

Leu Asn Phe Gly Glu Gly Asn Ala Lys Thr Ser Leu Gln Ala Ser
    2360            2365            2370

Ile Ser Leu Ala Asp Leu Gln Ile Arg His Asp Tyr Pro Glu Asn
    2375            2380            2385

Ser Gly Ala Gly Asn Val Arg Arg Ile Lys Gln Ile Ser Val Thr
    2390            2395            2400

Leu Pro Ala Leu Leu Gly Pro Tyr Gln Asp Val Gln Ala Ile Leu
    2405            2410            2415

Ser Tyr Gly Gly Asp Ala Thr Gly Leu Ala Lys Gly Cys Lys Ala
    2420            2425            2430

Leu Ala Val Ser His Gly Met Asn Asp Ser Gly Gln Phe Gln Leu
    2435            2440            2445

Asp Phe Asn Asp Gly Lys Phe Leu Pro Phe Glu Gly Ile Glu Ile
```

-continued

```
              2450                2455                2460

Asp Lys Gly Thr Leu Thr Leu Ser Phe Pro Asn Ala Thr Glu Lys
            2465                2470                2475

Gln Lys Thr Met Leu Glu Ser Ile Ser Asp Ile Ile Leu His Ile
        2480                2485                2490

Arg Tyr Thr Ile Arg Gln
        2495

<210> SEQ ID NO 63
<211> LENGTH: 2381
<212> TYPE: PRT
<213> ORGANISM: Photorhabdus luminescens

<400> SEQUENCE: 63

Met Asn Ser Tyr Val Lys Glu Ile Pro Asp Val Leu Gln Ser Gln Tyr
1               5                   10                  15

Gly Ile Asn Cys Leu Thr Asp Ile Cys His Tyr Ser Phe Asn Glu Phe
            20                  25                  30

Arg Gln Gln Val Ser Asp His Leu Ser Trp Ser Glu Thr Asn Arg Leu
        35                  40                  45

Tyr Arg Asp Ala Gln Gln Gln Lys Glu Asn Gln Leu Tyr Glu Ala
    50                  55                  60

Arg Ile Leu Lys Arg Ala Asn Pro Gln Leu Gln Asn Ala Val His Leu
65                  70                  75                  80

Gly Ile Thr Leu Pro His Ala Glu Leu Arg Gly Tyr Asn Ser Glu Phe
                85                  90                  95

Gly Gly Arg Ala Ser Gln Tyr Val Ala Pro Gly Ser Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr His Leu Asp Glu Arg Arg Pro Asp
    130                 135                 140

Leu Gln Ser Met Thr Leu Ser Gln Gln Asn Met Asp Thr Glu Leu Ser
145                 150                 155                 160

Thr Leu Ser Leu Ser Asn Glu Ile Leu Leu Lys Gly Ile Lys Ala Asn
                165                 170                 175

Gln Ser Asn Leu Asp Ser Asp Thr Lys Val Met Glu Met Leu Ser Thr
            180                 185                 190

Phe Arg Pro Ser Gly Thr Ile Pro Tyr His Asp Ala Tyr Glu Asn Val
        195                 200                 205

Arg Lys Ala Ile Gln Leu Gln Asp Pro Lys Leu Glu Gln Phe Gln Lys
    210                 215                 220

Ser Pro Ala Val Ala Gly Leu Met His Gln Ala Ser Leu Leu Gly Ile
225                 230                 235                 240

Asn Asn Ser Ile Ser Pro Glu Leu Phe Asn Ile Leu Thr Glu Glu Ile
                245                 250                 255

Thr Glu Ala Asn Ala Glu Ala Ile Tyr Lys Gln Asn Phe Gly Asp Ile
            260                 265                 270

Asp Pro Ala Cys Leu Ala Met Pro Glu Tyr Leu Lys Ser Tyr Tyr Asn
        275                 280                 285

Phe Ser Asp Glu Glu Leu Ser Gln Phe Ile Arg Lys Tyr Pro Asp Asn
    290                 295                 300

Glu Leu Asn Thr Gln Lys Ile His Leu Leu Lys Ile Asn Lys Ile Ile
305                 310                 315                 320
```

-continued

```
Leu Leu Ser Gln Ala Val Asn Leu Pro Phe Leu Lys Leu Asp Glu Ile
            325                 330                 335
Ile Pro Glu Gln Asn Ile Thr Pro Thr Val Leu Gly Lys Ile Phe Leu
            340                 345                 350
Val Lys Tyr Tyr Met Gln Lys Tyr Asn Ile Gly Thr Glu Thr Ala Leu
            355                 360                 365
Ile Leu Cys Asn Asp Ser Ile Ser Gln Tyr Ser Tyr Ser Asn Gln Pro
            370                 375                 380
Ser Gln Phe Asp Arg Leu Phe Asn Thr Ser Pro Leu Asn Gly Gln Tyr
385                 390                 395                 400
Phe Val Ile Glu Asp Thr Asn Ile Asp Leu Ser Leu Asn Ser Thr Asp
            405                 410                 415
Asn Trp His Lys Ala Val Leu Lys Arg Ala Phe Asn Val Asp Asp Ile
            420                 425                 430
Ser Leu Tyr Arg Leu Leu His Ile Ala Asn His Asn Asn Thr Asp Gly
            435                 440                 445
Lys Ile Ala Asn Asn Ile Lys Asn Leu Ser Asn Leu Tyr Met Thr Lys
            450                 455                 460
Leu Leu Ala Asp Ile His Gln Leu Thr Ile Asp Glu Leu Tyr Leu Leu
465                 470                 475                 480
Leu Ile Thr Ile Gly Glu Asp Lys Ile Asn Leu Tyr Asp Ile Asp Asp
            485                 490                 495
Lys Glu Leu Glu Lys Leu Ile Asn Arg Leu Asp Thr Leu Ser Asn Trp
            500                 505                 510
Leu His Thr Gln Lys Trp Ser Ile Tyr Gln Leu Phe Leu Met Thr Thr
            515                 520                 525
Thr Asn Tyr Asp Lys Thr Leu Thr Pro Glu Ile Gln Asn Leu Leu Asp
            530                 535                 540
Thr Val Tyr Asn Gly Leu Gln Asn Phe Asp Lys Asn Lys Thr Lys Leu
545                 550                 555                 560
Leu Ala Ala Ile Ala Pro Tyr Ile Ala Ala Thr Leu Gln Leu Pro Ser
            565                 570                 575
Glu Asn Val Ala His Ser Ile Leu Leu Trp Ala Asp Lys Ile Lys Pro
            580                 585                 590
Ser Glu Asn Lys Ile Thr Ala Glu Lys Phe Trp Ile Trp Leu Gln Asn
            595                 600                 605
Arg Asp Thr Thr Glu Leu Ser Lys Pro Pro Glu Met Gln Glu Gln Ile
            610                 615                 620
Ile Gln Tyr Cys His Cys Leu Ala Gln Leu Thr Met Ile Tyr Arg Ser
625                 630                 635                 640
Ser Gly Ile Asn Glu Asn Ala Phe Arg Leu Phe Ile Glu Lys Pro Thr
            645                 650                 655
Ile Phe Gly Ile Pro Asp Glu Pro Asn Lys Ala Thr Pro Ala His Asn
            660                 665                 670
Ala Pro Thr Leu Ile Ile Leu Thr Arg Phe Ala Asn Trp Val Asn Ser
            675                 680                 685
Leu Gly Glu Lys Ala Ser Pro Ile Leu Thr Ala Phe Glu Asn Lys Thr
            690                 695                 700
Leu Thr Ala Glu Lys Leu Ala Asn Ala Met Asn Leu Asp Ala Asn Leu
705                 710                 715                 720
Leu Glu Gln Ala Ser Ile Gln Ala Gln Asn Tyr Lys Gln Val Thr Lys
            725                 730                 735
Glu Asn Thr Phe Ser Asn Trp Gln Ser Ile Asp Ile Ile Leu Gln Trp
```

-continued

```
                740                 745                 750
Thr Asn Ile Ala Ser Asn Leu Asn Ile Ser Pro Gln Gly Ile Ser Pro
            755                 760                 765
Leu Ile Ala Leu Asp Tyr Ile Lys Pro Ala Gln Lys Thr Pro Thr Tyr
    770                 775                 780
Ala Gln Trp Glu Asn Ala Ala Ile Ala Leu Thr Ala Gly Leu Asp Thr
785                 790                 795                 800
Gln Gln Thr His Thr Leu His Val Phe Leu Asp Glu Ser Arg Ser Thr
                805                 810                 815
Ala Leu Ser Asn Tyr Tyr Ile Gly Lys Val Ala Asn Arg Ala Ala Ser
            820                 825                 830
Ile Lys Ser Arg Asp Asp Leu Tyr Gln Tyr Leu Leu Ile Asp Asn Gln
        835                 840                 845
Val Ser Ala Glu Ile Lys Thr Thr Arg Ile Ala Glu Ala Ile Ala Ser
850                 855                 860
Ile Gln Leu Tyr Val Asn Arg Ala Leu Glu Asn Ile Glu Ile His Ala
865                 870                 875                 880
Val Ser Asp Val Ile Thr Arg Gln Phe Phe Ile Asp Trp Asp Lys Tyr
                885                 890                 895
Asn Lys Arg Tyr Ser Thr Trp Ala Gly Val Ser Gln Leu Val Tyr Tyr
            900                 905                 910
Pro Glu Asn Tyr Ile Asp Pro Thr Met Arg Ile Gly Gln Thr Lys Met
        915                 920                 925
Met Asp Thr Leu Leu Gln Ser Val Ser Gln Ser Gln Leu Asn Ala Asp
    930                 935                 940
Thr Val Glu Asp Ala Phe Lys Ser Tyr Leu Thr Ser Phe Glu Gln Val
945                 950                 955                 960
Ala Asn Leu Glu Val Ile Ser Ala Tyr His Asp Asn Val Asn Asn Asp
                965                 970                 975
Gln Gly Leu Thr Tyr Phe Ile Gly Asn Ser Lys Thr Glu Val Asn Gln
            980                 985                 990
Tyr Tyr Trp Arg Ser Val Asp His  Ser Lys Phe Asn Asp  Gly Lys Phe
        995                 1000                1005
Ala Ala  Asn Ala Trp Ser Glu  Trp His Lys Ile Asp  Cys Ala Ile
    1010                1015                1020
Asn Pro  Tyr Gln Ser Thr Ile  Arg Pro Val Ile Tyr  Lys Ser Arg
    1025                1030                1035
Leu Tyr  Leu Ile Trp Leu Glu  Gln Lys Glu Thr Ala  Lys Gln Lys
    1040                1045                1050
Glu Asp  Asn Lys Val Thr Thr  Asp Tyr His Tyr Glu  Leu Lys Leu
    1055                1060                1065
Ala His  Ile Arg Tyr Asp Gly  Thr Trp Asn Val Pro  Ile Thr Phe
    1070                1075                1080
Asp Val  Asp Glu Lys Ile Leu  Ala Leu Glu Leu Thr  Lys Ser Gln
    1085                1090                1095
Ala Pro  Gly Leu Tyr Cys Ala  Gly Tyr Gln Gly Glu  Asp Thr Leu
    1100                1105                1110
Leu Ile  Met Phe Tyr Arg Lys  Lys Glu Lys Leu Asp  Asp Tyr Lys
    1115                1120                1125
Thr Ala  Pro Met Gln Gly Phe  Tyr Ile Phe Ser Asp  Met Ser Ser
    1130                1135                1140
Lys Asp  Met Thr Asn Glu Gln  Cys Asn Ser Tyr Arg  Asp Asn Gly
    1145                1150                1155
```

-continued

```
Tyr Thr His Phe Asp Thr Asn Ser Asp Thr Asn Ser Val Ile Arg
    1160                1165                1170

Ile Asn Asn Arg Tyr Ala Glu Asp Tyr Glu Ile Pro Ser Leu Ile
    1175                1180                1185

Asn His Ser Asn Ser His Asp Trp Gly Glu Tyr Asn Leu Ser Gln
    1190                1195                1200

Val Tyr Gly Gly Asn Ile Val Ile Asn Tyr Lys Val Thr Ser Asn
    1205                1210                1215

Asp Leu Lys Ile Tyr Ile Ser Pro Lys Leu Arg Ile Ile His Asp
    1220                1225                1230

Gly Lys Glu Gly Arg Glu Arg Ile Gln Ser Asn Leu Ile Lys Lys
    1235                1240                1245

Tyr Gly Lys Leu Gly Asp Lys Phe Ile Ile Tyr Thr Ser Leu Gly
    1250                1255                1260

Ile Asn Pro Asn Asn Ser Ser Asn Arg Phe Met Phe Tyr Pro Val
    1265                1270                1275

Tyr Gln Tyr Asn Gly Asn Thr Ser Gly Leu Ala Gln Gly Arg Leu
    1280                1285                1290

Leu Phe His Arg Asp Thr Ser Tyr Ser Ser Lys Val Ala Ala Trp
    1295                1300                1305

Ile Pro Gly Ala Gly Arg Ser Leu Ile Asn Glu Asn Ala Asn Ile
    1310                1315                1320

Gly Asp Asp Cys Ala Glu Asp Ser Val Asn Lys Pro Asp Asp Leu
    1325                1330                1335

Lys Gln Tyr Ile Tyr Met Thr Asp Ser Lys Gly Thr Ala Thr Asp
    1340                1345                1350

Val Ser Gly Pro Val Asp Ile Asn Thr Ala Ile Ser Ser Glu Lys
    1355                1360                1365

Val Gln Ile Thr Ile Lys Ala Gly Lys Glu Tyr Ser Leu Thr Ala
    1370                1375                1380

Asn Lys Asp Val Ser Val Gln Pro Ser Pro Ser Phe Glu Glu Met
    1385                1390                1395

Cys Tyr Gln Phe Asn Ala Leu Glu Ile Asp Gly Ser Asn Leu Asn
    1400                1405                1410

Phe Thr Asn Asn Ser Ala Ser Ile Asp Val Thr Phe Thr Ala Leu
    1415                1420                1425

Ala Asp Asp Gly Arg Lys Leu Gly Tyr Glu Ile Phe Asn Ile Pro
    1430                1435                1440

Val Ile Gln Lys Val Lys Thr Asp Asn Ala Leu Thr Leu Phe His
    1445                1450                1455

Asp Glu Asn Gly Ala Gln Tyr Met Gln Trp Gly Ala Tyr Arg Ile
    1460                1465                1470

Arg Leu Asn Thr Leu Phe Ala Arg Gln Leu Val Glu Arg Ala Asn
    1475                1480                1485

Thr Gly Ile Asp Thr Ile Leu Ser Met Glu Thr Gln Asn Ile Gln
    1490                1495                1500

Glu Pro Met Met Gly Ile Gly Ala Tyr Ile Glu Leu Ile Leu Asp
    1505                1510                1515

Lys Tyr Asn Pro Asp Ile His Gly Thr Asn Lys Ser Phe Lys Ile
    1520                1525                1530

Ile Tyr Gly Asp Ile Phe Lys Ala Gly Asp His Phe Pro Ile Tyr
    1535                1540                1545
```

-continued

```
Gln Gly Ala Leu Ser Asp Ile Thr Gln Thr Thr Val Lys Leu Phe
1550                1555                1560

Leu Pro Arg Val Asp Asn Ala Tyr Gly Asn Lys Asn Asn Leu Tyr
1565                1570                1575

Val Tyr Ala Ala Tyr Gln Lys Val Glu Thr Asn Phe Ile Arg Phe
1580                1585                1590

Val Lys Glu Asp Asn Lys Pro Ala Thr Phe Asp Thr Thr Tyr
1595                1600                1605

Lys Asn Gly Thr Phe Pro Gly Leu Ala Ser Ala Arg Val Ile Gln
1610                1615                1620

Thr Val Ser Glu Pro Met Asp Phe Ser Gly Ala Asn Ser Leu Tyr
1625                1630                1635

Phe Trp Glu Leu Phe Tyr Tyr Thr Pro Met Met Val Ala Gln Arg
1640                1645                1650

Leu Leu His Glu Gln Asn Phe Asp Glu Ala Asn Arg Trp Leu Lys
1655                1660                1665

Tyr Val Trp Ser Pro Ser Gly Tyr Ile Val Arg Gly Gln Ile Lys
1670                1675                1680

Asn Tyr His Trp Asn Val Arg Pro Leu Leu Glu Asn Thr Ser Trp
1685                1690                1695

Asn Ser Asp Pro Leu Asp Ser Val Asp Pro Asp Ala Val Ala Gln
1700                1705                1710

His Asp Pro Met His Tyr Lys Val Ala Thr Phe Met Arg Thr Leu
1715                1720                1725

Asp Leu Leu Met Ala Arg Gly Asp His Ala Tyr Arg Gln Leu Glu
1730                1735                1740

Arg Asp Thr Leu Asn Glu Ala Lys Met Trp Tyr Met Gln Ala Leu
1745                1750                1755

His Leu Leu Gly Asn Lys Pro Tyr Leu Pro Leu Ser Ser Val Trp
1760                1765                1770

Asn Asp Pro Arg Leu Asp Asn Ala Ala Ala Thr Thr Thr Gln Lys
1775                1780                1785

Ala His Ala Tyr Ala Ile Thr Ser Leu Arg Gln Gly Thr Gln Thr
1790                1795                1800

Pro Ala Leu Leu Leu Arg Ser Ala Asn Thr Leu Thr Asp Leu Phe
1805                1810                1815

Leu Pro Gln Ile Asn Asp Val Met Leu Ser Tyr Trp Asn Lys Leu
1820                1825                1830

Glu Leu Arg Leu Tyr Asn Leu Arg His Asn Leu Ser Ile Asp Gly
1835                1840                1845

Gln Pro Leu His Leu Pro Ile Tyr Ala Thr Pro Ala Asp Pro Lys
1850                1855                1860

Ala Leu Leu Ser Ala Ala Val Ala Thr Ser Gln Gly Gly Lys
1865                1870                1875

Leu Pro Glu Ser Phe Ile Ser Leu Trp Arg Phe Pro His Met Leu
1880                1885                1890

Glu Asn Ala Arg Ser Met Val Thr Gln Leu Ile Gln Phe Gly Ser
1895                1900                1905

Thr Leu Gln Asn Ile Ile Glu Arg Gln Asp Ala Glu Ser Leu Asn
1910                1915                1920

Ala Leu Leu Gln Asn Gln Ala Lys Glu Leu Ile Leu Thr Thr Leu
1925                1930                1935

Ser Ile Gln Asp Lys Thr Ile Glu Glu Ile Asp Ala Glu Lys Thr
```

-continued

```
          1940                1945                1950
Val Leu Glu Lys Ser Lys Ala  Gly Ala Lys Ser Arg  Phe Asp Asn
    1955                1960                1965

Tyr Ser Lys Leu Tyr Asp Glu  Asp Val Asn Ala Gly  Glu Arg Gln
    1970                1975                1980

Ala Leu Asp Met Arg Ile Ala  Ser Gln Ser Ile Thr  Ser Gly Leu
    1985                1990                1995

Lys Gly Leu His Met Ala Ala  Ala Ala Leu Glu Met  Val Pro Asn
    2000                2005                2010

Ile Tyr Gly Phe Ala Val Gly  Gly Thr Arg Tyr Gly  Ala Ile Ala
    2015                2020                2025

Asn Ala Ile Ala Ile Gly Gly  Gly Ile Ala Ala Glu  Gly Leu Leu
    2030                2035                2040

Ile Glu Ala Glu Lys Val Ser  Gln Ser Glu Ile Trp  Arg Arg Arg
    2045                2050                2055

Arg Gln Glu Trp Glu Ile Gln  Arg Asn Asn Ala Glu  Ala Glu Met
    2060                2065                2070

Lys Gln Ile Asp Ala Gln Leu  Lys Ser Leu Thr Val  Arg Arg Glu
    2075                2080                2085

Ala Ala Val Leu Gln Lys Thr  Gly Leu Lys Thr Gln  Gln Glu Gln
    2090                2095                2100

Thr Gln Ala Gln Leu Ala Phe  Leu Gln Arg Lys Phe  Ser Asn Gln
    2105                2110                2115

Ala Leu Tyr Asn Trp Leu Arg  Gly Arg Leu Ala Ala  Ile Tyr Phe
    2120                2125                2130

Gln Phe Tyr Asp Leu Val Val  Ala Arg Cys Leu Met  Ala Glu Gln
    2135                2140                2145

Ala Tyr Arg Trp Glu Thr Asn  Asp Ser Ser Ala Arg  Phe Ile Lys
    2150                2155                2160

Pro Gly Ala Trp Gln Gly Thr  Tyr Ala Gly Leu Leu  Ala Gly Glu
    2165                2170                2175

Thr Leu Met Leu Asn Leu Ala  Gln Met Glu Asp Ala  His Leu Lys
    2180                2185                2190

Gln Glu Gln Arg Ala Leu Glu  Val Glu Arg Thr Val  Ser Leu Ala
    2195                2200                2205

Gln Val Tyr Gln Ser Leu Gly  Glu Lys Ser Phe Ala  Leu Lys Asp
    2210                2215                2220

Lys Ile Glu Ala Leu Leu Gln  Gly Asp Lys Glu Thr  Ser Ala Gly
    2225                2230                2235

Asn Asp Gly Asn Gln Leu Lys  Leu Thr Asn Asn Thr  Leu Ser Ala
    2240                2245                2250

Thr Leu Thr Leu Gln Asp Leu  Lys Leu Lys Asp Asp  Tyr Pro Glu
    2255                2260                2265

Glu Met Gln Leu Gly Lys Thr  Arg Arg Ile Lys Gln  Ile Ser Val
    2270                2275                2280

Ser Leu Pro Ala Leu Leu Gly  Pro Tyr Gln Asp Val  Gln Ala Val
    2285                2290                2295

Leu Ser Tyr Gly Gly Asp Ala  Thr Gly Leu Ala Lys  Gly Cys Lys
    2300                2305                2310

Ala Leu Ala Val Ser His Gly  Leu Asn Asp Asn Gly  Gln Phe Gln
    2315                2320                2325

Leu Asp Phe Asn Asp Gly Lys  Phe Leu Pro Phe Glu  Gly Ile Asp
    2330                2335                2340
```

Ile Asn Asp Lys Gly Thr Phe Thr Leu Ser Phe Pro Asn Ala Ala
2345                2350                2355

Ser Lys Gln Lys Asn Ile Leu Gln Met Leu Thr Asp Ile Ile Leu
2360                2365                2370

His Ile Arg Tyr Thr Ile Leu Glu
2375                2380

<210> SEQ ID NO 64
<211> LENGTH: 949
<212> TYPE: PRT
<213> ORGANISM: Photorhabdus luminescens

<400> SEQUENCE: 64

Met Lys Asn Ile Asp Pro Lys Leu Tyr Gln His Thr Pro Thr Val Asn
1               5                   10                  15

Val Tyr Asp Asn Arg Gly Leu Thr Ile Arg Asn Ile Asp Phe His Arg
            20                  25                  30

Asp Val Ala Gly Gly Asp Thr Asp Thr Arg Ile Thr Arg His Gln Tyr
        35                  40                  45

Asp Thr Arg Gly His Leu Ser Gln Ser Ile Asp Pro Arg Leu Tyr Asp
    50                  55                  60

Ala Lys Gln Thr Asn Asn Ser Thr Asn Pro Asn Phe Leu Trp Gln Tyr
65                  70                  75                  80

Asn Leu Thr Gly Asp Thr Leu Arg Thr Glu Ser Val Asp Ala Gly Arg
                85                  90                  95

Thr Val Ala Leu Asn Asp Ile Glu Gly Arg Gln Val Leu Ile Val Thr
            100                 105                 110

Ala Thr Gly Ala Ile Gln Thr Arg Gln Tyr Glu Ala Asn Thr Leu Pro
        115                 120                 125

Gly Arg Leu Leu Ser Val Ser Glu Gln Ala Pro Gly Glu Gln Thr Pro
    130                 135                 140

Arg Val Thr Glu His Phe Ile Trp Ala Gly Asn Thr Gln Ala Glu Lys
145                 150                 155                 160

Asp His Asn Leu Ala Gly Gln Tyr Val Arg His Tyr Asp Thr Ala Gly
                165                 170                 175

Val Thr Gln Leu Glu Ser Leu Ser Leu Thr Glu Asn Ile Leu Ser Gln
            180                 185                 190

Ser Arg Gln Leu Leu Ala Asp Gly Gln Glu Ala Asp Trp Thr Gly Asn
        195                 200                 205

Asp Glu Thr Leu Trp Gln Thr Lys Leu Asn Ser Glu Thr Tyr Thr Thr
    210                 215                 220

Gln Ser Thr Phe Asp Ala Thr Gly Ala Leu Leu Thr Gln Thr Asp Ala
225                 230                 235                 240

Lys Gly Asn Met Gln Arg Leu Ala Tyr Asn Val Ala Gly Gln Leu Gln
                245                 250                 255

Gly Ser Trp Leu Thr Leu Lys Asn Gln Ser Glu Gln Val Ile Val Lys
            260                 265                 270

Ser Leu Thr Tyr Ser Ala Ala Gly Gln Lys Leu Arg Glu Glu His Gly
        275                 280                 285

Asn Gly Val Ile Thr Glu Tyr Ser Tyr Glu Pro Glu Thr Leu Arg Leu
    290                 295                 300

Ile Gly Thr Thr Thr Arg Arg Gln Ser Asp Ser Lys Val Leu Gln Asp
305                 310                 315                 320

Leu Arg Tyr Glu His Asp Pro Val Gly Asn Ile Ile Ser Val Arg Asn

-continued

```
                325                 330                 335
Asp Ala Glu Ala Thr Arg Phe Trp Arg Asn Gln Lys Ile Val Pro Glu
            340                 345                 350
Asn Thr Tyr Thr Tyr Asp Ser Leu Tyr Gln Leu Ile Ser Ala Thr Gly
        355                 360                 365
Arg Glu Met Ala Asn Ile Gly Gln Gln Ser Asn Gln Leu Pro Ser Pro
    370                 375                 380
Ile Ile Pro Leu Pro Thr Asp Glu Asn Ser Tyr Thr Asn Tyr Thr Arg
385                 390                 395                 400
Ser Tyr Asn Tyr Asp Arg Gly Gly Asn Leu Val Gln Ile Arg His Ser
                405                 410                 415
Ser Pro Ala Ala Gln Asn Asn Tyr Thr Thr Asp Ile Thr Val Ser Asn
            420                 425                 430
Arg Ser Asn Arg Ala Val Leu Ser Ser Leu Thr Ser Asp Pro Thr Gln
        435                 440                 445
Val Glu Ala Leu Phe Asp Ala Gly Gly His Gln Thr Lys Leu Leu Pro
    450                 455                 460
Gly Gln Glu Leu Ser Trp Asn Thr Arg Gly Glu Leu Lys Gln Val Thr
465                 470                 475                 480
Pro Val Ser Arg Glu Ser Ala Ser Asp Arg Glu Trp Tyr Arg Tyr Gly
                485                 490                 495
Asn Asp Gly Met Arg Arg Leu Lys Val Ser Glu Gln Gln Thr Gly Asn
            500                 505                 510
Ser Thr Gln Gln Gln Arg Val Thr Tyr Leu Pro Asp Leu Glu Leu Arg
        515                 520                 525
Thr Thr Gln Asn Gly Thr Thr Thr Ser Glu Asp Leu His Ala Ile Thr
    530                 535                 540
Val Gly Ala Ala Gly His Ala Gln Val Arg Val Leu His Trp Glu Thr
545                 550                 555                 560
Thr Pro Pro Ala Gly Ile Asn Asn Asn Gln Leu Arg Tyr Ser Tyr Asp
                565                 570                 575
Asn Leu Ile Gly Ser Ser Gln Leu Glu Leu Asp Asn Ala Gly Gln Ile
            580                 585                 590
Ile Ser Gln Glu Glu Tyr Tyr Pro Phe Gly Gly Thr Ala Leu Trp Ala
        595                 600                 605
Ala Arg Asn Gln Ile Glu Ala Ser Tyr Lys Ile Leu Arg Tyr Ser Gly
    610                 615                 620
Lys Glu Arg Asp Ala Thr Gly Leu Tyr Tyr Tyr Gly Tyr Arg Tyr Tyr
625                 630                 635                 640
Gln Pro Trp Val Gly Arg Trp Leu Ser Ala Asp Pro Ala Gly Thr Ile
                645                 650                 655
Asp Gly Leu Asn Leu Tyr Arg Met Val Arg Asn Asn Pro Ser Thr Leu
            660                 665                 670
Val Asp Ile Ser Gly Leu Ala Pro Thr Lys Tyr Asn Ile Pro Gly Phe
        675                 680                 685
Asp Phe Asp Val Glu Ile Asp Glu Gln Lys Arg Ser Lys Leu Lys Pro
    690                 695                 700
Thr Leu Ile Arg Ile Lys Asp Glu Phe Leu His Tyr Gly Pro Val Asp
705                 710                 715                 720
Lys Leu Leu Glu Glu Lys Lys Pro Gly Leu Asn Val Pro Glu Glu Leu
                725                 730                 735
Phe Asp Arg Gly Pro Ser Glu Asn Gly Val Ser Thr Leu Thr Phe Lys
            740                 745                 750
```

-continued

```
Lys Asp Leu Pro Ile Ser Cys Ile Ser Asn Thr Glu Tyr Thr Leu Asp
            755                 760                 765

Ile Leu Tyr Asn Lys His Glu Thr Lys Pro Phe Pro Tyr Glu Asn Glu
            770                 775                 780

Ala Thr Val Gly Ala Asp Leu Gly Val Ile Met Ser Val Glu Phe Gly
785                 790                 795                 800

Asn Lys Ser Ile Gly Asn Ala Ser Asp Glu Asp Leu Lys Glu Glu His
                805                 810                 815

Leu Pro Leu Gly Lys Ser Thr Met Asp Lys Thr Asp Leu Pro Asp Leu
                820                 825                 830

Lys Gln Gly Leu Met Ile Ala Glu Lys Ile Lys Ser Gly Lys Gly Ala
            835                 840                 845

Tyr Pro Phe His Phe Gly Ala Ala Ile Ala Val Val Tyr Gly Glu Asp
        850                 855                 860

Lys Lys Val Ala Ala Ser Ile Leu Thr Asp Leu Ser Glu Pro Lys Arg
865                 870                 875                 880

Asp Glu Gly Glu Tyr Leu Gln Ser Thr Arg Lys Val Ser Ala Met Phe
                885                 890                 895

Ile Thr Asn Val Asn Glu Phe Arg Gly His Asp Tyr Pro Lys Ser Lys
                900                 905                 910

Tyr Ser Ile Gly Leu Val Thr Ala Glu Lys Arg Gln Pro Val Ile Ser
            915                 920                 925

Lys Lys Arg Ala Asn Pro Glu Glu Ala Pro Ser Ser Ser Arg Asn Lys
            930                 935                 940

Lys Leu His Val His
945
```